United States Patent
Tanaka et al.

(10) Patent No.: US 9,598,411 B2
(45) Date of Patent: *Mar. 21, 2017

(54) SUBSTITUTED BENZIMIDAZOLE-TYPE PIPERIDINE COMPOUNDS AND USES THEREOF

(71) Applicant: Purdue Pharma L.P., Stamford, CT (US)

(72) Inventors: Nobuyuki Tanaka, Toyonaka (JP); Kenji Yamawaki, Toyonaka (JP); Jiangchao Yao, Monmouth Junction, NJ (US); Jianming Yu, Plainsboro, NJ (US); Xiaoming Zhou, Plainsboro, NJ (US)

(73) Assignee: Purdue Pharma L.P., Stamford, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/800,475

(22) Filed: Jul. 15, 2015

(65) Prior Publication Data
US 2015/0322066 A1    Nov. 12, 2015

Related U.S. Application Data

(63) Continuation of application No. 14/138,965, filed on Dec. 23, 2013, now Pat. No. 9,090,618.

(60) Provisional application No. 61/777,674, filed on Mar. 12, 2013, provisional application No. 61/746,505, filed on Dec. 27, 2012.

(51) Int. Cl.
  *C07D 471/08*   (2006.01)
  *C07D 401/04*   (2006.01)

(52) U.S. Cl.
  CPC ......... *C07D 471/08* (2013.01); *C07D 401/04* (2013.01)

(58) Field of Classification Search
  CPC ........................... C07D 471/08; C07D 401/04
  USPC ........................... 546/112; 514/299; 549/299
  See application file for complete search history.

(56) References Cited

U.S. PATENT DOCUMENTS

| | | |
|---|---|---|
| 3,536,809 A | 10/1970 | Applezweig |
| 3,598,123 A | 8/1971 | Zaffaroni |
| 3,845,770 A | 11/1974 | Theeuwes |
| 3,916,899 A | 11/1975 | Theeuwes et al. |
| 3,963,727 A | 6/1976 | Ueno et al. |
| 4,008,719 A | 2/1977 | Theeuwes et al. |
| 4,031,226 A | 6/1977 | Soudijn et al. |
| 4,223,137 A | 9/1980 | Yoshizaki et al. |
| 4,946,843 A | 8/1990 | Janssens et al. |
| 5,011,842 A | 4/1991 | Janssens et al. |
| 5,059,595 A | 10/1991 | Le Grazie |
| 5,073,543 A | 12/1991 | Marshall et al. |
| 5,086,056 A | 2/1992 | Janssens et al. |
| 5,120,548 A | 6/1992 | McClelland |
| 5,225,402 A | 7/1993 | Ogawa et al. |
| 5,354,556 A | 10/1994 | Sparks et al. |
| 5,591,767 A | 1/1997 | Mohr et al. |
| 5,639,476 A | 6/1997 | Oshlack et al. |
| 5,665,719 A | 9/1997 | Bock et al. |
| 5,674,533 A | 10/1997 | Santus et al. |
| 5,698,155 A | 12/1997 | Grosswald et al. |
| 5,733,566 A | 3/1998 | Lewis |
| 6,063,796 A | 5/2000 | Yang et al. |

(Continued)

FOREIGN PATENT DOCUMENTS

| | | |
|---|---|---|
| CA | 1085852 | 9/1980 |
| EP | 0029707 B1 | 2/1984 |

(Continued)

OTHER PUBLICATIONS

Allen (1999), "Orphanin-FQ/nociceptin (OFQ/N) modulates the activity of suprachiasmatic nucleus neurons," *J. Neurosci.* 19:2152-2160.

(Continued)

*Primary Examiner* — Niloofar Rahmani
(74) *Attorney, Agent, or Firm* — Dechert LLP

(57) ABSTRACT

The disclosure relates to Substituted Benzimidazole-Type Piperidine Compounds of Formula (I):

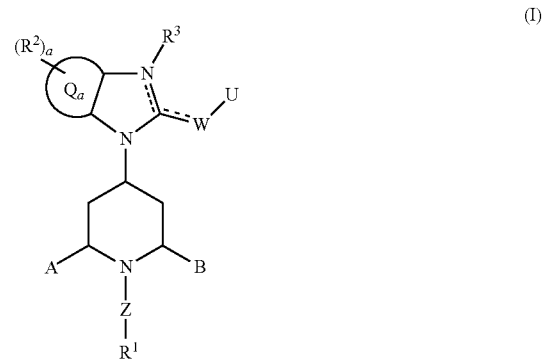

and pharmaceutically acceptable salts or solvates thereof, e.g., a pharmaceutically acceptable salt or solvate, wherein $R^1$, $R^2$, $R^3$, $Q_a$, W, U, A, B, Z, a, and the dashed lines are as defined herein, compositions comprising an effective amount of a Substituted Benzimidazole-Type Piperidine Compound, and methods to treat or prevent a condition, such as pain, comprising administering to an animal in need thereof an effective amount of a Substituted Benzimidazole-Type Piperidine Compound.

22 Claims, No Drawings

(56) References Cited

U.S. PATENT DOCUMENTS

| | | | |
|---|---|---|---|
| 6,136,839 A | 10/2000 | Isakson et al. | |
| 6,172,067 B1 | 1/2001 | Ito et al. | |
| 6,340,681 B1 | 1/2002 | Ito | |
| 6,423,716 B1 | 7/2002 | Matsuno et al. | |
| 6,531,484 B2 | 3/2003 | Willoughby | |
| 6,562,319 B2 | 5/2003 | Mishani et al. | |
| 6,635,653 B2 | 10/2003 | Goehring et al. | |
| 6,828,440 B2 | 12/2004 | Goehring et al. | |
| 6,855,724 B2* | 2/2005 | Basford ............... | C07D 519/00 514/217.07 |
| 6,861,421 B2 | 3/2005 | Goehring et al. | |
| 6,861,425 B2 | 3/2005 | Ito et al. | |
| 6,867,222 B2 | 3/2005 | Sun et al. | |
| 6,869,960 B2 | 3/2005 | Ito et al. | |
| 6,872,733 B2 | 3/2005 | Goehring et al. | |
| 6,916,805 B2 | 7/2005 | Dudley et al. | |
| 6,989,393 B2 | 1/2006 | Burrows et al. | |
| 7,105,505 B2 | 9/2006 | Zeng et al. | |
| 7,241,770 B2 | 7/2007 | Mentzel et al. | |
| 7,265,102 B2 | 9/2007 | Cai et al. | |
| 7,355,045 B2 | 4/2008 | Dey et al. | |
| 7,456,198 B2 | 11/2008 | Kyle et al. | |
| 7,495,109 B2 | 2/2009 | Sun et al. | |
| 7,563,809 B2 | 7/2009 | Goehring et al. | |
| 7,579,471 B2* | 8/2009 | Basford ............... | C07D 519/00 546/118 |
| 7,589,207 B2* | 9/2009 | Duan .................... | C07C 271/24 546/126 |
| 7,615,555 B2 | 11/2009 | Faull et al. | |
| 7,645,771 B2* | 1/2010 | Kazmierski .......... | C07D 451/04 514/304 |
| 7,678,809 B2 | 3/2010 | Kyle et al. | |
| 7,939,670 B2 | 5/2011 | Sun et al. | |
| 8,003,669 B2 | 8/2011 | Teshima et al. | |
| 8,110,602 B2 | 2/2012 | Brown et al. | |
| 8,476,271 B2 | 7/2013 | Fuchino et al. | |
| 9,090,618 B2 | 7/2015 | Yamawaki et al. | |
| 2002/0049212 A1 | 4/2002 | Ito et al. | |
| 2003/0069249 A1 | 4/2003 | Sun et al. | |
| 2003/0119869 A1 | 6/2003 | Burrows et al. | |
| 2004/0087641 A1 | 5/2004 | Goehring et al. | |
| 2004/0176361 A1 | 9/2004 | Fujio et al. | |
| 2005/0119308 A1 | 6/2005 | Teshima et al. | |
| 2005/0228023 A1 | 10/2005 | Zaveri et al. | |
| 2005/0256000 A1 | 11/2005 | Schaper et al. | |
| 2006/0030590 A1 | 2/2006 | Anderskewitz et al. | |
| 2006/0229336 A1 | 10/2006 | Kazmierski et al. | |
| 2006/0264638 A1 | 11/2006 | Kyle et al. | |
| 2008/0188478 A1 | 8/2008 | Bryans et al. | |
| 2008/0214827 A1 | 9/2008 | Goehring et al. | |
| 2008/0249101 A1 | 10/2008 | Bleicher et al. | |
| 2008/0287479 A1 | 11/2008 | Hutchings et al. | |
| 2009/0105274 A1 | 4/2009 | Kugimiya et al. | |
| 2010/0001007 A1 | 1/2010 | Ferraro | |
| 2010/0144591 A1 | 6/2010 | Aslanian et al. | |
| 2010/0216726 A1 | 8/2010 | Fuchino et al. | |
| 2014/0128346 A1 | 5/2014 | Tadesse et al. | |
| 2015/0011529 A1 | 1/2015 | Tadesse et al. | |

FOREIGN PATENT DOCUMENTS

| | | |
|---|---|---|
| EP | 1496058 A1 | 1/2005 |
| JP | 51-146474 | 12/1976 |
| WO | WO 99/32481 | 7/1999 |
| WO | WO 99/46260 | 9/1999 |
| WO | WO 00/01688 | 1/2000 |
| WO | WO 00/06545 | 2/2000 |
| WO | WO 00/38680 | 7/2000 |
| WO | WO 01/90102 | 11/2001 |
| WO | WO 03/062234 | 7/2003 |
| WO | WO 2004/069828 | 8/2004 |
| WO | WO 2005/028451 | 3/2005 |
| WO | WO 2005/075459 A1 | 8/2005 |
| WO | WO 2006/130426 | 12/2006 |
| WO | WO 2008/089201 | 7/2008 |
| WO | WO 2008/108958 | 9/2008 |
| WO | WO 2014/102594 A3 | 10/2014 |

OTHER PUBLICATIONS

Angeletti (1999), "Effect of nociceptin on morphine-induced conditioned place preference in rats," *Regulatory Peptides* 80:122.
Armstead (1999), "Nociceptin/orphanin FQ dilates pial arteries by K(ATP) and k(ca) channel activation," *Brain Res.* 835:315-323.
Arndt (1999), "Nociceptin/orphanin FQ increases blood pressure and heart rate via sympathetic activation in sheep," *Peptides* 20:465-470.
Bartho (1990), "Involvement of capsaicin-sensitive neurons in hyperalgesia and enhanced opioid antinociception in inflammation," *Naunyn-Schmiedeberg's Arch. Pharmacol.* 342:666-670.
Berdini (2002), "A Modified Palladium Catalyzed Reductive Amination Procedure," *Tetrahedron*, 58:5669-5674.
Bignan (2005), "Recent advances towards the discovery of ORL-1 receptor agonists and antagonists," *Expert Opinion on Therapeutic Patents* 15(4):357-388.
Bigoni (1999), "Characterization of nociceptin receptors in the periphery: in vitro and in vivo studies," *Naunyn-Schmiedeberg's Arch. Pharmacol.* 359:160-167.
Bingham (2001), "Over one hundred solvates of sulfathiazole," *Chem. Comm.*, pp. 603-604.
Bregola (1999), "Limbic seizures increase pronociceptin mRNA levels in the thalamic reticular nucleus," *Neuroreport* 19:541-546.
Briscini (2002), "Up-regulation of ORL-1 receptors in spinal tissue of allodynic rats after sciatic nerve injury," *Eur. J. Pharmacol.* 447:59-65.
Bucher (1998), "ORL1 receptor-mediated inhibition by nociceptin of noradrenaline release from perivascular sympathetic nerve endings of the rat tail artery," *Naunyn-Schmiedeberg's Arch. Pharmacol.* 358:682-685.
Buchwald (1980), "Long-term, Continuous Intravenous Heparin Administration by an Implantable Infusion Pump in Ambulatory Patients with Recurrent Venous Thrombosis," *Surgery* 88:507-516.
Caira (2004), "Preparation and Crystal Characterization of a Polymorph, a Monohydrate, and an Ethyl Acetate Solvate of the Antifungal Fluconazole," *J. Pharmaceut. Sci.*, 93(3):601-611.
Calo' (1996), "The mouse deferens: a pharmacological preparation sensitive to nociceptin," *Eur. J. Pharmacol.* 311:R3-R5.
Calo' (1999), "Characterization of nociceptin receptors modulating locomotor activity in mice," *Fund. Clin. Pharmacol.* 13:1-27.
Calo' (2000), "Pharmacology of nociceptin and its receptor: a novel therapeutic target," *Br. J. Pharmacol.* 129:1261-1283.
Champion (1997), "Nociceptin, a novel endogenous ligand for the ORL1 receptor, has potent erectile activity in the cat," *Am. J. Physiol.* 73:E214-E219.
Champion (1997), "Nociceptin, an endogenous ligand for the ORL1 receptor, has novel hypotensive activity in the rat," *Life Sci. Pharmacol. Lett.* 60(16):PL241-PL245.
Champion (1998), "Nociceptin, a novel endogenous ligand for the ORL1 receptor, dilates isolated resistance arteries from the rat," *Regul. Peptides* 78:69-74.
Chu (1999), "Inhibition of cardiovascular activity following microinjection of novel opioid-like neuropeptide nociceptin (orphanin FQ) into the rat rostral ventrolateral medulla," *Brain Res.* 829:134-142.
Chu (1999), "The nociceptin receptor-mediated inhibition of the rat rostral ventrolateral medulla neurons in vitro," *Eur. J. Pharmacol.* 364:49-53.
Ciccocioppo (1999), "Effect of nociceptin on alcohol intake in alcohol-preferring rats," *Psychopharmacol.* 141:220-224.
Corbett (1998), "The pharmacological actions of nociceptin in the isolated colon of rat, mouse, and man," *Naunyn-Schmiedeberg's Arch. Pharmacol.* 358(Suppl 1):4047.
Corboz (2000), "Nociceptin inhibits capsaicin-induced bronchoconstriction in isolated guinea pig lung," *Eur. J. Pharmacol.* 402:171-179.

(56) References Cited

OTHER PUBLICATIONS

Courteix (2004), "Evidence for an exclusive antinociceptive effect of nociceptin/orphanin FQ, an endogenous ligand for the ORL1 receptor, in two animal models of neuropathic pain," *Pain* 110:236-245.
Czapla (1997), "Decreases in systemic arterial and hindquarters perfusion pressure in response to nociceptin are not inhibited by naloxone in the rat," *Peptides* 18:1197-1200.
D'Amour (1941), "A Method for Determining Loss of Pain Sensation," *J. Pharmacol. Exp. Ther.* 72:74-79.
Devine (1996), "Rats rapidly develop tolerance to the locomotor-inhibiting effects of the novel neuropeptide orphanin FQ," *Neurochem. Res.* 21:1387-1396.
Devine (1996), "The novel neuropeptide orphanin FQ fails to produce conditioned place preference or aversion," *Brain Res.* 727:225-229.
During (1989), "Controlled Release of Dopamine from a Polymeric Brain Implant: In Vivo Characterization," *Ann. Neurol.* 25:351-356.
Faber (1996), "Depression of glutamatergic transmission by nociceptin in the neonatal rat hemisected spinal cord preparation in vitro," *Br. J. Pharmacol.* 119:189-190.
Filer (1987), "The Preparation and Characterization of Tritiated Neurochemicals," *Isotopes in the Physical and Biomedical Sciences*, vol. 1, Labeled Compounds (Part A), E. Buncel et al, eds., Chapter 6, pp. 155-192.
Fischer (1998), "Nociceptin-induced inhibition of tachykinergic neurotransmission in guinea pig bronchus," *J. Pharmacol. Ther.* 285:902-907.
Florin (1996), "Nociceptin stimulates locomotion and exploratory behavior in mice," *Eur. J. Pharmacol.* 317:9-13.
Gavioli (2003), "Blockade of nociceptin/orphanin FQ-NOP receptor signaling produces antidepressant-like effects: pharmacological and genetic evidences from the mouse forced swimming test," *Eur. J. Neurosci.* 17:1987 -1990.
Gavioli (2006), "Antidepressant—an anxiolytic-like effects of nociceptin/orphanin FQ receptor ligands," *Naunyn-Schmiedeberg's Arch. Pharmacol.* 372:319-330.
Giuliani (1997), "Effect of nociceptin on heart rate and blood pressure in anaesthetized rats," *Eur. J. Pharmacol.* 333:177-179.
Giuliani (1998), "The inhibitory effect of nociceptin on the micturition reflex in anaesthetized," *Br. J. Pharmacol.* 24:1566-1572.
Giuliani (1999), "Nociceptin protects capsaicin-sensitive afferent fibers in the rat urinary bladder from desensitization," *Nanyn-Schmiedeberg's Arch. Pharmacol.* 360:202-208.
Goeldner (2010), "Endogenous nociceptin/orphanin-FQ in the dorsal hippocampus facilitates despair-related behavior," *Hippocampus* 20:911-916.
Goodson (1984), "Dental Applications," in *Medical Applications of Controlled Release*, vol. 2, Applications and Evaluation, Langer and Wise, eds., CRC Press, Chapter 6, pp. 115-138.
Griebel (2000), "Orphanin FQ, a novel neuropeptide with anti-stress-like activity," *Brain Res.* 836:221-224 (1999).
Grupp (1999), "Protection against Hypoxia-reoxygenation in the Absence of Poly (ADP-ribose) Synthetase in Isolated Working Hearts," *J. Mol. Cell Cardiol.* 31:297-303.
Gumusel (1997), "Nociceptin: an endogenous agonist for central opioid-like 1 (ORL1) receptors possesses systemic vasorelaxant properties," *Life Sci. Pharmacol. Lett.* 69:PL141-PL145.
Gutierrez (2001), "Orphanin FQ/nociceptin inhibits kindling epileptogenesis and enhances hippocampal feed-forward inhibition," *Neuroscience* 105:325-333.
*Handbook of Pharmaceutical Excipients* (1986), (Amer. Pharmaceutical Ass'n, Washington, DC).
Hanson (1995), "Analgesic, Antipyretic and Anti-Inflammatory Drugs," pp. 1196-1221 in *Remington: The Science and Practice of Pharmacy* vol. II (Gennaro, ed., 19$^{th}$ Ed., Mack Publishing, Easton, PA).
Hargreaves (1988), "A New and Sensitive Method for Measuring Thermal Nociception in Cutaneous Hyperalgesia," *Pain* 32(1):77-88.

Hayashi (2009), "Novel Non-Peptide Nociceptin/Orphanin FQ Receptor Agonist, 1-[1-(1-Methylcyclooctyl)-4-piperidinyl]-2-[(3R)-3-piperidinyl]-1H-benzimidazole: Design, Synthesis, and Structure-Activity Relationship of Oral Receptor Occupancy in the Brain for Orally Potent Antianxiety Drug," *J. Med. Chem.* 52:610-625.
Hayashi (2009), "Discovery of 1-[1-Methylcyclooctyl)-4-piperidinyl]-2-[(3R)-3-piperidinyl]-1H-benzimidazole: Integrated Drug-Design and Structure-Activity Relationships for Orally Potent, Metabolically Stable and Potential-Risk Reduced Novel Non-Peptide Nociceptin/Orphanin FQ Receptor Agonist as Antianxiety Drug," *Chem. Biol. Drug Des.* 74:369-381.
Hayashi (2010), "Discovery of {1-[4-(2-{hexahydropyrrolo[3,4-c]pyrrol-2(1H)-yl}-1H-benzimidazol-1-yl)piperidin-1-yl]cyclooctyl}methanol, systemically potent novel non-peptide agonist of nociceptin/orphanin FQ receptor as analgesic for the treatment of neuropathic pain: Design, synthesis, and structure-activity relationships," *Bioorg. Med. Chem.* 18:7675-7699.
Helyes (1997), "Inhibition by nociceptin of neurogenic inflammation and the release of SP and CGRP from m sensory nerve terminals," *Br. J. Pharmacol.* 121:613-615.
Henderson (1997), "The orphan opioid receptor and its endogenous ligand—nociceptin/orphanin FQ," *Trends Pharmacol. Sci.* 18(8):293-300.
Hiramatsu (1999), "Effects of nocistatin on nociceptin-induced impairment of learning and memory in mice," *Eur. J. Pharmacol.* 367:151-155.
Hiramatsu (2000), "Improvement by low doses of nociceptin on scopolamine-induced impairment of learning and/or memory," *Eur. J. Pharmacol.* 395:149-156.
House (1979), *J. Org. Chem.* 44(16):2819-2824.
House (1980), *J. Org. Chem.* 45(10):1800-1806.
Howard (1989), "Intracerebral drug delivery in rats with lesion-induced memory deficits," *J. Neurosurg.* 71:105-112.
Insel (1996), "Analgesic-Antipyretic and Anti-inflammatory Agents and Drugs Employed in the Treatment of Gout," pp. 617-657 in *Goodman and Gilman's The Pharmacological Basis of Therapeutics* (Goodman et al., eds., 9$^{th}$ Ed., McGraw-Hill, New York).
Jenck (1997), "Orphanin FQ acts as an anxiolytic to attenuate behavioral responses to stress," *Proc. Natl. Acad. Sci., U.S.A.* 94:14854-14858.
Jenck (2000), "A synthetic agonist at the orphanin FQ/nociceptin receptor ORL1: Anxiolytic profile in the rat." *Proc. Natl. Acad. Sci.* 97:4938-4943.
Kapusta (1997), "Diuretic and antinatriuretic responses produced by the endogenous opioid-like peptide, nociceptin (orphanin FQ)," *Life Sci. Pharmacol. Lett.* 60:PL15-PL21.
Kapusta (1999), "Central administration of [Phe1psi(CH$_2$-NH)Gly2]nociceptin(1-13)-NH$_2$ and orphanin FQ/nociceptin (OFQ/N) produce similar cardiovascular and renal responses in conscious rats," *J. Pharmacol. Exp. Ther.* 289:176-180.
Kim (1992), "An Experimental Model for Peripheral Neuropathy Produced by Segmental Spinal Nerve Ligation in the Rat," *Pain* 50(3):355-363.
King (1980), "Tablets, Capsules, and Pills," pp. 1553-1593 in *Remington's Pharmaceutical Sciences* (Osol, ed., 16$^{th}$ Ed., Mack Publishing, Easton, PA).
Koster (1999), "Targeted disruption of the orphanin FQ/nociceptin gene increases stress susceptibility and impairs stress adaptation in mice." *Proc. Natl. Acad. Sci. U.S.A.* 96:10444-10449.
Langer (1990), "New Methods of Drug Delivery," *Science* 249:1527-1533.
Langer (1983), "Chemical and Physical Structure of Polymers as Carriers for Controlled Release of Bioactive Agents: A Review," *J. Macromol. Sci. Rev. Macromol. Chem.* C23(1):61-126.
Lazareno (1999), "Measurement of Agonist-stimulated [$^{35}$S]GTPγS Binding to Cell Membranes," *Methods Molec. Biol.* 106:231-245.
Lecci (2000), "Multiple sites of action in the inhibitory effect of nociceptin on the micturition reflex," *J. Urology* 163:638-645.
Lee (1997), "Nociceptin hyperpolarises neurones in the rt ventromedial hypothalamus," *Neurosci. Lett.* 239:37-40.

(56) References Cited

OTHER PUBLICATIONS

Levy (1985), "Inhibition of Calcification of Bioprosthetic Heart Valves by Local Controlled-Release Diphosphonate," *Science* 228:190-192.
Lewin (1998), "Molecular Features Associated with Polyamine Modulation of NMDA Receptors," *J. Med. Chem.* 41:988-995.
Li (2004), "Role of nociceptin in the modulation of nociception in the arcuate nucleus of rats," *Brain Res.* 1025:67-74.
Madeddu (1999), "Cardiovascular effects of nociceptin in unanaesthetized mice," *Hypertension* 33:914-919.
Mamiya (1999), "Nociceptin system plays a role in the memory retention: involvement of naloxone benzoylhydrazone binding sites," *Neuroreport* 10:1171-1175.
Manabe (1998), "Facilitation of long-term potentiation and memory in mice lacking nociceptin receptors," *Nature* 394:577-581.
McLeod (2001), "Nociceptin inhibits cough in the guinea-pig by activation of ORL1 receptors," *Br. J. Pharmacol.* 132:1175-1178.
Meunier (1995), "Isolation and structure of the endogenous agonist of opioid receptor-like ORL1 receptor." *Nature* 377:532-535.
Milligan (2003), "Principles: Extending the Utility of [$^{35}$S]GTP$\gamma$S Binding Assays," *TIPS* 24(2):87-90.
Miyakawa (2007), "ORL1 receptor-mediated down-regulation of mPER2 in the suprachiasmatic nucleus accelerates re-entrainment of the circadian clock following a shift in the environmental light/dark cycle," *Neuropharmacol.* 52:1055-1064.
Murphy (1999), "Orphanin FQ/nociceptin blocks acquisition of morphine place preference," *Brain Res.* 832:168-170.
Narayanan (1999), "Orphanin FQ and behavioral sensitization to cocaine," *Pharmacol. Biochem. Behav.* 63:271-277.
Narita (1999), "Identification of the G-protein Coupled ORL1 Receptor in the Mouse Spinal Cord by [$^{35}$S]-GTP$\gamma$S Binding and Immunohistochemistry," *Brit. J Pharmacol.* 128:1300-1306.
Nemeth (1998), "Inhibition of nociceptin on sensory neuropeptide release and mast cell-mediated plasma extravasation in rats," *Eur. J. Pharmacol.* 347:101-104.
Nicol (1996), "Nociceptin induced inhibition of K+ evoked glutamate release from rat cerebrocortical slices," *Br. J. Pharmacol.* 119:1081-1083.
Nicol (1998), "Nociceptin inhibits glutamate release from rat cerebellar slices," *Br. J. Pharmacol.* 123:217P.
Noble (1997), "Association of aminopeptidase N and endopeptidase 14.15 inhibitors potentiate behavioral effects mediated by nociceptin/orphanin FQ in mice," *FEBS Lett.* 401:227-229.
Osinski (1999), "Cloning, expression and functional role of a nociceptin/orphanin FQ receptor in the porcine gastrointestinal tract," *Eur. J. Pharmacol.* 365:281-289.
Osinski (1999), "Peripheral and central actions of orphanin FQ (nociceptin) on murine colon," *Am. J. Physiol.* 276:G125-G131.
Patel (1997), "Naloxone-insensitive inhibition of acetylcholine release from parasympathetic nerves innervating guinea-pig trachea by the novel opioid, nociceptin," *Br. J. Pharmacol.* 120:735-736.
*Pharmaceutical Dosage Forms: Disperse Systems* (1996 and 1998) (Lieberman et al., eds., 2$^{nd}$ Ed., Marcel Dekker, Inc.).
*Pharmaceutical Dosage Forms: Tablets* (1989 and 1990) (Lieberman et al., eds., 2$^{nd}$ Ed., Marcel Dekker, Inc.).
Pheng (2000), "[Nphe$^1$]nociceptin(1-13)NH$_2$ selectively antagonizes nociceptin effects in the rabbit isolated ileum," *Eur. J. Pharmacol.* 397:383-388.
Pieretti (1999), "Orphanin FQ effects on morphine-induced dopamine release in the accumbens of rats," *Neuroscience Letters*, vol. 272, Issue 3:183-186.
Polidori (1999), "Sensitivity of brain sites to the orexigenic effect of nociceptin or of its analog [Phe]psi(CH$_2$-NH)Gly2]NC(1-13)NH$_2$," *Regul. Peptides* 80:126.
Polidori (2000), "Pharmacological characterization of the nociceptin receptor mediating hyperphagia: identification of a selective antagonist," *Psychopharmacol.* 148:430-437.
Pomonis (1996), "Orphanin FQ, agonist of orphan opioid receptor ORL1, stimulates feeding in rats," *Neuroreport* 8:369-371.

Porter (1973), "The Zinin Reduction of Nitroarenes," *Org. Reactions*, 20:455-481.
Radebough (1995), "Preformulation," pp. 1447-1676 in *Remington's Pharmaceutical Sciences* vol. 2 (Gennaro, ed., 19$^{th}$ Ed., Mack Publishing, Easton, PA).
Reinscheid (1995), "Orphanin FQ: a neuropeptide that activates an opioid-like G protein-coupled receptor," *Science* 270:792-794.
Rizzi (1999), "[Nphe$^1$]nociceptin(1-13)NH$_2$ antagonizes nociceptin effects in the mouse colon," *Eur. J. Pharmacol* 285:R3-R5.
Rizzi (1999), "Nociceptin receptor activation inhibits tachykinergic non adrenergic non cholinergic contraction of guinea pig isolated bronchus," *Life Sci.* 64:L157-L163.
Rizzi (2011), "Nociceptin/orphanin FQ receptor knockout rats: in vitro and in vivo studies," *Neuropharmacol.* 60:572-579.
Ross (2001), "Pharmacodynamics: Mechanisms of Drug Action and the Relationship Between Drug Concentration and Effect," in *Goodman and Gilman's The Pharmacological Basis of Therapeutics* pp. 31-43 (Goodman et al., eds., 10$^{th}$ Ed., McGraw-Hill, New York).
Rowland (1996), "The physiology and brain mechanisms of feeding," *Nutrition* 12:626-639.
Rylander (1985), "Hydrogenation of Nitro Compounds," in *Hydrogenation Methods* pp. 104-116 (Academic Press, London).
Sandin (1997), "Nociceptin/orphanin FQ microinjected into hippocampus impairs spatial learning in rats," *Eur. J. Neurosci.* 9:194-197.
Sato (1978), "Psychotropic Agents," *J. Med. Chem.* 21(11):1116-1120.
Saudek (1989), "A Preliminary Trial of the Programmable Implantable Medication System for Insulin Delivery," *New Engl. J. Med.* 321:574-579.
Sefton (1987), "Implantable Pumps," in *CRC Crit. Rev. Biomed. Eng.* 14(3):201-240.
Seltzer (1990), "A Novel Behavioral Model of Neuropathic Pain Disorders Produced in Rats by Partial Sciatic Nerve Injury," *Pain* 43:205-218.
Shah (1998), "Nociceptin inhibits non-cholinergic contraction in guinea-pig airway," *Br. J. Pharmacol.* 125:510-516.
Shimohigashi (1996), "Sensitivity of Opioid Receptor-like Receptor ORL1 for Chemical Modification on Nociceptin, a Naturally Occurring Nociceptive Peptide," *J. Biol. Chem.* 271(39):23642-23645.
Sieklucka-Dziuba (2002), "Nociceptin, OP4 receptor ligand in different models of experimental epilepsy," *Peptides* 23:497-505.
Smolen (1984), "Drug Product Design and Performance," *Controlled Drug Bioavailability* vol. 1, John Wiley and Sons, New York.
Stein (1988), "Unilateral Inflammation of the Hindpaw in Rats as a Model of Prolonged Noxious Stimulation: Alterations in Behavior and Nociceptive Thresholds," *Pharmacol. Biochem. Behavior* 31:451-455.
Stratford (1997), "Injections of nociceptin into nucleus accumbens shell of ventromedial hypothalamic nucleus increase food intake," *Neuroreport* 8:423-426.
Tallent (2001), "Nociceptin reduces epileptiform events in CA3 hippocampus via presynaptic and postsynaptic mechanisms," *J. Neurosci.* 21:6940-6948.
Taniguchi (1998), "The effect of nociceptin an endogenous ligand for the ORL1 receptor, on rat colonic contraction and transit," *Eur. J. Pharmacol.* 353:265-271.
Tortolani (1999), "A Convenient Synthesis to N-Aryl-Substituted 4-Piperidones," *Org. Lett.* 1:1261-1262.
Treat (1989), "Liposome Encapsulated Doxorubicin Preliminary Results of Phase I and Phase II Trials," pp. 317-327 and 353-365 in *Liposomes in the Therapy of Infectious Disease and Cancer*.
Van Tonder (2004), "Preparation and Physicochemical Characterization of 5 Niclosamide Solvates and 1 Hemisolvate," *AAPS Pharm. Sci. Tech.*, 5(1):Article 12.
Vaughn (1997), "Actions of the ORL1 receptor ligand nociceptin on membrane properties of rat periaqueductal gray neurons in vitro," *J. Neurosci.* 17:996-1003.
Vitale (2009), "Chronic treatment with the selective NOP receptor antagonist [Nphe 1, Arg 14, Lys 15]N/OFQ-NH2 (UFP-101) reverses the behavioural and biochemical effects of unpredictable chronic mild stress in rats," *Psychopharmacol.* 207:173-189.

(56) References Cited

OTHER PUBLICATIONS

Walker (1998), "Nociceptin fails to affect heroin self-administration in the rat," *Neuroreport* 9:2243-2247.

Wang (1994), "cDNA cloning of an orphan opiate receptor gene family member and its splice variant," *FEBS Lett.* 348:75-79.

Wang (1996), "Nociceptin (orphanin FQ), and endogenous ligand for the ORL1 (opioid receptor-like1) receptor, modulates responses of trigeminal neurons evoked by excitatory amino acids and somatosensory stimuli," *J. Neurophysiol.* 76:3568-3572.

Yasdani (1999), "Functional significance of a newly discovered neuropeptide, orphanin FQ, in rat gastrointestinal motility," *Gastroenterology* 116:108-117.

Yu (1997), "Orphanin FQ inhibits synaptic transmission and long-term potentiation in rat hippocampus," *Hippocampus* 7:88-94.

Yu (1998), "Orphanin FQ/nociceptin inhibits synaptic transmission and long-term potentiation in rat dentate gyrus through postsynaptic mechanisms," *J. Neurophysiol.* 80:1277-1284.

Zambello (2008), "Acute stress differentially affects corticotropin-releasing hormone mRNA expression in the central amygdala of the 'epressed' flinders sensitive line and the control flinders resistant line rats," *Prog. Neuro-Psychopharmacol. Biolog. Psychiatry* 32:651-661.

Zhang (1997), "Orphanin FQ has an inhibitory effect on the guinea pig ileum and the mouse vas deferens," *Brain Res.* 772:102-106.

\* cited by examiner

SUBSTITUTED BENZIMIDAZOLE-TYPE PIPERIDINE COMPOUNDS AND USES THEREOF

CROSS REFERENCE TO RELATED APPLICATIONS

This application is a continuation of application Ser. No. 14/138,965, filed Dec. 23, 2013, now U.S. Pat. No. 9,090,618 B2, which claims the benefit under 35 U.S.C. §119(e) of provisional application No. 61/777,674, filed Mar. 12, 2013, and provisional application No. 61/746,505, filed Dec. 27, 2012, the contents of which are incorporated herein by reference.

1. FIELD

The disclosure relates to Substituted Benzimidazole-Type Piperidine Compounds, compositions comprising an effective amount of a Substituted Benzimidazole-Type Piperidine Compound and methods to treat or prevent a condition, such as pain, comprising administering to an animal in need thereof an effective amount of a Substituted Benzimidazole-Type Piperidine Compound.

2. BACKGROUND

Chronic pain is a major contributor to disability and is the cause of much suffering. The successful treatment of severe and chronic pain is a primary goal of the physician, with opioid analgesics being preferred drugs for doing so.

Three major classes of opioid receptors in the central nervous system (CNS) have long been known, with each class having subtype receptors. These receptor classes are known as µ, κ and δ. As opiates have a high affinity for these receptors while not being endogenous to the body, research followed in order to identify and isolate the endogenous ligands to these receptors. These ligands were identified as endorphins, dynorphins and enkephalins, respectively.

Experimentation eventually led to the identification of an opioid receptor-like (ORL-1) receptor with a high degree of homology to the known receptor classes. The ORL-1 receptor was classified as an opioid receptor based only on structural grounds, as the receptor did not exhibit pharmacological homology. It was initially demonstrated that non-selective ligands having a high affinity for µ, κ and δ receptors had low affinity for the ORL-1 receptor. This characteristic, along with the fact that an endogenous ligand had not yet been discovered, led to the term "orphan receptor." See, e.g., Henderson et al., "The orphan opioid receptor and its endogenous ligand-nociceptin/orphanin FQ," *Trends Pharmacol. Sci.* 18(8):293-300 (1997).

Subsequent research led to the isolation and structure of the endogenous ligand of the ORL-1 receptor (i.e., nociceptin; also known as orphanin FQ (OFQ)). This ligand is a seventeen amino acid peptide structurally similar to members of the opioid peptide family.

The discovery of the ORL-1 receptor presents an opportunity in drug discovery for novel compounds that can be administered for pain management or other syndromes modulated by this receptor.

U.S. Pat. Nos. 6,872,733, 7,456,198, 7,495,109, and 7,678,809 disclose benzoimidazolones or derivatives thereof as compounds having affinity for the ORL-1 receptor.

U.S. Pat. No. 6,867,222 and U.S. Pat. App. Pub. No. 2008/0214827 disclose cyanoimino-benzoimidazoles or derivatives thereof, and methods for making the same, as compounds for modulating the pharmacodynamic response from the ORL-1 receptor.

U.S. Pat. No. 7,939,670 discloses benzooxazolones or derivatives thereof as compounds for modulating the pharmacodynamic response from the ORL-1 receptor.

U.S. Pat. App. No. 2010/0144591 describes benzoimidazole derivatives and methods of using the same to treat or prevent pain.

U.S. Pat. No. 7,105,505 discloses benzoimidazole derivatives useful as histamine $H_3$ antagonists.

U.S. Pat. Nos. 6,172,067, 6,340,681, and 6,861,425 disclose certain piperidyl benzoimidazole compounds as ORL-1 receptor agonists.

U.S. Pat. App. Nos. 2003/0119869 and 2010/001007 describe certain benzoimidazole compounds or piperidine derivatives, respectively, as chemokine receptor CCR5 modulators.

U.S. Pat. App. No. 2008/0287479 describes certain benzimidazol-2-one compounds useful in the inhibition or modulation of serene palmitoyl transferase.

International PCT Publication No. WO 2004/069828 describes certain piperidine compounds as therapeutic agents for schizophrenia.

International PCT Publication Nos. WO 99/46260, WO 99/50254, WO 01/90102, WO 2005/028451, WO 2003/062234, and U.S. Pat. App. No. 2005/0256000, respectively, describe quinoxalines or derivatives thereof as (i) inhibitors of protein kinase C, (ii) serine protease inhibitors, (iii) herbicides, (iv) M2 acetylcholine receptor agonists, (v) medicaments for diseases involving poly(ADP-ribose) polymerase, and (vi) safeners for plants.

Hayashi et al. ("Discovery of 1-[1-(1-Methylcyclooctyl)-4-piperidinyl]-2-[(3R)-3-piperidinyl]-1H-benzimidazole: Integrated Thug-Design and Structure-Activity Relationships for Orally Potent, Metabolically Stable and Potential-Risk Reduced Novel Non-Peptide Nociceptin/Orphanin FQ Receptor Agonist as Antianxiety Drug," *Chem. Biol. Drug Des.* 74:369-381 (2009) and "Novel Non-Peptide Nociceptin/Orphanin FQ Receptor Agonist, 1-[1-(1-Methylcyclooctyl)-4-piperidinyl]-2-[(3R)-3-piperidinyl]-1H-benzimidazole: Design, Synthesis, and Structure-Activity Relationship of Oral Receptor Occupancy in the Brain for Orally Potent Antianxiety Drug," *J. Med. Chem.* 52:610-625 (2009)) disclose substituted 1-(1-(1-methylcyclooctyl)piperidin-4-yl)-2-(piperidin-3-yl)-1H-benzo[d]imidazoles said to be in vitro non-peptide full ORL-1 receptor agonists and oral anxiolytics in mice.

Hayashi et al., "Discovery of {1-[4-(2-{hexahydropyrrolo[3,4-c]pyrrol-2(1H)-yl}-1H-benzimidazol-1-yl)piperidin-1-yl]cyclooctyl}methanol, systemically potent novel non-peptide agonist of nociceptin/orphanin FQ receptor as analgesic for the treatment of neuropathic pain: Design, synthesis, and structure-activity relationships," *Bioorg. Med. Chem.* 18:7675-7699 (2010), disclose substituted 1-(1-cyclooctylpiperidin-4-yl)-2-(piperazin-1-yl)-1H-benzo[d]imidazoles said to be non-peptide ORL-1 receptor agonists and provide an inhibitory effect against mechanical allodynia in rats.

Citation of any reference in Section 2 of this application is not to be construed as an admission that such reference is prior art to the present application.

3. SUMMARY

In one aspect of the disclosure, new compounds that exhibit affinity for the ORL-1 receptor are described.

In some embodiments, such new compounds exhibit agonist activity or partial agonist activity at the ORL-1 receptor. In other embodiments, such new compounds exhibit agonist activity at the ORL-1 receptor. In other embodiments, such new compounds exhibit partial agonist activity at the ORL-1 receptor. In yet other embodiments, such new compounds exhibit antagonist activity at the ORL-1 receptor.

In another embodiment of the disclosure, such new compounds exhibit affinity for the ORL-1 receptor, and also for one or more of the μ, κ or δ receptors. In some embodiments, a new compound of the disclosure exhibits affinity for both the ORL-1 receptor and the μ receptor. In other embodiments, a new compound of the disclosure acts as an ORL-1 receptor agonist or partial agonist and as a μ receptor agonist or partial agonist. In other embodiments, a new compound of the disclosure acts as an ORL-1 receptor agonist and as a μ receptor agonist or partial agonist. In other embodiments, a new compound of the disclosure acts as an ORL-1 receptor partial agonist and as a μ receptor agonist or partial agonist. In other embodiments, a new compound of the disclosure acts as an ORL-1 receptor agonist or partial agonist and as μ receptor agonist. In other embodiments, a new compound of the disclosure acts as an ORL-1 receptor agonist or partial agonist and as a μ receptor partial agonist. In other embodiments, a new compound of the disclosure acts as an ORL-1 receptor agonist and as a μ receptor agonist. In other embodiments, a new compound of the disclosure acts as an ORL-1 receptor agonist and as a μ receptor partial agonist. In other embodiments, a new compound of the disclosure acts as an ORL-1 receptor partial agonist and as μ receptor agonist. In other embodiments, a new compound of the disclosure acts as an ORL-1 receptor partial agonist and as μ receptor partial agonist. In other embodiments, a new compound of the disclosure acts as an ORL-1 receptor agonist or partial agonist and as a μ receptor antagonist. In other embodiments, a new compound of the disclosure acts as an ORL-1 receptor agonist and as a μ receptor antagonist. In other embodiments, a new compound of the disclosure acts as an ORL-1 receptor partial agonist and as μ receptor antagonist. In other embodiments, a new compound of the disclosure acts as an ORL-1 receptor antagonist and as a μ receptor agonist or partial agonist. In other embodiments, a new compound of the disclosure acts as an ORL-1 receptor antagonist and as a μ receptor agonist. In other embodiments, a new compound of the disclosure acts as an ORL-1 receptor antagonist and as a μ receptor partial agonist.

Certain new compounds of the disclosure can be used to treat an animal suffering from chronic or acute pain.

In another embodiment of the disclosure, methods for treating chronic or acute pain in an animal by administering one or more Substituted Benzimidazole-Type Piperidine Compounds to an animal in need of such treatment are described. In certain embodiments, such new Substituted Benzimidazole-Type Piperidine Compounds effectively treat chronic or acute pain in the animal, while producing fewer or reduced side effects compared to previously available compounds.

Compounds of formula (I) are herein disclosed:

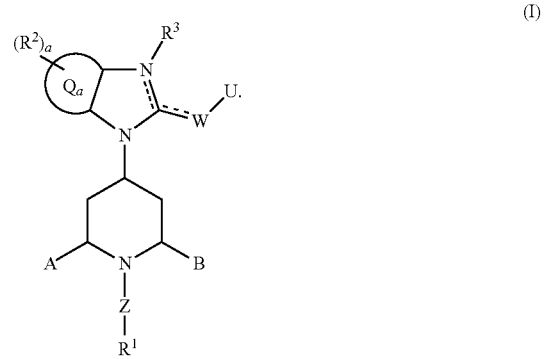

(I)

or a pharmaceutically acceptable salt or solvate thereof where:

the $Q_a$ ring is fused benzo or fused (5- or 6-membered) heteroaryl;

each $R^2$ is independently selected from:

(a) -halo, —CN, —NO$_2$, —OT$^3$, —C(=O)T$^3$, —C(=O)OT$^3$, —C(=O)N(T$^1$)(T$^2$), —S(=O)$_2$OT$^3$, —S(=O)T$^3$, —S(=O)$_2$T$^3$, —O—S(=O)$_2$T$^3$, —S(=O)$_2$N(T$^1$)(T$^2$), —N(T$^1$)(T$^2$), —N(T$^3$)C(=O)T$^3$, —N(T$^3$)C(=O)N(T$^1$)(T$^2$), —N(T$^3$)S(=O)T$^3$, —N(T$^3$)S(=O)$_2$T$^3$, —N(T$^3$)C(=O)OT$^3$, and —N(T$^3$)S(=O)$_2$N(T$^1$)(T$^2$); and (b) —(C$_1$-C$_6$)alkyl, —(C$_2$-C$_6$)alkenyl, —(C$_2$-C$_6$)alkynyl, —(C$_1$-C$_6$)alkoxy, —(C$_3$-C$_7$)cycloalkyl, —(C$_6$-C$_{10}$)bicycloalkyl, —(C$_5$-C$_{10}$)cycloalkenyl, —(C$_7$-C$_{10}$)bicycloalkenyl, and -(5- or 6-membered)heterocycle, each of which is unsubstituted or substituted with 1, 2, or 3 independently selected $R^8$ groups; and (c) -phenyl, -naphthalenyl, and -(5- or 6-membered)heteroaryl, each of which is unsubstituted or substituted with 1, 2, or 3 independently selected $R^7$ groups;

each dashed line denotes the presence or absence of a bond (i.e., when a dashed line is present there is a double bond at that position and when a dashed line is absent there is only a single bond at that position), provided that:

(a) one dashed line must denote the presence of a bond (i.e., there is a double bond at one position);

(b) when one dashed line denotes the presence of a bond (i.e., there is a double bond at that position) then the other dashed line denotes the absence of a bond (i.e., there is only a single bond at that other position);

(c) when the dashed line within the 5-membered, nitrogen-containing ring that is fused to the $Q_a$ ring is present (i.e., there is a double bond at that position), then $R^3$ is absent; and (d) when the dashed line within the 5-membered, nitrogen-containing ring that is fused to the $Q_a$ ring is absent (i.e., there is only a single bond at that position), then $R^3$ is present;

$R^3$, when present, is:

(a) —H; or (b) —(C$_1$-C$_4$)alkyl which is unsubstituted or substituted with 1, 2, or 3 groups independently selected from —OH, —(C$_1$-C$_4$)alkoxy, —N(R$^6$)$_2$, —C(=O)OR$^9$, and —C(=O)N(R$^6$)$_2$; or (c) —(C$_3$-C$_7$)cycloalkyl which is unsubstituted or substituted with 1, 2, or 3 groups independently selected from —OH, —(C$_1$-C$_4$)alkyl, —(C$_1$-C$_4$)alkoxy, —N(R$^6$)$_2$, —C(=O)OR$^9$, and —C(=O)N(R$^6$)$_2$;

---W— is a single bond, a double bond, =CH—, —CH$_2$—, =N—, —NH—, —O—, =CH—(C$_1$-C$_3$)alkylene-, —CH$_2$—(C$_1$-C$_3$)alkylene-, =N—(C$_1$-C$_3$)alkylene-, —NH—(C$_1$-C$_3$)alkylene-, —O—(C$_1$-C$_3$)alkylene-, =CH—(C$_2$-C$_3$)alkenylene-, —CH$_2$—(C$_2$-C$_3$)alkenylene-, =N—(C$_2$-C$_3$)alkenylene-, —NH—(C$_2$-C$_3$)alkenylene-, —O—(C$_2$-C$_3$)alkenylene-, =CH—(C$_1$-C$_3$)alkylene-N(R$^{11}$)—, —CH$_2$—(C$_1$-C$_3$)alkylene-N(R$^{11}$)—, =N—(C$_1$-C$_3$)alkylene-N(R$^{11}$)—, —NH—(C$_1$-C$_3$)alkylene-N(R$^{11}$)—, —O—(C$_1$-C$_3$)alkylene-N(R$^{11}$)—, =CH—N(R$^{11}$)—, —CH=N—, —CH$_2$—N(R$^{11}$)—, =CH—O—, —CH$_2$—O—, =CH—O—(C$_1$-C$_3$)alkylene-, or —CH$_2$—O—(C$_1$-C$_3$)alkylene-;

U is:
(a) —R$^{15}$; or
(b)

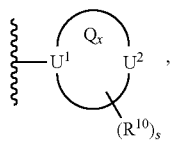

wherein when ---W— is a single bond or a double bond the Q$_x$ ring is a -(4-, 5-, 6-, or 7-membered)heterocycle containing one or two ring heteroatoms selected from N, N(R$^4$), O, and S provided that at least one ring heteroatom is N or N(R$^4$) and wherein either U$^1$ is N and U$^2$ is a bond or U$^1$ is C or CH and U$^2$ is N or N(R$^4$), provided that;

(1) when ---W— is a double bond and the Q$_x$ ring is present, U$^1$ is C; and
(2) when ---W— is =CH—, —CH$_2$—, =CH—(C$_1$-C$_3$)alkylene-, or —CH$_2$—(C$_1$-C$_3$)alkylene- and the Q$_x$ ring is present, the Q$_x$ ring is a (6-membered)heterocycle selected from:

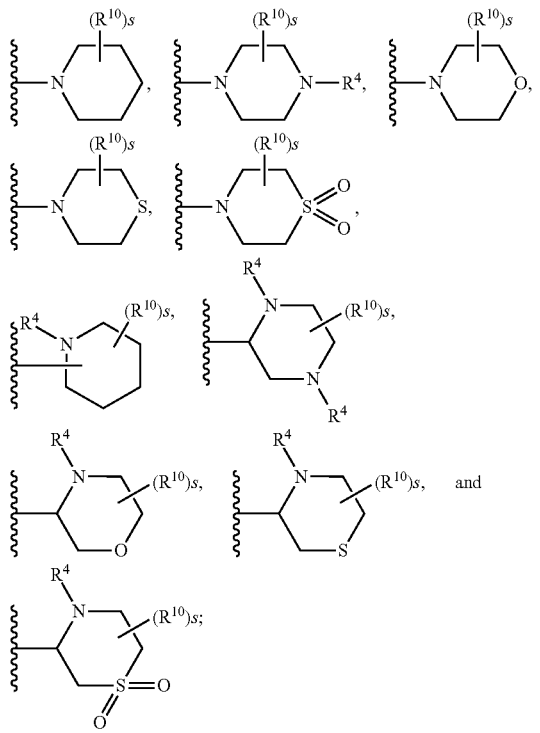

and
(3) when ---W— is =N—, —NH—, —O—, =N—(C$_1$-C$_3$)alkylene-, —NH—(C$_1$-C$_3$)alkylene-, —O—(C$_1$-C$_3$)alkylene-, =CH—(C$_2$-C$_3$)alkenylene-, —CH$_2$—(C$_2$-C$_3$)alkenylene-, =N—(C$_2$-C$_3$)alkenylene-, —NH—(C$_2$-C$_3$)alkenylene-, —O—(C$_2$-C$_3$)alkenylene-, =CH—(C$_1$-C$_3$)alkylene-N(R$^{11}$)—, —CH$_2$—(C$_1$-C$_3$)alkylene-N(R$^{11}$)—, =N—(C$_1$-C$_3$)alkylene-N(R$^{11}$)—, —NH—(C$_1$-C$_3$)alkylene-N(R$^{11}$)—, —O—(C$_1$-C$_3$)alkylene-N(R$^{11}$)—, =CH—N(R$^{11}$)—, —CH=N—, —CH$_2$—N(R$^{11}$)—, =CH—O—, —CH$_2$—O—, =CH—O—(C$_1$-C$_3$)alkylene-, or —CH$_2$—O—(C$_1$-C$_3$)alkylene-, then the Q$_x$ ring is absent;

each R$^4$, when present, is independently selected from:
(a) —H; and
(b) —X, —(C$_1$-C$_6$)alkyl-X, -(5- or 6-membered)heterocycle-X, or -(5- or 6-membered)heterocycle-(C$_1$-C$_6$)alkyl-X; and
(c) —(CH$_2$)$_d$—C(=Y)CN, —(CH$_2$)$_d$—C(=Y)X, —(CH$_2$)$_d$—C(=Y)T$^3$, —(CH$_2$)$_d$—C(=Y)YX, —(CH$_2$)$_d$—C(=Y)YT$^3$, —(CH$_2$)$_d$—C(=Y)N(T$^1$)(T$^2$), —(CH$_2$)$_d$—C(=Y)N(R$^9$)CN, —(CH$_2$)$_d$—C(=Y)N(R$^9$)X, —(CH$_2$)$_d$—C(=Y)N(R$^9$)YH, —(CH$_2$)$_d$—C(=Y)N(R$^9$)YX, —(CH$_2$)$_d$—C(=Y)N(R$^9$)YCH$_2$X, —(CH$_2$)$_d$—C(=Y)N(R$^9$)YCH$_2$CH$_2$X, or —(CH$_2$)$_d$—C(=Y)N(R$^9$)S(=O)$_2$T$^3$; and
(d) —[CH$_2$—O]$_b$—R$^{16}$, —[CH(CH$_3$)—O]$_b$—R$^{16}$, —[CH$_2$—CH$_2$—O]$_b$—R$^{16}$, —[CH(CH$_3$)—CH$_2$—O]$_b$—R$^{16}$, —[CH$_2$—CH(CH$_3$)—O]$_b$—R$^{16}$, —[CH$_2$—CH$_2$—CH$_2$—O]$_b$—R$^{16}$, —[CH(CH$_3$)—CH$_2$—CH$_2$—O]$_b$—R$^{16}$, —[CH$_2$—CH(CH$_3$)—CH$_2$—O]$_b$—R$^{16}$, or —[CH$_2$—CH$_2$—CH(CH$_3$)—O]$_b$—R$^{16}$;

X is selected from:
(a) —H, —(C$_1$-C$_6$)alkyl, —(C$_2$-C$_6$)alkenyl, —(C$_2$-C$_6$)alkynyl, —(C$_1$-C$_6$)alkoxy, —(C$_3$-C$_7$)cycloalkyl, —(C$_5$-C$_{10}$)cycloalkenyl, and -(5- or 6-membered)heterocycle, each of which is unsubstituted or substituted with 1, 2, or 3 independently selected R$^8$ groups; and
(b) -phenyl and -(5- or 6-membered)heteroaryl, each of which is unsubstituted or substituted with 1, 2, or 3 independently selected R$^7$ groups;

each Y is independently O or S;
each R$^{16}$ is independently H or CH$_3$;
s is an integer selected from 0, 1, and 2;
when s is 1, R$^{10}$ is —F, —CH$_3$, —CH$_2$CH$_3$, —(CH$_2$)$_d$—C(=Y)YT$^3$, or —(CH$_2$)$_d$—C(=Y)N(T$^1$)(T$^2$), and when s is 2, the R$^{10}$ groups together are gem-dimethyl, gem-difluoro, =O, or =S;

A and B are independently selected from:
(a) —H; and
(b) —(C$_1$-C$_6$)alkyl, —(C$_2$-C$_6$)alkenyl, and —(C$_1$-C$_6$)alkoxy, each of which is unsubstituted or substituted with 1 or 2 substituents independently selected from —OH, —S(=O)$_2$NH$_2$, —C(=O)OT$^3$, —C(=O)N(R$^6$)$_2$, and —N(R$^6$)C(=O)R$^9$, or 1, 2, or 3 independently selected -halo; or
(c) A-B can together form a (C$_2$-C$_6$) bridge, which is unsubstituted or substituted with 1, 2, 3, 4, 5, 6, 7, or 8 substituents independently selected from —OH, —(C$_1$-C$_4$)alkyl, -halo, and —C(halo)$_3$, and which bridge optionally contains —HC=CH— or —O— within the (C$_2$-C$_6$)bridge; wherein the 5-membered, nitrogen-containing ring that is fused to the Q$_a$ ring can be in the endo- or exo-configuration with respect to the A-B bridge;

Z is —[(C$_1$-C$_{10}$)alkyl optionally substituted by R$^{13}$]$_h$—, wherein h is 0 or 1; or —[(C$_2$-C$_{10}$)alkenyl optionally substituted by R$^{13}$]—, or —[(C$_1$-C$_{10}$)alkyl-NR$^6$C(=Y)]—;

R$^1$ is selected from:
(a) —H, -halo, —CN, —OH, —CH$_2$OH, —CH$_2$CH$_2$OH, —NO$_2$, —N(R$^6$)$_2$, —S(=O)NH$_2$, —S(=O)$_2$NH$_2$, —C(=O)OV$^1$, and —C(=O)CN; and
(b) —(C$_1$-C$_{10}$)alkyl, —(C$_2$-C$_{10}$)alkenyl, —(C$_2$-C$_{10}$)alkynyl, —O(C$_1$-C$_6$)alkyl, —(C$_3$-C$_7$)cycloalkoxy, —(C$_6$-C$_{14}$)bicycloalkyl, —(C$_8$-C$_{20}$)tricycloalkyl, —(C$_5$-C$_{10}$)cycloalkenyl, —(C$_7$-C$_{14}$)bicycloalkenyl, —(C$_8$-C$_{20}$)tricycloalkenyl, and -(3- to 7-membered)heterocycle, each of which is unsubstituted or substituted with 1, 2, 3, or 4 independently selected R$^8$ groups; and
(c)

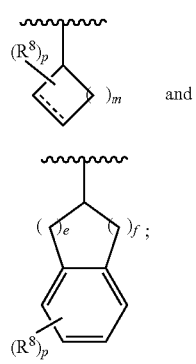

and (d) -phenyl, -naphthalenyl, —(C$_{14}$)aryl, and -(5- to 10-membered)heteroaryl, each of which is unsubstituted or substituted with 1, 2, 3, or 4 independently selected R$^7$ groups;

each R$^5$ is independently —(C$_1$-C$_4$)alkyl, —(C$_2$-C$_6$)alkenyl, —(C$_2$-C$_6$)alkynyl, -(5- or 6-membered)heteroaryl, —(C$_1$-C$_6$)alkyl-C(=O)OR$^9$, —OR$^9$, —SR$^9$, —C(halo)$_3$, —CH(halo)$_2$, —CH$_2$(halo), —CN, =O, =S, -halo, —N$_3$, —NO$_2$, —CH=N(R$^9$), —N(R$^9$)(C$_1$-C$_6$)alkyl-C(=O)OR$^9$, —N(R$^9$)$_2$, —N(R$^9$)OH, —N(R$^9$)S(=O)R$^{12}$, —N(R$^9$)S(=O)$_2$R$^{12}$, —N(R$^9$)C(=O)R$^{12}$, —N(R$^9$)C(=O)OR$^{12}$, —C(=O)R$^9$, —C(=O)OR$^9$, —OC(=O)R$^9$, —OC(=O)OR$^9$, —S(=O)R$^9$, or —S(=O)$_2$R$^9$;

each R$^6$ is independently —H, —(C$_1$-C$_6$)alkyl, or —(C$_3$-C$_7$)cycloalkyl, or two R$^6$ groups attached to the same nitrogen atom can together form a -(5- to 8-membered)heterocyclic ring, wherein the number of atoms in the ring includes the nitrogen atom, and in which one of the -(5- to 8-membered)heterocyclic ring carbon atoms is optionally replaced by O, S, or N(T$^3$);

each R$^7$ is independently —(C$_1$-C$_4$)alkyl, —(C$_2$-C$_6$)alkenyl, —(C$_2$-C$_6$)alkynyl, —OR$^9$, —SR$^9$, —C(halo)$_3$, —CH(halo)$_2$, —CH$_2$(halo), —CN, -halo, —N$_3$, —NO$_2$, —CH=N(R$^9$), —N(R$^9$)$_2$, —N(R$^9$)OH, —N(R$^9$)S(=O)R$^{12}$, —N(R$^9$)S(=O)$_2$R$^{12}$, —N(R$^9$)C(=O)R$^{12}$, —N(R$^9$)C(=O)N(T$^1$)(T$^2$), —N(R$^9$)C(=O)OR$^{12}$, —C(=O)R$^9$, —C(=O)N(T$^1$)(T$^2$), —C(=O)OR$^9$, —OC(=O)R$^9$, —OC(=O)N(T$^1$)(T$^2$), —OC(=O)OR$^9$, —S(=O)R$^9$, or —S(=O)$_2$R$^9$;

each R$^8$ is independently —(C$_1$-C$_4$)alkyl, —(C$_2$-C$_6$)alkenyl, —(C$_2$-C$_6$)alkynyl, -(5- or 6-membered)heteroaryl, —(C$_1$-C$_6$)alkyl-C(=O)OR$^9$, —N(R$^9$)(C$_1$-C$_6$)alkyl-C(=O)OR$^9$, —OR$^9$, —SR$^9$, —C(halo)$_3$, —CH(halo)$_2$, —CH$_2$(halo), —CN, =O, =S, =N(R$^9$), -halo, —N$_3$, —NO$_2$, —CH=N(R$^9$), —N(R$^9$)$_2$, —N(R$^9$)OR$^9$, —N(R$^9$)S(=O)R$^{12}$, —N(R$^9$)S(=O)$_2$R$^{12}$, —N(R$^9$)C(=O)R$^{12}$, —N(R$^9$)C(=O)N(T$^1$)(T$^2$), —N(R$^9$)C(=O)OR$^{12}$, —C(=O)R$^9$, —C(=O)N(T$^1$)(T$^2$), —C(=O)OR$^9$, —OC(=O)R$^9$, —OC(=O)N(T$^1$)(T$^2$), —OC(=O)OR$^9$, —S(=O)R$^9$, or —S(=O)$_2$R$^9$;

each R$^9$ is independently —H, —(C$_1$-C$_6$)alkyl, —(C$_2$-C$_6$)alkenyl, —(C$_2$-C$_6$)alkynyl, —(C$_3$-C$_8$)cycloalkyl, —(C$_8$-C$_8$)cycloalkenyl, -phenyl, -benzyl, -(3- to 7-membered)heterocycle, —C(halo)$_3$, —CH(halo)$_2$, or —CH$_2$(halo);

R$^{11}$ is —H, —CN, or —C(=O)N(R$^6$)$_2$ or R$^{11}$ is —(C$_1$-C$_4$)alkyl which is unsubstituted or substituted with —OH, —(C$_1$-C$_4$)alkoxy, or —N(R$^6$)$_2$;

each R$^{12}$ is independently —H or —(C$_1$-C$_4$)alkyl;

R$^{13}$ is selected from:
(a) -halo, —CN, —OH, —CH$_2$OH, —CH$_2$CH$_2$OH, —NO$_2$, —N(R$^6$)$_2$, —S(=O)NH$_2$, —S(=O)$_2$NH$_2$, —C(=O)OV$^1$, and —C(=O)CN; and
(b) —(C$_1$-C$_{10}$)alkyl, —(C$_2$-C$_{10}$)alkenyl, —(C$_2$-C$_{10}$)alkynyl, —O(C$_1$-C$_6$)alkyl, —(C$_3$-C$_7$)cycloalkoxy, —(C$_5$-C$_{10}$)cycloalkenyl, and -(3- to 7-membered)heterocycle, each of which is unsubstituted or substituted with 1, 2, 3, or 4 independently selected R$^8$ groups; and
(c)

and (d) -phenyl and -(5- to 10-membered)heteroaryl, each of which is unsubstituted or substituted with 1, 2, or 3 independently selected R$^7$ groups;

R$^{15}$, when present, is selected from:
(a) —H; and
(b) —(C$_1$-C$_4$)alkyl and —O—(C$_1$-C$_4$)alkyl, each of which is unsubstituted or substituted with 1, 2, 3, or 4 independently selected R$^8$ groups;
(c) provided that when --- W— is a single bond, a double bond, or —O—, R$^{15}$ is not —H;

each T$^1$ and T$^2$ is independently —H or —(C$_1$-C$_{10}$)alkyl which is unsubstituted or substituted with 1, 2, or 3 independently selected R$^5$ groups and, optionally, in which any —(C$_1$-C$_{10}$)alkyl carbon atom except the carbon atom bonded directly to the atom to which T$^1$ or T$^2$ is attached is independently replaced by O, S, or N(R$^6$), or T$^1$ and T$^2$ can together form a -(5- to 8-membered)heterocyclic ring wherein the number of atoms in the ring includes the nitrogen atom to which T$^1$ and T$^2$ are bonded, said -(5- to 8-membered)heterocyclic ring is unsubstituted or substituted with 1, 2, or 3 independently selected R$^5$ groups and, optionally, any 1 or 2 carbon atoms in said -(5- to 8-membered)heterocyclic ring is independently replaced by O, S, or N(R$^6$);

each T$^3$ is independently —H or —(C$_1$-C$_{10}$)alkyl which is unsubstituted or substituted with 1, 2, or 3 independently selected R$^5$ groups and, optionally, in which any —(C$_1$-C$_{10}$)alkyl carbon atom except the carbon atom bonded directly to the atom to which T$^3$ is attached is independently replaced by O, S, or N(R$^{12}$);

each V$^1$ is independently —H, —(C$_1$-C$_6$)alkyl, —(C$_3$-C$_7$)cycloalkyl, -phenyl, or -benzyl;

a is an integer selected from 0, 1, and 2;

each b is, independently, an integer selected from 1, 2, 3, 4, 5, and 6;

each d is, independently, an integer selected from 0, 1, 2, and 3;

m is an integer selected from 0, 1, 2, 3, 4, 5, 6, 7, 8, 9, 10, and 11;

n is an integer selected from 0, 1, 2, 3, 4, 5, 6, 7, 8, and 9;

e and f are each an integer independently selected from 0, 1, 2, 3, 4, and 5 provided that $2 \leq (e+f) \leq 5$;

each p is an integer independently selected from 0, 1, 2, 3, and 4; and each halo is independently —F, —Cl, —Br, or —I.

Compounds of formula (IA) are herein disclosed:

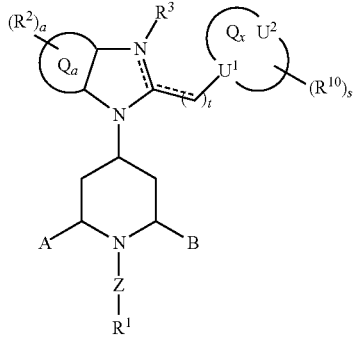

(IA)

or a pharmaceutically acceptable salt or solvate thereof where:

the $Q_a$ ring is fused benzo or fused (5- or 6-membered) heteroaryl;

each $R^2$ is independently selected from:

(a) -halo, —CN, —NO$_2$, —OT$^3$, —C(=O)T$^3$, —C(=O)T$^3$, —C(=O)N(T$^1$)(T$^2$), —S(=O)$_2$OT$^3$, —S(=O)T$^3$, —S(=O)$_2$T$^3$, —O—S(=O)$_2$T$^3$, —S(=O)$_2$N(T$^1$)(T$^2$), —N(T$^1$)(T$^2$), —N(T$^3$)C(=O)T$^3$, —N(T$^3$)C(=O)N(T$^1$)(T$^2$), —N(T$^3$)S(=O)T$^3$, —N(T$^3$)S(=O)$_2$T$^3$, —N(T$^3$)C(=O)OT$^3$, and —N(T$^3$)S(=O)$_2$N(T$^1$)(T$^2$); and (b) —(C$_1$-C$_6$)alkyl, —(C$_2$-C$_6$)alkenyl, —(C$_2$-C$_6$)alkynyl, —(C$_1$-C$_6$)alkoxy, —(C$_3$-C$_7$)cycloalkyl, —(C$_6$-C$_{10}$)bicycloalkyl, —(C$_5$-C$_{10}$)cycloalkenyl, —(C$_7$-C$_{10}$)bicycloalkenyl, and -(5- or 6-membered)heterocycle, each of which is unsubstituted or substituted with 1, 2, or 3 independently selected R$^8$ groups; and (c) -phenyl, -naphthalenyl, and -(5- or 6-membered)heteroaryl, each of which is unsubstituted or substituted with 1, 2, or 3 independently selected R$^7$ groups;

each dashed line denotes the presence or absence of a bond (i.e., when a dashed line is present there is a double bond at that position and when a dashed line is absent there is only a single bond at that position), provided that:

(a) one dashed line must denote the presence of a bond (i.e., there is a double bond at that position);

(b) when one dashed line denotes the presence of a bond (i.e., there is a double bond at that position) then the other dashed line denotes the absence of a bond (i.e., there is only a single bond at that other position);

(c) when the dashed line within the 5-membered, nitrogen-containing ring that is fused to the $Q_a$ ring is present (i.e., there is a double bond at that position), then $R^3$ is absent; and (d) when the dashed line within the 5-membered, nitrogen-containing ring that is fused to the $Q_a$ ring is absent (i.e., there is only a single bond at that position), then $R^3$ is present;

$R^3$, when present, is:

(a) —H; or (b) —(C$_1$-C$_4$)alkyl which is unsubstituted or substituted with 1, 2, or 3 groups independently selected from —OH, —(C$_1$-C$_4$)alkoxy, —N(R$^6$)$_2$, —C(=O)OR$^9$, and —C(=O)N(R$^6$)$_2$; or (c) —(C$_3$-C$_7$)cycloalkyl which is unsubstituted or substituted with 1, 2, or 3 groups independently selected from —OH, —(C$_1$-C$_4$)alkyl, —(C$_1$-C$_4$)alkoxy, —N(R$^6$)$_2$, —C(=O)OR$^9$, and —C(=O)N(R$^6$)$_2$;

t is an integer selected from 0, 1, 2, and 3;

when t is 0, the $Q_x$ ring is a -(4-, 5-, 6-, or 7-membered) heterocycle containing one or two ring heteroatoms selected from N, N(R$^4$), O, and S provided that at least one ring heteroatom is N or N(R$^4$) and provided that when the dashed line connecting the $Q_x$ ring to the 5-membered, nitrogen-containing ring that is fused to the $Q_a$ ring is present (i.e., there is a double bond at that position), U$^1$ is C or CH, and when t is 1, 2, or 3 the $Q_x$ ring is a (6-membered) heterocycle selected from:

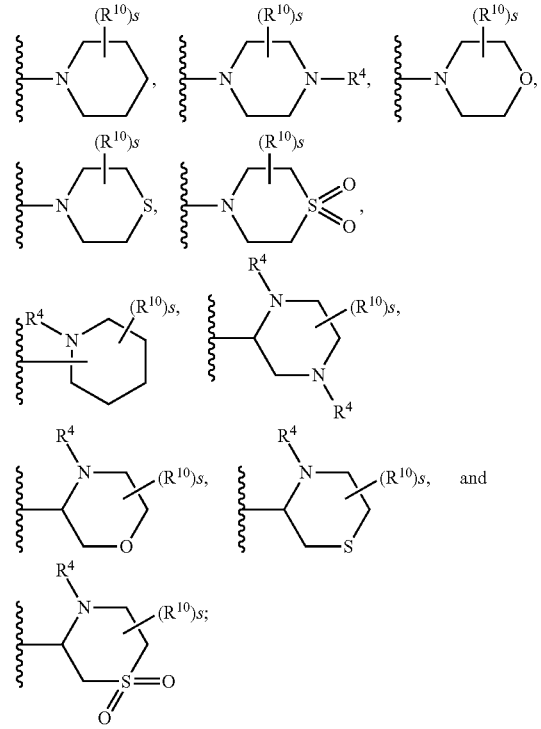

each R$^4$, when present, is independently selected from:

(a) —H; and (b) —X, —(C$_1$-C$_6$)alkyl-X, -(5- or 6-membered)heterocycle-X, or -(5- or 6-membered)heterocycle-(C$_1$-C$_6$)alkyl-X; and (c) —(CH$_2$)$_d$—C(=Y)CN, —(CH$_2$)$_d$—C(=Y)X, —(CH$_2$)$_d$—C(=Y)T$^3$, —(CH$_2$)$_d$—C(=Y)YX, —(CH$_2$)$_d$—C(=Y)YT$^3$, —(CH$_2$)$_d$—C(=Y)N(T$^1$)(T$^2$), —(CH$_2$)$_d$—C(=Y)N(R$^9$)CN, —(CH$_2$)$_d$—C(=Y)N(R$^9$)X, —(CH$_2$)$_d$—C(=Y)N(R$^9$)YH, —(CH$_2$)$_d$—C(=Y)N(R$^9$)YX, —(CH$_2$)$_d$—C(=Y)N ($R^9$)YCH$_2$X, —(CH$_2$)$_d$—C(=Y)N($R^9$)YCH$_2$CH$_2$X, or —(CH$_2$)$_d$—C(=Y)N($R^9$)S(=O)$_2$T$^3$; and (d) —[CH$_2$—O]$_b$—R$^{16}$, —[CH(CH$_3$)—O]$_b$—R$^{16}$, —[CH$_2$—CH$_2$—O]$_b$—R$^{16}$, —[CH(CH$_3$)—CH$_2$—O]$_b$—R$^{16}$, —[CH$_2$—CH(CH$_3$)—O]$_b$—R$^{16}$, —[CH$_2$—CH$_2$—CH$_2$—O]$_b$—R$^{16}$, —[CH(CH$_3$)—CH$_2$—CH$_2$—O]$_b$—R$^{16}$, —[CH$_2$—CH(CH$_3$)—CH$_2$—O]$_b$—R$^{16}$, or —[CH$_2$—CH$_2$—CH(CH$_3$)—O]$_b$—R$^{16}$;

X is selected from:

(a) —H, —(C$_1$-C$_6$)alkyl, —(C$_2$-C$_6$)alkenyl, —(C$_2$-C$_6$)alkynyl, —(C$_1$-C$_6$)alkoxy, —(C$_3$-C$_7$)cycloalkyl, —(C$_5$-C$_{10}$)cycloalkenyl, and -(5- or 6-membered)heterocycle, each of which is unsubstituted or substituted with 1, 2, or 3 independently selected R$^8$ groups; and (b) -phenyl and -(5- or 6-membered)heteroaryl, each of which is unsubstituted or substituted with 1, 2, or 3 independently selected R$^7$ groups;

each Y is independently O or S;

each R$^{16}$ is independently H or CH$_3$;

s is an integer selected from 0, 1, and 2;

when s is 1, R$^{10}$ is —F, —CH$_3$, —CH$_2$CH$_3$, —(CH$_2$)$_d$—C(=Y)YT$^3$, or —(CH$_2$)$_d$—C(=Y)N(T$^1$)(T$^2$), and when s is 2, the R$^{10}$ groups together are gem-dimethyl, gem-difluoro, =O, or =S;

A and B are independently selected from:

(a) —H; and (b) —(C$_1$-C$_6$)alkyl, —(C$_2$-C$_6$)alkenyl, and —(C$_1$-C$_6$)alkoxy, each of which is unsubstituted or substituted with 1 or 2 substituents independently selected from —OH, —S(=O)$_2$NH$_2$, —C(=O)OT$^3$, —C(=O)N(R$^6$)$_2$, and —N(R$^6$)C(=O)R$^9$, or 1, 2, or 3 independently selected -halo; or (c) A-B can together form a (C$_2$-C$_6$)bridge, which is unsubstituted or substituted with 1, 2, 3, 4, 5, 6, 7, or 8 substituents independently selected from —OH, —(C$_1$-C$_4$)alkyl, -halo, and —C(halo)$_3$, and which bridge optionally contains —HC=CH— or —O— within the (C$_2$-C$_6$)bridge; wherein the 5-membered, nitrogen-containing ring that is fused to the Q$_a$ ring can be in the endo- or exo-configuration with respect to the A-B bridge;

Z is —[(C$_1$-C$_{10}$)alkyl optionally substituted by R$^{13}$]$_h$—, wherein h is 0 or 1; or —[(C$_2$-C$_{10}$)alkenyl optionally substituted by R$^{13}$]—, or —[(C$_1$-C$_{10}$)alkyl-NR$^6$C(=Y)]—;

R$^1$ is selected from:

(a) —H, -halo, —CN, —OH, —CH$_2$OH, —CH$_2$CH$_2$OH, —NO$_2$, —N(R$^6$)$_2$, —S(=O)NH$_2$, —S(=O)$_2$NH$_2$, —C(=O)OV$^1$, and —C(=O)CN; and (b) —(C$_1$-C$_{10}$)alkyl, —(C$_2$-C$_{10}$)alkenyl, —(C$_2$-C$_{10}$)alkynyl, —O(C$_1$-C$_6$)alkyl, —(C$_3$-C$_7$)cycloalkoxy, —(C$_6$-C$_{14}$)bicycloalkyl, —(C$_8$-C$_{20}$)tricycloalkyl, —(C$_5$-C$_{10}$)cycloalkenyl, —(C$_7$-C$_{17}$)bicycloalkenyl, —(C$_8$-C$_{20}$)tricycloalkenyl, and -(3- to 7-membered)heterocycle, each of which is unsubstituted or substituted with 1, 2, 3, or 4 independently selected R$^8$ groups; and (c)

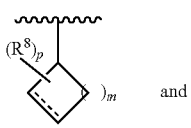

and

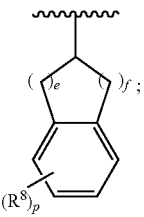

and (d) -phenyl, -naphthalenyl, —(C$_{14}$)aryl, and -(5- to 10-membered)heteroaryl, each of which is unsubstituted or substituted with 1, 2, 3, or 4 independently selected R$^7$ groups;

each R$^5$ is independently —(C$_1$-C$_4$)alkyl, —(C$_2$-C$_6$)alkenyl, —(C$_2$-C$_6$)alkynyl, -(5- or 6-membered)heteroaryl, —(C$_1$-C$_6$)alkyl-C(=O)OR$^9$, —OR$^9$, —SR$^9$, —C(halo)$_3$, —CH(halo)$_2$, —CH$_2$(halo), —CN, =O, =S, -halo, —N$_3$, —NO$_2$, —CH=N(R$^9$), —N(R$^9$)(C$_1$-C$_6$)alkyl-C(=O)OR$^9$, —N(R$^9$)$_2$, —N(R$^9$)OH, —N(R$^9$)S(=O)R$^{12}$, —N(R$^9$)S(=O)R$^{12}$, —N(R$^9$)C(=O)R$^{12}$, —N(R$^9$)C(=O)OR$^{12}$, —C(=O)R$^9$, —C(=O)OR$^9$, —OC(=O)R$^9$, —OC(=O)OR$^9$, —S(=O)R$^9$, or —S(=O)$_2$R$^9$;

each R$^6$ is independently —H, —(C$_1$-C$_6$)alkyl, or —(C$_3$-C$_7$)cycloalkyl, or two R$^6$ groups attached to the same nitrogen atom can together form a -(5- to 8-membered)heterocyclic ring, wherein the number of atoms in the ring includes the nitrogen atom, and in which one of the -(5- to 8-membered)heterocyclic ring carbon atoms is optionally replaced by O, S, or N(T$^3$);

each R$^7$ is independently —(C$_1$-C$_4$)alkyl, —(C$_2$-C$_6$)alkenyl, —(C$_2$-C$_6$)alkynyl, —OR$^9$, —SR$^9$, —C(halo)$_3$, —CH(halo)$_2$, —CH$_2$(halo), —CN, -halo, —N$_3$, —NO$_2$, —CH=N(R$^9$), —N(R$^9$)$_2$, —N(R$^9$)OH, —N(R$^9$)S(=O)R$^{12}$, —N(R$^9$)S(=O)$_2$R$^{12}$, —N(R$^9$)C(=O)R$^{12}$, —N(R$^9$)C(=O)N(T$^1$)(T$^2$), —N(R$^9$)C(=O)OR$^{12}$, —C(=O)R$^9$, —C(=O)N(T$^1$)(T$^2$), —C(=O)OR$^9$, —OC(=O)R$^9$, —OC(=O)N(T$^1$)(T$^2$), —OC(=O)OR$^9$, —S(=O)R$^9$, or —S(=O)$_2$R$^9$;

each R$^8$ is independently —(C$_1$-C$_4$)alkyl, —(C$_2$-C$_6$)alkenyl, —(C$_2$-C$_6$)alkynyl, -(5- or 6-membered)heteroaryl, —(C$_1$-C$_6$)alkyl-C(=O)OR$^9$, —N(R$^9$)(C$_1$-C$_6$)alkyl-C(=O)OR$^9$, —OR$^9$, —SR$^9$, —C(halo)$_3$, —CH(halo)$_2$, —CH$_2$(halo), —CN, =O, =S, =N(R$^9$), -halo, —N$_3$, —NO$_2$, —CH=N(R$^9$), —N(R$^9$)$_2$, —N(R$^9$)OR$^9$, —N(R$^9$)S(=O)R$^{12}$, —N(R$^9$)S(=O)$_2$R$^{12}$, —N(R$^9$)C(=O)R$^{12}$, —N(R$^9$)C(=O)N(T$^1$)(T$^2$), —N(R$^9$)C(=O)OR$^{12}$, —C(=O)R$^9$, —C(=O)N(T$^1$)(T$^2$), —C(=O)OR$^9$, —OC(=O)R$^9$, —OC(=O)N(T$^1$)(T$^2$), —OC(=O)OR$^9$, —S(=O)R$^9$, or —S(=O)$_2$R$^9$;

each R$^9$ is independently —H, —(C$_1$-C$_6$)alkyl, —(C$_2$-C$_6$)alkenyl, —(C$_2$-C$_6$)alkynyl, —(C$_3$-C$_8$)cycloalkyl, —(C$_5$-C$_8$)cycloalkenyl, -phenyl, -benzyl, -(3- to 7-membered)heterocycle, —C(halo)$_3$, —CH(halo)$_2$, or —CH$_2$(halo);

each R$^{12}$ is independently —H or —(C$_1$-C$_4$)alkyl;

R$^{13}$ is selected from:

(a) -halo, —CN, —OH, —CH$_2$OH, —CH$_2$CH$_2$OH, —NO$_2$, —N(R$^6$)$_2$, —S(=O)NH$_2$, —S(=O)$_2$NH$_2$, —C(=O)OV$^1$, and —C(=O)CN; and (b) —(C$_1$-C$_{10}$)alkyl, —(C$_2$-C$_{10}$)alkenyl, —(C$_2$-C$_{10}$)alkynyl, —O(C$_1$-C$_6$)alkyl, —(C$_3$-C$_7$)cycloalkoxy, —(C$_5$-C$_{10}$)cycloalkenyl, and -(3- to 7-membered)heterocycle, each of which is unsubstituted or substituted with 1, 2, 3, or 4 independently selected R$^8$ groups; and (c)

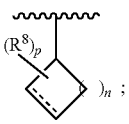

and (d) -phenyl and -(5- to 10-membered)heteroaryl, each of which is unsubstituted or substituted with 1, 2, or 3 independently selected $R^7$ groups;

each $T^1$ and $T^2$ is independently —H or —$(C_1\text{-}C_{10})$alkyl which is unsubstituted or substituted with 1, 2, or 3 independently selected $R^5$ groups and, optionally, in which any —$(C_1\text{-}C_{10})$alkyl carbon atom except the carbon atom bonded directly to the atom to which $T^1$ or $T^2$ is attached is independently replaced by O, S, or $N(R^6)$, or $T^1$ and $T^2$ can together form a -(5- to 8-membered)heterocyclic ring wherein the number of atoms in the ring includes the nitrogen atom to which $T^1$ and $T^2$ are bonded, said -(5- to 8-membered)heterocyclic ring is unsubstituted or substituted with 1, 2, or 3 independently selected $R^5$ groups and, optionally, any 1 or 2 carbon atoms in said -(5- to 8-membered)heterocyclic ring is independently replaced by O, S, or $N(R^6)$;

each $T^3$ is independently —H or —$(C_1\text{-}C_{10})$alkyl which is unsubstituted or substituted with 1, 2, or 3 independently selected $R^5$ groups and, optionally, in which any —$(C_1\text{-}C_{10})$alkyl carbon atom except the carbon atom bonded directly to the atom to which $T^3$ is attached is independently replaced by O, S, or $N(R^{12})$;

each $V^1$ is independently —H, —$(C_1\text{-}C_6)$alkyl, —$(C_3\text{-}C_7)$cycloalkyl, -phenyl, or -benzyl;

a is an integer selected from 0, 1, and 2;

each b is, independently, an integer selected from 1, 2, 3, 4, 5, and 6;

each d is, independently, an integer selected from 0, 1, 2, and 3;

m is an integer selected from 0, 1, 2, 3, 4, 5, 6, 7, 8, 9, 10, and 11;

n is an integer selected from 0, 1, 2, 3, 4, 5, 6, 7, 8, and 9;

e and f are each an integer independently selected from 0, 1, 2, 3, 4, and 5 provided that $2 \leq (e+f) \leq 5$;

each p is an integer independently selected from 0, 1, 2, 3, and 4; and each halo is independently —F, —Cl, —Br, or —I.

Compounds of formula (I*) are herein disclosed:

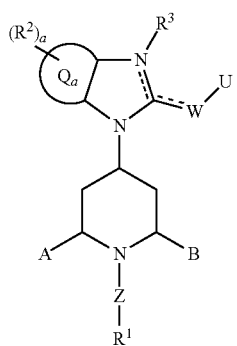

(I*)

or a pharmaceutically acceptable salt or solvate thereof wherein:

the $Q_a$ ring is fused benzo or fused (5- or 6-membered) heteroaryl;

each $R^2$ is independently selected from:

(a) -halo, —CN, —$NO_2$, —$OT^3$, —$C(=O)T^3$, —$C(=O)OT^3$, —$C(=O)N(T^1)(T^2)$, —$S(=O)_2OT^3$, —$S(=O)T^3$, —$S(=O)_2T^3$, —O—$S(=O)_2T^3$, —$S(=O)_2N(T^1)(T^2)$, —$N(T^1)(T^2)$, —$N(T^3)C(=O)T^3$, —$N(T^3)C(=O)N(T^1)(T^2)$, —$N(T^3)S(=O)T^3$, —$N(T^3)S(=O)_2T^3$, —$N(T^3)C(=O)OT^3$, and —$N(T^3)S(=O)_2N(T^1)(T^2)$; and (b) —$(C_1\text{-}C_6)$alkyl, —$(C_2\text{-}C_6)$alkenyl, —$(C_2\text{-}C_6)$alkynyl, —$(C_1\text{-}C_6)$alkoxy, —$(C_3\text{-}C_7)$cycloalkyl, —$(C_6\text{-}C_{10})$bicycloalkyl, —$(C_5\text{-}C_{10})$cycloalkenyl, —$(C_7\text{-}C_{10})$bicycloalkenyl, and -(5- or 6-membered)heterocycle, each of which is unsubstituted or substituted with 1, 2, or 3 independently selected $R^8$ groups; and (c) -phenyl, -naphthalenyl, and -(5- or 6-membered)heteroaryl, each of which is unsubstituted or substituted with 1, 2, or 3 independently selected $R^2$ groups;

each dashed line denotes the presence or absence of a bond, provided that:

(a) one dashed line must denote the presence of a bond;

(b) when one dashed line denotes the presence of a bond then the other dashed line denotes the absence of a bond;

(c) when the dashed line within the 5-membered, nitrogen-containing ring that is fused to the $Q_a$ ring is present, then $R^3$ is absent; and (d) when the dashed line within the 5-membered, nitrogen-containing ring that is fused to the $Q_a$ ring is absent, then $R^3$ is present;

$R^3$, when present, is:

(a) —H; or (b) —$(C_1\text{-}C_4)$alkyl which is unsubstituted or substituted with 1, 2, or 3 groups independently selected from —OH, —$(C_1\text{-}C_4)$alkoxy, —$N(R^6)_2$, —$C(=O)OR^9$, and —$C(=O)N(R^6)_2$; or (c) —$(C_3\text{-}C_7)$cycloalkyl which is unsubstituted or substituted with 1, 2, or 3 groups independently selected from —OH, —$(C_1\text{-}C_4)$alkyl, —$(C_1\text{-}C_4)$alkoxy, —$N(R^6)_2$, —$C(=O)OR^9$, and —$C(=O)N(R^6)_2$;

---W— is a single bond, a double bond, =CH—, —$CH_2$—, =N—, —NH—, —O—, =CH—$(C_1\text{-}C_3)$alkylene-, —$CH_2$—$(C_1\text{-}C_3)$alkylene-, =N—$(C_1\text{-}C_3)$alkylene-, —NH—$(C_1\text{-}C_3)$alkylene-, —O—$(C_1\text{-}C_3)$alkylene-, =CH—$(C_2\text{-}C_3)$alkenylene-, —$CH_2$—$(C_2\text{-}C_3)$alkenylene-, =N—$(C_2\text{-}C_3)$alkenylene-, —NH—$(C_2\text{-}C_3)$alkenylene-, —O—$(C_2\text{-}C_3)$alkenylene-, =CH—$(C_1\text{-}C_3)$alkylene-N$(R^{11})$—, —$CH_2$—$(C_1\text{-}C_3)$alkylene-N$(R^{11})$—, =N—$(C_1\text{-}C_3)$alkylene-N$(R^{11})$—, —NH—$(C_1\text{-}C_3)$alkylene-N$(R^{11})$—, —O—$(C_1\text{-}C_3)$alkylene-N$(R^{11})$—, =CH—N$(R^{11})$—, —CH=N—, —$CH_2$—N$(R^{11})$—, =CH—O—, —$CH_2$—O—, =CH—O—$(C_1\text{-}C_3)$alkylene-, or —$CH_2$—O—$(C_1\text{-}C_3)$alkylene-;

U is:

(a) —$R^{15}$; or (b)

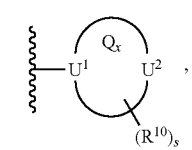

wherein when ---W— is a single bond or a double bond the Q$_x$ ring is a -(3-, 4-, 5-, 6-, or 7-membered)heterocycle containing 1, 2, 3, or 4 ring heteroatoms independently selected from N, N(R$^4$), O, and S, wherein said heterocycle is unsubstituted or substituted with)(R$^{10}$)$_s$, provided that at least one ring heteroatom is N or N(R$^4$) and wherein either U$^1$ is N and U$^2$ is a bond or U$^1$ is C or CH and U$^2$ is N or N(R$^4$), provided that;

(1) when ---W— is a double bond and the Q$_x$ ring is present, U$^1$ is C; and (2) when ---W— is =CH—, —CH$_2$—, =CH—(C$_1$-C$_3$)alkylene-, or —CH$_2$—(C$_1$-C$_3$)alkylene- and the Q$_a$ ring is present, the Q$_x$ ring is a -(5- or 6-membered)heterocycle selected from:

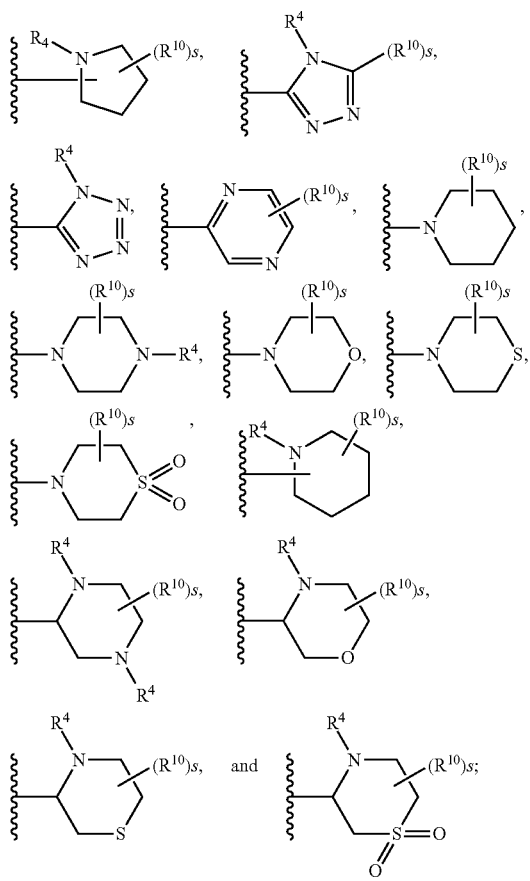

and (3) when ---W— is =N—, —NH—, —O—, =N—(C$_1$-C$_3$)alkylene-, —NH—(C$_1$-C$_3$)alkylene-, —O—(C$_1$-C$_3$)alkylene-, =CH—(C$_2$-C$_3$)alkenylene-, —CH$_2$—(C$_2$-C$_3$)alkenylene-, =N—(C$_2$-C$_3$)alkenylene-, —NH—(C$_2$-C$_3$)alkenylene-, —O—(C$_2$-C$_3$)alkenylene-, =CH—(C$_1$-C$_3$)alkylene-N(R$^{11}$)—, —CH$_2$—(C$_1$-C$_3$)alkylene-N(R$^{11}$)—, =N—(C$_1$-C$_3$)alkylene-N(R$^{11}$)—, —NH—(C$_1$-C$_3$)alkylene-N(R$^{11}$)—, —O—(C$_1$-C$_3$)alkylene-N(R$^{11}$)—, =CH—N(R$^{11}$)—, —CH=N—, —CH$_2$—N(R$^{11}$)—, =CH—O—, —CH$_2$—O—, =CH—O—(C$_1$-C$_3$)alkylene-, or —CH$_2$—O—(C$_1$-C$_3$)alkylene-, then the Q$_x$ ring is absent;

each R$^4$, when present, is independently selected from:
(a) —H; and
(b) —X, —(C$_1$-C$_6$)alkyl-X, -(5- or 6-membered)heterocycle-X, or -(5- or 6-membered)heterocycle-(C$_1$-C$_6$)alkyl-X; and
(c) —(CH$_2$)$_d$—C(=Y)CN, —(CH$_2$)$_d$—C(=Y)X, —(CH$_2$)$_d$—C(=Y)T$^3$, —(CH$_2$)$_d$—C(=Y)YX, —(CH$_2$)$_d$—C(=Y)YT$^3$, —(CH$_2$)$_d$—C(=Y)N(T$^1$)(T$^2$), —(CH$_2$)$_d$—C(=Y)N(R$^9$)CN, —(CH$_2$)$_d$—C(=Y)N(R$^9$)X, —(CH$_2$)$_d$—C(=Y)N(R$^9$)YH, —(CH$_2$)$_d$—C(=Y)N(R$^9$)YX, —(CH$_2$)$_d$—C(=Y)N(R$^9$)YCH$_2$X, —(CH$_2$)$_d$—C(=Y)N(R$^9$)YCH$_2$CH$_2$X, —(CH$_2$)$_d$—C(=Y)N(R$^9$)S(=O)$_2$T$^3$, —(CH$_2$)$_d$—N(R$^9$)S(=O)$_2$T$^3$, or —(CH$_2$)$_d$S(=O)$_2$T$^4$; and
(d) —[CH$_2$—O]$_b$—R$^{16}$, —[CH(CH$_3$)—O]$_b$—R$^{16}$, —[CH$_2$—CH$_2$—O]$_b$—R$^{16}$, —[CH(CH$_3$)—CH$_2$—O]$_b$—R$^{16}$, —[CH$_2$—CH(CH$_3$)—O]$_b$—R$^{16}$, —[CH$_2$—CH$_2$—CH$_2$—O]$_b$—R$^{16}$, —[CH(CH$_3$)—CH$_2$—CH$_2$—O]$_b$—R$^{16}$, —[CH$_2$—CH(CH$_3$)—CH$_2$—O]$_b$—R$^{16}$, or —[CH$_2$—CH$_2$—CH(CH$_3$)—O]$_b$—R$^{16}$;

X is selected from:
(a) —H, —(C$_1$-C$_6$)alkyl, —(C$_2$-C$_6$)alkenyl, —(C$_2$-C$_6$)alkynyl, —(C$_1$-C$_6$)alkoxy, —(C$_3$-C$_7$)cycloalkyl, —(C$_5$-C$_{10}$)cycloalkenyl, and -(5- or 6-membered)heterocycle, each of which is unsubstituted or substituted with 1, 2, or 3 independently selected R$^8$ groups; and
(b) -phenyl and -(5- or 6-membered)heteroaryl, each of which is unsubstituted or substituted with 1, 2, or 3 independently selected R$^7$ groups;

each Y is independently O or S;
each R$^{16}$ is independently H or CH$_3$;
s is an integer selected from 0, 1, 2, 3, and 4;
when s is 1, 2, 3, or 4, each R$^{10}$ is independently —F, —Cl, —CH$_3$, —CH$_2$CH$_3$, —OCH$_3$, —OCH$_2$CH$_3$, —(CH$_2$)$_d$—C(=Y)YT$^3$, or —(CH$_2$)$_d$—C(=Y)N(T$^1$)(T$^2$), and when s is 2, 3, or 4, each R$^{10}$ is independently —F, —Cl, —CH$_3$, —CH$_2$CH$_3$, —OCH$_3$, —OCH$_2$CH$_3$, —(CH$_2$)$_d$—C(=Y)YT$^3$, or —(CH$_2$)$_d$—C(=Y)N(T$^1$)(T$^2$) or two R$^{10}$ groups attached to the same carbon atom and are gem-dimethyl, gem-difluoro, =O, or =S;

A and B are independently selected from:
(a) —H; and
(b) —(C$_1$-C$_6$)alkyl, —(C$_2$-C$_6$)alkenyl, and —(C$_1$-C$_6$)alkoxy, each of which is unsubstituted or substituted with 1 or 2 substituents independently selected from —OH, —S(=O)$_2$NH$_2$, —C(=O)OT$^3$, —C(=O)N(R$^6$)$_2$, and —N(R$^6$)C(=O)R$^9$, or 1, 2, or 3 independently selected -halo; or
(c) A-B can together form a (C$_2$-C$_6$)bridge, which is unsubstituted or substituted with 1, 2, 3, 4, 5, 6, 7, or 8 substituents independently selected from —OH, —(C$_1$-C$_4$)alkyl, -halo, and —C(halo)$_3$, and which bridge optionally contains —HC=CH— or —O— within the (C$_2$-C$_6$)bridge; wherein the 5-membered, nitrogen-containing ring that is fused to the Q$_a$ ring can be in the endo- or exo-configuration with respect to the A-B bridge;

Z is —[(C$_1$-C$_{10}$)alkyl optionally substituted by R$^{13}$]$_h$—, wherein h is 0 or 1; or —[(C$_2$-C$_{10}$)alkenyl optionally substituted by R$^{13}$]—, or —[(C$_1$-C$_{10}$)alkyl-NR$^6$C(=Y)]—;

R$^1$ is selected from:
(a) —H, -halo, —CN, —OH, —CH$_2$OH, —CH$_2$CH$_2$OH, —NO$_2$, —N(R$^6$)$_2$, —S(=O)NH$_2$, —S(=O)$_2$NH$_2$, —C(=O)OV$^1$, and —C(=O)CN; and
(b) —(C$_1$-C$_{10}$)alkyl, —(C$_2$-C$_{10}$)alkenyl, —(C$_2$-C$_{10}$)alkynyl, —O(C$_1$-C$_6$)alkyl, —(C$_3$-C$_7$)cycloalkoxy, —(C$_6$-C$_{14}$)bicycloalkyl, —(C$_8$-C$_{20}$)tricycloalkyl, —(C$_5$-C$_{10}$)cycloalkenyl, —(C$_7$-C$_{14}$)bicycloalkenyl, —(C$_8$-C$_{20}$)tricycloalkenyl, and -(3- to 7-membered)heterocycle, each of which is unsubstituted or substituted with 1, 2, 3, or 4 independently selected R⁸ groups; and (c)

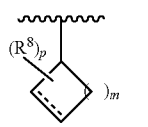

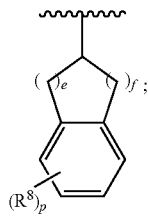

and (d) -phenyl, -naphthalenyl, —(C₁₄)aryl, and -(5- to 10-membered)heteroaryl, each of which is unsubstituted or substituted with 1, 2, 3, or 4 independently selected R⁷ groups;

each R⁵ is independently —(C₁-C₄)alkyl, —(C₂-C₆)alkenyl, —(C₂-C₆)alkynyl, -(5- or 6-membered)heteroaryl, —(C₁-C₆)alkyl-C(=O)OR⁹, —OR⁹, —SR⁹, —C(halo)₃, —CH(halo)₂, —CH₂(halo), —CN, =O, =S, -halo, —N₃, —NO₂, —CH=N(R⁹), —N(R⁹)(C₁-C₆)alkyl-C(=O)OR⁹, —N(R⁹)₂, —N(R⁹)OH, —N(R⁹)S(=O)R¹², —N(R⁹)S(=O)₂R¹², —N(R⁹)C(=O)R¹², —N(R⁹)C(=O)OR¹², —C(=O)R⁹, —C(=O)OR⁹, —OC(=O)R⁹, —OC(=O)OR⁹, —S(=O)R⁹, or —S(=O)₂R⁹;

each R⁶ is independently —H, —(C₁-C₆)alkyl, or —(C₃-C₇)cycloalkyl, or two R⁶ groups attached to the same nitrogen atom can together form a -(5- to 8-membered)heterocyclic ring, wherein the number of atoms in the ring includes the nitrogen atom, and in which one of the -(5- to 8-membered)heterocyclic ring carbon atoms is optionally replaced by O, S, or N(T³);

each R⁷ is independently —(C₁-C₄)alkyl, —(C₂-C₆)alkenyl, —(C₂-C₆)alkynyl, —OR⁹, —SR⁹, —C(halo)₃, —CH(halo)₂, —CH₂(halo), —CN, -halo, —N₃, —NO₂, —CH=N(R⁹), —N(R⁹)₂, —N(R⁹)OH, —N(R⁹)S(=O)R¹², —N(R⁹)S(=O)₂R¹², —N(R⁹)C(=O)R¹², —N(R⁹)C(=O)N(T¹)(T²), —N(R⁹)C(=O)OR¹², —C(=O)R⁹, —C(=O)N(T¹)(T²), —C(=O)OR⁹, —OC(=O)R⁹, —OC(=O)N(T¹)(T²), —OC(=O)OR⁹, —S(=O)R⁹, or —S(=O)₂R⁹;

each R⁸ is independently —(C₁-C₄)alkyl, —(C₂-C₆)alkenyl, —(C₂-C₆)alkynyl, -(5- or 6-membered)heteroaryl, —(C₁-C₆)alkyl-C(=O)OR⁹, —N(R⁹)(C₁-C₆)alkyl-C(=O)OR⁹, —OR⁹, —SR⁹, —C(halo)₃, —CH(halo)₂, —CH₂(halo), —CN, =O, =S, =N(R⁹), -halo, —N₃, —NO₂, —CH=N(R⁹), —N(R⁹)₂, —N(R⁹)OR⁹, —N(R⁹)S(=O)R¹², —N(R⁹)S(=O)₂R¹², —N(R⁹)C(=O)R¹², —N(R⁹)C(=O)N(T¹)(T²), —N(R⁹)C(=O)OR¹², —C(=O)R⁹, —C(=O)N(T¹)(T²), —C(=O)OR⁹, —OC(=O)R⁹, —OC(=O)N(T¹)(T²), —OC(=O)OR⁹, —S(=O)R⁹, or —S(=O)₂R⁹;

each R⁹ is independently —H, —(C₁-C₆)alkyl, —(C₂-C₆)alkenyl, —(C₂-C₆)alkynyl, —(C₃-C₈)cycloalkyl, —(C₅-C₈)cycloalkenyl, -phenyl, -benzyl, -(3- to 7-membered)heterocycle, —C(halo)₃, —CH(halo)₂, or —CH₂(halo);

R¹¹ is —H, —CN, or —C(=O)N(R⁶)₂ or is —(C₁-C₄)alkyl which is unsubstituted or substituted with —OH, —(C₁-C₄)alkoxy, or —N(R⁶)₂;

each R¹² is independently —H or —(C₁-C₄)alkyl;

R¹³ is selected from:
(a) -halo, —CN, —OH, —CH₂OH, —CH₂CH₂OH, —NO₂, —N(R⁶)₂, —S(=O)NH₂, —S(=O)₂NH₂, —C(=O)OV¹, and —C(=O)CN; and
(b) —(C₁-C₁₀)alkyl, —(C₂-C₁₀)alkenyl, —(C₂-C₁₀)alkynyl, —O(C₁-C₆)alkyl, —(C₃-C₇)cycloalkoxy, —(C₅-C₁₀)cycloalkenyl, and -(3- to 7-membered)heterocycle, each of which is unsubstituted or substituted with 1, 2, 3, or 4 independently selected R⁸ groups; and (c)

and (d) -phenyl and -(5- to 10-membered)heteroaryl, each of which is unsubstituted or substituted with 1, 2, or 3 independently selected R⁷ groups;

R¹⁵, when present, is selected from:
(a) —H; and
(b) —(C₁-C₄)alkyl and —O—(C₁-C₄)alkyl, each of which is unsubstituted or substituted with 1, 2, 3, or 4 independently selected R⁸ groups;
(c) provided that when ---W— is a single bond, a double bond, or —O—, R¹⁵ is not —H;

each T¹ and T² is independently —H or —(C₁-C₁₀)alkyl which is unsubstituted or substituted with 1, 2, or 3 independently selected R⁵ groups and, optionally, in which any —(C₁-C₁₀)alkyl carbon atom except the carbon atom bonded directly to the atom to which T¹ or T² is attached is independently replaced by O, S, or N(R⁶), or T¹ and T² can together form a -(5- to 8-membered)heterocyclic ring wherein the number of atoms in the ring includes the nitrogen atom to which T¹ and T² are bonded, said -(5- to 8-membered)heterocyclic ring is unsubstituted or substituted with 1, 2, or 3 independently selected R⁵ groups and, optionally, any 1 or 2 carbon atoms in said -(5- to 8-membered)heterocyclic ring is independently replaced by O, S, or N(R⁶);

each T³ is independently —H or —(C₁-C₁₀)alkyl which is unsubstituted or substituted with 1, 2, or 3 independently selected R⁵ groups and, optionally, in which any —(C₁-C₁₀)alkyl carbon atom except the carbon atom bonded directly to the atom to which T³ is attached is independently replaced by O, S, or N(R¹²);

each T⁴ is independently a -(5- or 6-membered)heteroaryl which is unsubstituted or substituted with 1 or 2 independently selected R¹² groups;

each V¹ is independently —H, —(C₁-C₆)alkyl, —(C₃-C₇)cycloalkyl, -phenyl, or -benzyl;

a is an integer selected from 0, 1, and 2;

each b is, independently, an integer selected from 1, 2, 3, 4, 5, and 6;

each d is, independently, an integer selected from 0, 1, 2, and 3;

m is an integer selected from 0, 1, 2, 3, 4, 5, 6, 7, 8, 9, 10, and 11;

n is an integer selected from 0, 1, 2, 3, 4, 5, 6, 7, 8, and 9;

e and f are each an integer independently selected from 0, 1, 2, 3, 4, and 5 provided that 2≤(e+f)≤5;

each p is an integer independently selected from 0, 1, 2, 3, and 4; and each halo is independently —F, —Cl, —Br, or —I.

Compounds of formula (I‡A) are herein disclosed:

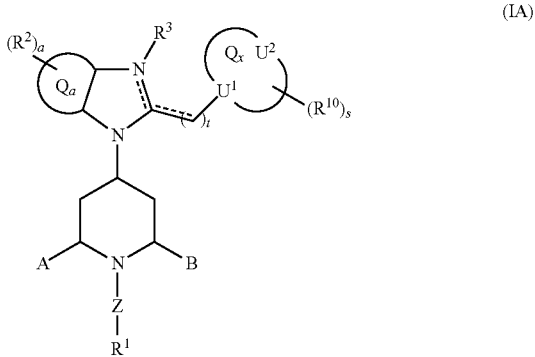

(IA)

or a pharmaceutically acceptable salt or solvate thereof where:

the $Q_a$ ring is fused benzo or fused (5- or 6-membered) heteroaryl;

each $R^2$ is independently selected from:
- (a) -halo, —CN, —NO$_2$, —OT$^3$, —C(=O)T$^3$, —C(=O)OT$^3$, —C(=O)N(T$^1$)(T$^2$), —S(=O)$_2$OT$^3$, —S(=O)T$^3$, —S(=O)$_2$T$^3$, —O—S(=O)$_2$T$^3$, —S(=O)$_2$N(T$^1$)(T$^2$), —N(T$^1$)(T$^2$), —N(T$^3$)C(=O)T$^3$, —N(T$^3$)C(=O)N(T$^1$)(T$^2$), —N(T$^3$)S(=O)T$^3$, —N(T$^3$)S(=O)$_2$T$^3$, —N(T$^3$)C(=O)OT$^3$, and —N(T$^3$)S(=O)$_2$N(T$^1$)(T$^2$); and
- (b) —(C$_1$-C$_6$)alkyl, —(C$_2$-C$_6$)alkenyl, —(C$_2$-C$_6$)alkynyl, —(C$_1$-C$_6$)alkoxy, —(C$_3$-C$_7$)cycloalkyl, —(C$_6$-C$_{10}$)bicycloalkyl, —(C$_5$-C$_{10}$)cycloalkenyl, —(C$_7$-C$_{10}$)bicycloalkenyl, and -(5- or 6-membered)heterocycle, each of which is unsubstituted or substituted with 1, 2, or 3 independently selected $R^8$ groups; and
- (c) -phenyl, -naphthalenyl, and -(5- or 6-membered)heteroaryl, each of which is unsubstituted or substituted with 1, 2, or 3 independently selected $R^7$ groups;

each dashed line denotes the presence or absence of a bond (i.e., when a dashed line is present there is a double bond at that position and when a dashed line is absent there is only a single bond at that position), provided that:
- (a) one dashed line must denote the presence of a bond (i.e., there is a double bond at that position);
- (b) when one dashed line denotes the presence of a bond (i.e., there is a double bond at that position) then the other dashed line denotes the absence of a bond (i.e., there is only a single bond at that other position);
- (c) when the dashed line within the 5-membered, nitrogen-containing ring that is fused to the $Q_a$ ring is present (i.e., there is a double bond at that position), then $R^3$ is absent; and
- (d) when the dashed line within the 5-membered, nitrogen-containing ring that is fused to the $Q_a$ ring is absent (i.e., there is only a single bond at that position), then $R^3$ is present;

$R^3$, when present, is:
- (a) —H; or
- (b) —(C$_1$-C$_4$)alkyl which is unsubstituted or substituted with 1, 2, or 3 groups independently selected from —OH, —(C$_1$-C$_4$)alkoxy, —N(R$^6$)$_2$, —C(=O)OR$^9$, and —C(=O)N(R$^6$)$_2$; or
- (c) —(C$_3$-C$_7$)cycloalkyl which is unsubstituted or substituted with 1, 2, or 3 groups independently selected from —OH, —(C$_1$-C$_4$)alkyl, —(C$_1$-C$_4$)alkoxy, —N(R$^6$)$_2$, —C(=O)OR$^9$, and —C(=O)N(R$^6$)$_2$;

t is an integer selected from 0, 1, 2, and 3;

when t is 0, the $Q_x$ ring is a -(3-, 4-, 5-, 6-, or 7-membered) heterocycle containing 1, 2, 3, or 4 ring heteroatoms independently selected from N, N(R$^4$), O, and S wherein said heterocycle is unsubstituted or substituted with (R$^{10}$)$_s$ groups provided that at least one ring heteroatom is N or N(R$^4$) and provided that when the dashed line connecting the $Q_x$ ring to the 5-membered, nitrogen-containing ring that is fused to the $Q_a$ ring is present (i.e., there is a double bond at that position), U$^1$ is C or CH, and when t is 1, 2, or 3 the $Q_x$ ring is a (5- or 6-membered) heterocycle selected from:

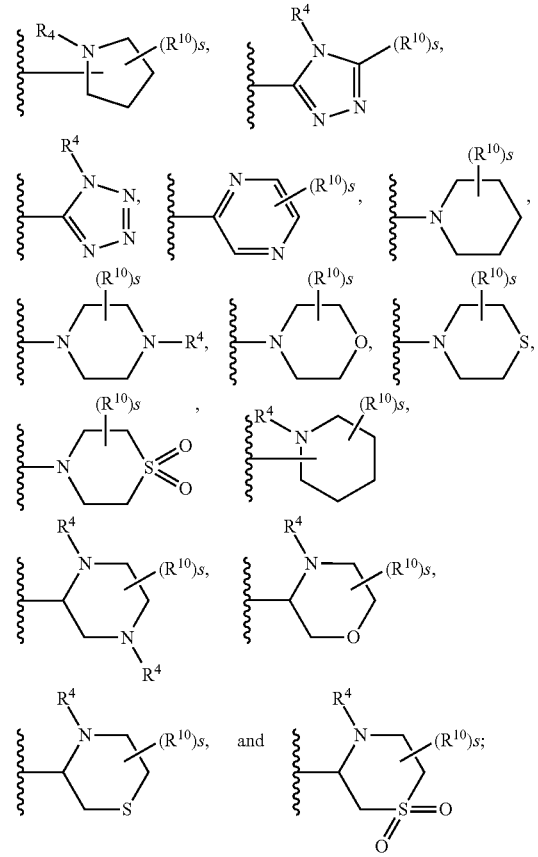

each $R^4$, when present, is independently selected from:
- (a) —H; and
- (b) —X, —(C$_1$-C$_6$)alkyl-X, -(5- or 6-membered)heterocycle-X, or -(5- or 6-membered)heterocycle-(C$_1$-C$_6$)alkyl-X; and
- (c) —(CH$_2$)$_d$—C(=Y)CN, —(CH$_2$)$_d$—C(=Y)X, —(CH$_2$)$_d$—C(=Y)T$^3$, —(CH$_2$)$_d$—C(=Y)YX, —(CH$_2$)$_d$—C(=Y)YT$^3$, —(CH$_2$)$_d$—C(=Y)N(T$^1$)(T$^2$), —(CH$_2$)$_d$—C(=Y)N(R$^9$)CN, —(CH$_2$)$_d$—C(=Y)N(R$^9$)X, —(CH$_2$)$_d$—C(=Y)N(R$^9$)YH, —(CH$_2$)$_d$—C(=Y)N(R$^9$)YX, —(CH$_2$)$_d$—C(=Y)N(R$^9$)YCH$_2$X, —(CH$_2$)$_d$—C(=Y)N(R$^9$)YCH$_2$CH$_2$X, —(CH$_2$)$_d$—C(=Y)N(R$^9$)S(=O)$_2$T$^3$; —(CH$_2$)$_d$—N(R$^9$)S(=O)$_2$T$^3$; or —(CH$_2$)$_d$—S(=O)$_2$T$^4$; and (d) —[CH$_2$—O]$_b$—R$^{16}$, —[CH(CH$_3$)—O]$_b$—R$^{16}$, —[CH$_2$—CH$_2$—O]$_b$—R$^{16}$, —[CH(CH$_3$)—CH$_2$—O]$_b$—R$^{16}$, —[CH$_2$—CH(CH$_3$)—O]$_b$—R$^{16}$, —[CH$_2$—CH$_2$—CH$_2$—O]$_b$—R$^{16}$, —[CH(CH$_3$)—CH$_2$—CH$_2$—O]$_b$—R$^{16}$, —[CH$_2$—CH(CH$_3$)—CH$_2$—O]$_b$—R$^{16}$, or —[CH$_2$—CH$_2$—CH(CH$_3$)—O]$_b$—R$^{16}$;

X is selected from:
(a) —H, —(C$_1$-C$_6$)alkyl, —(C$_2$-C$_6$)alkenyl, —(C$_2$-C$_6$)alkynyl, —(C$_1$-C$_6$)alkoxy, —(C$_3$-C$_7$)cycloalkyl, —(C$_5$-C$_{10}$)cycloalkenyl, and -(5- or 6-membered)heterocycle, each of which is unsubstituted or substituted with 1, 2, or 3 independently selected R$^8$ groups; and
(b) -phenyl and -(5- or 6-membered)heteroaryl, each of which is unsubstituted or substituted with 1, 2, or 3 independently selected R$^7$ groups;

each Y is independently O or S;
each R$^{16}$ is independently H or CH$_3$;
s is an integer selected from 0, 1, 2, 3, and 4;
when s is 1, 2, or 4, each R$^{10}$ is independently —F, —Cl, —CH$_3$, —CH$_2$CH$_3$, —OCH$_3$, —OCH$_2$CH$_3$, —(CH$_2$)$_d$—C(=Y)YT$^3$, or —(CH$_2$)$_d$—C(=Y)N(T$^1$)(T$^2$), and when s is 2, 3, or 4, each R$^{10}$ is independently —F, —Cl, —CH$_3$, —CH$_2$CH$_3$, —OCH$_3$, —OCH$_2$CH$_3$, —(CH$_2$)$_d$—C(=Y)YT$^3$, or —(CH$_2$)$_d$—C(=Y)N(T$^1$)(T$^2$) or two R$^{10}$ groups attached to the same carbon atom and are gem-dimethyl, gem-difluoro, =O, or =S;

A and B are independently selected from:
(a) —H; and
(b) —(C$_1$-C$_6$)alkyl, —(C$_2$-C$_6$)alkenyl, and —(C$_1$-C$_6$)alkoxy, each of which is unsubstituted or substituted with 1 or 2 substituents independently selected from —OH, —S(=O)$_2$NH$_2$, —C(=O)OT$^3$, —C(=O)N(R$^6$)$_2$, and —N(R$^6$)C(=O)R$^9$, or 1, 2, or 3 independently selected -halo; or
(c) A-B can together form a (C$_2$-C$_6$)bridge, which is unsubstituted or substituted with 1, 2, 3, 4, 5, 6, 7, or 8 substituents independently selected from —OH, —(C$_1$-C$_4$)alkyl, -halo, and —C(halo)$_3$, and which bridge optionally contains —HC=CH— or —O— within the (C$_2$-C$_6$)bridge; wherein the 5-membered, nitrogen-containing ring that is fused to the Q$_a$ ring can be in the endo- or exo-configuration with respect to the A-B bridge;

Z is —[(C$_1$-C$_{10}$)alkyl optionally substituted by R$^{13}$]$_h$—, wherein h is 0 or 1; or —[(C$_2$-C$_{10}$)alkenyl optionally substituted by R$^{13}$]—, or —[(C$_1$-C$_{10}$)alkyl-NR$^6$C(=Y)]—;

R$^1$ is selected from:
(a) —H, -halo, —CN, —OH, —CH$_2$OH, —CH$_2$CH$_2$OH, —NO$_2$, —N(R$^6$)$_2$, —S(=O)NH$_2$, —S(=O)$_2$NH$_2$, —C(=O)OV$^1$, and —C(=O)CN; and
(b) —(C$_1$-C$_{10}$)alkyl, —(C$_2$-C$_{10}$)alkenyl, —(C$_2$-C$_{10}$)alkynyl, —O(C$_1$-C$_6$)alkyl, —(C$_3$-C$_7$)cycloalkoxy, —(C$_6$-C$_{14}$)bicycloalkyl, —(C$_8$-C$_{20}$)tricycloalkyl, —(C$_5$-C$_{10}$)cycloalkenyl, —(C$_7$-C$_{14}$)bicycloalkenyl, —(C$_8$-C$_{20}$)tricycloalkenyl, and -(3- to 7-membered)heterocycle, each of which is unsubstituted or substituted with 1, 2, 3, or 4 independently selected R$^8$ groups; and
(c)

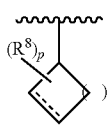
(i)

and

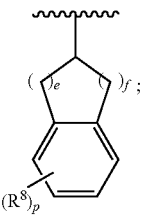
(ii)

and
(d) -phenyl, -naphthalenyl, —(C$_{14}$)aryl, and -(5- to 10-membered)heteroaryl, each of which is unsubstituted or substituted with 1, 2, 3, or 4 independently selected R$^7$ groups;

each R$^5$ is independently —(C$_1$-C$_4$)alkyl, —(C$_2$-C$_6$)alkenyl, —(C$_2$-C$_6$)alkynyl, -(5- or 6-membered)heteroaryl, —(C$_1$-C$_6$)alkyl-C(=O)OR$^9$, —OR$^9$, —SR$^9$, —C(halo)$_3$, —CH(halo)$_2$, —CH$_2$(halo), —CN, =O, =S, -halo, —N$_3$, —NO$_2$, —CH=N(R$^9$), —N(R$^9$)(C$_1$-C$_6$)alkyl-C(=O)OR$^9$, —N(R$^9$)$_2$, —N(R$^9$)OH, —N(R$^9$)S(=O)R$^{12}$, —N(R$^9$)S(=O)R$^{12}$, —N(R$^9$)C(=O)R$^{12}$, —N(R$^9$)C(=O)OR$^{12}$, —C(=O)R$^9$, —C(=O)OR$^9$, —OC(=O)R$^9$, —OC(=O)OR$^9$, —S(=O)R$^9$, or —S(=O)$_2$R$^9$;

each R$^6$ is independently —H, —(C$_1$-C$_6$)alkyl, or —(C$_3$-C$_7$)cycloalkyl, or two R$^6$ groups attached to the same nitrogen atom can together form a -(5- to 8-membered)heterocyclic ring, wherein the number of atoms in the ring includes the nitrogen atom, and in which one of the -(5- to 8-membered)heterocyclic ring carbon atoms is optionally replaced by O, S, or N(T$^3$);

each R$^7$ is independently —(C$_1$-C$_4$)alkyl, —(C$_2$-C$_6$)alkenyl, —(C$_2$-C$_6$)alkynyl, —OR$^9$, —SR$^9$, —C(halo)$_3$, —CH(halo)$_2$, —CH$_2$(halo), —CN, -halo, —N$_3$, —NO$_2$, —CH=N(R$^9$), —N(R$^9$)$_2$, —N(R$^9$)OH, —N(R$^9$)S(=O)R$^{12}$, —N(R$^9$)S(=O)$_2$R$^{12}$, —N(R$^9$)C(=O)R$^{12}$, —N(R$^9$)C(=O)N(T$^1$)(T$^2$), —N(R$^9$)C(=O)OR$^{12}$, —C(=O)R$^9$, —C(=O)N(T$^1$)(T$^2$), —C(=O)OR$^9$, —OC(=O)R$^9$, —OC(=O)N(T$^1$)(T$^2$), —OC(=O)OR$^9$, —S(=O)R$^9$, or —S(=O)$_2$R$^9$;

each R$^8$ is independently —(C$_1$-C$_4$)alkyl, —(C$_2$-C$_6$)alkenyl, —(C$_2$-C$_6$)alkynyl, -(5- or 6-membered)heteroaryl, —(C$_1$-C$_6$)alkyl-C(=O)OR$^9$, —N(R$^9$)(C$_1$-C$_6$)alkyl-C(=O)OR$^9$, —OR$^9$, —SR$^9$, —C(halo)$_3$, —CH(halo)$_2$, —CH$_2$(halo), —CN, =O, =S, =N(R$^9$), -halo, —N$_3$, —NO$_2$, —CH=N(R$^9$), —N(R$^9$)$_2$, —N(R$^9$)OR$^9$, —N(R$^9$)S(=O)R$^{12}$, —N(R$^9$)S(=O)$_2$R$^{12}$, —N(R$^9$)C(=O)R$^{12}$, —N(R$^9$)C(=O)N(T$^1$)(T$^2$), —N(R$^9$)C(=O)OR$^{12}$, —C(=O)R$^9$, —C(=O)N(T$^1$)(T$^2$), —C(=O)OR$^9$, —OC(=O)R$^9$, —OC(=O)N(T$^1$)(T$^2$), —OC(=O)OR$^9$, —S(=O)R$^9$, or —S(=O)$_2$R$^9$;

each R$^9$ is independently —H, —(C$_1$-C$_6$)alkyl, —(C$_2$-C$_6$)alkenyl, —(C$_2$-C$_6$)alkynyl, —(C$_3$-C$_8$)cycloalkyl, —(C$_5$-C$_8$)cycloalkenyl, -phenyl, -benzyl, -(3- to 7-membered)heterocycle, —C(halo)$_3$, —CH(halo)$_2$, or —CH$_2$(halo);

each R$^{12}$ is independently —H or —(C$_1$-C$_4$)alkyl;

R$^{13}$ is selected from:
(a) -halo, —CN, —OH, —CH$_2$OH, —CH$_2$CH$_2$OH, —NO$_2$, —N(R$^6$)$_2$, —S(=O)NH$_2$, —S(=O)$_2$NH$_2$, —C(=O)OV$^1$, and —C(=O)CN; and
(b) —(C$_1$-C$_{10}$)alkenyl, —(C$_2$-C$_{10}$)alkynyl, —O(C$_1$-C$_6$)alkyl, —(C$_3$-C$_7$)cycloalkoxy, —(C$_5$-C$_{10}$)cycloalkenyl, and -(3- to 7-membered)heterocycle, each of which is unsubstituted or substituted with 1, 2, 3, or 4 independently selected R$^8$ groups; and (c)

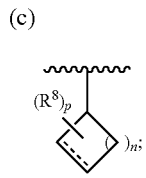

and (d) -phenyl and -(5- to 10-membered)heteroaryl, each of which is unsubstituted or substituted with 1, 2, or 3 independently selected $R^7$ groups;

each $T^1$ and $T^2$ is independently —H or —$(C_1$-$C_{10})$alkyl which is unsubstituted or substituted with 1, 2, or 3 independently selected $R^5$ groups and, optionally, in which any —$(C_1$-$C_{10})$alkyl carbon atom except the carbon atom bonded directly to the atom to which $T^1$ or $T^2$ is attached is independently replaced by O, S, or N($R^6$), or $T^1$ and $T^2$ can together form a -(5- to 8-membered)heterocyclic ring wherein the number of atoms in the ring includes the nitrogen atom to which $T^1$ and $T^2$ are bonded, said -(5- to 8-membered)heterocyclic ring is unsubstituted or substituted with 1, 2, or 3 independently selected $R^5$ groups and, optionally, any 1 or 2 carbon atoms in said -(5- to 8-membered)heterocyclic ring is independently replaced by O, S, or N($R^6$);

each $T^3$ is independently —H or —$(C_1$-$C_{10})$alkyl which is unsubstituted or substituted with 1, 2, or 3 independently selected $R^5$ groups and, optionally, in which any —$(C_1$-$C_{10})$alkyl carbon atom except the carbon atom bonded directly to the atom to which $T^3$ is attached is independently replaced by O, S, or N($R^{12}$);

each $T^4$ is independently a -(5- or 6-membered)heteroaryl which is unsubstituted or substituted with 1 or 2 independently selected $R^{12}$ groups;

each $V^1$ is independently —H, —$(C_1$-$C_6)$alkyl, —$(C_3$-$C_7)$ cycloalkyl, -phenyl, or -benzyl;

a is an integer selected from 0, 1, and 2;

each b is, independently, an integer selected from 1, 2, 3, 4, 5, and 6;

each d is, independently, an integer selected from 0, 1, 2, and 3;

m is an integer selected from 0, 1, 2, 3, 4, 5, 6, 7, 8, 9, 10, and 11;

n is an integer selected from 0, 1, 2, 3, 4, 5, 6, 7, 8, and 9;

e and f are each an integer independently selected from 0, 1, 2, 3, 4, and 5 provided that 2≤(e+f)≤5;

each p is an integer independently selected from 0, 1, 2, 3, and 4; and each halo is independently —F, —Cl, —Br, or —I.

Compounds of formula (IB) are herein disclosed:

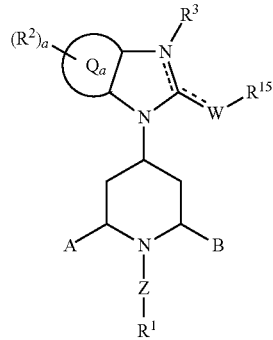

(IB)

or a pharmaceutically acceptable salt or solvate thereof where:

the $Q_a$ ring is fused benzo or fused (5- or 6-membered) heteroaryl;

each $R^2$ is independently selected from:

(a) -halo, —CN, —$NO_2$, —$OT^3$, —C(=O)$T^3$, —C(=O) $OT^3$, —C(=O)N($T^1$)($T^2$), —S(=O)$_2OT^3$, —S(=O) $T^3$, —S(=O)$_2T^3$, —O—S(=O)$_2T^3$, —S(=O)$_2$N($T^1$) ($T^2$), —N($T^1$)($T^2$), —N($T^3$)C(=O)$T^3$, —N($T^3$)C(=O) N($T^1$)($T^2$), —N($T^3$)S(=O)T, —N($T^3$)S(=O)$_2T^3$, —N($T^3$)C(=O)$OT^3$, and —N($T^3$)S(=O)$_2$N($T^1$)($T^2$); and (b) —$(C_1$-$C_6)$alkyl, —$(C_2$-$C_6)$alkenyl, —$(C_2$-$C_6)$alkynyl, —$(C_1$-$C_6)$alkoxy, —$(C_3$-$C_7)$cycloalkyl, —$(C_6$-$C_{10})$bicycloalkyl, —$(C_5$-$C_{10})$cycloalkenyl, —$(C_7$-$C_{10})$bicycloalkenyl, and -(5- or 6-membered)heterocycle, each of which is unsubstituted or substituted with 1, 2, or 3 independently selected $R^8$ groups; and (c) -phenyl, -naphthalenyl, and -(5- or 6-membered)heteroaryl, each of which is unsubstituted or substituted with 1, 2, or 3 independently selected $R^7$ groups;

each dashed line denotes the presence or absence of a bond (i.e., when a dashed line is present there is a double bond at that position and when a dashed line is absent there is only a single bond at that position), provided that:

(a) one dashed line must denote the presence of a bond (i.e., there is a double bond at that position);

(b) when one dashed line denotes the presence of a bond (i.e., there is a double bond at that position) then the other dashed line denotes the absence of a bond (i.e., there is only a single bond at that other position);

(c) when the dashed line within the 5-membered, nitrogen-containing ring that is fused to the $Q_a$ ring is present (i.e., there is a double bond at that position), then $R^3$ is absent; and (d) when the dashed line within the 5-membered, nitrogen-containing ring that is fused to the $Q_a$ ring is absent (i.e., there is only a single bond at that position), then $R^3$ is present;

$R^3$, when present, is:

(a) —H; or (b) —$(C_1$-$C_4)$alkyl which is unsubstituted or substituted with 1, 2, or 3 groups independently selected from —OH, —$(C_1$-$C_4)$alkoxy, —N($R^6)_2$, —C(=O)$OR^9$, and —C(=O)N($R^6)_2$; or (c) —$(C_3$-$C_7)$cycloalkyl which is unsubstituted or substituted with 1, 2, or 3 groups independently selected from —OH, —$(C_1$-$C_4)$alkyl, —$(C_1$-$C_4)$alkoxy, —N($R^6)_2$, —C(=O)$OR^9$, and —C(=O)N($R^6)_2$;

---W— is =CH—, —$CH_2$—, =N—, —NH—, —O—, =CH—$(C_1$-$C_3)$alkylene-, —$CH_2$—$(C_1$-$C_3)$alkylene-, =N—$(C_1$-$C_3)$alkylene-, —NH—$(C_1$-$C_3)$alkylene-, —O— $(C_1$-$C_3)$alkylene-, =CH—$(C_2$-$C_3)$alkenylene-, —$CH_2$— $(C_2$-$C_3)$alkylene-N($R^{11}$)—, —$CH_2$—$(C_1$-$C_3)$alkylene-N ($R^{11}$)—, =N—$(C_1$-$C_3)$alkylene-N($R^{11}$)—, —NH—$(C_1$-$C_3)$ alkylene-N($R^{11}$)—, —O—$(C_1$-$C_3)$alkylene-N($R^{11}$)—, =CH—N($R^{11}$)—, —CH=N—, —$CH_2$—N($R^{11}$)—, =CH—O—, —$CH_2$—O—, =CH—O—$(C_1$-$C_3)$alkylene-, or —$CH_2$—O—$(C_1$-$C_3)$alkylene-;

each Y is independently O or S;

A and B are independently selected from:

(a) —H; and (b) —$(C_1$-$C_6)$alkyl, —$(C_2$-$C_6)$alkenyl, and —$(C_1$-$C_6)$ alkoxy, each of which is unsubstituted or substituted with 1 or 2 substituents independently selected from —OH, —S(=O)₂NH₂, —C(=O)OT³, —C(=O)N(R⁶)₂, and —N(R⁶)C(=O)R⁹, or 1, 2, or 3 independently selected -halo; or (c) A-B can together form a (C₂-C₆)bridge, which is unsubstituted or substituted with 1, 2, 3, 4, 5, 6, 7, or 8 substituents independently selected from —OH, —(C₁-C₄)alkyl, -halo, and —C(halo)₃, and which bridge optionally contains —HC=CH— or —O— within the (C₂-C₆)bridge; wherein the 5-membered, nitrogen-containing ring that is fused to the $Q_a$ ring can be in the endo- or exo-configuration with respect to the A-B bridge;

Z is —[(C₁-C₁₀)alkyl optionally substituted by $R^{13}$]ₕ—, wherein h is 0 or 1; or —[(C₂-C₁₀)alkenyl optionally substituted by $R^{13}$]—, or —[(C₁-C₁₀)alkyl-NR⁶C(=Y)]—;

$R^1$ is selected from:
(a) —H, -halo, —CN, —OH, —CH₂OH, —CH₂CH₂OH, —NO₂, —N(R⁶)₂, —S(=O)NH₂, —S(=O)₂NH₂, —C(=O)OV¹, and —C(=O)CN; and
(b) —(C₁-C₁₀)alkyl, —(C₂-C₁₀)alkenyl, —(C₂-C₁₀)alkynyl, —O(C₁-C₆)alkyl, —(C₃-C₇)cycloalkoxy, —(C₆-C₁₄)bicycloalkyl, —(C₈-C₂₀)tricycloalkyl, —(C₅-C₁₀)cycloalkenyl, —(C₇-C₁₄)bicycloalkenyl, —(C₈-C₂₀)tricycloalkenyl, and -(3- to 7-membered)heterocycle, each of which is unsubstituted or substituted with 1, 2, 3, or 4 independently selected $R^8$ groups; and
(c)

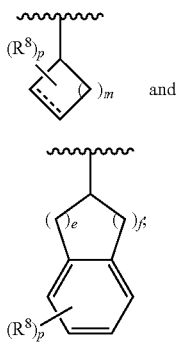

and (d) -phenyl, -naphthalenyl, —(C₁₄)aryl, and -(5- to 10-membered)heteroaryl, each of which is unsubstituted or substituted with 1, 2, 3, or 4 independently selected $R^7$ groups;

each $R^5$ is independently —(C₁-C₄)alkyl, —(C₂-C₆)alkenyl, —(C₂-C₆)alkynyl, -(5- or 6-membered)heteroaryl, —(C₁-C₆)alkyl-C(=O)OR⁹, —OR⁹, —SR⁹, —C(halo)₃, —CH(halo)₂, —CH₂(halo), —CN, =O, =S, -halo, —N₃, —NO₂, —CH=N(R⁹), —N(R⁹)(C₁-C₆)alkyl-C(=O)OR⁹, —N(R⁹)₂, —N(R⁹)OH, —N(R⁹)S(=O)R¹², —N(R⁹)S(=O)R¹², —N(R⁹)C(=O)R¹², —N(R⁹)C(=O)OR¹², —C(=O)R⁹, —C(=O)OR⁹, —OC(=O)R⁹, —OC(=O)OR⁹, —S(=O)R⁹, or —S(=O)₂R⁹;

each $R^6$ is independently —H, —(C₁-C₆)alkyl, or —(C₃-C₇)cycloalkyl, or two $R^6$ groups attached to the same nitrogen atom can together form a -(5- to 8-membered)heterocyclic ring, wherein the number of atoms in the ring includes the nitrogen atom, and in which one of the -(5- to 8-membered)heterocyclic ring carbon atoms is optionally replaced by O, S, or N(T³);

each $R^7$ is independently —(C₁-C₄)alkyl, —(C₂-C₆)alkenyl, —(C₂-C₆)alkynyl, —OR⁹, —SR⁹, —C(halo)₃, —CH(halo)₂, —CH₂(halo), —CN, -halo, —N₃, —NO₂, —CH=N(R⁹), —N(R⁹)₂, —N(R⁹)OH, —N(R⁹)S(=O)R¹², —N(R⁹)S(=O)R¹², —N(R⁹)C(=O)R¹², —N(R⁹)C(=O)N(T¹)(T²), —N(R⁹)C(=O)OR¹², —C(=O)R⁹, —C(=O)N(T¹)(T²), —C(=O)OR⁹, —OC(=O)R⁹, —OC(=O)N(T¹)(T²), —OC(=O)OR⁹, —S(=O)R⁹, or —S(=O)₂R⁹;

each $R^8$ is independently —(C₁-C₄)alkyl, —(C₂-C₆)alkenyl, —(C₂-C₆)alkynyl, -(5- or 6-membered)heteroaryl, —(C₁-C₆)alkyl-C(=O)OR⁹, —N(R⁹)(C₁-C₆)alkyl-C(=O)OR⁹, —OR⁹, —SR⁹, —C(halo)₃, —CH(halo)₂, —CH₂(halo), —CN, =O, =S, =N(R⁹), -halo, —N₃, —NO₂, —CH=N(R⁹), —N(R⁹)₂, —N(R⁹)OR⁹, —N(R⁹)S(=O)R¹², —N(R⁹)S(=O)₂R¹², —N(R⁹)C(=O)R¹², —N(R⁹)C(=O)N(T¹)(T²), —N(R⁹)C(=O)OR¹², —C(=O)R⁹, —C(=O)N(T¹)(T²), —C(=O)OR⁹, —OC(=O)R⁹, —OC(=O)N(T¹)(T²), —OC(=O)OR⁹, —S(=O)R⁹, or —S(=O)₂R⁹;

each $R^9$ is independently —H, —(C₁-C₆)alkyl, —(C₂-C₆)alkenyl, —(C₂-C₆)alkynyl, —(C₃-C₈)cycloalkyl, —(C₅-C₈)cycloalkenyl, -phenyl, -benzyl, -(3- to 7-membered)heterocycle, —C(halo)₃, —CH(halo)₂, or —CH₂(halo);

$R^{11}$ is —H, —CN, or —C(=O)N(R⁶)₂ or $R^{11}$ is —(C₁-C₄)alkyl which is unsubstituted or substituted with —OH, —(C₁-C₄)alkoxy, or —N(R⁶)₂;

each $R^{12}$ is independently —H or —(C₁-C₄)alkyl;

$R^{13}$ is selected from:
(a) -halo, —CN, —OH, —CH₂OH, —CH₂CH₂OH, —NO₂, —N(R⁶)₂, —S(=O)NH₂, —S(=O)₂NH₂, —C(=O)OV¹, and —C(=O)CN; and
(b) —(C₁-C₁₀)alkyl, —(C₂-C₁₀)alkenyl, —(C₂-C₁₀)alkynyl, —O(C₁-C₆)alkyl, —(C₃-C₇)cycloalkoxy, —(C₅-C₁₀)cycloalkenyl, and -(3- to 7-membered)heterocycle, each of which is unsubstituted or substituted with 1, 2, 3, or 4 independently selected $R^8$ groups; and
(c)

and (d) -phenyl and -(5- to 10-membered)heteroaryl, each of which is unsubstituted or substituted with 1, 2, or 3 independently selected $R^7$ groups;

$R^{15}$ is selected from:
(a) —H; and
(b) —(C₁-C₄)alkyl and —O—(C₁-C₄)alkyl, each of which is unsubstituted or substituted with 1, 2, 3, or 4 independently selected $R^8$ groups;
(c) provided that when ---W— is a single bond, a double bond, or —O—, $R^{15}$ is not —H; each $T^1$ and $T^2$ is independently —H or —(C₁-C₁₀)alkyl which is unsubstituted or substituted with 1, 2, or 3 independently selected $R^5$ groups and, optionally, in which any —(C₁-C₁₀)alkyl carbon atom except the carbon atom bonded directly to the atom to which $T^1$ or $T^2$ is attached is independently replaced by O, S, or N(R⁶), or $T^1$ and $T^2$ can together form a -(5- to 8-membered)heterocyclic ring wherein the number of atoms in the ring includes the nitrogen atom to which $T^1$ and $T^2$ are bonded, said -(5- to 8-membered)heterocyclic ring is unsubstituted or substituted with 1, 2, or 3 independently selected $R^5$ groups and, optionally, any 1 or 2 carbon atoms in said -(5- to 8-membered)heterocyclic ring is independently replaced by O, S, or N(R$^6$);

each T$^3$ is independently —H or —(C$_1$-C$_{10}$)alkyl which is unsubstituted or substituted with 1, 2, or 3 independently selected R$^5$ groups and, optionally, in which any —(C$_1$-C$_{10}$) alkyl carbon atom except the carbon atom bonded directly to the atom to which T$^3$ is attached is independently replaced by O, S, or N(R$^{12}$);

each V$^1$ is independently —H, —(C$_1$-C$_6$)alkyl, —(C$_3$-C$_7$)cycloalkyl, -phenyl, or -benzyl;

a is an integer selected from 0, 1, and 2;

each b is, independently, an integer selected from 1, 2, 3, 4, 5, and 6;

each d is, independently, an integer selected from 0, 1, 2, and 3;

m is an integer selected from 0, 1, 2, 3, 4, 5, 6, 7, 8, 9, 10, and 11;

n is an integer selected from 0, 1, 2, 3, 4, 5, 6, 7, 8, and 9;

e and f are each an integer independently selected from 0, 1, 2, 3, 4, and 5 provided that 2≤(e+f)≤5;

each p is an integer independently selected from 0, 1, 2, 3, and 4; and each halo is independently —F, —Cl, —Br, or —I.

A compound of formula (I) and the like or a pharmaceutically acceptable derivative thereof (an "Substituted Benzimidazole-Type Piperidine Compound") is useful, e.g., as an analgesic, anti-inflammatory, diuretic, anesthetic agent, neuroprotective agent, anti-hypertensive, an anxiolytic agent, an agent for appetite control, hearing regulator, anti-tussive, anti-asthmatic, modulator of locomotor activity, modulator of learning and memory, regulator of neurotransmitter release, regulator of hormone release, kidney function modulator, anti-depressant, agent to treat memory loss due to Alzheimer's disease and/or other dementias and/or disruption of spatial memory, anti-epileptic, anticonvulsant, agent to treat withdrawal from alcohol, agent to treat withdrawal from drug(s) of addiction, agent to control water balance, agent to control sodium excretion, and/or agent to control arterial blood pressure disorder(s).

A Substituted Benzimidazole-Type Piperidine Compound, a pharmaceutically acceptable salt or solvate thereof, a composition containing a Substituted Benzimidazole-Type Piperidine Compound, and/or a composition containing a pharmaceutically acceptable salt or solvate of a Substituted Benzimidazole-Type Piperidine Compound is useful for treating and/or preventing (each hereafter being a "Condition"):

pain (see, for example: Courteix et al., "Evidence for an exclusive antinociceptive effect of nociceptin/orphanin FQ, an endogenous ligand for the ORL1 receptor, in two animal models of neuropathic pain," *Pain* 110:236-245 (2004); Reinscheid et al., "Orphanin FQ: a neuropeptide that activates an opioid-like G protein-coupled receptor," *Science* 270:792-794 (1995); Bignan et al., "Recent advances towards the discovery of ORL-1 receptor agonists and antagonists," *Expert Opinion on Therapeutic Patents* 15(4):357-388 (2005); Meunier et al., "Isolation and structure of the endogenous agonist of opioid receptor-like ORL1 receptor." *Nature* 377:532-535 (1995); Briscini, et al., "Up-regulation of ORL-1 receptors in spinal tissue of allodynic rats after sciatic nerve injury," *Eur. J. Pharmacol.* 447:59-65 (2002); Li et al., "Role of nociceptin in the modulation of nociception in the arcuate nucleus of rats," *Brain Res.* 1025:67-74 (2004));

anxiety (see, for example: Jenck et al., "Orphanin FQ acts as an anxiolytic to attenuate behavioral responses to stress," *Proc. Natl. Acad. Sci., U.S.A.* 94:14854-14858 (1997); Koster et al., "Targeted disruption of the orphanin FQ/nociceptin gene increases stress susceptibility and impairs stress adaptation in mice." *Proc. Natl. Acad. Sci. U.S.A.* 96:10444-10449 (1999); Griebel et al., "Orphanin FQ, a novel neuropeptide with anti-stress-like activity," *Brain Res.* 836:221-224 (1999); Jenck et al., "A synthetic agonist at the orphanin FQ/nociceptin receptor ORL1: Anxiolytic profile in the rat." *Proc. Natl. Acad. Sci.* 97:4938-4943 (2000));

cough (see, for example: Fischer et al., "Nociceptin-induced inhibition of tachykinergic neurotransmission in guinea pig bronchus," *J. Pharmacol. Ther.* 285:902-907 (1998); Rizzi et al., "Nociceptin receptor activation inhibits tachykinergic non adrenergic non cholinergic contraction of guinea pig isolated bronchus," *Life Sci.* 64:L157-L163 (1999); Shah et al., "Nociceptin inhibits non-cholinergic contraction in guinea-pig airway," *Br. J. Pharmacol.* 125:510-516 (1998); Patel et al., "Naloxone-insensitive inhibition of acetylcholine release from parasympathetic nerves innervating guinea-pig trachea by the novel opioid, nociceptin," *Br. J. Pharmacol.* 120:735-736 (1997); Helyes et al., "Inhibition by nociceptin of neurogenic inflammation and the release of SP and CGRP from sensory nerve terminals," *Br. J. Pharmacol.* 121:613-615 (1997); Nemeth et al., "Inhibition of nociceptin on sensory neuropeptide release and mast cell-mediated plasma extravasation in rats," *Eur. J. Pharmacol.* 347:101-104 (1998); McLeod et al., "Nociceptin inhibits cough in the guinea-pig by activation of ORL1 receptors," *Br. J. Pharmacol.* 132:1175-1178 (2001); Corboz et al., "Nociceptin inhibits capsaicin-induced bronchoconstriction in isolated guinea pig lung," *Eur. J. Pharmacol.* 402:171-179 (2000));

gut motility disorders (such as diarrhea and constipation) (see, for example: Wang et al., "cDNA cloning of an orphan opiate receptor gene family member and its splice variant," *FEBS Lett.* 348:75-79 (1994); Calo' et al., "The mouse deferens: a pharmacological preparation sensitive to nociceptin," *Eur. J. Pharmacol.* 311:R3-R5 (1996); Zhang et al., "Orphanin FQ has an inhibitory effect on the guinea pig ileum and the mouse vas deferens," *Brain Res.* 772:102-106 (1997); Osinski et al., "Cloning, expression and functional role of a nociceptin/orphanin FQ receptor in the porcine gastrointestinal tract," *Eur. J. Pharmacol.* 365:281-289 (1999); Yasdani et al., "Functional significance of a newly discovered neuropeptide, orphanin FQ, in rat gastrointestinal motility," *Gastroenterology* 116:108-117 ((1999); Corbett et al., "The pharmacological actions of nociceptin in the isolated colon of rat, mouse, and man," *Naunyn-Schmiedeberg's Arch. Pharmacol.* 358 (Suppl 1):4047 (1998); Osinski et al., "Peripheral and central actions of orphanin FQ (nociceptin) on murine colon," *Am. J. Physiol.* 276:G125-G131 (1999); Rizzi et al., "[Nphe$^1$]nociceptin(1-13)NH$_2$ antagonizes nociceptin effects in the mouse colon," *Eur. J. Pharmacol* 285:R3-R5 (1999); Taniguchi et al., "The effect of nociceptin an endogenous ligand for the ORL1 receptor, on rat colonic contraction and transit," *Eur. J. Pharmacol.* 353:265-271 (1998); Pheng et al., "[Nphe$^1$]nociceptin(1-13)NH$_2$ selectively antagonizes nociceptin effects in the rabbit isolated ileum," *Eur. J. Pharmacol.* 397:383-388 (2000));

high blood pressure (see, for example: Champion et al., "Nociceptin, an endogenous ligand for the ORL1 receptor, has novel hypotensive activity in the rat," *Life Sci.* 60:PL 241-245 (1997); Giuliani et al., "Effect of nociceptin on heart rate and blood pressure in anaesthetized rats," *Eur. J. Pharmacol.* 333:177-179 (1997); Kapusta et al., "Diuretic and antinatriuretic responses produced by the endogenous opioid-like peptide, nociceptin (orphanin FQ)," *Life Sci.* 60:PL15-PL21 (1997); Kapusta et al., "Central administration of [Phe1psi(CH$_2$—NH)Gly2]nociceptin(1-13)-NH$_2$ and orphanin FQ/nociceptin (OFQ/N) produce similar cardiovascular and renal responses in conscious rats," *J. Pharmacol. Exp. Ther.* 289:173-180 (1999); Madeddu et al., "Cardiovascular effects of nociceptin in unanaesthetized mice," *Hypertension* 33:914-919 (1999); Bigoni et al., "Characterization of nociceptin receptors in the periphery: in vitro and in vivo studies," *Naunyn-Schmiedeberg's Arch. Pharmacol.* 359:160-167 (1999); Chu et al., "Inhibition of cardiovascular activity following microinjection of novel opioid-like neuropeptide nociceptin (orphanin FQ) into the rat rostral ventrolateral medulla," *Brain Res.* 829:134-142 (1999); Chu et al., "The nociceptin receptor-mediated inhibition of the rat rostral ventrolateral medulla neurons in vitro," *Eur. J. Pharmacol.* 364:49-53 (1999); Arndt et al., "Nociceptin/orphanin FQ increases blood pressure and heart rate via sympathetic activation in sheep," *Peptides* 20:465-470 (1999); Gumusel et al., "Nociceptin: an endogenous agonist for central opioid-like1 (ORL1) receptors possesses systemic vasorelaxant properties," *Life Sci.* 69:PL141-PL145 (1997); Champion et al., "Nociceptin, a novel endogenous ligand for the ORL1 receptor, dilates isolated resistance arteries from the rat," *Regul. Peptides* 78:69-74 (1998); Czapla et al., "Decreases in systemic arterial and hindquarters perfusion pressure in response to nociceptin are not inhibited by naloxone in the rat," *Peptides* 18:1197-1200 (1997); Armstead, "Nociceptin/orphanin FQ dilates pial arteries by K(ATP) and k(ca) channel activation," *Brain Res.* 835:315-323 (1999); Bucher, "ORL1 receptor-mediated inhibition by nociceptin of noradrenaline release from perivascular sympathetic nerve endings of the rat tail artery," *Naunyn-Schmiedeberg's Arch. Pharmacol.* 358:682-685 (1998); Champion et al., "Nociceptin, a novel endogenous ligand for the ORL1 receptor, has potent erectile activity in the cat," *Am. J. Physiol.* 73:E214-E219 (1997));

epilepsy (see, for example: Nicol et al., "Nociceptin induced inhibition of K+ evoked glutamate release from rat cerebrocortical slices," *Br. J. Pharmacol.* 119:1081-1083 (1996); Nicol et al., "Nociceptin inhibits glutamate release from rat cerebellar slices," *Br. J. Pharmacol.* 123:217P (1998); Allen et al., "Orphanin-FQ/nociceptin (OFQ/N) modulates the activity of suprachiasmatic nucleus neurons," *J. Neurosci.* 19:2152-2160 (1999); Faber et al., "Depression of glutamatergic transmission by nociceptin in the neonatal rat hemisected spinal cord preparation in vitro," *Br. J. Pharmacol.* 119:189-190 (1996); Vaughn et al., "Actions of the ORL1 receptor ligand nociceptin on membrane properties of rat periaqueductal gray neurons in vitro," *J. Neurosci.* 17:996-1003 (1997); Wang et al., "Nociceptin (orphanin FQ), and endogenous ligand for the ORL1 (opioid receptor-like1) receptor, modulates responses of trigeminal neurons evoked by excitatory amino acids and somatosensory stimuli," *J. Neurophysiol.* 76:3568-3572 (1996); Yu et al., "Orphanin FQ/nociceptin inhibits synaptic transmission and long-term potentiation in rat dentate gyrus through postsynaptic mechanisms," *J. Neurophysiol.* 80:1277-1284 (1998); Bregola et al., "Limbic seizures increase pronociceptin mRNA levels in the thalamic reticular nucleus," *Neuroreport* 19:541-546 (1999); Sieklucka-Dziuba et al., "Nociceptin, OP4 receptor ligand in different models of experimental epilepsy," *Peptides* 23:497-505 (2002); Gutierrez, et al., "Orphanin FQ/nociceptin inhibits kindling epileptogenesis and enhances hippocampal feed-forward inhibition," *Neuroscience* 105:325-333 (2001); Tallent et al., "Nociceptin reduces epileptiform events in CA3 hippocampus via presynaptic and postsynaptic mechanisms," *J. Neurosci.* 21:6940-6948 (2001));

eating-related disorders (such as anorexia/cachexia and obesity) (see, for example: Pomonis et al., "Orphanin FQ, agonist of orphan opioid receptor ORL1, stimulates feeding in rats," *Neuroreport* 8:369-371 (1996); Stratford et al., "Injections of nociceptin into nucleus accumbens shell of ventromedial hypothalamic nucleus increase food intake," *Neuroreport* 8:423-426 (1997); Lee et al., "Nociceptin hyperpolarises neurones in the rt ventromedial hypothalamus," *Neurosci. Lett.* 239:37-40 (1997); Polidori et al., "Sensitivity of brain sites to the orexigenic effect of nociceptin or of its analog [Phe]psi(CH$_2$—NH)Gly2]NC(1-13)NH$_2$," *Regul. Peptides* 80:126 (1999); Polidori et al., "Pharmacological characterization of the nociceptin receptor mediating hyperphagia: identification of a selective antagonist," *Psychopharmacol.* 148:430-437 (2000); Rowland et al., "The physiology and brain mechanisms of feeding," *Nutrition* 12:626-639 (1996));

urinary incontinence (see, for example: Giuliani et al., "The inhibitory effect of nociceptin on the micturition reflex in anaesthetized," *Br. J. Pharmacol.* 24:1566-1572 (1998); Giuliani et al., "Nociceptin protects capsaicin-sensitive afferent fibers in the rat urinary bladder from desensitization," *Nanyn-Schmiedeberg's Arch. Pharmacol.* 360:202-208 (1999); Lecci et al., "Multiple sites of action in the inhibitory effect of nociceptin on the micturition reflex," *J. Urology* 163:638-645 (2000));

renal function (see, for example: Kapusta et al., "Diuretic and antinatriuretic responses produced by the endogenous opioid-like peptide, nociceptin (orphanin FQ)," *Life Sci.* 60:PL15-PL21 (1997); Kapusta et al., "Central administration of [Phe1psi(CH$_2$—NH)Gly2]nociceptin (1-13)-NH2 and orphanin FQ/nociceptin (OFQ/N) produce similar cardiovascular and renal responses in conscious rats," *J. Pharmacol. Exp. Ther.* 289:173-180 (1999));

drug abuse (see, for example: Devine et al., "The novel neuropeptide orphanin FQ fails to produce conditioned place preference or aversion," *Brain Res.* 727:225-229 (1996); Ciccocioppo et al., "Effect of nociceptin on alcohol intake in alcohol-preferring rats," *Psychopharmacol.* 141:220-224 (1999); Angeletti et al., "Effect of nociceptin on morphine-induced conditioned place preference in rats," *Regulatory Peptides* 80:122 (1999); Murphy et al., "Orphanin FQ/nociceptin blocks acquisition of morphine place preference," *Brain Res.* 832: 168-170 (1999); Pieretti et al., "Orphanin FQ effects on morphine-induced dopamine release in the accumbens of rats," *Regulatory Peptides* 80:126 (1999); Walker et al., "Nociceptin fails to affect heroin self-administration in the rat," *Neuroreport* 9:2243-2247 (1998); Narayanan et al., "Orphanin FQ and behavioral sensitization to cocaine," *Pharmacol. Biochem. Behav.* 63:271-277 (1999));

memory disorders (see, for example: Sandin et al., "Nociceptin/orphanin FQ microinjected into hippocampus impairs spatial learning in rats," *Eur. J. Neurosci.* 9:194-197 (1997); Yu et al., "Orphanin FQ inhibits synaptic transmission and long-term potentiation in rat hippocampus," *Hippocampus* 7:88-94 (1997); Yu et al., "Orphanin FQ/nociceptin inhibits synaptic transmission and long-term potentiation in rat dentate gyrus through postsynaptic mechanisms," *J. Neurophysiol.* 80:1277-1284 (1998); Manabe et al., "Facilitation of long-term potentiation and memory in mice lacking nociceptin receptors," *Nature* 394:577-581 (1998); Hiramatsu et al., "Effects of nocistatin on nociceptin-induced impairment of learning and memory in mice," *Eur. J. Pharmacol.* 367:151-155 (1999); Mamiya et al., "Nociceptin system plays a role in the memory retention: involvement of naloxone benzoylhydrazone binding sites," *Neuroreport* 10:1171-1175 (1999); Hiramatsu et al., "Improvement by low doses of nociceptin on scopolamine-induced impairment of learning and/or memory," *Eur. J. Pharmacol.* 395:149-156 (2000));

depression (see, for example: Rizzi et al., "Nociceptin/orphanin FQ receptor knockout rats: in vitro and in vivo studies," *Neuropharmacology* 60:572-579 (2011); Goeldner et al., "Endogenous nociceptin/orphanin-FQ in the dorsal hippocampus facilitates despair-related behavior," *Hippocampus* 20:911-916 (2010); Vitale et al., "Chronic treatment with the selective NOP receptor antagonist [Nphe 1, Arg 14, Lys 15]N/OFQ-NH2 (UFP-101) reverses the behavioural and biochemical effects of unpredictable chronic mild stress in rats," *Psychopharmacol.* 207:173-189 (2009); Zambello et al., "Acute stress differentially affects corticotropin-releasing hormone mRNA expression in the central amygdala of the 'epressed' Hinders sensitive line and the control Hinders resistant line rats," *Prog. Neuro-Psychopharmacol. Biolog. Psychiatry* 32:651-661 (2008); Gavioli et al., "Antidepressant—an anxiolytic-like effects of nociceptin/orphanin FQ receptor ligands," *Naunyn-Schmiedeberg's Arch. Pharmacol.* 372:319-330 (2006); Gavioli et al., "Blockade of nociceptin/orphanin FQ-NOP receptor signaling produces antidepressant-like effects: pharmacological and genetic evidences from the mouse forced swimming test," *Eur. J. Neurosci.* 17:1987-1990 (2003)); and/or dementia or locomotor disorders (such as Parkinsonism) (see, for example: Reinscheid et al., "Orphanin FQ: a neuropeptide that activates an opioidlike G protein-coupled receptor," *Science* 270:792-794 (1995); Calo' et al., "Characterization of nociceptin receptors modulating locomotor activity in mice," *Fund. Clin. Pharmacol.* 13:1-27 (1999); Devine et al., "Rats rapidly develop tolerance to the locomotor-inhibiting effects of the novel neuropeptide orphanin FQ," *Neurochem. Res.* 21:1387-1396 (1996); Noble et al., "Association of aminopeptidase N and endopeptidase 14.15 inhibitors potentiate behavioral effects mediated by nociceptin/orphanin FQ in mice," *FEBS Lett.* 401:227-229 (1997); Florin et al., "Nociceptin stimulates locomotion and exploratory behavior in mice," *Eur. J. Pharmacol.* 317:9-13 (1996)).

For a general discussion of ORL1 receptors see Calo' et al., "Pharmacology of nociceptin and its receptor: a novel therapeutic target," *Br. J. Pharmacol.* 129:1261-1283 (2000).

Compositions comprising an effective amount of a Substituted Benzimidazole-Type Piperidine Compound or a pharmaceutically acceptable salt or solvate thereof and a pharmaceutically acceptable carrier or excipient are disclosed. The compositions are useful for treating or preventing a Condition in an animal.

Methods for treating or preventing a Condition, comprising administering to an animal in need thereof an effective amount of a Substituted Benzimidazole-Type Piperidine Compound, a pharmaceutically acceptable salt or solvate thereof, a composition containing a Substituted Benzimidazole-Type Piperidine Compound, and/or a composition containing a pharmaceutically acceptable salt or solvate of a Substituted Benzimidazole-Type Piperidine Compound are disclosed.

Substituted Benzimidazole-Type Piperidine Compounds, e.g., of formula (I), may also be used in the manufacture of a medicament useful for treating a Condition or for preventing a Condition.

Methods for inhibiting ORL-1 receptor function in a cell, comprising contacting a cell capable of expressing the ORL-1 receptor with an ORL-1 receptor function-inhibiting amount of a Substituted Benzimidazole-Type Piperidine Compound or a pharmaceutically acceptable salt or solvate thereof are disclosed. In further embodiments of the disclosure, methods for activating ORL-1 receptor function in a cell, comprising contacting a cell capable of expressing the ORL-1 receptor with an ORL-1 receptor function-activating amount of a Substituted Benzimidazole-Type Piperidine Compound or a pharmaceutically acceptable salt or solvate thereof are disclosed. In yet another embodiment, methods for preparing a composition, comprising the step of admixing a Substituted Benzimidazole-Type Piperidine Compound or a pharmaceutically acceptable salt or solvate thereof and a pharmaceutically acceptable carrier or excipient, are disclosed.

An embodiment of the disclosure relates to a kit comprising a container containing an effective amount of a Substituted Benzimidazole-Type Piperidine Compound or a pharmaceutically acceptable salt or solvate thereof.

Another embodiment of the disclosure provides novel intermediates for use in making the Substituted Benzimidazole-Type Piperidine Compounds.

The disclosure can be understood more fully by reference to the following detailed description and illustrative examples, which are intended to exemplify non-limiting embodiments of the disclosure.

4. DETAILED DESCRIPTION

The invention includes the following:
(1) A compound of formula (I):

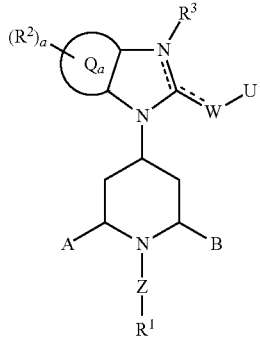

(IB)

or a pharmaceutically acceptable derivative thereof wherein:
the $Q_a$ ring is fused benzo or fused (5- or 6-membered) heteroaryl;
each $R^2$ is independently selected from:
(a) -halo, —CN, —NO$_2$, —OT$^3$, —C(=O)T$^3$, —C(=O) OT$^3$, —C(=O)N(T$^1$)(T$^2$), —S(=O)$_2$OT$^3$, —S(=O) T$^3$, —S(=O)$_2$T$^3$, —O—S(=O)$_2$T$^3$, —S(=O)$_2$N(T$^1$)(T$^2$), —N(T$^1$)(T$^2$), —N(T$^3$)C(=O)T$^3$, —N(T$^3$)C(=O)N(T$^1$)(T$^2$), —N(T$^3$)S(=O)T$^3$, —N(T$^3$)S(=O)$_2$T$^3$, —N(T$^3$)C(=O)OT$^3$, and —N(T$^3$)S(=O)$_2$N(T$^1$)(T$^2$); and
(b) —(C$_1$-C$_6$)alkyl, —(C$_2$-C$_6$)alkenyl, —(C$_2$-C$_6$)alkynyl, —(C$_1$-C$_6$)alkoxy, —(C$_3$-C$_7$)cycloalkyl, —(C$_6$-C$_{10}$)bicycloalkyl, —(C$_5$-C$_{10}$)cycloalkenyl, —(C$_7$-C$_{10}$)bicycloalkenyl, and -(5- or 6-membered)heterocycle, each of which is unsubstituted or substituted with 1, 2, or 3 independently selected $R^8$ groups; and
(c) -phenyl, -naphthalenyl, and -(5- or 6-membered)heteroaryl, each of which is unsubstituted or substituted with 1, 2, or 3 independently selected $R^7$ groups;
each dashed line denotes the presence or absence of a bond, provided that:
(a) one dashed line must denote the presence of a bond;
(b) when one dashed line denotes the presence of a bond then the other dashed line denotes the absence of a bond;
(c) when the dashed line within the 5-membered, nitrogen-containing ring that is fused to the $Q_a$ ring is present, then $R^3$ is absent; and
(d) when the dashed line within the 5-membered, nitrogen-containing ring that is fused to the $Q_a$ ring is absent, then $R^3$ is present;
$R^3$, when present, is:
(a) —H; or
(b) —(C$_1$-C$_4$)alkyl which is unsubstituted or substituted with 1, 2, or 3 groups independently selected from —OH, —(C$_1$-C$_4$)alkoxy, —N(R$^6$)$_2$, —C(=O)OR$^9$, and —C(=O)N(R$^6$)$_2$; or
(c) —(C$_3$-C$_7$)cycloalkyl which is unsubstituted or substituted with 1, 2, or 3 groups independently selected from —OH, —(C$_1$-C$_4$)alkyl, —(C$_1$-C$_4$)alkoxy, —N(R$^6$)$_2$, —C(=O)OR$^9$, and —C(=O)N(R$^6$)$_2$;
---W— is a single bond, a double bond, =CH—, —CH$_2$—, =N—, —NH—, —O—, =CH—(C$_1$-C$_3$)alkylene-, —CH$_2$—(C$_1$-C$_3$)alkylene-, =N—(C$_1$-C$_3$)alkylene-, —NH—(C$_1$-C$_3$)alkylene-, —O—(C$_1$-C$_3$)alkylene-, =CH—(C$_2$-C$_3$)alkenylene-, —CH$_2$—(C$_2$-C$_3$)alkenylene-, =N—(C$_2$-C$_3$)alkenylene-, —NH—(C$_2$-C$_3$)alkenylene-, —O—(C$_2$-C$_3$)alkenylene-, =CH—(C$_1$-C$_3$)alkylene-N(R$^{11}$)—, —CH$_2$—(C$_1$-C$_3$)alkylene-N(R$^{11}$)—, =N—(C$_1$-C$_3$)alkylene-N(R$^{11}$)—, —NH—(C$_1$-C$_3$)alkylene-N(R$^{11}$)—, —O—(C$_1$-C$_3$)alkylene-N(R$^{11}$)—, =CH—N(R$^{11}$)—, —CH=N—, —CH$_2$—N(R$^{11}$)—, =CH—O—, —CH$_2$—O—, =CH—O—(C$_1$-C$_3$)alkylene-, or —CH$_2$—O—(C$_1$-C$_3$)alkylene-;
U is:
(a) —R$^{15}$; or
(b)

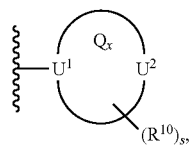

wherein when ---W— is a single bond or a double bond the $Q_x$ ring is a -(4-, 5-, 6-, or 7-membered)heterocycle containing one or two ring heteroatoms selected from N, N(R$^4$), O, and S provided that at least one ring heteroatom is N or N(R$^4$) and wherein either U$^1$ is N and U$^2$ is a bond or U$^1$ is C or CH and U$^2$ is N or N(R$^4$), provided that;
(1) when ---W— is a double bond and the $Q_x$ ring is present, U$^1$ is C; and
(2) when ---W— is =CH—, —CH$_2$—, =CH—(C$_1$-C$_3$)alkylene-, or —CH$_2$—(C$_1$-C$_3$)alkylene- and the $Q_x$ ring is present, the $Q_x$ ring is a (6-membered)heterocycle selected from:

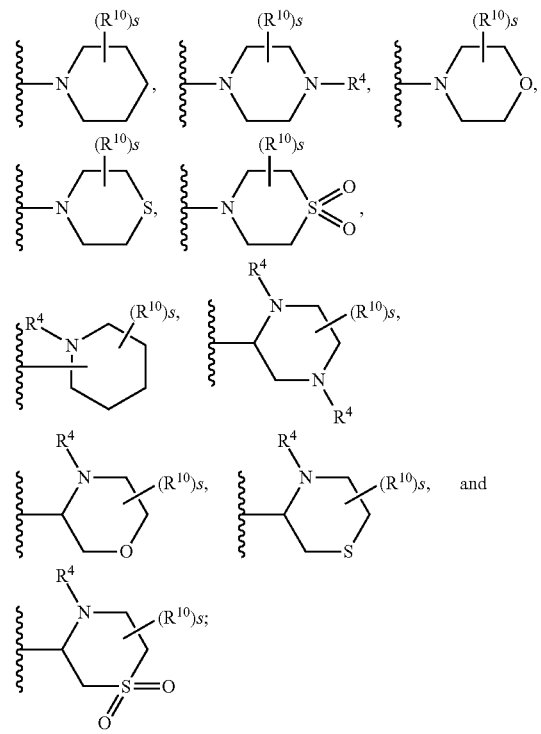

and
(3) when ---W— is =N—, —NH—, —O—, =N—(C$_1$-C$_3$)alkylene-, —NH—(C$_1$-C$_3$)alkylene-, —O—(C$_1$-C$_3$)alkylene-, =CH—(C$_2$-C$_3$)alkenylene-, —CH$_2$—(C$_2$-C$_3$)alkenylene-, =N—(C$_2$-C$_3$)alkenylene-, —NH—(C$_2$-C$_3$)alkenylene-, —O—(C$_2$-C$_3$)alkenylene-, =CH—(C$_1$-C$_3$)alkylene-N(R$^{11}$)—, —CH$_2$—(C$_1$-C$_3$)alkylene-N(R$^{11}$)—, =N—(C$_1$-C$_3$)alkylene-N(R$^{11}$)—, —NH—(C$_1$-C$_3$)alkylene-N(R$^{11}$)—, —O—(C$_1$-C$_3$)alkylene-N(R$^{11}$)—, =CH—N(R$^{11}$)—, —CH=N—, —CH$_2$—N(R$^{11}$)—, =CH—O—, —CH$_2$—O—, =CH—O—(C$_1$-C$_3$)alkylene-, or —CH$_2$—O—(C$_1$-C$_3$)alkylene-, then the $Q_x$ ring is absent;
each R$^4$, when present, is independently selected from:
(a) —H; and
(b) —X, —(C$_1$-C$_6$)alkyl-X, -(5- or 6-membered)heterocycle-X, or -(5- or 6-membered)heterocycle-(C$_1$-C$_6$)alkyl-X; and
(c) —(CH$_2$)$_d$—C(=Y)CN, —(CH$_2$)$_d$—C(=Y)X, —(CH$_2$)$_d$—C(=Y)T$^3$, —(CH$_2$)$_d$—C(=Y)YX, —(CH$_2$)$_d$—C(=Y)YT$^3$, —(CH$_2$)$_d$—C(=Y)N(T$^1$)(T$^2$), —(CH$_2$)$_d$—C(=Y)N(R$^9$)CN, —(CH$_2$)$_d$—C(=Y)N(R$^9$)X, —(CH$_2$)$_d$—C(=Y)N(R$^9$)YH, —(CH$_2$)$_d$—C(=Y)N(R$^9$)YX, —(CH$_2$)$_d$—C(=Y)N(R$^9$)YCH$_2$X, —(CH$_2$)$_d$—C(=Y)N(R$^9$)YCH$_2$CH$_2$X, or —(CH$_2$)$_d$—C(=Y)N(R$^9$)S(=O)$_2$T$^3$; and (d) —[CH$_2$—O]$_b$—R$^{16}$, —[CH(CH$_3$)—O]$_b$—R$^{16}$, —[CH$_2$—CH$_2$—O]$_b$—R$^{16}$, —[CH(CH$_3$)—CH$_2$—O]$_b$—R$^{16}$, —[CH$_2$—CH(CH$_3$)—O]$_b$—R$^{16}$, —[CH$_2$—CH$_2$—CH$_2$—O]$_b$—R$^{16}$, —[CH(CH$_3$)—CH$_2$—CH$_2$—O]$_b$—R$^{16}$, —[CH$_2$—CH(CH$_3$)—CH$_2$—O]$_b$—R$^{16}$, or —[CH$_2$—CH$_2$—CH(CH$_3$)—O]$_b$—R$^{16}$;

X is selected from:

(a) —H, —(C$_1$-C$_6$)alkyl, —(C$_2$-C$_6$)alkenyl, —(C$_2$-C$_6$)alkynyl, —(C$_1$-C$_6$)alkoxy, —(C$_3$-C$_7$)cycloalkyl, —(C$_5$-C$_{10}$)cycloalkenyl, and -(5- or 6-membered)heterocycle, each of which is unsubstituted or substituted with 1, 2, or 3 independently selected R$^8$ groups; and (b) -phenyl and -(5- or 6-membered)heteroaryl, each of which is unsubstituted or substituted with 1, 2, or 3 independently selected R$^7$ groups;

each Y is independently O or S;

each R$^{16}$ is independently H or CH$_3$;

s is an integer selected from 0, 1, and 2;

when s is 1, R$^{10}$ is —F, —CH$_3$, —CH$_2$CH$_3$, —(CH$_2$)$_d$—C(=Y)YT$^3$, or —(CH$_2$)$_d$—C(=Y)N(T$^1$)(T$^2$), and when s is 2, the R$^{10}$ groups together are gem-dimethyl, gem-difluoro, =O, or =S;

A and B are independently selected from:

(a) —H; and (b) —(C$_1$-C$_6$)alkyl, —(C$_2$-C$_6$)alkenyl, and —(C$_1$-C$_6$)alkoxy, each of which is unsubstituted or substituted with 1 or 2 substituents independently selected from —OH, —S(=O)$_2$NH$_2$, —C(=O)OT$^3$, —C(=O)N(R$^6$)$_2$, and —N(R$^6$)C(=O)R$^9$, or 1, 2, or 3 independently selected -halo; or (c) A-B can together form a (C$_2$-C$_6$)bridge, which is unsubstituted or substituted with 1, 2, 3, 4, 5, 6, 7, or 8 substituents independently selected from —OH, —(C$_1$-C$_4$)alkyl, -halo, and —C(halo)$_3$, and which bridge optionally contains —HC=CH— or —O— within the (C$_2$-C$_6$)bridge; wherein the 5-membered, nitrogen-containing ring that is fused to the Q$_a$ ring can be in the endo- or exo-configuration with respect to the A-B bridge;

Z is —[(C$_1$-C$_{10}$)alkyl optionally substituted by R$^{13}$]$_h$—, wherein h is 0 or 1; or —[(C$_2$-C$_{10}$)alkenyl optionally substituted by R$^{13}$]—, or —[(C$_1$-C$_{10}$)alkyl-NR$^6$C(=Y)]—;

R$^1$ is selected from:

(a) —H, -halo, —CN, —OH, —CH$_2$OH, —CH$_2$CH$_2$OH, —NO$_2$, —N(R$^6$)$_2$, —S(=O)NH$_2$, —S(=O)$_2$NH$_2$, —C(=O)OV$^1$, and —C(=O)CN; and (b) —(C$_1$-C$_{10}$)alkyl, —(C$_2$-C$_{10}$)alkenyl, —(C$_2$-C$_{10}$)alkynyl, —O(C$_1$-C$_6$)alkyl, —(C$_3$-C$_7$)cycloalkoxy, —(C$_6$-C$_{14}$)bicycloalkyl, —(C$_8$-C$_{20}$)tricycloalkyl, —(C$_5$-C$_{10}$)cycloalkenyl, —(C$_7$-C$_{14}$)bicycloalkenyl, —(C$_8$-C$_{20}$)tricycloalkenyl, and -(3- to 7-membered)heterocycle, each of which is unsubstituted or substituted with 1, 2, 3, or 4 independently selected R$^8$ groups; and (c)

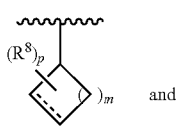

(i)

and

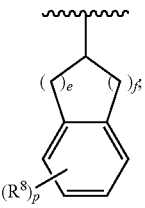

(ii)

and (d) -phenyl, -naphthalenyl, —(C$_{14}$)aryl, and -(5- to 10-membered)heteroaryl, each of which is unsubstituted or substituted with 1, 2, 3, or 4 independently selected R$^7$ groups;

each R$^5$ is independently —(C$_1$-C$_4$)alkyl, —(C$_2$-C$_6$)alkenyl, —(C$_2$-C$_6$)alkynyl, -(5- or 6-membered)heteroaryl, —(C$_1$-C$_6$)alkyl-C(=O)OR$^9$, —OR$^9$, —SR$^9$, —C(halo)$_3$, —CH(halo)$_2$, —CH$_2$(halo), —CN, =O, =S, -halo, —N$_3$, —NO$_2$, —CH=N(R$^9$), —N(R$^9$)(C$_1$-C$_6$)alkyl-C(=O)OR$^9$, —N(R$^9$)$_2$, —N(R$^9$)OH, —N(R$^9$)S(=O)R$^{12}$, —N(R$^9$)S(=O)$_2$R$^{12}$, —N(R$^9$)C(=O)R$^{12}$, —N(R$^9$)C(=O)OR$^{12}$, —C(=O)R$^9$, —C(=O)OR$^9$, —OC(=O)R$^9$, —OC(=O)OR$^9$, —S(=O)R$^9$, or —S(=O)$_2$R$^9$;

each R$^6$ is independently —H, —(C$_1$-C$_6$)alkyl, or —(C$_3$-C$_7$)cycloalkyl, or two R$^6$ groups attached to the same nitrogen atom can together form a -(5- to 8-membered)heterocyclic ring, wherein the number of atoms in the ring includes the nitrogen atom, and in which one of the -(5- to 8-membered)heterocyclic ring carbon atoms is optionally replaced by O, S, or N(T$^3$);

each R$^7$ is independently —(C$_1$-C$_4$)alkyl, —(C$_2$-C$_6$)alkenyl, —(C$_2$-C$_6$)alkynyl, —OR$^9$, —SR$^9$, —C(halo)$_3$, —CH(halo)$_2$, —CH$_2$(halo), —CN, -halo, —N$_3$, —NO$_2$, —CH=N(R$^9$), —N(R$^9$)$_2$, —N(R$^9$)OH, —N(R$^9$)S(=O)R$^{12}$, —N(R$^9$)S(=O)$_2$R$^{12}$, —N(R$^9$)C(=O)R$^{12}$, —N(R$^9$)C(=O)N(T$^1$)(T$^2$), —N(R$^9$)C(=O)OR$^{12}$, —C(=O)R$^9$, —C(=O)N(T$^1$)(T$^2$), —C(=O)OR$^9$, —OC(=O)R$^9$, —OC(=O)N(T$^1$)(T$^2$), —OC(=O)OR$^9$, —S(=O)R$^9$, or —S(=O)$_2$R$^9$;

each R$^8$ is independently —(C$_1$-C$_4$)alkyl, —(C$_2$-C$_6$)alkenyl, —(C$_2$-C$_6$)alkynyl, -(5- or 6-membered)heteroaryl, —(C$_1$-C$_6$)alkyl-C(=O)OR$^9$, —N(R$^9$)(C$_1$-C$_6$)alkyl-C(=O)OR$^9$, —OR$^9$, —SR$^9$, —C(halo)$_3$, —CH(halo)$_2$, —CH$_2$(halo), —CN, =O, =S, =N(R$^9$), -halo, —N$_3$, —NO$_2$, —CH=N(R$^9$), —N(R$^9$)$_2$, —N(R$^9$)OR$^9$, —N(R$^9$)S(=O)R$^{12}$, —N(R$^9$)S(=O)$_2$R$^{12}$, —N(R$^9$)C(=O)R$^{12}$, —N(R$^9$)C(=O)N(T$^1$)(T$^2$), —N(R$^9$)C(=O)OR$^{12}$, —C(=O)R$^9$, —C(=O)N(T$^1$)(T$^2$), —C(=O)OR$^9$, —OC(=O)R$^9$, —OC(=O)N(T$^1$)(T$^2$), —OC(=O)OR$^9$, —S(=O)R$^9$, or —S(=O)$_2$R$^9$;

each R$^9$ is independently —H, —(C$_1$-C$_6$)alkyl, —(C$_2$-C$_6$)alkenyl, —(C$_2$-C$_6$)alkynyl, —(C$_3$-C$_8$)cycloalkyl, —(C$_5$-C$_8$)cycloalkenyl, -phenyl, -benzyl, -(3- to 7-membered)heterocycle, —C(halo)$_3$, —CH(halo)$_2$, or —CH$_2$(halo);

R$^{11}$ is —H, —CN, or —C(=O)N(R$^6$)$_2$ or R$^{11}$ is —(C$_1$-C$_4$)alkyl which is unsubstituted or substituted with —OH, —(C$_1$-C$_4$)alkoxy, or —N(R$^6$)$_2$;

each R$^{12}$ is independently —H or —(C$_1$-C$_4$)alkyl;

R$^{13}$ is selected from:

(a) -halo, —CN, —OH, —CH$_2$OH, —CH$_2$CH$_2$OH, —NO$_2$, —N(R$^6$)$_2$, —S(=O)NH$_2$, —S(=O)$_2$NH$_2$, —C(=O)OV$^1$, and —C(=O)CN; and (b) —(C$_1$-C$_{10}$)alkyl, —(C$_2$-C$_{10}$)alkenyl, —(C$_2$-C$_{10}$)alkynyl, —O(C$_1$-C$_6$)alkyl, —(C$_3$-C$_7$)cycloalkoxy, —(C$_5$-C$_{10}$)cycloalkenyl, and -(3- to 7-membered)heterocycle, each of which is unsubstituted or substituted with 1, 2, 3, or 4 independently selected R⁸ groups; and (c)

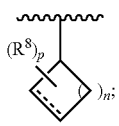

(iv)

and (d) -phenyl and -(5- to 10-membered)heteroaryl, each of which is unsubstituted or substituted with 1, 2, or 3 independently selected R⁷ groups;

R¹⁵, when present, is selected from:

(a) —H; and (b) —(C₁-C₄)alkyl and —O—(C₁-C₄)alkyl, each of which is unsubstituted or substituted with 1, 2, 3, or 4 independently selected R⁸ groups;

(c) provided that when --- W— is a single bond, a double bond, or —O—, R¹⁵ is not —H;

each T¹ and T² is independently —H or —(C₁-C₁₀)alkyl which is unsubstituted or substituted with 1, 2, or 3 independently selected R⁵ groups and, optionally, in which any —(C₁-C₁₀)alkyl carbon atom except the carbon atom bonded directly to the atom to which T¹ or T² is attached is independently replaced by O, S, or N(R⁶), or T¹ and T² can together form a -(5- to 8-membered)heterocyclic ring wherein the number of atoms in the ring includes the nitrogen atom to which T¹ and T² are bonded, said -(5- to 8-membered)heterocyclic ring is unsubstituted or substituted with 1, 2, or 3 independently selected R⁵ groups and, optionally, any 1 or 2 carbon atoms in said -(5- to 8-membered)heterocyclic ring is independently replaced by O, S, or N(R⁶);

each T³ is independently —H or —(C₁-C₁₀)alkyl which is unsubstituted or substituted with 1, 2, or 3 independently selected R⁵ groups and, optionally, in which any —(C₁-C₁₀) alkyl carbon atom except the carbon atom bonded directly to the atom to which T³ is attached is independently replaced by O, S, or N(R¹²);

each V¹ is independently —H, —(C₁-C₆)alkyl, —(C₃-C₇)cycloalkyl, -phenyl, or -benzyl;

a is an integer selected from 0, 1, and 2;

each b is, independently, an integer selected from 1, 2, 3, 4, 5, and 6;

each d is, independently, an integer selected from 0, 1, 2, and 3;

m is an integer selected from 0, 1, 2, 3, 4, 5, 6, 7, 8, 9, 10, and 11;

n is an integer selected from 0, 1, 2, 3, 4, 5, 6, 7, 8, and 9;

e and f are each an integer independently selected from 0, 1, 2, 3, 4, and 5 provided that 2≤(e+f)≤5;

each p is an integer independently selected from 0, 1, 2, 3, and 4; and each halo is independently —F, —Cl, —Br, or —I.

(2) The compound of the above (1) which is a compound of formula (IA):

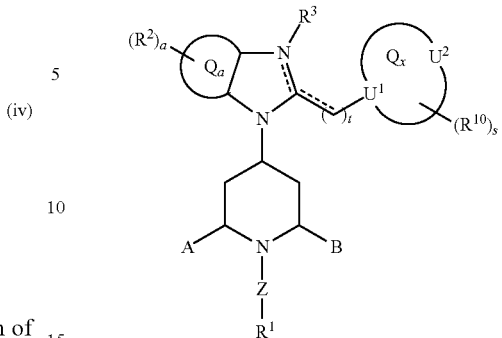

(IA)

or a pharmaceutically acceptable derivative thereof wherein:

t is an integer selected from 0, 1, 2, and 3;

when t is 0, the Q_x ring is a -(4-, 5-, 6-, or 7-membered) heterocycle containing one or two ring heteroatoms selected from N, N(R⁴), O, and S provided that at least one ring heteroatom is N or N(R⁴) and provided that when the dashed line connecting the Q_x ring to the 5-membered, nitrogen-containing ring that is fused to the Q_a ring is present, U¹ is C or CH, and when t is 1, 2, or 3 the Q_x ring is a (6-membered) heterocycle selected from:

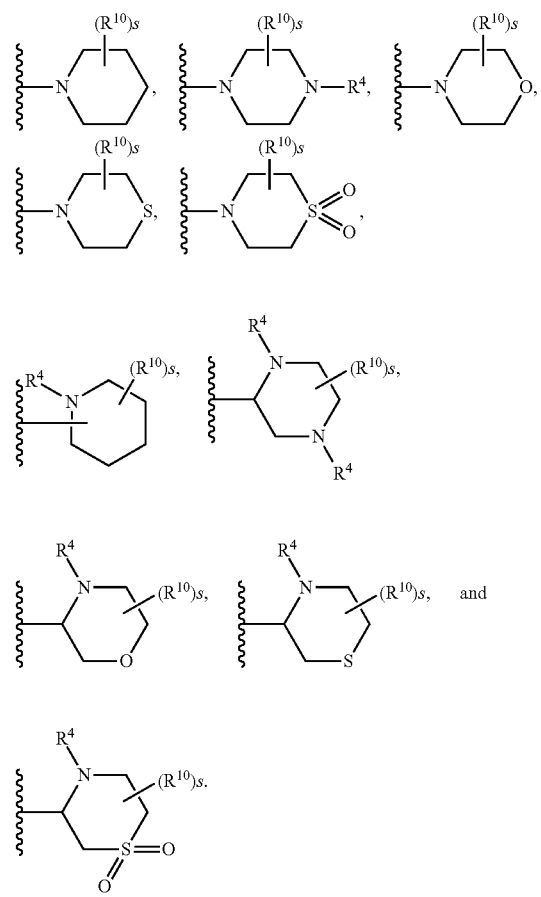

(3) The compound of the above (1) which is a compound of formula (IB)

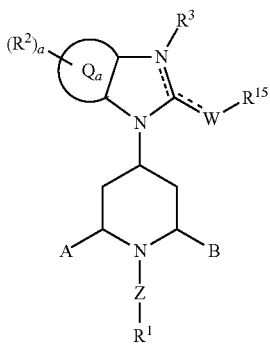
(IB)

or a pharmaceutically acceptable derivative thereof.

(4) The compound of any one of the above (1)-(3) or a pharmaceutically acceptable salt or solvate thereof, wherein $Q_a$ is benzo, pyridino, pyrimidino, pyrazino, or pyridazino, and preferably $Q_a$ is benzo or pyridino, wherein preferably the 2- and 3-positions of the pyridino are fused to the 5-membered, nitrogen-containing ring.

(5) The compound of any one of the above (1)-(4) or a pharmaceutically acceptable salt or solvate thereof, wherein $Q_a$ is benzo.

(6) The compound of any one of the above (1)-(5) or a pharmaceutically acceptable salt or solvate thereof, wherein a is 0.

(7) The compound of any one of the above (1)-(6) or a pharmaceutically acceptable salt or solvate thereof, wherein:

$Q_a$ is benzo;

a is 0;

A-B together form a $(C_2-C_6)$bridge, which is unsubstituted or substituted with 1, 2, 3, 4, 5, 6, 7 or 8 substituents independently selected from —OH, —$(C_1-C_4)$alkyl, -halo, and —C(halo)$_3$, and which bridge optionally contains —HC=CH— or —O— within the $(C_2-C_6)$bridge; wherein the A-B bridge can be in the endo- or exo-configuration with respect to the 5-membered, nitrogen-containing ring that is fused to the $Q_a$ ring;

Z is —[$(C_1-C_{10})$alkyl]$_h$-, wherein h is 0 or 1; and $R^1$ is selected from:

(a) —CN, —OH, —CH$_2$OH, —CH$_2$CH$_2$OH, —NO$_2$, —N(R$^6$)$_2$, —S(=O)NH$_2$, —S(=O)$_2$NH$_2$, —C(=O)OV$^1$, and —C(=O)CN; and (b) —$(C_1-C_{10})$alkyl, —O$(C_1-C_6)$alkyl, —$(C_3-C_7)$cycloalkoxy, —$(C_3-C_{14})$cycloalkyl, —$(C_6-C_{14})$bicycloalkyl, —$(C_8-C_{20})$tricycloalkyl, —$(C_5-C_{14})$cycloalkenyl, —$(C_7-C_{14})$bicycloalkenyl, —$(C_8-C_{20})$tricycloalkenyl, and -(3- to 7-membered)heterocycle, each of which is unsubstituted or substituted with 1, 2, 3, or 4 independently selected $R^8$ groups; and (c)

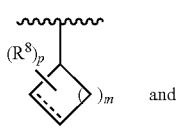
and
(i)

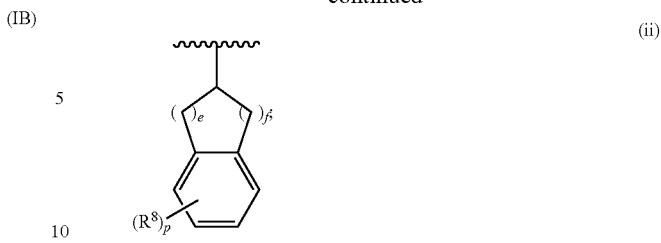
and (d) -phenyl and -(5- to 10-membered)heteroaryl, each of which is unsubstituted or substituted with 1, 2, or 3 independently selected $R^7$ groups.

(8) The compound of any one of the above (1)-(7) or a pharmaceutically acceptable salt or solvate thereof, wherein each b is, independently, an integer selected from 2, 3, and 4.

(9) The compound of any one of the above (1)-(8) or a pharmaceutically acceptable salt or solvate thereof, wherein each b is, independently, an integer selected from 2 and 3.

(10) The compound of any one of the above (1)-(9) or a pharmaceutically acceptable salt or solvate thereof, wherein each b is 3.

(11) The compound of any one of the above (1), (2), or (4)-(10) or a pharmaceutically acceptable salt or solvate thereof, wherein t is 1 and the $Q_x$ ring is selected from:

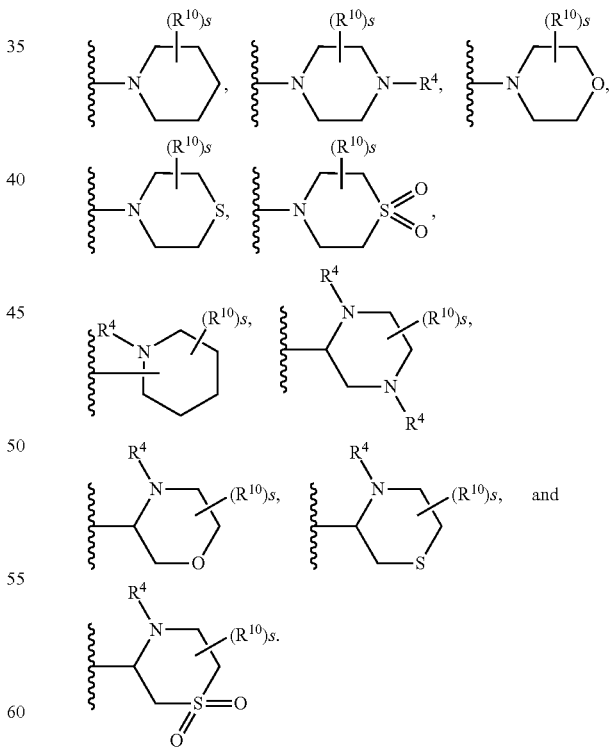

(12) The compound of any one of the above (1), (2), or (4)-(11) or a pharmaceutically acceptable salt or solvate thereof, wherein t is 1, 2, or 3 and the $Q_x$ ring is selected from:

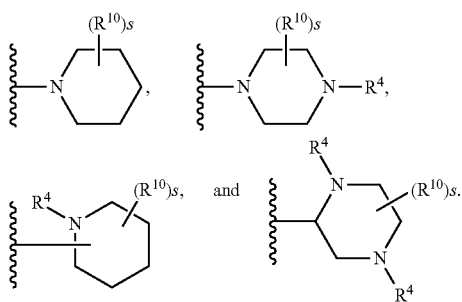

(13) The compound of any one of the above (1), (2), or (4)-(12) or a pharmaceutically acceptable salt or solvate thereof, wherein t is 1 and the $Q_x$ ring is selected from:

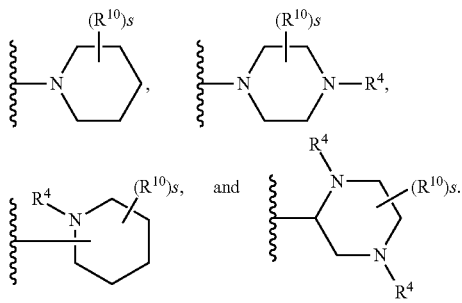

(14) The compound of any one of the above (1), (2), or (4)-(10) or a pharmaceutically acceptable salt or solvate thereof, wherein t is 0 and the $Q_x$ ring is selected from:

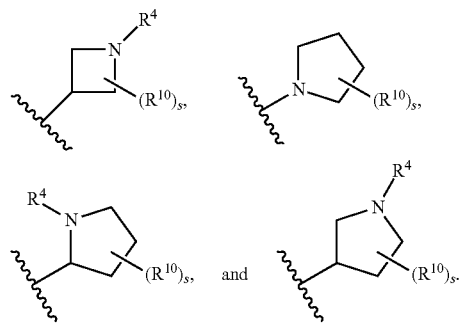

(15) The compound of any one of the above (1), (2), or (4)-(14) or a pharmaceutically acceptable salt or solvate thereof, wherein s is 0.

(16) The compound of any one of the above (1)-(15) or a pharmaceutically acceptable salt or solvate thereof, wherein the dashed line within the 5-membered, nitrogen-containing ring that is fused to the $Q_a$ ring is present to provide one bond of a double bond.

(17) The compound of any one of the above (1) or (3)-(10) or a pharmaceutically acceptable salt or solvate thereof, wherein =W— is a single bond, a double bond, —CH$_2$—, =N—, —CH=N—, or —NH—.

(18) The compound of any one of the above (1), (3)-(10), or (17) or a pharmaceutically acceptable salt or solvate thereof, wherein $R^{15}$ is —OH, —C(=O)OH, —C(=O)OCH$_3$, —C(=O)OC$_2$H$_5$, —C(=O)NH$_2$, —CH$_2$C(=O)OH, —CH$_2$C(=O)OCH$_3$, —CH$_2$C(=O)OC$_2$H$_5$, —OC(=O)CH$_3$, —OC(=O)C$_2$H$_5$, —OCH$_2$C(=O)OH, —OCH$_2$C(=O)OCH$_3$, —OCH$_2$C(=O)OC$_2$H$_5$, —C(=NH)OCH$_3$, —C(=NH)OC$_2$H$_5$, —C(=NH)NHOCH$_3$, or —C(=NH)NHOC$_2$H$_5$.

(19) The compound of any one of the above (1), (3)-(10), (17), or (18) or a pharmaceutically acceptable salt or solvate thereof, wherein =W— is —CH$_2$—, =N—, —CH=N—, or —NH— and $R^{15}$ is —C(=O)OH, —C(=O)OCH$_3$, —C(=O)OC$_2$H$_5$, —C(=O)NH$_2$, —CH$_2$C(=O)OH, —CH$_2$C(=O)OCH$_3$, —CH$_2$C(=O)OC$_2$H$_5$, —OC(=O)CH$_3$, —OC(=O)C$_2$H$_5$, —OCH$_2$C(=O)OH, —OCH$_2$C(=O)OCH$_3$, —OCH$_2$C(=O)OC$_2$H$_5$, —C(=NH)OCH$_3$, —C(=NH)OC$_2$H$_5$, —C(=NH)NHOCH$_3$, or —C(=NH)NHOC$_2$H$_5$.

(20) The compound of any one of the above (1), (3)-(10), (17), or (18) or a pharmaceutically acceptable salt or solvate thereof, wherein =W— is —CH$_2$—, =N—, —CH=N—, or —NH— and $R^{15}$ is —C(=O)OCH$_3$, —C(=O)NH$_2$, —CH$_2$C(=O)OH, —CH$_2$C(=O)OC$_2$H$_5$, —OC(=O)CH$_3$, —OCH$_2$C(=O)OH, —C(=NH)OC$_2$H$_5$, or —C(=NH)NHOCH$_3$.

(21) The compound of any one of the above (1), (3)-(10), (17), or (18) or a pharmaceutically acceptable salt or solvate thereof, wherein =W— is —CH$_2$— or —CH=N— and $R^{15}$ is —C(=O)OH, —C(=O)OCH$_3$, —C(=O)OC$_2$H$_5$, —C(=O)NH$_2$, —CH$_2$C(=O)OH, —CH$_2$C(=O)OC$_2$H$_5$, —OC(=O)CH$_3$, —OC(=O)C$_2$H$_5$, —OCH$_2$C(=O)OH, —OCH$_2$C(=O)OCH$_3$, —OCH$_2$C(=O)OC$_2$H$_5$, —C(=NH)OCH$_3$, —C(=NH)OC$_2$H$_5$, —C(=NH)NHOCH$_3$, or —C(=NH)NHOC$_2$H$_5$.

(22) The compound of any one of the above (1), (3)-(10), (17), or (18) or a pharmaceutically acceptable salt or solvate thereof, wherein =W— is =N— or —NH— and $R^{15}$ is —C(=O)OCH$_3$, —C(=O)OC$_2$H$_5$, —C(=O)OH$_2$, —CH$_2$C(=O)OH, —CH$_2$C(=O)OCH$_3$, —CH$_2$C(=O)OC$_2$H$_5$, —OC(=O)CH$_3$, —OC(=O)C$_2$H$_5$, —OCH$_2$C(=O)OH, —OCH$_2$C(=O)OCH$_3$, —OCH$_2$C(=O)OC$_2$H$_5$, —C(=NH)OCH$_3$, —C(=NH)OC$_2$H$_5$, —C(=NH)NHOCH$_3$, or —C(=NH)NHOC$_2$H$_5$.

(23) The compound of any one of the above (1), (3)-(10), (17), or (18) or a pharmaceutically acceptable salt or solvate thereof, wherein =W— is —CH=N— or —NH— and $R^{15}$ is —C(=O)OCH$_3$, —C(=O)OC$_2$H$_5$, —C(=O)NH$_2$, —CH$_2$C(=O)OH, —CH$_2$C(=O)OCH$_3$, —CH$_2$C(=O)OC$_2$H$_5$, —OC(=O)CH$_3$, —OC(=O)C$_2$H$_5$, —OCH$_2$C(=O)OH, —OCH$_2$C(=O)OCH$_3$, —OCH$_2$C(=O)OC$_2$H$_5$, —C(=NH)OCH$_3$, —C(=NH)OC$_2$H$_5$, —C(=NH)NHOCH$_3$, or —C(=NH)NHOC$_2$H$_5$.

(24) The compound of any one of the above (1)-(3), which is:

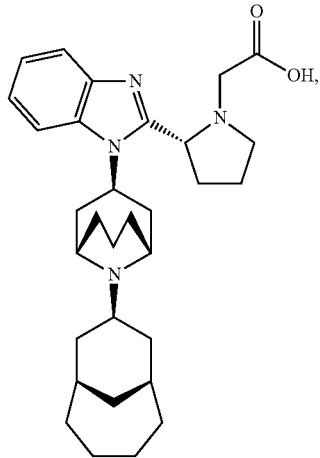

-continued
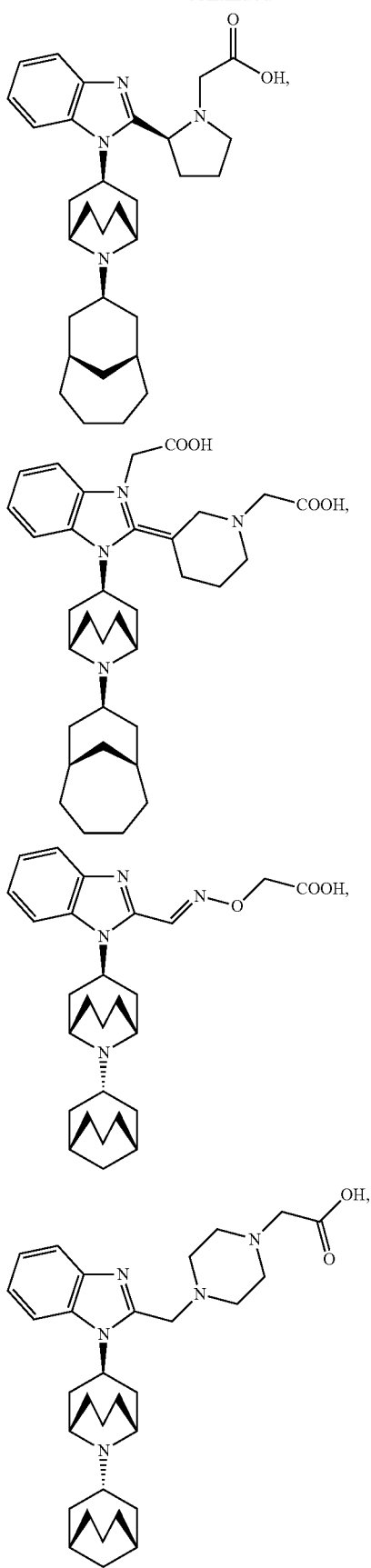
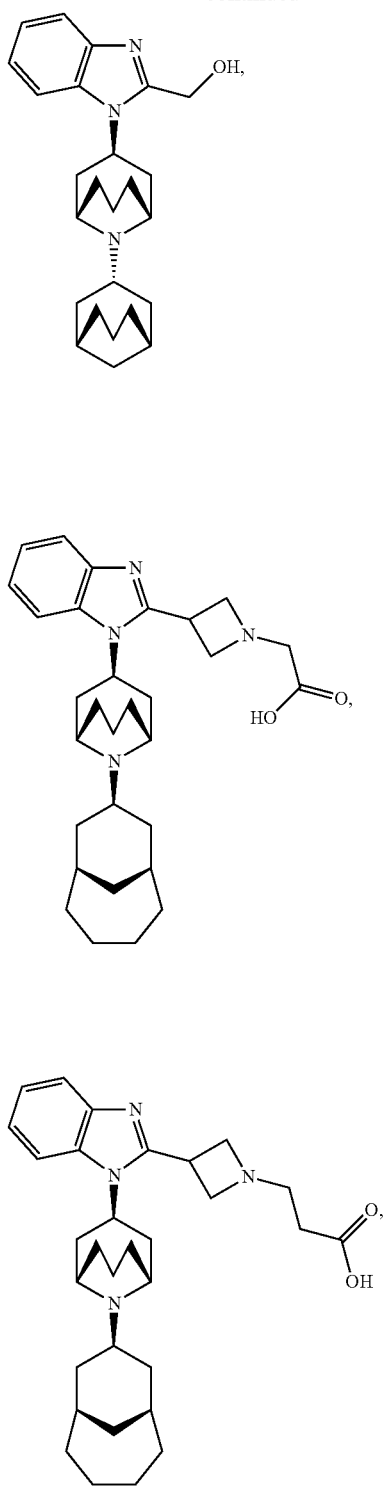
or a pharmaceutically acceptable salt or solvate thereof.
(25) The compound of any one of the above (1)-(3) or (24), which is:

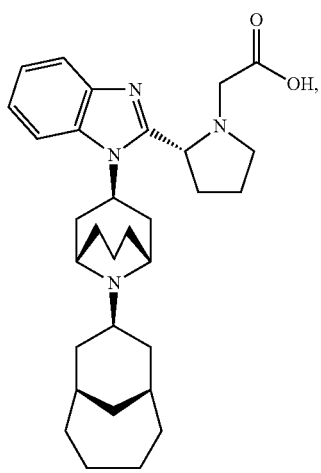
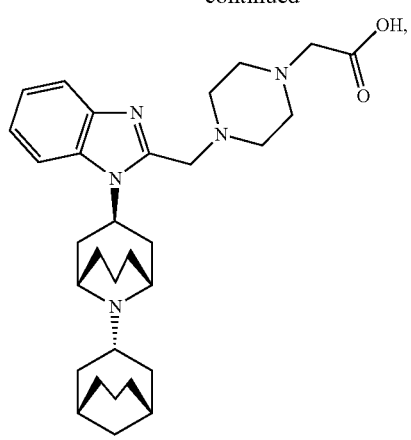
or a pharmaceutically acceptable salt or solvate thereof.
(26) The compound of any one of the above (1)-(3), (24), or (25), which is:

-continued

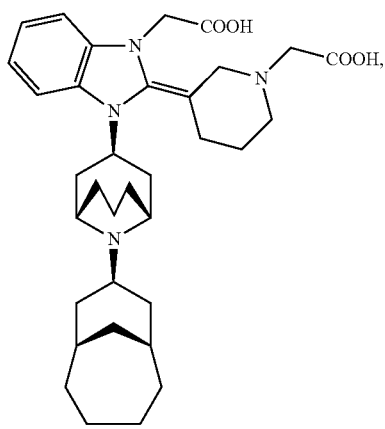

or a pharmaceutically acceptable salt or solvate thereof.

(27) The compound of any one of the above (1)-(23) or a pharmaceutically acceptable salt or solvate thereof, wherein h is 1.

(28) The compound of any one of the above (1)-(23) or (27) or a pharmaceutically acceptable salt or solvate thereof, wherein Z is —($C_1$-$C_3$)alkyl- optionally substituted by $R^{13}$.

(29) The compound of any one of the above (1)-(28) or a pharmaceutically acceptable salt or solvate thereof, wherein $R^{13}$ is absent.

(30) The compound of any one of the above (1)-(23) or (27)-(29) or a pharmaceutically acceptable salt or solvate thereof, wherein $R^{13}$ is absent and Z is —$CH_2$—$CH_2$—.

(31) The compound of any one of the above (1)-(23) or (27)-(30) or a pharmaceutically acceptable salt or solvate thereof, wherein —Z—$R^1$ is:

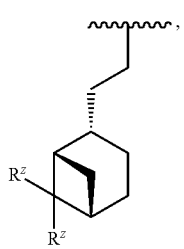

wherein each $R^z$ is independently —H, —($C_1$-$C_4$)alkyl, —OH, or —CN and preferably each $R^z$ is independently —H, —$CH_3$, or —$CH_2CH_3$.

(32) The compound of any one of the above (1)-(26) or a pharmaceutically acceptable salt or solvate thereof, wherein h is 0.

(33) The compound of any one of the above (1)-(23) or (27)-(32) or a pharmaceutically acceptable salt or solvate thereof, wherein A and B are independently —H or —($C_1$-$C_6$)alkyl and preferably A and B are each —H or A is —H and B is —$CH_3$ or A is —$CH_3$ and B is —H.

(34) The compound of any one of the above (1)-(32) or a pharmaceutically acceptable salt or solvate thereof, wherein A and B together form a bridge such that the bridged-piperidine is:

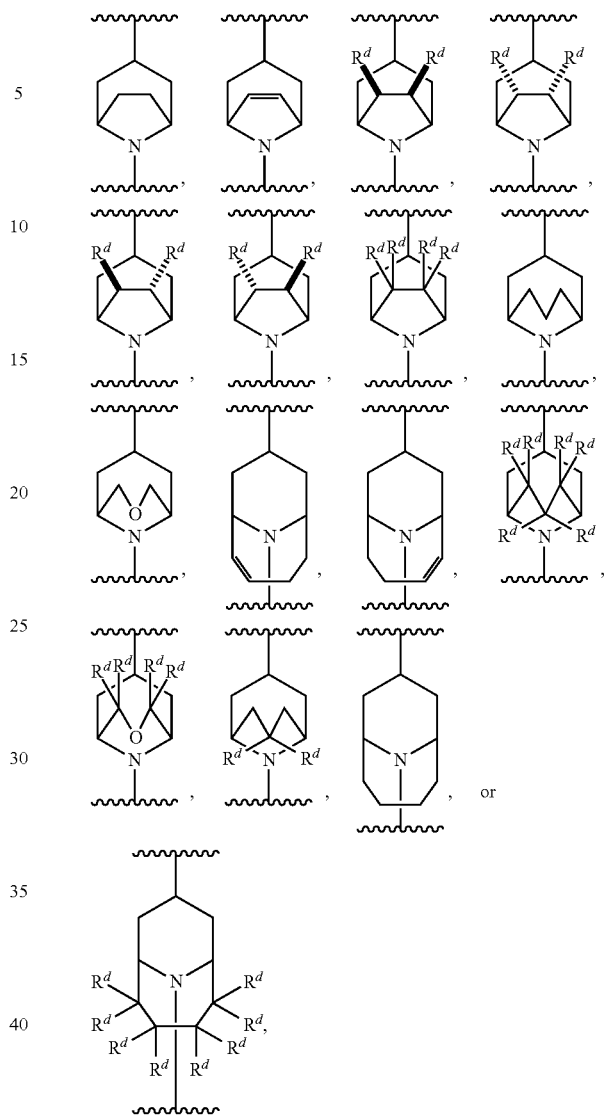

wherein each $R^d$ is independently —H, —($C_1$-$C_4$)alkyl, -halo, or —C(halo)$_3$.

(35) The compound of any one of the above (1)-(32) or (34) or a pharmaceutically acceptable salt or solvate thereof, wherein A and B together form a bridge such that the bridged-piperidine is:

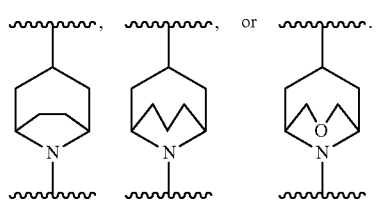

(36) The compound of any one of the above (1)-(32), (34), or (35) or a pharmaceutically acceptable salt or solvate thereof, wherein A and B together form a bridge such that the bridged-piperidine is:

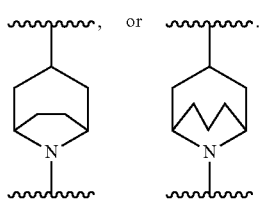 [SMILES: *C1CC2CCC(C1)N2* ; *C1CC2CCCC(C1)N2*] 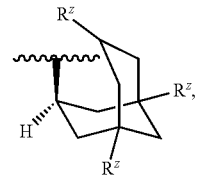

(37) The compound of any one of the above (1)-(32) or (34)-(36) or a pharmaceutically acceptable salt or solvate thereof, wherein the A-B bridge of the bridged-piperidine is in the endo-configuration with respect to the 5-membered, nitrogen-containing ring that is fused to the $Q_a$ ring.

(38) The compound of any one of the above (1)-(26) or (32)-(37) or a pharmaceutically acceptable salt or solvate thereof, wherein:

(a) h is 0;

(b) $R^1$ is —$(C_1-C_{10})$alkyl, —$(C_3-C_{14})$cycloalkyl, —$(C_5-C_{14})$cycloalkenyl, —$(C_6-C_{14})$bicycloalkyl, —$(C_7-C_{14})$bicycloalkenyl, or —$(C_8-C_{20})$tricycloalkyl, each of which is unsubstituted or substituted with 1, 2, 3, or 4 independently selected $R^8$ groups and preferably $R^1$ is —$(C_3-C_{14})$cycloalkyl, —$(C_8-C_{14})$cycloalkenyl, —$(C_6-C_{14})$bicycloalkyl, —$(C_7-C_{14})$bicycloalkenyl, or —$(C_8-C_{20})$tricycloalkyl, each of which is unsubstituted or substituted with 1, 2, 3, or 4 independently selected $R^8$ groups; and (c) each $R^8$ is independently —$(C_1-C_4)$alkyl, —$(C_1-C_6)$alkyl-C(=O)OR$^9$, —N(R$^9$)(C$_1$-C$_6$)alkyl-C(=O)OR$^9$, —OR$^9$, —C(halo)$_3$, —CH(halo)$_2$, —CH$_2$(halo), -halo, —N(R$^9$)$_2$, —C(=O)N(T$^1$)(T$^2$), or —C(=O)OR$^9$.

(39) The compound of any one of the above (1)-(23) or (32)-(38) or a pharmaceutically acceptable salt or solvate thereof; wherein —Z—R$^1$ is:

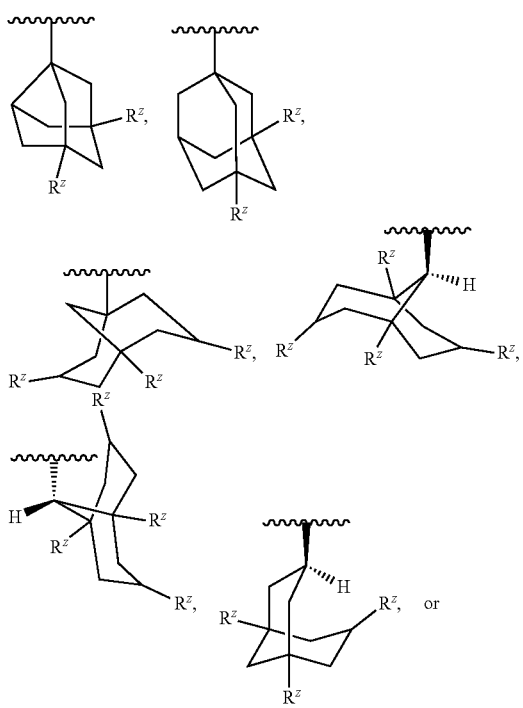

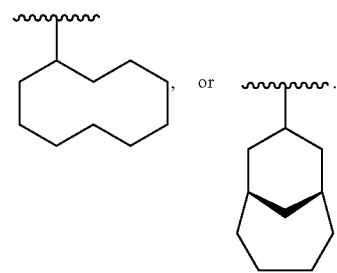

wherein each $R^z$ is independently —H, —(C$_1$-C$_4$)alkyl, —OH, or —CN and preferably each $R^z$ is independently —H, —CH$_3$, or —CH$_2$CH$_3$.

(40) The compound of any one of the above (1)-(23) or (32)-(38) or a pharmaceutically acceptable salt or solvate thereof, wherein —Z—R$^1$ is:

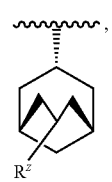

(41) The compound of any one of the above (1)-(23) or (32)-(39) or a pharmaceutically acceptable salt or solvate thereof, wherein —Z—R$^1$ is:

wherein $R^z$ is —H, —CH$_3$, or —CH$_2$CH$_3$.

(42) The compound of any one of the above (1)-(5) or (8)-(41) or a pharmaceutically acceptable salt or solvate thereof, wherein a is 1 and $R^2$ is -halo, preferably $R^2$ is —F.

(43) The compound of any one of the above (1)-(23) or (32)-(38) or a pharmaceutically acceptable salt or solvate thereof, wherein the $R^1$ group is in the exo-configuration with respect to the A-B bridge of the bridged piperidine.

(44) A compound which is:

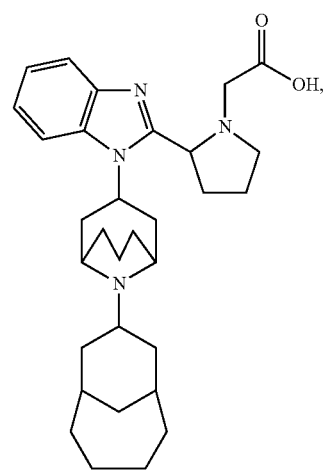

51

-continued

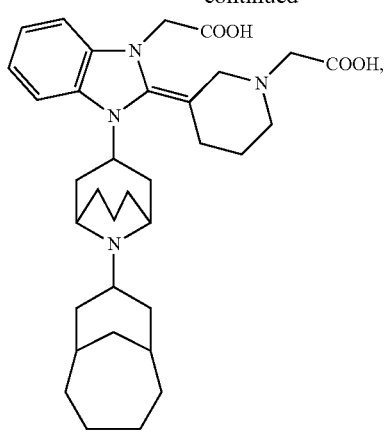

or a pharmaceutically acceptable salt thereof.

(45) The compound of the above (44), which is:

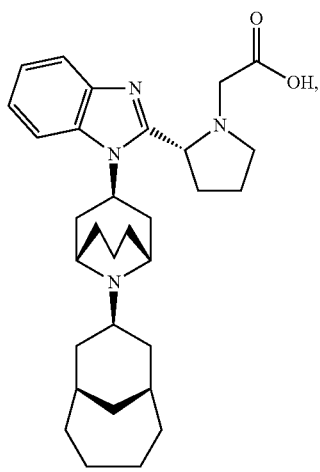 [SMILES: O=C(O)CN1CCC[C@@H]1c1nc2ccccc2n1[C@H]1C[C@H]2CCC[C@@H](C1)N2[C@@H]1C[C@@H]2CCCC[C@@H](C2)C1]

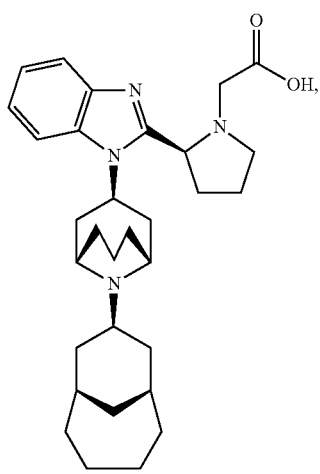

52

-continued

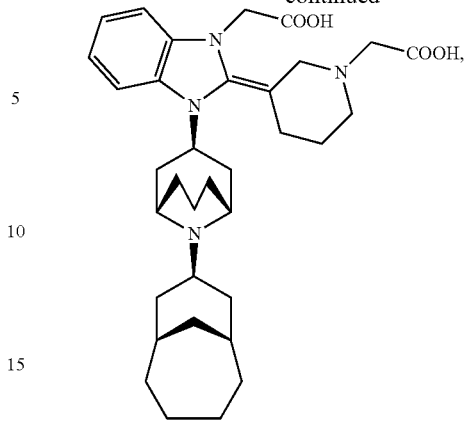

or a pharmaceutically acceptable salt thereof.

(46) The compound of the above (45) having the formula:

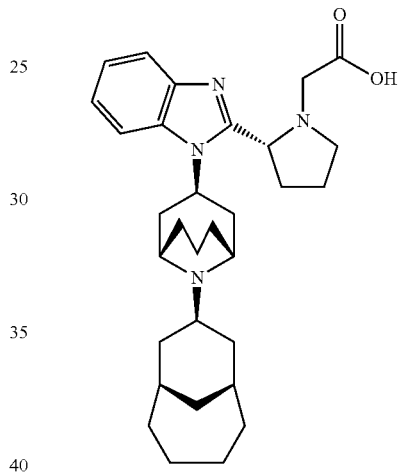

or a pharmaceutically acceptable salt thereof.

(47) The compound of any one of the above (1)-(46) or a pharmaceutically acceptable salt or solvate thereof, which is radiolabeled.

(48) The compound of any one of the above (1)-(47), wherein the pharmaceutically acceptable salt is a hydrochloride-salt, a sodium-salt, a potassium-salt, or a para-toluene-sulfonic acid-salt.

(49) The compound of any one of the above (1)-(48) or a pharmaceutically acceptable salt thereof, wherein the % de of the compound is at least about 95%.

(50) The compound of the above (49) or a pharmaceutically acceptable salt thereof, wherein the % de of the compound is at least about 99%.

(51) A composition comprising an effective amount of the compound or a pharmaceutically acceptable salt or solvate of the compound of any one of the above (1)-(50) and a pharmaceutically acceptable carrier or excipient.

(52) A method for preparing a composition, comprising the step of admixing a compound or a pharmaceutically acceptable salt or solvate of the compound of any one of the above (1)-(50) and a pharmaceutically acceptable carrier or excipient.

(53) A method for modulating ORL-1 receptor function in a cell, comprising contacting a cell capable of expressing the ORL-1 receptor with an effective amount of the composition or the compound or a pharmaceutically acceptable salt or solvate of the compound of any one of the above (1)-(51).

(54) The method of the above (53) wherein the composition or the compound or the pharmaceutically acceptable salt or solvate of the compound acts as an agonist at the ORL-1 receptor.

(55) The method of the above (53), wherein the composition or the compound or the pharmaceutically acceptable salt or solvate of the compound acts as a partial agonist at the ORL-1 receptor.

(56) A method for treating pain in an animal, comprising administering to an animal in need thereof an effective amount of the composition or the compound or a pharmaceutically acceptable salt or solvate of the compound of any one of the above (1)-(51).

(57) A method for treating a memory disorder, obesity, constipation, depression, dementia, Parkinsonism, anxiety, cough, diarrhea, high blood pressure, epilepsy, anorexia/cachexia, urinary incontinence, or drug abuse in an animal, comprising administering to an animal in need thereof an effective amount of the composition or the compound or a pharmaceutically acceptable salt or solvate of the compound of any one of the above (1)-(51).

(58) Use of a compound or the pharmaceutically acceptable salt or solvate of the compound of any one of the above (1)-(50) for the manufacture of a medicament useful for treating pain, a memory disorder, obesity, constipation, depression, dementia, Parkinsonism, anxiety, cough, diarrhea, high blood pressure, epilepsy, anorexia/cachexia, urinary incontinence, or drug abuse.

(59) The compound or the pharmaceutically acceptable salt or solvate of the compound of any one of the above (1)-(50) for use in the treatment of pain, a memory disorder, obesity, constipation, depression, dementia, Parkinsonism, anxiety, cough, diarrhea, high blood pressure, epilepsy, anorexia/cachexia, urinary incontinence, or drug abuse.

(60) A kit, comprising a container containing an effective amount of the composition or the compound or a pharmaceutically acceptable salt or solvate of the compound of any one of the above (1)-(51).

(61) The compound of any one of the above (1)-(47) or (49)-(60), wherein the compound is present as a pharmaceutically acceptable salt.

(62) The compound of any one of the above (1)-(6), (8)-(23), (27)-(30), (32)-(37), (42), (43), or (47)-(61), wherein $R^1$ is selected from:
(a) -halo, —CN, —OH, —CH$_2$OH, —CH$_2$CH$_2$OH, —NO$_2$, —N(R$^6$)$_2$, —S(=O)NH$_2$, —S(=O)$_2$NH$_2$, —C(=O)OV$^1$, and —C(=O)CN; and
(b) —(C$_2$-C$_{10}$)alkyl, —(C$_2$-C$_{10}$)alkenyl, —(C$_2$-C$_{10}$)alkynyl, —O(C$_1$-C$_6$)alkyl, —(C$_3$-C$_7$)cycloalkoxy, —(C$_6$-C$_{14}$)bicycloalkyl, —(C$_8$-C$_{20}$)tricycloalkyl, —(C$_5$-C$_{10}$)cycloalkenyl, —(C$_7$-C$_{14}$)bicycloalkenyl, —(C$_8$-C$_{20}$)tricycloalkenyl, -(3- to 5-membered)heterocycle, and -(7-membered)heterocycle, each of which is unsubstituted or substituted with 1, 2, 3, or 4 independently selected R$^8$ groups; and
(c)

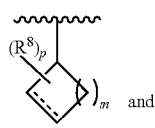
and (i)

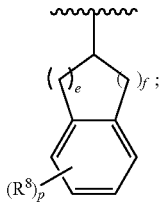

(ii)

and
(d) -naphthalenyl, —(C$_{14}$)aryl, and -(5- to 10-membered)heteroaryl, each of which is unsubstituted or substituted with 1, 2, 3, or 4 independently selected R$^7$ groups.

(63) The compound of any one of the above (1)-(6), (8)-(23), (27), (28), (32)-(37), (42), (43), or (47)-(62), wherein R$^{13}$ is selected from:
(a) -halo, —CN, —OH, —CH$_2$OH, —CH$_2$CH$_2$OH, —NO$_2$, —N(R$^6$)$_2$, —S(=O)NH$_2$, —S(=O)$_2$NH$_2$, —C(=O)OV$^1$, and —C(=O)CN; and
(b) —(C$_2$-C$_{10}$)alkyl, —(C$_2$-C$_{10}$)alkenyl, —(C$_2$-C$_{10}$)alkynyl, —O(C$_1$-C$_6$)alkyl, —(C$_3$-C$_7$)cycloalkoxy, —(C$_5$-C$_{10}$)cycloalkenyl, and -(3- to 7-membered)heterocycle, each of which is unsubstituted or substituted with 1, 2, 3, or 4 independently selected R$^8$ groups; and
(c)

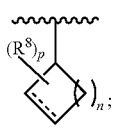

(iv)

and
(d) -(5- to 10-membered)heteroaryl, each of which is unsubstituted or substituted with 1, 2, or 3 independently selected R$^7$ groups wherein p is 0 or 1, optionally 0.

(64) The compound of any one of the above (1)-(23), (27)-(43), or (47)-(63), wherein p is 0.

(65) The compound of any one of the above (1), (3)-(10), (16)-(23), (27)-(43), or (47)-(64), wherein R$^{15}$, when present, is selected from:
(a) —H; and
(b) —(C$_1$-C$_2$)alkyl which is substituted with 1, 2, or 3 independently selected R$^8$ groups; and
(c) —(C$_3$-C$_4$)alkyl and —O—(C$_1$-C$_4$)alkyl, each of which is unsubstituted or substituted with 1, 2, 3, or 4 independently selected R$^8$ groups;
(d) provided that when ---W— is a single bond, a double bond, or —O—, R$^{15}$ is not —H.

(66) The compound of any one of the above (1)-(23), (27)-(37), (39)-(43), or (47)-(65), wherein each R$^8$ is independently —(C$_1$-C$_4$)alkyl, —(C$_2$-C$_6$)alkenyl, —(C$_2$-C$_6$)alkynyl, -(5- or 6-membered)heteroaryl, —(C$_1$-C$_6$)alkyl-C(=O)OR$^9$, —N(R$^9$)(C$_1$-C$_6$)alkyl-C(=O)OR$^9$, —OR$^9$, —SR$^9$, —C(halo)$_3$, —CH(halo)$_2$, —CH$_2$(halo), —CN, =O, =S, =N(R$^9$), —N$_3$, —NO$_2$, —CH=N(R$^9$), —N(R$^9$)$_2$, —N(R$^9$)OR$^9$, —N(R$^9$)S(=O)R$^{12}$, —N(R$^9$)S(=O)$_2$R$^{12}$, —N(R$^9$)C(=O)R$^{12}$, —N(R$^9$)C(=O)N(T$^1$)(T$^2$), —N(R$^9$)C(=O)OR$^{12}$, —C(=O)R$^9$, —C(=O)N(T$^1$)(T$^2$), —OC(=O)R$^9$, —OC(=O)N(T$^1$)(T$^2$), —OC(=O)OR$^9$, or —S(=O)R$^9$.

(101) A compound of formula (I‡A):

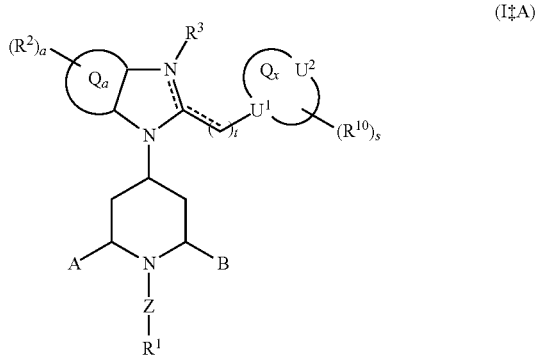

or a pharmaceutically acceptable salt or solvate thereof where:

the $Q_a$ ring is fused benzo or fused (5- or 6-membered) heteroaryl;

each $R^2$ is independently selected from:

(a) -halo, —CN, —$NO_2$, —$OT^3$, —C(=O)$T^3$, —C(=O)$OT^3$, —C(=O)N($T^1$)($T^2$), —S(=O)$_2OT^3$, —S(=O)$T^3$, —S(=O)$_2T^3$, —O—S(=O)$_2T^3$, —S(=O)$_2$N($T^1$)($T^2$), —N($T^1$)($T^2$), —N($T^3$)C(=O)$T^3$, —N($T^3$)C(=O)N($T^1$)($T^2$), —N($T^3$)S(=O)$T^3$, —N($T^3$)S(=O)$_2T^3$, —N($T^3$)C(=O)$OT^3$, and —N($T^3$)S(=O)$_2$N($T^1$)($T^2$); and (b) —($C_1$-$C_6$)alkyl, —($C_2$-$C_6$)alkenyl, —($C_2$-$C_6$)alkynyl, —($C_1$-$C_6$)alkoxy, —($C_3$-$C_7$)cycloalkyl, —($C_6$-$C_{10}$)bicycloalkyl, —($C_5$-$C_{10}$)cycloalkenyl, —($C_7$-$C_{10}$)bicycloalkenyl, and -(5- or 6-membered)heterocycle, each of which is unsubstituted or substituted with 1, 2, or 3 independently selected $R^8$ groups; and (c) -phenyl, -naphthalenyl, and -(5- or 6-membered)heteroaryl, each of which is unsubstituted or substituted with 1, 2, or 3 independently selected $R^7$ groups;

each dashed line denotes the presence or absence of a bond (i.e., when a dashed line is present there is a double bond at that position and when a dashed line is absent there is only a single bond at that position), provided that:

(a) one dashed line must denote the presence of a bond (i.e., there is a double bond at that position);

(b) when one dashed line denotes the presence of a bond (i.e., there is a double bond at that position) then the other dashed line denotes the absence of a bond (i.e., there is only a single bond at that other position);

(c) when the dashed line within the 5-membered, nitrogen-containing ring that is fused to the $Q_a$ ring is present (i.e., there is a double bond at that position), then $R^3$ is absent; and (d) when the dashed line within the 5-membered, nitrogen-containing ring that is fused to the $Q_a$ ring is absent (i.e., there is only a single bond at that position), then $R^3$ is present;

$R^3$, when present, is:

(a) —H; or (b) —($C_1$-$C_4$)alkyl which is unsubstituted or substituted with 1, 2, or 3 groups independently selected from —OH, —($C_1$-$C_4$)alkoxy, —N($R^6$)$_2$, —C(=O)$OR^9$, and —C(=O)N($R^6$)$_2$; or (c) —($C_3$-$C_7$)cycloalkyl which is unsubstituted or substituted with 1, 2, or 3 groups independently selected from —OH, —($C_1$-$C_4$)alkyl, —($C_1$-$C_4$)alkoxy, —N($R^6$)$_2$, —C(=O)$OR^9$, and —C(=O)N($R^6$)$_2$;

t is an integer selected from 0, 1, 2, and 3;

when t is 0, the $Q_x$ ring is a -(3-, 4-, 5-, 6-, or 7-membered) heterocycle containing 1, 2, 3, or 4 ring heteroatoms independently selected from N, N($R^4$), O, and S wherein said heterocycle is unsubstituted or substituted with ($R^{10}$)$_s$ groups provided that at least one ring heteroatom is N or N($R^4$) and provided that when the dashed line connecting the $Q_x$ ring to the 5-membered, nitrogen-containing ring that is fused to the $Q_a$ ring is present (i.e., there is a double bond at that position), $U^1$ is C or CH, and when t is 1, 2, or 3 the $Q_x$ ring is a (5- or 6-membered) heterocycle selected from:

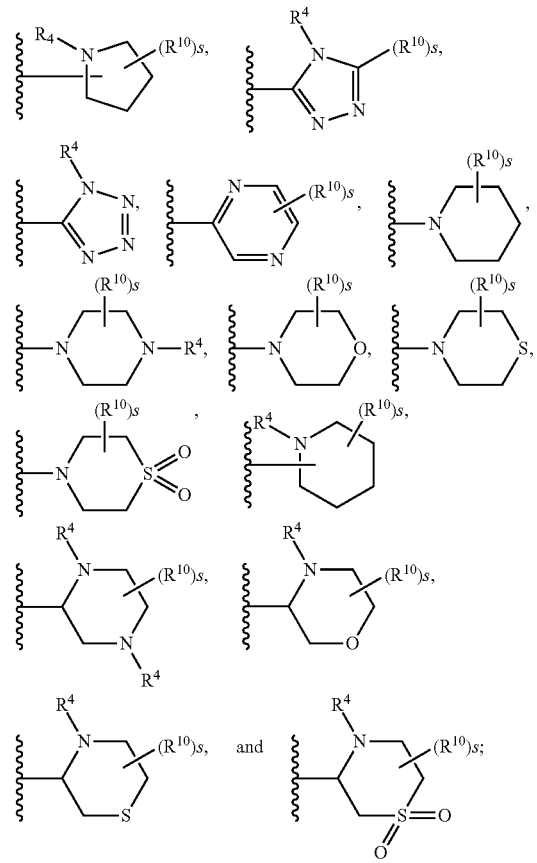

each $R^4$, when present, is independently selected from:

(a) —H; and (b) —X, —($C_1$-$C_6$)alkyl-X, -(5- or 6-membered)heterocycle-X, or -(5- or 6-membered)heterocycle-($C_1$-$C_6$)alkyl-X; and (c) —($CH_2$)$_d$—C(Y)CN, —($CH_2$)$_d$—C(Y)X, —($CH_2$)$_d$—C(Y)$T^3$, —($CH_2$)$_d$—C(=Y)YX, —($CH_2$)$_d$—C(=Y)$YT^3$, —($CH_2$)$_d$—C(=Y)N($T^1$)($T^2$), —($CH_2$)$_d$—C(=Y)N($R^9$)CN, —($CH_2$)$_d$—C(=Y)N($R^9$)X, —($CH_2$)$_d$—C(=Y)N($R^9$)YH, —($CH_2$)$_d$—C(=Y)N($R^9$)YX, —($CH_2$)$_d$—C(=Y)N($R^9$)YCH$_2$X, —($CH_2$)$_d$—C(=Y)N($R^9$)YCH$_2$CH$_2$X, —($CH_2$)$_d$—C(=Y)N($R^9$)S(=O)$_2T^3$; —($CH_2$)$_d$—N($R^9$)S(=O)$_2T^3$; or —($CH_2$)$_d$—S(=O)$_2T^4$; and (d) —[CH$_2$—O]$_b$—R$^{16}$, —[CH(CH$_3$)—O]$_b$—R$^{16}$, —[CH$_2$—CH$_2$—O]$_b$—R$^{16}$, —[CH(CH$_3$)—CH$_2$—O]$_b$—R$^{16}$, —[CH$_2$—CH(CH$_3$)—O]$_b$—R$^{16}$, —[CH$_2$—CH$_2$—CH$_2$—O]$_b$—R$^{16}$, —[CH(CH$_3$)—CH$_2$—CH$_2$—O]$_b$—R$^{16}$, —[CH$_2$—CH(CH$_3$)—CH$_2$—O]$_b$—R$^{16}$, or —[CH$_2$—CH$_2$—CH(CH$_3$)—O]$_b$—R$^{16}$;

X is selected from:
(a) —H, —(C$_1$-C$_6$)alkyl, —(C$_2$-C$_6$)alkenyl, —(C$_2$-C$_6$)alkynyl, —(C$_1$-C$_6$)alkoxy, —(C$_3$-C$_7$)cycloalkyl, —(C$_5$-C$_{10}$)cycloalkenyl, and -(5- or 6-membered)heterocycle, each of which is unsubstituted or substituted with 1, 2, or 3 independently selected R$^8$ groups; and
(b) -phenyl and -(5- or 6-membered)heteroaryl, each of which is unsubstituted or substituted with 1, 2, or 3 independently selected R$^7$ groups;

each Y is independently O or S;
each R$^{16}$ is independently H or CH$_3$;
s is an integer selected from 0, 1, 2, 3, and 4;
when s is 1, 2, 3, or 4, each R$^{10}$ is independently —F, —CH$_3$, —CH$_2$CH$_3$, —OCH$_3$, —OCH$_2$CH$_3$, —(CH$_2$)$_d$—C(=Y)YT$^3$, or —(CH$_2$)$_d$—C(=Y)N(T$^1$)(T$^2$), and when s is 2, 3, or 4, each R$^{10}$ is independently —F, —Cl, —CH$_3$, —CH$_2$CH$_3$, —OCH$_3$, —OCH$_2$CH$_3$, —(CH$_2$)$_d$—C(=Y)YT$^3$, or —(CH$_2$)$_d$—C(=Y)N(T$^1$)(T$^2$) or two R$^{10}$ groups attached to the same carbon atom and are gem-dimethyl, gem-difluoro, =O, or =S;

A and B are independently selected from:
(a) —H; and
(b) —(C$_1$-C$_6$)alkyl, —(C$_2$-C$_6$)alkenyl, and —(C$_1$-C$_6$)alkoxy, each of which is unsubstituted or substituted with 1 or 2 substituents independently selected from —OH, —S(=O)$_2$NH$_2$, —C(=O)OT$^3$, —C(=O)N(R$^6$)$_2$, and —N(R$^6$)C(=O)R$^9$, or 1, 2, or 3 independently selected -halo; or
(c) A-B can together form a (C$_2$-C$_6$)bridge, which is unsubstituted or substituted with 1, 2, 3, 4, 5, 6, 7, or 8 substituents independently selected from —OH, —(C$_1$-C$_4$)alkyl, -halo, and —C(halo)$_3$, and which bridge optionally contains —HC=CH— or —O— within the (C$_2$-C$_6$)bridge; wherein the 5-membered, nitrogen-containing ring that is fused to the Q$_a$ ring can be in the endo- or exo-configuration with respect to the A-B bridge;

Z is —[(C$_1$-C$_{10}$)alkyl optionally substituted by R$^{13}$]$_h$—, wherein h is 0 or 1; or —[(C$_2$-C$_{10}$)alkenyl optionally substituted by R$^{13}$]—, or —[(C$_1$-C$_{10}$)alkyl-NR$^6$C(=Y)]—;

R$^1$ is selected from:
(a) —H, -halo, —CN, —OH, —CH$_2$OH, —CH$_2$CH$_2$OH, —NO$_2$, —N(R$^6$)$_2$, —S(=O)NH$_2$, —S(=O)$_2$NH$_2$, —C(=O)OV$^1$, and —C(=O)CN; and
(b) —(C$_1$-C$_{10}$)alkyl, —(C$_2$-C$_{10}$)alkenyl, —(C$_2$-C$_{10}$)alkynyl, —O(C$_1$-C$_6$)alkyl, —(C$_3$-C$_7$)cycloalkoxy, —(C$_6$-C$_{14}$)bicycloalkyl, —(C$_8$-C$_{20}$)tricycloalkyl, —(C$_5$-C$_{10}$)cycloalkenyl, —(C$_7$-C$_{14}$)bicycloalkenyl, —(C$_8$-C$_{20}$)tricycloalkenyl, and -(3- to 7-membered)heterocycle, each of which is unsubstituted or substituted with 1, 2, 3, or 4 independently selected R$^8$ groups; and
(c)

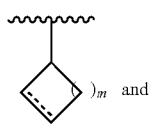

)$_m$ and

-continued

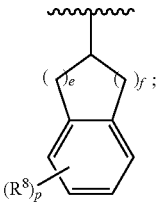

(ii)

and
(d) -phenyl, -naphthalenyl, —(C$_{14}$)aryl, and -(5- to 10-membered)heteroaryl, each of which is unsubstituted or substituted with 1, 2, 3, or 4 independently selected R$^7$ groups;

each R$^5$ is independently —(C$_1$-C$_4$)alkyl, —(C$_2$-C$_6$)alkenyl, —(C$_2$-C$_6$)alkynyl, -(5- or 6-membered)heteroaryl, —(C$_1$-C$_6$)alkyl-C(=O)OR$^9$, —OR$^9$, —SR$^9$, —C(halo)$_3$, —CH(halo)$_2$, —CH$_2$(halo), —CN, =O, =S, -halo, —N$_3$, —NO$_2$, —CH=N(R$^9$), —N(R$^9$)(C$_1$-C$_6$)alkyl-C(=O)OR$^9$, —N(R$^9$)$_2$, —N(R$^9$)OH, —N(R$^9$)S(=O)R$^{12}$, —N(R$^9$)S(=O)$_2$R$^{12}$, —N(R$^9$)C(=O)R$^{12}$, —N(R$^9$)C(=O)OR$^{12}$, —C(=O)R$^9$, —C(=O)OR$^9$, —OC(=O)R$^9$, —OC(=O)OR$^9$, —S(=O)R$^9$, or —S(=O)$_2$R$^9$;

each R$^6$ is independently —H, —(C$_1$-C$_6$)alkyl, or —(C$_3$-C$_7$)cycloalkyl, or two R$^6$ groups attached to the same nitrogen atom can together form a -(5- to 8-membered)heterocyclic ring, wherein the number of atoms in the ring includes the nitrogen atom, and in which one of the -(5- to 8-membered)heterocyclic ring carbon atoms is optionally replaced by O, S, or N(T$^3$);

each R$^7$ is independently —(C$_1$-C$_4$)alkyl, —(C$_2$-C$_6$)alkenyl, —(C$_2$-C$_6$)alkynyl, —OR$^9$, —SR$^9$, —C(halo)$_3$, —CH(halo)$_2$, —CH$_2$(halo), —CN, -halo, —N$_3$, —NO$_2$, —CH=N(R$^9$), —N(R$^9$)$_2$, —N(R$^9$)OH, —N(R$^9$)S(=O)R$^{12}$, —N(R$^9$)S(=O)$_2$R$^{12}$, —N(R$^9$)C(=O)R$^{12}$, —N(R$^9$)C(=O)N(T$^1$)(T$^2$), —N(R$^9$)C(=O)OR$^{12}$, —C(=O)R$^9$, —C(=O)N(T$^1$)(T$^2$), —C(=O)OR$^9$, —OC(=O)R$^9$, —OC(=O)N(T$^1$)(T$^2$), —OC(=O)OR$^9$, —S(=O)R$^9$, or —S(=O)$_2$R$^9$;

each R$^8$ is independently —(C$_1$-C$_4$)alkyl, —(C$_2$-C$_6$)alkenyl, —(C$_2$-C$_6$)alkynyl, -(5- or 6-membered)heteroaryl, —(C$_1$-C$_6$)alkyl-C(=O)OR$^9$, —N(R$^9$)(C$_1$-C$_6$)alkyl-C(=O)OR$^9$, —OR$^9$, —SR$^9$, —C(halo)$_3$, —CH(halo)$_2$, —CH$_2$(halo), —CN, =O, =S, =N(R$^9$), -halo, —N$_3$, —NO$_2$, —CH=N(R$^9$), —N(R$^9$)$_2$, —N(R$^9$)OR$^9$, —N(R$^9$)S(=O)R$^{12}$, —N(R$^9$)S(=O)$_2$R$^{12}$, —N(R$^9$)C(=O)R$^{12}$, —N(R$^9$)C(=O)N(T$^1$)(T$^2$), —N(R$^9$)C(=O)OR$^{12}$, —C(=O)R$^9$, —C(=O)N(T$^1$)(T$^2$), —C(=O)OR$^9$, —OC(=O)R$^9$, —OC(=O)N(T$^1$)(T$^2$), —OC(=O)OR$^9$, —S(=O)R$^9$, or —S(=O)$_2$R$^9$;

each R$^9$ is independently —H, —(C$_1$-C$_6$)alkyl, —(C$_2$-C$_6$)alkenyl, —(C$_2$-C$_6$)alkynyl, —(C$_3$-C$_8$)cycloalkyl, —(C$_5$-C$_8$)cycloalkenyl, -phenyl, -benzyl, -(3- to 7-membered)heterocycle, —C(halo)$_3$, —CH(halo)$_2$, or —CH$_2$(halo);

each R$^{12}$ is independently —H or —(C$_1$-C$_4$)alkyl;

R$^{13}$ is selected from:
(a) -halo, —CN, —OH, —CH$_2$OH, —CH$_2$CH$_2$OH, —NO$_2$, —N(R$^6$)$_2$, —S(=O)NH$_2$, —S(=O)$_2$NH$_2$, —C(=O)OV$^1$, and —C(=O)CN; and
(b) —(C$_2$-C$_{10}$)alkenyl, —(C$_2$-C$_{10}$)alkynyl, —O(C$_1$-C$_6$)alkyl, —(C$_3$-C$_7$)cycloalkoxy, —(C$_5$-C$_{10}$)cycloalkenyl, and -(3- to 7-membered)heterocycle, each of which is unsubstituted or substituted with 1, 2, 3, or 4 independently selected R$^8$ groups; and (c)

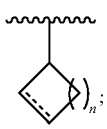

and (d) -phenyl and -(5- to 10-membered)heteroaryl, each of which is unsubstituted or substituted with 1, 2, or 3 independently selected $R^7$ groups;

each $T^1$ and $T^2$ is independently —H or —$(C_1$-$C_{10})$alkyl which is unsubstituted or substituted with 1, 2, or 3 independently selected $R^5$ groups and, optionally, in which any —$(C_1$-$C_{10})$alkyl carbon atom except the carbon atom bonded directly to the atom to which $T^1$ or $T^2$ is attached is independently replaced by O, S, or N($R^6$), or $T^1$ and $T^2$ can together form a -(5- to 8-membered)heterocyclic ring wherein the number of atoms in the ring includes the nitrogen atom to which $T^1$ and $T^2$ are bonded, said -(5- to 8-membered)heterocyclic ring is unsubstituted or substituted with 1, 2, or 3 independently selected $R^5$ groups and, optionally, any 1 or 2 carbon atoms in said -(5- to 8-membered)heterocyclic ring is independently replaced by O, S, or N($R^6$);

each $T^3$ is independently —H or —$(C_1$-$C_{10})$alkyl which is unsubstituted or substituted with 1, 2, or 3 independently selected $R^5$ groups and, optionally, in which any —$(C_1$-$C_{10})$alkyl carbon atom except the carbon atom bonded directly to the atom to which $T^3$ is attached is independently replaced by O, S, or N($R^{12}$);

each $T^4$ is independently a -(5- or 6-membered)heteroaryl which is unsubstituted or substituted with 1 or 2 independently selected $R^{12}$ groups;

each $V^1$ is independently —H, —$(C_1$-$C_6)$alkyl, —$(C_3$-$C_7)$cycloalkyl, -phenyl, or -benzyl;

a is an integer selected from 0, 1, and 2;

each b is, independently, an integer selected from 1, 2, 3, 4, 5, and 6;

each d is, independently, an integer selected from 0, 1, 2, and 3;

m is an integer selected from 0, 1, 2, 3, 4, 5, 6, 7, 8, 9, 10, and 11;

n is an integer selected from 0, 1, 2, 3, 4, 5, 6, 7, 8, and 9;

e and f are each an integer independently selected from 0, 1, 2, 3, 4, and 5 provided that 2≤(e+f)≤5;

each p is an integer independently selected from 0, 1, 2, 3, and 4; and each halo is independently —F, —Cl, —Br, or —I.

(102) The compound of the above (101) or a pharmaceutically acceptable salt or solvate thereof, wherein $Q_a$ is benzo, pyridino, pyrimidino, pyrazino, or pyridazino, and preferably $Q_a$ is benzo or pyridino, wherein preferably the 2- and 3-positions of the pyridino are fused to the 5-membered, nitrogen-containing ring.

(103) The compound of the above (101) or (102) or a pharmaceutically acceptable salt or solvate thereof, wherein $Q_a$ is benzo.

(104) The compound of any one of the above (101)-(103) or a pharmaceutically acceptable salt or solvate thereof, wherein a is 0.

(105) The compound of any one of the above (101)-(104) or a pharmaceutically acceptable salt or solvate thereof, wherein:

$Q_a$ is benzo;

a is 0;

A-B together form a $(C_2$-$C_6)$bridge, which is unsubstituted or substituted with 1, 2, 3, 4, 5, 6, 7 or 8 substituents independently selected from —OH, —$(C_1$-$C_4)$alkyl, -halo, and —C(halo)$_3$, and which bridge optionally contains —HC=CH— or —O— within the $(C_2$-$C_6)$bridge; wherein the A-B bridge can be in the endo- or exo-configuration with respect to the 5-membered, nitrogen-containing ring that is fused to the $Q_a$ ring;

Z is —[$(C_1$-$C_{10})$alkyl]$_h$-, wherein h is 0 or 1; and $R^1$ is selected from:

(a) —CN, —OH, —CH$_2$OH, —CH$_2$CH$_2$OH, —NO$_2$, —N($R^6$)$_2$, —S(=O)NH$_2$, —S(=O)$_2$NH$_2$, —C(=O)OV$^1$, and —C(=O)CN; and (b) —$(C_1$-$C_{10})$alkyl, —O$(C_1$-$C_6)$alkyl, —$(C_3$-$C_7)$cycloalkoxy, —$(C_3$-$C_{14})$cycloalkyl, —$(C_6$-$C_{14})$bicycloalkyl, —$(C_8$-$C_{20})$tricycloalkyl, —$(C_5$-$C_{14})$cycloalkenyl, —$(C_7$-$C_{14})$bicycloalkenyl, —$(C_8$-$C_{20})$tricycloalkenyl, and -(3- to 7-membered)heterocycle, each of which is unsubstituted or substituted with 1, 2, 3, or 4 independently selected $R^8$ groups; and (c)

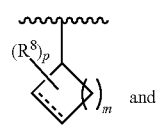

and

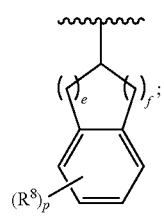

and (d) -phenyl and -(5- to 10-membered)heteroaryl, each of which is unsubstituted or substituted with 1, 2, or 3 independently selected $R^7$ groups.

(106) The compound of any one of the above (101)-(105) or a pharmaceutically acceptable salt or solvate thereof, wherein each b is, independently, an integer selected from 2, 3, and 4.

(107) The compound of any one of the above (101)-(106) or a pharmaceutically acceptable salt or solvate thereof, wherein each b is, independently, an integer selected from 2 and 3.

(108) The compound of any one of the above (101)-(107) or a pharmaceutically acceptable salt or solvate thereof, wherein each b is 3.

(109) The compound of any one of the above (101)-(108) or a pharmaceutically acceptable salt or solvate thereof, wherein t is 1, 2, or 3, s is 0, 1, or 2, and the $Q_x$ ring is selected from:

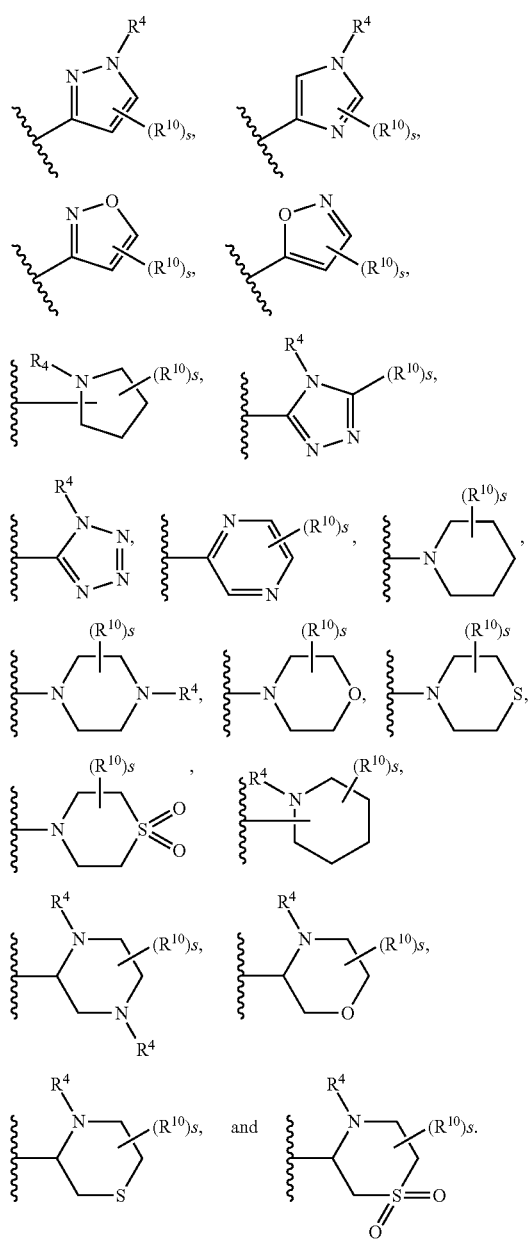
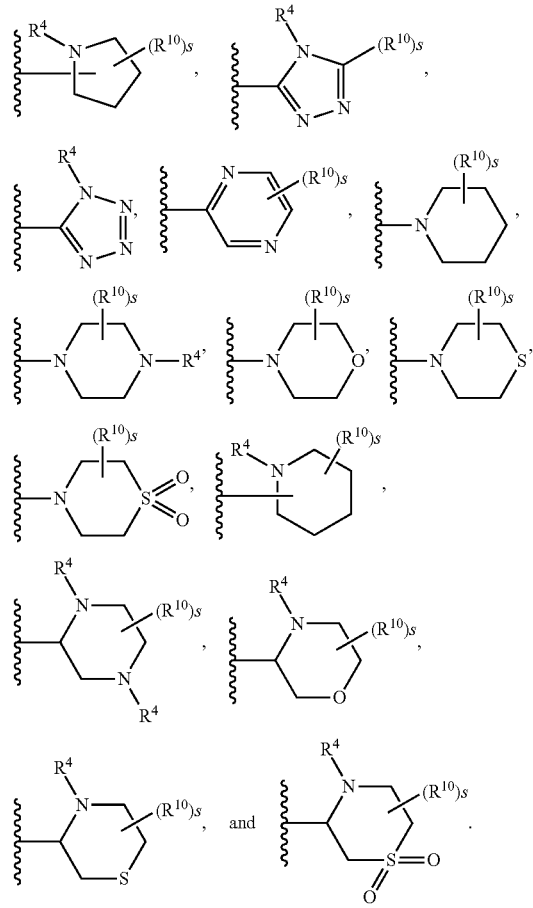
(110) The compound of any one of the above (101)-(109) or a pharmaceutically acceptable salt or solvate thereof, wherein t is 1, s is 0, 1, or 2, and the $Q_x$ ring is selected from:
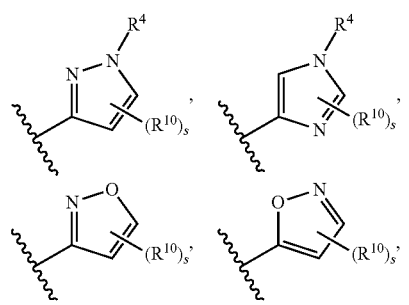
(111) The compound of any one of the above (101)-(108) or a pharmaceutically acceptable salt or solvate thereof, wherein t is 1, s is 0, 1, or 2, and the $Q_x$ ring is selected from:
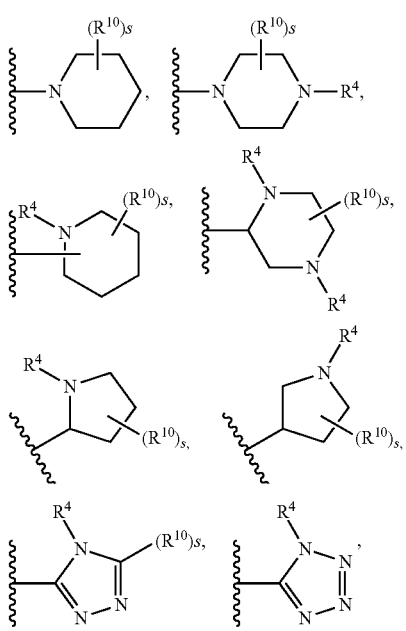

-continued

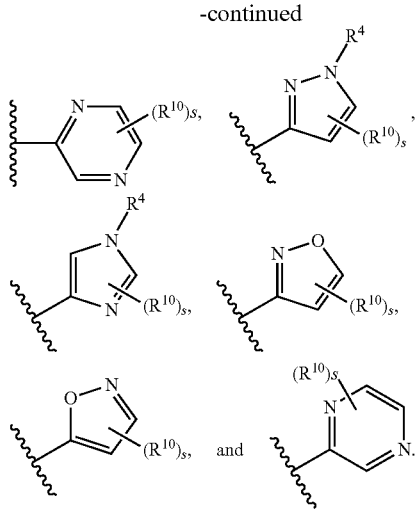

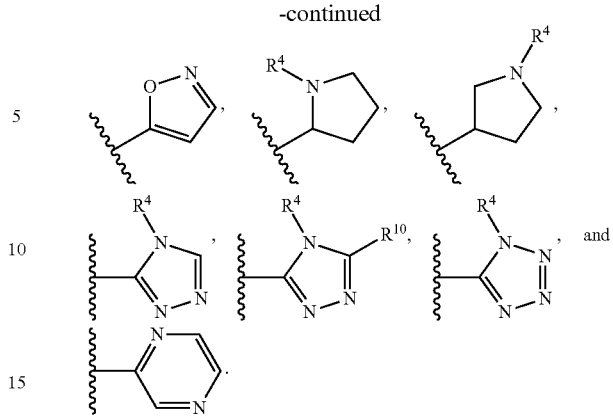

(112) The compound of any one of the above (101)-(108) or (111) or a pharmaceutically acceptable salt or solvate thereof, wherein t is 1, s is 0, 1, or 2, and the $Q_x$ ring is selected from:

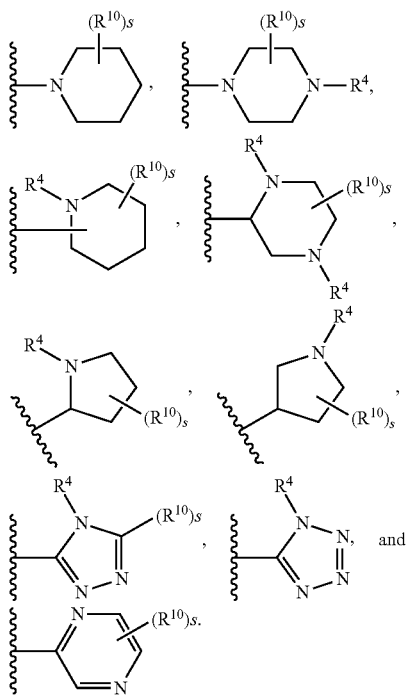

(113) The compound of any one of the above (101)-(108) or a pharmaceutically acceptable salt or solvate thereof, wherein t is 1 and the $Q_x$ ring is selected from:

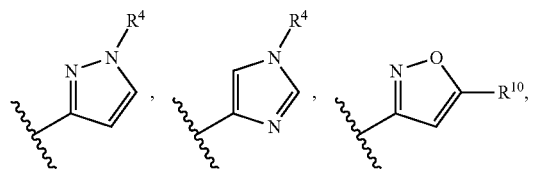

(114) The compound of any one of the above (101)-(108) or a pharmaceutically acceptable salt or solvate thereof, wherein t is 0, s is 0, 1, or 2, and the $Q_x$ ring is selected from:

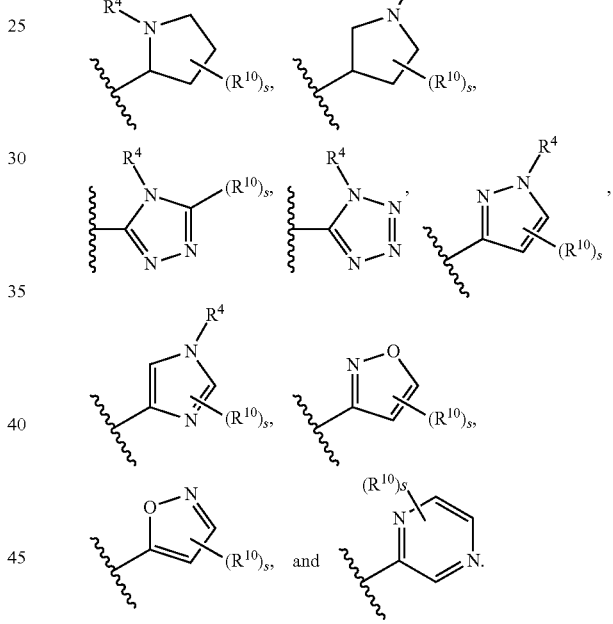

(115) The compound of any one of the above (101)-(108) or (114) or a pharmaceutically acceptable salt or solvate thereof, wherein t is 0, s is 0, 1, or 2, and the $Q_x$ ring is selected from:

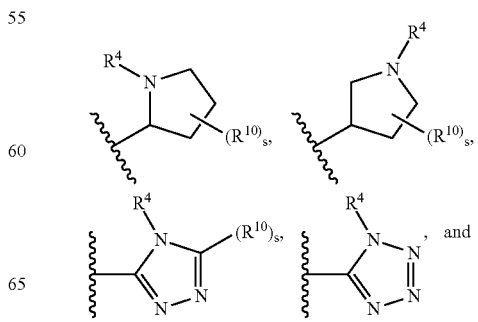

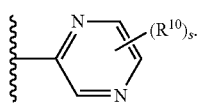

(116) The compound of any one of the above (101)-(108) or a pharmaceutically acceptable salt or solvate thereof, wherein t is 0 and the $Q_x$ ring is selected from:

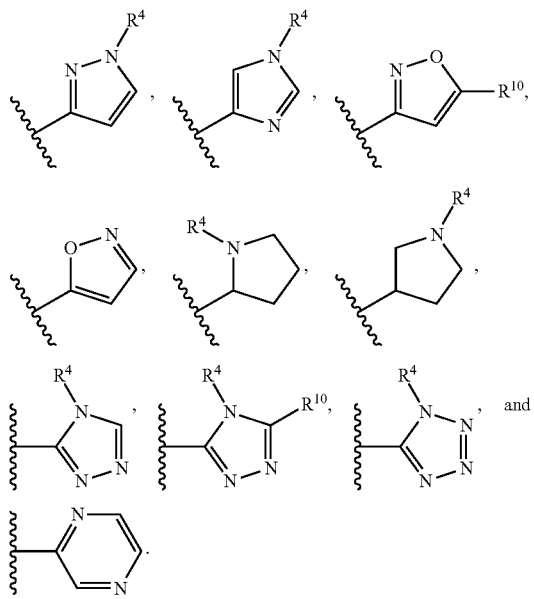

(117) The compound of any one of the above (101)-(108) or (116) or a pharmaceutically acceptable salt or solvate thereof, wherein t is 0 and the $Q_x$ ring is selected from:

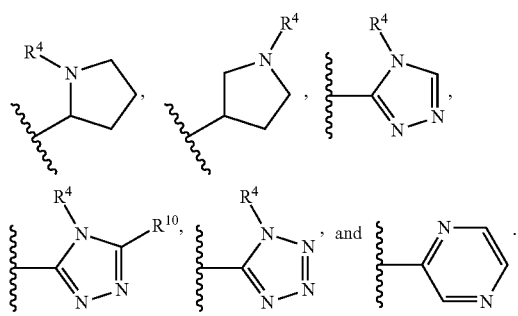

(118) The compound of any one of the above (101)-(108), (116), or (117) or a pharmaceutically acceptable salt or solvate thereof, wherein In another embodiment, t is 0 and the $Q_x$ ring is selected from:

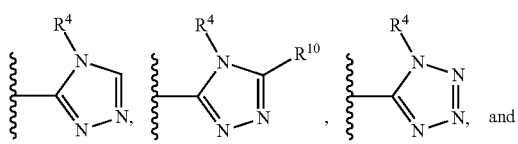

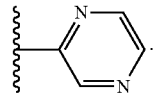

(119) The compound of any one of the above (101)-(112), (114), or (115) or a pharmaceutically acceptable salt or solvate thereof, wherein s is 0.

(120) The compound of any one of the above (101)-(119) or a pharmaceutically acceptable salt or solvate thereof, wherein the dashed line within the 5-membered, nitrogen-containing ring that is fused to the $Q_a$ ring is present to provide one bond of a double bond.

(121) The compound of any one of the above (101)-(120) or a pharmaceutically acceptable salt or solvate thereof, wherein h is 1.

(122) The compound of any one of the above (101)-(121) or a pharmaceutically acceptable salt or solvate thereof, wherein Z is —($C_1$-$C_3$)alkyl- optionally substituted by $R^{13}$.

(123) The compound of any one of the above (101)-(122) or a pharmaceutically acceptable salt or solvate thereof; wherein $R^3$ is absent.

(124) The compound of any one of the above (101)-(123) or a pharmaceutically acceptable salt or solvate thereof, wherein $R^{13}$ is absent and Z is —$CH_2$—$CH_2$—.

(125) The compound of any one of the above (101)-(124) or a pharmaceutically acceptable salt or solvate thereof, wherein —Z—$R^1$ is:

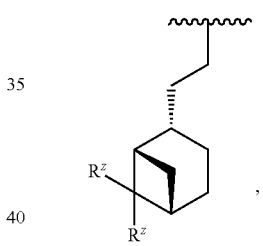

wherein each $R^z$ is independently —H, —($C_1$-$C_4$)alkyl, —OH, or —CN and preferably each $R^z$ is independently —H, —$CH_3$, or —$CH_2CH_3$.

(126) The compound of any one of the above (101)-(120) or a pharmaceutically acceptable salt or solvate thereof, wherein h is 0.

(127) The compound of any one of the above (101)-(126) or a pharmaceutically acceptable salt or solvate thereof, wherein A and B are independently —H or —($C_1$-$C_6$)alkyl and preferably A and B are each —H or A is —H and B is —$CH_3$ or A is —$CH_3$ and B is —H.

(128) The compound of any one of the above (101)-(126) or a pharmaceutically acceptable salt or solvate thereof, wherein A and B together form a bridge such that the bridged-piperidine is:

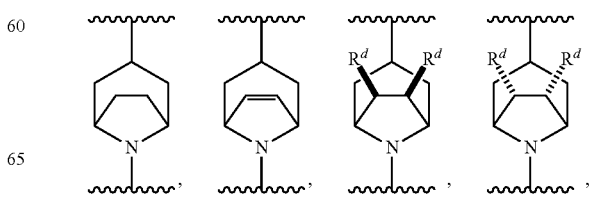

-continued

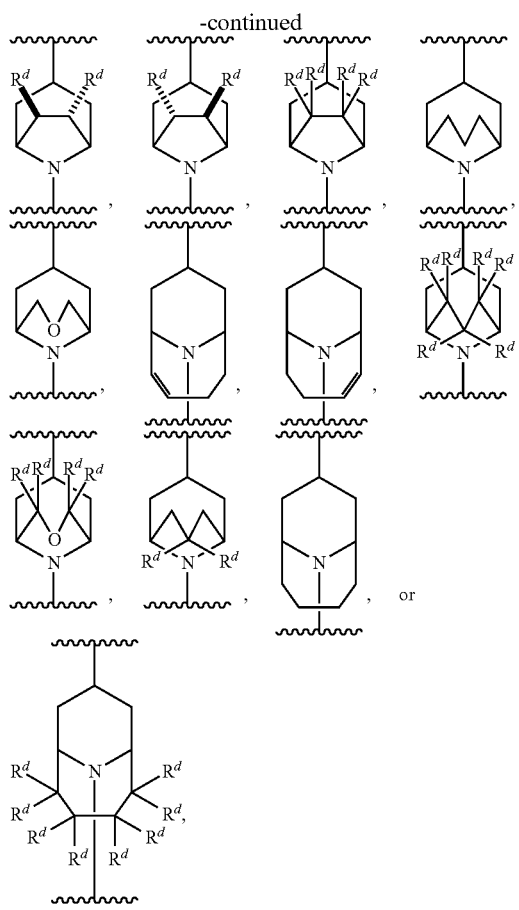

wherein each $R^d$ is independently —H, —($C_1$-$C_4$)alkyl, -halo, or —C(halo)$_3$.

(129) The compound of any one of the above (101)-(126) or (128) or a pharmaceutically acceptable salt or solvate thereof, wherein A and B together form a bridge such that the bridged-piperidine is:

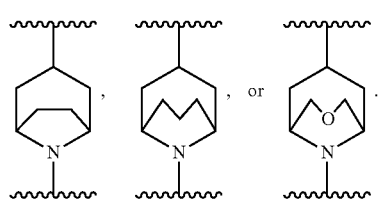

(130) The compound of any one of the above (101)-(126), (128), or (129) or a pharmaceutically acceptable salt or solvate thereof, wherein A and B together form a bridge such that the bridged-piperidine is:

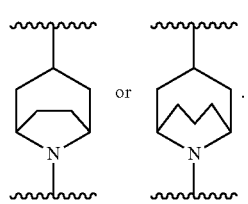 [SMILES: *C1CC2CCC(C1)N2* ; *C1CC2CCCC(C1)N2*]

(131) The compound of any one of the above (101)-(126) or (128)-(130) or a pharmaceutically acceptable salt or solvate thereof, wherein the A-B bridge of the bridged-piperidine is in the endo-configuration with respect to the 5-membered, nitrogen-containing ring that is fused to the $Q_a$ ring.

(132) The compound of any one of the above (101)-(120) or (126)-(131) or a pharmaceutically acceptable salt or solvate thereof, wherein:

(a) h is 0;

(b) $R^1$ is —($C_1$-$C_{10}$)alkyl, —($C_3$-$C_{14}$)cycloalkyl, —($C_8$-$C_{14}$)cycloalkenyl, —($C_6$-$C_{14}$)bicycloalkyl, —($C_7$-$C_{14}$)bicycloalkenyl, or —($C_8$-$C_{20}$)tricycloalkyl, each of which is unsubstituted or substituted with 1, 2, 3, or 4 independently selected $R^8$ groups and preferably $R^1$ is —($C_3$-$C_{14}$)cycloalkyl, —($C_5$-$C_{14}$)cycloalkenyl, —($C_6$-$C_{14}$)bicycloalkyl, —($C_7$-$C_{14}$)bicycloalkenyl, or —($C_8$-$C_{20}$)tricycloalkyl, each of which is unsubstituted or substituted with 1, 2, 3, or 4 independently selected $R^8$ groups; and (c) each $R^8$ is independently —($C_1$-$C_4$)alkyl, —($C_1$-$C_6$)alkyl-C(=O)O$R^9$, —N($R^9$)($C_1$-$C_6$)alkyl-C(=O)O$R^9$, —O$R^9$, —C(halo)$_3$, —CH(halo)$_2$, —CH$_2$(halo), -halo, —N($R^9$)$_2$, —C(=O)N($T^1$)($T^2$), or —C(=O)O$R^9$.

(133) The compound of any one of the above (101)-(120) or (126)-(132) or a pharmaceutically acceptable salt or solvate thereof, wherein —Z—$R^1$ is:

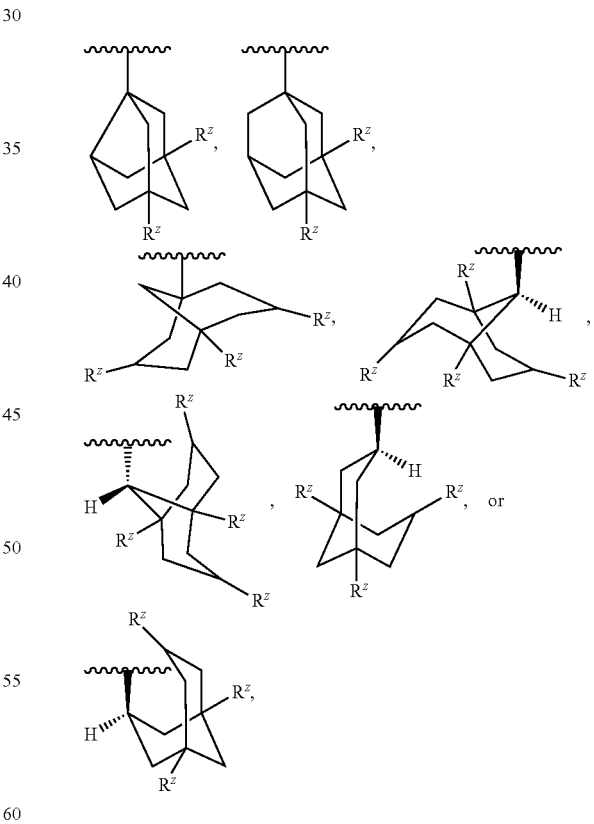

wherein each $R^z$ is independently —H, —OH, or —CN and preferably each $R^z$ is independently —H, —CH$_3$, or —CH$_2$CH$_3$.

(134) The compound of any one of the above (101)-(120) or (126)-(132) or a pharmaceutically acceptable salt or solvate thereof, wherein —Z—$R^1$ is:

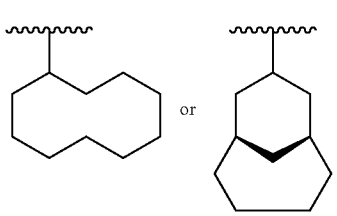

(135) The compound of any one of the above (101)-(120) or (126)-(133) or a pharmaceutically acceptable salt or solvate thereof, wherein —Z—R¹ is:

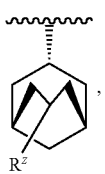

wherein R$^z$ is —H, —CH$_3$, or —CH$_2$CH$_3$.

(136) The compound of any one of the above (101)-(103) or (106)-(135) or a pharmaceutically acceptable salt or solvate thereof, wherein a is 1 and R² is -halo, preferably R² is —F.

(137) The compound of any one of the above (101)-(120) or (126)-(136) or a pharmaceutically acceptable salt or solvate thereof, wherein the R¹ group is in the exo-configuration with respect to the A-B bridge of the bridged piperidine.

(138) The compound of any one of the above (101)-(104), (106)-(124), (126)-(132), (136), or (137) or a pharmaceutically acceptable salt or solvate thereof, wherein R¹ is selected from:
(a) -halo, —CN, —OH, —CH$_2$OH, —CH$_2$CH$_2$OH, —NO$_2$, —N(R$^6$)$_2$, —S(=O)NH$_2$, —S(=O)$_2$NH$_2$, —C(=O)OV¹, and —C(=O)CN; and
(b) —(C$_2$-C$_{10}$)alkyl, —(C$_2$-C$_{10}$)alkenyl, —(C$_2$-C$_{10}$)alkynyl, —O(C$_1$-C$_6$)alkyl, —(C$_3$-C$_7$)cycloalkoxy, —(C$_6$-C$_{14}$)bicycloalkyl, —(C$_8$-C$_{20}$)tricycloalkyl, —(C$_5$-C$_{10}$)cycloalkenyl, —(C$_7$-C$_{14}$)bicycloalkenyl, —(C$_8$-C$_{20}$)tricycloalkenyl, -(3- to 5-membered)heterocycle, and -(7-membered)heterocycle, each of which is unsubstituted or substituted with 1, 2, 3, or 4 independently selected R⁸ groups; and
(c)

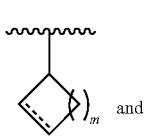 (i')

and

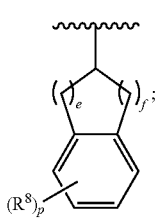 (ii)

and
(d) -naphthalenyl, —(C$_{14}$)aryl, and -(5- to 10-membered)heteroaryl, each of which is unsubstituted or substituted with 1, 2, 3, or 4 independently selected R⁷ groups.

(139) The compound of any one of the above (101)-(104), (106)-(122), (126)-(131), or (136) or a pharmaceutically acceptable salt or solvate thereof, wherein R¹³ is selected from:
(a) -halo, —CN, —OH, —CH$_2$OH, —CH$_2$CH$_2$OH, —NO$_2$, —N(R$^6$)$_2$, —S(=O)NH$_2$, —S(=O)$_2$NH$_2$, —C(=O)OV¹, and —C(=O)CN; and
(b) —(C$_2$-C$_{10}$)alkyl, —(C$_2$-C$_{10}$)alkenyl, —(C$_2$-C$_{10}$)alkynyl, —O(C$_1$-C$_6$)alkyl, —(C$_3$-C$_7$)cycloalkoxy, —(C$_5$-C$_{10}$)cycloalkenyl, and -(3- to 7-membered)heterocycle, each of which is unsubstituted or substituted with 1, 2, 3, or 4 independently selected R⁸ groups; and
(c)

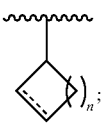 (iv')

and
(d) -(5- to 10-membered)heteroaryl, each of which is unsubstituted or substituted with 1, 2, or 3 independently selected R⁷ groups.

(140) The compound of any one of the above (101)-(139) or a pharmaceutically acceptable salt or solvate thereof, which is radiolabeled.

(141) The compound of any one of the above (101)-(140), wherein the pharmaceutically acceptable salt is a hydrochloride-salt, a sodium-salt, a potassium-salt, or a para-toluenesulfonic acid-salt.

(142) The compound of any one of the above (101)-(141) or a pharmaceutically acceptable salt thereof, wherein the % de of the compound is at least about 95%.

(143) The compound of the above (142) or a pharmaceutically acceptable salt thereof, wherein the % de of the compound is at least about 99%.

(144) A composition comprising an effective amount of the compound or a pharmaceutically acceptable salt or solvate of the compound of any one of the above (101)-(143) and a pharmaceutically acceptable carrier or excipient.

(145) A method for preparing a composition, comprising the step of admixing a compound or a pharmaceutically acceptable salt or solvate of the compound of any one of the above (101)-(143) and a pharmaceutically acceptable carrier or excipient.

(146) A method for modulating ORL-1 receptor function in a cell, comprising contacting a cell capable of expressing the ORL-1 receptor with an effective amount of the composition or the compound or a pharmaceutically acceptable salt or solvate of the compound of any one of the above (101)-(144).

(147) The method of the above (146) wherein the composition or the compound or the pharmaceutically acceptable salt or solvate of the compound acts as an agonist at the ORL-1 receptor.

(148) The method of the above (146), wherein the composition or the compound or the pharmaceutically acceptable salt or solvate of the compound acts as a partial agonist at the ORL-1 receptor.

(149) A method for treating pain in an animal, comprising administering to an animal in need thereof an effective amount of the composition or the compound or a pharmaceutically acceptable salt or solvate of the compound of any one of the above (101)-(144).

(150) A method for treating a memory disorder, obesity, constipation, depression, dementia, Parkinsonism, anxiety, cough, diarrhea, high blood pressure, epilepsy, anorexia/cachexia, urinary incontinence, or drug abuse in an animal, comprising administering to an animal in need thereof an effective amount of the composition or the compound or a pharmaceutically acceptable salt or solvate of the compound of any one of the above (101)-(144).

(151) Use of a compound or the pharmaceutically acceptable salt or solvate of the compound of any one of the above (101)-(143) for the manufacture of a medicament useful for treating pain, a memory disorder, obesity, constipation, depression, dementia, Parkinsonism, anxiety, cough, diarrhea, high blood pressure, epilepsy, anorexia/cachexia, urinary incontinence, or drug abuse.

(152) The compound or the pharmaceutically acceptable salt or solvate of the compound of any one of the above (101)-(143) for use in the treatment of pain, a memory disorder, obesity, constipation, depression, dementia, Parkinsonism, anxiety, cough, diarrhea, high blood pressure, epilepsy, anorexia/cachexia, urinary incontinence, or drug abuse.

(153) A kit, comprising a container containing an effective amount of the composition or the compound or a pharmaceutically acceptable salt or solvate of the compound of any one of the above (101)-(144).

(154) The compound of any one of the above (101)-(140) or (142)-(153), wherein the compound is present as a pharmaceutically acceptable salt.

(200) A compound of formula (I*)

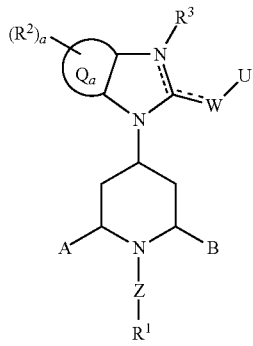

(I*)

or a pharmaceutically acceptable salt or solvate thereof wherein:
the $Q_a$ ring is fused benzo or fused (5- or 6-membered) heteroaryl;
each $R^2$ is independently selected from:
(a) -halo, —CN, —NO$_2$, —OT$^3$, —C(=O)T$^3$, —C(=O)OT$^3$, —C(=O)N(T$^1$)(T$^2$), —S(=O)$_2$OT$^3$, —S(=O)T$^3$, —S(=O)$_2$T$^3$, —O—S(=O)$_2$T$^3$, —S(=O)$_2$N(T$^1$)(T$^2$), —N(T$^1$)(T$^2$), —N(T$^3$)C(=O)T$^3$, —N(T$^3$)C(=O)N(T$^1$)(T$^2$), —N(T$^3$)S(=O)T$^3$, —N(T$^3$)S(=O)$_2$T$^3$, —N(T$^3$)C(=O)OT$^3$, and —N(T$^3$)S(=O)$_2$N(T$^1$)(T$^2$); and
(b) —(C$_1$-C$_6$)alkyl, —(C$_2$-C$_6$)alkenyl, —(C$_2$-C$_6$)alkynyl, —(C$_1$-C$_6$)alkoxy, —(C$_3$-C$_7$)cycloalkyl, —(C$_6$-C$_{10}$)bicycloalkyl, —(C$_5$-C$_{10}$)cycloalkenyl, —(C$_7$-C$_{10}$)bicycloalkenyl, and -(5- or 6-membered)heterocycle, each of which is unsubstituted or substituted with 1, 2, or 3 independently selected $R^8$ groups; and
(c) -phenyl, -naphthalenyl, and -(5- or 6-membered)heteroaryl, each of which is unsubstituted or substituted with 1, 2, or 3 independently selected $R^7$ groups;
each dashed line denotes the presence or absence of a bond, provided that:
(a) one dashed line must denote the presence of a bond;
(b) when one dashed line denotes the presence of a bond then the other dashed line denotes the absence of a bond;
(c) when the dashed line within the 5-membered, nitrogen-containing ring that is fused to the $Q_a$ ring is present, then $R^3$ is absent; and
(d) when the dashed line within the 5-membered, nitrogen-containing ring that is fused to the $Q_a$ ring is absent, then $R^3$ is present;
$R^3$, when present, is:
(a) —H; or
(b) —(C$_1$-C$_4$)alkyl which is unsubstituted or substituted with 1, 2, or 3 groups independently selected from —OH, —(C$_1$-C$_4$)alkoxy, —N(R$^6$)$_2$, —C(=O)OR$^9$, and —C(=O)N(R$^6$)$_2$; or
(c) —(C$_3$-C$_7$)cycloalkyl which is unsubstituted or substituted with 1, 2, or 3 groups independently selected from —OH, —(C$_1$-C$_4$)alkyl, —(C$_1$-C$_4$)alkoxy, —N(R$^6$)$_2$, —C(=O)OR$^9$, and —C(=O)N(R$^6$)$_2$;
---W--- is a single bond, a double bond, =CH—, —CH$_2$—, =N—, —NH—, —O—, =CH—(C$_1$-C$_3$)alkylene-, —CH$_2$—(C$_1$-C$_3$)alkylene-, =N—(C$_1$-C$_3$)alkylene-, —NH—(C$_1$-C$_3$)alkylene-, —O—(C$_1$-C$_3$)alkylene-, =CH—(C$_2$-C$_3$)alkenylene-, —CH$_2$—(C$_2$-C$_3$)alkenylene-, =N—(C$_2$-C$_3$)alkenylene-, —NH—(C$_2$-C$_3$)alkenylene-, —O—(C$_2$-C$_3$)alkenylene-, =CH—(C$_1$-C$_3$)alkylene-N(R$^{11}$)—, —CH$_2$—(C$_1$-C$_3$)alkylene-N(R$^{11}$)—, =N—(C$_1$-C$_3$)alkylene-N(R$^{11}$)—, —NH—(C$_1$-C$_3$)alkylene-N(R$^{11}$)—, —O—(C$_1$-C$_3$)alkylene-N(R$^{11}$)—, =CH—N(R$^{11}$)—, —CH=N—, —CH$_2$—N(R$^{11}$)—, =CH—O—, —CH$_2$—O—, =CH—O—(C$_1$-C$_3$)alkylene-, or —CH$_2$—O—(C$_1$-C$_3$)alkylene-;
U is:
(a) —R$^{15}$; or
(b)

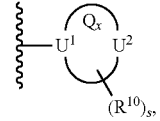

wherein when ---W--- is a single bond or a double bond the $Q_x$ ring is a -(3-, 4-, 5-, 6-, or 7-membered)heterocycle containing 1, 2, 3, or 4 ring heteroatoms independently selected from N, N(R$^4$), O, and S, wherein said heterocycle is unsubstituted or substituted with (R$^{10}$)$_s$, provided that at least one ring heteroatom is N or N(R$^4$) and wherein either U$^1$ is N and U$^2$ is a bond or U$^1$ is C or CH and U$^2$ is N or N(R$^4$), provided that;
(1) when ---W--- is a double bond and the $Q_x$ ring is present, U$^1$ is C; and
(2) when ---W--- is =CH—, —CH$_2$—, =CH—(C$_1$-C$_3$) alkylene-, or —CH$_2$—(C$_1$-C$_3$)alkylene- and the $Q_x$ ring is present, the $Q_x$ ring is a -(5- or 6-membered)heterocycle selected from:

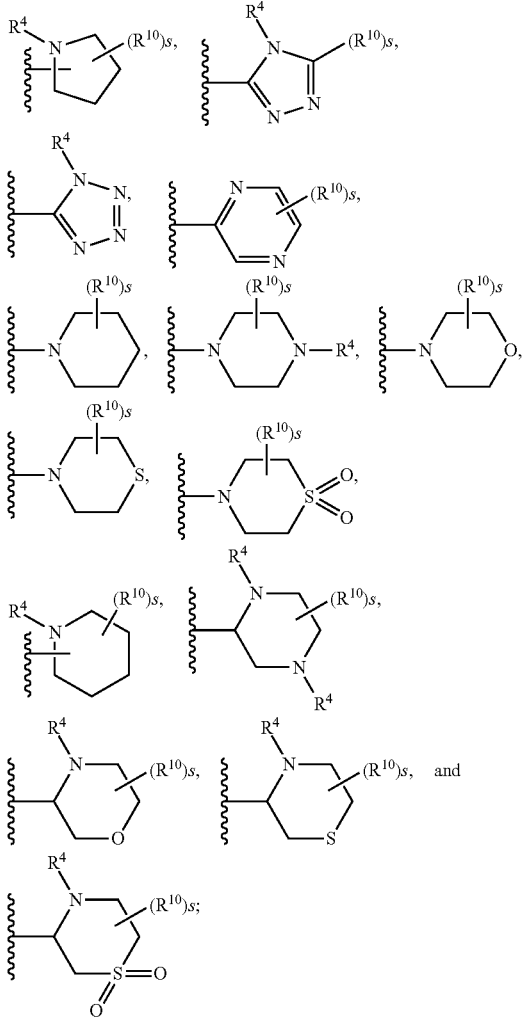

and (3) when ---W— is =N—, —NH—, —O—, =N—(C$_1$-C$_3$)alkylene-, —NH—(C$_1$-C$_3$)alkylene-, —O—(C$_1$-C$_3$)alkylene-, =CH—(C$_2$-C$_3$)alkenylene-, —CH$_2$—(C$_2$-C$_3$)alkenylene-, =N—(C$_2$-C$_3$)alkenylene-, —NH—(C$_2$-C$_3$)alkenylene-, —O—(C$_2$-C$_3$)alkenylene-, =CH—(C$_1$-C$_3$)alkylene-N(R$^{11}$)—, —CH$_2$—(C$_1$-C$_3$)alkylene-N(R$^{11}$)—, =N—(C$_1$-C$_3$)alkylene-N(R$^{11}$)—, —NH—(C$_1$-C$_3$)alkylene-N(R$^{11}$)—, —O—(C$_1$-C$_3$)alkylene-N(R$^{11}$)—, =CH—N(R$^{11}$)—, —CH$_2$—N(R$^{11}$)—, =CH—O—, —CH$_2$—O—, =CH—O—(C$_1$-C$_3$)alkylene-, or —CH$_2$—O—(C$_1$-C$_3$)alkylene-, then the Q$_x$ ring is absent;

each R$^4$, when present, is independently selected from:
(a) —H; and
(b) —X, —(C$_1$-C$_6$)alkyl-X, -(5- or 6-membered)heterocycle-X, or -(5- or 6-membered)heterocycle-(C$_1$-C$_6$)alkyl-X; and
(c) —(CH$_2$)$_d$—C(=Y)CN, —(CH$_2$)$_d$—C(=Y)X, —(CH$_2$)$_d$—C(=Y)T$^3$, —(CH$_2$)$_d$—C(=Y)YX, —(CH$_2$)$_d$—C(=Y)YT$^3$, —(CH$_2$)$_d$—C(=Y)N(T$^1$)(T$^2$), —(CH$_2$)$_d$—C(=Y)N(R$^9$)CN, —(CH$_2$)$_d$—C(=Y)N(R$^9$)X, —(CH$_2$)$_d$—C(=Y)N(R$^9$)YH, —(CH$_2$)$_d$—C(=Y)N(R$^9$)YX, —(CH$_2$)$_d$—C(=Y)N(R$^9$)YCH$_2$X, —(CH$_2$)$_d$—C(=Y)N(R$^9$)YCH$_2$CH$_2$X, —(CH$_2$)$_d$—C(=Y)N(R$^9$)S(=O)$_2$T$^3$, —(CH$_2$)$_d$—N(R$^9$)S(=O)$_2$T$^3$, or —(CH$_2$)$_d$S(=O)$_2$T$^4$; and (d) —[CH$_2$—O]$_b$—R$^{16}$, —[CH(CH$_3$)—O]$_b$—R$^{16}$, —[CH$_2$—CH$_2$—O]$_b$—R$^{16}$, —[CH(CH$_3$)—CH$_2$—O]$_b$—R$^{16}$, —[CH$_2$—CH(CH$_3$)—O]$_b$—R$^{16}$, —[CH$_2$—CH$_2$—CH$_2$—O]$_b$—R$^{16}$, —[CH(CH$_3$)—CH$_2$—CH$_2$—O]$_b$—R$^{16}$, —[CH$_2$—CH(CH$_3$)—CH$_2$—O]$_b$—R$^{16}$, or —[CH$_2$—CH$_2$—CH(CH$_3$)—O]$_b$—R$^{16}$;

X is selected from:
(a) —H, —(C$_1$-C$_6$)alkyl, —(C$_2$-C$_6$)alkenyl, —(C$_2$-C$_6$)alkynyl, —(C$_1$-C$_6$)alkoxy, —(C$_3$-C$_7$)cycloalkyl, —(C$_5$-C$_{10}$)cycloalkenyl, and -(5- or 6-membered)heterocycle, each of which is unsubstituted or substituted with 1, 2, or 3 independently selected R$^8$ groups; and
(b) -phenyl and -(5- or 6-membered)heteroaryl, each of which is unsubstituted or substituted with 1, 2, or 3 independently selected R$^7$ groups;

each Y is independently O or S;
each R$^{16}$ is independently H or CH$_3$;
s is an integer selected from 0, 1, 2, 3, and 4;
when s is 1, 2, 3, or 4, each R$^{10}$ is independently —F, —Cl, —CH$_3$, —CH$_2$CH$_3$, —OCH$_3$, —OCH$_2$CH$_3$, —(CH$_2$)$_d$—C(=Y)YT$^3$, or —(CH$_2$)$_d$—C(=Y)N(T$^1$)(T$^2$), and when s is 2, 3, or 4, each R$^{10}$ is independently —F, —Cl, —CH$_3$, —CH$_2$CH$_3$, —OCH$_3$, —OCH$_2$CH$_3$, —(CH$_2$)$_d$—C(=Y)YT$^3$, or —(CH$_2$)$_d$—C(=Y)N(T$^1$)(T$^2$) or two R$^{10}$ groups attached to the same carbon atom and are gem-dimethyl, gem-difluoro, =O, or =S;

A and B are independently selected from:
(a) —H; and
(b) —(C$_1$-C$_6$)alkyl, —(C$_2$-C$_6$)alkenyl, and —(C$_1$-C$_6$)alkoxy, each of which is unsubstituted or substituted with 1 or 2 substituents independently selected from —OH, —S(=O)$_2$NH$_2$, —C(=O)OT$^3$, —C(=O)N(R$^6$)$_2$, and —N(R$^6$)C(=O)R$^9$, or 1, 2, or 3 independently selected -halo; or
(c) A-B can together form a (C$_2$-C$_6$)bridge, which is unsubstituted or substituted with 1, 2, 3, 4, 5, 6, 7, or 8 substituents independently selected from —OH, —(C$_1$-C$_4$)alkyl, -halo, and —C(halo)$_3$, and which bridge optionally contains —HC=CH— or —O— within the (C$_2$-C$_6$)bridge; wherein the 5-membered nitrogen-containing ring that is fused to the Q$_a$ ring can be in the endo- or exo-configuration with respect to the A-B bridge;

Z is —[(C$_1$-C$_{10}$)alkyl optionally substituted by R$^{13}$]$_h$—, wherein h is 0 or 1; or —[(C$_2$-C$_{10}$)alkenyl optionally substituted by R$^{13}$]—, or —[(C$_1$-C$_{10}$)alkyl-NR$^6$C(=Y)]—;

R$^1$ is selected from:
(a) —H, -halo, —CN, —OH, —CH$_2$OH, —CH$_2$CH$_2$OH, —NO$_2$, —N(R$^6$)$_2$, —S(=O)NH$_2$, —S(=O)$_2$NH$_2$, —C(=O)OV$^1$, and —C(=O)CN; and
(b) —(C$_1$-C$_{10}$)alkyl, —(C$_2$-C$_{10}$)alkenyl, —(C$_2$-C$_{10}$)alkynyl, —O(C$_1$-C$_6$)alkyl, —(C$_3$-C$_7$)cycloalkoxy, —(C$_6$-C$_{14}$)bicycloalkyl, —(C$_8$-C$_{20}$)tricycloalkyl, —(C$_8$-C$_{10}$)cycloalkenyl, —(C$_7$-C$_{14}$)bicycloalkenyl, —(C$_8$-C$_{20}$)tricycloalkenyl, and -(3- to 7-membered)heterocycle, each of which is unsubstituted or substituted with 1, 2, 3, or 4 independently selected R$^8$ groups; and
(c)

and

-continued

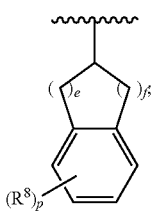
(ii)

and (d) -phenyl, -naphthalenyl, —($C_{14}$)aryl, and -(5- to 10-membered)heteroaryl, each of which is unsubstituted or substituted with 1, 2, 3, or 4 independently selected $R^7$ groups;

each $R^5$ is independently —($C_1$-$C_4$)alkyl, —($C_2$-$C_6$)alkenyl, —($C_2$-$C_6$)alkynyl, -(5- or 6-membered)heteroaryl, —($C_1$-$C_6$)alkyl-C(=O)O$R^9$, —O$R^9$, —S$R^9$, —C(halo)$_3$, —CH(halo)$_2$, —CH$_2$(halo), —CN, =O, =S, -halo, —$N_3$, —$NO_2$, —CH=N($R^9$), —N($R^9$)($C_1$-$C_6$)alkyl-C(=O)O$R^9$, —N($R^9$)$_2$, —N($R^9$)OH, —N($R^9$)S(=O)$R^{12}$, —N($R^9$)S(=O)$_2R^{12}$, —N($R^9$)C(=O)$R^{12}$, —N($R^9$)C(=O)O$R^{12}$, —C(=O)$R^9$, —C(=O)O$R^9$, —OC(=O)$R^9$, —OC(=O)O$R^9$, —S(=O)$R^9$, or —S(=O)$_2R^9$;

each $R^6$ is independently —H, —($C_1$-$C_6$)alkyl, or —($C_3$-$C_7$)cycloalkyl, or two $R^6$ groups attached to the same nitrogen atom can together form a -(5- to 8-membered)heterocyclic ring, wherein the number of atoms in the ring includes the nitrogen atom, and in which one of the -(5- to 8-membered)heterocyclic ring carbon atoms is optionally replaced by O, S, or N($T^3$);

each $R^7$ is independently —($C_1$-$C_4$)alkyl, —($C_2$-$C_6$)alkenyl, —($C_2$-$C_6$)alkynyl, —O$R^9$, —S$R^9$, —C(halo)$_3$, —CH(halo)$_2$, —CH$_2$(halo), —CN, -halo, —$N_3$, —$NO_2$, —CH=N($R^9$), —N($R^9$)$_2$, —N($R^9$)OH, —N($R^9$)S(=O)$R^{12}$, —N($R^9$)S(=O)$_2R^{12}$, —N($R^9$)C(=O)$R^{12}$, —N($R^9$)C(=O)N($T^1$)($T^2$), —N($R^9$)C(=O)O$R^{12}$, —C(=O)$R^9$, —C(=O)N($T^1$)($T^2$), —C(=O)O$R^9$, —OC(=O)$R^9$, —OC(=O)N($T^1$)($T^2$), —OC(=O)O$R^9$, —S(=O)$R^9$, or —S(=O)$_2R^9$;

each $R^8$ is independently —($C_1$-$C_4$)alkyl, —($C_2$-$C_6$)alkenyl, —($C_2$-$C_6$)alkynyl, -(5- or 6-membered)heteroaryl, —($C_1$-$C_6$)alkyl-C(=O)O$R^9$, —N($R^9$)($C_1$-$C_6$)alkyl-C(=O)O$R^9$, —O$R^9$, —S$R^9$, —C(halo)$_3$, —CH(halo)$_2$, —CH$_2$(halo), —CN, =O, =S, =N($R^9$), -halo, —$N_3$, —$NO_2$, —CH=N($R^9$), —N($R^9$)$_2$, —N($R^9$)O$R^9$, —N($R^9$)S(=O)$R^{12}$, —N($R^9$)S(=O)$_2R^{12}$, —N($R^9$)C(=O)$R^{12}$, —N($R^9$)C(=O)N($T^1$)($T^2$), —N($R^9$)C(=O)O$R^{12}$, —C(=O)$R^9$, —C(=O)N($T^1$)($T^2$), —C(=O)O$R^9$, —OC(=O)$R^9$, —OC(=O)N($T^1$)($T^2$), —OC(=O)O$R^9$, —S(=O)$R^9$, or —S(=O)$_2R^9$;

each $R^9$ is independently —H, —($C_1$-$C_6$)alkyl, —($C_2$-$C_6$)alkenyl, —($C_2$-$C_6$)alkynyl, —($C_3$-$C_8$)cycloalkyl, —($C_5$-$C_8$)cycloalkenyl, -phenyl, -benzyl, -(3- to 7-membered)heterocycle, —C(halo)$_3$, —CH(halo)$_2$, or —CH$_2$(halo);

$R^{11}$ is —H, —CN, or —C(=O)N($R^6$)$_2$ or $R^{11}$ is —($C_1$-$C_4$)alkyl which is unsubstituted or substituted with —OH, —($C_1$-$C_4$)alkoxy, or —N($R^6$)$_2$;

each $R^{12}$ is independently —H or —($C_1$-$C_4$)alkyl;

$R^{13}$ is selected from:

(a) -halo, —CN, —OH, —CH$_2$OH, —CH$_2$CH$_2$OH, —$NO_2$, —N($R^6$)$_2$, —S(=O)NH$_2$, —S(=O)$_2$NH$_2$, —C(=O)O$V^1$, and —C(=O)CN; and (b) —($C_1$-$C_{10}$)alkyl, —($C_2$-$C_{10}$)alkenyl, —($C_2$-$C_{10}$)alkynyl, —O($C_1$-$C_6$)alkyl, —($C_3$-$C_7$)cycloalkoxy, —($C_5$-$C_{10}$)cycloalkenyl, and -(3- to 7-membered)heterocycle, each of which is unsubstituted or substituted with 1, 2, 3, or 4 independently selected $R^8$ groups; and (c)

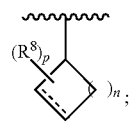
(iv)

and (d) -phenyl and -(5- to 10-membered)heteroaryl, each of which is unsubstituted or substituted with 1, 2, or 3 independently selected $R^7$ groups;

$R^{15}$, when present, is selected from:

(a) —H; and (b) —($C_1$-$C_4$)alkyl and —O—($C_1$-$C_4$)alkyl, each of which is unsubstituted or substituted with 1, 2, 3, or 4 independently selected $R^8$ groups;

(c) provided that when ---W— is a single bond, a double bond, or —O—, $R^{15}$ is not —H;

each $T^1$ and $T^2$ is independently —H or —($C_1$-$C_{10}$)alkyl which is unsubstituted or substituted with 1, 2, or 3 independently selected $R^5$ groups and, optionally, in which any —($C_1$-$C_{10}$)alkyl carbon atom except the carbon atom bonded directly to the atom to which $T^1$ or $T^2$ is attached is independently replaced by O, S, or N($R^6$), or $T^1$ and $T^2$ can together form a -(5- to 8-membered)heterocyclic ring wherein the number of atoms in the ring includes the nitrogen atom to which $T^1$ and $T^2$ are bonded, said -(5- to 8-membered)heterocyclic ring is unsubstituted or substituted with 1, 2, or 3 independently selected $R^5$ groups and, optionally, any 1 or 2 carbon atoms in said -(5- to 8-membered)heterocyclic ring is independently replaced by O, S, or N($R^6$);

each $T^3$ is independently —H or —($C_1$-$C_{10}$)alkyl which is unsubstituted or substituted with 1, 2, or 3 independently selected $R^5$ groups and, optionally, in which any —($C_1$-$C_{10}$) alkyl carbon atom except the carbon atom bonded directly to the atom to which $T^3$ is attached is independently replaced by O, S, or N($R^{12}$);

each $T^4$ is independently a -(5- or 6-membered)heteroaryl which is unsubstituted or substituted with 1 or 2 independently selected $R^{12}$ groups;

each $V^1$ is independently —H, —($C_1$-$C_6$)alkyl, —($C_3$-$C_7$) cycloalkyl, -phenyl, or -benzyl;

a is an integer selected from 0, 1, and 2;

each b is, independently, an integer selected from 1, 2, 3, 4, 5, and 6;

each d is, independently, an integer selected from 0, 1, 2, and 3;

m is an integer selected from 0, 1, 2, 3, 4, 5, 6, 7, 8, 9, 10, and 11;

n is an integer selected from 0, 1, 2, 3, 4, 5, 6, 7, 8, and 9;

e and f are each an integer independently selected from 0, 1, 2, 3, 4, and 5 provided that 2≤(e+f)≤5;

each p is an integer independently selected from 0, 1, 2, 3, and 4; and each halo is independently —F, —Cl, —Br, or —I.

(201) A compound of formula (I‡A):

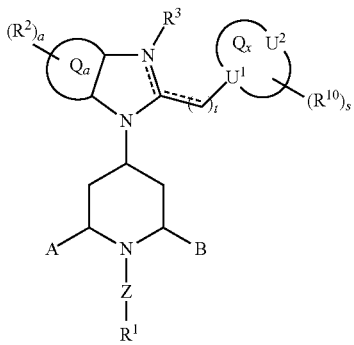

or a pharmaceutically acceptable salt or solvate thereof where:

the $Q_a$ ring is fused benzo or fused (5- or 6-membered) heteroaryl;

each $R^2$ is independently selected from:

(a) -halo, —CN, —NO$_2$, —OT$^3$, —C(=O)T$^3$, —C(=O)OT$^3$, —C(=O)N(T$^1$)(T$^2$), —S(=O)$_2$OT$^3$, —S(=O)T$^3$, —S(=O)$_2$T$^3$, —O—S(=O)$_2$T$^3$, —S(=O)$_2$N(T$^1$)(T$^2$), —N(T$^1$)(T$^2$), —N(T$^3$)C(=O)T$^3$, —N(T$^3$)C(=O)N(T$^1$)(T$^2$), —N(T$^3$)S(=O)T$^3$, —N(T$^3$)S(=O)$_2$T$^3$, —N(T$^3$)C(=O)OT$^3$, and —N(T$^3$)S(=O)$_2$N(T$^1$)(T$^2$); and (b) —(C$_1$-C$_6$)alkyl, —(C$_2$-C$_6$)alkenyl, —(C$_2$-C$_6$)alkynyl, —(C$_1$-C$_6$)alkoxy, —(C$_3$-C$_7$)cycloalkyl, —(C$_6$-C$_{10}$)bicycloalkyl, —(C$_5$-C$_{10}$)cycloalkenyl, —(C$_7$-C$_{10}$)bicycloalkenyl, and -(5- or 6-membered)heterocycle, each of which is unsubstituted or substituted with 1, 2, or 3 independently selected $R^8$ groups; and (c) -phenyl, -naphthalenyl, and -(5- or 6-membered)heteroaryl, each of which is unsubstituted or substituted with 1, 2, or 3 independently selected $R^7$ groups;

each dashed line denotes the presence or absence of a bond (i.e., when a dashed line is present there is a double bond at that position and when a dashed line is absent there is only a single bond at that position), provided that:

(a) one dashed line must denote the presence of a bond (i.e., there is a double bond at that position);

(b) when one dashed line denotes the presence of a bond (i.e., there is a double bond at that position) then the other dashed line denotes the absence of a bond (i.e., there is only a single bond at that other position);

(c) when the dashed line within the 5-membered, nitrogen-containing ring that is fused to the $Q_a$ ring is present (i.e., there is a double bond at that position), then $R^3$ is absent; and (d) when the dashed line within the 5-membered, nitrogen-containing ring that is fused to the $Q_a$ ring is absent (i.e., there is only a single bond at that position), then $R^3$ is present;

$R^3$, when present, is:

(a) —H; or (b) —(C$_1$-C$_4$)alkyl which is unsubstituted or substituted with 1, 2, or 3 groups independently selected from —OH, —(C$_1$-C$_4$)alkoxy, —N(R$^6$)$_2$, —C(=O)OR$^9$, and —C(=O)N(R$^6$)$_2$; or (c) —(C$_3$-C$_7$)cycloalkyl which is unsubstituted or substituted with 1, 2, or 3 groups independently selected from —OH, —(C$_1$-C$_4$)alkoxy, —N(R$^6$)$_2$, —C(=O)OR$^9$, and —C(=O)N(R$^6$)$_2$;

t is an integer selected from 0, 1, 2, and 3;

when t is 0, the $Q_x$ ring is a -(3-, 4-, 5-, 6-, or 7-membered) heterocycle containing 1, 2, 3, or 4 ring heteroatoms independently selected from N, N(R$^4$), O, and S wherein said heterocycle is unsubstituted or substituted with (R$^1$)$_s$ provided that at least one ring heteroatom is N or N(R$^4$) and provided that when the dashed line connecting the $Q_x$ ring to the 5-membered, nitrogen-containing ring that is fused to the $Q_a$ ring is present (i.e., there is a double bond at that position), U$^1$ is C or CH, and when t is 1, 2, or 3 the $Q_x$ ring is a (5- or 6-membered) heterocycle selected from:

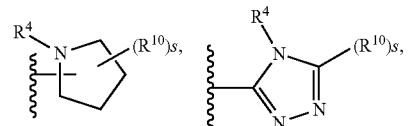

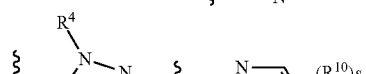

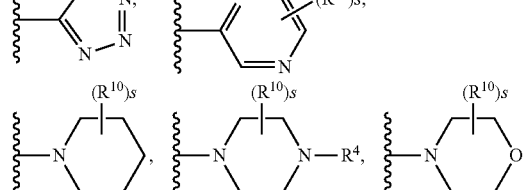

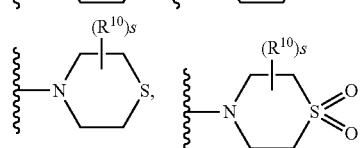

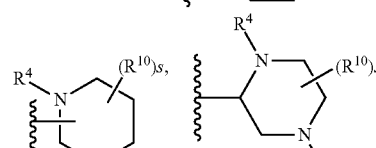

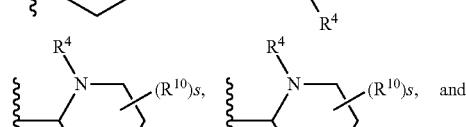

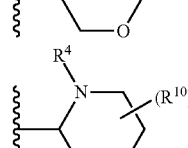

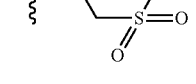

each $R^4$, when present, is independently selected from:

(a) —H; and (b) —X, —(C$_1$-C$_6$)alkyl-X, -(5- or 6-membered)heterocycle-X, or -(5- or 6-membered)heterocycle-(C$_1$-C$_6$)alkyl-X; and (c) —(CH$_2$)$_d$—C(Y)CN, —(CH$_2$)$_d$—C(Y)X, —(CH$_2$)$_d$—C(Y)T$^3$, —(CH$_2$)$_d$—C(Y)YX, —(CH$_2$)$_d$—C(=Y)YT$^3$, —(CH$_2$)$_d$—C(=Y)N(T$^1$)(T$^2$), —(CH$_2$)$_d$—C(=Y)N(R$^9$)CN, —(CH$_2$)$_d$—C(=Y)N(R$^9$)X, —(CH$_2$)$_d$—C(=Y)N(R$^9$)YH, —(CH$_2$)$_d$—C(=Y)N(R$^9$)YX, —(CH$_2$)$_d$—C(=Y)N(R$^9$)YCH$_2$X, —(CH$_2$)$_d$—C(=Y)N(R$^9$)YCH$_2$CH$_2$X, —(CH$_2$)$_d$—C(=Y)N(R$^9$)S(=O)$_2$T$^3$; —(CH$_2$)$_d$—N(R$^9$)S(=O)$_2$T$^3$; or —(CH$_2$)$_d$—S(=O)$_2$T$^4$; and (d) —[CH$_2$—O]$_b$—R$^{16}$, —[CH(CH$_3$)—O]$_b$—R$^{16}$, —[CH$_2$—CH$_2$—O]$_b$—R$^{16}$, —[CH(CH$_3$)—CH$_2$—O]$_b$—R$^{16}$, —[CH$_2$—CH(CH$_3$)—O]$_b$—R$^{16}$, —[CH$_2$—CH$_2$—CH$_2$—O]$_b$—R$^{16}$, —[CH(CH$_3$)—CH$_2$—CH$_2$—O]$_b$—R$^{16}$, —[CH$_2$—CH(CH$_3$)—CH$_2$—O]$_b$—R$^{16}$, or —[CH$_2$—CH$_2$—CH(CH$_3$)—O]$_b$—R$^{16}$;

X is selected from:

(a) —H, —(C$_1$-C$_6$)alkyl, —(C$_2$-C$_6$)alkenyl, —(C$_2$-C$_6$)alkynyl, —(C$_1$-C$_6$)alkoxy, —(C$_3$-C$_7$)cycloalkyl, —(C$_5$-C$_{10}$)cycloalkenyl, and -(5- or 6-membered)heterocycle, each of which is unsubstituted or substituted with 1, 2, or 3 independently selected R$^8$ groups; and (b) -phenyl and -(5- or 6-membered)heteroaryl, each of which is unsubstituted or substituted with 1, 2, or 3 independently selected R$^7$ groups;

each Y is independently O or S;

each R$^{16}$ is independently H or CH$_3$;

s is an integer selected from 0, 1, 2, 3, and 4;

when s is 1, 2, 3, or 4, each R$^{10}$ is independently —F, —CH$_3$, —CH$_2$CH$_3$, —OCH$_3$, —OCH$_2$CH$_3$, —(CH$_2$)$_d$—C(=Y)YT$^3$, or —(CH$_2$)$_d$—C(=Y)N(T$^1$)(T$^2$), and when s is 2, 3, or 4, each R$^{10}$ is independently —F, —Cl, —CH$_3$, —CH$_2$CH$_3$, —OCH$_3$, —OCH$_2$CH$_3$, —(CH$_2$)$_d$—C(=Y)YT$^3$, or —(CH$_2$)$_d$—C(=Y)N(T$^1$)(T$^2$) or two R$^{10}$ groups attached to the same carbon atom and are gem-dimethyl, gem-difluoro, =O, or =S;

A and B are independently selected from:

(a) —H; and (b) —(C$_1$-C$_6$)alkyl, —(C$_2$-C$_6$)alkenyl, and —(C$_1$-C$_6$)alkoxy, each of which is unsubstituted or substituted with 1 or 2 substituents independently selected from —OH, —S(=O)$_2$NH$_2$, —C(=O)OT$^3$, —C(=O)N(R$^6$)$_2$, and —N(R$^6$)C(=O)R$^9$, or 1, 2, or 3 independently selected -halo; or (c) A-B can together form a (C$_2$-C$_6$)bridge, which is unsubstituted or substituted with 1, 2, 3, 4, 5, 6, 7, or 8 substituents independently selected from —OH, —(C$_1$-C$_4$)alkyl, -halo, and —C(halo)$_3$, and which bridge optionally contains —HC=CH— or —O— within the (C$_2$-C$_6$)bridge; wherein the 5-membered, nitrogen-containing ring that is fused to the Q$_a$ ring can be in the endo- or exo-configuration with respect to the A-B bridge;

Z is —[(C$_1$-C$_{10}$)alkyl optionally substituted by R$^{13}$]$_h$—, wherein h is 0 or 1; or —[(C$_2$-C$_{10}$)alkenyl optionally substituted by R$^{13}$]—, or —[(C$_1$-C$_{10}$)alkyl-NR$^6$C(=Y)]—;

R$^1$ is selected from:

(a) —H, -halo, —CN, —OH, —CH$_2$OH, —CH$_2$CH$_2$OH, —NO$_2$, —N(R$^6$)$_2$, —S(=O)NH$_2$, —S(=O)$_2$NH$_2$, —C(=O)OV$^1$, and —C(=O)CN; and (b) —(C$_1$-C$_{10}$)alkyl, —(C$_2$-C$_{10}$)alkenyl, —(C$_2$-C$_{10}$)alkynyl, —O(C$_1$-C$_6$)alkyl, —(C$_3$-C$_7$)cycloalkoxy, —(C$_6$-C$_{14}$)bicycloalkyl, —(C$_8$-C$_{20}$)tricycloalkyl, —(C$_5$-C$_{10}$)cycloalkenyl, —(C$_7$-C$_{14}$)bicycloalkyl, —(C$_8$-C$_{20}$)tricycloalkenyl, and -(3- to 7-membered)heterocycle, each of which is unsubstituted or substituted with 1, 2, 3, or 4 independently selected R$^8$ groups; and (c)

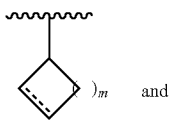

(i')

and

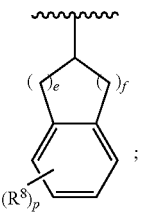

(ii)

and (d) -phenyl, -naphthalenyl, —(C$_{14}$)aryl, and -(5- to 10-membered)heteroaryl, each of which is unsubstituted or substituted with 1, 2, 3, or 4 independently selected R$^7$ groups;

each R$^5$ is independently —(C$_1$-C$_4$)alkyl, —(C$_2$-C$_6$)alkenyl, —(C$_2$-C$_6$)alkynyl, -(5- or 6-membered)heteroaryl, —(C$_1$-C$_6$)alkyl-C(=O)OR$^9$, —OR$^9$, —SR$^9$, —C(halo)$_3$, —CH(halo)$_2$, —CH$_2$(halo), —CN, =O, =S, -halo, —N$_3$, —NO$_2$, —CH=N(R$^9$), —N(R$^9$)(C$_1$-C$_6$)alkyl-C(=O)OR$^9$, —N(R$^9$)$_2$, —N(R$^9$)OH, —N(R$^9$)S(=O)R$^{12}$, —N(R$^9$)S(=O)$_2$R$^{12}$, —N(R$^9$)C(=O)R$^{12}$, —N(R$^9$)C(=O)OR$^{12}$, —C(=O)R$^9$, —C(=O)OR$^9$, —OC(=O)R$^9$, —OC(=O)OR$^9$, —S(=O)R$^9$, or —S(=O)$_2$R$^9$;

each R$^6$ is independently —H, —(C$_1$-C$_6$)alkyl, or —(C$_3$-C$_7$)cycloalkyl, or two R$^6$ groups attached to the same nitrogen atom can together form a -(5- to 8-membered)heterocyclic ring, wherein the number of atoms in the ring includes the nitrogen atom, and in which one of the -(5- to 8-membered)heterocyclic ring carbon atoms is optionally replaced by O, S, or N(T$^3$);

each R$^7$ is independently —(C$_1$-C$_4$)alkyl, —(C$_2$-C$_6$)alkenyl, —(C$_2$-C$_6$)alkynyl, —OR$^9$, —SR$^9$, —C(halo)$_3$, —CH(halo)$_2$, —CH$_2$(halo), —CN, -halo, —N$_3$, —NO$_2$, —CH=N(R$^9$), —N(R$^9$)$_2$, —N(R$^9$)OH, —N(R$^9$)S(=O)R$^{12}$, —N(R$^9$)S(=O)$_2$R$^{12}$, —N(R$^9$)C(=O)R$^{12}$, —N(R$^9$)C(=O)N(T$^1$)(T$^2$), —N(R$^9$)C(=O)OR$^{12}$, —C(=O)R$^9$, —C(=O)N(T$^1$)(T$^2$), —C(=O)OR$^9$, —OC(=O)R$^9$, —OC(=O)N(T$^1$)(T$^2$), —OC(=O)OR$^9$, —S(=O)R$^9$, or —S(=O)$_2$R$^9$;

each R$^8$ is independently —(C$_1$-C$_4$)alkyl, —(C$_2$-C$_6$)alkenyl, —(C$_2$-C$_6$)alkynyl, -(5- or 6-membered)heteroaryl, —(C$_1$-C$_6$)alkyl-C(=O)OR$^9$, —N(R$^9$)(C$_1$-C$_6$)alkyl-C(=O)OR$^9$, —OR$^9$, —SR$^9$, —C(halo)$_3$, —CH(halo)$_2$, —CH$_2$(halo), —CN, =O, =S, =N(R$^9$), -halo, —N$_3$, —NO$_2$, —CH=N(R$^9$), —N(R$^9$)$_2$, —N(R$^9$)OR$^9$, —N(R$^9$)S(=O)R$^{12}$, —N(R$^9$)S(=O)$_2$R$^{12}$, —N(R$^9$)C(=O)R$^{12}$, —N(R$^9$)C(=O)N(T$^1$)(T$^2$), —N(R$^9$)C(=O)OR$^{12}$, —C(=O)R$^9$, —C(=O)N(T$^1$)(T$^2$), —C(=O)OR$^9$, —OC(=O)R$^9$, —OC(=O)N(T$^1$)(T$^2$), —OC(=O)OR$^9$, —S(=O)R$^9$, or —S(=O)$_2$R$^9$;

each R$^9$ is independently —H, —(C$_1$-C$_6$)alkyl, —(C$_2$-C$_6$)alkenyl, —(C$_2$-C$_6$)alkynyl, —(C$_3$-C$_8$)cycloalkyl, —(C$_5$-C$_8$)cycloalkenyl, -phenyl, -benzyl, -(3- to 7-membered)heterocycle, —C(halo)$_3$, —CH(halo)$_2$, or —CH$_2$(halo);

each R$^{12}$ is independently —H or —(C$_1$-C$_4$)alkyl;

R$^{13}$ is selected from:

(a) -halo, —CN, —OH, —CH$_2$OH, —CH$_2$CH$_2$OH, —NO$_2$, —N(R$^6$)$_2$, —S(=O)NH$_2$, —S(=O)$_2$NH$_2$, —C(=O)OV$^1$, and —C(=O)CN; and (b) —(C$_1$-C$_{10}$)alkyl, —(C$_2$-C$_{10}$)alkenyl, —(C$_2$-C$_{10}$)alkynyl, —O(C$_1$-C$_6$)alkyl, —(C$_3$-C$_7$)cycloalkoxy, —(C$_5$-C$_{10}$)cycloalkenyl, and -(3- to 7-membered)heterocycle, each of which is unsubstituted or substituted with 1, 2, 3, or 4 independently selected R$^8$ groups; and (c)

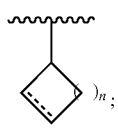

and (d) -phenyl and -(5- to 10-membered)heteroaryl, each of which is unsubstituted or substituted with 1, 2, or 3 independently selected $R^7$ groups;

each $T^1$ and $T^2$ is independently —H or —$(C_1-C_{10})$alkyl which is unsubstituted or substituted with 1, 2, or 3 independently selected $R^5$ groups and, optionally, in which any —$(C_1-C_{10})$alkyl carbon atom except the carbon atom bonded directly to the atom to which $T^1$ or $T^2$ is attached is independently replaced by O, S, or $N(R^6)$, or $T^1$ and $T^2$ can together form a -(5- to 8-membered)heterocyclic ring wherein the number of atoms in the ring includes the nitrogen atom to which $T^1$ and $T^2$ are bonded, said -(5- to 8-membered)heterocyclic ring is unsubstituted or substituted with 1, 2, or 3 independently selected $R^5$ groups and, optionally, any 1 or 2 carbon atoms in said -(5- to 8-membered)heterocyclic ring is independently replaced by O, S, or $N(R^6)$;

each $T^3$ is independently —H or —$(C_1-C_{10})$alkyl which is unsubstituted or substituted with 1, 2, or 3 independently selected $R^5$ groups and, optionally, in which any —$(C_1-C_{10})$alkyl carbon atom except the carbon atom bonded directly to the atom to which $T^3$ is attached is independently replaced by O, S, or $N(R^{12})$;

each $T^4$ is independently a -(5- or 6-membered)heteroaryl which is unsubstituted or substituted with 1 or 2 independently selected $R^{12}$ groups;

each $V^1$ is independently —H, —$(C_1-C_6)$alkyl, —$(C_3-C_7)$cycloalkyl, -phenyl, or -benzyl;

a is an integer selected from 0, 1, and 2;

each b is, independently, an integer selected from 1, 2, 3, 4, 5, and 6;

each d is, independently, an integer selected from 0, 1, 2, and 3;

m is an integer selected from 0, 1, 2, 3, 4, 5, 6, 7, 8, 9, 10, and 11;

n is an integer selected from 0, 1, 2, 3, 4, 5, 6, 7, 8, and 9;

e and f are each an integer independently selected from 0, 1, 2, 3, 4, and 5 provided that $2 \leq (e+f) \leq 5$;

each p is an integer independently selected from 0, 1, 2, 3, and 4; and each halo is independently —F, —Cl, —Br, or —I.

(202) The compound of the above (200) or (201) or a pharmaceutically acceptable salt or solvate thereof, wherein $Q_a$ is benzo, pyridino, pyrimidino, pyrazino, or pyridazino, and preferably $Q_a$ is benzo or pyridino, wherein preferably the 2- and 3-positions of the pyridino are fused to the 5-membered, nitrogen-containing ring.

(203) The compound of the above (200) or (202) or a pharmaceutically acceptable salt or solvate thereof, wherein $Q_a$ is benzo.

(204) The compound of any one of the above (200)-(203) or a pharmaceutically acceptable salt or solvate thereof, wherein a is 0.

(205) The compound of any one of the above (200)-(204) or a pharmaceutically acceptable salt or solvate thereof, wherein:

$Q_a$ is benzo;

a is 0;

A-B together form a $(C_2-C_6)$bridge, which is unsubstituted or substituted with 1, 2, 3, 4, 5, 6, 7 or 8 substituents independently selected from —OH, —$(C_1-C_4)$alkyl, -halo, and —C(halo)$_3$, and which bridge optionally contains —HC=CH— or —O— within the $(C_2-C_6)$bridge; wherein the A-B bridge can be in the endo- or exo-configuration with respect to the 5-membered, nitrogen-containing ring that is fused to the $Q_a$ ring;

Z is —$[(C_1-C_{10})$alkyl$]_h$-, wherein h is 0 or 1; and $R^1$ is selected from:

(a) —CN, —OH, —CH$_2$OH, —CH$_2$CH$_2$OH, —NO$_2$, —N(R$^6$)$_2$, —S(=O)NH$_2$, —S(=O)$_2$NH$_2$, —C(=O)OV$^1$, and —C(=O)CN; and (b) —$(C_1-C_{10})$alkyl, —O$(C_1-C_6)$alkyl, —$(C_3-C_7)$cycloalkoxy, —$(C_3-C_{14})$cycloalkyl, —$(C_6-C_{14})$bicycloalkyl, —$(C_8-C_{20})$tricycloalkyl, —$(C_5-C_{14})$cycloalkenyl, —$(C_7-C_{14})$bicycloalkenyl, —$(C_8-C_{20})$tricycloalkenyl, and -(3- to 7-membered)heterocycle, each of which is unsubstituted or substituted with 1, 2, 3, or 4 independently selected $R^8$ groups; and (c)

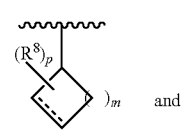 and

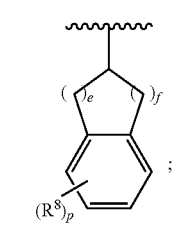

and (d) -phenyl and -(5- to 10-membered)heteroaryl, each of which is unsubstituted or substituted with 1, 2, or 3 independently selected $R^7$ groups.

(206) The compound of any one of the above (200)-(205) or a pharmaceutically acceptable salt or solvate thereof, wherein each b is, independently, an integer selected from 2, 3, and 4.

(207) The compound of any one of the above (200)-(206) or a pharmaceutically acceptable salt or solvate thereof, wherein each b is, independently, an integer selected from 2 and 3.

(208) The compound of any one of the above (200)-(207) or a pharmaceutically acceptable salt or solvate thereof, wherein each b is 3.

(209) The compound of any one of the above (200)-(208) or a pharmaceutically acceptable salt or solvate thereof, wherein t is 1, 2, or 3, s is 0, 1, or 2, and the $Q_x$ ring is selected from:

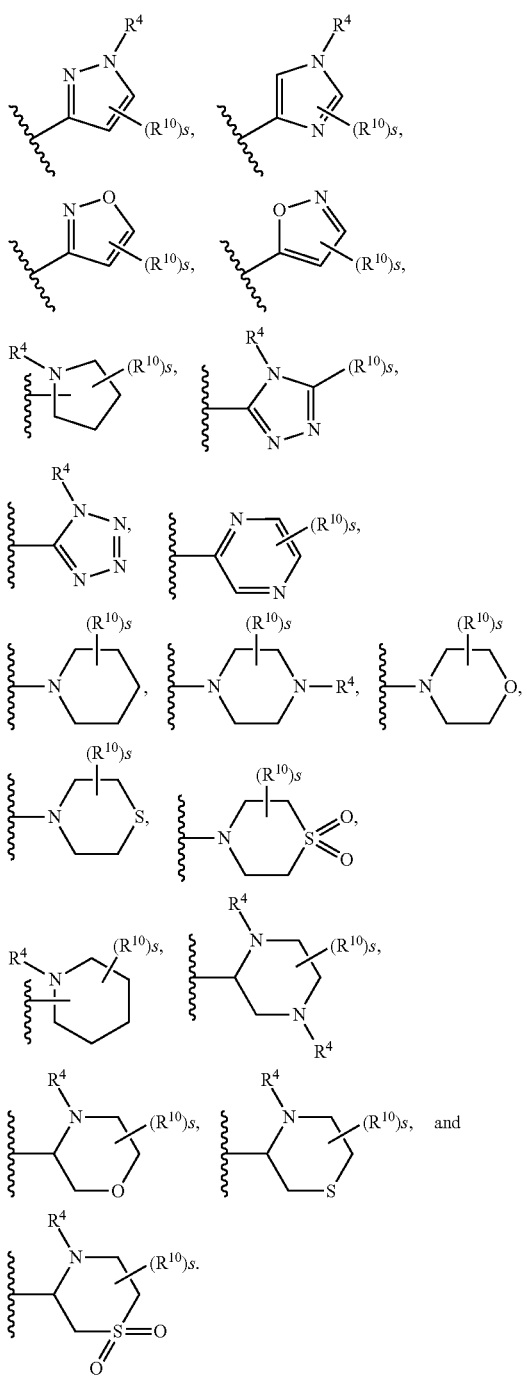
(210) The compound of any one of the above (201)-(209) or a pharmaceutically acceptable salt or solvate thereof, wherein t is 1, s is 0, 1, or 2, and the Q$_x$ ring is selected from:
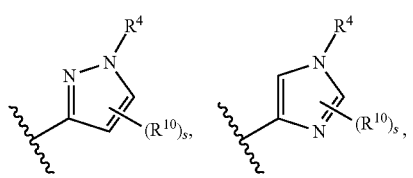
(211) The compound of any one of the above (201)-(208) or a pharmaceutically acceptable salt or solvate thereof, wherein t is 1, s is 0, 1, or 2, and the Q$_x$ ring is selected from:
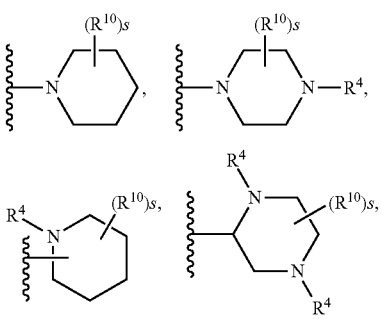

-continued

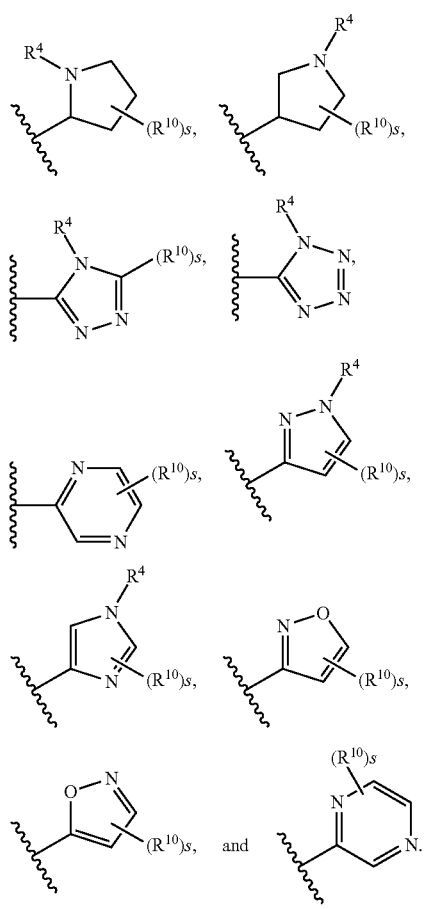

(212) The compound of any one of the above (200)-(208) or (211) or a pharmaceutically acceptable salt or solvate thereof, wherein t is 1, s is 0, 1, or 2, and the $Q_x$ ring is selected from:

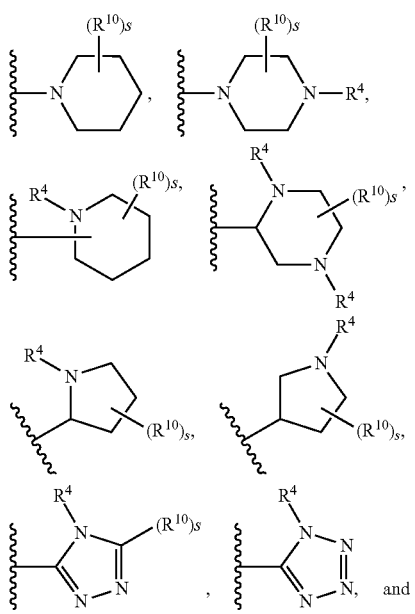

-continued

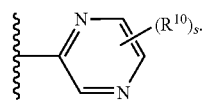

(213) The compound of any one of the above (200)-(208) or a pharmaceutically acceptable salt or solvate thereof, wherein t is 1 and the $Q_x$ ring is selected from:

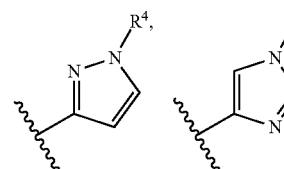

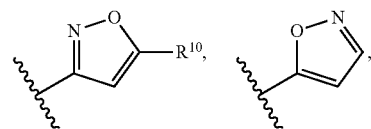

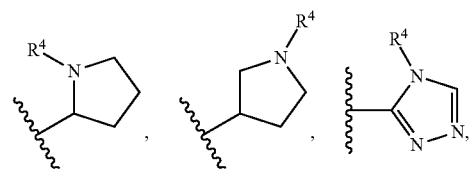

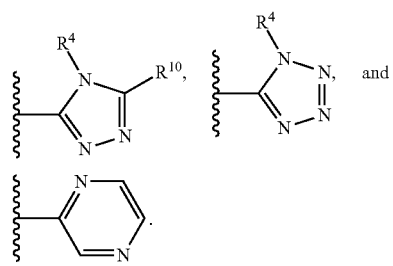

(214) The compound of any one of the above (200)-(208) or a pharmaceutically acceptable salt or solvate thereof, wherein t is 0, s is 0, 1, or 2, and the $Q_x$ ring is selected from:

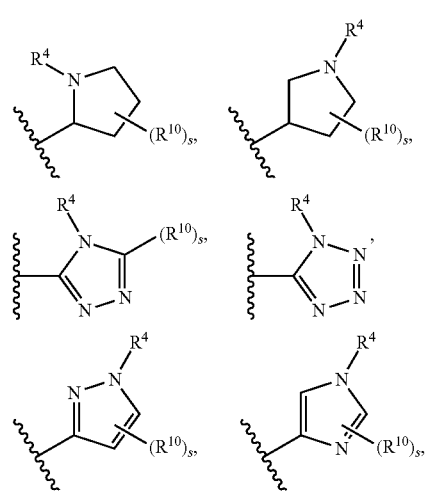

-continued

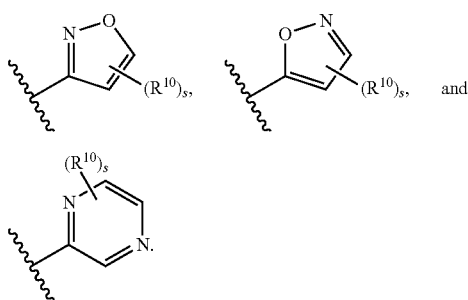

(215) The compound of any one of the above (200)-(208) or (214) or a pharmaceutically acceptable salt or solvate thereof, wherein t is 0, s is 0, 1, or 2, and the $Q_x$ ring is selected from:

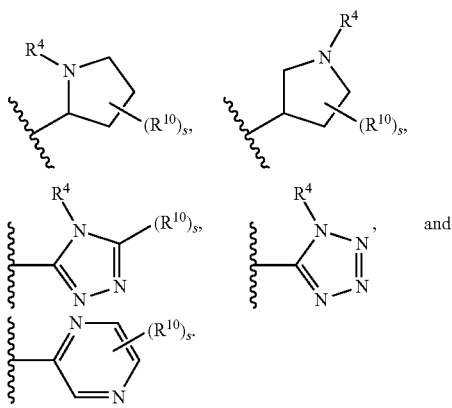

(216) The compound of any one of the above (200)-(208) or a pharmaceutically acceptable salt or solvate thereof, wherein t is 0 and the $Q_x$ ring is selected from:

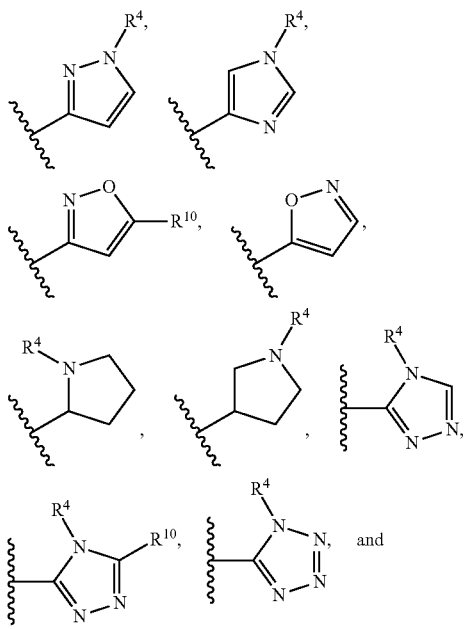

-continued

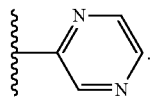

(217) The compound of any one of the above (200)-(208) or (216) or a pharmaceutically acceptable salt or solvate thereof, wherein t is 0 and the $Q_x$ ring is selected from:

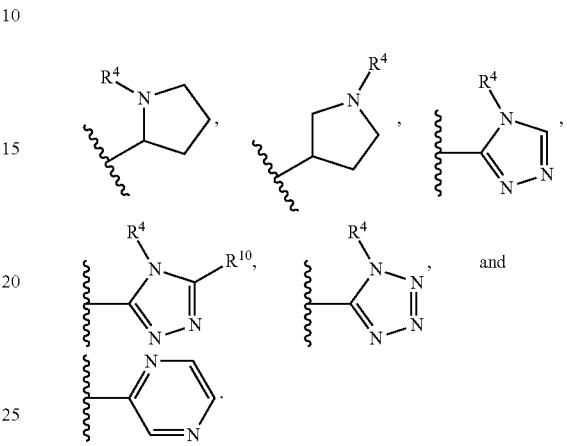

(218) The compound of any one of the above (200)-(208), (216), or (217) or a pharmaceutically acceptable salt or solvate thereof, wherein In another embodiment, t is 0 and the $Q_x$ ring is selected from:

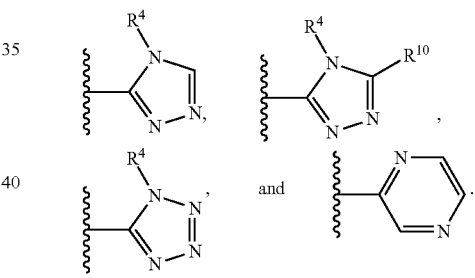

(219) The compound of any one of the above (200)-(212), (214), or (215) or a pharmaceutically acceptable salt or solvate thereof, wherein s is 0.

(220) The compound of any one of the above (200)-(219) or a pharmaceutically acceptable salt or solvate thereof, wherein the dashed line within the 5-membered, nitrogen-containing ring that is fused to the $Q_a$ ring is present to provide one bond of a double bond.

(221) The compound of any one of the above (200)-(220) or a pharmaceutically acceptable salt or solvate thereof, wherein h is 1.

(222) The compound of any one of the above (200)-(221) or a pharmaceutically acceptable salt or solvate thereof, wherein Z is —($C_1$-$C_3$)alkyl- optionally substituted by $R^{13}$.

(223) The compound of any one of the above (200)-(222) or a pharmaceutically acceptable salt or solvate thereof, wherein $R^{13}$ is absent.

(224) The compound of any one of the above (200)-(223) or a pharmaceutically acceptable salt or solvate thereof, wherein $R^{13}$ is absent and Z is —$CH_2$—$CH_2$—.

(225) The compound of any one of the above (200)-(224) or a pharmaceutically acceptable salt or solvate thereof, wherein —Z—$R^1$ is:

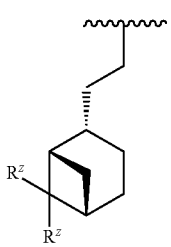

wherein each $R^z$ is independently —H, —$(C_1$-$C_4)$alkyl, —OH, or —CN and preferably each $R^z$ is independently —H, —$CH_3$, or —$CH_2CH_3$.

(226) The compound of any one of the above (200)-(220) or a pharmaceutically acceptable salt or solvate thereof, wherein h is 0.

(227) The compound of any one of the above (200)-(226) or a pharmaceutically acceptable salt or solvate thereof, wherein A and B are independently —H or —$(C_1$-$C_6)$alkyl and preferably A and B are each —H or A is —H and B is —$CH_3$ or A is —$CH_3$ and B is —H.

(228) The compound of any one of the above (200)-(226) or a pharmaceutically acceptable salt or solvate thereof, wherein A and B together form a bridge such that the bridged-piperidine is:

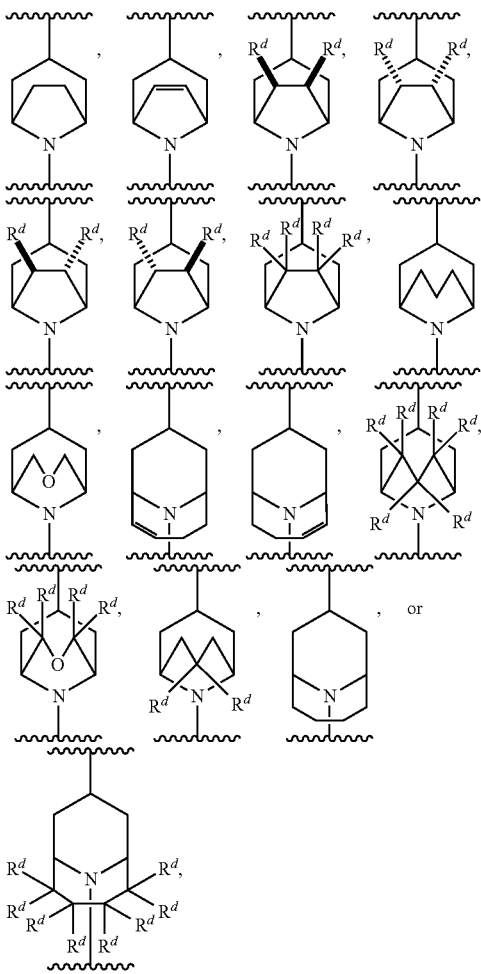

wherein each $R^d$ is independently —H, —$(C_1$-$C_4)$alkyl, -halo, or —C(halo)$_3$.

(229) The compound of any one of the above (200)-(226) or (228) or a pharmaceutically acceptable salt or solvate thereof, wherein A and B together form a bridge such that the bridged-piperidine is:

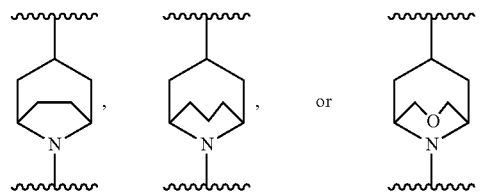

(230) The compound of any one of the above (200)-(226), (228), or (229) or a pharmaceutically acceptable salt or solvate thereof, wherein A and B together form a bridge such that the bridged-piperidine is:

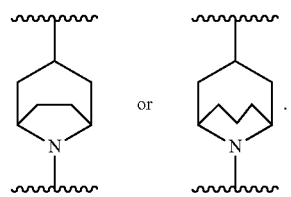 [SMILES: *C1CC2CCC(C1)N2* ; *C1CC2CCCC(C1)N2*]

(231) The compound of any one of the above (200)-(226) or (228)-(230) or a pharmaceutically acceptable salt or solvate thereof, wherein the A-B bridge of the bridged-piperidine is in the endo-configuration with respect to the 5-membered, nitrogen-containing ring that is fused to the $Q_a$ ring.

(232) The compound of any one of the above (200)-(220) or (226)-(231) or a pharmaceutically acceptable salt or solvate thereof, wherein:
  (a) h is 0;
  (b) $R^1$ is —$(C_1$-$C_{10})$alkyl, —$(C_3$-$C_{14})$cycloalkyl, —$(C_5$-$C_{14})$cycloalkenyl, —$(C_6$-$C_{14})$bicycloalkyl, —$(C_2$-$C_{14})$bicycloalkenyl, or —$(C_8$-$C_{20})$tricycloalkyl, each of which is unsubstituted or substituted with 1, 2, 3, or 4 independently selected $R^8$ groups and preferably $R^1$ is —$(C_3$-$C_{14})$cycloalkyl, —$(C_5$-$C_{14})$cycloalkenyl, —$(C_6$-$C_{14})$bicycloalkyl, —$(C_2$-$C_{14})$bicycloalkenyl, or —$(C_8$-$C_{20})$tricycloalkyl, each of which is unsubstituted or substituted with 1, 2, 3, or 4 independently selected $R^8$ groups; and
  (c) each $R^8$ is independently —$(C_1$-$C_4)$alkyl, —$(C_1$-$C_6)$alkyl-C(=O)O$R^9$, —N($R^9$)($C_1$-$C_6$)alkyl-C(=O)O$R^9$, —O$R^9$, —C(halo)$_3$, —CH(halo)$_2$, —$CH_2$(halo), -halo, —N($R^9$)$_2$, —C(=O)N($T^1$)($T^2$), or —C(=O)O$R^9$.

(233) The compound of any one of the above (200)-(220) or (226)-(232) or a pharmaceutically acceptable salt or solvate thereof, wherein —Z—$R^1$ is:

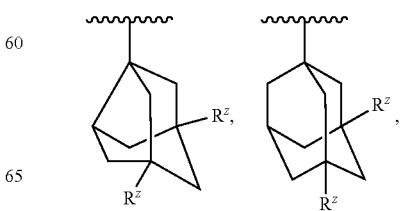

-continued

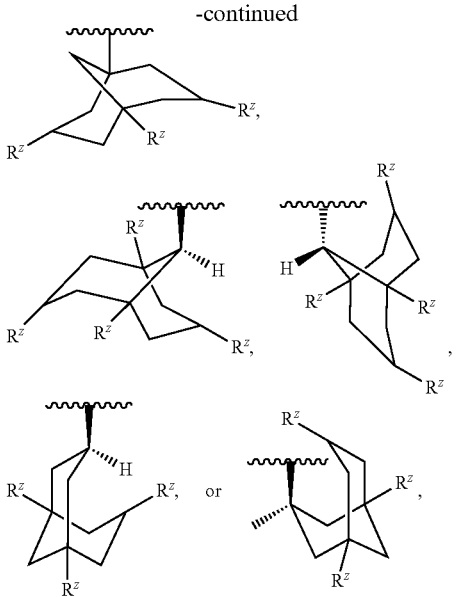

wherein each $R^z$ is independently —H, —$(C_1$-$C_4)$alkyl, —OH, or —CN and preferably each $R^z$ is independently —H, —$CH_3$, or —$CH_2CH_3$.

(234) The compound of any one of the above (200)-(220) or (226)-(232) or a pharmaceutically acceptable salt or solvate thereof, wherein —Z—$R^1$ is:

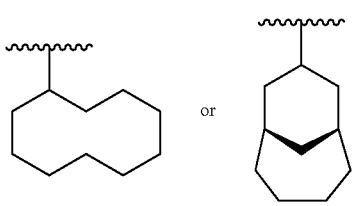

(235) The compound of any one of the above (200)-(220) or (226)-(233) or a pharmaceutically acceptable salt or solvate thereof, wherein —Z—$R^1$ is:

wherein $R^z$ is —H, —$CH_3$, or —$CH_2CH_3$.

(236) The compound of any one of the above (200)-(203) or (206)-(235) or a pharmaceutically acceptable salt or solvate thereof, wherein a is 1 and $R^2$ is -halo, preferably $R^2$ is —F.

(237) The compound of any one of the above (200)-(220) or (226)-(236) or a pharmaceutically acceptable salt or solvate thereof, wherein the $R^1$ group is in the exo-configuration with respect to the A-B bridge of the bridged piperidine.

(238) The compound of any one of the above (200)-(204), (206)-(224), (226)-(232), (236), or (237) or a pharmaceutically acceptable salt or solvate thereof, wherein $R^1$ is selected from:

(a) -halo, —CN, —OH, —$CH_2OH$, —$CH_2CH_2OH$, —$NO_2$, —$N(R^6)_2$, —$S(\!=\!O)NH_2$, —$S(\!=\!O)_2NH_2$, —$C(\!=\!O)OV^1$, and —$C(\!=\!O)CN$; and (b) —$(C_2$-$C_{10})$alkyl, —$(C_2$-$C_{10})$alkenyl, —$(C_2$-$C_{10})$alkynyl, —$O(C_1$-$C_6)$alkyl, —$(C_3$-$C_7)$cycloalkoxy, —$(C_6$-$C_{14})$bicycloalkyl, —$(C_8$-$C_{20})$tricycloalkyl, —$(C_5$-$C_{10})$cycloalkenyl, —$(C_7$-$C_{14})$bicycloalkenyl, —$(C_8$-$C_{20})$tricycloalkenyl, -(3- to 5-membered)heterocycle, and -(7-membered)heterocycle, each of which is unsubstituted or substituted with 1, 2, 3, or 4 independently selected $R^8$ groups; and (c)

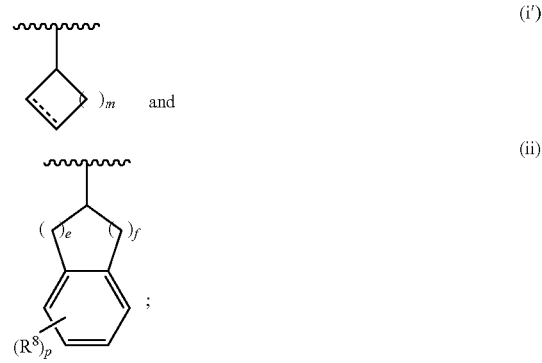

and (d) -naphthalenyl, —$(C_{14})$aryl, and -(5- to 10-membered)heteroaryl, each of which is unsubstituted or substituted with 1, 2, 3, or 4 independently selected $R^7$ groups.

(239) The compound of any one of the above (200)-(204), (206)-(222), (226)-(231), or (236) or a pharmaceutically acceptable salt or solvate thereof, wherein $R^{13}$ is selected from:

(a) -halo, —CN, —OH, —$CH_2OH$, —$CH_2CH_2OH$, —$NO_2$, —$N(R^6)_2$, —$S(\!=\!O)NH_2$, —$S(\!=\!O)_2NH_2$, —$C(\!=\!O)OV^1$, and —$C(\!=\!O)CN$; and (b) —$(C_2$-$C_{10})$alkyl, —$(C_2$-$C_{10})$alkenyl, —$(C_2$-$C_{10})$alkynyl, —$O(C_1$-$C_6)$alkyl, —$(C_3$-$C_7)$cycloalkoxy, —$(C_5$-$C_{10})$cycloalkenyl, and -(3- to 7-membered)heterocycle, each of which is unsubstituted or substituted with 1, 2, 3, or 4 independently selected $R^8$ groups; and (c)

and (d) -(5- to 10-membered)heteroaryl, each of which is unsubstituted or substituted with 1, 2, or 3 independently selected $R^7$ groups.

(240) The compound of any one of the above (200)-(239) or a pharmaceutically acceptable salt or solvate thereof, which is radiolabeled.

(241) The compound of any one of the above (200)-(240), wherein the pharmaceutically acceptable salt is a hydrochloride-salt, a sodium-salt, a potassium-salt, or a para-toluenesulfonic acid-salt.

(242) The compound of any one of the above (200)-(241) or a pharmaceutically acceptable salt thereof, wherein the % de of the compound is at least about 95%.

(243) The compound of the above (242) or a pharmaceutically acceptable salt thereof, wherein the % de of the compound is at least about 99%.

(244) A composition comprising an effective amount of the compound or a pharmaceutically acceptable salt or solvate of the compound of any one of the above (200)-(243) and a pharmaceutically acceptable carrier or excipient.

(245) A method for preparing a composition, comprising the step of admixing a compound or a pharmaceutically acceptable salt or solvate of the compound of any one of the above (200)-(243) and a pharmaceutically acceptable carrier or excipient.

(246) A method for modulating ORL-1 receptor function in a cell, comprising contacting a cell capable of expressing the ORL-1 receptor with an effective amount of the composition or the compound or a pharmaceutically acceptable salt or solvate of the compound of any one of the above (200)-(244).

(247) The method of the above (246) wherein the composition or the compound or the pharmaceutically acceptable salt or solvate of the compound acts as an agonist at the ORL-1 receptor.

(248) The method of the above (246), wherein the composition or the compound or the pharmaceutically acceptable salt or solvate of the compound acts as a partial agonist at the ORL-1 receptor.

(249) A method for treating pain in an animal, comprising administering to an animal in need thereof an effective amount of the composition or the compound or a pharmaceutically acceptable salt or solvate of the compound of any one of the above (200)-(244).

(250) A method for treating a memory disorder, obesity, constipation, depression, dementia, Parkinsonism, anxiety, cough, diarrhea, high blood pressure, epilepsy, anorexia/cachexia, urinary incontinence, or drug abuse in an animal, comprising administering to an animal in need thereof an effective amount of the composition or the compound or a pharmaceutically acceptable salt or solvate of the compound of any one of the above (200)-(244).

(251) Use of a compound or the pharmaceutically acceptable salt or solvate of the compound of any one of the above (200)-(243) for the manufacture of a medicament useful for treating pain, a memory disorder, obesity, constipation, depression, dementia, Parkinsonism, anxiety, cough, diarrhea, high blood pressure, epilepsy, anorexia/cachexia, urinary incontinence, or drug abuse.

(252) The compound or the pharmaceutically acceptable salt or solvate of the compound of any one of the above (200)-(243) for use in the treatment of pain, a memory disorder, obesity, constipation, depression, dementia, Parkinsonism, anxiety, cough, diarrhea, high blood pressure, epilepsy, anorexia/cachexia, urinary incontinence, or drug abuse.

(253) A kit, comprising a container containing an effective amount of the composition or the compound or a pharmaceutically acceptable salt or solvate of the compound of any one of the above (200)-(244).

(254) The compound of any one of the above (200)-(240) or (242)-(253), wherein the compound is present as a pharmaceutically acceptable salt.

4.1 Substituted Benzimidazole-Type Piperidine Compounds of Formula (I)

Compounds of formula (I) are herein disclosed:

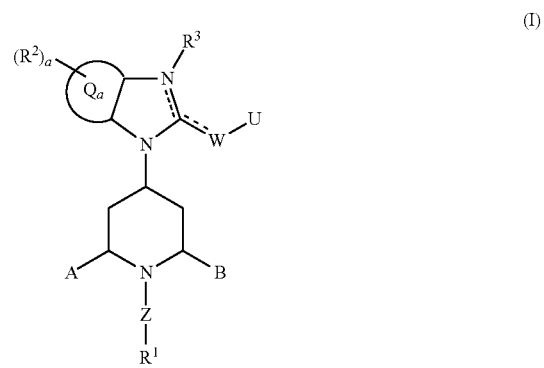

or a pharmaceutically acceptable derivative thereof where each dashed line, $Q_a$, $R^1$, $R^2$, $R^3$, A, B, U, W, Z, and a are defined above for the Substituted Benzimidazole-Type Piperidine Compounds of Formula (I).

In one embodiment, a is 0 or 1. In another embodiment, a is 0. In another embodiment, a is 1. In another embodiment, a is 2.

In another embodiment, each $R^2$ is independently -halo, —OH, —NH$_2$, —CN, —(C$_1$-C$_6$)alkyl, —(C$_3$-C$_7$)cycloalkyl, -(5- or 6-membered)heterocycle, -phenyl, -naphthalenyl, or -(5- or 6-membered)heteroaryl.

In another embodiment, a is 1 and $R^2$ is -halo, —OH, —NH$_2$, —CN, —(C$_1$-C$_6$)alkyl, —(C$_3$-C$_7$)cycloalkyl, -(5- or 6-membered)heterocycle, -phenyl, -naphthalenyl, or -(5- or 6-membered)heteroaryl. In another embodiment, a is 1 and $R^2$ is -halo, —OH, —NH$_2$, —CN, methyl, ethyl, n-propyl, iso-propyl, cyclopentyl, cyclohexyl, cycloheptyl, or phenyl. In another embodiment, a is 1 and $R^2$ is -halo. In another embodiment, a is 1 and $R^2$ is —F or —Cl. In another embodiment, a is 1 and $R^2$ is —F. In another embodiment, a is 1 and $R^2$ is —Cl.

In another embodiment, a is 2 and each $R^2$ is independently -halo, —OH, —NH$_2$, —CN, —(C$_1$-C$_6$)alkyl, —(C$_3$-C$_7$)cycloalkyl, -(5- or 6-membered)heterocycle, -phenyl, -naphthalenyl, or -(5- or 6-membered)heteroaryl. In another embodiment, a is 2 and each $R^2$ is independently -halo, —OH, —NH$_2$, —CN, methyl, ethyl, n-propyl, iso-propyl, cyclopentyl, cyclohexyl, cycloheptyl, or phenyl. In another embodiment, a is 2 and each $R^2$ is -halo. In another embodiment, a is 2 and each $R^2$ is —F or —Cl. In another embodiment, a is 2 and each $R^2$ is —F. In another embodiment, a is 2 and each $R^2$ is —Cl.

In another embodiment, the compound of formula (I) is a compound of formula (I'):

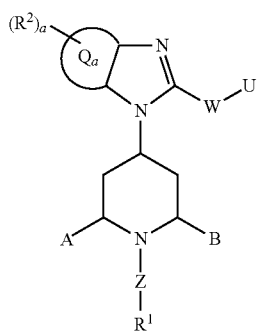
(I')

or a pharmaceutically acceptable salt or solvate thereof where —W— is a single bond, —CH$_2$—, —NH—, —O—, —CH$_2$—(C$_1$-C$_3$)alkylene-, —NH—(C$_1$-C$_3$)alkylene-, —O—(C$_1$-C$_3$)alkylene-, =CH—(C$_2$-C$_3$)alkenylene-, —CH$_2$—(C$_2$-C$_3$)alkenylene-, —NH—(C$_2$-C$_3$)alkenylene-, —O—(C$_2$-C$_3$)alkenylene-, —CH$_2$—(C$_1$-C$_3$)alkylene-N(R$^{11}$)—, —NH—(C$_1$-C$_3$)alkylene-N(R$^{11}$)—, —O—(C$_1$-C$_3$)alkylene-N(R$^{11}$)—, —CH=N—, —CH$_2$—N(R$^{11}$)—, —CH$_2$—O—, or —CH$_2$—O—(C$_1$-C$_3$)alkylene- and Q$_a$, R$^1$, R$^2$, R$^{11}$, A, B, U, Z, and a are as defined for the compounds of formula (I).

In another embodiment, the compound of formula (I) is a compound of formula (I''):

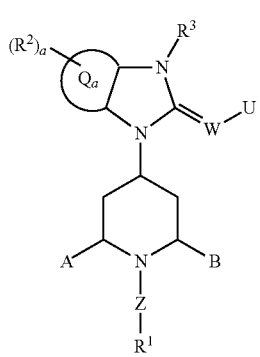
(I'')

or a pharmaceutically acceptable salt or solvate thereof where =W— is a double bond, =CH—, =N—, =CH—(C$_1$-C$_3$)alkylene-, =N—(C$_1$-C$_3$)alkylene-, =CH—(C$_2$-C$_3$)alkenylene-, =N—(C$_2$-C$_3$)alkenylene-, =CH—(C$_1$-C$_3$)alkylene-N(R$^{11}$)—, =N—(C$_1$-C$_3$)alkylene-N(R$^{11}$)—, =CH—N(R$^{11}$)—, =CH—O—, OR=CH—O—(C$_1$-C$_3$)alkylene- and Q$_a$, R$^1$, R$^2$, R$^3$, R$^{11}$, A, B, U, Z, and a are as defined for the compounds of formula (I).

In another embodiment, Q$_a$ is benzo, pyridino, pyrimidino, pyrazino, pyridazino, pyrrolino, imidazolino, pyrazolino, triazolino, furano, oxazolino, isoxazolino, oxadiazolino, thiopheno, thiazolino, isothiazolino, or thiadiazolino. In another embodiment, Q$_a$ is benzo, pyrrolino, imidazolino, pyrazolino, triazolino, furano, oxazolino, isoxazolino, oxadiazolino, thiopheno, thiazolino, isothiazolino, or thiadiazolino. In another embodiment, Q$_a$ is benzo, imidazolino, pyrazolino, triazolino, oxazolino, isoxazolino, oxadiazolino, thiazolino, isothiazolino, or thiadiazolino. In another embodiment, Q$_a$ is benzo, pyrrolino, imidazolino, pyrazolino, or triazolino. In another embodiment, Q$_a$ is benzo, furano, oxazolino, isoxazolino, or oxadiazolino. In another embodiment, Q$_a$ is benzo, oxazolino, isoxazolino, or oxadiazolino. In another embodiment, Q$_a$ is benzo, thiopheno, thiazolino, isothiazolino, or thiadiazolino. In another embodiment, Q$_a$ is benzo, thiazolino, isothiazolino, or thiadiazolino. In another embodiment, Q$_a$ is benzo, pyrrolino, furano, or thiopheno. In another embodiment, Q$_a$ is pyridino, pyrimidino, pyrazino, pyridazino, pyrrolino, imidazolino, pyrazolino, triazolino, furano, oxazolino, isoxazolino, oxadiazolino, thiopheno, thiazolino, isothiazolino, or thiadiazolino. In another embodiment, Q$_a$ is pyrrolino, imidazolino, pyrazolino, triazolino, furano, oxazolino, isoxazolino, oxadiazolino, thiopheno, thiazolino, isothiazolino, or thiadiazolino. In another embodiment, Q$_a$ is imidazolino, pyrazolino, triazolino, oxazolino, isoxazolino, oxadiazolino, thiazolino, isothiazolino, or thiadiazolino. In another embodiment, Q$_a$ is pyrrolino, imidazolino, pyrazolino, or triazolino. In another embodiment, Q$_a$ is furano, oxazolino, isoxazolino, or oxadiazolino. In another embodiment, Q$_a$ is oxazolino, isoxazolino, or oxadiazolino. In another embodiment, Q$_a$ is thiopheno, thiazolino, isothiazolino, or thiadiazolino. In another embodiment, Q$_a$ is thiazolino, isothiazolino, or thiadiazolino. In another embodiment, Q$_a$ is pyrrolino, furano, or thiopheno. In another embodiment, Q$_a$ is benzo, pyridino, pyrimidino, pyrazino, or pyridazino. In another embodiment, Q$_a$ is benzo, pyrimidino, pyrazino, or pyridazino. In another embodiment, Q$_a$ is pyridino, pyrimidino, pyrazino, or pyridazino. In another embodiment, Q$_a$ is pyrimidino, pyrazino, or pyridazino. In another embodiment, Q$_a$ is benzo or pyridino. In another embodiment, Q$_a$ is benzo. In another embodiment, Q$_a$ is pyridino.

In another embodiment, a is 1, Q$_a$ is benzo or pyridino, and R$^2$ is attached at the position shown below, denoted for purposes of the R$^2$-attachment-position herein as the "6-position", of the benzo or pyridino, e.g., as illustrated below:

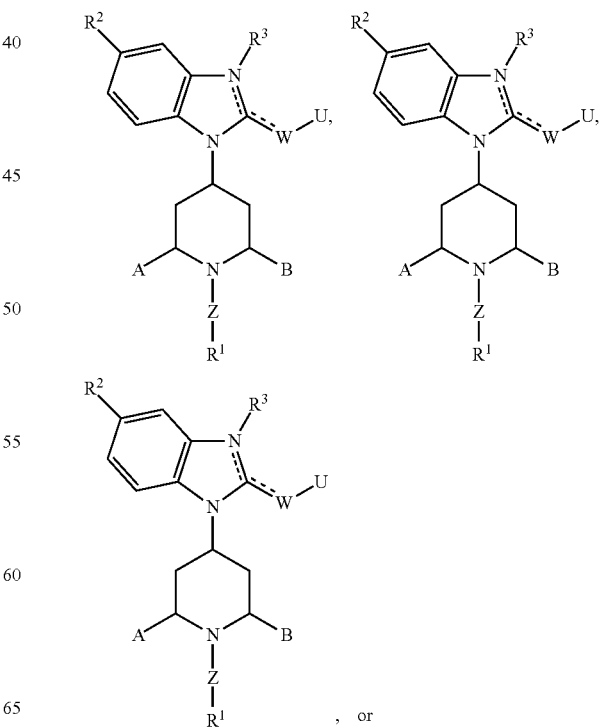

, or

-continued

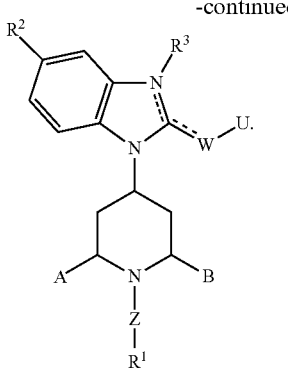

In another embodiment, a is 1, $Q_a$ is benzo or pyridino, $R^2$ is -halo, and $R^2$ is attached at the 6-position of the benzo or pyridino as illustrated immediately above. In another embodiment, a is 1, $Q_a$ is benzo or pyridino, $R^2$ is —F or —Cl, and $R^2$ is attached at the 6-position of the benzo or pyridino as illustrated immediately above. In another embodiment, a is 1, $Q_a$ is benzo or pyridino, $R^2$ is —F, and $R^2$ is attached at the 6-position of the benzo or pyridino as illustrated immediately above.

In another embodiment, $Q_a$ is benzo. In another embodiment, $Q_a$ is pyridino. In another embodiment, $Q_a$ is pyridino and the 2- and 3-positions of the pyridino are fused to the 6-membered, nitrogen-containing ring as illustrated, inter alia, for compounds according to Formula (I) in Table 1 and for compounds according to Formula (IB) in Table 17, and the like.

In another embodiment, each $R^7$ is independently selected from —($C_1$-$C_4$)alkyl, —$OR^9$, —$SR^9$, —C(halo)$_3$, —CH(halo)$_2$, —CH$_2$(halo), -halo, —N($R^9$)$_2$, —N($R^9$)C(=O)$OR^{12}$, —C(=O)$OR^9$, and —OC(=O)$R^9$. In another embodiment, each $R^7$ is independently selected from —($C_1$-$C_4$)alkyl, —$OR^9$, —C(halo)$_3$, —CH(halo)$_2$, —CH$_2$(halo), -halo, —N($R^9$)$_2$, —C(=O)$OR^9$, and —OC(=O)$R^9$. In another embodiment, each $R^7$ is independently selected from —($C_1$-$C_4$)alkyl, —$OR^9$, —C(halo)$_3$, -halo, —N($R^9$)$_2$, and —C(=O)$OR^9$.

In another embodiment, each $R^8$ is independently selected from —($C_1$-$C_4$)alkyl, —($C_2$-$C_6$)alkenyl, —($C_2$-$C_6$)alkynyl, -(5- or 6-membered)heteroaryl, —($C_1$-$C_6$)alkyl-C(=O)$OR^9$, —N($R^9$)($C_1$-$C_6$)alkyl-C(=O)$OR^9$, —C(halo)$_3$, —CH(halo)$_2$, —CH$_2$(halo), —CN, =O, =S, =N($R^9$), -halo, —NO$_2$, —CH=N($R^9$), —N($R^9$)$_2$, —N($R^9$)$OR^9$, —N($R^9$)S(=O)$R^{12}$, —N($R^9$)S(=O)$_2R^{12}$, —N($R^9$)C(=O)$R^{12}$, —N($R^9$)C(=O)N($T^1$)($T^2$), —N($R^9$)C(=O)$OR^{12}$, —C(=O)$R^9$, —C(=O)N($T^1$)($T^2$), —C(=O)$OR^9$, —OC(=O)$R^9$, —OC(=O)N($T^1$)($T^2$), —OC(=O)$OR^9$, —S(=O)$R^9$, and —S(=O)$_2R^9$. In another embodiment, each $R^8$ is independently selected from —($C_1$-$C_4$)alkyl, —($C_2$-$C_6$)alkenyl, —($C_2$-$C_6$)alkynyl, -(5- or 6-membered)heteroaryl, —($C_1$-$C_6$)alkyl-C(=O)$OR^9$, —N($R^9$)($C_1$-$C_6$)alkyl-C(=O)$OR^9$, —$OR^9$, —$SR^9$, —C(halo)$_3$, —CH(halo)$_2$, —CH$_2$(halo), —CN, =N($R^9$), -halo, —NO$_2$, —CH=N($R^9$), —N($R^9$)$_2$, —N($R^9$)$OR^9$, —N($R^9$)S(=O)$R^{12}$, —N($R^9$)S(=O)$_2R^{12}$, —N($R^9$)C(=O)$R^{12}$, —N($R^9$)C(=O)N($T^1$)($T^2$), —N($R^9$)C(=O)$OR^{12}$, —C(=O)$R^9$, —C(=O)N($T^1$)($T^2$), —C(=O)$OR^9$, —OC(=O)$R^9$, —OC(=O)N($T^1$)($T^2$), —OC(=O)$OR^9$, —S(=O)$R^9$, and —S(=O)$_2R^9$. In another embodiment, each $R^8$ is independently selected from —($C_1$-$C_4$)alkyl, —($C_2$-$C_6$)alkenyl, —($C_2$-$C_6$)alkynyl, -(5- or 6-membered)heteroaryl, —($C_1$-$C_6$)alkyl-C(=O)$OR^9$, —N($R^9$)($C_1$-$C_6$)alkyl-C(=O)$OR^9$, —$OR^9$, —$SR^9$, —C(halo)$_3$, —CH(halo)$_2$, —CH$_2$(halo), —CN, =N($R^9$), —NO$_2$, —CH=N($R^9$), —N($R^9$)$_2$, —N($R^9$)$OR^9$, —N($R^9$)S(=O)$R^{12}$, —N($R^9$)S(=O)$_2R^{12}$, —N($R^9$)C(=O)$R^{12}$, —N($R^9$)C(=O)N($T^1$)($T^2$), —N($R^9$)C(=O)$OR^{12}$, —C(=O)$R^9$, —C(=O)N($T^1$)($T^2$), —C(=O)$OR^9$, —OC(=O)$R^9$, —OC(=O)N($T^1$)($T^2$), —OC(=O)$OR^9$, —S(=O)$R^9$, and —S(=O)$_2R^9$. In another embodiment, each $R^8$ is independently selected from —($C_1$-$C_4$)alkyl, —($C_2$-$C_6$)alkenyl, —($C_2$-$C_6$)alkynyl, -(5- or 6-membered)heteroaryl, —($C_1$-$C_6$)alkyl-C(=O)$OR^9$, —N($R^9$)($C_1$-$C_6$)alkyl-C(=O)$OR^9$, —C(halo)$_3$, —CH(halo)$_2$, —CH$_2$(halo), —CN, =N($R^9$), —NO$_2$, —CH=N($R^9$), —N($R^9$)$_2$, —N($R^9$)$OR^9$, —N($R^9$)S(=O)$R^{12}$, —N($R^9$)S(=O)$_2R^{12}$, —N($R^9$)C(=O)$R^{12}$, —N($R^9$)C(=O)N($T^1$)($T^2$), —N($R^9$)C(=O)$OR^{12}$, —C(=O)$R^9$, —C(=O)N($T^1$)($T^2$), —C(=O)$OR^9$, —OC(=O)$R^9$, —OC(=O)N($T^1$)($T^2$), —OC(=O)$OR^9$, —S(=O)$R^9$, and —S(=O)$_2R^9$.

In another embodiment, each $R^8$ is independently selected from —($C_1$-$C_4$)alkyl, —($C_2$-$C_6$)alkenyl, —($C_2$-$C_6$)alkynyl, -(5- or 6-membered)heteroaryl, —($C_1$-$C_6$)alkyl-C(=O)$OR^9$, —N($R^9$)($C_1$-$C_6$)alkyl-C(=O)$OR^9$, —$OR^9$, —$SR^9$, —C(halo)$_3$, —CH(halo)$_2$, —CH$_2$(halo), —CN, =O, =S, =N($R^9$), -halo, —NO$_2$, —CH=N($R^9$), —N($R^9$)$_2$, —N($R^9$)$OR^9$, —N($R^9$)S(=O)$R^{12}$, —N($R^9$)S(=O)$_2R^{12}$, —N($R^9$)C(=O)$R^{12}$, —N($R^9$)C(=O)N($T^1$)($T^2$), —N($R^9$)C(=O)$OR^{12}$, —C(=O)$R^9$, —C(=O)N($T^1$)($T^2$), —C(=O)$OR^9$, —OC(=O)$R^9$, —S(=O)$R^9$, and —S(=O)$_2R^9$. In another embodiment, each $R^8$ is independently selected from —($C_1$-$C_4$)alkyl, —($C_2$-$C_6$)alkenyl, -(5- or 6-membered)heteroaryl, —($C_1$-$C_6$)alkyl-C(=O)$OR^9$, —N($R^9$)($C_1$-$C_6$)alkyl-C(=O)$OR^9$, —$OR^9$, —$SR^9$, —C(halo)$_3$, —CH(halo)$_2$, —CH$_2$(halo), =O, =S, =N($R^9$), -halo, —CH=N($R^9$), —N($R^9$)$_2$, —N($R^9$)$OR^9$, —N($R^9$)S(=O)$R^{12}$, —N($R^9$)S(=O)$_2R^{12}$, —N($R^9$)C(=O)$R^{12}$, —N($R^9$)C(=O)N($T^1$)($T^2$), —N($R^9$)C(=O)$OR^{12}$, —C(=O)$R^9$, —C(=O)N($T^1$)($T^2$), —C(=O)$OR^9$, —OC(=O)$R^9$, —S(=O)$R^9$, and —S(=O)$_2R^9$. In another embodiment, each $R^8$ is independently selected from —$(C_1-C_4)$alkyl, —$(C_2-C_6)$alkenyl, -(5- or 6-membered)heteroaryl, —$(C_1-C_6)$alkyl-C(=O)OR$^9$, —N(R$^9$)(C$_1$-C$_6$)alkyl-C(=O)OR$^9$, —OR$^9$, —SR$^9$, —C(halo)$_3$, —CH(halo)$_2$, —CH$_2$(halo), -halo, —CH=N(R$^9$), —N(R$^9$)$_2$, —N(R$^9$)OR$^9$, —N(R$^9$)S(=O)$_2$R$^{12}$, —N(R$^9$)C(=O)R$^{12}$, —N(R$^9$)C(=O)N(T$^1$)(T$^2$), —N(R$^9$)C(=O)OR$^{12}$, —C(=O)R$^9$, —C(=O)N(T$^1$)(T$^2$), —C(=O)OR$^9$, —OC(=O)R$^9$, and —S(=O)$_2$R$^9$. In another embodiment, each $R^8$ is independently selected from —(C$_1$-C$_4$)alkyl, -(5- or 6-membered)heteroaryl, —(C$_1$-C$_6$)alkyl-C(=O)OR$^9$, —N(R$^9$)(C$_1$-C$_6$)alkyl-C(=O)OR$^9$, —OR$^9$, —SR$^9$, —C(halo)$_3$, —CH(halo)$_2$, —CH$_2$(halo), -halo, —N(R$^9$)$_2$, —N(R$^9$)S(=O)$_2$R$^{12}$, —N(R$^9$)C(=O)R$^{12}$, —N(R$^9$)C(=O)N(T$^1$)(T$^2$), —N(R$^9$)C(=O)OR$^{12}$, —C(=O)R$^9$, —C(=O)N(T$^1$)(T$^2$), —C(=O)OR$^9$, —OC(=O)R$^9$, and —S(=O)$_2$R$^9$. In another embodiment, each $R^8$ is independently selected from —(C$_1$-C$_4$)alkyl, -(5- or 6-membered)heteroaryl, —(C$_1$-C$_6$)alkyl-C(=O)OR$^9$, —N(R$^9$)(C$_1$-C$_6$)alkyl-C(=O)OR$^9$, —OR$^9$, —SR$^9$, —C(halo)$_3$, —CH(halo)$_2$, —CH$_2$(halo), -halo, —N(R$^9$)$_2$, —N(R$^9$)S(=O)$_2$R$^{12}$, —N(R$^9$)C(=O)R$^{12}$, —C(=O)R$^9$, —C(=O)N(T$^1$)(T$^2$), —C(=O)OR$^9$, —OC(=O)R$^9$, and —S(=O)$_2$R$^9$. In another embodiment, each $R^8$ is independently selected from —(C$_1$-C$_4$)alkyl, —(C$_1$-C$_6$)alkyl-C(=O)OR$^9$, —N(R$^9$)(C$_1$-C$_6$)alkyl-C(=O)OR$^9$, —OR$^9$, —C(halo)$_3$, —CH(halo)$_2$, —CH$_2$(halo), -halo, —N(R$^9$)$_2$, —C(=O)N(T$^1$)(T$^2$), and —C(=O)OR$^9$.

In another embodiment, each $R^9$ is independently —H, —(C$_1$-C$_6$)alkyl, —(C$_2$-C$_6$)alkenyl, —(C$_3$-C$_8$)cycloalkyl, -phenyl, -benzyl, -(3- to 7-membered)heterocycle, —C(halo)$_3$, —CH(halo)$_2$, or —CH$_2$(halo). In another embodiment, each $R^9$ is independently —H, —(C$_1$-C$_6$)alkyl, —(C$_3$-C$_8$)cycloalkyl, -phenyl, -benzyl, -(3- to 7-membered)heterocycle, —C(halo)$_3$, —CH(halo)$_2$, or —CH$_2$(halo). In another embodiment, each $R^9$ is independently —H, —(C$_1$-C$_6$)alkyl, —C(halo)$_3$, —CH(halo)$_2$, or —CH$_2$(halo). In another embodiment, each $R^9$ is independently —H or —(C$_1$-C$_3$)alkyl.

In another embodiment, each T$^1$ and T$^2$ is independently —H or —(C$_1$-C$_3$)alkyl which is unsubstituted or substituted with an independently selected R$^5$ group. In another embodiment, each T$^1$ and T$^2$ is independently —H or —(C$_1$-C$_3$)alkyl which is unsubstituted. In another embodiment, each T$^1$ and T$^2$ is independently —H or —CH$_3$. In another embodiment, each T$^3$ is independently —H or —(C$_1$-C$_3$)alkyl which is unsubstituted or substituted with an independently selected R$^5$ group. In another embodiment, each T$^3$ is independently —H or —(C$_1$-C$_3$)alkyl which is unsubstituted. In another embodiment, each T$^3$ is independently —H or —CH$_3$.

In another embodiment, each R$^5$ is independently selected from —(C$_1$-C$_4$)alkyl, —(C$_2$-C$_6$)alkenyl, —(C$_2$-C$_6$)alkynyl, -(5- or 6-membered)heteroaryl, —(C$_1$-C$_6$)alkyl-C(=O)OR$^9$, —N(R$^9$)(C$_1$-C$_6$)alkyl-C(=O)OR$^9$, —OR$^9$, —SR$^9$, —C(halo)$_3$, —CH(halo)$_2$, —CH$_2$(halo), —CN, =O, =S, -halo, —NO$_2$, —CH=N(R$^9$), —N(R$^9$)$_2$, —N(R$^9$)OH, —N(R$^9$)S(=O)R$^{12}$, —N(R$^9$)S(=O)$_2$R$^{12}$, —N(R$^9$)C(=O)R$^{12}$, —N(R$^9$)C(=O)OR$^{12}$, —C(=O)R$^9$, —C(=O)OR$^9$, —OC(=O)R$^9$, —S(=O)R$^9$, and —S(=O)$_2$R$^9$. In another embodiment, each R$^5$ is independently selected from —(C$_1$-C$_4$)alkyl, —(C$_2$-C$_6$)alkenyl, -(5- or 6-membered)heteroaryl, —(C$_1$-C$_6$)alkyl-C(=O)OR$^9$, —N(R$^9$)(C$_1$-C$_6$)alkyl-C(=O)OR$^9$, —OR$^9$, —SR$^9$, —C(halo)$_3$, —CH(halo)$_2$, —CH$_2$(halo), =O, =S, -halo, —CH=N(R$^9$), —N(R$^9$)$_2$, —N(R$^9$)OH, —N(R$^9$)S(=O)R$^{12}$, —N(R$^9$)S(=O)$_2$R$^{12}$, —N(R$^9$)C(=O)R$^{12}$, —N(R$^9$)C(=O)OR$^{12}$, —C(=O)R$^9$, —C(=O)OR$^9$, —OC(=O)R$^9$, —S(=O)R$^9$, and —S(=O)$_2$R$^9$. In another embodiment, each R$^5$ is independently selected from —(C$_1$-C$_4$)alkyl, —(C$_2$-C$_6$)alkenyl, -(5- or 6-membered)heteroaryl, —(C$_1$-C$_6$)alkyl-C(=O)OR$^9$, —N(R$^9$)(C$_1$-C$_6$)alkyl-C(=O)OR$^9$, —OR$^9$, —SR$^9$, —C(halo)$_3$, —CH(halo)$_2$, —CH$_2$(halo), -halo, —N(R$^9$)$_2$, —N(R$^9$)OH, —N(R$^9$)S(=O)$_2$R$^{12}$, —N(R$^9$)C(=O)R$^{12}$, —N(R$^9$)C(=O)OR$^{12}$, —C(=O)R$^9$, —C(=O)OR$^9$, —OC(=O)R$^9$, and —S(=O)$_2$R$^9$. In another embodiment, each R$^5$ is independently selected from —(C$_1$-C$_4$)alkyl, -(5- or 6-membered)heteroaryl, —(C$_1$-C$_6$)alkyl-C(=O)OR$^9$, —N(R$^9$)(C$_1$-C$_6$)alkyl-C(=O)OR$^9$, —OR$^9$, —SR$^9$, —C(halo)$_3$, —CH(halo)$_2$, —CH$_2$(halo), -halo, —N(R$^9$)$_2$, —N(R$^9$)S(=O)$_2$R$^{12}$, —N(R$^9$)C(=O)R$^{12}$, —N(R$^9$)C(=O)OR$^{12}$, —C(=O)R$^9$, —C(=O)OR$^9$, —OC(=O)R$^9$, and —S(=O)$_2$R$^9$. In another embodiment, each R$^5$ is independently selected from —(C$_1$-C$_4$)alkyl, -(5- or 6-membered)heteroaryl, —(C$_1$-C$_6$)alkyl-C(=O)OR$^9$, —N(R$^9$)(C$_1$-C$_6$)alkyl-C(=O)OR$^9$, —OR$^9$, —SR$^9$, —C(halo)$_3$, —CH(halo)$_2$, —CH$_2$(halo), -halo, —N(R$^9$)$_2$, —N(R$^9$)S(=O)$_2$R$^{12}$, —N(R$^9$)C(=O)R$^{12}$, —C(=O)R$^9$, —C(=O)OR$^9$, —OC(=O)R$^9$, and —S(=O)$_2$R$^9$. In another embodiment, each R$^5$ is independently selected from —(C$_1$-C$_4$)alkyl, —(C$_1$-C$_6$)alkyl-C(=O)OR$^9$, —N(R$^9$)(C$_1$-C$_6$)alkyl-C(=O)OR$^9$, —OR$^9$, —C(halo)$_3$, —CH(halo)$_2$, —CH$_2$(halo), -halo, —N(R$^9$)$_2$, and —C(=O)OR$^9$.

In another embodiment, R$^{11}$ is —H or —(C$_1$-C$_4$)alkyl which is unsubstituted or substituted with —OH, —(C$_1$-C$_4$)alkoxy, or —N(R$^6$)$_2$. In another embodiment, R$^{11}$ is —H. In another embodiment, R$^{11}$ is not —C(=O)OH.

In another embodiment, h is 0. In another embodiment, h is 1. In another embodiment, h is 1 and R$^{13}$ is absent. In another embodiment, h is 0 and R$^{11}$ is —H. In another embodiment, h is 1 and R$^{11}$ is —H. In another embodiment, h is 0 or 1 and Z is —(C$_1$-C$_{10}$)alkyl unsubstituted by R$^{13}$, i.e., Z is —[(C$_1$-C$_{10}$)alkyl]$_h$.

In another embodiment, h is 1 and Z is —(C$_1$-C$_3$)alkyl optionally substituted by R$^{13}$. In another embodiment, h is 1, R$^{13}$ is absent, and Z is —CH$_2$—. In another embodiment, h is 1, R$^{13}$ is absent, and Z is —CH$_2$—CH$_2$—. In another embodiment, h is 1, R$^{13}$ is absent and Z is —CH$_2$—CH$_2$—CH$_2$—. In another embodiment, h is 1, Z is —(C$_1$-C$_3$)alkyl-, R$^1$ is phenyl, and the Z group (i.e., —(C$_1$-C$_3$)alkyl-) is substituted by R$^{13}$. In another embodiment, h is 1, Z is a —(C$_1$-C$_3$)alkyl-, R$^1$ is optionally-substituted phenyl, and the Z group is substituted by R$^{13}$ which is optionally-substituted phenyl. In another embodiment, h is 1, Z is a —(C$_1$-C$_3$)alkyl-, R$^1$ is unsubstituted phenyl, and the Z group is substituted by R$^{13}$ which is unsubstituted phenyl. In another embodiment, h is 1, Z is a —(C$_1$-C$_3$)alkyl-, and the Z group is substituted by R$^{13}$ which is —CF$_3$. In another embodiment, h is 1 and Z—R$^{13}$ is —CH$_2$—CH(CF$_3$)—CH$_2$—.

In another embodiment, R$^1$ is —(C$_1$-C$_6$)alkyl, —(C$_2$-C$_6$)alkenyl, —(C$_2$-C$_6$)alkynyl, —O(C$_1$-C$_6$)alkyl, —(C$_3$-C$_7$)cycloalkoxy, —(C$_6$-C$_{14}$)bicycloalkyl, —(C$_8$-C$_{20}$)tricycloalkyl, —(C$_5$-C$_{14}$)cycloalkenyl, —(C$_7$-C$_{14}$)bicycloalkenyl, —(C$_8$-C$_{20}$)tricycloalkenyl, -(3- to 7-membered)heterocycle, or -(7- to 10-membered)bicycloheterocycle, each of which is unsubstituted or substituted with 1, 2, 3, or 4 independently selected R$^8$ groups.

In another embodiment, Z is —(C$_2$-C$_{10}$)alkenyl-. In another embodiment, Z is —(C$_2$-C$_6$)alkenyl-. In another embodiment, Z is —CH$_2$—CH=CH—. In another embodiment, Z is —CH$_2$—CH=CH—CH$_2$—. In another embodiment, Z is a —(C$_3$)alkenyl-. In another embodiment, Z is n-prop-1,3-diyl and R$^1$ is an optionally substituted —(C$_6$-C$_{14}$)bicycloalkyl or optionally substituted —(C$_8$-C$_{20}$)tricycloalkyl. In another embodiment, Z—R$^1$ is —CH$_2$—

CH=$R^1$. In another embodiment, Z—$R^1$ is —$CH_2$—$CH_2$—CH=$R^1$ or —CH($CH_3$)—CH=$R^1$ where $R^1$ is —($C_6$-$C_{14}$)bicycloalkyl or —($C_8$-$C_{20}$)tricycloalkyl, each of which is optionally substituted. In another embodiment, h is 1, and Z—$R^1$ is

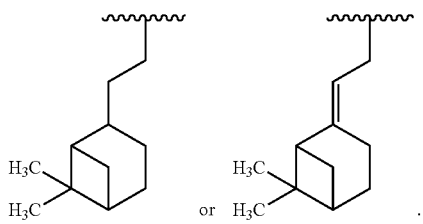 [SMILES: *CCC1CCC2CC1C2(C)C ; *C/C=C1\CCC2CC1C2(C)C]

In another embodiment, Y is O. In another embodiment, Y is S.

In another embodiment, Z is —$CH_2$—NH—C(=O)—. In another embodiment, Z is —$CH_2$—$CH_2$—NH—C(=O)—. In another embodiment, Z is —$CH_2$—NH—C(=S)—. In another embodiment, Z is —$CH_2$—$CH_2$—NH—C(=S)—. In another embodiment, Z is —$CH_2$—N($CH_3$)—C(=O)—. In another embodiment, Z is —$CH_2$—$CH_2$—N($CH_3$)—C(=O)—. In another embodiment, Z is —$CH_2$—N($CH_3$)—C(=S)—. In another embodiment, Z is —$CH_2$—$CH_2$—N($CH_3$)—C(=S)—.

In another embodiment, $R^1$ is selected from:
(a) -halo, —CN, —OH, —$CH_2OH$, —$CH_2CH_2OH$, —$NO_2$, —N($R^6$)$_2$, —S(=O)$NH_2$, —S(=O)$_2NH_2$, —C(=O)$OV^1$, and —C(=O)CN; and
(b) —($C_1$-$C_{10}$)alkyl, —O($C_1$-$C_6$)alkyl, —($C_3$-$C_7$)cycloalkoxy, —($C_3$-$C_{14}$)cycloalkyl, —($C_6$-$C_{14}$)bicycloalkyl, —($C_8$-$C_{20}$)tricycloalkyl, —($C_5$-$C_{14}$)cycloalkenyl, —($C_7$-$C_{14}$)bicycloalkenyl, —($C_r$-$C_{20}$)tricycloalkenyl, and -(3- to 7-membered)heterocycle, each of which is unsubstituted or substituted with 1, 2, 3, or 4 independently selected $R^8$ groups; and
(c) -phenyl, -naphthalenyl, —($C_{14}$)aryl, and -(5- to 10-membered)heteroaryl, each of which is unsubstituted or substituted with 1, 2, or 3 independently selected $R^7$ groups.

In another embodiment, $R^1$ is selected from:
(a) -halo, —CN, —OH, —$CH_2OH$, —$CH_2CH_2OH$, —$NO_2$, —N($R^6$)$_2$, —S(=O)$NH_2$, —S(=O)$_2NH_2$, —C(=O)$OV^1$, and —C(=O)CN; and
(b) —($C_1$-$C_{10}$)alkyl, —($C_2$-$C_{10}$)alkenyl, —($C_2$-$C_{10}$)alkynyl, —O($C_1$-$C_6$)alkyl, —($C_3$-$C_7$)cycloalkoxy, —($C_6$-$C_{14}$)bicycloalkyl, —($C_8$-$C_{20}$)tricycloalkyl, —($C_5$-$C_{14}$)cycloalkenyl, —($C_7$-$C_{14}$)bicycloalkenyl, —($C_8$-$C_{20}$)tricycloalkenyl, and -(3- to 7-membered)heterocycle, each of which is unsubstituted or substituted with 1, 2, 3, or 4 independently selected $R^8$ groups; and
(c)

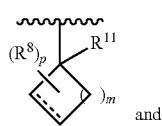

(i)

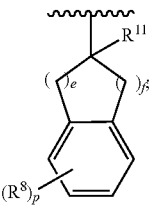

(ii)

and
(d) -phenyl, -naphthalenyl, —($C_{14}$)aryl, and -(5- to 10-membered)heteroaryl, each of which is unsubstituted or substituted with 1, 2, or 3 independently selected $R^7$ groups.

In another embodiment, $R^1$ is selected from:
(a) -halo, —CN, —OH, —$CH_2OH$, —$CH_2CH_2OH$, —$NO_2$, —N($R^6$)$_2$, —S(=O)$NH_2$, —S(=O)$_2NH_2$, —C(=O)$OV^1$, and —C(=O)CN; and
(b) —($C_1$-$C_{10}$)alkyl, —O($C_1$-$C_6$)alkyl, —($C_3$-$C_7$)cycloalkoxy, —($C_6$-$C_{14}$)bicycloalkyl, —($C_8$-$C_{20}$)tricycloalkyl, —($C_5$-$C_{14}$)cycloalkenyl, —($C_7$-$C_{14}$)bicycloalkenyl, —($C_8$-$C_{20}$)tricycloalkenyl, and -(3- to 7-membered)heterocycle, each of which is unsubstituted or substituted with 1, 2, 3, or 4 independently selected $R^8$ groups; and
(c)

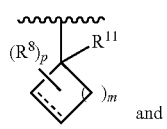

(i)

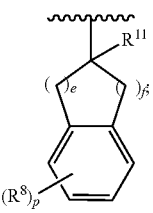

(ii)

and
(d) -phenyl and -(5- to 10-membered)heteroaryl, each of which is unsubstituted or substituted with 1, 2, or 3 independently selected $R^7$ groups.

In another embodiment, m is 1, 2, 3, 4, 5, 6, 7, 8, or 9. In another embodiment, m is 2, 3, 4, 5, 6, 7, or 8. In another embodiment, m is 2, 3, 4, 5, 6, or 7. In another embodiment, m is 2, 3, 4, 5, or 6. In another embodiment, m is 2, 3, 4, or 5. In another embodiment, m is 2. In another embodiment, m is 3. In another embodiment, m is 4. In another embodiment, m is 5. In another embodiment, m is 6. In another embodiment, m is 7.

In another embodiment, n is 2, 3, 4, 5, 6, 7, or 8. In another embodiment, n is 2, 3, 4, 5, 6, or 7. In another embodiment, n is 2, 3, 4, 5, or 6. In another embodiment, n is 2, 3, 4, or 5. In another embodiment, n is 2. In another embodiment, n is 3. In another embodiment, n is 4. In another embodiment, n is 5. In another embodiment, n is 6. In another embodiment, n is 7.

In another embodiment, m is 1, 2, 3, 4, 5, 6, 7, 8, or 9 and n is 2, 3, 4, 5, 6, 7, or 8. In another embodiment, m is 2, 3, 4, 5, 6, 7, or 8 and n is 2, 3, 4, 5, 6, 7, or 8. In another embodiment, m is 2, 3, 4, 5, 6, or 7 and n is 2, 3, 4, 5, 6, or 7. In another embodiment, m is 2, 3, 4, 5, or 6 and n is 2, 3, 4, 5, or 6. In another embodiment, m is 2, 3, 4, or 5 and n is 2, 3, 4, or 5. In another embodiment, m=n. In another embodiment, m and n are each 2. In another embodiment, m and n are each 3. In another embodiment, m and n are each 4. In another embodiment, m and n are each 5. In another embodiment, m and n are each 6. In another embodiment, m and n are each 7.

In another embodiment, e is 0 and f is 0. In another embodiment, e is 0 and f is 1. In another embodiment, e is 1 and f is 0. In another embodiment, e is 1 and f is 1. In another embodiment, e is 1 and f is 2. In another embodiment, e is 2 and f is 1. In another embodiment, e is 2 and f is 2.

In another embodiment, p is 0, 1, 2, or 3. In another embodiment, p is 0, 1, or 2. In another embodiment, p is 1 or 2. In another embodiment, p is 2. In another embodiment, p is 1. In another embodiment, p is 0.

In another embodiment, $R^1$ is optionally substituted cyclooctyl. In another embodiment, $R^1$ is optionally substituted cyclooctenyl. In another embodiment, $R^1$ is optionally substituted anthryl.

In another embodiment, h is 0 and $R^1$ is optionally substituted cyclooctyl. In another embodiment, h is 0 and $R^1$ is optionally substituted cycloundecyl. In another embodiment, h is 0 and $R^1$ is optionally substituted cyclooctenyl. In another embodiment, h is 0 and $R^1$ is optionally substituted anthryl. In another embodiment, h is 0 and $R^1$ is optionally substituted —$(C_6$-$C_{14})$bicycloalkyl. In another embodiment, h is 0 and $R^1$ is optionally substituted bicyclo[3.3.1]nonyl. In another embodiment, h is 0 and $R^1$ is optionally substituted bicyclo[2.2.1.]hepyl. In another embodiment, h is 0 and $R^1$ is optionally substituted —$(C_8$-$C_{20})$tricycloalkyl. In another embodiment, h is 0 and $R^1$ is optionally substituted adamantyl. In another embodiment, h is 0 and $R^1$ is optionally substituted noradamantyl.

In another embodiment, —Z—$R^1$ is:

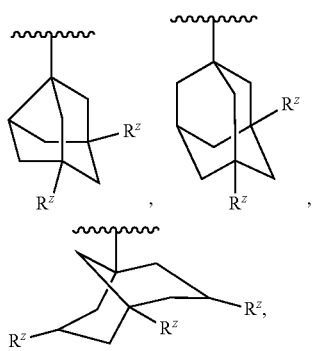

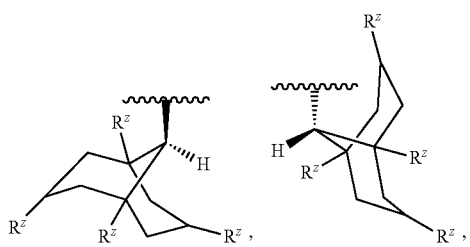

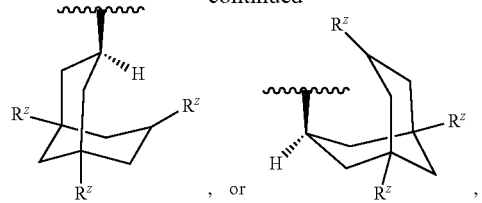

where each $R^z$ is independently —H, —$(C_1$-$C_4)$alkyl, —OH, or —CN and preferably each $R^z$ is independently —H, —$CH_3$, or —$CH_2CH_3$. In another embodiment, —Z—$R^1$ is:

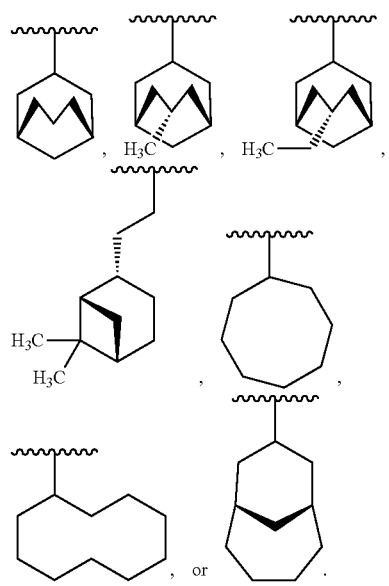

In another embodiment, —Z—$R^1$ is:

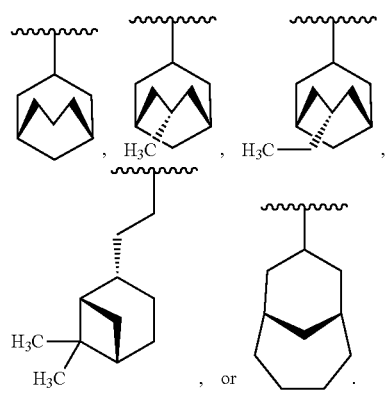

In another embodiment, —Z—$R^1$ is:

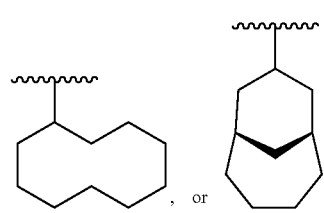 [SMILES: *C1CCCCCCCCC1 ; *C1C[C@H]2CCCC[C@@H](C1)C2]

In another embodiment, —Z—R¹ is:

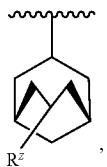

where $R^z$ is —H, —CH₃, or —CH₂CH₃.

In another embodiment, $Y_1$ is O, A and B are each H, and a is 0 or 1. In another embodiment, $Y_1$ is S, A and B are each H, and a is 0 or 1. In another embodiment, $Y_1$ is O, A and B are each H, and a is 0. In another embodiment, $Y_1$ is S, A and B are each H, and a is 0. In another embodiment, $Y_1$ is O, A and B are each H, and a is 1. In another embodiment, $Y_1$ is S, A and B are each H, and a is 1.

In another embodiment, $Y_1$ is O, A and B are each H, h is 0, and a is 0 or 1. In another embodiment, $Y_1$ is S, A and B are each H, h is 0, and a is 0 or 1. In another embodiment, $Y_1$ is O, A and B are each H, h is 0, and a is 0. In another embodiment, $Y_1$ is S, A and B are each H, h is 0, and a is 0. In another embodiment, $Y_1$ is O, A and B are each H, h is 0, and a is 1. In another embodiment, $Y_1$ is S, A and B are each H, h is 0, and a is 1. In another embodiment, $Y_1$ is O, A and B are each H, h is 1, Z is $(C_1-C_4)$alkyl unsubstituted by $R^{13}$, and a is 0 or 1. In another embodiment, $Y_1$ is S, A and B are each H, h is 1, Z is $(C_1-C_4)$alkyl unsubstituted by $R^{13}$, and a is 0 or 1. In another embodiment, $Y_1$ is O, A and B are each H, h is 1, Z is $(C_1-C_4)$alkyl unsubstituted by $R^{13}$, and a is 0. In another embodiment, $Y_1$ is S, A and B are each H, h is 1, Z is $(C_1-C_4)$alkyl unsubstituted by $R^{13}$, and a is 0. In another embodiment, $Y_1$ is O, A and B are each H, h is 1, Z is $(C_1-C_4)$alkyl unsubstituted by $R^{13}$, and a is 1. In another embodiment, $Y_1$ is S, A and B are each H, h is 1, Z is $(C_1-C_4)$alkyl unsubstituted by $R^{13}$, and a is 1.

In another embodiment, A and B are independently selected from:
- (a) —H, —CN, —C(=O)OT³, and —C(=O)N(T¹)(T²); and
- (b) —$(C_3-C_{12})$cycloalkyl, —$(C_3-C_{12})$cycloalkoxy, —$(C_1-C_6)$alkyl, —$(C_2-C_6)$alkenyl, —$(C_2-C_6)$alkynyl, and —$(C_1-C_6)$alkoxy, each of which is unsubstituted or is substituted with 1 or 2 substituents independently selected from —OH, —S(=O)₂NH₂, —N(R⁶)₂, =NR⁶, —C(=O)OT³, —C(=O)N(R⁶)₂, —N(R⁶)C(=O)R⁹, and -(5- or 6-membered)heterocycle, or 1, 2, or 3 independently selected -halo; or
- (c) A-B can together form a $(C_2-C_6)$bridge, which is unsubstituted or substituted with 1, 2, 3, 4, 5, 6, 7 or 8 substituents independently selected from —OH, —$(C_1-C_4)$alkyl, -halo, and —C(halo)₃, and which bridge optionally contains —HC=CH— or —O— within the $(C_2-C_6)$bridge; wherein the 6-membered, nitrogen-containing ring that is fused to the $Q_a$ ring can be in the endo- or exo-configuration with respect to the A-B bridge.

In another embodiment, A and B are each independently —H or —$(C_1-C_6)$alkyl. In another embodiment, A is —$(C_1-C_6)$alkyl. In another embodiment, B is —$(C_1-C_6)$alkyl. In another embodiment, A and B are each independently —$(C_1-C_6)$alkyl. In another embodiment, A is —$(C_1-C_6)$alkyl and B is H.

In another embodiment, A is —H and B is —$(C_1-C_6)$alkyl. In another embodiment, A and B are each independently —H or —CH₃. In another embodiment, A is —CH₃. In another embodiment, B is —CH₃. In another embodiment, A and B are each —CH₃. In another embodiment, A is —CH₃ and B is H. In another embodiment, A is —H and B is —CH₃. In another embodiment, A is H. In another embodiment, B is H. In another embodiment, A and B are each H.

In another embodiment, A-B together form a $(C_2)$bridge which bridge is substituted or unsubstituted. In another embodiment, A-B together form a $(C_2)$bridge which bridge is unsubstituted. In another embodiment, A-B together form a $(C_2)$bridge which bridge is substituted by one or two methyl groups. In another embodiment, A-B together form a $(C_3)$bridge which bridge is substituted or unsubstituted. In another embodiment, A-B together form a $(C_3)$bridge which bridge is unsubstituted. In another embodiment, A-B together form a $(C_3)$bridge which bridge is substituted by one or two methyl groups. In another embodiment, A-B together form a $(C_4)$bridge which bridge is substituted or unsubstituted. In another embodiment, A-B together form a $(C_4)$bridge which bridge is unsubstituted. In another embodiment, A-B together form a $(C_4)$bridge which bridge is substituted by one or two methyl groups. In another embodiment, A-B together form a $(C_5)$bridge which bridge is substituted or unsubstituted. In another embodiment, A-B together form a $(C_5)$bridge which bridge is unsubstituted. In another embodiment, A-B together form a $(C_5)$bridge which bridge is substituted by one or two methyl groups. In another embodiment, A-B together form a $(C_6)$bridge which bridge is substituted or unsubstituted. In another embodiment, A-B together form a $(C_6)$bridge which bridge is unsubstituted. In another embodiment, A-B together form a $(C_6)$bridge which bridge is substituted by one or two methyl groups.

In another embodiment, A-B together form a $(C_2)$bridge which bridge is —HC=CH— and is substituted or unsubstituted. In another embodiment, A-B together form a $(C_2)$bridge which bridge is —HC=CH— and is unsubstituted. In another embodiment, A-B together form a $(C_2)$bridge which is —HC=CH— and is substituted by one or two methyl groups. In another embodiment, A-B together form a $(C_3)$bridge which is —CH₂—HC=CH— or —HC=CH—CH₂— and is substituted or unsubstituted. In another embodiment, A-B together form a $(C_3)$bridge which is —CH₂—HC=CH— or —HC=CH—CH₂— and is unsubstituted. In another embodiment, A-B together form a $(C_3)$bridge which is —CH₂—HC=CH— or —HC=CH—CH₂— and is substituted by one or two methyl groups. In another embodiment, A-B together form a $(C_4)$bridge which is —CH₂—CH₂—HC=CH—, —CH₂—HC=CH—CH₂—, or —HC=CH—CH₂—CH₂— and is substituted or unsubstituted. In another embodiment, A-B together form a $(C_4)$bridge which is —CH₂—CH₂—HC=CH—, —CH₂—HC=CH—CH₂—, or —HC=CH—CH₂—CH₂— and is unsubstituted. In another embodiment, A-B together form a $(C_4)$bridge which is —CH₂—CH₂—HC=CH—, —CH₂—HC=CH—CH₂—, or —HC=CH—CH₂—CH₂— and is substituted by one or two methyl groups.

In another embodiment, A-B together form a $(C_2)$bridge which is —CH₂—O—CH₂— and is substituted or unsubstituted. In another embodiment, A-B together form a $(C_2)$bridge which is —CH₂—O—CH₂— and is unsubstituted. In another embodiment, A-B together form a $(C_2)$bridge which is —CH₂—O—CH₂— and is substituted by one or two methyl groups. In another embodiment, A-B together form a $(C_3)$bridge which is —CH₂—O—CH₂—CH₂— or —CH₂—CH₂—O—CH₂— and is substituted or unsubstituted. In another embodiment, A-B together form a $(C_3)$ bridge which is —CH₂—O—CH₂—CH₂— or —CH₂—CH₂—O—CH₂— and is unsubstituted. In another embodiment, A-B together form a (C₃)bridge which is —CH₂—O—CH₂—CH₂— or —CH₂—CH₂—O—CH₂— and is substituted by one or two methyl groups. In another embodiment, A-B together form a (C₄)bridge which is —CH₂—O—CH₂—CH₂—CH₂—, —CH₂—CH₂—O—CH₂—CH₂—, or —CH₂—CH₂—CH₂—O—CH₂— and is substituted or unsubstituted. In another embodiment, A-B together form a (C₄)bridge which is —CH₂—O—CH₂—CH₂—CH₂—, —CH₂—CH₂—O—CH₂—CH₂—, or —CH₂—CH₂—CH₂—O—CH₂— and is unsubstituted. In another embodiment, A-B together form a (C₄)bridge which is —CH₂—O—CH₂—CH₂—CH₂—, —CH₂—CH₂—O—CH₂—CH₂—, or —CH₂—CH₂—CH₂—O—CH₂— and is substituted by one or two methyl groups.

In another embodiment, A and B together form a bridge such that the bridged-piperidine is:

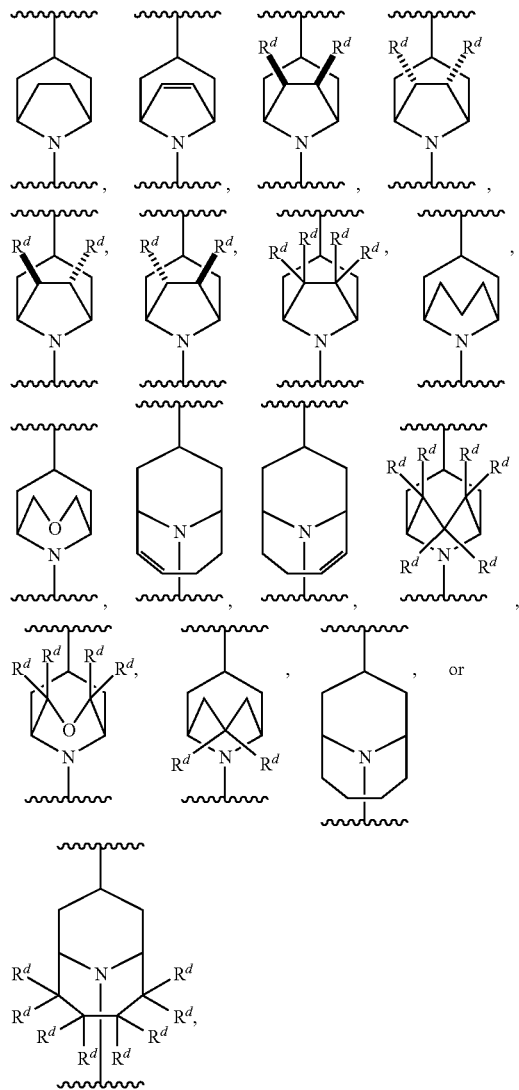

wherein each $R^d$ is independently —H, —(C₁-C₄)alkyl, -halo, or —C(halo)₃. In another embodiment, A and B together form a bridge such that the bridged-piperidine is:

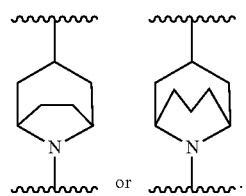

In another embodiment, A and B together form a bridge such that the bridged-piperidine is:

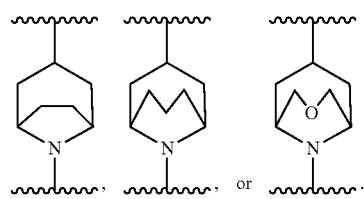

In another embodiment, the A-B bridge of the bridged-piperidine is in the endo-configuration with respect to the 6-membered, nitrogen-containing ring that is fused to the $Q_a$ ring.

In another embodiment, the pharmaceutically acceptable salt or solvate of a compounds of Formula (I) is a pharmaceutically acceptable salt. In another embodiment, the pharmaceutically acceptable salt is a hydrochloride salt. In another embodiment, the pharmaceutically acceptable salt is a sodium salt. In another embodiment, the pharmaceutically acceptable salt is a potassium salt. In another embodiment, the pharmaceutically acceptable salt is a para-toluenesulfonic acid salt.

In other embodiments, the Substituted Benzimidazole-Type Piperidine Compound of Formula (I) has one of the formulae of Table 1.

TABLE 1

| Formula | Compound |
|---|---|
| IAA | (structure with $(R^2)_a$, W, U, $R^1$, Z) |
| IAB | (structure with $(R^2)_a$, W, U, $R^1$, Z) |

TABLE 1-continued

| Formula | Compound |
|---|---|
| IAC | |
| IAD | |
| IAD$_1$† | |
| IAD$_2$‡ | |
| IAE | |
| IAE$_1$† | |
| IAE$_2$‡ | |
| IAF | |
| IAF$_1$† | |
| IAF$_2$‡ | |

TABLE 1-continued

| Formula | Compound |
|---|---|
| IAG | |
| IAG$_1$† | |
| IAG$_2$‡ | |
| IAH | |
| IAH$_1$† | |
| IAH$_2$‡ | |
| IAJ | |
| IAJ$_1$† | |
| IAJ$_2$‡ | |
| IAK | |

TABLE 1-continued

| Formula | Compound |
|---|---|
| IAK$_1$[†] | 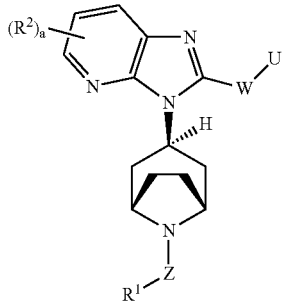 |
| IAK$_2$[‡] | 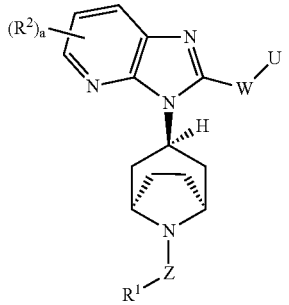 |
| IAL | 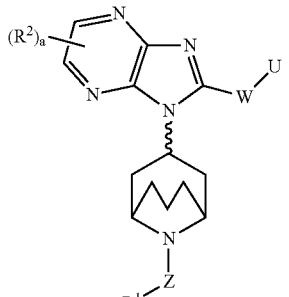 |
| IAL$_1$[†] | 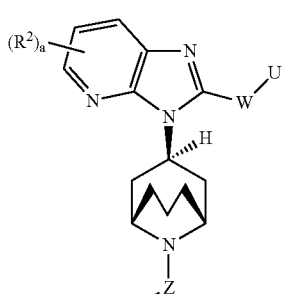 |
| IAL$_2$[‡] | 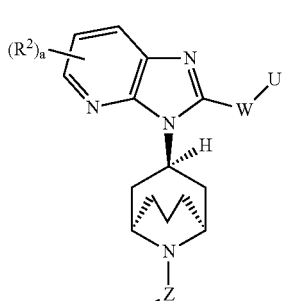 |
| IAM | 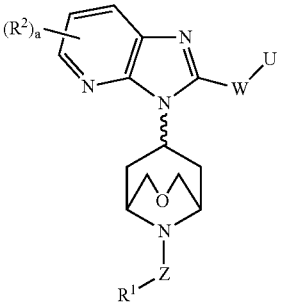 |
| IAM$_1$[†] | 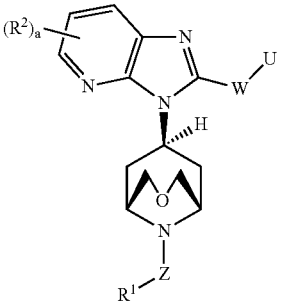 |
| IAM$_2$[‡] | 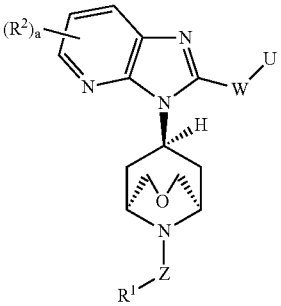 |

[†]indicates the 5-membered, nitrogen-containing ring that is fused to the benzo or pyridino is in the endo-configuration with respect to the alkyl or —CH$_2$—O—CH$_2$— bridge.
[‡]indicates the 5-membered, nitrogen-containing ring that is fused to the benzo or pyridino is in the exo-configuration with respect to the alkyl or —CH$_2$—O—CH$_2$— bridge.

where $R^1$, $R^2$, $R^{11}$, U, Z, and a are as defined above for the Substituted Benzimidazole-Type Piperidine Compounds of Formula (I) and —W— is a single bond, —CH$_2$—, —NH—, —O—, —CH$_2$—(C$_1$-C$_3$)alkylene-, —NH—(C$_1$-C$_3$)alkylene-, —O—(C$_1$-C$_3$)alkylene-, —CH$_2$—(C$_2$-C$_3$)alkenylene-, —NH—(C$_2$-C$_3$)alkenylene-, —O—(C$_2$-C$_3$)alkenylene-, —CH$_2$—(C$_1$-C$_3$)alkylene-N(R$^{11}$)—, —NH—(C$_1$-C$_3$)alkylene-N(R$^{11}$)—, —O—(C$_1$-C$_3$)alkylene-N(R$^{11}$)—, —CH$_2$—N(R$^{11}$)—, —CH$_2$—O—, or —CH$_2$—O—(C$_1$-C$_3$)alkylene-.

4.2 Substituted Benzimidazole-Type Piperidine Compounds of Formula (IA)

As stated above, the disclosure encompasses Substituted Benzimidazole-Type Piperidine Compounds of Formula (IA):

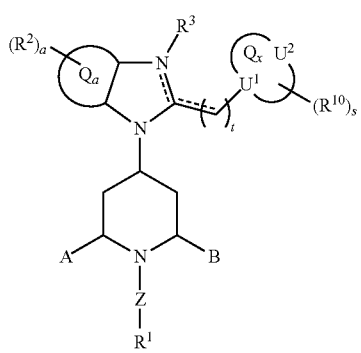

(IA)

or a pharmaceutically acceptable derivative thereof where each dashed line, $Q_a$, $Q_x$, $R^1$, $R^2$, $R^3$, $R^{10}$, A, B, $U^1$, $U^2$, Z, a, s, and t are defined above for the Substituted Benzimidazole-Type Piperidine Compounds of Formula (IA).

In one embodiment, the compound of formula (IA) is a compound of formula (IA'):

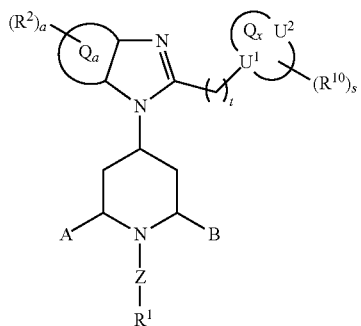

(IA')

or a pharmaceutically acceptable salt or solvate thereof where $R^1$, $R^2$, $R^{10}$, $Q_a$, $Q_x$, $U^1$, $U^2$, A, B, Z, a, s, and t are as defined for the compounds of formula (IA).

In another embodiment, the compound of formula (IA) is a compound of formula (IA"):

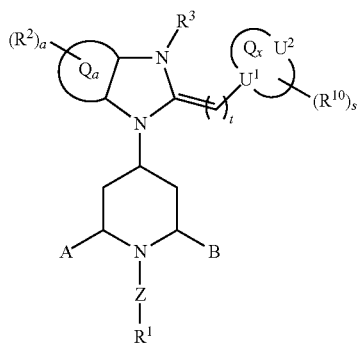

(IA")

or a pharmaceutically acceptable salt or solvate thereof where $R^1$, $R^2$, $R^3$, $R^{10}$, $Q_a$, $Q_x$, $U^1$, $U^2$, A, B, Z, a, s, and t are as defined for the compounds of formula (IA).

4.2a Substituted Benzimidazole-Type Piperidine Compounds of Formulae (IA), (IA'), and (IA")

In one embodiment, t is 1 and the $Q_x$ ring is selected from:

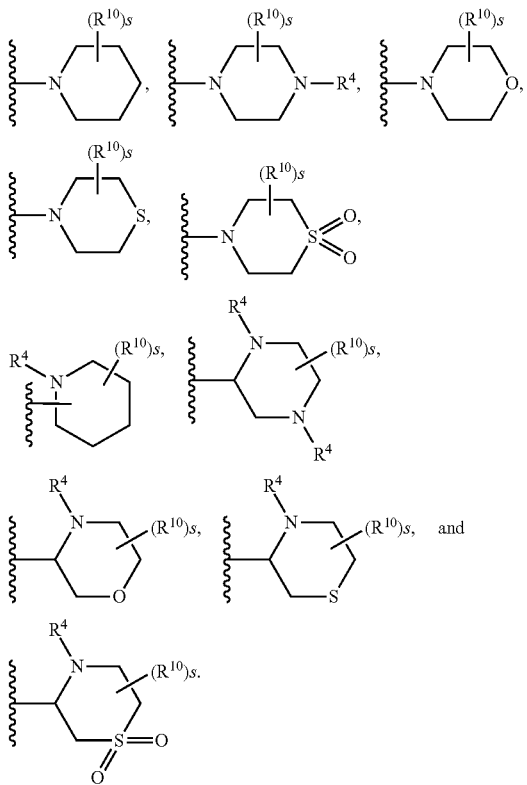

In another embodiment, t is 1, 2, or 3 and the $Q_x$ ring is selected from:

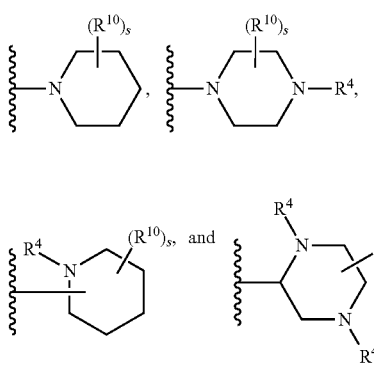

In another embodiment, t is 1 and the $Q_x$ ring is selected from:

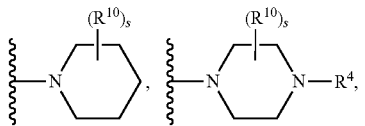

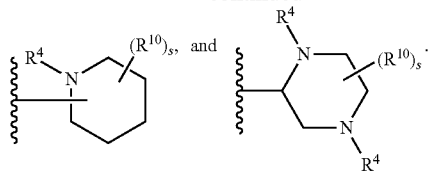

In another embodiment, t is 0, 1, 2, or 3 and the $Q_x$ ring is selected from:

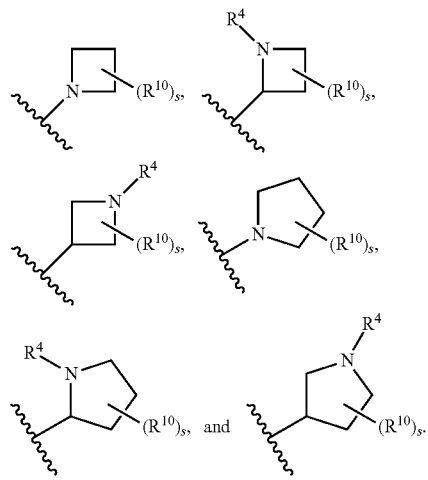

In another embodiment, t is 0 and the $Q_x$ ring is selected from:

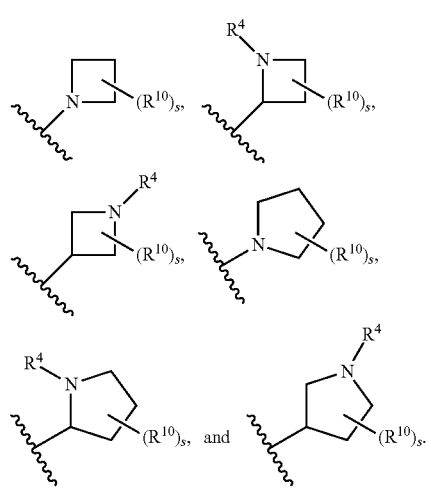

In another embodiment, t is 0 and the $Q_x$ ring is selected from:

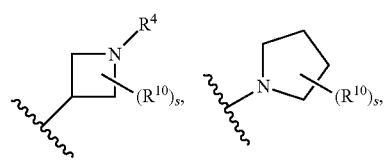

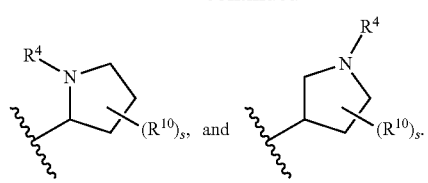

In another embodiment, t is 1 and the $Q_x$ ring is selected from:

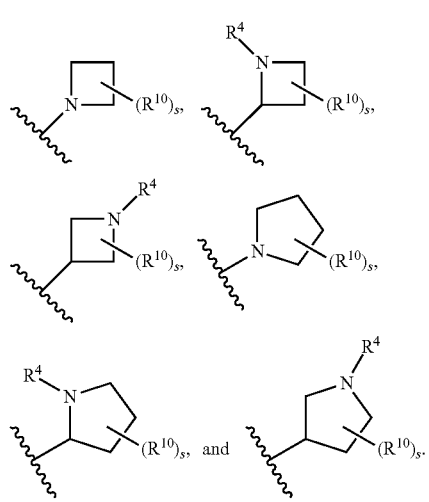

In another embodiment, t is 1 and the $Q_x$ ring is selected from:

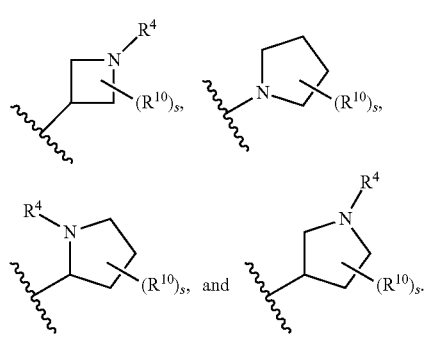

In another embodiment, s is 0, t is 1, and the $Q_x$ ring is selected from:

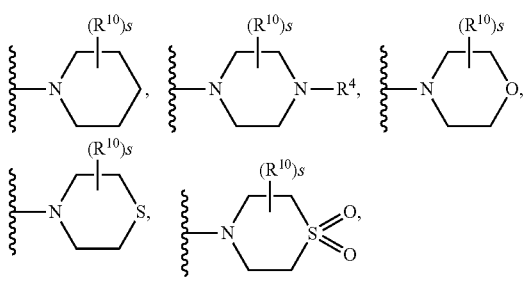

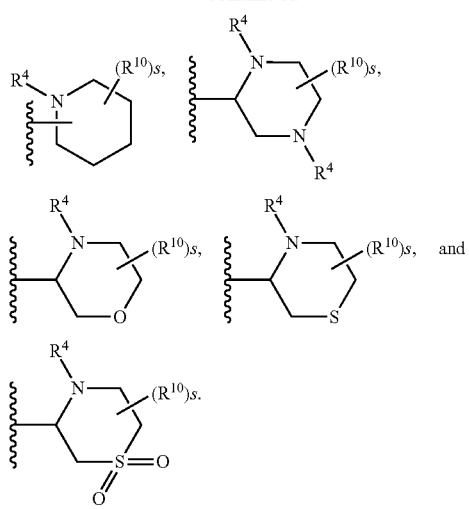

In another embodiment, s is 0, t is 1, 2, or 3, and the $Q_x$ ring is selected from:

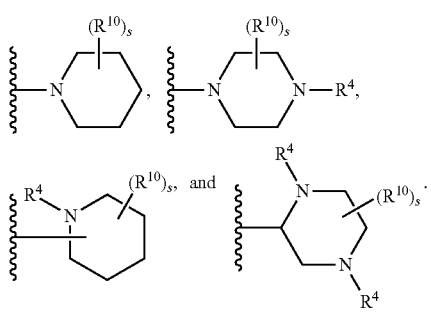

In another embodiment, s is 0, t is 1, and the $Q_x$ ring is selected from:

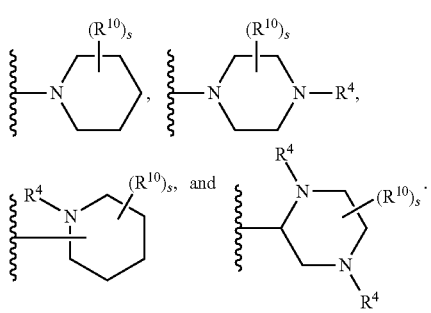

In another embodiment, s is 0, t is 0, 1, 2, or 3, and the $Q_x$ ring is selected from:

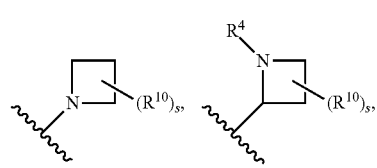

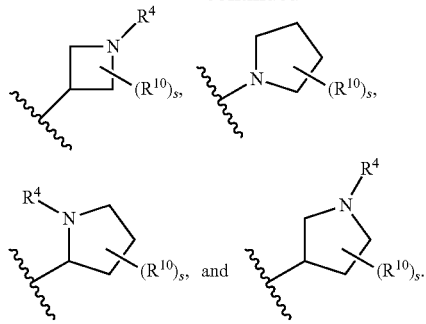

In another embodiment, s is 0, t is 0, and the $Q_x$ ring is selected from:

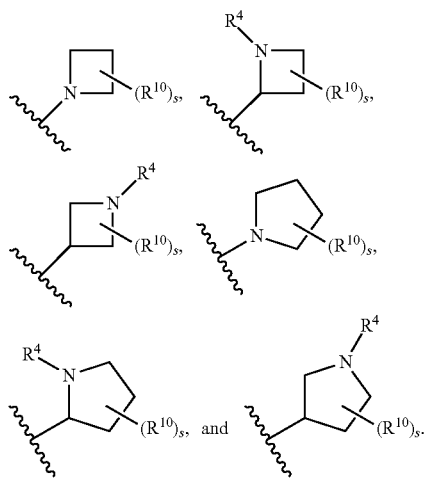

In another embodiment, s is 0, t is 0, and the $Q_x$ ring is selected from:

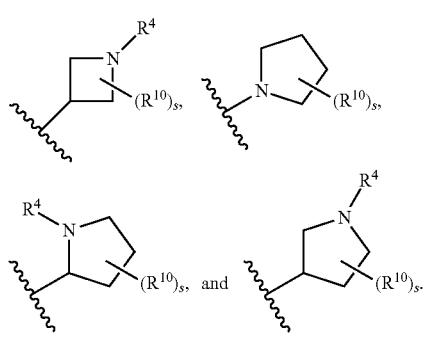

In another embodiment, s is 0, t is 1, and the $Q_x$ ring is selected from:

-continued

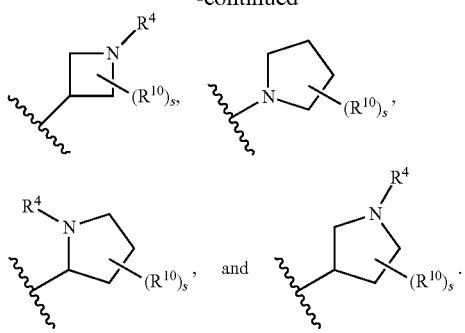

In another embodiment, s is 0, t is 1, and the $Q_x$ ring is selected from:

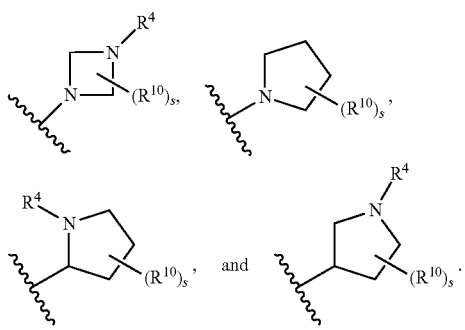

In another embodiment, s is 1, t is 1, and the $Q_x$ ring is selected from:

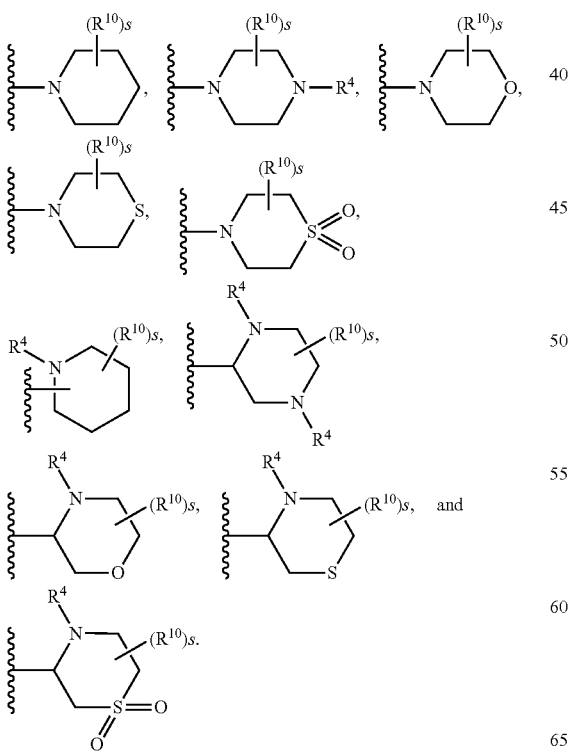

In another embodiment, s is 1, t is 1, 2, or 3, and the $Q_x$ ring is selected from:

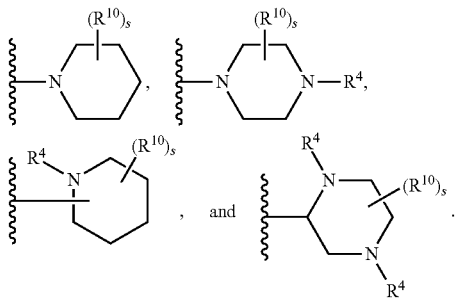

In another embodiment, s is 1, t is 1, and the $Q_x$ ring is selected from:

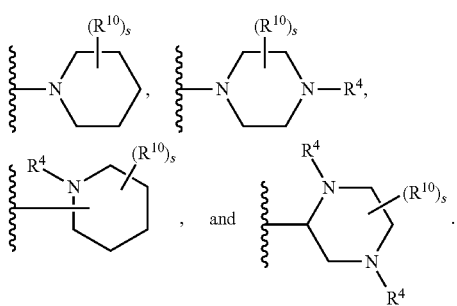

In another embodiment, s is 1, t is 0, 1, 2, or 3, and the $Q_x$ ring is selected from:

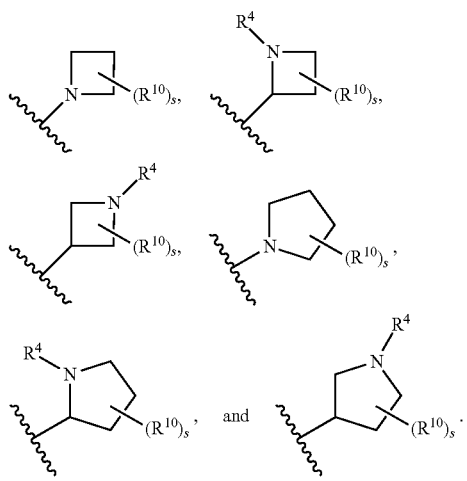

In another embodiment, s is 1, t is 0, and the $Q_x$ ring is selected from:

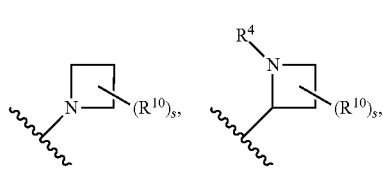

In another embodiment, s is 1, t is 0, and the $Q_x$ ring is selected from:

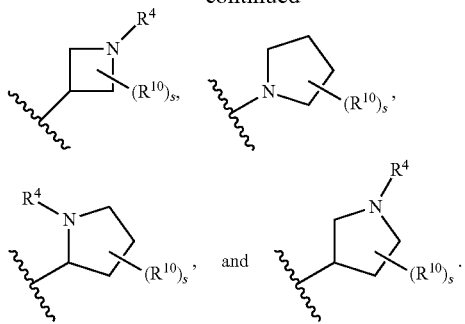

In another embodiment, s is 1, t is 1, and the $Q_x$ ring is selected from:

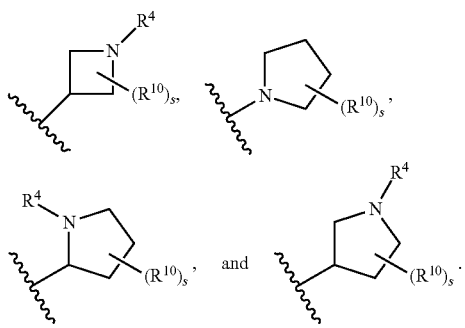

In another embodiment, s is 1, t is 1, and the $Q_x$ ring is selected from:

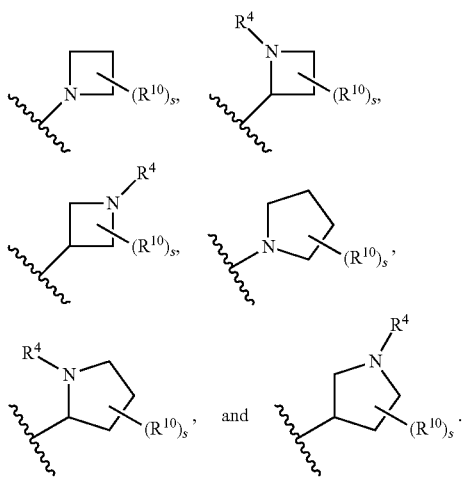

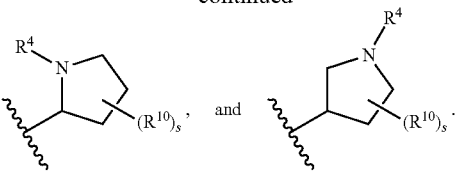

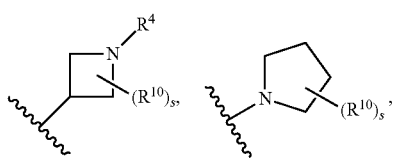

In another embodiment, $R^4$ is $CH_2CH_2C(=O)O-(C_1-C_6)$alkyl, $CH_2CH_2C(=O)OH$, $CH_2C(=O)O-(C_1-C_6)$alkyl, $CH_2C(=O)OH$, $C(=O)O-(C_1-C_6)$alkyl, $C(=O)OH$, or $CH_2C(=O)NH(C_1-C_6)$alkyl. In another embodiment, $R^4$ is $CH_2CH_2C(=O)OH$, $CH_2C(=O)O-(C_1-C_6)$alkyl, $CH_2C(=O)OH$, $C(=O)O-(C_1-C_6)$alkyl, $C(=O)OH$, or $CH_2C(=O)NH(C_1-C_6)$alkyl. In another embodiment, $R^4$ is $CH_2CH_2C(=O)O-(C_1-C_6)$alkyl, $CH_2C(=O)O-(C_1-C_6)$alkyl, $CH_2C(=O)OH$, $C(=O)O-(C_1-C_6)$alkyl, $C(=O)OH$, or $CH_2C(=O)NH(C_1-C_6)$alkyl. In another embodiment, $R^4$ is $CH_2CH_2C(=O)O-(C_1-C_6)$alkyl, $CH_2CH_2C(=O)OH$, $CH_2C(=O)OH$, $C(=O)O-(C_1-C_6)$alkyl, $C(=O)OH$, or $CH_2C(=O)NH(C_1-C_6)$alkyl. In another embodiment, $R^4$ is $CH_2CH_2C(=O)O-(C_1-C_6)$alkyl, $CH_2CH_2C(=O)OH$, $CH_2C(=O)O-(C_1-C_6)$alkyl, $C(=O)O-(C_1-C_6)$alkyl, $C(=O)OH$, or $CH_2C(=O)NH(C_1-C_6)$alkyl. In another embodiment, $R^4$ is $CH_2CH_2C(=O)O-(C_1-C_6)$alkyl, $CH_2CH_2C(=O)OH$, $CH_2C(=O)O-(C_1-C_6)$alkyl, $CH_2C(=O)OH$, $C(=O)OH$, or $CH_2C(=O)NH(C_1-C_6)$alkyl. In another embodiment, $R^4$ is $CH_2CH_2C(=O)O-(C_1-C_6)$alkyl, $CH_2CH_2C(=O)OH$, $CH_2C(=O)O-(C_1-C_6)$alkyl, $CH_2C(=O)OH$, $C(=O)O-(C_1-C_6)$alkyl, or $CH_2C(=O)NH(C_1-C_6)$alkyl. In another embodiment, $R^4$ is $CH_2CH_2C(=O)O-(C_1-C_6)$alkyl, $CH_2CH_2C(=O)OH$, $CH_2C(=O)O-(C_1-C_6)$alkyl, $CH_2C(=O)OH$, $C(=O)O-(C_1-C_6)$alkyl, or $C(=O)OH$.

In another embodiment, $R^4$ is $CH_2CH_2C(=O)O-(C_1-C_6)$alkyl or $CH_2CH_2C(=O)OH$. In another embodiment, $R^4$ is $CH_2CH_2C(=O)OH$ or $CH_2C(=O)O-(C_1-C_6)$alkyl. In another embodiment, $R^4$ is $CH_2C(=O)O-(C_1-C_6)$alkyl or $CH_2C(=O)OH$. In another embodiment, $R^4$ is $CH_2C(=O)OH$ or $C(=O)O-(C_1-C_6)$alkyl. In another embodiment, $R^4$ is $C(=O)O-(C_1-C_6)$alkyl or $C(=O)OH$. In another embodiment, $R^4$ is $CH_2CH_2C(=O)O-(C_1-C_6)$alkyl or $CH_2C(=O)NH(C_1-C_6)$alkyl.

In another embodiment, $R^4$ is $CH_2CH_2C(=O)OH$, $CH_2C(=O)O-(C_1-C_4)$alkyl, $CH_2C(=O)OH$, $C(=O)O-(C_1-C_4)$alkyl, $C(=O)OH$, or $CH_2C(=O)NH(C_1-C_4)$alkyl. In another embodiment, $R^4$ is $CH_2CH_2C(=O)O-(C_1-C_4)$alkyl, $CH_2C(=O)O-(C_1-C_4)$alkyl, $CH_2C(=O)OH$, $C(=O)O-(C_1-C_4)$alkyl, $C(=O)OH$, or $CH_2C(=O)NH(C_1-C_4)$alkyl. In another embodiment, $R^4$ is $CH_2CH_2C(=O)O-(C_1-C_4)$alkyl, $CH_2CH_2C(=O)OH$, $CH_2C(=O)OH$, $C(=O)O-(C_1-C_4)$alkyl, $C(=O)OH$, or $CH_2C(=O)NH(C_1-C_4)$alkyl. In another embodiment, $R^4$ is $CH_2CH_2C(=O)O-(C_1-C_4)$alkyl, $CH_2CH_2C(=O)OH$, $CH_2C(=O)O-(C_1-C_4)$alkyl, $C(=O)O-(C_1-C_4)$alkyl, $C(=O)OH$, or $CH_2C(=O)NH(C_1-C_4)$alkyl. In another embodiment, $R^4$ is $CH_2CH_2C(=O)O-(C_1-C_4)$alkyl, $CH_2CH_2C(=O)OH$, $CH_2C(=O)O-(C_1-C_4)$alkyl, $CH_2C(=O)OH$, $C(=O)OH$, or $CH_2C(=O)NH(C_1-C_4)$alkyl. In another embodiment, $R^4$ is $CH_2CH_2C(=O)O-(C_1-C_4)$alkyl, $CH_2CH_2C(=O)OH$, $CH_2C(=O)O-(C_1-C_4)$alkyl, $CH_2C(=O)OH$, $C(=O)O-(C_1-C_4)$alkyl, or $CH_2C(=O)NH(C_1-C_4)$alkyl. In another embodiment, $R^4$ is $CH_2CH_2C(=O)O-(C_1-C_4)$alkyl, $CH_2CH_2C(=O)OH$, $CH_2C(=O)O-(C_1-C_4)$alkyl, $CH_2C(=O)OH$, $C(=O)O-(C_1-C_4)$alkyl, or $C(=O)OH$.

In another embodiment, $R^4$ is $CH_2CH_2C(=O)O-(C_1-C_4)$alkyl or $CH_2CH_2C(=O)OH$. In another embodiment, $R^4$ is $CH_2CH_2C(=O)OH$ or $CH_2C(=O)O-(C_1-C_4)$alkyl. In another embodiment, $R^4$ is $CH_2C(=O)O-(C_1-C_4)$alkyl or $CH_2C(=O)OH$. In another embodiment, $R^4$ is $CH_2C(=O)OH$ or $C(=O)O-(C_1-C_4)$alkyl. In another embodiment, $R^4$ is $C(=O)O-(C_1-C_4)$alkyl or $C(=O)OH$. In another embodiment, $R^4$ is $CH_2CH_2C(=O)O-(C_1-C_4)$alkyl or $CH_2C(=O)NH(C_1-C_4)$alkyl.

In another embodiment, $R^4$ is $CH_2CH_2C(=O)O-(C_1-C_6)$alkyl. In another embodiment, $R^4$ is $CH_2CH_2C(=O)OH$. In another embodiment, $R^4$ is $CH_2C(=O)O-(C_1-C_6)$alkyl. In another embodiment, $R^4$ is $CH_2C(=O)OH$. In another embodiment, $R^4$ is $C(=O)O-(C_1-C_6)$alkyl. In another embodiment, $R^4$ is $C(=O)OH$. In another embodiment, $R^4$ is $CH_2C(=O)NH(C_1-C_6)$alkyl. In another embodiment, $R^4$ is $CH_2CH_2C(=O)O-(C_1-C_4)$alkyl. In another embodiment, $R^4$ is $CH_2C(=O)O-(C_1-C_4)$alkyl. In another embodiment, $R^4$ is $C(=O)O-(C_1-C_4)$alkyl. In another embodiment, $R^4$ is $CH_2C(=O)NH(C_1-C_4)$alkyl. In another embodiment, $R^4$ is H. In another embodiment, $R^4$ is absent.

In another embodiment, $R^{10}$ is $CH_2C(=O)O-(C_1-C_6)$alkyl, $CH_2C(=O)OH$, $C(=O)O-(C_1-C_6)$alkyl, $C(=O)OH$, or $CH_2C(=O)NH(C_1-C_6)$alkyl. In another embodiment, $R^{10}$ is $CH_2C(=O)OH$, $C(=O)O-(C_1-C_6)$alkyl, $C(=O)OH$, or $CH_2C(=O)NH(C_1-C_6)$alkyl. In another embodiment, $R^{10}$ is $CH_2C(=O)O-(C_1-C_6)$alkyl, $C(=O)OH$, or $CH_2C(=O)NH(C_1-C_6)$alkyl. In another embodiment, $R^{10}$ is $CH_2C(=O)O-(C_1-C_6)$alkyl, $CH_2C(=O)OH$, $C(=O)O-(C_1-C_6)$alkyl, or $CH_2C(=O)NH(C_1-C_6)$alkyl. In another embodiment, $R^{10}$ is $CH_2C(=O)O-(C_1-C_6)$alkyl, $CH_2C(=O)OH$, $C(=O)O-(C_1-C_6)$alkyl, or $C(=O)OH$.

In another embodiment, $R^{10}$ is $CH_2C(=O)O-(C_1-C_6)$alkyl, $CH_2C(=O)OH$, or $C(=O)O-(C_1-C_6)$alkyl. In another embodiment, $R^{10}$ is $CH_2C(=O)OH$, $C(=O)O-(C_1-C_6)$alkyl, or $C(=O)OH$. In another embodiment, $R^{10}$ is $C(=O)OH$ or $CH_2C(=O)NH(C_1-C_6)$alkyl. In another embodiment, $R^{10}$ is $CH_2C(=O)O-(C_1-C_6)$alkyl or $CH_2C(=O)NH(C_1-C_6)$alkyl.

In another embodiment, $R^{10}$ is $CH_2C(=O)OH$, $C(=O)O-(C_1-C_4)$alkyl, $C(=O)OH$, or $CH_2C(=O)NH(C_1-C_4)$alkyl. In another embodiment, $R^{10}$ is $CH_2C(=O)O-(C_1-C_4)$alkyl, $C(=O)OH$, or $CH_2C(=O)NH(C_1-C_4)$alkyl. In another embodiment, $R^{10}$ is $CH_2C(=O)O-(C_1-C_4)$alkyl, $CH_2C(=O)OH$, $C(=O)O-(C_1-C_4)$alkyl, or $CH_2C(=O)NH(C_1-C_4)$alkyl. In another embodiment, $R^{10}$ is $CH_2C(=O)O-(C_1-C_4)$alkyl, $CH_2C(=O)OH$, $C(=O)O-(C_1-C_4)$alkyl, or $C(=O)OH$.

In another embodiment, $R^{10}$ is $CH_2C(=O)O-(C_1-C_4)$alkyl or $CH_2C(=O)OH$, $C(=O)O-(C_1-C_4)$alkyl. In another embodiment, $R^{10}$ is $CH_2C(=O)OH$, $C(=O)O-(C_1-C_4)$alkyl or $C(=O)OH$. In another embodiment, $R^{10}$ is $C(=O)OH$ or $CH_2C(=O)NH(C_1-C_4)$alkyl. In another embodiment, $R^{10}$ is $CH_2C(=O)O-(C_1-C_4)$alkyl or $CH_2C(=O)NH(C_1-C_4)$alkyl.

In another embodiment, $R^{10}$ is $CH_2C(=O)O-(C_1-C_6)$alkyl. In another embodiment, $R^{10}$ is $CH_2C(=O)OH$. In another embodiment, $R^{10}$ is $C(=O)O-(C_1-C_6)$alkyl. In another embodiment, $R^{10}$ is $C(=O)OH$. In another embodiment, $R^{10}$ is $CH_2C(=O)NH(C_1-C_6)$alkyl. In another embodiment, $R^{10}$ is $CH_2C(=O)O-(C_1-C_4)$alkyl. In another embodiment, $R^{10}$ is $C(=O)O-(C_1-C_4)$alkyl. In another embodiment, $R^{10}$ is $CH_2C(=O)NH(C_1-C_4)$alkyl. In another embodiment, $R^{10}$ is $CH_3$ or $CH_2CH_3$. In another embodiment, $R^{10}$ is $CH_3$. In another embodiment, $R^{10}$ is $CH_2CH_3$.

In another embodiment, s is 0 or 1. In another embodiment, s is 1 or 2. In another embodiment, s is 0. In another embodiment, s is 1. In another embodiment, s is 2.

In another embodiment, s is 1 and $R^{10}$ is $CH_2C(=O)NH(C_1-C_4)$alkyl.

In another embodiment, s is 2 and each $R^{10}$ is, independently, $CH_2C(=O)O-(C_1-C_6)$alkyl, $CH_2C(=O)OH$, $C(=O)O-(C_1-C_6)$alkyl, $C(=O)OH$, or $CH_2C(=O)NH(C_1-C_6)$alkyl. In another embodiment, s is 2 and each $R^{10}$ is, independently, $CH_2C(=O)OH$, $C(=O)O-(C_1-C_6)$alkyl, $C(=O)OH$, or $CH_2C(=O)NH(C_1-C_6)$alkyl. In another embodiment, s is 2 and each $R^{10}$ is, independently, $CH_2C(=O)O-(C_1-C_6)$alkyl, $C(=O)OH$, or $CH_2C(=O)NH(C_1-C_6)$alkyl. In another embodiment, s is 2 and each $R^{10}$ is, independently, $CH_2C(=O)O-(C_1-C_6)$alkyl, $CH_2C(=O)OH$, $C(=O)O-(C_1-C_6)$alkyl, or $CH_2C(=O)NH(C_1-C_6)$alkyl. In another embodiment, s is 2 and each $R^{10}$ is, independently, $CH_2C(=O)O-(C_1-C_6)$alkyl, $CH_2C(=O)OH$, $C(=O)O-(C_1-C_6)$alkyl, or $C(=O)OH$.

In another embodiment, s is 2 and each $R^{10}$ is, independently, $CH_2C(=O)O-(C_1-C_6)$alkyl, $CH_2C(=O)OH$, or $C(=O)O-(C_1-C_6)$alkyl. In another embodiment, s is 2 and each $R^{10}$ is, independently, $CH_2C(=O)OH$, $C(=O)O-(C_1-C_6)$alkyl, or $C(=O)OH$. In another embodiment, s is 2 and each $R^{10}$ is, independently, $C(=O)OH$ or $CH_2C(=O)NH(C_1-C_6)$alkyl. In another embodiment, s is 2 and each $R^{10}$ is, independently, $CH_2C(=O)O-(C_1-C_6)$alkyl or $CH_2C(=O)NH(C_1-C_6)$alkyl.

In another embodiment, s is 2 and each $R^{10}$ is, independently, $CH_2C(=O)OH$, $C(=O)O-(C_1-C_4)$alkyl, $C(=O)OH$, or $CH_2C(=O)NH(C_1-C_4)$alkyl. In another embodiment, s is 2 and each $R^{10}$ is, independently, $CH_2C(=O)O-(C_1-C_4)$alkyl, $C(=O)OH$, or $CH_2C(=O)NH(C_1-C_4)$alkyl. In another embodiment, s is 2 and each $R^{10}$ is, independently, $CH_2C(=O)O-(C_1-C_4)$alkyl, $CH_2C(=O)OH$, $C(=O)O-(C_1-C_4)$alkyl, or $CH_2C(=O)NH(C_1-C_4)$alkyl. In another embodiment, s is 2 and each $R^{10}$ is, independently, $CH_2C(=O)O-(C_1-C_4)$alkyl, $CH_2C(=O)OH$, $C(=O)O-(C_1-C_4)$alkyl, or $C(=O)OH$.

In another embodiment, s is 2 and each $R^{10}$ is, independently, $CH_2C(=O)O-(C_1-C_4)$alkyl or $CH_2C(=O)OH$, $C(=O)O-(C_1-C_4)$alkyl. In another embodiment, s is 2 and each $R^{10}$ is, independently, $CH_2C(=O)OH$, $C(=O)O-(C_1-C_4)$alkyl or $C(=O)OH$. In another embodiment, s is 2 and each $R^{10}$ is, independently, $C(=O)OH$ or $CH_2C(=O)NH(C_1-C_4)$alkyl. In another embodiment, s is 2 and each $R^{10}$ is, independently, $CH_2C(=O)O-(C_1-C_4)$alkyl or $CH_2C(=O)NH(C_1-C_4)$alkyl.

In another embodiment, s is 2 and each $R^{10}$ is, independently, $CH_2C(=O)O-(C_1-C_6)$alkyl. In another embodiment, s is 2 and each $R^{10}$ is, independently, $CH_2C(=O)OH$. In another embodiment, s is 2 and each $R^{10}$ is, independently, $C(=O)O-(C_1-C_6)$alkyl. In another embodiment, s is 2 and each $R^{10}$ is, independently, $C(=O)OH$. In another embodiment, s is 2 and each $R^{10}$ is, independently, $CH_2C(=O)NH(C_1-C_6)$alkyl. In another embodiment, s is 2 and each $R^{10}$ is, independently, $CH_2C(=O)O-(C_1-C_4)$alkyl. In another embodiment, s is 2 and each $R^{10}$ is, independently, $C(=O)O-(C_1-C_4)$alkyl.

In another embodiment, $R^3$ is absent. In another embodiment, $R^3$ is H, $CH_2C(=O)OH$, $CH_2C(=O)OCH_3$, $CH_2C(=O)NH_2$, $CH_2C(=O)NHCH_3$, or $CH_2C(=O)NH(CH_3)_2$. In another embodiment, $R^3$ is H, $CH_2C(=O)OH$, $CH_2C(=O)OCH_3$, $CH_2C(=O)NH_2$, or $CH_2C(=O)NHCH_3$. In another embodiment, $R^3$ is H, $CH_2C(=O)OH$, or $CH_2C(=O)NH_2$. In another embodiment, $R^3$ is H or $CH_2C(=O)OH$. In another embodiment, $R^3$ is H or $CH_2C(=O)NH_2$. In another embodiment, $R^3$ is H. In another embodiment, $R^3$ is $CH_2C(=O)OH$. In another embodiment, $R^3$ is $CH_2C(=O)NH_2$.

Each and every embodiment set forth in Section 4.1 relating to the piperidine ring and the A, B, Z, and $R^1$ substituents thereto, and to the $Q_a$, $R^2$, $R^3$, and a variable groups referenced therein also relate to the Substituted Benzimidazole-Type Piperidine Compounds in this section; therefore, those embodiments are not repeated here but are instead incorporated by reference in their entirety.

4.2b Substituted Benzimidazole-Type Piperidine Compounds of Formulae (IA), (IA'), and (IA")

In another embodiment, t is 1, 2, or 3, s is 0 or 1, and the $Q_x$ ring is selected from:

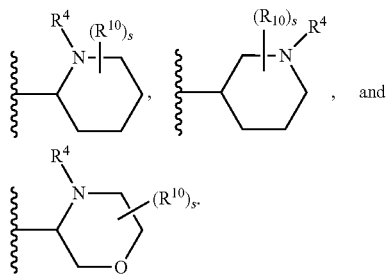

In another embodiment, t is 1, s is 0 or 1, and the $Q_x$ ring is selected from:

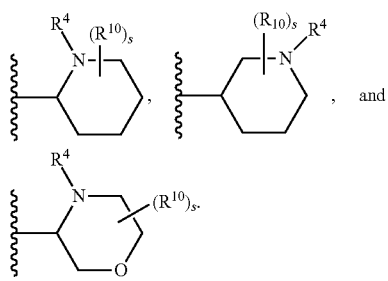

In another embodiment, t is 0, s is 0 or 1, and the $Q_x$ ring is selected from pyrrolyl, pyrazolyl, imidazolyl, oxazolyl, isoxazolyl, thiazolyl, isothiazolyl, pyridyl, pyridazyl, pyrimidyl, and pyrazyl.

In another embodiment, t is 0, s is 0 or 1, and the $Q_x$ ring is selected from pyrazolyl, imidazolyl, isoxazolyl, and pyrazyl.

In another embodiment, t is 0, s is 0 or 1, and the $Q_x$ ring is selected from pyrrolyl, oxazolyl, thiazolyl, isothiazolyl, pyridyl, pyridazyl, and pyrimidyl.

In another embodiment, t is 0, s is 0 or 1, and the $Q_x$ ring is selected from:

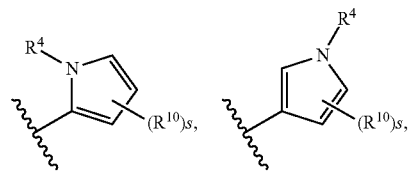

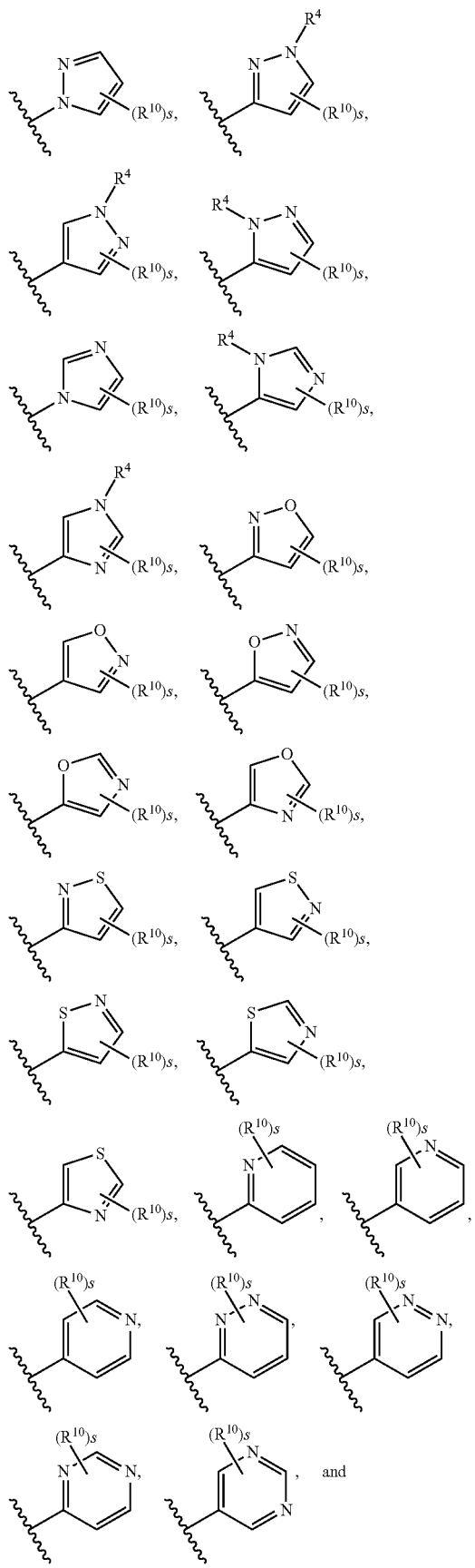

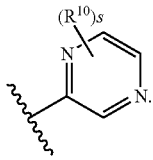

In another embodiment, t is 0, s is 0 or 1, and the $Q_x$ ring is selected from:

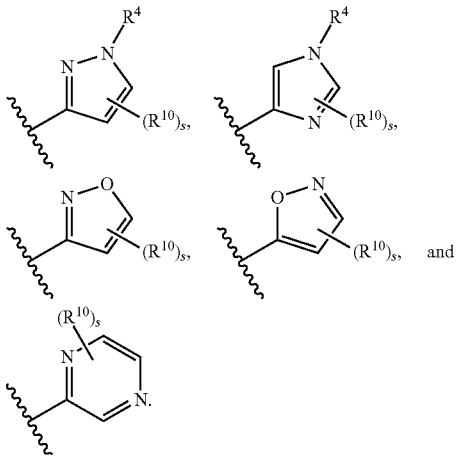

In another embodiment, t is 0, s is 0 or 1, and the $Q_x$ ring is selected from:

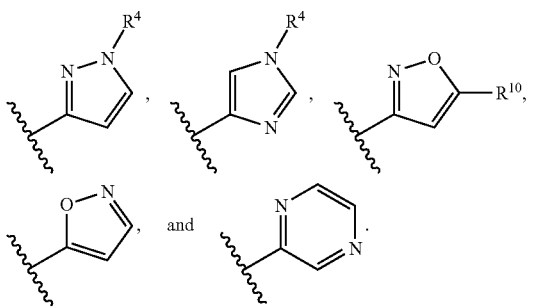

In another embodiment, $R^4$ is H, 2-(1H-imidazole), 2-(1-methyl-1H-imidazole), $CH_2CH_2C(=O)O—(C_1-C_4)$alkyl, $CH_2CH_2C(=O)OH$, $CH_2C(=O)O—(C_1-C_4)$alkyl, $CH_2C(=O)OH$, $C(=O)O—(C_1-C_4)$alkyl, $C(=O)OH$, $CH_2C(=O)NH(C_1-C_4)$alkyl, or $CH_2C(=O)N[(C_1-C_4)alkyl]_2$. In another embodiment, $R^4$ is H, 2-(1H-imidazole), 2-(1-methyl-1H-imidazole), $CH_2CH_2C(=O)OH$, $CH_2C(=O)O—(C_1-C_4)$alkyl, $CH_2C(=O)OH$, $C(=O)O—(C_1-C_4)$alkyl, $C(=O)OH$, $CH_2C(=O)NH(C_1-C_4)$alkyl, or $CH_2C(=O)N[(C_1-C_4)alkyl]_2$. In another embodiment, $R^4$ is H, 2-(1H-imidazole), 2-(1-methyl-1H-imidazole), $CH_2CH_2C(=O)O—(C_1-C_4)$alkyl, $CH_2C(=O)O—(C_1-C_4)$alkyl, $CH_2C(=O)OH$, $C(=O)O—(C_1-C_4)$alkyl, $CH_2C(=O)NH(C_1-C_4)$alkyl, or $CH_2C(=O)N[(C_1-C_4)alkyl]_2$. In another embodiment, $R^4$ is H, 2-(1H-imidazole), 2-(1-methyl-1H-imidazole), $CH_2CH_2C(=O)O—(C_1-C_4)$alkyl, $CH_2CH_2C(=O)OH$, $CH_2C(=O)O—(C_1-C_4)$alkyl, $CH_2C(=O)OH$, $C(=O)O—(C_1-C_4)$alkyl, $CH_2C(=O)NH(C_1-C_4)$alkyl, or $CH_2C(=O)N[(C_1-C_4)alkyl]_2$. In another embodiment, $R^4$ is H, H, 2-(1H-imidazole), 2-(1-methyl-1H-imidazole), $CH_2CH_2C(=O)O—(C_1-C_4)$alkyl, $CH_2CH_2C(=O)OH$, $CH_2C(=O)O—(C_1-C_4)$alkyl, $C(=O)O—(C_1-C_4)$alkyl, $C(=O)OH$, $CH_2C(=O)NH(C_1-C_4)$alkyl, or $CH_2C(=O)N[(C_1-C_4)alkyl]_2$. In another embodiment, $R^4$ is H, 2-(1H-imidazole), 2-(1-methyl-1H-imidazole), $CH_2CH_2C(=O)O—(C_1-C_4)$alkyl, $CH_2CH_2C(=O)OH$, $CH_2C(=O)O—(C_1-C_4)$alkyl, $CH_2C(=O)OH$, $C(=O)OH$, $CH_2C(=O)NH(C_1-C_4)$alkyl, or $CH_2C(=O)N[(C_1-C_4)alkyl]_2$. In another embodiment, $R^4$ is H, 2-(1H-imidazole), 2-(1-methyl-1H-imidazole), $CH_2CH_2C(=O)O—(C_1-C_4)$alkyl, $CH_2CH_2C(=O)OH$, $CH_2C(=O)O—(C_1-C_4)$alkyl, $CH_2C(=O)OH$, $C(=O)O—(C_1-C_4)$alkyl, $CH_2C(=O)NH(C_1-C_4)$alkyl, or $CH_2C(=O)N[(C_1-C_4)alkyl]_2$. In another embodiment, $R^4$ is H, 2-(1H-imidazole), 2-(1-methyl-1H-imidazole), $CH_2CH_2C(=O)O—(C_1-C_4)$alkyl, $CH_2CH_2C(=O)OH$, $CH_2C(=O)O—(C_1-C_4)$alkyl, $CH_2C(=O)OH$, $C(=O)O—(C_1-C_4)$alkyl, or $C(=O)OH$.

In another embodiment, $R^4$ is H, 2-(1H-imidazole), 2-(1-methyl-1H-imidazole), $CH_2CH_2C(=O)O—(C_1-C_4)$alkyl or $CH_2CH_2C(=O)OH$. In another embodiment, $R^4$ is H, 2-(1H-imidazole), 2-(1-methyl-1H-imidazole), $CH_2CH_2C(=O)OH$ or $CH_2C(=O)O(C_1-C_4)$alkyl. In another embodiment, $R^4$ is H, 2-(1H-imidazole), 2-(1-methyl-1H-imidazole), $CH_2C(=O)O(C_1-C_4)$alkyl or $CH_2C(=O)OH$. In another embodiment, $R^4$ is H, 2-(1H-imidazole), 2-(1-methyl-1H-imidazole), $CH_2C(=O)OH$ or $C(=O)O(C_1-C_4)$alkyl. In another embodiment, $R^4$ is H, 2-(1H-imidazole), 2-(1-methyl-1H-imidazole), $C(=O)O(C_1-C_4)$alkyl or $C(=O)OH$. In another embodiment, $R^4$ is H, 2-(1H-imidazole), 2-(1-methyl-1H-imidazole), $CH_2CH_2C(=O)O(C_1-C_4)$alkyl, $CH_2C(=O)NH(C_1-C_4)$alkyl, or $CH_2C(=O)N[(C_1-C_4)alkyl]_2$.

In another embodiment, $R^4$ is H, 2-(1H-imidazole), 2-(1-methyl-1H-imidazole), $CH_2CH_2C(=O)OH$, $CH_2C(=O)O(C_1-C_4)$alkyl, $CH_2C(=O)OH$, $C(=O)O(C_1-C_4)$alkyl, $C(=O)OH$, or $CH_2C(=O)NH(C_1-C_4)$alkyl. In another embodiment, $R^4$ is H, 2-(1H-imidazole), 2-(1-methyl-1H-imidazole), $CH_2CH_2C(=O)O(C_1-C_4)$alkyl, $CH_2C(=O)O—(C_1-C_4)$alkyl, $CH_2C(=O)OH$, $C(=O)O—(C_1-C_4)$alkyl, $C(=O)OH$, or $CH_2C(=O)NH(C_1-C_4)$alkyl. In another embodiment, $R^4$ is H, 2-(1H-imidazole), 2-(1-methyl-1H-imidazole), $CH_2CH_2C(=O)O(C_1-C_4)$alkyl, $CH_2CH_2C(=O)OH$, $CH_2C(=O)OH$, $C(=O)O(C_1-C_4)$alkyl, $C(=O)OH$, or $CH_2C(=O)NH(C_1-C_4)$alkyl. In another embodiment, $R^4$ is H, 2-(1H-imidazole), 2-(1-methyl-1H-imidazole), $CH_2CH_2C(=O)O(C_1-C_4)$alkyl, $CH_2CH_2C(=O)OH$, $CH_2C(=O)O(C_1-C_4)$alkyl, $C(=O)O(C_1-C_4)$alkyl, $C(=O)OH$, or $CH_2C(=O)NH(C_1-C_4)$alkyl. In another embodiment, $R^4$ is H, 2-(1H-imidazole), 2-(1-methyl-1H-imidazole), $CH_2CH_2C(=O)O(C_1-C_4)$alkyl, $CH_2CH_2C(=O)OH$, $CH_2C(=O)O(C_1-C_4)$alkyl, $CH_2C(=O)OH$, $C(=O)OH$, or $CH_2C(=O)NH(C_1-C_4)$alkyl. In another embodiment, $R^4$ is H, 2-(1H-imidazole), 2-(1-methyl-1H-imidazole), $CH_2CH_2C(=O)O(C_1-C_4)$alkyl, $CH_2CH_2C(=O)OH$, $CH_2C(=O)O(C_1-C_4)$alkyl, $CH_2C(=O)OH$, $C(=O)O—(C_1-C_4)$alkyl, or $CH_2C(=O)NH(C_1-C_4)$alkyl. In another embodiment, $R^4$ is H, 2-(1H-imidazole), 2-(1-methyl-1H-imidazole), $CH_2CH_2C(=O)O(C_1-C_4)$alkyl, $CH_2CH_2C(=O)OH$, $CH_2C(=O)O(C_1-C_4)$alkyl, $CH_2C(=O)OH$, $C(=O)O(C_1-C_4)$alkyl, or $C(=O)OH$.

In another embodiment, $R^4$ is H, 2-(1-methyl-1H-imidazole), $CH_2CH_2C(=O)O—(C_1-C_4)$alkyl, or $CH_2CH_2C(=O)OH$. In another embodiment, $R^4$ is H, 2-(1-methyl-1H-imidazole), $CH_2C(=O)OH$, or $CH_2C(=O)O—(C_1-C_4)$alkyl. In another embodiment, $R^4$ is H, 2-(1-methyl-1H-imidazole), $CH_2C(=O)O—(C_1-C_4)$alkyl, or $CH_2C(=O)$ OH. In another embodiment, $R^4$ is H, 2-(1-methyl-1H-imidazole), $CH_2C(=O)OH$, or $C(=O)O(C_1-C_4)$alkyl. In another embodiment, $R^4$ is H, 2-(1-methyl-1H-imidazole), $C(=O)O(C_1-C_4)$alkyl, or $C(=O)OH$. In another embodiment, $R^4$ is H, 2-(1-methyl-1H-imidazole), $CH_2CH_2C(=O)O(C_1-C_4)$alkyl, or $CH_2C(=O)NH(C_1-C_4)$alkyl.

In another embodiment, $R^4$ is H or $CH_2CH_2C(=O)O—(C_1-C_4)$alkyl. In another embodiment, $R^4$ is H or $CH_2CH_2C(=O)OH$. In another embodiment, $R^4$ is H or $CH_2C(=O)O—(C_1-C_4)$alkyl. In another embodiment, $R^4$ is H or $CH_2C(=O)OH$. In another embodiment, $R^4$ is H or $C(=O)O(C_1-C_4)$alkyl. In another embodiment, $R^4$ is H or $C(=O)OH$. In another embodiment, $R^4$ is H, 2-(1-methyl-1H-imidazole), $CH_2C(=O)NH(C_1-C_4)$alkyl, or $CH_2C(=O)N[(C_1-C_4)$alkyl$]_2$. In another embodiment, $R^4$ is H or $CH_2CH_2C(=O)O—(C_1-C_4)$alkyl. In another embodiment, $R^4$ is H or $CH_2C(=O)O—(C_1-C_4)$alkyl. In another embodiment, $R^4$ is H or $C(=O)O—(C_1-C_4)$alkyl. In another embodiment, $R^4$ is H or $CH_2C(=O)NH(C_1-C_4)$alkyl. In another embodiment, $R^4$ is H, 2-(1H-imidazole), or 2-(1-methyl-1H-imidazole).

In another embodiment, $R^4$ is H or 2-(1H-imidazole). In another embodiment, $R^4$ is H or 2-(1-methyl-1H-imidazole). In another embodiment, $R^4$ is 2-(1H-imidazole). In another embodiment, $R^4$ is 2-(1-methyl-1H-imidazole).

In another embodiment, s is 1 and $R^{10}$ is $CH_2C(=O)O—(C_1-C_6)$alkyl, $CH_2C(=O)OH$, $C(=O)O—(C_1-C_6)$alkyl, $C(=O)OH$, or $CH_2C(=O)NH(C_1-C_6)$alkyl. In another embodiment, s is 1 and $R^{10}$ is $CH_2C(=O)OH$, $C(=O)O—(C_1-C_6)$alkyl, $C(=O)OH$, or $CH_2C(=O)NH(C_1-C_6)$alkyl. In another embodiment, s is 1 and $R^{10}$ is $CH_2C(=O)O—(C_1-C_6)$alkyl, $C(=O)OH$, or $CH_2C(=O)NH(C_1-C_6)$alkyl. In another embodiment, s is 1 and $R^{10}$ is $CH_2C(=O)O—(C_1-C_6)$alkyl, $CH_2C(=O)OH$, $C(=O)O—(C_1-C_6)$alkyl, or $CH_2C(=O)NH(C_1-C_6)$alkyl. In another embodiment, s is 1 and $R^{10}$ is $CH_2C(=O)O—(C_1-C_6)$alkyl, $CH_2C(=O)OH$, $C(=O)O—(C_1-C_6)$alkyl, or $C(=O)OH$.

In another embodiment, s is 1 and $R^{10}$ is $CH_2C(=O)O—(C_1-C_6)$alkyl, $CH_2C(=O)OH$, or $C(=O)O—(C_1-C_6)$alkyl. In another embodiment, s is 1 and $R^{10}$ is $CH_2C(=O)OH$, $C(=O)O—(C_1-C_6)$alkyl, or $C(=O)OH$. In another embodiment, s is 1 and $R^{10}$ is $C(=O)OH$ or $CH_2C(=O)NH(C_1-C_6)$alkyl. In another embodiment, s is 1 and $R^{10}$ is $CH_2C(=O)O—(C_1-C_6)$alkyl or $CH_2C(=O)NH(C_1-C_6)$alkyl.

In another embodiment, s is 1 and $R^{10}$ is $CH_2C(=O)OH$, $C(=O)O—(C_1-C_4)$alkyl, $C(=O)OH$, or $CH_2C(=O)NH(C_1-C_4)$alkyl. In another embodiment, s is 1 and $R^{10}$ is $CH_2C(=O)O—(C_1-C_4)$alkyl, $C(=O)OH$, or $CH_2C(=O)NH(C_1-C_4)$alkyl. In another embodiment, s is 1 and $R^{10}$ is $CH_2C(=O)O—(C_1-C_4)$alkyl, $CH_2C(=O)OH$, $C(=O)O—(C_1-C_4)$alkyl, or $CH_2C(=O)NH(C_1-C_4)$alkyl. In another embodiment, s is 1 and $R^{10}$ is $CH_2C(=O)O—(C_1-C_4)$alkyl, $CH_2C(=O)OH$, $C(=O)O—(C_1-C_4)$alkyl, or $C(=O)OH$.

In another embodiment, s is 1 and $R^{10}$ is $CH_2C(=O)O—(C_1-C_4)$alkyl or $CH_2C(=O)OH$, $C(=O)O—(C_1-C_4)$alkyl. In another embodiment, s is 1 and $R^{10}$ is $CH_2C(=O)OH$, $C(=O)O—(C_1-C_4)$alkyl or $C(=O)OH$. In another embodiment, s is 1 and $R^{10}$ is $C(=O)OH$ or $CH_2C(=O)NH(C_1-C_4)$alkyl. In another embodiment, s is 1 and $R^{10}$ is $CH_2C(=O)O—(C_1-C_4)$alkyl or $CH_2C(=O)NH(C_1-C_4)$alkyl.

In another embodiment, s is 1 and $R^{10}$ is $CH_2C(=O)O—(C_1-C_6)$alkyl. In another embodiment, s is 1 and $R^{10}$ is $CH_2C(=O)OH$. In another embodiment, s is 1 and $R^{10}$ is $C(=O)O—(C_1-C_6)$alkyl. In another embodiment, s is 1 and $R^{10}$ is $C(=O)OH$. In another embodiment, s is 1 and $R^{10}$ is $CH_2C(=O)NH(C_1-C_6)$alkyl. In another embodiment, s is 1 and $R^{10}$ is $CH_2C(=O)O—(C_1-C_4)$alkyl. In another embodiment, s is 1 and $R^{10}$ is $C(=O)O—(C_1-C_4)$alkyl.

In another embodiment, s is 1 and $R^{10}$ is $CH_3$, $CH_2CH_3$, $CH_2C(=O)O—(C_1-C_4)$alkyl, $CH_2C(=O)OH$, $C(=O)O—(C_1-C_4)$alkyl, $C(=O)OH$, or $CH_2C(=O)NH(C_1-C_4)$alkyl. In another embodiment, s is 1 and $R^{10}$ is $CH_3$, $CH_2CH_3$, $CH_2C(=O)OH$, $C(=O)O—(C_1-C_4)$alkyl, $C(=O)OH$, or $CH_2C(=O)NH(C_1-C_4)$alkyl. In another embodiment, s is 1 and $R^{10}$ is $CH_3$, $CH_2CH_3$, $CH_2C(=O)O—(C_1-C_4)$alkyl, $C(=O)OH$, or $CH_2C(=O)NH(C_1-C_4)$alkyl. In another embodiment, s is 1 and $R^{10}$ is $CH_3$, $CH_2CH_3$, $CH_2C(=O)O—(C_1-C_4)$alkyl, $CH_2C(=O)OH$, $C(=O)O—(C_1-C_4)$alkyl, or $CH_2C(=O)NH(C_1-C_4)$alkyl. In another embodiment, s is 1 and $R^{10}$ is $CH_3$, $CH_2CH_3$, $CH_2C(=O)O—(C_1-C_4)$alkyl, $CH_2C(=O)OH$, $C(=O)O—(C_1-C_4)$alkyl, or $C(=O)OH$.

In another embodiment, s is 1 and $R^{10}$ is $CH_3$, $CH_2CH_3$, $CH_2C(=O)O—(C_1-C_4)$alkyl or $CH_2C(=O)OH$, $C(=O)O—(C_1-C_4)$alkyl. In another embodiment, s is 1 and $R^{10}$ is $CH_3$, $CH_2CH_3$, $CH_2C(=O)OH$, $C(=O)O—(C_1-C_4)$alkyl or $C(=O)OH$. In another embodiment, s is 1 and $R^{10}$ is $CH_3$, $CH_2CH_3$, $C(=O)OH$ or $CH_2C(=O)NH(C_1-C_4)$alkyl. In another embodiment, s is 1 and $R^{10}$ is $CH_3$, $CH_2CH_3$, $CH_2C(=O)O—(C_1-C_4)$alkyl or $CH_2C(=O)NH(C_1-C_4)$alkyl.

In another embodiment, s is 1 and $R^{10}$ is $CH_3$, $CH_2CH_3$, $CH_2C(=O)OH$, $C(=O)O—(C_1-C_4)$alkyl, $C(=O)OH$, or $CH_2C(=O)NH(C_1-C_4)$alkyl. In another embodiment, s is 1 and $R^{10}$ is $CH_3$, $CH_2CH_3$, $CH_2C(=O)O—(C_1-C_4)$alkyl, $C(=O)OH$, or $CH_2C(=O)NH(C_1-C_4)$alkyl. In another embodiment, s is 1 and $R^{10}$ is $CH_3$, $CH_2CH_3$, $CH_2C(=O)O—(C_1-C_4)$alkyl, $CH_2C(=O)OH$, $C(=O)O—(C_1-C_4)$alkyl, or $CH_2C(=O)NH(C_1-C_4)$alkyl. In another embodiment, s is 1 and $R^{10}$ is $CH_3$, $CH_2CH_3$, $CH_2C(=O)O—(C_1-C_4)$alkyl, $CH_2C(=O)OH$, $C(=O)O—(C_1-C_4)$alkyl, or $C(=O)OH$.

In another embodiment, s is 1 and $R^{10}$ is $CH_3$, $CH_2C(=O)O—(C_1-C_4)$alkyl or $CH_2C(=O)OH$, $C(=O)O—(C_1-C_4)$alkyl. In another embodiment, s is 1 and $R^{10}$ is $CH_3$, $CH_2C(=O)OH$, $C(=O)O—(C_1-C_4)$alkyl or $C(=O)OH$. In another embodiment, s is 1 and $R^{10}$ is $CH_3$, $C(=O)OH$ or $CH_2C(=O)NH(C_1-C_4)$alkyl. In another embodiment, s is 1 and $R^{10}$ is $CH_3$, $CH_2C(=O)O—(C_1-C_4)$alkyl or $CH_2C(=O)NH(C_1-C_4)$alkyl.

In another embodiment, s is 1 and $R^{10}$ is $CH_2C(=O)O—(C_1-C_4)$alkyl. In another embodiment, s is 1 and $R^{10}$ is $CH_2C(=O)OH$. In another embodiment, s is 1 and $R^{10}$ is $C(=O)O—(C_1-C_4)$alkyl. In another embodiment, s is 1 and $R^{10}$ is $C(=O)OH$. In another embodiment, s is 1 and $R^{10}$ is $CH_2C(=O)NH(C_1-C_4)$alkyl. In another embodiment, s is 1 and $R^{10}$ is $CH_2C(=O)O—(C_1-C_4)$alkyl. In another embodiment, s is 1 and $R^{10}$ is $C(=O)O—(C_1-C_4)$alkyl. In another embodiment, s is 1 and $R^{10}$ is $CH_2C(=O)NH(C_1-C_4)$alkyl. In another embodiment, s is 1 and $R^{10}$ is $CH_3$ or $CH_2CH_3$. In another embodiment, s is 1 and $R^{10}$ is $CH_3$. In another embodiment, s is 1 and $R^{10}$ is $CH_2CH_3$.

In another embodiment, $R^1$ is selected from:
(a) -halo, —CN, —OH, —$CH_2OH$, —$CH_2CH_2OH$, —$NO_2$, —$N(R^6)_2$, —$S(=O)NH_2$, —$S(=O)_2NH_2$, —$C(=O)OV^1$, and —$C(=O)CN$; and
(b) —$(C_2-C_{10})$alkyl, —$(C_2-C_{10})$alkenyl, —$(C_2-C_{10})$alkynyl, —$O(C_1-C_6)$alkyl, —$(C_3-C_7)$cycloalkoxy, —$(C_6-C_{14})$bicycloalkyl, —$(C_8-C_{20})$tricycloalkyl, —$(C_5-C_{10})$cycloalkenyl, —$(C_7-C_{14})$bicycloalkenyl, —$(C_8-C_{20})$tricycloalkenyl, -(3- to 5-membered)heterocycle, and -(7-membered)heterocycle, each of which is unsubstituted or substituted with 1, 2, 3, or 4 independently selected $R^8$ groups; and (c)

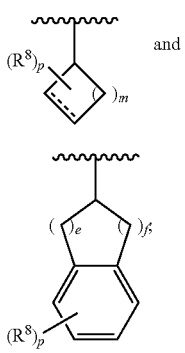

and (d) -naphthalenyl, —($C_{14}$)aryl, and -(5- to 10-membered) heteroaryl, each of which is unsubstituted or substituted with 1, 2, 3, or 4 independently selected $R^7$ groups.

In another embodiment, $R^{13}$ is selected from:

(a) -halo, —CN, —OH, —$CH_2OH$, —$CH_2CH_2OH$, —$NO_2$, —$N(R^6)_2$, —$S(=O)NH_2$, —$S(=O)_2NH_2$, —$C(=O)OV^1$, and —$C(=O)CN$; and (b) —($C_2$-$C_{10}$)alkyl, —($C_2$-$C_{10}$)alkenyl, —($C_2$-$C_{10}$)alkynyl, —$O(C_1$-$C_6$)alkyl, —($C_3$-$C_7$)cycloalkoxy, —($C_5$-$C_{10}$)cycloalkenyl, and -(3- to 7-membered)heterocycle, each of which is unsubstituted or substituted with 1, 2, 3, or 4 independently selected $R^8$ groups; and (c)

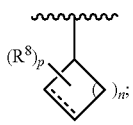

and (d) -(5- to 10-membered)heteroaryl, each of which is unsubstituted or substituted with 1, 2, or 3 independently selected $R^7$ groups wherein p is 0 or 1, optionally 0.

Each and every embodiment set forth in Sections 4.1 and 4.2a relating to the piperidine ring and the A, B, Z, and $R^1$ substituents thereto, and to the $Q_a$, $Q_x$, $R^2$, $R^3$, $R^4$, $R^{10}$, a, s, and t variable groups referenced therein also relate to the Substituted Benzimidazole-Type Piperidine Compounds in this section; therefore, those embodiments are not repeated here but are instead incorporated by reference in their entirety.

4.2c Substituted Benzimidazole-Type Piperidine Compounds of Formula (IA)

Illustrative compounds of formula (IA) are listed below in Tables 2-16.

TABLE 2

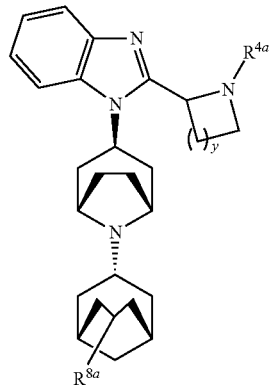
(a)

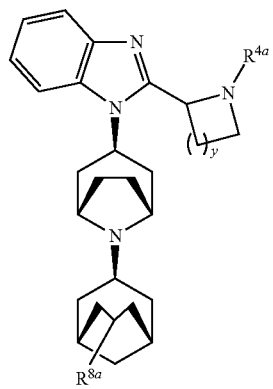
(b)

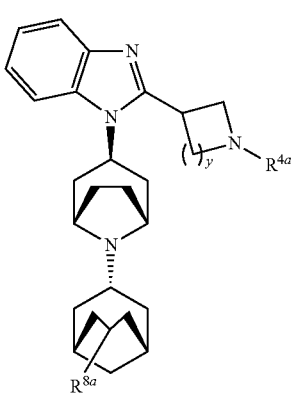
(c)

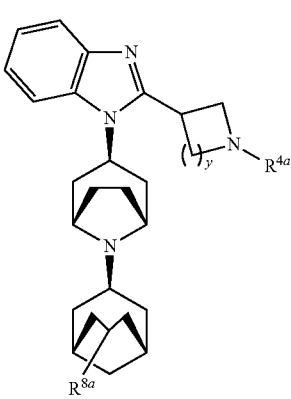
(d)

TABLE 2-continued

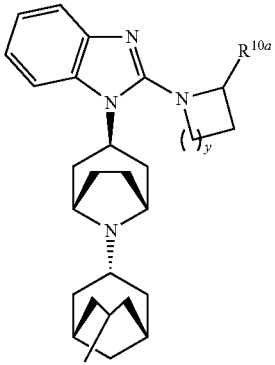
(e)

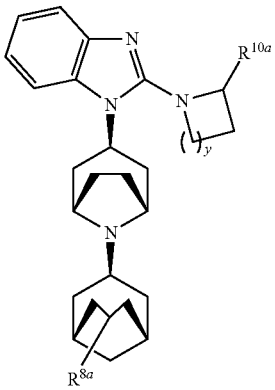
(f)

and pharmaceutically acceptable salts or solvates thereof, where:

| Compound* | $R^{4a}$ or $R^{10a}$ | $R^{8a}$ | y |
|---|---|---|---|
| A A1 a, b, c, d, e, or f | H | H | 1 |
| A2 a, b, c, d, e, or f | C(=O)OH | H | 1 |
| A3 a, b, c, d, e, or f | C(=O)OCH$_3$ | H | 1 |
| A4 a, b, c, d, e, or f | CH$_2$C(=O)OH | H | 1 |
| A5 a, b, c, d, e, or f | CH$_2$C(=O)OCH$_3$ | H | 1 |
| A6 a, b, c, d, e, or f | CH$_2$CH$_2$C(=O)OH | H | 1 |
| A7 a, b, c, d, e, or f | CH$_2$CH$_2$C(=O)OCH$_3$ | H | 1 |
| A8 a, b, c, d, e, or f | C(=O)NH$_2$ | H | 1 |
| A9 a, b, c, d, e, or f | C(=O)NHCH$_3$ | H | 1 |
| A10 a, b, c, d, e, or f | CH$_2$C(=O)NH$_2$ | H | 1 |
| A11 a, b, c, d, e, or f | CH$_2$C(=O)NHCH$_3$ | H | 1 |
| A12 a, b, c, d, e, or f | CH$_2$CH$_2$C(=O)NH$_2$ | H | 1 |
| A13 a, b, c, d, e, or f | CH$_2$CH$_2$C(=O)NHCH$_3$ | H | 1 |
| A14 a, b, c, d, e, or f | H | CH$_3$ | 1 |
| A15 a, b, c, d, e, or f | C(=O)OH | CH$_3$ | 1 |
| A16 a, b, c, d, e, or f | C(=O)OCH$_3$ | CH$_3$ | 1 |
| A17 a, b, c, d, e, or f | CH$_2$C(=O)OH | CH$_3$ | 1 |
| A18 a, b, c, d, e, or f | CH$_2$C(=O)OCH$_3$ | CH$_3$ | 1 |
| A19 a, b, c, d, e, or f | CH$_2$CH$_2$C(=O)OH | CH$_3$ | 1 |
| A20 a, b, c, d, e, or f | CH$_2$CH$_2$C(=O)OCH$_3$ | CH$_3$ | 1 |
| A21 a, b, c, d, e, or f | C(=O)NH$_2$ | CH$_3$ | 1 |
| A22 a, b, c, d, e, or f | C(=O)NHCH$_3$ | CH$_3$ | 1 |
| A23 a, b, c, d, e, or f | CH$_2$C(=O)NH$_2$ | CH$_3$ | 1 |
| A24 a, b, c, d, e, or f | CH$_2$C(=O)NHCH$_3$ | CH$_3$ | 1 |
| A25 a, b, c, d, e, or f | CH$_2$CH$_2$C(=O)NH$_2$ | CH$_3$ | 1 |
| A26 a, b, c, d, e, or f | CH$_2$CH$_2$C(=O)NHCH$_3$ | CH$_3$ | 1 |
| A27 a, b, c, d, e, or f | H | H | 2 |
| A28 a, b, c, d, e, or f | C(=O)OH | H | 2 |
| A29 a, b, c, d, e, or f | C(=O)OCH$_3$ | H | 2 |
| A30 a, b, c, d, e, or f | CH$_2$C(=O)OH | H | 2 |
| A31 a, b, c, d, e, or f | CH$_2$C(=O)OCH$_3$ | H | 2 |
| A32 a, b, c, d, e, or f | CH$_2$CH$_2$C(=O)OH | H | 2 |
| A33 a, b, c, d, e, or f | CH$_2$CH$_2$C(=O)OCH$_3$ | H | 2 |
| A34 a, b, c, d, e, or f | C(=O)NH$_2$ | H | 2 |
| A35 a, b, c, d, e, or f | C(=O)NHCH$_3$ | H | 2 |
| A36 a, b, c, d, e, or f | CH$_2$C(=O)NH$_2$ | H | 2 |
| A37 a, b, c, d, e, or f | CH$_2$C(=O)NHCH$_3$ | H | 2 |
| A38 a, b, c, d, e, or f | CH$_2$CH$_2$C(=O)NH$_2$ | H | 2 |
| A39 a, b, c, d, e, or f | CH$_2$CH$_2$C(=O)NHCH$_3$ | H | 2 |
| A40 a, b, c, d, e, or f | H | CH$_3$ | 2 |
| A41 a, b, c, d, e, or f | C(=O)OH | CH$_3$ | 2 |
| A42 a, b, c, d, e, or f | C(=O)OCH$_3$ | CH$_3$ | 2 |
| A43 a, b, c, d, e, or f | CH$_2$C(=O)OH | CH$_3$ | 2 |
| A44 a, b, c, d, e, or f | CH$_2$C(=O)OCH$_3$ | CH$_3$ | 2 |
| A45 a, b, c, d, e, or f | CH$_2$CH$_2$C(=O)OH | CH$_3$ | 2 |
| A46 a, b, c, d, e, or f | CH$_2$CH$_2$C(=O)OCH$_3$ | CH$_3$ | 2 |
| A47 a, b, c. d, e, or f | C(=O)NH$_2$ | CH$_3$ | 2 |
| A48 a, b, c, d, e, or f | C(=O)NHCH$_3$ | CH$_3$ | 2 |
| A49 a, b, c, d, e, or f | CH$_2$C(=O)NH$_2$ | CH$_3$ | 2 |
| A50 a, b, c, d, e, or f | CH$_2$C(=O)NHCH$_3$ | CH$_3$ | 2 |
| A51 a, b, c, d, e, or f | CH$_2$CH$_2$C(=O)NH$_2$ | CH$_3$ | 2 |
| A52 a, b, c, d, e, or f | CH$_2$CH$_2$C(=O)NHCH$_3$ | CH$_3$ | 2 |
| A53 a, b, c, d, e, or f | H | H | 3 |
| A54 a, b, c, d, e, or f | C(=O)OH | H | 3 |
| A55 a, b, c, d, e, or f | C(=O)OCH$_3$ | H | 3 |
| A56 a, b, c, d, e, or f | CH$_2$C(=O)OH | H | 3 |
| A57 a, b, c, d, e, or f | CH$_2$C(=O)OCH$_3$ | H | 3 |
| A58 a, b, c, d, e, or f | CH$_2$CH$_2$C(=O)OH | H | 3 |
| A59 a, b, c, d, e, or f | CH$_2$CH$_2$C(=O)OCH$_3$ | H | 3 |
| A60 a, b, c, d, e, or f | C(=O)NH$_2$ | H | 3 |
| A61 a, b, c, d, e, or f | C(=O)NHCH$_3$ | H | 3 |
| A62 a, b, c, d, e, or f | CH$_2$C(=O)NH$_2$ | H | 3 |
| A63 a, b, c, d, e, or f | CH$_2$C(=O)NHCH$_3$ | H | 3 |
| A64 a, b, c, d, e, or f | CH$_2$CH$_2$C(=O)NH$_2$ | H | 3 |
| A65 a, b, c, d, e, or f | CH$_2$CH$_2$C(=O)NHCH$_3$ | H | 3 |
| A66 a, b, c, d, e, or f | H | CH$_3$ | 3 |
| A67 a, b, c, d, e, or f | C(=O)OH | CH$_3$ | 3 |
| A68 a, b, c, d, e, or f | C(O)OCH$_3$ | CH$_3$ | 3 |
| A69 a, b, c, d, e, or f | CH$_2$C(=O)OH | CH$_3$ | 3 |
| A70 a, b, c, d, e, or f | CH$_2$C(=O)OCH$_3$ | CH$_3$ | 3 |
| A71 a, b, c, d, e, or f | CH$_2$CH$_2$C(=O)OH | CH$_3$ | 3 |
| A72 a, b, c, d, e, or f | CH$_2$CH$_2$C(=O)OCH$_3$ | CH$_3$ | 3 |
| A73 a, b, c, d, e, or f | C(=O)NH$_2$ | CH$_3$ | 3 |
| A74 a, b, c, d, e, or f | C(=O)NHCH$_3$ | CH$_3$ | 3 |
| A75 a, b, c, d, e, or f | CH$_2$C(=O)NH$_2$ | CH$_3$ | 3 |
| A76 a, b, c, d, e, or f | CH$_2$C(=O)NHCH$_3$ | CH$_3$ | 3 |
| A77 a, b, c, d, e, or f | CH$_2$CH$_2$C(=O)NH$_2$ | CH$_3$ | 3 |
| A78 a, b, c, d, e, or f | CH$_2$CH$_2$C(=O)NHCH$_3$ | CH$_3$ | 3 |

*(i) Indicates that $Q_x$ ring carbon atom that is bonded to the 5-membered, nitrogen-containing ring that is fused to benzo is in the (R)-conformation, (ii) indicates that $Q_x$ ring carbon atom that is bonded to the 5-membered, nitrogen-containing ring that is fused to benzo is in the (S)-conformation.

TABLE 3

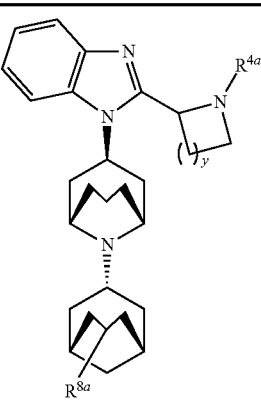
(a)

TABLE 3-continued (b) 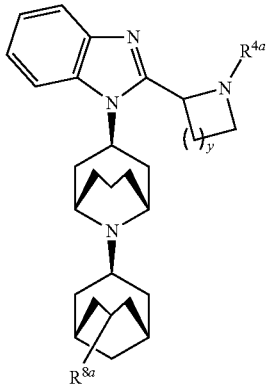

(c) 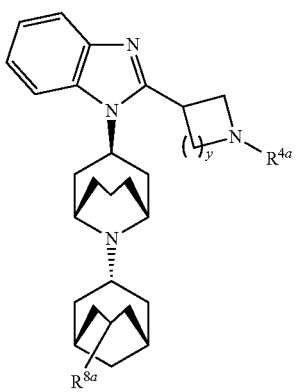

(d) 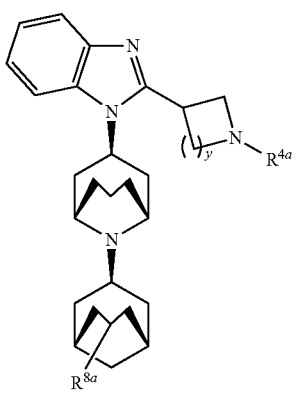

(e) 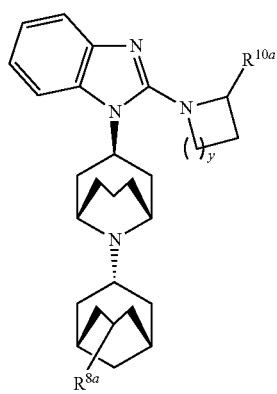

(f) 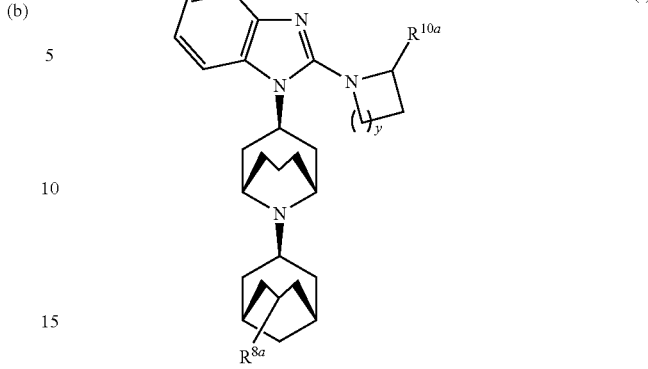

and pharmaceutically acceptable salts or solvates thereof, where:

| | Compound* | $R^{4a}$ or $R^{10a}$ | $R^{8a}$ | y |
|---|---|---|---|---|
| B | B1 a, b, c, d, e, or f | H | H | 1 |
| | B2 a, b, c, d, e, or f | C(=O)OH | H | 1 |
| | B3 a, b, c, d, e, or f | C(=O)OCH$_3$ | H | 1 |
| | B4 a, b, c, d, e, or f | CH$_2$C(=O)OH | H | 1 |
| | B5 a, b, c, d, e, or f | CH$_2$C(=O)OCH$_3$ | H | 1 |
| | B6 a, b, c, d, e, or f | CH$_2$CH$_2$C(=O)OH | H | 1 |
| | B7 a, b, c, d, e, or f | CH$_2$CH$_2$C(=O)OCH$_3$ | H | 1 |
| | B8 a, b, c, d, e, or f | C(=O)NH$_2$ | H | 1 |
| | B9 a, b, c, d, e, or f | C(=O)NHCH$_3$ | H | 1 |
| | B10 a, b, c, d, e, or f | CH$_2$C(=O)NH$_2$ | H | 1 |
| | B11 a, b, c, d, e, or f | CH$_2$C(=O)NHCH$_3$ | H | 1 |
| | B12 a, b, c, d, e, or f | CH$_2$CH$_2$C(=O)NH$_2$ | H | 1 |
| | B13 a, b, c, d, e, or f | CH$_2$CH$_2$C(=O)NHCH$_3$ | H | 1 |
| | B14 a, b, c, d, e, or f | H | CH$_3$ | 1 |
| | B15 a, b, c, d, e, or f | C(=O)OH | CH$_3$ | 1 |
| | B16 a, b, c, d, e, or f | C(=O)OCH$_3$ | CH$_3$ | 1 |
| | B17 a, b, c, d, e, or f | CH$_2$C(=O)OH | CH$_3$ | 1 |
| | B18 a, b, c, d, e, or f | CH$_2$C(=O)OCH$_3$ | CH$_3$ | 1 |
| | B19 a, b, c, d, e, or f | CH$_2$CH$_2$C(=O)OH | CH$_3$ | 1 |
| | B20 a, b, c, d, e, or f | CH$_2$CH$_2$C(=O)OCH$_3$ | CH$_3$ | 1 |
| | B21 a, b, c, d, e, or f | C(=O)NH$_2$ | CH$_3$ | 1 |
| | B22 a, b, c, d, e, or f | C(=O)NHCH$_3$ | CH$_3$ | 1 |
| | B23 a, b, c, d, e, or f | CH$_2$C(=O)NH$_2$ | CH$_3$ | 1 |
| | B24 a, b, c, d, e, or f | CH$_2$C(=O)NHCH$_3$ | CH$_3$ | 1 |
| | B25 a, b, c, d, e, or f | CH$_2$CH$_2$C(=O)NH$_2$ | CH$_3$ | 1 |
| | B26 a, b, c, d, e, or f | CH$_2$CH$_2$C(=O)NHCH$_3$ | CH$_3$ | 1 |
| | B27 a, b, c, d, e, or f | H | H | 2 |
| | B28 a, b, c, d, e, or f | C(=O)OH | H | 2 |
| | B29 a, b, c, d, e, or f | C(=O)OCH$_3$ | H | 2 |
| | B30 a, b, c, d, e, or f | CH$_2$C(=O)OH | H | 2 |
| | B31 a, b, c, d, e, or f | CH$_2$C(=O)OCH$_3$ | H | 2 |
| | B32 a, b, c, d, e, or f | CH$_2$CH$_2$C(=O)OH | H | 2 |
| | B33 a, b, c, d, e, or f | CH$_2$CH$_2$C(=O)OCH$_3$ | H | 2 |
| | B34 a, b, c, d, e, or f | C(=O)NH$_2$ | H | 2 |
| | B35 a, b, c, d, e, or f | C(=O)NHCH$_3$ | H | 2 |
| | B36 a, b, c, d, e, or f | CH$_2$C(=O)NH$_2$ | H | 2 |
| | B37 a, b, c, d, e, or f | CH$_2$C(=O)NHCH$_3$ | H | 2 |
| | B38 a, b, c, d, e, or f | CH$_2$CH$_2$C(=O)NH$_2$ | H | 2 |
| | B39 a, b, c, d, e, or f | CH$_2$CH$_2$C(=O)NHCH$_3$ | H | 2 |
| | B40 a, b, c, d, e, or f | H | CH$_3$ | 2 |
| | B41 a, b, c, d, e, or f | C(=O)OH | CH$_3$ | 2 |
| | B42 a, b, c, d, e, or f | C(=O)OCH$_3$ | CH$_3$ | 2 |
| | B43 a, b, c, d, e, or f | CH$_2$C(=O)OH | CH$_3$ | 2 |
| | B44 a, b, c, d, e, or f | CH$_2$C(=O)OCH$_3$ | CH$_3$ | 2 |
| | B45 a, b, c, d, e, or f | CH$_2$CH$_2$C(=O)OH | CH$_3$ | 2 |
| | B46 a, b, c, d, e, or f | CH$_2$CH$_2$C(=O)OCH$_3$ | CH$_3$ | 2 |
| | B47 a, b, c, d, e, or f | C(=O)NH$_2$ | CH$_3$ | 2 |
| | B48 a, b, c, d, e, or f | C(=O)NHCH$_3$ | CH$_3$ | 2 |
| | B49 a, b, c, d, e, or f | CH$_2$C(=O)NH$_2$ | CH$_3$ | 2 |
| | B50 a, b, c, d, e, or f | CH$_2$C(=O)NHCH$_3$ | CH$_3$ | 2 |
| | B51 a, b, c, d, e, or f | CH$_2$CH$_2$C(=O)NH$_2$ | CH$_3$ | 2 |
| | B52 a, b, c, d, e, or f | CH$_2$CH$_2$C(=O)NHCH$_3$ | CH$_3$ | 2 |
| | B53 a, b, c, d, e, or f | H | H | 3 |

139
-continued

| Compound* | $R^{4a}$ or $R^{10a}$ | $R^{8a}$ | y |
|---|---|---|---|
| B54 a, b, c, d, e, or f | C(=O)OH | H | 3 |
| B55 a, b, c, d, e, or f | C(=O)OCH$_3$ | H | 3 |
| B56 a, b, c, d, e, or f | CH$_2$C(=O)OH | H | 3 |
| B57 a, b, c, d, e, or f | CH$_2$C(=O)OCH$_3$ | H | 3 |
| B58 a, b, c, d, e, or f | CH$_2$CH$_2$C(=O)OH | H | 3 |
| B59 a, b, c, d, e, or f | CH$_2$CH$_2$C(=O)OCH$_3$ | H | 3 |
| B60 a, b, c, d, e, or f | C(=O)NH$_2$ | H | 3 |
| B61 a, b, c, d, e, or f | C(=O)NHCH$_3$ | H | 3 |
| B62 a, b, c, d, e, or f | CH$_2$C(=O)NH$_2$ | H | 3 |
| B63 a, b, c, d, e, or f | CH$_2$C(=O)NHCH$_3$ | H | 3 |
| B64 a, b, c, d, e, or f | CH$_2$CH$_2$C(=O)NH$_2$ | H | 3 |
| B65 a, b, c, d, e, or f | CH$_2$CH$_2$C(=O)NHCH$_3$ | H | 3 |
| B66 a, b, c, d, e, or f | H | CH$_3$ | 3 |
| B67 a, b, c, d, e, or f | C(=O)OH | CH$_3$ | 3 |
| B68 a, b, c, d, e, or f | C(=O)OCH$_3$ | CH$_3$ | 3 |
| B69 a, b, c, d, e, or f | CH$_2$C(=O)OH | CH$_3$ | 3 |
| B70 a, b, c, d, e, or f | CH$_2$C(=O)OCH$_3$ | CH$_3$ | 3 |
| B71 a. b, c, d, e, or f | CH$_2$CH$_2$C(=O)OH | CH$_3$ | 3 |
| B72 a, b, c, d, e, or f | CH$_2$CH$_2$C(=O)OCH$_3$ | CH$_3$ | 3 |
| B73 a, b, c, d, e, or f | C(=O)NH$_2$ | CH$_3$ | 3 |
| B74 a, b, c, d, e, or f | C(=O)NHCH$_3$ | CH$_3$ | 3 |
| B75 a, b, c, d, e, or f | CH$_2$C(=O)NH$_2$ | CH$_3$ | 3 |
| B76 a, b, c, d, e, or f | CH$_2$C(=O)NHCH$_3$ | CH$_3$ | 3 |
| B77 a, b, c, d, e, or f | CH$_2$CH$_2$C(=O)NH$_2$ | CH$_3$ | 3 |
| B78 a, b, c, d, e, or f | CH$_2$CH$_2$C(=O)NHCH$_3$ | CH$_3$ | 3 |

*(i) Indicates that Q$_x$ ring carbon atom that is bonded to the 5-membered, nitrogen-containing ring that is fused to benzo is in the (R)-conformation, (ii) indicates that Q$_x$ ring carbon atom that is bonded to the 5-membered, nitrogen-containing ring that is fused to benzo is in the (S)-conformation.

TABLE 4

(a)

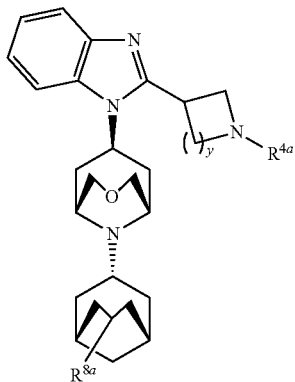

(b)

(c)

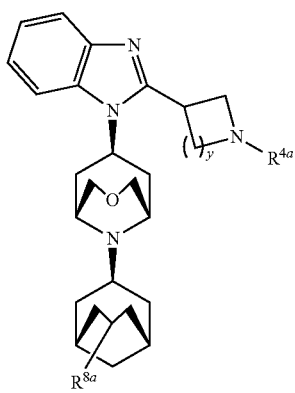

(d)

(e)

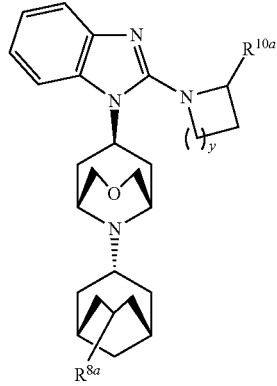

(f)

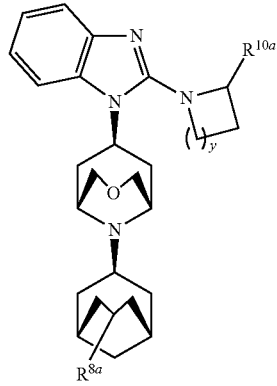

and pharmaceutically acceptable salts or solvates thereof, where:

| Compound* | $R^{4a}$ or $R^{10a}$ | $R^{8a}$ | y |
|---|---|---|---|
| C C1 a, b, c, d, e, or f | H | H | 1 |
| C2 a, b, c, d, e, or f | C(=O)OH | H | 1 |
| C3 a, b, c, d, e, or f | C(=O)OCH$_3$ | H | 1 |
| C4 a, b, c, d, e, or f | CH$_2$C(=O)OH | H | 1 |
| C5 a, b, c, d, e, or f | CH$_2$C(=O)OCH$_3$ | H | 1 |
| C6 a, b, c, d, e, or f | CH$_2$CH$_2$C(=O)OH | H | 1 |
| C7 a, b, c, d, e, or f | CH$_2$CH$_2$C(=O)OCH$_3$ | H | 1 |
| C8 a, b, c, d, e, or f | C(=O)NH$_2$ | H | 1 |
| C9 a, b, c, d, e, or f | C(=O)NHCH$_3$ | H | 1 |
| C10 a, b, c, d, e, or f | CH$_2$C(=O)NH$_2$ | H | 1 |
| C11 a, b, c, d, e, or f | CH$_2$C(=O)NHCH$_3$ | H | 1 |
| C12 a, b, c, d, e, or f | CH$_2$CH$_2$C(=O)NH$_2$ | H | 1 |
| C13 a, b, c, d, e, or f | CH$_2$CH$_2$C(=O)NHCH$_3$ | H | 1 |
| C14 a, b, c, d, e, or f | H | CH$_3$ | 1 |
| C15 a, b, c, d, e, or f | C(=O)OH | CH$_3$ | 1 |
| C16 a, b, c, d, e, or f | C(=O)OCH$_3$ | CH$_3$ | 1 |
| C17 a, b, c, d, e, or f | CH$_2$C(=O)OH | CH$_3$ | 1 |
| C18 a, b, c, d, e, or f | CH$_2$C(=O)OCH$_3$ | CH$_3$ | 1 |
| C19 a, b, c, d, e, or f | CH$_2$CH$_2$C(=O)OH | CH$_3$ | 1 |
| C20 a, b, c, d, e, or f | CH$_2$CH$_2$C(O)OCH$_3$ | CH$_3$ | 1 |
| C21 a, b, c, d, e, or f | C(=O)NH$_2$ | CH$_3$ | 1 |
| C22 a, b, c, d, e, or f | C(=O)NHCH$_3$ | CH$_3$ | 1 |
| C23 a, b, c, d, e, or f | CH$_2$C(=O)NH$_2$ | CH$_3$ | 1 |
| C24 a, b, c, d, e, or f | CH$_2$C(=O)NHCH$_3$ | CH$_3$ | 1 |
| C25 a, b, c, d, e, or f | CH$_2$CH$_2$C(=O)NH$_2$ | CH$_3$ | 1 |
| C26 a, b, c, d, e, or f | CH$_2$CH$_2$C(=O)NHCH$_3$ | CH$_3$ | 1 |
| C27 a, b, c, d, e, or f | H | H | 2 |
| C28 a, b, c, d, e, or f | C(=O)OH | H | 2 |
| C29 a, b, c, d, e, or f | C(=O)OCH$_3$ | H | 2 |
| C30 a, b, c, d, e, or f | CH$_2$C(=O)OH | H | 2 |
| C31 a, b, c, d, e, or f | CH$_2$C(=O)OCH$_3$ | H | 2 |
| C32 a, b, c, d, e, or f | CH$_2$CH$_2$C(=O)OH | H | 2 |
| C33 a, b, c, d, e, or f | CH$_2$CH$_2$C(=O)OCH$_3$ | H | 2 |
| C34 a, b, c, d, e, or f | C(=O)NH$_2$ | H | 2 |
| C35 a, b, c, d, e, or f | C(=O)NHCH$_3$ | H | 2 |
| C36 a, b, c, d, e, or f | CH$_2$C(=O)NH$_2$ | H | 2 |
| C37 a, b, c, d, e, or f | CH$_2$C(=O)NHCH$_3$ | H | 2 |
| C38 a, b, c, d, e, or f | CH$_2$CH$_2$C(=O)NH$_2$ | H | 2 |
| C39 a, b, c, d, e, or f | CH$_2$CH$_2$C(=O)NHCH$_3$ | H | 2 |
| C40 a, b, c, d, e, or f | H | CH$_3$ | 2 |
| C41 a, b, c, d, e, or f | C(=O)OH | CH$_3$ | 2 |
| C42 a, b, c, d, e, or f | C(=O)OCH$_3$ | CH$_3$ | 2 |
| C43 a, b, c, d, e, or f | CH$_2$C(=O)OH | CH$_3$ | 2 |
| C44 a, b, c, d, e, or f | CH$_2$C(=O)OCH$_3$ | CH$_3$ | 2 |
| C45 a, b, c, d, e, or f | CH$_2$CH$_2$C(=O)OH | CH$_3$ | 2 |
| C46 a, b, c, d, e, or f | CH$_2$CH$_2$C(=O)OCH$_3$ | CH$_3$ | 2 |
| C47 a, b, c, d, e, or f | C(=O)NH$_2$ | CH$_3$ | 2 |
| C48 a, b, c, d, e, or f | C(=O)NHCH$_3$ | CH$_3$ | 2 |
| C49 a, b, c, d, e, or f | CH$_2$C(=O)NH$_2$ | CH$_3$ | 2 |
| C50 a, b, c, d, e, or f | CH$_2$C(=O)NHCH$_3$ | CH$_3$ | 2 |
| C51 a, b, c, d, e, or f | CH$_2$CH$_2$C(=O)NH$_2$ | CH$_3$ | 2 |
| C52 a, b, c, d, e, or f | CH$_2$CH$_2$C(=O)NHCH$_3$ | CH$_3$ | 2 |
| C53 a, b, c, d, e, or f | H | H | 3 |
| C54 a, b, c, d, e, or f | C(=O)OH | H | 3 |
| C55 a, b, c, d, e, or f | C(=O)OCH$_3$ | H | 3 |
| C56 a, b, c, d, e, or f | CH$_2$C(=O)OH | H | 3 |
| C57 a, b, c, d, e, or f | CH$_2$C(=O)OCH$_3$ | H | 3 |
| C58 a, b, c, d, e, or f | CH$_2$CH$_2$C(=O)OH | H | 3 |
| C59 a, b, c, d, e, or f | CH$_2$CH$_2$C(=O)OCH$_3$ | H | 3 |
| C60 a, b, c, d, e, or f | C(=O)NH$_2$ | H | 3 |
| C61 a, b, c, d, e, or f | C(=O)NHCH$_3$ | H | 3 |
| C62 a, b, c, d, e, or f | CH$_2$C(=O)NH$_2$ | H | 3 |
| C63 a, b, c, d, e, or f | CH$_2$C(=O)NHCH$_3$ | H | 3 |
| C64 a, b, c, d, e, or f | CH$_2$CH$_2$C(-O)NH$_2$ | H | 3 |
| C65 a, b, c, d, e, or f | CH$_2$CH$_2$C(=O)NHCH$_3$ | H | 3 |
| C66 a, b, c, d, e, or f | H | CH$_3$ | 3 |
| C67 a, b, c, d, e, or f | C(=O)OH | CH$_3$ | 3 |
| C68 a, b, c, d, e, or f | C(=O)OCH$_3$ | CH$_3$ | 3 |
| C69 a, b, c, d, e, or f | CH$_2$C(=O)OH | CH$_3$ | 3 |
| C70 a, b, c, d, e, or f | CH$_2$C(=O)OCH$_3$ | CH$_3$ | 3 |
| C71 a, b, c, d, e, or f | CH$_2$CH$_2$C(=O)OH | CH$_3$ | 3 |
| C72 a. b, c, d, e, or f | CH$_2$CH$_2$C(=O)OCH$_3$ | CH$_3$ | 3 |
| C73 a, b, c, d, e, or f | C(=O)NH$_2$ | CH$_3$ | 3 |
| C74 a, b, c, d, e, or f | C(=O)NHCH$_3$ | CH$_3$ | 3 |
| C75 a, b, c, d, e, or f | CH$_2$C(=O)NH$_2$ | CH$_3$ | 3 |
| C76 a, b, c, d, e, or f | CH$_2$C(=O)NHCH$_3$ | CH$_3$ | 3 |
| C77 a, b, c, d, e, or f | CH$_2$CH$_2$C(=O)NH$_2$ | CH$_3$ | 3 |
| C78 a, b, c, d, e, or f | CH$_2$CH$_2$C(=O)NHCH$_3$ | CH$_3$ | 3 |

*(i) Indicates that $Q_x$ ring carbon atom that is bonded to the 5-membered, nitrogen-containing ring that is fused to benzo is in the (R)-conformation, (ii) indicates that $Q_x$ ring carbon atom that is bonded to the 5-membered, nitrogen-containing ring that is fused to benzo is in the (S)-conformation.

TABLE 5

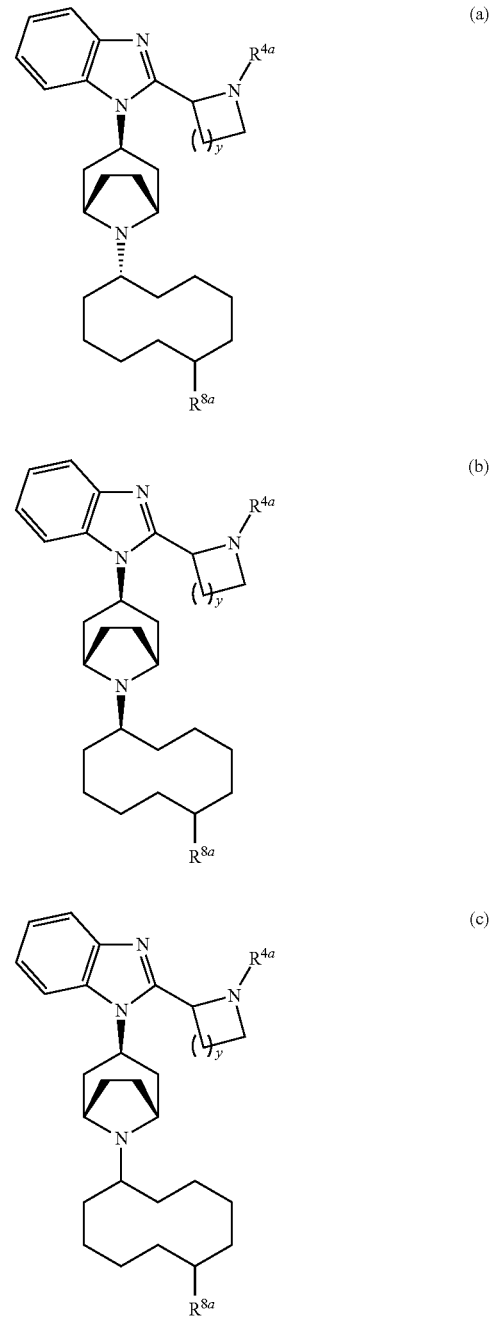

(a)

(b)

(c)

TABLE 5-continued (d), (e), (f): structures with benzimidazole linked to azetidine (N-R^4a) via (CH_2)_y, and bicyclic azabicyclic system connected to cyclohexyl bearing R^8a.

and pharmaceutically acceptable salts or solvates thereof, where:

| Compound* | | R^4a | R^8a | y |
|---|---|---|---|---|
| D | D1 c or f | H | H | 1 |
|   | D2 c or f | C(=O)OH | H | 1 |
|   | D3 c or f | C(=O)OCH_3 | H | 1 |
|   | D4 c or f | CH_2C(=O)OH | H | 1 |
|   | D5 c or f | CH_2C(=O)OCH_3 | H | 1 |
|   | D6 c or f | CH_2CH_2C(=O)OH | H | 1 |
|   | D7 c or f | CH_2CH_2C(=O)OCH_3 | H | 1 |
|   | D8 c or f | C(=O)NH_2 | H | 1 |
|   | D9 c or f | C(=O)NHCH_3 | H | 1 |
|   | D10 c or f | CH_2C(=O)NH_2 | H | 1 |
|   | D11 c or f | CH_2C(=O)NHCH_3 | H | 1 |
|   | D12 c or f | CH_2CH_2C(=O)NH_2 | H | 1 |
|   | D13 c or f | CH_2CH_2C(=O)NHCH_3 | H | 1 |
|   | D14 a, b, c, d, e, or f | H | CH_3 | 1 |
|   | D15 a, b, c, d, e, or f | C(=O)OH | CH_3 | 1 |
|   | D16 a, b, c, d, e, or f | C(=O)OCH_3 | CH_3 | 1 |
|   | D17 a, b, c, d, e, or f | CH_2C(=O)OH | CH_3 | 1 |
|   | D18 a, b, c, d, e, or f | CH_2C(=O)OCH_3 | CH_3 | 1 |
|   | D19 a, b, c, d, e, or f | CH_2CH_2C(=O)OH | CH_3 | 1 |
|   | D20 a, b, c, d, e, or f | CH_2CH_2C(=O)OCH_3 | CH_3 | 1 |
|   | D21 a, b, c, d, e, or f | C(=O)NH_2 | CH_3 | 1 |
|   | D22 a, b, c, d, e, or f | C(=O)NHCH_3 | CH_3 | 1 |
|   | D23 a, b, c, d, e, or f | CH_2C(=O)NH_2 | CH_3 | 1 |
|   | D24 a, b, c, d, e, or f | CH_2C(=O)NHCH_3 | CH_3 | 1 |
|   | D25 a, b, c, d, e, or f | CH_2CH_2C(=O)NH_2 | CH_3 | 1 |
|   | D26 a, b, c, d, e, or f | CH_2CH_2C(=O)NHCH_3 | CH_3 | 1 |
|   | D27 c or f | H | H | 2 |
|   | D28 c or f | C(=O)OH | H | 2 |
|   | D29 c or f | C(=O)OCH_3 | H | 2 |
|   | D30 c or f | CH_2C(=O)OH | H | 2 |
|   | D31 c or f | CH_2C(=O)OCH_3 | H | 2 |
|   | D32 c or f | CH_2CH_2C(=O)OH | H | 2 |
|   | D33 c or f | CH_2CH_2C(=O)OCH_3 | H | 2 |
|   | D34 c or f | C(=O)NH_2 | H | 2 |
|   | D35 c or f | C(=O)NHCH_3 | H | 2 |
|   | D36 c or f | CH_2C(=O)NH_2 | H | 2 |
|   | D37 c or f | CH_2C(=O)NHCH_3 | H | 2 |
|   | D38 c or f | CH_2CH_2C(=O)NH_2 | H | 2 |
|   | D39 c or f | CH_2CH_2C(=O)NHCH_3 | H | 2 |
|   | D40 a, b, c, d, e, or f | H | CH_3 | 2 |
|   | D41 a, b, c, d, e, or f | C(=O)OH | CH_3 | 2 |
|   | D42 a, b, c, d, e, or f | C(=O)OCH_3 | CH_3 | 2 |
|   | D43 a, b, c, d, e, or f | CH_2C(=O)OH | CH_3 | 2 |
|   | D44 a, b, c, d, e, or f | CH_2C(=O)OCH_3 | CH_3 | 2 |
|   | D45 a, b, c, d, e, or f | CH_2CH_2C(=O)OH | CH_3 | 2 |
|   | D46 a, b, c, d, e, or f | CH_2CH_2C(=O)OCH_3 | CH_3 | 2 |
|   | D47 a, b, c, d, e, or f | C(=O)NH_2 | CH_3 | 2 |
|   | D48 a, b, c, d, e, or f | C(=O)NHCH_3 | CH_3 | 2 |
|   | D49 a, b, c, d, e, or f | CH_2C(=O)NH_2 | CH_3 | 2 |
|   | D50 a, b, c, d, e, or f | CH_2C(=O)NHCH_3 | CH_3 | 2 |
|   | D51 a, b, c, d, e, or f | CH_2CH_2C(=O)NH_2 | CH_3 | 2 |
|   | D52 a, b, c, d, e, or f | CH_2CH_2C(=O)NHCH_3 | CH_3 | 2 |
|   | D53 c or f | H | H | 3 |
|   | D54 c or f | C(=O)OH | H | 3 |
|   | D55 c or f | C(=O)OCH_3 | H | 3 |
|   | D56 c or f | CH_2C(=O)OH | H | 3 |
|   | D57 c or f | CH_2C(=O)OCH_3 | H | 3 |
|   | D58 c or f | CH_2CH_2C(=O)OH | H | 3 |
|   | D59 c or f | CH_2CH_2C(=O)OCH_3 | H | 3 |
|   | D60 c or f | C(=O)NH_2 | H | 3 |
|   | D61 c or f | C(=O)NHCH_3 | H | 3 |
|   | D62 c or f | CH_2C(=O)NH_2 | H | 3 |
|   | D63 c or f | CH_2C(=O)NHCH_3 | H | 3 |
|   | D64 c or f | CH_2CH_2C(=O)NH_2 | H | 3 |
|   | D65 c or f | CH_2CH_2C(=O)NHCH_3 | H | 3 |
|   | D66 a, b, c, d, e, or f | H | CH_3 | 3 |
|   | D67 a, b, c, d, e, or f | C(=O)OH | CH_3 | 3 |
|   | D68 a, b, c, d, e, or f | C(=O)OCH_3 | CH_3 | 3 |
|   | D69 a, b, c, d, e, or f | CH_2C(=O)OH | CH_3 | 3 |
|   | D70 a, b, c, d, e, or f | CH_2C(=O)OCH_3 | CH_3 | 3 |
|   | D71 a, b, c, d, e, or f | CH_2CH_2C(=O)OH | CH_3 | 3 |
|   | D72 a, b, c, d, e, or f | CH_2CH_2C(=O)OCH_3 | CH_3 | 3 |
|   | D73 a, b, c, d, e, or f | C(=O)NH_2 | CH_3 | 3 |
|   | D74 a, b, c, d, e, or f | C(=O)NHCH_3 | CH_3 | 3 |
|   | D75 a, b, c, d, e, or f | CH_2C(=O)NH_2 | CH_3 | 3 |
|   | D76 a, b, c, d, e, or f | CH_2C(=O)NHCH_3 | CH_3 | 3 |
|   | D77 a, b, c, d, e, or f | CH_2CH_2C(=O)NH_2 | CH_3 | 3 |
|   | D78 a, b, c, d, e, or f | CH_2CH_2C(=O)NHCH_3 | CH_3 | 3 |

*(i) Indicates that $Q_x$ ring carbon atom that is bonded to the 5-membered, nitrogen-containing ring that is fused to benzo is in the (R)-conformation, (ii) indicates that $Q_x$ ring carbon atom that is bonded to the 5-membered, nitrogen-containing ring that is fused to benzo is in the (S)-conformation.

TABLE 6

(a) 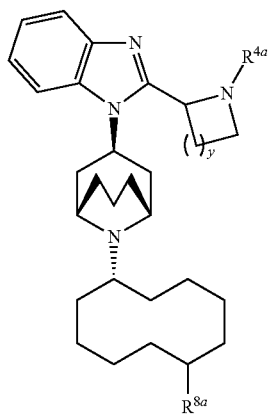

(b) 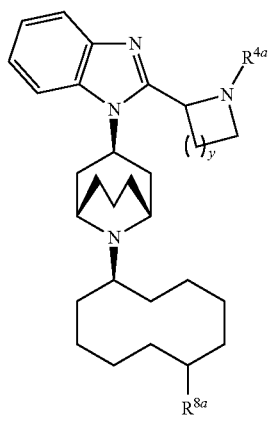

(c) 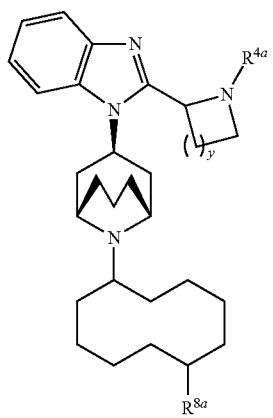

(d) 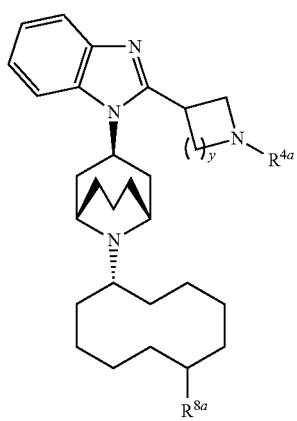

TABLE 6-continued

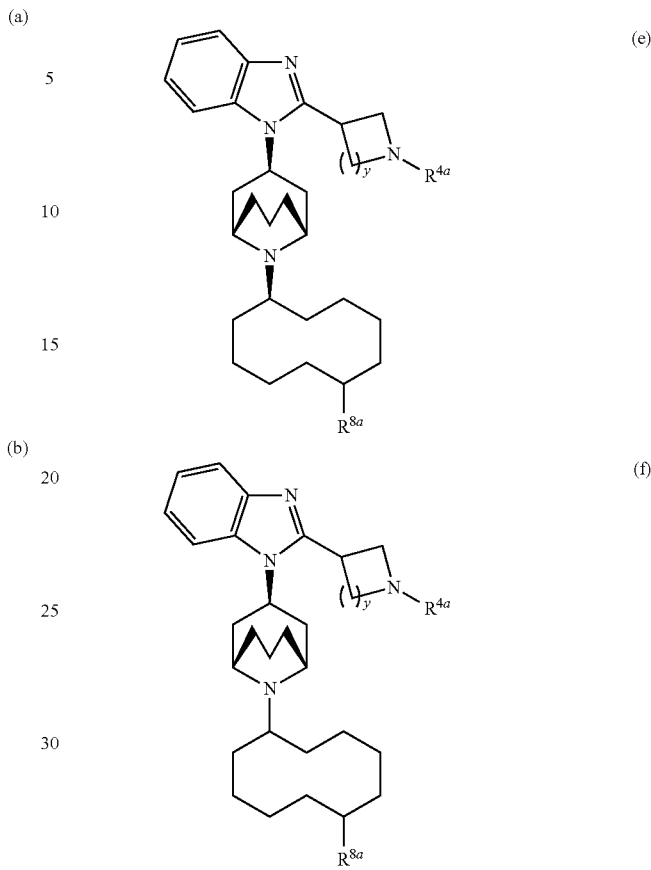

and pharmaceutically acceptable salts or solvates thereof, where:

| | Compound* | | $R^{4a}$ | $R^{8a}$ | y |
|---|---|---|---|---|---|
| E | E1 | c or f | H | H | 1 |
| | E2 | c or f | C(=O)OH | H | 1 |
| | E3 | c or f | C(=O)OCH$_3$ | H | 1 |
| | E4 | c or f | CH$_2$C(=O)OH | H | 1 |
| | E5 | c or f | CH$_2$C(=O)OCH$_3$ | H | 1 |
| | E6 | c or f | CH$_2$CH$_2$C(=O)OH | H | 1 |
| | E7 | c or f | CH$_2$CH$_2$C(=O)OCH$_3$ | H | 1 |
| | E8 | c or f | C(=O)NH$_2$ | H | 1 |
| | E9 | c or f | C(=O)NHCH$_3$ | H | 1 |
| | E10 | c or f | CH$_2$C(=O)NH$_2$ | H | 1 |
| | E11 | c or f | CH$_2$C(=O)NHCH$_3$ | H | 1 |
| | E12 | c or f | CH$_2$CH$_2$C(=O)NH$_2$ | H | 1 |
| | E13 | c or f | CH$_2$CH$_2$C(=O)NHCH$_3$ | H | 1 |
| | E14 | a, b, c, d, e, or f | H | CH$_3$ | 1 |
| | E15 | a, b, c, d, e, or f | C(=O)OH | CH$_3$ | 1 |
| | E16 | a, b, c, d, e, or f | C(=O)OCH$_3$ | CH$_3$ | 1 |
| | E17 | a, b, c, d, e, or f | CH$_2$C(=O)OH | CH$_3$ | 1 |
| | E18 | a, b, c, d, e, or f | CH$_2$C(=O)OCH$_3$ | CH$_3$ | 1 |
| | E19 | a, b, c, d, e, or f | CH$_2$CH$_2$C(=O)OH | CH$_3$ | 1 |
| | E20 | a, b, c, d, e, or f | CH$_2$CH$_2$C(=O)OCH$_3$ | CH$_3$ | 1 |
| | E21 | a, b, c, d, e, or f | C(=O)NH$_2$ | CH$_3$ | 1 |
| | E22 | a, b, c, d, e, or f | C(=O)NHCH$_3$ | CH$_3$ | 1 |
| | E23 | a, b, c, d, e, or f | CH$_2$C(=O)NH$_2$ | CH$_3$ | 1 |
| | E24 | a, b, c, d, e, or f | CH$_2$C(=O)NHCH$_3$ | CH$_3$ | 1 |
| | E25 | a, b, c, d, e, or f | CH$_2$CH$_2$C(=O)NH$_2$ | CH$_3$ | 1 |
| | E26 | a, b, c, d, e, or f | CH$_2$CH$_2$C(=O)NHCH$_3$ | CH$_3$ | 1 |
| | E27 | c or f | H | H | 2 |
| | E28 | c or f | C(=O)OH | H | 2 |
| | E29 | c or f | C(=O)OCH$_3$ | H | 2 |
| | E30 | c or f | CH$_2$C(=O)OH | H | 2 |
| | E31 | c or f | CH$_2$C(=O)OCH$_3$ | H | 2 |

-continued

| Compound* | R$^{4a}$ | R$^{8a}$ | y |
|---|---|---|---|
| E32 c or f | CH$_2$CH$_2$C(=O)OH | H | 2 |
| E33 c or f | CH$_2$CH$_2$C(=O)OCH$_3$ | H | 2 |
| E34 c or f | C(=O)NH$_2$ | H | 2 |
| E35 c or f | C(=O)NHCH$_3$ | H | 2 |
| E36 c or f | CH$_2$C(=O)NH$_2$ | H | 2 |
| E37 c or f | CH$_2$C(=O)NHCH$_3$ | H | 2 |
| E38 c or f | CH$_2$CH$_2$C(=O)NH$_2$ | H | 2 |
| E39 c or f | CH$_2$CH$_2$C(=O)NHCH$_3$ | H | 2 |
| E40 a, b, c, d, e, or f | H | CH$_3$ | 2 |
| E41 a, b, c, d, e, or f | C(=O)OH | CH$_3$ | 2 |
| E42 a, b, c, d, e, or f | C(=O)OCH$_3$ | CH$_3$ | 2 |
| E43 a, b, c, d, e, or f | CH$_2$C(=O)OH | CH$_3$ | 2 |
| E44 a, b, c, d, e, or f | CH$_2$C(=O)OCH$_3$ | CH$_3$ | 2 |
| E45 a, b, c, d, e, or f | CH$_2$CH$_2$C(=O)OH | CH$_3$ | 2 |
| E46 a, b, c, d, e, or f | CH$_2$CH$_2$C(=O)OCH$_3$ | CH$_3$ | 2 |
| E47 a, b, c, d, e, or f | C(=O)NH$_2$ | CH$_3$ | 2 |
| E48 a, b, c, d, e, or f | C(=O)NHCH$_3$ | CH$_3$ | 2 |
| E49 a, b, c, d, e, or f | CH$_2$C(=O)NH$_2$ | CH$_3$ | 2 |
| E50 a, b, c, d, e, or f | CH$_2$C(=O)NHCH$_3$ | CH$_3$ | 2 |
| E51 a, b, c, d, e, or f | CH$_2$CH$_2$C(=O)NH$_2$ | CH$_3$ | 2 |
| E52 a, b, c, d, e, or f | CH$_2$CH$_2$C(=O)NHCH$_3$ | CH$_3$ | 2 |
| E53 c or f | H | H | 3 |
| E54 c or f | C(=O)OH | H | 3 |
| E55 c or f | C(=O)OCH$_3$ | H | 3 |
| E56 c or f | CH$_2$C(=O)OH | H | 3 |
| E57 c or f | CH$_2$C(=O)OCH$_3$ | H | 3 |
| E58 c or f | CH$_2$CH$_2$C(=O)OH | H | 3 |
| E59 c or f | CH$_2$CH$_2$C(=O)OCH$_3$ | H | 3 |
| E60 c or f | C(=O)NH$_2$ | H | 3 |
| E61 c or f | C(=O)NHCH$_3$ | H | 3 |
| E62 c or f | CH$_2$C(=O)NH$_2$ | H | 3 |
| E63 c or f | CH$_2$C(=O)NHCH$_3$ | H | 3 |
| E64 c or f | CH$_2$CH$_2$C(=O)NH$_2$ | H | 3 |
| E65 c or f | CH$_2$CH$_2$C(=O)NHCH$_3$ | H | 3 |
| E66 a, b, c, d, e, or f | H | CH$_3$ | 3 |
| E67 a, b, c, d, e, or f | C(=O)OH | CH$_3$ | 3 |
| E68 a, b, c, d, e, or f | C(=O)OCH$_3$ | CH$_3$ | 3 |
| E69 a, b, c, d, e, or f | CH$_2$C(=O)OH | CH$_3$ | 3 |
| E70 a, b, c, d, e, or f | CH$_2$C(=O)OCH$_3$ | CH$_3$ | 3 |
| E71 a, b, c, d, e, or f | CH$_2$CH$_2$C(=O)OH | CH$_3$ | 3 |
| E72 a, b, c, d, e, or f | CH$_2$CH$_2$C(=O)OCH$_3$ | CH$_3$ | 3 |
| E73 a, b, c, d, e, or f | C(=O)NH$_2$ | CH$_3$ | 3 |
| E74 a, b, c, d, e, or f | C(=O)NHCH$_3$ | CH$_3$ | 3 |
| E75 a, b, c, d, e, or f | CH$_2$C(=O)NH$_2$ | CH$_3$ | 3 |
| E76 a, b, c, d, e, or f | CH$_2$C(=O)NHCH$_3$ | CH$_3$ | 3 |
| E77 a, b, c, d, e, or f | CH$_2$CH$_2$C(=O)NH$_2$ | CH$_3$ | 3 |
| E78 a, b, c, d, e, or f | CH$_2$CH$_2$C(=O)NHCH$_3$ | CH$_3$ | 3 |

*(i) Indicates that Q$_x$ ring carbon atom that is bonded to the 5-membered, nitrogen-containing ring that is fused to benzo is in the (R)-conformation, (ii) indicates that Q$_x$ ring carbon atom that is bonded to the 5-membered, nitrogen-containing ring that is fused to benzo is in the (S)-conformation.

TABLE 7

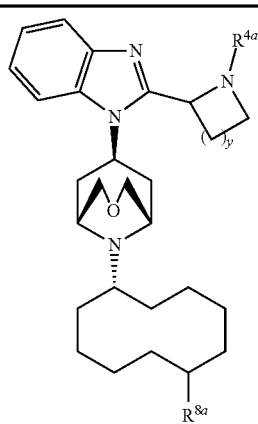

(a)

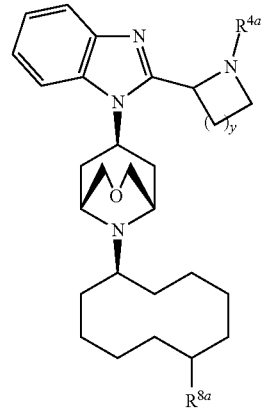

(b)

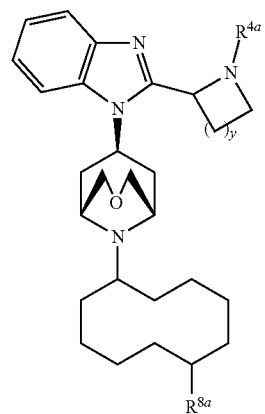

(c)

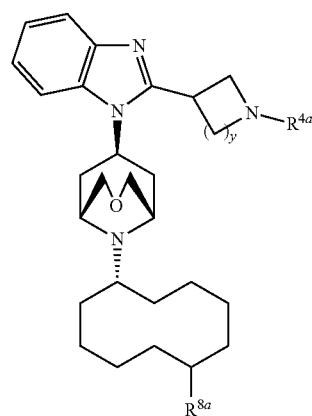

(d)

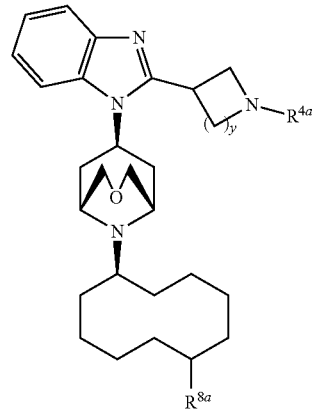

(e)

TABLE 7-continued

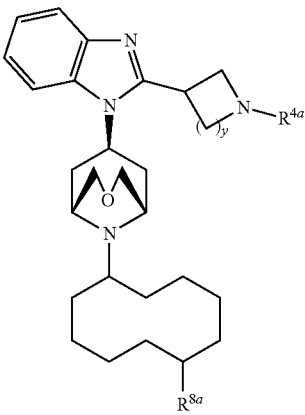
(f)

and pharmaceutically acceptable salts or solvates thereof, where:

| Compound* | | $R^{4a}$ | $R^{8a}$ | y |
|---|---|---|---|---|
| F | F1 c or f | H | H | 1 |
| | F2 c or f | C(=O)OH | H | 1 |
| | F3 c or f | C(=O)OCH$_3$ | H | 1 |
| | F4 c or f | CH$_2$C(=O)OH | H | 1 |
| | F5 c or f | CH$_2$C(=O)OCH$_3$ | H | 1 |
| | F6 c or f | CH$_2$CH$_2$C(=O)OH | H | 1 |
| | F7 c or f | CH$_2$CH$_2$C(=O)OCH$_3$ | H | 1 |
| | F8 c or f | C(=O)NH$_2$ | H | 1 |
| | F9 c or f | C(=O)NHCH$_3$ | H | 1 |
| | F10 c or f | CH$_2$C(=O)NH$_2$ | H | 1 |
| | F11 c or f | CH$_2$C(=O)NHCH$_3$ | H | 1 |
| | F12 c or f | CH$_2$CH$_2$C(=O)NH$_2$ | H | 1 |
| | F13 c or f | CH$_2$CH$_2$C(=O)NHCH$_3$ | H | 1 |
| | F14 a, b, c, d, e, or f | H | CH$_3$ | 1 |
| | F15 a, b, c, d, e, or f | C(=O)OH | CH$_3$ | 1 |
| | F16 a, b, c, d, e, or f | C(=O)OCH$_3$ | CH$_3$ | 1 |
| | F17 a, b, c, d, e, or f | CH$_2$C(=O)OH | CH$_3$ | 1 |
| | F18 a, b, c, d, e, or f | CH$_2$C(=O)OCH$_3$ | CH$_3$ | 1 |
| | F19 a, b, c, d, e, or f | CH$_2$CH$_2$C(=O)OH | CH$_3$ | 1 |
| | F20 a, b, c, d, e, or f | CH$_2$CH$_2$C(=O)OCH$_3$ | CH$_3$ | 1 |
| | F21 a, b, c, d, e, or f | C(=O)NH$_2$ | CH$_3$ | 1 |
| | F22 a, b, c, d, e, or f | C(=O)NHCH$_3$ | CH$_3$ | 1 |
| | F23 a, b, c, d, e, or f | CH$_2$C(=O)NH$_2$ | CH$_3$ | 1 |
| | F24 a, b, c, d, e, or f | CH$_2$C(=O)NHCH$_3$ | CH$_3$ | 1 |
| | F25 a, b, c, d, e, or f | CH$_2$CH$_2$C(=O)NH$_2$ | CH$_3$ | 1 |
| | F26 a, b, c, d, e, or f | CH$_2$CH$_2$C(=O)NHCH$_3$ | CH$_3$ | 1 |
| | F27 c or f | H | H | 2 |
| | F28 c or f | C(=O)OH | H | 2 |
| | F29 c or f | C(=O)OCH$_3$ | H | 2 |
| | F30 c or f | CH$_2$C(=O)OH | H | 2 |
| | F31 c or f | CH$_2$C(=O)OCH$_3$ | H | 2 |
| | F32 c or f | CH$_2$CH$_2$C(=O)OH | H | 2 |
| | F33 c or f | CH$_2$CH$_2$C(=O)OCH$_3$ | H | 2 |
| | F34 c or f | C(=O)NH$_2$ | H | 2 |
| | F35 c or f | C(=O)NHCH$_3$ | H | 2 |
| | F36 c or f | CH$_2$C(=O)NH$_2$ | H | 2 |
| | F37 c or f | CH$_2$C(=O)NHCH$_3$ | H | 2 |
| | F38 c or f | CH$_2$CH$_2$C(=O)NH$_2$ | H | 2 |
| | F39 c or f | CH$_2$CH$_2$C(=O)NHCH$_3$ | H | 2 |
| | F40 a, b, c, d, e, or f | H | CH$_3$ | 2 |
| | F41 a, b, c, d, e, or f | C(=O)OH | CH$_3$ | 2 |
| | F42 a, b, c, d, e, or f | C(=O)OCH$_3$ | CH$_3$ | 2 |
| | F43 a, b, c, d, e, or f | CH$_2$C(=O)OH | CH$_3$ | 2 |
| | F44 a, b, c, d, e, or f | CH$_2$C(=O)OCH$_3$ | CH$_3$ | 2 |
| | F45 a, b, c, d, e, or f | CH$_2$CH$_2$C(=O)OH | CH$_3$ | 2 |
| | F46 a, b, c, d, e, or f | CH$_2$CH$_2$C(=O)OCH$_3$ | CH$_3$ | 2 |
| | F47 a, b, c, d, e, or f | C(=O)NH$_2$ | CH$_3$ | 2 |
| | F48 a, b, c, d, e, or f | C(=O)NHCH$_3$ | CH$_3$ | 2 |
| | F49 a, b, c, d, e, or f | CH$_2$C(=O)NH$_2$ | CH$_3$ | 2 |
| | F50 a, b, c, d, e, or f | CH$_2$C(=O)NHCH$_3$ | CH$_3$ | 2 |
| | F51 a, b, c, d, e, or f | CH$_2$CH$_2$C(=O)NH$_2$ | CH$_3$ | 2 |

-continued

| Compound* | | $R^{4a}$ | $R^{8a}$ | y |
|---|---|---|---|---|
| | F52 a, b, c, d, e, or f | CH$_2$CH$_2$C(=O)NHCH$_3$ | CH$_3$ | 2 |
| | F53 c or f | H | H | 3 |
| | F54 c or f | C(=O)OH | H | 3 |
| | F55 c or f | C(=O)OCH$_3$ | H | 3 |
| | F56 c or f | CH$_2$C(=O)OH | H | 3 |
| | F57 c or f | CH$_2$C(=O)OCH$_3$ | H | 3 |
| | F58 c or f | CH$_2$CH$_2$C(=O)OH | H | 3 |
| | F59 c or f | CH$_2$CH$_2$C(=O)OCH$_3$ | H | 3 |
| | F60 c or f | C(=O)NH$_2$ | H | 3 |
| | F61 c or f | C(=O)NHCH$_3$ | H | 3 |
| | F62 c or f | CH$_2$C(=O)NH$_2$ | H | 3 |
| | F63 c or f | CH$_2$C(=O)NHCH$_3$ | H | 3 |
| | F64 c or f | CH$_2$CH$_2$C(=O)NH$_2$ | H | 3 |
| | F65 c or f | CH$_2$CH$_2$C(=O)NHCH$_3$ | H | 3 |
| | F66 a, b, c, d, e, or f | H | CH$_3$ | 3 |
| | F67 a, b, c, d, e, or f | C(=O)OH | CH$_3$ | 3 |
| | F68 a, b, c, d, e, or f | C(=O)OCH$_3$ | CH$_3$ | 3 |
| | F69 a, b, c, d, e, or f | CH$_2$C(=O)OH | CH$_3$ | 3 |
| | F70 a, b, c, d, e, or f | CH$_2$C(=O)OCH$_3$ | CH$_3$ | 3 |
| | F71 a, b, c, d, e, or f | CH$_2$CH$_2$C(=O)OH | CH$_3$ | 3 |
| | F72 a, b, c, d, e, or f | CH$_2$CH$_2$C(=O)OCH$_3$ | CH$_3$ | 3 |
| | F73 a, b, c, d, e, or f | C(=O)NH$_2$ | CH$_3$ | 3 |
| | F74 a, b, c, d, e, or f | C(=O)NHCH$_3$ | CH$_3$ | 3 |
| | F75 a, b, c, d, e, or f | CH$_2$C(=O)NH$_2$ | CH$_3$ | 3 |
| | F76 a, b, c, d, e, or f | CH$_2$C(=O)NHCH$_3$ | CH$_3$ | 3 |
| | F77 a, b, c, d, e, or f | CH$_2$CH$_2$C(=O)NH$_2$ | CH$_3$ | 3 |
| | F78 a, b, c, d, e, or f | CH$_2$CH$_2$C(=O)NHCH$_3$ | CH$_3$ | 3 |

*(i) Indicates that $Q_x$ ring carbon atom that is bonded to the 5-membered, nitrogen-containing ring that is fused to benzo is in the (R)-conformation, (ii) indicates that $Q_x$ ring carbon atom that is bonded to the 5-membered, nitrogen-containing ring that is fused to benzo is in the (S)-conformation.

TABLE 8

(a)

TABLE 8-continued (b) [structure: benzimidazole with N-R^4a azetidine, azabicyclic, and adamantyl-R^8a]

(c) [structure variant]

(d) [structure variant]

and pharmaceutically acceptable salts or solvates thereof, where:

| Compound* | R^4a | R^8a | y |
|---|---|---|---|
| G G1 a, b, c, or d | H | H | 1 |
| G2 a, b, c, or d | C(=O)OH | H | 1 |
| G3 a, b, c, or d | C(=O)OCH$_3$ | H | 1 |
| G4 a, b, c, or d | CH$_2$C(=O)OH | H | 1 |
| G5 a, b, c, or d | CH$_2$C(=O)OCH$_3$ | H | 1 |
| G6 a, b, c, or d | CH$_2$CH$_2$C(=O)OH | H | 1 |
| G7 a, b, c, or d | CH$_2$CH$_2$C(=O)OCH$_3$ | H | 1 |
| G8 a, b, c, or d | C(=O)NH$_2$ | H | 1 |
| G9 a, b, c, or d | C(=O)NHCH$_3$ | H | 1 |
| G10 a, b, c, or d | CH$_2$C(=O)NH$_2$ | H | 1 |
| G11 a, b, c, or d | CH$_2$C(=O)NHCH$_3$ | H | 1 |
| G12 a, b, c, or d | CH$_2$CH$_2$C(=O)NH$_2$ | H | 1 |
| G13 a, b, c, or d | CH$_2$CH$_2$C(=O)NHCH$_3$ | H | 1 |
| G14 a, b, c, or d | H | CH$_3$ | 1 |
| G15 a, b, c, or d | C(=O)OH | CH$_3$ | 1 |
| G16 a, b, c, or d | C(=O)OCH$_3$ | CH$_3$ | 1 |
| G17 a, b, c, or d | CH$_2$C(=O)OH | CH$_3$ | 1 |
| G18 a, b, c, or d | CH$_2$C(=O)OCH$_3$ | CH$_3$ | 1 |
| G19 a, b, c, or d | CH$_2$CH$_2$C(=O)OH | CH$_3$ | 1 |
| G20 a, b, c, or d | CH$_2$CH$_2$C(=O)OCH$_3$ | CH$_3$ | 1 |
| G21 a, b, c, or d | C(=O)NH$_2$ | CH$_3$ | 1 |
| G22 a, b, c, or d | C(=O)NHCH$_3$ | CH$_3$ | 1 |
| G23 a, b, c, or d | CH$_2$C(=O)NH$_2$ | CH$_3$ | 1 |
| G24 a, b, c, or d | CH$_2$C(=O)NHCH$_3$ | CH$_3$ | 1 |
| G25 a, b, c, or d | CH$_2$CH$_2$C(=O)NH$_2$ | CH$_3$ | 1 |
| G26 a, b, c, or d | CH$_2$CH$_2$C(=O)NHCH$_3$ | CH$_3$ | 1 |
| G27 a, b, c, or d | H | H | 2 |
| G28 a, b, c, or d | C(=O)OH | H | 2 |
| G29 a, b, c, or d | C(=O)OCH$_3$ | H | 2 |
| G30 a, b, c, or d | CH$_2$C(=O)OH | H | 2 |
| G31 a, b, c, or d | CH$_2$C(=O)OCH$_3$ | H | 2 |
| G32 a, b, c, or d | CH$_2$CH$_2$C(=O)OH | H | 2 |
| G33 a, b, c, or d | CH$_2$CH$_2$C(=O)OCH$_3$ | H | 2 |
| G34 a, b, c, or d | C(=O)NH$_2$ | H | 2 |
| G35 a, b, c, or d | C(=O)NHCH$_3$ | H | 2 |
| G36 a, b, c, or d | CH$_2$C(=O)NH$_2$ | H | 2 |
| G37 a, b, c, or d | CH$_2$C(=O)NHCH$_3$ | H | 2 |
| G38 a, b, c, or d | CH$_2$CH$_2$C(=O)NH$_2$ | H | 2 |
| G39 a, b, c, or d | CH$_2$CH$_2$C(=O)NHCH$_3$ | H | 2 |
| G40 a, b, c, or d | H | CH$_3$ | 2 |
| G41 a, b, c, or d | C(=O)OH | CH$_3$ | 2 |
| G42 a, b, c, or d | C(=O)OCH$_3$ | CH$_3$ | 2 |
| G43 a, b, c, or d | CH$_2$C(=O)OH | CH$_3$ | 2 |
| G44 a, b, c, or d | CH$_2$C(=O)OCH$_3$ | CH$_3$ | 2 |
| G45 a, b, c, or d | CH$_2$CH$_2$C(=O)OH | CH$_3$ | 2 |
| G46 a, b, c, or d | CH$_2$CH$_2$C(=O)OCH$_3$ | CH$_3$ | 2 |
| G47 a, b, c, or d | C(=O)NH$_2$ | CH$_3$ | 2 |
| G48 a, b, c, or d | C(=O)NHCH$_3$ | CH$_3$ | 2 |
| G49 a, b, c, or d | CH$_2$C(=O)NH$_2$ | CH$_3$ | 2 |
| G50 a, b, c, or d | CH$_2$C(=O)NHCH$_3$ | CH$_3$ | 2 |
| G51 a, b, c, or d | CH$_2$CH$_2$C(=O)NH$_2$ | CH$_3$ | 2 |
| G52 a, b, c, or d | CH$_2$CH$_2$C(=O)NHCH$_3$ | CH$_3$ | 2 |
| G53 a, b, c, or d | H | H | 3 |
| G54 a, b, c, or d | C(=O)OH | H | 3 |
| G55 a, b, c, or d | C(=O)OCH$_3$ | H | 3 |
| G56 a, b, c, or d | CH$_2$C(=O)OH | H | 3 |
| G57 a, b, c, or d | CH$_2$C(=O)OCH$_3$ | H | 3 |
| G58 a, b, c, or d | CH$_2$CH$_2$C(=O)OH | H | 3 |
| G59 a, b, c, or d | CH$_2$CH$_2$C(=O)OCH$_3$ | H | 3 |
| G60 a, b, c, or d | C(=O)NH$_2$ | H | 3 |
| G61 a, b, c, or d | C(=O)NHCH$_3$ | H | 3 |
| G62 a, b, c, or d | CH$_2$C(=O)NH$_2$ | H | 3 |
| G63 a, b, c, or d | CH$_2$C(=O)NHCH$_3$ | H | 3 |
| G64 a, b, c, or d | CH$_2$CH$_2$C(=O)NH$_2$ | H | 3 |
| G65 a, b, c, or d | CH$_2$CH$_2$C(=O)NHCH$_3$ | H | 3 |
| G66 a, b, c, or d | H | CH$_3$ | 3 |
| G67 a, b, c, or d | C(=O)OH | CH$_3$ | 3 |
| G68 a, b, c, or d | C(=O)OCH$_3$ | CH$_3$ | 3 |
| G69 a, b, c, or d | CH$_2$C(=O)OH | CH$_3$ | 3 |
| G70 a, b, c, or d | CH$_2$C(=O)OCH$_3$ | CH$_3$ | 3 |
| G71 a, b, c, or d | CH$_2$CH$_2$C(=O)OH | CH$_3$ | 3 |
| G72 a, b, c, or d | CH$_2$CH$_2$C(=O)OCH$_3$ | CH$_3$ | 3 |
| G73 a, b, c, or d | C(=O)NH$_2$ | CH$_3$ | 3 |
| G74 a, b, c, or d | C(=O)NHCH$_3$ | CH$_3$ | 3 |
| G75 a, b, c, or d | CH$_2$C(=O)NH$_2$ | CH$_3$ | 3 |
| G76 a, b, c, or d | CH$_2$C(=O)NHCH$_3$ | CH$_3$ | 3 |
| G77 a, b, c, or d | CH$_2$CH$_2$C(=O)NH$_2$ | CH$_3$ | 3 |
| G78 a, b, c, or d | CH$_2$CH$_2$C(=O)NHCH$_3$ | CH$_3$ | 3 |

*(i) Indicates that $Q_x$ ring carbon atom that is bonded to the 5-membered, nitrogen-containing ring that is fused to benzo is in the (R)-conformation, (ii) indicates that $Q_x$ ring carbon atom that is bonded to the 5-membered, nitrogen-containing ring that is fused to benzo is in the (S)-conformation.

TABLE 9

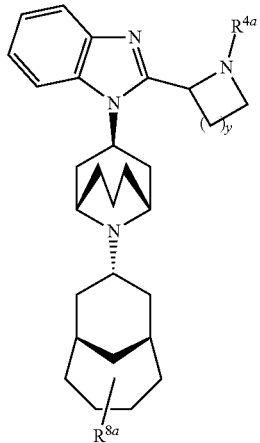
(a)

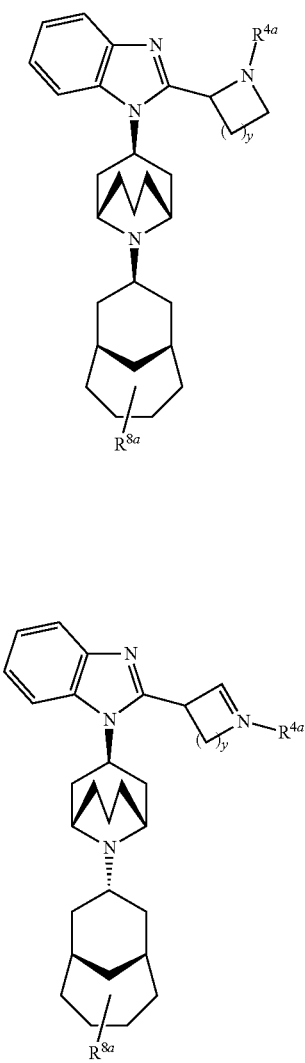

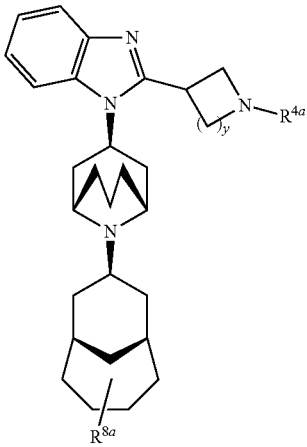
(d)

and pharmaceutically acceptable salts or solvates thereof, where:

| Compound* | | $R^{4a}$ | $R^{8a}$ | y |
|---|---|---|---|---|
| H | H1 a, b, c, or d | H | H | 1 |
| | H2 a, b, c, or d | C(=O)OH | H | 1 |
| | H3 a, b, c, or d | C(=O)OCH$_3$ | H | 1 |
| | H4 a, b, c, or d | CH$_2$C(=O)OH | H | 1 |
| | H5 a, b, c, or d | CH$_2$C(=O)OCH$_3$ | H | 1 |
| | H6 a, b, c, or d | CH$_2$CH$_2$C(=O)OH | H | 1 |
| | H7 a, b, c, or d | CH$_2$CH$_2$C(=O)OCH$_3$ | H | 1 |
| | H8 a, b, c, or d | C(=O)NH$_2$ | H | 1 |
| | H9 a, b, c, or d | C(=O)NHCH$_3$ | H | 1 |
| | H10 a, b, c, or d | CH$_2$C(=O)NH$_2$ | H | 1 |
| | H11 a, b, c, or d | CH$_2$C(=O)NHCH$_3$ | H | 1 |
| | H12 a, b, c, or d | CH$_2$CH$_2$C(=O)NH$_2$ | H | 1 |
| | H13 a, b, c, or d | CH$_2$CH$_2$C(=O)NHCH$_3$ | H | 1 |
| | H14 a, b, c, or d | H | CH$_3$ | 1 |
| | H15 a, b, c, or d | C(=O)OH | CH$_3$ | 1 |
| | H16 a, b, c, or d | C(=O)OCH$_3$ | CH$_3$ | 1 |
| | H17 a, b, c, or d | CH$_2$C(=O)OH | CH$_3$ | 1 |
| | H18 a, b, c, or d | CH$_2$C(=O)OCH$_3$ | CH$_3$ | 1 |
| | H19 a, b, c, or d | CH$_2$CH$_2$C(=O)OH | CH$_3$ | 1 |
| | H20 a, b, c, or d | CH$_2$CH$_2$C(=O)OCH$_3$ | CH$_3$ | 1 |
| | H21 a, b, c, or d | C(=O)NH$_2$ | CH$_3$ | 1 |
| | H22 a, b, c, or d | C(=O)NHCH$_3$ | CH$_3$ | 1 |
| | H23 a, b, c, or d | CH$_2$C(=O)NH$_2$ | CH$_3$ | 1 |
| | H24 a, b, c, or d | CH$_2$C(=O)NHCH$_3$ | CH$_3$ | 1 |
| | H25 a, b, c, or d | CH$_2$CH$_2$C(=O)NH$_2$ | CH$_3$ | 1 |
| | H26 a, b, c, or d | CH$_2$CH$_2$C(=O)NHCH$_3$ | CH$_3$ | 1 |
| | H27 a, b, c, or d | H | H | 2 |
| | H28 a, b, c, or d | C(=O)OH | H | 2 |
| | H29 a, b, c, or d | C(=O)OCH$_3$ | H | 2 |
| | H30 a, b, c, or d | CH$_2$C(=O)OH | H | 2 |
| | H31 a, b, c, or d | CH$_2$C(=O)OCH$_3$ | H | 2 |
| | H32 a, b, c, or d | CH$_2$CH$_2$C(=O)OH | H | 2 |
| | H33 a, b, c, or d | CH$_2$CH$_2$C(=O)OCH$_3$ | H | 2 |
| | H34 a, b, c, or d | C(=O)NH$_2$ | H | 2 |
| | H35 a, b, c, or d | C(=O)NHCH$_3$ | H | 2 |
| | H36 a, b, c, or d | CH$_2$C(=O)NH$_2$ | H | 2 |
| | H37 a, b, c, or d | CH$_2$C(=O)NHCH$_3$ | H | 2 |
| | H38 a, b, c, or d | CH$_2$CH$_2$C(=O)NH$_2$ | H | 2 |
| | H39 a, b, c, or d | CH$_2$CH$_2$C(=O)NHCH$_3$ | H | 2 |
| | H40 a, b, c, or d | H | CH$_3$ | 2 |
| | H41 a, b, c, or d | C(=O)OH | CH$_3$ | 2 |
| | H42 a, b, c, or d | C(=O)OCH$_3$ | CH$_3$ | 2 |
| | H43 a, b, c, or d | CH$_2$C(=O)OH | CH$_3$ | 2 |
| | H44 a, b, c, or d | CH$_2$C(=O)OCH$_3$ | CH$_3$ | 2 |
| | H45 a, b, c, or d | CH$_2$CH$_2$C(=O)OH | CH$_3$ | 2 |
| | H46 a, b, c, or d | CH$_2$CH$_2$C(=O)OCH$_3$ | CH$_3$ | 2 |
| | H47 a, b, c, or d | C(=O)NH$_2$ | CH$_3$ | 2 |
| | H48 a, b, c, or d | C(=O)NHCH$_3$ | CH$_3$ | 2 |
| | H49 a, b, c, or d | CH$_2$C(=O)NH$_2$ | CH$_3$ | 2 |
| | H50 a, b, c, or d | CH$_2$C(=O)NHCH$_3$ | CH$_3$ | 2 |

-continued

| Compound* | $R^{4a}$ | $R^{8a}$ | y |
|---|---|---|---|
| H51 a, b, c, or d | $CH_2CH_2C(=O)NH_2$ | $CH_3$ | 2 |
| H52 a, b, c, or d | $CH_2CH_2C(=O)NHCH_3$ | $CH_3$ | 2 |
| H53 a, b, c, or d | H | H | 3 |
| H54 a, b, c, or d | $C(=O)OH$ | H | 3 |
| H55 a, b, c, or d | $C(=O)OCH_3$ | H | 3 |
| H56 a, b, c, or d | $CH_2C(=O)OH$ | H | 3 |
| H57 a, b, c, or d | $CH_2C(=O)OCH_3$ | H | 3 |
| H58 a, b, c, or d | $CH_2CH_2C(=O)OH$ | H | 3 |
| H59 a, b, c, or d | $CH_2CH_2C(=O)OCH_3$ | H | 3 |
| H60 a, b, c, or d | $C(=O)NH_2$ | H | 3 |
| H61 a, b, c, or d | $C(=O)NHCH_3$ | H | 3 |
| H62 a, b, c, or d | $CH_2C(=O)NH_2$ | H | 3 |
| H63 a, b, c, or d | $CH_2C(=O)NHCH_3$ | H | 3 |
| H64 a, b, c, or d | $CH_2CH_2C(=O)NH_2$ | H | 3 |
| H65 a, b, c, or d | $CH_2CH_2C(=O)NHCH_3$ | H | 3 |
| H66 a, b, c, or d | H | $CH_3$ | 3 |
| H67 a, b, c, or d | $C(=O)OH$ | $CH_3$ | 3 |
| H68 a, b, c, or d | $C(=O)OCH_3$ | $CH_3$ | 3 |
| H69 a, b, c, or d | $CH_2C(=O)OH$ | $CH_3$ | 3 |
| H70 a, b, c, or d | $CH_2C(=O)OCH_3$ | $CH_3$ | 3 |
| H71 a, b, c, or d | $CH_2CH_2C(=O)OH$ | $CH_3$ | 3 |
| H72 a, b, c, or d | $CH_2CH_2C(=O)OCH_3$ | $CH_3$ | 3 |
| H73 a, b, c, or d | $C(=O)NH_2$ | $CH_3$ | 3 |
| H74 a, b, c, or d | $C(=O)NHCH_3$ | $CH_3$ | 3 |
| H75 a, b, c, or d | $CH_2C(=O)NH_2$ | $CH_3$ | 3 |
| H76 a, b, c, or d | $CH_2C(=O)NHCH_3$ | $CH_3$ | 3 |
| H77 a, b, c, or d | $CH_2CH_2C(=O)NH_2$ | $CH_3$ | 3 |
| H78 a, b, c, or d | $CH_2CH_2C(=O)NHCH_3$ | $CH_3$ | 3 |

*(i) Indicates that $Q_x$ ring carbon atom that is bonded to the 5-membered, nitrogen-containing ring that is fused to benzo is in the (R)-conformation, (ii) indicates that $Q_x$ ring carbon atom that is bonded to the 5-membered, nitrogen-containing ring that is fused to benzo is in the (S)-conformation.

TABLE 10

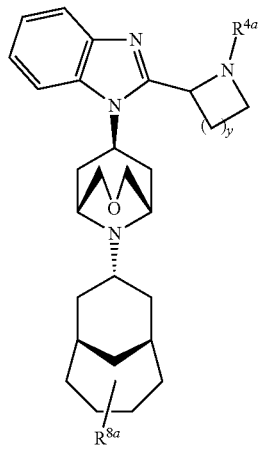

(a)

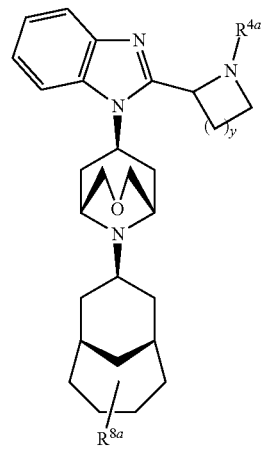

(b)

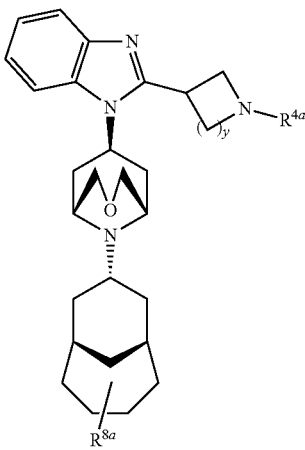

(c)

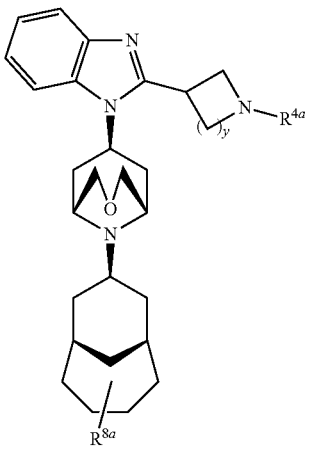

(d)

and pharmaceutically acceptable salts or solvates thereof, where:

| | Compound* | $R^{4a}$ | $R^{8a}$ | y |
|---|---|---|---|---|
| J | J1 a, b, c, or d | H | H | 1 |
| | J2 a, b, c, or d | $C(=O)OH$ | H | 1 |
| | J3 a, b, c, or d | $C(=O)OCH_3$ | H | 1 |
| | J4 a, b, c, or d | $CH_2C(=O)OH$ | H | 1 |
| | J5 a, b, c, or d | $CH_2C(=O)OCH_3$ | H | 1 |
| | J6 a, b, c, or d | $CH_2CH_2C(=O)OH$ | H | 1 |

-continued

| Compound* | R⁴ᵃ | R⁸ᵃ | y |
|---|---|---|---|
| J7 a, b, c, or d | CH₂CH₂C(=O)OCH₃ | H | 1 |
| J8 a, b, c, or d | C(=O)NH₂ | H | 1 |
| J9 a, b, c, or d | C(=O)NHCH₃ | H | 1 |
| J10 a, b, c, or d | CH₂C(=O)NH₂ | H | 1 |
| J11 a, b, c, or d | CH₂C(=O)NHCH₃ | H | 1 |
| J12 a, b, c, or d | CH₂CH₂C(=O)NH₂ | H | 1 |
| J13 a, b, c, or d | CH₂CH₂C(=O)NHCH₃ | H | 1 |
| J14 a, b, c, or d | H | CH₃ | 1 |
| J15 a, b, c, or d | C(=O)OH | CH₃ | 1 |
| J16 a, b, c, or d | C(=O)OCH₃ | CH₃ | 1 |
| J17 a, b, c, or d | CH₂C(=O)OH | CH₃ | 1 |
| J18 a, b, c, or d | CH₂C(=O)OCH₃ | CH₃ | 1 |
| J19 a, b, c, or d | CH₂CH₂C(=O)OH | CH₃ | 1 |
| J20 a, b, c, or d | CH₂CH₂C(=O)OCH₃ | CH₃ | 1 |
| J21 a, b, c, or d | C(=O)NH₂ | CH₃ | 1 |
| J22 a, b, c, or d | C(=O)NHCH₃ | CH₃ | 1 |
| J23 a, b, c, or d | CH₂C(=O)NH₂ | CH₃ | 1 |
| J24 a, b, c, or d | CH₂C(=O)NHCH₃ | CH₃ | 1 |
| J25 a, b, c, or d | CH₂CH₂C(=O)NH₂ | CH₃ | 1 |
| J26 a, b, c, or d | CH₂CH₂C(=O)NHCH₃ | CH₃ | 1 |
| J27 a, b, c, or d | H | H | 2 |
| J28 a, b, c, or d | C(=O)OH | H | 2 |
| J29 a, b, c, or d | C(=O)OCH₃ | H | 2 |
| J30 a, b, c, or d | CH₂C(=O)OH | H | 2 |
| J31 a, b, c, or d | CH₂C(=O)OCH₃ | H | 2 |
| J32 a, b, c, or d | CH₂CH₂C(=O)OH | H | 2 |
| J33 a, b, c, or d | CH₂CH₂C(=O)OCH₃ | H | 2 |
| J34 a, b, c, or d | C(=O)NH₂ | H | 2 |
| J35 a, b, c, or d | C(=O)NHCH₃ | H | 2 |
| J36 a, b, c, or d | CH₂C(=O)NH₂ | H | 2 |
| J37 a, b, c, or d | CH₂C(=O)NHCH₃ | H | 2 |
| J38 a, b, c, or d | CH₂CH₂C(=O)NH₂ | H | 2 |
| J39 a, b, c, or d | CH₂CH₂C(=O)NHCH₃ | H | 2 |
| J40 a, b, c, or d | H | CH₃ | 2 |
| J41 a, b, c, or d | C(=O)OH | CH₃ | 2 |
| J42 a, b, c, or d | C(=O)OCH₃ | CH₃ | 2 |
| J43 a, b, c, or d | CH₂C(=O)OH | CH₃ | 2 |
| J44 a, b, c, or d | CH₂C(=O)OCH₃ | CH₃ | 2 |
| J45 a, b, c, or d | CH₂CH₂C(=O)OH | CH₃ | 2 |
| J46 a, b, c, or d | CH₂CH₂C(=O)OCH₃ | CH₃ | 2 |
| J47 a, b, c, or d | C(=O)NH₂ | CH₃ | 2 |
| J48 a, b, c, or d | C(=O)NHCH₃ | CH₃ | 2 |
| J49 a, b, c, or d | CH₂C(=O)NH₂ | CH₃ | 2 |
| J50 a, b, c, or d | CH₂C(=O)NHCH₃ | CH₃ | 2 |
| J51 a, b, c, or d | CH₂CH₂C(=O)NH₂ | CH₃ | 2 |
| J52 a, b, c, or d | CH₂CH₂C(=O)NHCH₃ | CH₃ | 2 |
| J53 a, b, c, or d | H | H | 3 |
| J54 a, b, c, or d | C(=O)OH | H | 3 |
| J55 a, b, c, or d | C(=O)OCH₃ | H | 3 |
| J56 a, b, c, or d | CH₂C(=O)OH | H | 3 |
| J57 a, b, c, or d | CH₂C(=O)OCH₃ | H | 3 |
| J58 a, b, c, or d | CH₂CH₂C(=O)OH | H | 3 |
| J59 a, b, c, or d | CH₂CH₂C(=O)OCH₃ | H | 3 |
| J60 a, b, c, or d | C(=O)NH₂ | H | 3 |
| J61 a, b, c, or d | C(=O)NHCH₃ | H | 3 |
| J62 a, b, c, or d | CH₂C(=O)NH₂ | H | 3 |
| J63 a, b, c, or d | CH₂C(=O)NHCH₃ | H | 3 |
| J64 a, b, c, or d | CH₂CH₂C(=O)NH₂ | H | 3 |
| J65 a, b, c, or d | CH₂CH₂C(=O)NHCH₃ | H | 3 |
| J66 a, b, c, or d | H | CH₃ | 3 |
| J67 a, b, c, or d | C(=O)OH | CH₃ | 3 |
| J68 a, b, c, or d | C(=O)OCH₃ | CH₃ | 3 |
| J69 a, b, c, or d | CH₂C(=O)OH | CH₃ | 3 |
| J70 a, b, c, or d | CH₂C(=O)OCH₃ | CH₃ | 3 |
| J71 a, b, c, or d | CH₂CH₂C(=O)OH | CH₃ | 3 |
| J72 a, b, c, or d | CH₂CH₂C(=O)OCH₃ | CH₃ | 3 |
| J73 a, b, c, or d | C(=O)NH₂ | CH₃ | 3 |
| J74 a, b, c, or d | C(=O)NHCH₃ | CH₃ | 3 |
| J75 a, b, c, or d | CH₂C(=O)NH₂ | CH₃ | 3 |
| J76 a, b, c, or d | CH₂C(=O)NHCH₃ | CH₃ | 3 |
| J77 a, b, c, or d | CH₂CH₂C(=O)NH₂ | CH₃ | 3 |
| J78 a, b, c, or d | CH₂CH₂C(=O)NHCH₃ | CH₃ | 3 |

*(i) Indicates that $Q_x$ ring carbon atom that is bonded to the 5-membered, nitrogen-containing ring that is fused to benzo is in the (R)-conformation, (ii) indicates that $Q_x$ ring carbon atom that is bonded to the 5-membered, nitrogen-containing ring that is fused to benzo is in the (S)-conformation.

TABLE 11

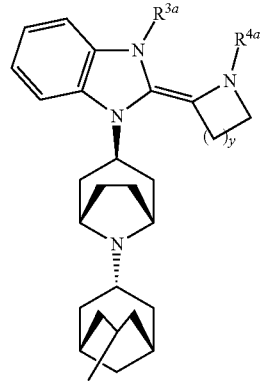

(a)

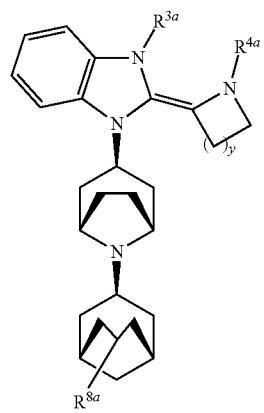

(b)

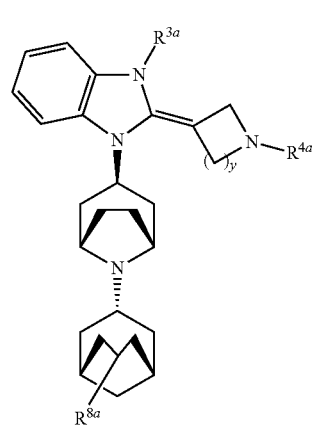

(c)

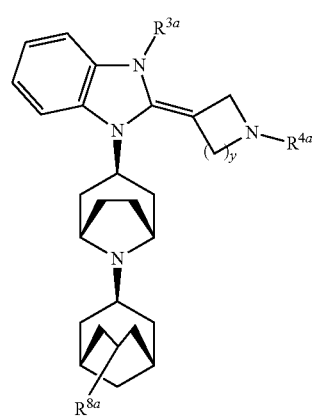

(d)

and pharmaceutically acceptable salts or solvates thereof, where:

| | Compound | $R^{4a}$ | $R^{3a}$ | $R^{8a}$ | y |
|---|---|---|---|---|---|
| K | K1 a, b, c, or d | H | H | H | 1 |
| | K2 a, b, c, or d | $CH_2C(=O)OH$ | H | H | 1 |
| | K3 a, b, c, or d | $CH_2C(=O)OCH_3$ | H | H | 1 |
| | K4 a, b, c, or d | $CH_2CH_2C(=O)OH$ | H | H | 1 |
| | K5 a, b, c, or d | $CH_2CH_2C(=O)OCH_3$ | H | H | 1 |
| | K6 a, b, c, or d | $CH_2C(=O)NH_2$ | H | H | 1 |
| | K7 a, b, c, or d | $CH_2CH_2C(=O)NH_2$ | H | H | 1 |
| | K8 a, b, c, or d | H | $CH_2C(=O)OH$ | H | 1 |
| | K9 a, b, c, or d | $CH_2C(=O)OH$ | $CH_2C(=O)OH$ | H | 1 |
| | K10 a, b, c, or d | $CH_2CH_2C(=O)OH$ | $CH_2C(=O)OH$ | H | 1 |
| | K11 a, b, c, or d | $CH_2C(=O)NH_2$ | $CH_2C(=O)OH$ | H | 1 |
| | K12 a, b, c, or d | $CH_2CH_2C(=O)NH_2$ | $CH_2C(=O)OH$ | H | 1 |
| | K13 a, b, c, or d | H | $CH_2C(=O)NH_2$ | H | 1 |
| | K14 a, b, c, or d | $CH_2C(=O)OH$ | $CH_2C(=O)NH_2$ | H | 1 |
| | K15 a, b, c, or d | $CH_2C(=O)OCH_3$ | $CH_2C(=O)NH_2$ | H | 1 |
| | K16 a, b, c, or d | $CH_2CH_2C(=O)OH$ | $CH_2C(=O)NH_2$ | H | 1 |
| | K17 a, b, c, or d | $CH_2CH_2C(=O)OCH_3$ | $CH_2C(=O)NH_2$ | H | 1 |
| | K18 a, b, c, or d | $CH_2C(=O)NH_2$ | $CH_2C(=O)NH_2$ | H | 1 |
| | K19 a, b, c, or d | $CH_2CH_2C(=O)NH_2$ | $CH_2C(=O)NH_2$ | H | 1 |
| | K20 a, b, c, or d | H | H | $CH_3$ | 1 |
| | K21 a, b, c, or d | $CH_2C(=O)OH$ | H | $CH_3$ | 1 |
| | K22 a, b, c, or d | $CH_2C(=O)OCH_3$ | H | $CH_3$ | 1 |
| | K23 a, b, c, or d | $CH_2CH_2C(=O)OH$ | H | $CH_3$ | 1 |
| | K24 a, b, c, or d | $CH_2CH_2C(=O)OCH_3$ | H | $CH_3$ | 1 |
| | K25 a, b, c, or d | $CH_2C(=O)NH_2$ | H | $CH_3$ | 1 |
| | K26 a, b, c, or d | $CH_2CH_2C(=O)NH_2$ | H | $CH_3$ | 1 |
| | K27 a, b, c, or d | H | $CH_2C(=O)OH$ | $CH_3$ | 1 |
| | K28 a, b, c, or d | $CH_2C(=O)OH$ | $CH_2C(=O)OH$ | $CH_3$ | 1 |
| | K29 a, b, c, or d | $CH_2CH_2C(=O)OH$ | $CH_2C(=O)OH$ | $CH_3$ | 1 |
| | K30 a, b, c, or d | $CH_2C(=O)NH_2$ | $CH_2C(=O)OH$ | $CH_3$ | 1 |
| | K31 a, b, c, or d | $CH_2CH_2C(=O)NH_2$ | $CH_2C(=O)OH$ | $CH_3$ | 1 |
| | K32 a, b, c, or d | H | $CH_2C(=O)NH_2$ | $CH_3$ | 1 |
| | K33 a, b, c, or d | $CH_2C(=O)OH$ | $CH_2C(=O)NH_2$ | $CH_3$ | 1 |
| | K34 a, b, c, or d | $CH_2C(=O)OCH_3$ | $CH_2C(=O)NH_2$ | $CH_3$ | 1 |
| | K35 a, b, c, or d | $CH_2CH_2C(=O)OH$ | $CH_2C(=O)NH_2$ | $CH_3$ | 1 |
| | K36 a, b, c, or d | $CH_2CH_2C(=O)OCH_3$ | $CH_2C(=O)NH_2$ | $CH_3$ | 1 |
| | K37 a, b, c, or d | $CH_2C(=O)NH_2$ | $CH_2C(=O)NH_2$ | $CH_3$ | 1 |
| | K38 a, b, c, or d | $CH_2CH_2C(=O)NH_2$ | $CH_2C(=O)NH_2$ | $CH_3$ | 1 |
| | K39 a, b, c, or d | H | H | H | 2 |
| | K40 a, b, c, or d | $CH_2C(=O)OH$ | H | H | 2 |
| | K41 a, b, c, or d | $CH_2C(=O)OCH_3$ | H | H | 2 |
| | K42 a, b, c, or d | $CH_2CH_2C(=O)OH$ | H | H | 2 |
| | K43 a, b, c, or d | $CH_2CH_2C(=O)OCH_3$ | H | H | 2 |
| | K44 a, b, c, or d | $CH_2C(=O)NH_2$ | H | H | 2 |
| | K45 a, b, c, or d | $CH_2CH_2C(=O)NH_2$ | H | H | 2 |
| | K46 a, b, c, or d | H | $CH_2C(=O)OH$ | H | 2 |
| | K47 a, b, c, or d | $CH_2C(=O)OH$ | $CH_2C(=O)OH$ | H | 2 |
| | K48 a, b, c, or d | $CH_2CH_2C(=O)OH$ | $CH_2C(=O)OH$ | H | 2 |
| | K49 a, b, c, or d | $CH_2C(=O)NH_2$ | $CH_2C(=O)OH$ | H | 2 |
| | K50 a, b, c, or d | $CH_2CH_2C(=O)NH_2$ | $CH_2C(=O)OH$ | H | 2 |
| | K51 a, b, c, or d | H | $CH_2C(=O)NH_2$ | H | 2 |
| | K52 a, b, c, or d | $CH_2C(=O)OH$ | $CH_2C(=O)NH_2$ | H | 2 |
| | K53 a, b, c, or d | $CH_2C(=O)OCH_3$ | $CH_2C(=O)NH_2$ | H | 2 |
| | K54 a, b, c, or d | $CH_2CH_2C(=O)OH$ | $CH_2C(=O)NH_2$ | H | 2 |
| | K55 a, b, c, or d | $CH_2CH_2C(=O)OCH_3$ | $CH_2C(=O)NH_2$ | H | 2 |
| | K56 a, b, c, or d | $CH_2C(=O)NH_2$ | $CH_2C(=O)NH_2$ | H | 2 |
| | K57 a, b, c, or d | $CH_2CH_2C(=O)NH_2$ | $CH_2C(=O)NH_2$ | H | 2 |
| | K58 a, b, c, or d | H | H | $CH_3$ | 2 |
| | K59 a, b, c, or d | $CH_2C(=O)OH$ | H | $CH_3$ | 2 |
| | K60 a, b, c, or d | $CH_2C(=O)OCH_3$ | H | $CH_3$ | 2 |
| | K61 a, b, c, or d | $CH_2CH_2C(=O)OH$ | H | $CH_3$ | 2 |
| | K62 a, b, c, or d | $CH_2CH_2C(=O)OCH_3$ | H | $CH_3$ | 2 |
| | K63 a, b, c, or d | $CH_2C(=O)NH_2$ | H | $CH_3$ | 2 |
| | K64 a, b, c, or d | $CH_2CH_2C(=O)NH_2$ | H | $CH_3$ | 2 |
| | K65 a, b, c, or d | H | $CH_2C(=O)OH$ | $CH_3$ | 2 |
| | K66 a, b, c, or d | $CH_2C(=O)OH$ | $CH_2C(=O)OH$ | $CH_3$ | 2 |
| | K67 a, b, c, or d | $CH_2CH_2C(=O)OH$ | $CH_2C(=O)OH$ | $CH_3$ | 2 |
| | K68 a, b, c, or d | $CH_2C(=O)NH_2$ | $CH_2C(=O)OH$ | $CH_3$ | 2 |
| | K69 a, b, c, or d | $CH_2CH_2C(=O)NH_2$ | $CH_2C(=O)OH$ | $CH_3$ | 2 |

-continued

| Compound | $R^{4a}$ | $R^{3a}$ | $R^{8a}$ | y |
|---|---|---|---|---|
| K70 a, b, c, or d | H | $CH_2C(=O)NH_2$ | $CH_3$ | 2 |
| K71 a, b, c, or d | $CH_2C(=O)OH$ | $CH_2C(=O)NH_2$ | $CH_3$ | 2 |
| K72 a, b, c, or d | $CH_2C(=O)OCH_3$ | $CH_2C(=O)NH_2$ | $CH_3$ | 2 |
| K73 a, b, c, or d | $CH_2CH_2C(=O)OH$ | $CH_2C(=O)NH_2$ | $CH_3$ | 2 |
| K74 a, b, c, or d | $CH_2CH_2C(=O)OCH_3$ | $CH_2C(=O)NH_2$ | $CH_3$ | 2 |
| K75 a, b, c, or d | $CH_2C(=O)NH_2$ | $CH_2C(=O)NH_2$ | $CH_3$ | 2 |
| K76 a, b, c, or d | $CH_2CH_2C(=O)NH_2$ | $CH_2C(=O)NH_2$ | $CH_3$ | 2 |
| K77 a, b, c, or d | H | H | H | 3 |
| K78 a, b, c, or d | $CH_2C(=O)OH$ | H | H | 3 |
| K79 a, b, c, or d | $CH_2C(=O)OCH_3$ | H | H | 3 |
| K80 a, b, c, or d | $CH_2CH_2C(=O)OH$ | H | H | 3 |
| K81 a, b, c, or d | $CH_2CH_2C(=O)OCH_3$ | H | H | 3 |
| K82 a, b, c, or d | $CH_2C(=O)NH_2$ | H | H | 3 |
| K83 a, b, c, or d | $CH_2CH_2C(=O)NH_2$ | H | H | 3 |
| K84 a, b, c, or d | H | $CH_2C(=O)OH$ | H | 3 |
| K85 a, b, c, or d | $CH_2C(=O)OH$ | $CH_2C(=O)OH$ | H | 3 |
| K86 a, b, c, or d | $CH_2CH_2C(=O)OH$ | $CH_2C(=O)OH$ | H | 3 |
| K87 a, b, c, or d | $CH_2C(=O)NH_2$ | $CH_2C(=O)OH$ | H | 3 |
| K88 a, b, c, or d | $CH_2CH_2C(=O)NH_2$ | $CH_2C(=O)OH$ | H | 3 |
| K89 a, b, c, or d | H | $CH_2C(=O)NH_2$ | H | 3 |
| K90 a, b, c, or d | $CH_2C(=O)OH$ | $CH_2C(=O)NH_2$ | H | 3 |
| K91 a, b, c, or d | $CH_2C(=O)OCH_3$ | $CH_2C(=O)NH_2$ | H | 3 |
| K92 a, b, c, or d | $CH_2CH_2C(=O)OH$ | $CH_2C(=O)NH_2$ | H | 3 |
| K93 a, b, c, or d | $CH_2CH_2C(=O)OCH_3$ | $CH_2C(=O)NH_2$ | H | 3 |
| K94 a, b, c, or d | $CH_2C(=O)NH_2$ | $CH_2C(=O)NH_2$ | H | 3 |
| K95 a, b, c, or d | $CH_2CH_2C(=O)NH_2$ | $CH_2C(=O)NH_2$ | H | 3 |
| K96 a, b, c, or d | H | H | $CH_3$ | 3 |
| K97 a, b, c, or d | $CH_2C(=O)OH$ | H | $CH_3$ | 3 |
| K98 a, b, c, or d | $CH_2C(=O)OCH_3$ | H | $CH_3$ | 3 |
| K99 a, b, c, or d | $CH_2CH_2C(=O)OH$ | H | $CH_3$ | 3 |
| K100 a, b, c, or d | $CH_2CH_2C(=O)OCH_3$ | H | $CH_3$ | 3 |
| K101 a, b, c, or d | $CH_2C(=O)NH_2$ | H | $CH_3$ | 3 |
| K102 a, b, c, or d | $CH_2CH_2C(=O)NH_2$ | H | $CH_3$ | 3 |
| K103 a, b, c, or d | H | $CH_2C(=O)OH$ | $CH_3$ | 3 |
| K104 a, b, c, or d | $CH_2C(=O)OH$ | $CH_2C(=O)OH$ | $CH_3$ | 3 |
| K105 a, b, c, or d | $CH_2CH_2C(=O)OH$ | $CH_2C(=O)OH$ | $CH_3$ | 3 |
| K106 a, b, c, or d | $CH_2C(=O)NH_2$ | $CH_2C(=O)OH$ | $CH_3$ | 3 |
| K107 a, b, c, or d | $CH_2CH_2C(=O)NH_2$ | $CH_2C(=O)OH$ | $CH_3$ | 3 |
| K108 a, b, c, or d | H | $CH_2C(=O)NH_2$ | $CH_3$ | 3 |
| K109 a, b, c, or d | $CH_2C(=O)OH$ | $CH_2C(=O)NH_2$ | $CH_3$ | 3 |
| K110 a, b, c, or d | $CH_2C(=O)OCH_3$ | $CH_2C(=O)NH_2$ | $CH_3$ | 3 |
| K111 a, b, c, or d | $CH_2CH_2C(=O)OH$ | $CH_2C(=O)NH_2$ | $CH_3$ | 3 |
| K112 a, b, c, or d | $CH_2CH_2C(=O)OCH_3$ | $CH_2C(=O)NH_2$ | $CH_3$ | 3 |
| K113 a, b, c, or d | $CH_2C(=O)NH_2$ | $CH_2C(=O)NH_2$ | $CH_3$ | 3 |
| K114 a, b, c, or d | $CH_2CH_2C(=O)NH_2$ | $CH_2C(=O)NH_2$ | $CH_3$ | 3 |

TABLE 12

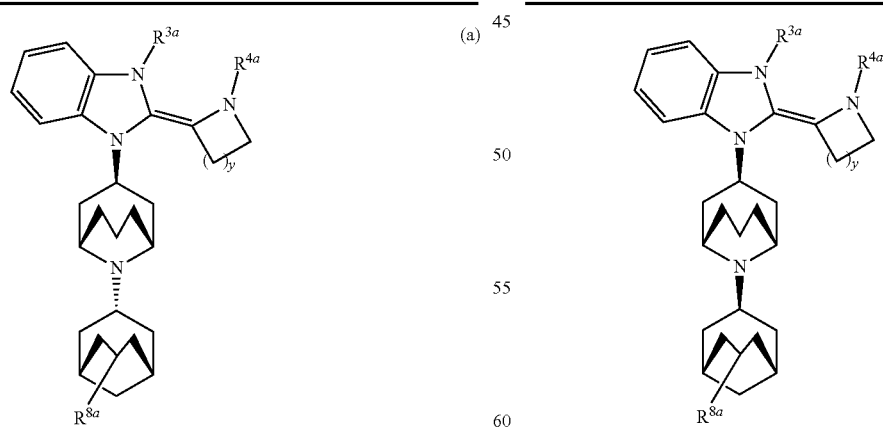

TABLE 12-continued

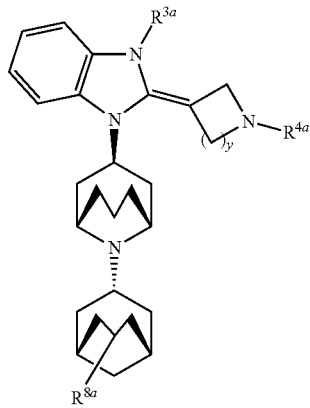

(c)

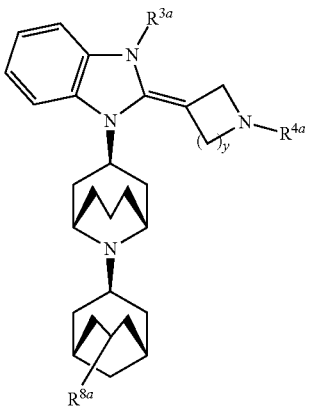

(d)

and pharmaceutically acceptable salts or solvates thereof, where:

| | Compound | $R^{4a}$ | $R^{3a}$ | $R^{8a}$ | y |
|---|---|---|---|---|---|
| L | L1 a, b, c, or d | H | H | H | 1 |
| | L2 a, b, c, or d | $CH_2C(=O)OH$ | H | H | 1 |
| | L3 a, b, c, or d | $CH_2C(=O)OCH_3$ | H | H | 1 |
| | L4 a, b, c, or d | $CH_2CH_2C(=O)OH$ | H | H | 1 |
| | L5 a, b, c, or d | $CH_2CH_2C(=O)OCH_3$ | H | H | 1 |
| | L6 a, b, c, or d | $CH_2C(=O)NH_2$ | H | H | 1 |
| | L7 a, b, c, or d | $CH_2CH_2C(=O)NH_2$ | H | H | 1 |
| | L8 a, b, c, or d | H | $CH_2C(=O)OH$ | H | 1 |
| | L9 a, b, c, or d | $CH_2C(=O)OH$ | $CH_2C(=O)OH$ | H | 1 |
| | L10 a, b, c, or d | $CH_2CH_2C(=O)OH$ | $CH_2C(=O)OH$ | H | 1 |
| | L11 a, b, c, or d | $CH_2C(=O)NH_2$ | $CH_2C(=O)OH$ | H | 1 |
| | L12 a, b, c, or d | $CH_2CH_2C(=O)NH_2$ | $CH_2C(=O)OH$ | H | 1 |
| | L13 a, b, c, or d | H | $CH_2C(=O)NH_2$ | H | 1 |
| | L14 a, b, c, or d | $CH_2C(=O)OH$ | $CH_2C(=O)NH_2$ | H | 1 |
| | L15 a, b, c, or d | $CH_2C(=O)OCH_3$ | $CH_2C(=O)NH_2$ | H | 1 |
| | L16 a, b, c, or d | $CH_2CH_2C(=O)OH$ | $CH_2C(=O)NH_2$ | H | 1 |
| | L17 a, b, c, or d | $CH_2CH_2C(=O)OCH_3$ | $CH_2C(=O)NH_2$ | H | 1 |
| | L18 a, b, c, or d | $CH_2C(=O)NH_2$ | $CH_2C(=O)NH_2$ | H | 1 |
| | L19 a, b, c, or d | $CH_2CH_2C(=O)NH_2$ | $CH_2C(=O)NH_2$ | H | 1 |
| | L20 a, b, c, or d | H | H | $CH_3$ | 1 |
| | L21 a, b, c, or d | $CH_2C(=O)OH$ | H | $CH_3$ | 1 |
| | L22 a, b, c, or d | $CH_2C(=O)OCH_3$ | H | $CH_3$ | 1 |
| | L23 a, b, c, or d | $CH_2CH_2C(=O)OH$ | H | $CH_3$ | 1 |
| | L24 a, b, c, or d | $CH_2CH_2C(=O)OCH_3$ | H | $CH_3$ | 1 |
| | L25 a, b, c, or d | $CH_2C(=O)NH_2$ | H | $CH_3$ | 1 |
| | L26 a, b, c, or d | $CH_2CH_2C(=O)NH_2$ | H | $CH_3$ | 1 |
| | L27 a, b, c, or d | H | $CH_2C(=O)OH$ | $CH_3$ | 1 |
| | L28 a, b, c, or d | $CH_2C(=O)OH$ | $CH_2C(=O)OH$ | $CH_3$ | 1 |
| | L29 a, b, c, or d | $CH_2CH_2C(=O)OH$ | $CH_2C(=O)OH$ | $CH_3$ | 1 |
| | L30 a, b, c, or d | $CH_2C(=O)NH_2$ | $CH_2C(=O)OH$ | $CH_3$ | 1 |
| | L31 a, b, c, or d | $CH_2CH_2C(=O)NH_2$ | $CH_2C(=O)OH$ | $CH_3$ | 1 |
| | L32 a, b, c, or d | H | $CH_2C(=O)NH_2$ | $CH_3$ | 1 |
| | L33 a, b, c, or d | $CH_2C(=O)OH$ | $CH_2C(=O)NH_2$ | $CH_3$ | 1 |
| | L34 a, b, c, or d | $CH_2C(=O)OCH_3$ | $CH_2C(=O)NH_2$ | $CH_3$ | 1 |
| | L35 a, b, c, or d | $CH_2CH_2C(=O)OH$ | $CH_2C(=O)NH_2$ | $CH_3$ | 1 |
| | L36 a, b, c, or d | $CH_2CH_2C(=O)OCH_3$ | $CH_2C(=O)NH_2$ | $CH_3$ | 1 |
| | L37 a, b, c, or d | $CH_2C(=O)NH_2$ | $CH_2C(=O)NH_2$ | $CH_3$ | 1 |
| | L38 a, b, c, or d | $CH_2CH_2C(=O)NH_2$ | $CH_2C(=O)NH_2$ | $CH_3$ | 1 |
| | L39 a, b, c, or d | H | H | H | 2 |
| | L40 a, b, c, or d | $CH_2C(=O)OH$ | H | H | 2 |
| | L41 a, b, c, or d | $CH_2C(=O)OCH_3$ | H | H | 2 |
| | L42 a, b, c, or d | $CH_2CH_2C(=O)OH$ | H | H | 2 |
| | L43 a, b, c, or d | $CH_2CH_2C(=O)OCH_3$ | H | H | 2 |
| | L44 a, b, c, or d | $CH_2C(=O)NH_2$ | H | H | 2 |
| | L45 a, b, c, or d | $CH_2CH_2C(=O)NH_2$ | H | H | 2 |
| | L46 a, b, c, or d | H | $CH_2C(=O)OH$ | H | 2 |
| | L47 a, b, c, or d | $CH_2C(=O)OH$ | $CH_2C(=O)OH$ | H | 2 |
| | L48 a, b, c, or d | $CH_2C(=O)OH$ | $CH_2C(=O)OH$ | H | 2 |
| | L49 a, b, c, or d | $CH_2C(=O)NH_2$ | $CH_2C(=O)OH$ | H | 2 |
| | L50 a, b, c, or d | $CH_2CH_2C(=O)NH_2$ | $CH_2C(=O)OH$ | H | 2 |
| | L51 a, b, c, or d | H | $CH_2C(=O)NH_2$ | H | 2 |
| | L52 a, b, c, or d | $CH_2C(=O)OH$ | $CH_2C(=O)NH_2$ | H | 2 |
| | L53 a, b, c, or d | $CH_2C(=O)OCH_3$ | $CH_2C(=O)NH_2$ | H | 2 |

-continued

| Compound | $R^{4a}$ | $R^{3a}$ | $R^{8a}$ | y |
|---|---|---|---|---|
| L54 a, b, c, or d | $CH_2CH_2C(=O)OH$ | $CH_2C(=O)NH_2$ | H | 2 |
| L55 a, b, c, or d | $CH_2CH_2C(=O)OCH_3$ | $CH_2C(=O)NH_2$ | H | 2 |
| L56 a, b, c, or d | $CH_2C(=O)NH_2$ | $CH_2C(=O)NH_2$ | H | 2 |
| L57 a, b, c, or d | $CH_2CH_2C(=O)NH_2$ | $CH_2C(=O)NH_2$ | H | 2 |
| L58 a, b, c, or d | H | H | $CH_3$ | 2 |
| L59 a, b, c, or d | $CH_2C(=O)OH$ | H | $CH_3$ | 2 |
| L60 a, b, c, or d | $CH_2C(=O)OCH_3$ | H | $CH_3$ | 2 |
| L61 a, b, c, or d | $CH_2CH_2C(=O)OH$ | H | $CH_3$ | 2 |
| L62 a, b, c, or d | $CH_2CH_2C(=O)OCH_3$ | H | $CH_3$ | 2 |
| L63 a, b, c, or d | $CH_2C(=O)NH_2$ | H | $CH_3$ | 2 |
| L64 a, b, c, or d | $CH_2CH_2C(=O)NH_2$ | H | $CH_3$ | 2 |
| L65 a, b, c, or d | H | $CH_2C(=O)OH$ | $CH_3$ | 2 |
| L66 a, b, c, or d | $CH_2C(=O)OH$ | $CH_2C(=O)OH$ | $CH_3$ | 2 |
| L67 a, b, c, or d | $CH_2CH_2C(=O)OH$ | $CH_2C(=O)OH$ | $CH_3$ | 2 |
| L68 a, b, c, or d | $CH_2C(=O)NH_2$ | $CH_2C(=O)OH$ | $CH_3$ | 2 |
| L69 a, b, c, or d | $CH_2CH_2C(=O)NH_2$ | $CH_2C(=O)OH$ | $CH_3$ | 2 |
| L70 a, b, c, or d | H | $CH_2C(=O)NH_2$ | $CH_3$ | 2 |
| L71 a, b, c, or d | $CH_2C(=O)OH$ | $CH_2C(=O)NH_2$ | $CH_3$ | 2 |
| L72 a, b, c, or d | $CH_2C(=O)OCH_3$ | $CH_2C(=O)NH_2$ | $CH_3$ | 2 |
| L73 a, b, c, or d | $CH_2CH_2C(=O)OH$ | $CH_2C(=O)NH_2$ | $CH_3$ | 2 |
| L74 a, b, c, or d | $CH_2CH_2C(=O)OCH_3$ | $CH_2C(=O)NH_2$ | $CH_3$ | 2 |
| L75 a, b, c, or d | $CH_2C(=O)NH_2$ | $CH_2C(=O)NH_2$ | $CH_3$ | 2 |
| L76 a, b, c, or d | $CH_2CH_2C(=O)NH_2$ | $CH_2C(=O)NH_2$ | $CH_3$ | 2 |
| L77 a, b, c, or d | H | H | H | 3 |
| L78 a, b, c, or d | $CH_2C(=O)OH$ | H | H | 3 |
| L79 a, b, c, or d | $CH_2C(=O)OCH_3$ | H | H | 3 |
| L80 a, b, c, or d | $CH_2CH_2C(=O)OH$ | H | H | 3 |
| L81 a, b, c, or d | $CH_2CH_2C(=O)OCH_3$ | H | H | 3 |
| L82 a, b, c, or d | $CH_2C(=O)NH_2$ | H | H | 3 |
| L83 a, b, c, or d | $CH_2CH_2C(=O)NH_2$ | H | H | 3 |
| L84 a, b, c, or d | H | $CH_2C(=O)OH$ | H | 3 |
| L85 a, b, c, or d | $CH_2C(=O)OH$ | $CH_2C(=O)OH$ | H | 3 |
| L86 a, b, c, or d | $CH_2CH_2C(=O)OH$ | $CH_2C(=O)OH$ | H | 3 |
| L87 a, b, c, or d | $CH_2C(=O)NH_2$ | $CH_2C(=O)OH$ | H | 3 |
| L88 a, b, c, or d | $CH_2CH_2C(=O)NH_2$ | $CH_2C(=O)OH$ | H | 3 |
| L89 a, b, c, or d | H | $CH_2C(=O)NH_2$ | H | 3 |
| L90 a, b, c, or d | $CH_2C(=O)OH$ | $CH_2C(=O)NH_2$ | H | 3 |
| L91 a, b, c, or d | $CH_2C(=O)OCH_3$ | $CH_2C(=O)NH_2$ | H | 3 |
| L92 a, b, c, or d | $CH_2CH_2C(=O)OH$ | $CH_2C(=O)NH_2$ | H | 3 |
| L93 a, b, c, or d | $CH_2CH_2C(=O)OCH_3$ | $CH_2C(=O)NH_2$ | H | 3 |
| L94 a, b, c, or d | $CH_2C(=O)NH_2$ | $CH_2C(=O)NH_2$ | H | 3 |
| L95 a, b, c, or d | $CH_2CH_2C(=O)NH_2$ | $CH_2C(=O)NH_2$ | H | 3 |
| L96 a, b, c, or d | H | H | $CH_3$ | 3 |
| L97 a, b, c, or d | $CH_2C(=O)OH$ | H | $CH_3$ | 3 |
| L98 a, b, c, or d | $CH_2C(=O)OCH_3$ | H | $CH_3$ | 3 |
| L99 a, b, c, or d | $CH_2CH_2C(=O)OH$ | H | $CH_3$ | 3 |
| L100 a, b, c, or d | $CH_2CH_2C(=O)OCH_3$ | H | $CH_3$ | 3 |
| L101 a, b, c, or d | $CH_2C(=O)NH_2$ | H | $CH_3$ | 3 |
| L102 a, b, c, or d | $CH_2CH_2C(=O)NH_2$ | H | $CH_3$ | 3 |
| L103 a, b, c, or d | H | $CH_2C(=O)OH$ | $CH_3$ | 3 |
| L104 a, b, c, or d | $CH_2C(=O)OH$ | $CH_2C(=O)OH$ | $CH_3$ | 3 |
| L105 a, b, c, or d | $CH_2CH_2C(=O)OH$ | $CH_2C(=O)OH$ | $CH_3$ | 3 |
| L106 a, b, c, or d | $CH_2C(=O)NH_2$ | $CH_2C(=O)OH$ | $CH_3$ | 3 |
| L107 a, b, c, or d | $CH_2CH_2C(=O)NH_2$ | $CH_2C(=O)OH$ | $CH_3$ | 3 |
| L108 a, b, c, or d | H | $CH_2C(=O)NH_2$ | $CH_3$ | 3 |
| L109 a, b, c, or d | $CH_2C(=O)OH$ | $CH_2C(=O)NH_2$ | $CH_3$ | 3 |
| L110 a, b, c, or d | $CH_2C(=O)OCH_3$ | $CH_2C(=O)NH_2$ | $CH_3$ | 3 |
| L111 a, b, c, or d | $CH_2CH_2C(=O)OH$ | $CH_2C(=O)NH_2$ | $CH_3$ | 3 |
| L112 a, b, c, or d | $CH_2CH_2C(=O)OCH_3$ | $CH_2C(=O)NH_2$ | $CH_3$ | 3 |
| L113 a, b, c, or d | $CH_2C(=O)NH_2$ | $CH_2C(=O)NH_2$ | $CH_3$ | 3 |
| L114 a, b, c, or d | $CH_2CH_2C(=O)NH_2$ | $CH_2C(=O)NH_2$ | $CH_3$ | 3 |

TABLE 13

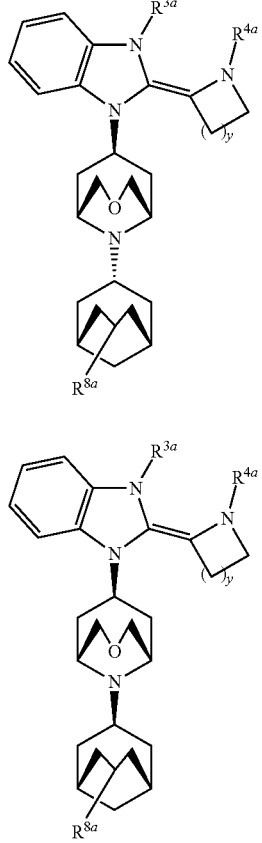

(a)

(b)

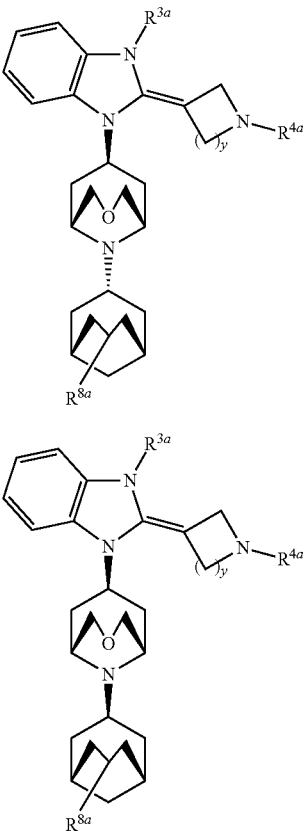

(c)

(d)

and pharmaceutically acceptable salts or solvates thereof, where:

| Compound | | $R^{4a}$ | $R^{3a}$ | $R^{8a}$ | y |
|---|---|---|---|---|---|
| M | M1 a, b, c, or d | H | H | H | 1 |
| | M2 a, b, c, or d | $CH_2C(=O)OH$ | H | H | 1 |
| | M3 a, b, c, or d | $CH_2C(=O)OCH_3$ | H | H | 1 |
| | M4 a, b, c, or d | $CH_2CH_2C(=O)OH$ | H | H | 1 |
| | M5 a, b, c, or d | $CH_2CH_2C(=O)OCH_3$ | H | H | 1 |
| | M6 a, b, c, or d | $CH_2C(=O)NH_2$ | H | H | 1 |
| | M7 a, b, c, or d | $CH_2CH_2C(=O)NH_2$ | H | H | 1 |
| | M8 a, b, c, or d | H | $CH_2C(=O)OH$ | H | 1 |
| | M9 a, b, c, or d | $CH_2C(=O)OH$ | $CH_2C(=O)OH$ | H | 1 |
| | M10 a, b, c, or d | $CH_2CH_2C(=O)OH$ | $CH_2C(=O)OH$ | H | 1 |
| | M11 a, b, c, or d | $CH_2C(=O)NH_2$ | $CH_2C(=O)OH$ | H | 1 |
| | M12 a, b, c, or d | $CH_2CH_2C(=O)NH_2$ | $CH_2C(=O)OH$ | H | 1 |
| | M13 a, b, c, or d | H | $CH_2C(=O)NH_2$ | H | 1 |
| | M14 a, b, c, or d | $CH_2C(=O)OH$ | $CH_2C(=O)NH_2$ | H | 1 |
| | M15 a, b, c, or d | $CH_2C(=O)OCH_3$ | $CH_2C(=O)NH_2$ | H | 1 |
| | M16 a, b, c, or d | $CH_2CH_2C(=O)OH$ | $CH_2C(=O)NH_2$ | H | 1 |
| | M17 a, b, c, or d | $CH_2CH_2C(=O)OCH_3$ | $CH_2C(=O)NH_2$ | H | 1 |
| | M18 a, b, c, or d | $CH_2C(=O)NH_2$ | $CH_2C(=O)NH_2$ | H | 1 |
| | M19 a, b, c, or d | $CH_2CH_2C(=O)NH_2$ | $CH_2C(=O)NH_2$ | H | 1 |
| | M20 a, b, c, or d | H | H | $CH_3$ | 1 |
| | M21 a, b, c, or d | $CH_2C(=O)OH$ | H | $CH_3$ | 1 |
| | M22 a, b, c, or d | $CH_2C(=O)OCH_3$ | H | $CH_3$ | 1 |
| | M23 a, b, c, or d | $CH_2CH_2C(=O)OH$ | H | $CH_3$ | 1 |
| | M24 a, b, c, or d | $CH_2CH_2C(=O)OCH_3$ | H | $CH_3$ | 1 |
| | M25 a, b, c, or d | $CH_2C(=O)NH_2$ | H | $CH_3$ | 1 |
| | M26 a, b, c, or d | $CH_2CH_2C(=O)NH_2$ | H | $CH_3$ | 1 |
| | M27 a, b, c, or d | H | $CH_2C(=O)OH$ | $CH_3$ | 1 |
| | M28 a, b, c, or d | $CH_2C(=O)OH$ | $CH_2C(=O)OH$ | $CH_3$ | 1 |
| | M29 a, b, c, or d | $CH_2CH_2C(=O)OH$ | $CH_2C(=O)OH$ | $CH_3$ | 1 |
| | M30 a, b, c, or d | $CH_2C(=O)NH_2$ | $CH_2C(=O)OH$ | $CH_3$ | 1 |
| | M31 a, b, c, or d | $CH_2CH_2C(=O)NH_2$ | $CH_2C(=O)OH$ | $CH_3$ | 1 |
| | M32 a, b, c, or d | H | $CH_2C(=O)NH_2$ | $CH_3$ | 1 |
| | M33 a, b, c, or d | $CH_2C(=O)OH$ | $CH_2C(=O)NH_2$ | $CH_3$ | 1 |

-continued

| Compound | $R^{4a}$ | $R^{3a}$ | $R^{8a}$ | y |
|---|---|---|---|---|
| M34 a, b, c, or d | CH$_2$C(=O)OCH$_3$ | CH$_2$C(=O)NH$_2$ | CH$_3$ | 1 |
| M35 a, b, c, or d | CH$_2$CH$_2$C(=O)OH | CH$_2$C(=O)NH$_2$ | CH$_3$ | 1 |
| M36 a, b, c, or d | CH$_2$CH$_2$C(=O)OCH$_3$ | CH$_2$C(=O)NH$_2$ | CH$_3$ | 1 |
| M37 a, b, c, or d | CH$_2$C(=O)NH$_2$ | CH$_2$C(=O)NH$_2$ | CH$_3$ | 1 |
| M38 a, b, c, or d | CH$_2$CH$_2$C(=O)NH$_2$ | CH$_2$C(=O)NH$_2$ | CH$_3$ | 1 |
| M39 a, b, c, or d | H | H | H | 2 |
| M40 a, b, c, or d | CH$_2$C(=O)OH | H | H | 2 |
| M41 a, b, c, or d | CH$_2$C(=O)OCH$_3$ | H | H | 2 |
| M42 a, b, c, or d | CH$_2$CH$_2$C(=O)OH | H | H | 2 |
| M43 a, b, c, or d | CH$_2$CH$_2$C(=O)OCH$_3$ | H | H | 2 |
| M44 a, b, c, or d | CH$_2$C(=O)NH$_2$ | H | H | 2 |
| M45 a, b, c, or d | CH$_2$CH$_2$C(=O)NH$_2$ | H | H | 2 |
| M46 a, b, c, or d | H | CH$_2$C(=O)OH | H | 2 |
| M47 a, b, c, or d | CH$_2$C(=O)OH | CH$_2$C(=O)OH | H | 2 |
| M48 a, b, c, or d | CH$_2$CH$_2$C(=O)OH | CH$_2$C(=O)OH | H | 2 |
| M49 a, b, c, or d | CH$_2$C(=O)NH$_2$ | CH$_2$C(=O)OH | H | 2 |
| M50 a, b, c, or d | CH$_2$CH$_2$C(=O)NH$_2$ | CH$_2$C(=O)OH | H | 2 |
| M51 a, b, c, or d | H | CH$_2$C(=O)NH$_2$ | H | 2 |
| M52 a, b, c, or d | CH$_2$C(=O)OH | CH$_2$C(=O)NH$_2$ | H | 2 |
| M53 a, b, c, or d | CH$_2$C(=O)OCH$_3$ | CH$_2$C(=O)NH$_2$ | H | 2 |
| M54 a, b, c, or d | CH$_2$CH$_2$C(=O)OH | CH$_2$C(=O)NH$_2$ | H | 2 |
| M55 a, b, c, or d | CH$_2$CH$_2$C(=O)OCH$_3$ | CH$_2$C(=O)NH$_2$ | H | 2 |
| M56 a, b, c, or d | CH$_2$C(=O)NH$_2$ | CH$_2$C(=O)NH$_2$ | H | 2 |
| M57 a, b, c, or d | CH$_2$CH$_2$C(=O)NH$_2$ | CH$_2$C(=O)NH$_2$ | H | 2 |
| M58 a, b, c, or d | H | H | CH$_3$ | 2 |
| M59 a, b, c, or d | CH$_2$C(=O)OH | H | CH$_3$ | 2 |
| M60 a, b, c, or d | CH$_2$C(=O)OCH$_3$ | H | CH$_3$ | 2 |
| M61 a, b, c, or d | CH$_2$CH$_2$C(=O)OH | H | CH$_3$ | 2 |
| M62 a, b, c, or d | CH$_2$CH$_2$C(=O)OCH$_3$ | H | CH$_3$ | 2 |
| M63 a, b, c, or d | CH$_2$C(=O)NH$_2$ | H | CH$_3$ | 2 |
| M64 a, b, c, or d | CH$_2$CH$_2$C(=O)NH$_2$ | H | CH$_3$ | 2 |
| M65 a, b, c, or d | H | CH$_2$C(=O)OH | CH$_3$ | 2 |
| M66 a, b, c, or d | CH$_2$C(=O)OH | CH$_2$C(=O)OH | CH$_3$ | 2 |
| M67 a, b, c, or d | CH$_2$CH$_2$C(=O)OH | CH$_2$C(=O)OH | CH$_3$ | 2 |
| M68 a, b, c, or d | CH$_2$C(=O)NH$_2$ | CH$_2$C(=O)OH | CH$_3$ | 2 |
| M69 a, b, c, or d | CH$_2$CH$_2$C(=O)NH$_2$ | CH$_2$C(=O)OH | CH$_3$ | 2 |
| M70 a, b, c, or d | H | CH$_2$C(=O)NH$_2$ | CH$_3$ | 2 |
| M71 a, b, c, or d | CH$_2$C(=O)OH | CH$_2$C(=O)NH$_2$ | CH$_3$ | 2 |
| M72 a, b, c, or d | CH$_2$C(=O)OCH$_3$ | CH$_2$C(=O)NH$_2$ | CH$_3$ | 2 |
| M73 a, b, c, or d | CH$_2$CH$_2$C(=O)OH | CH$_2$C(=O)NH$_2$ | CH$_3$ | 2 |
| M74 a, b, c, or d | CH$_2$CH$_2$C(=O)OCH$_3$ | CH$_2$C(=O)NH$_2$ | CH$_3$ | 2 |
| M75 a, b, c, or d | CH$_2$C(=O)NH$_2$ | CH$_2$C(=O)NH$_2$ | CH$_3$ | 2 |
| M76 a, b, c, or d | CH$_2$CH$_2$C(=O)NH$_2$ | CH$_2$C(=O)NH$_2$ | CH$_3$ | 2 |
| M77 a, b, c, or d | H | H | H | 3 |
| M78 a, b, c, or d | CH$_2$C(=O)OH | H | H | 3 |
| M79 a, b, c, or d | CH$_2$C(=O)OCH$_3$ | H | H | 3 |
| M80 a, b, c, or d | CH$_2$CH$_2$C(=O)OH | H | H | 3 |
| M81 a, b, c, or d | CH$_2$CH$_2$C(=O)OCH$_3$ | H | H | 3 |
| M82 a, b, c, or d | CH$_2$C(=O)NH$_2$ | H | H | 3 |
| M83 a, b, c, or d | CH$_2$CH$_2$C(=O)NH$_2$ | H | H | 3 |
| M84 a, b, c, or d | H | CH$_2$C(=O)OH | H | 3 |
| M85 a, b, c, or d | CH$_2$C(=O)OH | CH$_2$C(=O)OH | H | 3 |
| M86 a, b, c, or d | CH$_2$CH$_2$C(=O)OH | CH$_2$C(=O)OH | H | 3 |
| M87 a, b, c, or d | CH$_2$C(=O)NH$_2$ | CH$_2$C(=O)OH | H | 3 |
| M88 a, b, c, or d | CH$_2$CH$_2$C(=O)NH$_2$ | CH$_2$C(=O)OH | H | 3 |
| M89 a, b, c, or d | H | CH$_2$C(=O)NH$_2$ | H | 3 |
| M90 a, b, c, or d | CH$_2$C(=O)OH | CH$_2$C(=O)NH$_2$ | H | 3 |
| M91 a, b, c, or d | CH$_2$C(=O)OCH$_3$ | CH$_2$C(=O)NH$_2$ | H | 3 |
| M92 a, b, c, or d | CH$_2$CH$_2$C(=O)OH | CH$_2$C(=O)NH$_2$ | H | 3 |
| M93 a, b, c, or d | CH$_2$CH$_2$C(=O)OCH$_3$ | CH$_2$C(=O)NH$_2$ | H | 3 |
| M94 a, b, c, or d | CH$_2$C(=O)NH$_2$ | CH$_2$C(=O)NH$_2$ | H | 3 |
| M95 a, b, c, or d | CH$_2$CH$_2$C(=O)NH$_2$ | CH$_2$C(=O)NH$_2$ | H | 3 |
| M96 a, b, c, or d | H | H | CH$_3$ | 3 |
| M97 a, b, c, or d | CH$_2$C(=O)OH | H | CH$_3$ | 3 |
| M98 a, b, c, or d | CH$_2$C(=O)OCH$_3$ | H | CH$_3$ | 3 |
| M99 a, b, c, or d | CH$_2$CH$_2$C(=O)OH | H | CH$_3$ | 3 |
| M100 a, b, c, or d | CH$_2$CH$_2$C(=O)OCH$_3$ | H | CH$_3$ | 3 |
| M101 a, b, c, or d | CH$_2$C(=O)NH$_2$ | H | CH$_3$ | 3 |
| M102 a, b, c, or d | CH$_2$CH$_2$C(=O)NH$_2$ | H | CH$_3$ | 3 |
| M103 a, b, c, or d | H | CH$_2$C(=O)OH | CH$_3$ | 3 |
| M104 a, b, c, or d | CH$_2$C(=O)OH | CH$_2$C(=O)OH | CH$_3$ | 3 |
| M105 a, b, c, or d | CH$_2$CH$_2$C(=O)OH | CH$_2$C(=O)OH | CH$_3$ | 3 |
| M106 a, b, c, or d | CH$_2$C(=O)NH$_2$ | CH$_2$C(=O)OH | CH$_3$ | 3 |
| M107 a, b, c, or d | CH$_2$CH$_2$C(=O)NH$_2$ | CH$_2$C(=O)OH | CH$_3$ | 3 |
| M108 a, b, c, or d | H | CH$_2$C(=O)NH$_2$ | CH$_3$ | 3 |
| M109 a, b, c, or d | CH$_2$C(=O)OH | CH$_2$C(=O)NH$_2$ | CH$_3$ | 3 |
| M110 a, b, c, or d | CH$_2$C(=O)OCH$_3$ | CH$_2$C(=O)NH$_2$ | CH$_3$ | 3 |

-continued

| Compound | $R^{4a}$ | $R^{3a}$ | $R^{8a}$ | y |
|---|---|---|---|---|
| M111 a, b, c, or d | $CH_2CH_2C(=O)OH$ | $CH_2C(=O)NH_2$ | $CH_3$ | 3 |
| M112 a, b, c, or d | $CH_2CH_2C(=O)OCH_3$ | $CH_2C(=O)NH_2$ | $CH_3$ | 3 |
| M113 a, b, c, or d | $CH_2C(=O)NH_2$ | $CH_2C(=O)NH_2$ | $CH_3$ | 3 |
| M114 a, b, c, or d | $CH_2CH_2C(=O)NH_2$ | $CH_2C(=O)NH_2$ | $CH_3$ | 3 |

TABLE 14

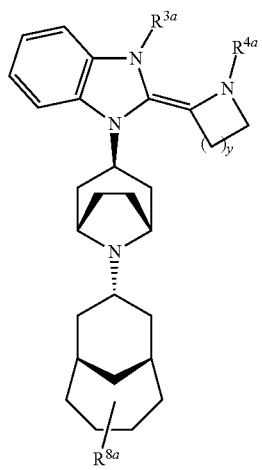
(a)

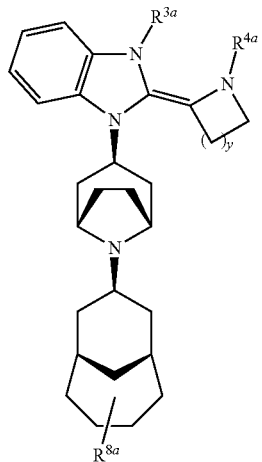
(b)

TABLE 14-continued

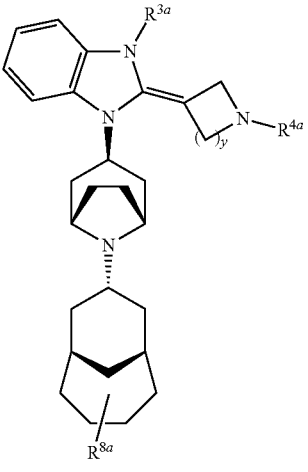
(c)

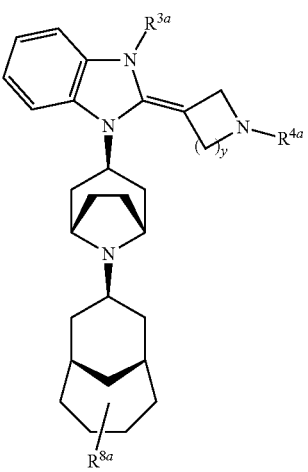
(d)

and pharmaceutically acceptable salts or solvates thereof, where:

| | Compound | $R^{4a}$ | $R^{3a}$ | $R^{8a}$ | y |
|---|---|---|---|---|---|
| N | N1 a, b, c, or d | H | H | H | 1 |
| | N2 a, b, c, or d | $CH_2C(=O)OH$ | H | H | 1 |
| | N3 a, b, c, or d | $CH_2C(=O)OCH_3$ | H | H | 1 |
| | N4 a, b, c, or d | $CH_2CH_2C(=O)OH$ | H | H | 1 |
| | N5 a, b, c, or d | $CH_2CH_2C(=O)OCH_3$ | H | H | 1 |
| | N6 a, b, c, or d | $CH_2C(=O)NH_2$ | H | H | 1 |
| | N7 a, b, c, or d | $CH_2CH_2C(=O)NH_2$ | H | H | 1 |
| | N8 a, b, c, or d | H | $CH_2C(=O)OH$ | H | 1 |
| | N9 a, b, c, or d | $CH_2C(=O)OH$ | $CH_2C(=O)OH$ | H | 1 |
| | N10 a, b, c, or d | $CH_2CH_2C(=O)OH$ | $CH_2C(=O)OH$ | H | 1 |
| | N11 a, b, c, or d | $CH_2C(=O)NH_2$ | $CH_2C(=O)OH$ | H | 1 |
| | N12 a, b, c, or d | $CH_2CH_2C(=O)NH_2$ | $CH_2C(=O)OH$ | H | 1 |
| | N13 a, b, c, or d | H | $CH_2C(=O)NH_2$ | H | 1 |
| | N14 a, b, c, or d | $CH_2C(=O)OH$ | $CH_2C(=O)NH_2$ | H | 1 |
| | N15 a, b, c, or d | $CH_2C(=O)OCH_3$ | $CH_2C(=O)NH_2$ | H | 1 |
| | N16 a, b, c, or d | $CH_2CH_2C(=O)OH$ | $CH_2C(=O)NH_2$ | H | 1 |

-continued

| Compound | $R^{4a}$ | $R^{3a}$ | $R^{8a}$ | y |
|---|---|---|---|---|
| N17 a, b, c, or d | $CH_2CH_2C(=O)OCH_3$ | $CH_2C(=O)NH_2$ | H | 1 |
| N18 a, b, c, or d | $CH_2C(=O)NH_2$ | $CH_2C(=O)NH_2$ | H | 1 |
| N19 a, b, c, or d | $CH_2CH_2C(=O)NH_2$ | $CH_2C(=O)NH_2$ | H | 1 |
| N20 a, b, c, or d | H | H | $CH_3$ | 1 |
| N21 a, b, c, or d | $CH_2C(=O)OH$ | H | $CH_3$ | 1 |
| N22 a, b, c, or d | $CH_2C(=O)OCH_3$ | H | $CH_3$ | 1 |
| N23 a, b, c, or d | $CH_2CH_2C(=O)OH$ | H | $CH_3$ | 1 |
| N24 a, b, c, or d | $CH_2CH_2C(=O)OCH_3$ | H | $CH_3$ | 1 |
| N25 a, b, c, or d | $CH_2C(=O)NH_2$ | H | $CH_3$ | 1 |
| N26 a, b, c, or d | $CH_2CH_2C(=O)NH_2$ | H | $CH_3$ | 1 |
| N27 a, b, c, or d | H | $CH_2C(=O)OH$ | $CH_3$ | 1 |
| N28 a, b, c, or d | $CH_2C(=O)OH$ | $CH_2C(=O)OH$ | $CH_3$ | 1 |
| N29 a, b, c, or d | $CH_2CH_2C(=O)OH$ | $CH_2C(=O)OH$ | $CH_3$ | 1 |
| N30 a, b, c, or d | $CH_2C(=O)NH_2$ | $CH_2C(=O)OH$ | $CH_3$ | 1 |
| N31 a, b, c, or d | $CH_2CH_2C(=O)NH_2$ | $CH_2C(=O)OH$ | $CH_3$ | 1 |
| N32 a, b, c, or d | H | $CH_2C(=O)NH_2$ | $CH_3$ | 1 |
| N33 a, b, c, or d | $CH_2C(=O)OH$ | $CH_2C(=O)NH_2$ | $CH_3$ | 1 |
| N34 a, b, c, or d | $CH_2C(=O)OCH_3$ | $CH_2C(=O)NH_2$ | $CH_3$ | 1 |
| N35 a, b, c, or d | $CH_2CH_2C(=O)OH$ | $CH_2C(=O)NH_2$ | $CH_3$ | 1 |
| N36 a, b, c, or d | $CH_2CH_2C(=O)OCH_3$ | $CH_2C(=O)NH_2$ | $CH_3$ | 1 |
| N37 a, b, c, or d | $CH_2C(=O)NH_2$ | $CH_2C(=O)NH_2$ | $CH_3$ | 1 |
| N38 a, b, c, or d | $CH_2CH_2C(=O)NH_2$ | $CH_2C(=O)NH_2$ | $CH_3$ | 1 |
| N39 a, b, c, or d | H | H | H | 2 |
| N40 a, b, c, or d | $CH_2C(=O)OH$ | H | H | 2 |
| N41 a, b, c, or d | $CH_2C(=O)OCH_3$ | H | H | 2 |
| N42 a, b, c, or d | $CH_2CH_2C(=O)OH$ | H | H | 2 |
| N43 a, b, c, or d | $CH_2CH_2C(=O)OCH_3$ | H | H | 2 |
| N44 a, b, c, or d | $CH_2C(=O)NH_2$ | H | H | 2 |
| N45 a, b, c, or d | $CH_2CH_2C(=O)NH_2$ | H | H | 2 |
| N46 a, b, c, or d | H | $CH_2C(=O)OH$ | H | 2 |
| N47 a, b, c, or d | $CH_2C(=O)OH$ | $CH_2C(=O)OH$ | H | 2 |
| N48 a, b, c, or d | $CH_2C(=O)OH$ | $CH_2C(=O)OH$ | H | 2 |
| N49 a, b, c, or d | $CH_2C(=O)NH_2$ | $CH_2C(=O)OH$ | H | 2 |
| N50 a, b, c, or d | $CH_2CH_2C(=O)NH_2$ | $CH_2C(=O)OH$ | H | 2 |
| N51 a, b, c, or d | H | $CH_2C(=O)NH_2$ | H | 2 |
| N52 a, b, c, or d | $CH_2C(=O)OH$ | $CH_2C(=O)NH_2$ | H | 2 |
| N53 a, b, c, or d | $CH_2C(=O)OCH_3$ | $CH_2C(=O)NH_2$ | H | 2 |
| N54 a, b, c, or d | $CH_2CH_2C(=O)OH$ | $CH_2C(=O)NH_2$ | H | 2 |
| N55 a, b, c, or d | $CH_2CH_2C(=O)OCH_3$ | $CH_2C(=O)NH_2$ | H | 2 |
| N56 a, b, c, or d | $CH_2C(=O)NH_2$ | $CH_2C(=O)NH_2$ | H | 2 |
| N57 a, b, c, or d | $CH_2CH_2C(=O)NH_2$ | $CH_2C(=O)NH_2$ | H | 2 |
| N58 a, b, c, or d | H | H | $CH_3$ | 2 |
| N59 a, b, c, or d | $CH_2C(=O)OH$ | H | $CH_3$ | 2 |
| N60 a, b, c, or d | $CH_2C(=O)OCH_3$ | H | $CH_3$ | 2 |
| N61 a, b, c, or d | $CH_2CH_2C(=O)OH$ | H | $CH_3$ | 2 |
| N62 a, b, c, or d | $CH_2CH_2C(=O)OCH_3$ | H | $CH_3$ | 2 |
| N63 a, b, c, or d | $CH_2C(=O)NH_2$ | H | $CH_3$ | 2 |
| N64 a, b, c, or d | $CH_2CH_2C(=O)NH_2$ | H | $CH_3$ | 2 |
| N65 a, b, c, or d | H | $CH_2C(=O)OH$ | $CH_3$ | 2 |
| N66 a, b, c, or d | $CH_2C(=O)OH$ | $CH_2C(=O)OH$ | $CH_3$ | 2 |
| N67 a, b, c, or d | $CH_2CH_2C(=O)OH$ | $CH_2C(=O)OH$ | $CH_3$ | 2 |
| N68 a, b, c, or d | $CH_2C(=O)NH_2$ | $CH_2C(=O)OH$ | $CH_3$ | 2 |
| N69 a, b, c, or d | $CH_2CH_2C(=O)NH_2$ | $CH_2C(=O)OH$ | $CH_3$ | 2 |
| N70 a, b, c, or d | H | $CH_2C(=O)NH_2$ | $CH_3$ | 2 |
| N71 a, b, c, or d | $CH_2C(=O)OH$ | $CH_2C(=O)NH_2$ | $CH_3$ | 2 |
| N72 a, b, c, or d | $CH_2C(=O)OCH_3$ | $CH_2C(=O)NH_2$ | $CH_3$ | 2 |
| N73 a, b, c, or d | $CH_2CH_2C(=O)OH$ | $CH_2C(=O)NH_2$ | $CH_3$ | 2 |
| N74 a, b, c, or d | $CH_2CH_2C(=O)OCH_3$ | $CH_2C(=O)NH_2$ | $CH_3$ | 2 |
| N75 a, b, c, or d | $CH_2C(=O)NH_2$ | $CH_2C(=O)NH_2$ | $CH_3$ | 2 |
| N76 a, b, c, or d | $CH_2CH_2C(=O)NH_2$ | $CH_2C(=O)NH_2$ | $CH_3$ | 2 |
| N77 a, b, c, or d | H | H | H | 3 |
| N78 a, b, c, or d | $CH_2C(=O)OH$ | H | H | 3 |
| N79 a, b, c, or d | $CH_2C(=O)OCH_3$ | H | H | 3 |
| N80 a, b, c, or d | $CH_2CH_2C(=O)OH$ | H | H | 3 |
| N81 a, b, c, or d | $CH_2CH_2C(=O)OCH_3$ | H | H | 3 |
| N82 a, b, c, or d | $CH_2C(=O)NH_2$ | H | H | 3 |
| N83 a, b, c, or d | $CH_2CH_2C(=O)NH_2$ | H | H | 3 |
| N84 a, b, c, or d | H | $CH_2C(=O)OH$ | H | 3 |
| N85 a, b, c, or d | $CH_2C(=O)OH$ | $CH_2C(=O)OH$ | H | 3 |
| N86 a, b, c, or d | $CH_2CH_2C(=O)OH$ | $CH_2C(=O)OH$ | H | 3 |
| N87 a, b, c, or d | $CH_2C(=O)NH_2$ | $CH_2C(=O)OH$ | H | 3 |
| N88 a, b, c, or d | $CH_2CH_2C(=O)NH_2$ | $CH_2C(=O)OH$ | H | 3 |
| N89 a, b, c, or d | H | $CH_2C(=O)NH_2$ | H | 3 |
| N90 a, b, c, or d | $CH_2C(=O)OH$ | $CH_2C(=O)NH_2$ | H | 3 |
| N91 a, b, c, or d | $CH_2C(=O)OCH_3$ | $CH_2C(=O)NH_2$ | H | 3 |
| N92 a, b, c, or d | $CH_2CH_2C(=O)OH$ | $CH_2C(=O)NH_2$ | H | 3 |
| N93 a, b, c, or d | $CH_2CH_2C(=O)OCH_3$ | $CH_2C(=O)NH_2$ | H | 3 |

-continued

| Compound | $R^{4a}$ | $R^{3a}$ | $R^{8a}$ | y |
|---|---|---|---|---|
| N94 a, b, c, or d | $CH_2C(=O)NH_2$ | $CH_2C(=O)NH_2$ | H | 3 |
| N95 a, b, c, or d | $CH_2CH_2C(=O)NH_2$ | $CH_2CH_2C(=O)NH_2$ | H | 3 |
| N96 a, b, c, or d | H | H | $CH_3$ | 3 |
| N97 a, b, c, or d | $CH_2C(=O)OH$ | H | $CH_3$ | 3 |
| N98 a, b, c, or d | $CH_2C(=O)OCH_3$ | H | $CH_3$ | 3 |
| N99 a, b, c, or d | $CH_2CH_2C(=O)OH$ | H | $CH_3$ | 3 |
| N100 a, b, c, or d | $CH_2CH_2C(=O)OCH_3$ | H | $CH_3$ | 3 |
| N101 a, b, c, or d | $CH_2C(=O)NH_2$ | H | $CH_3$ | 3 |
| N102 a, b, c, or d | $CH_2CH_2C(=O)NH_2$ | H | $CH_3$ | 3 |
| N103 a, b, c, or d | H | $CH_2C(=O)OH$ | $CH_3$ | 3 |
| N104 a, b, c, or d | $CH_2C(=O)OH$ | $CH_2C(=O)OH$ | $CH_3$ | 3 |
| N105 a, b, c, or d | $CH_2CH_2C(=O)OH$ | $CH_2C(=O)OH$ | $CH_3$ | 3 |
| N106 a, b, c, or d | $CH_2C(=O)NH_2$ | $CH_2C(=O)OH$ | $CH_3$ | 3 |
| N107 a, b, c, or d | $CH_2CH_2C(=O)NH_2$ | $CH_2C(=O)OH$ | $CH_3$ | 3 |
| N108 a, b, c, or d | H | $CH_2C(=O)NH_2$ | $CH_3$ | 3 |
| N109 a, b, c, or d | $CH_2C(=O)OH$ | $CH_2C(=O)NH_2$ | $CH_3$ | 3 |
| N110 a, b, c, or d | $CH_2C(=O)OCH_3$ | $CH_2C(=O)NH_2$ | $CH_3$ | 3 |
| N111 a, b, c, or d | $CH_2CH_2C(=O)OH$ | $CH_2C(=O)NH_2$ | $CH_3$ | 3 |
| N112 a, b, c, or d | $CH_2CH_2C(=O)OCH_3$ | $CH_2C(=O)NH_2$ | $CH_3$ | 3 |
| N113 a, b, c, or d | $CH_2C(=O)NH_2$ | $CH_2C(=O)NH_2$ | $CH_3$ | 3 |
| N114 a, b, c, or d | $CH_2CH_2C(=O)NH_2$ | $CH_2C(=O)NH_2$ | $CH_3$ | 3 |

TABLE 15

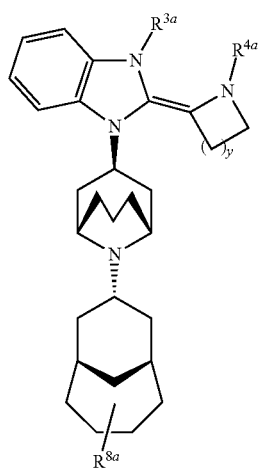

(a)

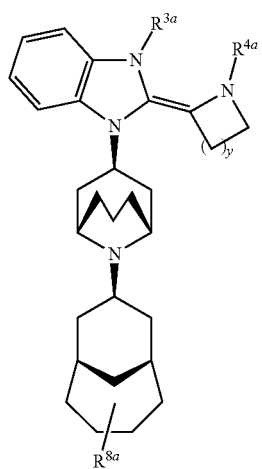

(b)

TABLE 15-continued

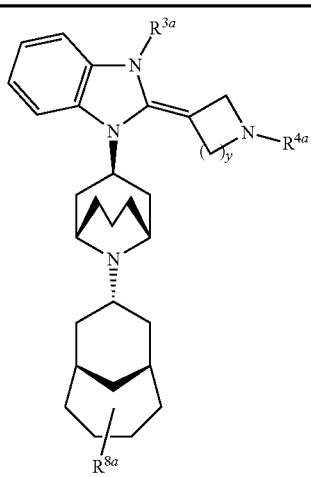

(c)

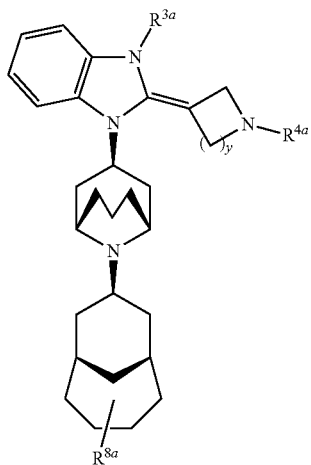

(d)

and pharmaceutically acceptable salts or solvates thereof, where:

| | Compound | R$^{4a}$ | R$^{3a}$ | R$^{8a}$ | y |
|---|---|---|---|---|---|
| O | O1 a, b, c, or d | H | H | H | 1 |
| | O2 a, b, c, or d | CH$_2$C(=O)OH | H | H | 1 |
| | O3 a, b, c, or d | CH$_2$C(=O)OCH$_3$ | H | H | 1 |
| | O4 a, b, c, or d | CH$_2$CH$_2$C(=O)OH | H | H | 1 |
| | O5 a, b, c, or d | CH$_2$CH$_2$C(=O)OCH$_3$ | H | H | 1 |
| | O6 a, b, c, or d | CH$_2$C(=O)NH$_2$ | H | H | 1 |
| | O7 a, b, c, or d | CH$_2$CH$_2$C(=O)NH$_2$ | H | H | 1 |
| | O8 a, b, c, or d | H | CH$_2$C(=O)OH | H | 1 |
| | O9 a, b, c, or d | CH$_2$C(=O)OH | CH$_2$C(=O)OH | H | 1 |
| | O10 a, b, c, or d | CH$_2$CH$_2$C(=O)OH | CH$_2$C(=O)OH | H | 1 |
| | O11 a, b, c, or d | CH$_2$C(=O)NH$_2$ | CH$_2$C(=O)OH | H | 1 |
| | O12 a, b, c, or d | CH$_2$CH$_2$C(=O)NH$_2$ | CH$_2$C(=O)OH | H | 1 |
| | O13 a, b, c, or d | H | CH$_2$C(=O)NH$_2$ | H | 1 |
| | O14 a, b, c, or d | CH$_2$C(=O)OH | CH$_2$C(=O)NH$_2$ | H | 1 |
| | O15 a, b, c, or d | CH$_2$C(=O)OCH$_3$ | CH$_2$C(=O)NH$_2$ | H | 1 |
| | O16 a, b, c, or d | CH$_2$CH$_2$C(=O)OH | CH$_2$C(=O)NH$_2$ | H | 1 |
| | O17 a, b, c, or d | CH$_2$CH$_2$C(=O)OCH$_3$ | CH$_2$C(=O)NH$_2$ | H | 1 |
| | O18 a, b, c, or d | CH$_2$C(=O)NH$_2$ | CH$_2$C(=O)NH$_2$ | H | 1 |
| | O19 a, b, c, or d | CH$_2$CH$_2$C(=O)NH$_2$ | CH$_2$C(=O)NH$_2$ | H | 1 |
| | O20 a, b, c, or d | H | H | CH$_3$ | 1 |
| | O21 a, b, c, or d | CH$_2$C(=O)OH | H | CH$_3$ | 1 |
| | O22 a, b, c, or d | CH$_2$C(=O)OCH$_3$ | H | CH$_3$ | 1 |
| | O23 a, b, c, or d | CH$_2$CH$_2$C(=O)OH | H | CH$_3$ | 1 |
| | O24 a, b, c, or d | CH$_2$CH$_2$C(=O)OCH$_3$ | H | CH$_3$ | 1 |
| | O25 a, b, c, or d | CH$_2$C(=O)NH$_2$ | H | CH$_3$ | 1 |
| | O26 a, b, c, or d | CH$_2$CH$_2$C(=O)NH$_2$ | H | CH$_3$ | 1 |
| | O27 a, b, c, or d | H | CH$_2$C(=O)OH | CH$_3$ | 1 |
| | O28 a, b, c, or d | CH$_2$C(=O)OH | CH$_2$C(=O)OH | CH$_3$ | 1 |
| | O29 a, b, c, or d | CH$_2$CH$_2$C(=O)OH | CH$_2$C(=O)OH | CH$_3$ | 1 |
| | O30 a, b, c, or d | CH$_2$C(=O)NH$_2$ | CH$_2$C(=O)OH | CH$_3$ | 1 |
| | O31 a, b, c, or d | CH$_2$CH$_2$C(=O)NH$_2$ | CH$_2$C(=O)OH | CH$_3$ | 1 |
| | O32 a, b, c, or d | H | CH$_2$C(=O)NH$_2$ | CH$_3$ | 1 |
| | O33 a, b, c, or d | CH$_2$C(=O)OH | CH$_2$C(=O)NH$_2$ | CH$_3$ | 1 |
| | O34 a, b, c, or d | CH$_2$C(=O)OCH$_3$ | CH$_2$C(=O)NH$_2$ | CH$_3$ | 1 |
| | O35 a, b, c, or d | CH$_2$CH$_2$C(=O)OH | CH$_2$C(=O)NH$_2$ | CH$_3$ | 1 |
| | O36 a, b, c, or d | CH$_2$CH$_2$C(=O)OCH$_3$ | CH$_2$C(=O)NH$_2$ | CH$_3$ | 1 |
| | O37 a, b, c, or d | CH$_2$C(=O)NH$_2$ | CH$_2$C(=O)NH$_2$ | CH$_3$ | 1 |
| | O38 a, b, c, or d | CH$_2$CH$_2$C(=O)NH$_2$ | CH$_2$C(=O)NH$_2$ | CH$_3$ | 1 |
| | O39 a, b, c, or d | H | H | H | 2 |
| | O40 a, b, c, or d | CH$_2$C(=O)OH | H | H | 2 |
| | O41 a, b, c, or d | CH$_2$C(=O)OCH$_3$ | H | H | 2 |
| | O42 a, b, c, or d | CH$_2$CH$_2$C(=O)OH | H | H | 2 |
| | O43 a, b, c, or d | CH$_2$CH$_2$C(=O)OCH$_3$ | H | H | 2 |
| | O44 a, b, c, or d | CH$_2$C(=O)NH$_2$ | H | H | 2 |
| | O45 a, b, c, or d | CH$_2$CH$_2$C(=O)NH$_2$ | H | H | 2 |
| | O46 a, b, c, or d | H | CH$_2$C(=O)OH | H | 2 |
| | O47 a, b, c, or d | CH$_2$C(=O)OH | CH$_2$C(=O)OH | H | 2 |
| | O48 a, b, c, or d | CH$_2$CH$_2$C(=O)OH | CH$_2$C(=O)OH | H | 2 |
| | O49 a, b, c, or d | CH$_2$C(=O)NH$_2$ | CH$_2$C(=O)OH | H | 2 |
| | O50 a, b, c, or d | CH$_2$CH$_2$C(=O)NH$_2$ | CH$_2$C(=O)OH | H | 2 |
| | O51 a, b, c, or d | H | CH$_2$C(=O)NH$_2$ | H | 2 |
| | O52 a, b, c, or d | CH$_2$C(=O)OH | CH$_2$C(=O)NH$_2$ | H | 2 |
| | O53 a, b, c, or d | CH$_2$C(=O)OCH$_3$ | CH$_2$C(=O)NH$_2$ | H | 2 |
| | O54 a, b, c, or d | CH$_2$CH$_2$C(=O)OH | CH$_2$C(=O)NH$_2$ | H | 2 |
| | O55 a, b, c, or d | CH$_2$CH$_2$C(=O)OCH$_3$ | CH$_2$C(=O)NH$_2$ | H | 2 |
| | O56 a, b, c, or d | CH$_2$C(=O)NH$_2$ | CH$_2$C(=O)NH$_2$ | H | 2 |
| | O57 a, b, c, or d | CH$_2$CH$_2$C(=O)NH$_2$ | CH$_2$C(=O)NH$_2$ | H | 2 |
| | O58 a, b, c, or d | H | H | CH$_3$ | 2 |
| | O59 a, b, c, or d | CH$_2$C(=O)OH | H | CH$_3$ | 2 |
| | O60 a, b, c, or d | CH$_2$C(=O)OCH$_3$ | H | CH$_3$ | 2 |
| | O61 a, b, c, or d | CH$_2$CH$_2$C(=O)OH | H | CH$_3$ | 2 |
| | O62 a, b, c, or d | CH$_2$CH$_2$C(=O)OCH$_3$ | H | CH$_3$ | 2 |
| | O63 a, b, c, or d | CH$_2$C(=O)NH$_2$ | H | CH$_3$ | 2 |
| | O64 a, b, c, or d | CH$_2$CH$_2$C(=O)NH$_2$ | H | CH$_3$ | 2 |
| | O65 a, b, c, or d | H | CH$_2$C(=O)OH | CH$_3$ | 2 |
| | O66 a, b, c, or d | CH$_2$C(=O)OH | CH$_2$C(=O)OH | CH$_3$ | 2 |

-continued

| Compound | R⁴ᵃ | R³ᵃ | R⁸ᵃ | y |
|---|---|---|---|---|
| O67 a, b, c, or d | CH₂CH₂C(=O)OH | CH₂C(=O)OH | CH₃ | 2 |
| O68 a, b, c, or d | CH₂C(=O)NH₂ | CH₂C(=O)OH | CH₃ | 2 |
| O69 a, b, c, or d | CH₂CH₂C(=O)NH₂ | CH₂C(=O)OH | CH₃ | 2 |
| O70 a, b, c, or d | H | CH₂C(=O)NH₂ | CH₃ | 2 |
| O71 a, b, c, or d | CH₂C(=O)OH | CH₂C(=O)NH₂ | CH₃ | 2 |
| O72 a, b, c, or d | CH₂C(=O)OCH₃ | CH₂C(=O)NH₂ | CH₃ | 2 |
| O73 a, b, c, or d | CH₂CH₂C(=O)OH | CH₂C(=O)NH₂ | CH₃ | 2 |
| O74 a, b, c, or d | CH₂CH₂C(=O)OCH₃ | CH₂C(=O)NH₂ | CH₃ | 2 |
| O75 a, b, c, or d | CH₂C(=O)NH₂ | CH₂C(=O)NH₂ | CH₃ | 2 |
| O76 a, b, c, or d | CH₂CH₂C(=O)NH₂ | CH₂C(=O)NH₂ | CH₃ | 2 |
| O77 a, b, c, or d | H | H | H | 3 |
| O78 a, b, c, or d | CH₂C(=O)OH | H | H | 3 |
| O79 a, b, c, or d | CH₂C(=O)OCH₃ | H | H | 3 |
| O80 a, b, c, or d | CH₂CH₂C(=O)OH | H | H | 3 |
| O81 a, b, c, or d | CH₂CH₂C(=O)OCH₃ | H | H | 3 |
| O82 a, b, c, or d | CH₂C(=O)NH₂ | H | H | 3 |
| O83 a, b, c, or d | CH₂CH₂C(=O)NH₂ | H | H | 3 |
| O84 a, b, c, or d | H | CH₂C(=O)OH | H | 3 |
| O85 a, b, c, or d | CH₂C(=O)OH | CH₂C(=O)OH | H | 3 |
| O86 a, b, c, or d | CH₂CH₂C(=O)OH | CH₂C(=O)OH | H | 3 |
| O87 a, b, c, or d | CH₂C(=O)NH₂ | CH₂C(=O)OH | H | 3 |
| O88 a, b, c, or d | CH₂CH₂C(=O)NH₂ | CH₂C(=O)OH | H | 3 |
| O89 a, b, c, or d | H | CH₂C(=O)NH₂ | H | 3 |
| O90 a, b, c, or d | CH₂C(=O)OH | CH₂C(=O)NH₂ | H | 3 |
| O91 a, b, c, or d | CH₂C(=O)OCH₃ | CH₂C(=O)NH₂ | H | 3 |
| O92 a, b, c, or d | CH₂CH₂C(=O)OH | CH₂C(=O)NH₂ | H | 3 |
| O93 a, b, c, or d | CH₂CH₂C(=O)OCH₃ | CH₂C(=O)NH₂ | H | 3 |
| O94 a, b, c, or d | CH₂C(=O)NH₂ | CH₂C(=O)NH₂ | H | 3 |
| O95 a, b, c, or d | CH₂CH₂C(=O)NH₂ | CH₂C(=O)NH₂ | H | 3 |
| O96 a, b, c, or d | H | H | CH₃ | 3 |
| O97 a, b, c, or d | CH₂C(=O)OH | H | CH₃ | 3 |
| O98 a, b, c, or d | CH₂C(=O)OCH₃ | H | CH₃ | 3 |
| O99 a, b, c, or d | CH₂CH₂C(=O)OH | H | CH₃ | 3 |
| O100 a, b, c, or d | CH₂CH₂C(=O)OCH₃ | H | CH₃ | 3 |
| O101 a, b, c, or d | CH₂C(=O)NH₂ | H | CH₃ | 3 |
| O102 a, b, c, or d | CH₂CH₂C(=O)NH₂ | H | CH₃ | 3 |
| O103 a, b, c, or d | H | CH₂C(=O)OH | CH₃ | 3 |
| O104 a, b, c, or d | CH₂C(=O)OH | CH₂C(=O)OH | CH₃ | 3 |
| O105 a, b, c, or d | CH₂CH₂C(=O)OH | CH₂C(=O)OH | CH₃ | 3 |
| O106 a, b, c, or d | CH₂C(=O)NH₂ | CH₂C(=O)OH | CH₃ | 3 |
| O107 a, b, c, or d | CH₂CH₂C(=O)NH₂ | CH₂C(=O)OH | CH₃ | 3 |
| O108 a, b, c, or d | H | CH₂C(=O)NH₂ | CH₃ | 3 |
| O109 a, b, c, or d | CH₂C(=O)OH | CH₂C(=O)NH₂ | CH₃ | 3 |
| O110 a, b, c, or d | CH₂C(=O)OCH₃ | CH₂C(=O)NH₂ | CH₃ | 3 |
| O111 a, b, c, or d | CH₂CH₂C(=O)OH | CH₂C(=O)NH₂ | CH₃ | 3 |
| O112 a, b, c, or d | CH₂CH₂C(=O)OCH₃ | CH₂C(=O)NH₂ | CH₃ | 3 |
| O113 a, b, c, or d | CH₂C(=O)NH₂ | CH₂C(=O)NH₂ | CH₃ | 3 |
| O114 a, b, c, or d | CH₂CH₂C(=O)NH₂ | CH₂C(=O)NH₂ | CH₃ | 3 |

TABLE 16

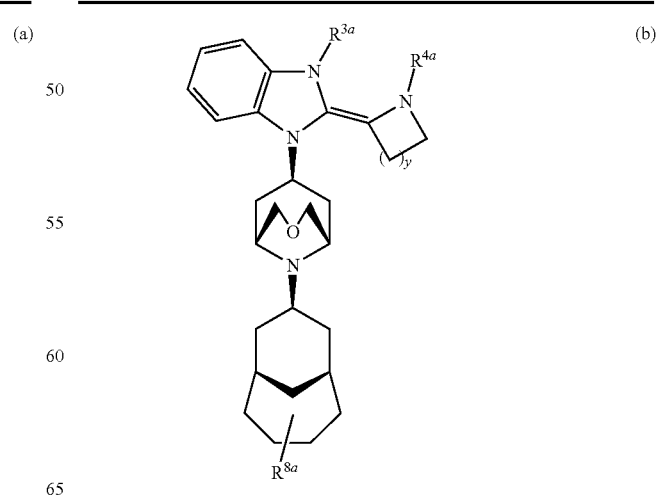

(a)

TABLE 16-continued (b)

TABLE 16-continued

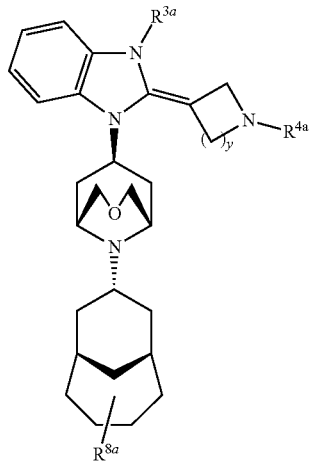
(c)

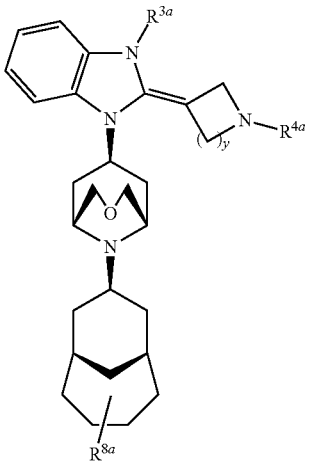
(d)

and pharmaceutically acceptable salts or solvates thereof, where:

| Compound | $R^{4a}$ | $R^{3a}$ | $R^{8a}$ | y |
|---|---|---|---|---|
| P P1 a, b, c, or d | H | H | H | 1 |
| P2 a, b, c, or d | $CH_2C(=O)OH$ | H | H | 1 |
| P3 a, b, c, or d | $CH_2C(=O)OCH_3$ | H | H | 1 |
| P4 a, b, c, or d | $CH_2CH_2C(=O)OH$ | H | H | 1 |
| P5 a, b, c, or d | $CH_2CH_2C(=O)OCH_3$ | H | H | 1 |
| P6 a, b, c, or d | $CH_2C(=O)NH_2$ | H | H | 1 |
| P7 a, b, c, or d | $CH_2CH_2C(=O)NH_2$ | H | H | 1 |
| P8 a, b, c, or d | H | $CH_2C(=O)OH$ | H | 1 |
| P9 a, b, c, or d | $CH_2C(=O)OH$ | $CH_2C(=O)OH$ | H | 1 |
| P10 a, b, c, or d | $CH_2CH_2C(=O)OH$ | $CH_2C(=O)OH$ | H | 1 |
| P11 a, b, c, or d | $CH_2C(=O)NH_2$ | $CH_2C(=O)OH$ | H | 1 |
| P12 a, b, c, or d | $CH_2CH_2C(=O)NH_2$ | $CH_2C(=O)OH$ | H | 1 |
| P13 a, b, c, or d | H | $CH_2C(=O)NH_2$ | H | 1 |
| P14 a, b, c, or d | $CH_2C(=O)OH$ | $CH_2C(=O)NH_2$ | H | 1 |
| P15 a, b, c, or d | $CH_2C(=O)OCH_3$ | $CH_2C(=O)NH_2$ | H | 1 |
| P16 a, b, c, or d | $CH_2CH_2C(=O)OH$ | $CH_2C(=O)NH_2$ | H | 1 |
| P17 a, b, c, or d | $CH_2CH_2C(=O)OCH_3$ | $CH_2C(=O)NH_2$ | H | 1 |
| P18 a, b, c, or d | $CH_2C(=O)NH_2$ | $CH_2C(=O)NH_2$ | H | 1 |
| P19 a, b, c, or d | $CH_2CH_2C(=O)NH_2$ | $CH_2C(=O)NH_2$ | H | 1 |
| P20 a, b, c, or d | H | H | $CH_3$ | 1 |
| P21 a, b, c, or d | $CH_2C(=O)OH$ | H | $CH_3$ | 1 |
| P22 a, b, c, or d | $CH_2C(=O)OCH_3$ | H | $CH_3$ | 1 |
| P23 a, b, c, or d | $CH_2CH_2C(=O)OH$ | H | $CH_3$ | 1 |
| P24 a, b, c, or d | $CH_2CH_2C(=O)OCH_3$ | H | $CH_3$ | 1 |
| P25 a, b, c, or d | $CH_2C(=O)NH_2$ | H | $CH_3$ | 1 |
| P26 a, b, c, or d | $CH_2CH_2C(=O)NH_2$ | H | $CH_3$ | 1 |
| P27 a, b, c, or d | H | $CH_2C(=O)OH$ | $CH_3$ | 1 |
| P28 a, b, c, or d | $CH_2C(=O)OH$ | $CH_2C(=O)OH$ | $CH_3$ | 1 |
| P29 a, b, c, or d | $CH_2CH_2C(=O)OH$ | $CH_2C(=O)OH$ | $CH_3$ | 1 |
| P30 a, b, c, or d | $CH_2C(=O)NH_2$ | $CH_2C(=O)OH$ | $CH_3$ | 1 |
| P31 a, b, c, or d | $CH_2CH_2C(=O)NH_2$ | $CH_2C(=O)OH$ | $CH_3$ | 1 |
| P32 a, b, c, or d | H | $CH_2C(=O)NH_2$ | $CH_3$ | 1 |
| P33 a, b, c, or d | $CH_2C(=O)OH$ | $CH_2C(=O)NH_2$ | $CH_3$ | 1 |
| P34 a, b, c, or d | $CH_2C(=O)OCH_3$ | $CH_2C(=O)NH_2$ | $CH_3$ | 1 |
| P35 a, b, c, or d | $CH_2CH_2C(=O)OH$ | $CH_2C(=O)NH_2$ | $CH_3$ | 1 |
| P36 a, b, c, or d | $CH_2CH_2C(=O)OCH_3$ | $CH_2C(=O)NH_2$ | $CH_3$ | 1 |
| P37 a, b, c, or d | $CH_2C(=O)NH_2$ | $CH_2C(=O)NH_2$ | $CH_3$ | 1 |
| P38 a, b, c, or d | $CH_2CH_2C(=O)NH_2$ | $CH_2C(=O)NH_2$ | $CH_3$ | 1 |
| P39 a, b, c, or d | H | H | H | 2 |
| P40 a, b, c, or d | $CH_2C(=O)OH$ | H | H | 2 |
| P41 a, b, c, or d | $CH_2C(=O)OCH_3$ | H | H | 2 |
| P42 a, b, c, or d | $CH_2CH_2C(=O)OH$ | H | H | 2 |
| P43 a, b, c, or d | $CH_2CH_2C(=O)OCH_3$ | H | H | 2 |
| P44 a, b, c, or d | $CH_2C(=O)NH_2$ | H | H | 2 |
| P45 a, b, c, or d | $CH_2CH_2C(=O)NH_2$ | H | H | 2 |
| P46 a, b, c, or d | H | $CH_2C(=O)OH$ | H | 2 |
| P47 a, b, c, or d | $CH_2C(=O)OH$ | $CH_2C(=O)OH$ | H | 2 |
| P48 a, b, c, or d | $CH_2CH_2C(=O)OH$ | $CH_2C(=O)OH$ | H | 2 |
| P49 a, b, c, or d | $CH_2C(=O)NH_2$ | $CH_2C(=O)OH$ | H | 2 |
| P50 a, b, c, or d | $CH_2CH_2C(=O)NH_2$ | $CH_2C(=O)OH$ | H | 2 |

-continued

| Compound | $R^{4a}$ | $R^{3a}$ | $R^{8a}$ | y |
|---|---|---|---|---|
| P51 a, b, c, or d | H | $CH_2C(=O)NH_2$ | H | 2 |
| P52 a, b, c, or d | $CH_2C(=O)OH$ | $CH_2C(=O)NH_2$ | H | 2 |
| P53 a, b, c, or d | $CH_2C(=O)OCH_3$ | $CH_2C(=O)NH_2$ | H | 2 |
| P54 a, b, c, or d | $CH_2CH_2C(=O)OH$ | $CH_2C(=O)NH_2$ | H | 2 |
| P55 a, b, c, or d | $CH_2CH_2C(=O)OCH_3$ | $CH_2C(=O)NH_2$ | H | 2 |
| P56 a, b, c, or d | $CH_2C(=O)NH_2$ | $CH_2C(=O)NH_2$ | H | 2 |
| P57 a, b, c, or d | $CH_2CH_2C(=O)NH_2$ | $CH_2C(=O)NH_2$ | H | 2 |
| P58 a, b, c, or d | H | H | $CH_3$ | 2 |
| P59 a, b, c, or d | $CH_2C(=O)OH$ | H | $CH_3$ | 2 |
| P60 a, b, c, or d | $CH_2C(=O)OCH_3$ | H | $CH_3$ | 2 |
| P61 a, b, c, or d | $CH_2CH_2C(=O)OH$ | H | $CH_3$ | 2 |
| P62 a, b, c, or d | $CH_2CH_2C(=O)OCH_3$ | H | $CH_3$ | 2 |
| P63 a, b, c, or d | $CH_2C(=O)NH_2$ | H | $CH_3$ | 2 |
| P64 a, b, c, or d | $CH_2CH_2C(=O)NH_2$ | H | $CH_3$ | 2 |
| P65 a, b, c, or d | H | $CH_2C(=O)OH$ | $CH_3$ | 2 |
| P66 a, b, c, or d | $CH_2C(=O)OH$ | $CH_2C(=O)OH$ | $CH_3$ | 2 |
| P67 a, b, c, or d | $CH_2CH_2C(=O)OH$ | $CH_2C(=O)OH$ | $CH_3$ | 2 |
| P68 a, b, c, or d | $CH_2C(=O)NH_2$ | $CH_2C(=O)OH$ | $CH_3$ | 2 |
| P69 a, b, c, or d | $CH_2CH_2C(=O)NH_2$ | $CH_2C(=O)OH$ | $CH_3$ | 2 |
| P70 a, b, c, or d | H | $CH_2C(=O)NH_2$ | $CH_3$ | 2 |
| P71 a, b, c, or d | $CH_2C(=O)OH$ | $CH_2C(=O)NH_2$ | $CH_3$ | 2 |
| P72 a, b, c, or d | $CH_2C(=O)OCH_3$ | $CH_2C(=O)NH_2$ | $CH_3$ | 2 |
| P73 a, b, c, or d | $CH_2CH_2C(=O)OH$ | $CH_2C(=O)NH_2$ | $CH_3$ | 2 |
| P74 a, b, c, or d | $CH_2CH_2C(=O)OCH_3$ | $CH_2C(=O)NH_2$ | $CH_3$ | 2 |
| P75 a, b, c, or d | $CH_2C(=O)NH_2$ | $CH_2C(=O)NH_2$ | $CH_3$ | 2 |
| P76 a, b, c, or d | $CH_2CH_2C(=O)NH_2$ | $CH_2C(=O)NH_2$ | $CH_3$ | 2 |
| P77 a, b, c, or d | H | H | H | 3 |
| P78 a, b, c, or d | $CH_2C(=O)OH$ | H | H | 3 |
| P79 a, b, c, or d | $CH_2C(=O)OCH_3$ | H | H | 3 |
| P80 a, b, c, or d | $CH_2CH_2C(=O)OH$ | H | H | 3 |
| P81 a, b, c, or d | $CH_2CH_2C(=O)OCH_3$ | H | H | 3 |
| P82 a, b, c, or d | $CH_2C(=O)NH_2$ | H | H | 3 |
| P83 a, b, c, or d | $CH_2CH_2C(=O)NH_2$ | H | H | 3 |
| P84 a, b, c, or d | H | $CH_2C(=O)OH$ | H | 3 |
| P85 a, b, c, or d | $CH_2C(=O)OH$ | $CH_2C(=O)OH$ | H | 3 |
| P86 a, b, c, or d | $CH_2CH_2C(=O)OH$ | $CH_2C(=O)OH$ | H | 3 |
| P87 a, b, c, or d | $CH_2C(=O)NH_2$ | $CH_2C(=O)OH$ | H | 3 |
| P88 a, b, c, or d | $CH_2CH_2C(=O)NH_2$ | $CH_2C(=O)OH$ | H | 3 |
| P89 a, b, c, or d | H | $CH_2C(=O)NH_2$ | H | 3 |
| P90 a, b, c, or d | $CH_2C(=O)OH$ | $CH_2C(=O)NH_2$ | H | 3 |
| P91 a, b, c, or d | $CH_2C(=O)OCH_3$ | $CH_2C(=O)NH_2$ | H | 3 |
| P92 a, b, c, or d | $CH_2CH_2C(=O)OH$ | $CH_2C(=O)NH_2$ | H | 3 |
| P93 a, b, c, or d | $CH_2CH_2C(=O)OCH_3$ | $CH_2C(=O)NH_2$ | H | 3 |
| P94 a, b, c, or d | $CH_2C(=O)NH_2$ | $CH_2C(=O)NH_2$ | H | 3 |
| P95 a, b, c, or d | $CH_2CH_2C(=O)NH_2$ | $CH_2C(=O)NH_2$ | H | 3 |
| P96 a, b, c, or d | H | H | $CH_3$ | 3 |
| P97 a, b, c, or d | $CH_2C(=O)OH$ | H | $CH_3$ | 3 |
| P98 a, b, c, or d | $CH_2C(=O)OCH_3$ | H | $CH_3$ | 3 |
| P99 a, b, c, or d | $CH_2CH_2C(=O)OH$ | H | $CH_3$ | 3 |
| P100 a, b, c, or d | $CH_2CH_2C(=O)OCH_3$ | H | $CH_3$ | 3 |
| P101 a, b, c, or d | $CH_2C(=O)NH_2$ | H | $CH_3$ | 3 |
| P102 a, b, c, or d | $CH_2CH_2C(=O)NH_2$ | H | $CH_3$ | 3 |
| P103 a, b, c, or d | H | $CH_2C(=O)OH$ | $CH_3$ | 3 |
| P104 a, b, c, or d | $CH_2C(=O)OH$ | $CH_2C(=O)OH$ | $CH_3$ | 3 |
| P105 a, b, c, or d | $CH_2CH_2C(=O)OH$ | $CH_2C(=O)OH$ | $CH_3$ | 3 |
| P106 a, b, c, or d | $CH_2C(=O)NH_2$ | $CH_2C(=O)OH$ | $CH_3$ | 3 |
| P107 a, b, c, or d | $CH_2CH_2C(=O)NH_2$ | $CH_2C(=O)OH$ | $CH_3$ | 3 |
| P108 a, b, c, or d | H | $CH_2C(=O)NH_2$ | $CH_3$ | 3 |
| P109 a, b, c, or d | $CH_2C(=O)OH$ | $CH_2C(=O)NH_2$ | $CH_3$ | 3 |
| P110 a, b, c, or d | $CH_2C(=O)OCH_3$ | $CH_2C(=O)NH_2$ | $CH_3$ | 3 |
| P111 a, b, c, or d | $CH_2CH_2C(=O)OH$ | $CH_2C(=O)NH_2$ | $CH_3$ | 3 |
| P112 a, b, c, or d | $CH_2CH_2C(=O)OCH_3$ | $CH_2C(=O)NH_2$ | $CH_3$ | 3 |
| P113 a, b, c, or d | $CH_2C(=O)NH_2$ | $CH_2C(=O)NH_2$ | $CH_3$ | 3 |
| P114 a, b, c, or d | $CH_2CH_2C(=O)NH_2$ | $CH_2C(=O)NH_2$ | $CH_3$ | 3 |

4.2d Substituted Benzimidazole-Type Piperidine Compounds of Formulae (I‡A), (I‡A'), and (I‡A")

Compounds of formula (I‡A) are herein disclosed:

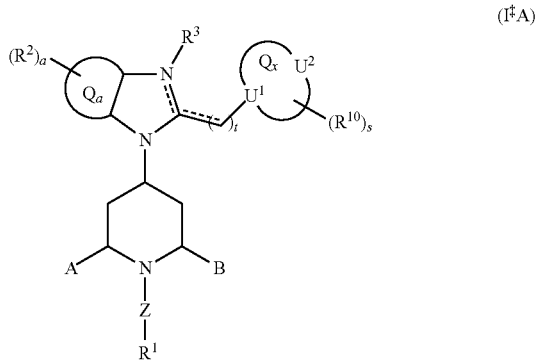

(I‡A)

or a pharmaceutically acceptable salt or solvate thereof where:

the $Q_a$ ring is fused benzo or fused (5- or 6-membered) heteroaryl;

each $R^2$ is independently selected from:
  (a) -halo, —CN, —NO$_2$, —OT$^3$, —C(=O)T$^3$, —C(=O)OT$^3$, —C(=O)N(T$^1$)(T$^2$), —S(=O)$_2$OT$^3$, —S(=O)T$^3$, —S(=O)$_2$T$^3$, —O—S(=O)$_2$T$^3$, —S(=O)$_2$N(T$^1$)(T$^2$), —N(T$^1$)(T$^2$), —N(T$^3$)C(=O)T$^3$, —N(T$^3$)C(=O)N(T$^1$)(T$^2$), —N(T$^3$)S(=O)T$^3$, —N(T$^3$)S(=O)$_2$T$^3$, —N(T$^3$)C(=O)OT$^3$, and —N(T$^3$)S(=O)$_2$N(T$^1$)(T$^2$); and
  (b) —(C$_1$-C$_6$)alkyl, —(C$_2$-C$_6$)alkenyl, —(C$_2$-C$_6$)alkynyl, —(C$_1$-C$_6$)alkoxy, —(C$_3$-C$_7$)cycloalkyl, —(C$_6$-C$_{10}$)bicycloalkyl, —(C$_5$-C$_{10}$)cycloalkenyl, —(C$_7$-C$_{10}$)bicycloalkenyl, and -(5- or 6-membered)heterocycle, each of which is unsubstituted or substituted with 1, 2, or 3 independently selected $R^8$ groups; and
  (c) -phenyl, -naphthalenyl, and -(5- or 6-membered)heteroaryl, each of which is unsubstituted or substituted with 1, 2, or 3 independently selected $R^7$ groups;

each dashed line denotes the presence or absence of a bond (i.e., when a dashed line is present there is a double bond at that position and when a dashed line is absent there is only a single bond at that position), provided that:
  (a) one dashed line must denote the presence of a bond (i.e., there is a double bond at that position);
  (b) when one dashed line denotes the presence of a bond (i.e., there is a double bond at that position) then the other dashed line denotes the absence of a bond (i.e., there is only a single bond at that other position);
  (c) when the dashed line within the 5-membered, nitrogen-containing ring that is fused to the $Q_a$ ring is present (i.e., there is a double bond at that position), then $R^3$ is absent; and
  (d) when the dashed line within the 5-membered, nitrogen-containing ring that is fused to the $Q_a$ ring is absent (i.e., there is only a single bond at that position), then $R^3$ is present;

$R^3$, when present, is:
  (a) —H; or
  (b) —(C$_1$-C$_4$)alkyl which is unsubstituted or substituted with 1, 2, or 3 groups independently selected from —OH, —(C$_1$-C$_4$)alkoxy, —N(R$^6$)$_2$, —C(=O)OR$^9$, and —C(=O)N(R$^6$)$_2$; or (c) —(C$_3$-C$_7$)cycloalkyl which is unsubstituted or substituted with 1, 2, or 3 groups independently selected from —OH, —(C$_1$-C$_4$)alkoxy, —N(R$^6$)$_2$, —C(=O)OR$^9$, and —C(=O)N(R$^6$)$_2$;

t is an integer selected from 0, 1, 2, and 3;

when t is 0, the $Q_x$ ring is a -(3-, 4-, 5-, 6-, or 7-membered) heterocycle containing 1, 2, 3, or 4 ring heteroatoms independently selected from N, N(R$^4$), O, and S wherein said heterocycle is unsubstituted or substituted with (R$^{10}$)$_s$ groups provided that at least one ring heteroatom is N or N(R$^4$) and provided that when the dashed line connecting the $Q_x$ ring to the 5-membered, nitrogen-containing ring that is fused to the $Q_a$ ring is present (i.e., there is a double bond at that position), U$^1$ is C or CH, and when t is 1, 2, or 3 the $Q_x$ ring is a (5- or 6-membered) heterocycle selected from:

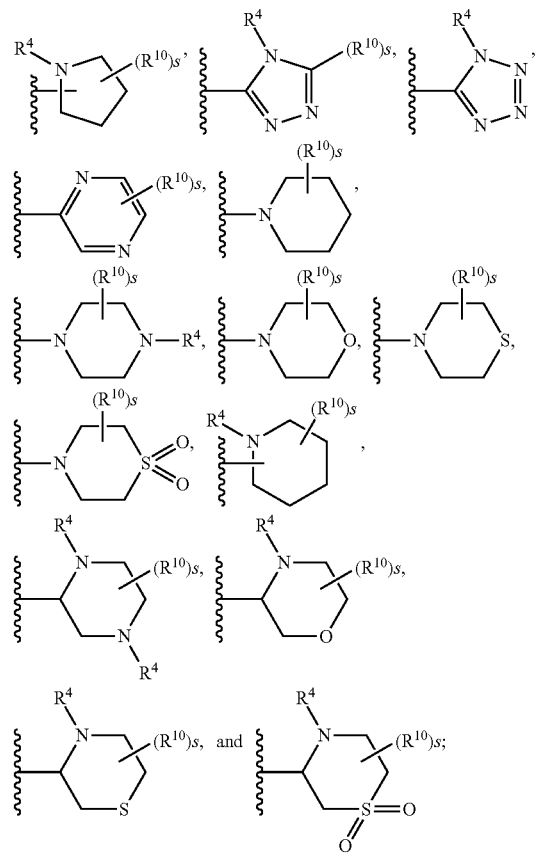

each $R^4$, when present, is independently selected from:
  (a) —H; and
  (b) —X, —(C$_1$-C$_6$)alkyl-X, -(5- or 6-membered)heterocycle-X, or -(5- or 6-membered)heterocycle-(C$_1$-C$_6$)alkyl-X; and
  (c) —(CH$_2$)$_d$—C(Y)CN, —(CH$_2$)$_d$—C(Y)X, —(CH$_2$)$_d$—C(=Y)T$^3$, —(CH$_2$)$_d$—C(=Y)YX, —(CH$_2$)$_d$—C(Y)YT$^3$, —(CH$_2$)$_d$—C(=Y)N(T$^1$)(T$^2$), —(CH$_2$)$_d$—C(=Y)N(R$^9$)CN, —(CH$_2$)$_d$—C(=Y)N(R$^9$)X, —(CH$_2$)$_d$—C(=Y)N(R$^9$)YH, —(CH$_2$)$_d$—C(=Y)N(R$^9$)YX, —(CH$_2$)$_d$—C(=Y)N(R$^9$)YCH$_2$X, —(CH$_2$)$_d$—C(=Y)N(R$^9$)YCH$_2$CH$_2$X, —(CH$_2$)$_d$—C(=Y)N(R$^9$)S(=O)$_2$T$^3$; —(CH$_2$)$_d$—N(R$^9$)S(=O)$_2$T$^3$; or —(CH$_2$)$_d$—S(=O)$_2$T$^4$; and
  (d) —[CH$_2$—O]$_b$—R$^{16}$, —[CH(CH$_3$)—O]$_b$—R$^{16}$, —[CH$_2$—CH$_2$—O]$_b$—R$^{16}$, —[CH(CH$_3$)—CH$_2$—

O]$_b$—R$^{16}$, —[CH$_2$—CH(CH$_3$)—O]$_b$—R$^{16}$, —[CH$_2$—CH$_2$—CH$_2$—O]$_b$—R$^{16}$, —[CH(CH$_3$)—CH$_2$—CH$_2$—O]$_b$—R$^{16}$, —[CH$_2$—CH(CH$_3$)—CH$_2$—O]$_b$—R$^{16}$, or —[CH$_2$—CH$_2$—CH(CH$_3$)—O]$_b$—R$^{16}$;

X is selected from:
(a) —H, —(C$_1$-C$_6$)alkyl, —(C$_2$-C$_6$)alkenyl, —(C$_2$-C$_6$)alkynyl, —(C$_1$-C$_6$)alkoxy, —(C$_3$-C$_7$)cycloalkyl, —(C$_5$-C$_{10}$)cycloalkenyl, and -(5- or 6-membered)heterocycle, each of which is unsubstituted or substituted with 1, 2, or 3 independently selected R$^8$ groups; and
(b) -phenyl and -(5- or 6-membered)heteroaryl, each of which is unsubstituted or substituted with 1, 2, or 3 independently selected R$^7$ groups;

each Y is independently O or S;
each R$^{16}$ is independently H or CH$_3$;
s is an integer selected from 0, 1, 2, 3, and 4;
when s is 1, 2, 3, or 4, each R$^{10}$ is independently —F, —Cl, —CH$_3$, —CH$_2$CH$_3$, —OCH$_3$, —OCH$_2$CH$_3$, —(CH$_2$)$_d$—C(=Y)YT$^3$, or —(CH$_2$)$_d$—C(=Y)N(T$^1$)(T$^2$), and when s is 2, 3, or 4, each R$^{10}$ is independently —F, —Cl, —CH$_3$, —CH$_2$CH$_3$, —OCH$_3$, —OCH$_2$CH$_3$, —(CH$_2$)$_d$—C(=Y)YT$^3$, or —(CH$_2$)$_d$—C(=Y)N(T$^1$)(T$^2$) or two R$^{10}$ groups attached to the same carbon atom and are gem-dimethyl, gem-difluoro, =O, or =S;

A and B are independently selected from:
(a) —H; and
(b) —(C$_1$-C$_6$)alkyl, —(C$_2$-C$_6$)alkenyl, and —(C$_1$-C$_6$)alkoxy, each of which is unsubstituted or substituted with 1 or 2 substituents independently selected from —OH, —S(=O)$_2$NH$_2$, —C(=O)OT$^3$, —C(=O)N(R$^6$)$_2$, and —N(R$^6$)C(=O)R$^9$, or 1, 2, or 3 independently selected -halo; or
(c) A-B can together form a (C$_2$-C$_6$)bridge, which is unsubstituted or substituted with 1, 2, 3, 4, 5, 6, 7, or 8 substituents independently selected from —OH, —(C$_1$-C$_4$)alkyl, -halo, and —C(halo)$_3$, and which bridge optionally contains —HC=CH— or —O— within the (C$_2$-C$_6$)bridge; wherein the 5-membered, nitrogen-containing ring that is fused to the Q$_a$ ring can be in the endo- or exo-configuration with respect to the A-B bridge;

Z is —[(C$_1$-C$_{10}$)alkyl optionally substituted by R$^{13}$]$_h$—, wherein h is 0 or 1; or —[(C$_2$-C$_{10}$)alkenyl optionally substituted by R$^{13}$]—, or —[(C$_1$-C$_{10}$)alkyl-NR$^6$C(=Y)]—;

R$^1$ is selected from:
(a) —H, -halo, —CN, —OH, —CH$_2$OH, —CH$_2$CH$_2$OH, —NO$_2$, —N(R$^6$)$_2$, —S(=O)NH$_2$, —S(=O)$_2$NH$_2$, —C(=O)OV$^1$, and —C(=O)CN; and
(b) —(C$_1$-C$_{10}$)alkyl, —(C$_2$-C$_{10}$)alkenyl, —(C$_2$-C$_{10}$)alkynyl, —O(C$_1$-C$_6$)alkyl, —(C$_3$-C$_7$)cycloalkoxy, —(C$_6$-C$_{14}$)bicycloalkyl, —(C$_8$-C$_{20}$)tricycloalkyl, —(C$_5$-C$_{10}$)cycloalkenyl, —(C$_7$-C$_{14}$)bicycloalkenyl, —(C$_8$-C$_{20}$)tricycloalkenyl, and -(3- to 7-membered)heterocycle, each of which is unsubstituted or substituted with 1, 2, 3, or 4 independently selected R$^8$ groups; and
(c)

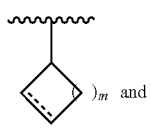 )$_m$ and

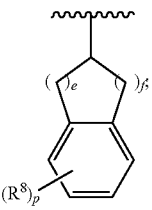

-continued (ii)

and
(d) -phenyl, -naphthalenyl, —(C$_{14}$)aryl, and -(5- to 10-membered)heteroaryl, each of which is unsubstituted or substituted with 1, 2, 3, or 4 independently selected R$^7$ groups;

each R$^5$ is independently —(C$_1$-C$_4$)alkyl, —(C$_2$-C$_6$)alkenyl, —(C$_2$-C$_6$)alkynyl, -(5- or 6-membered)heteroaryl, —(C$_1$-C$_6$)alkyl-C(=O)OR$^9$, —OR$^9$, —SR$^9$, —C(halo)$_3$, —CH(halo)$_2$, —CH$_2$(halo), —CN, =O, =S, -halo, —N$_3$, —NO$_2$, —CH=N(R$^9$), —N(R$^9$)(C$_1$-C$_6$)alkyl-C(=O)OR$^9$, —N(R$^9$)$_2$, —N(R$^9$)OH, —N(R$^9$)S(=O)R$^{12}$, —N(R$^9$)S(=O)R$^{12}$, —N(R$^9$)C(=O)R$^{12}$, —N(R$^9$)C(=O)OR$^{12}$, —C(=O)R$^9$, —C(=O)OR$^9$, —OC(=O)R$^9$, —OC(=O)OR$^9$, —S(=O)R$^9$, or —S(=O)$_2$R$^9$;

each R$^6$ is independently —H, —(C$_1$-C$_6$)alkyl, or —(C$_3$-C$_7$)cycloalkyl, or two R$^6$ groups attached to the same nitrogen atom can together form a -(5- to 8-membered)heterocyclic ring, wherein the number of atoms in the ring includes the nitrogen atom, and in which one of the -(5- to 8-membered)heterocyclic ring carbon atoms is optionally replaced by O, S, or N(T$^3$);

each R$^7$ is independently —(C$_1$-C$_4$)alkyl, —(C$_2$-C$_6$)alkenyl, —(C$_2$-C$_6$)alkynyl, —OR$^9$, —SR$^9$, —C(halo)$_3$, —CH(halo)$_2$, —CH$_2$(halo), —CN, -halo, —N$_3$, —NO$_2$, —CH=N(R$^9$), —N(R$^9$)$_2$, —N(R$^9$)OH, —N(R$^9$)S(=O)R$^{12}$, —N(R$^9$)S(=O)R$^{12}$, —N(R$^9$)C(=O)R$^{12}$, —N(R$^9$)C(=O)N(T$^1$)(T$^2$), —N(R$^9$)C(=O)OR$^{12}$, —C(=O)R$^9$, —C(=O)N(T$^1$)(T$^2$), —C(=O)OR$^9$, —OC(=O)R$^9$, —OC(=O)N(T$^1$)(T$^2$), —OC(=O)OR$^9$, —S(=O)R$^9$, or —S(=O)$_2$R$^9$;

each R$^8$ is independently —(C$_1$-C$_4$)alkyl, —(C$_2$-C$_6$)alkenyl, —(C$_2$-C$_6$)alkynyl, -(5- or 6-membered)heteroaryl, —(C$_1$-C$_6$)alkyl-C(=O)OR$^9$, —N(R$^9$)(C$_1$-C$_6$)alkyl-C(=O)OR$^9$, —OR$^9$, —SR$^9$, —C(halo)$_3$, —CH(halo)$_2$, —CH$_2$(halo), —CN, =O, =S, =N(R$^9$), -halo, —N$_3$, —NO$_2$, —CH=N(R$^9$), —N(R$^9$)$_2$, —N(R$^9$)OR$^9$, —N(R$^9$)S(=O)R$^{12}$, —N(R$^9$)S(=O)$_2$R$^{12}$, —N(R$^9$)C(=O)R$^{12}$, —N(R$^9$)C(=O)N(T$^1$)(T$^2$), —N(R$^9$)C(=O)OR$^{12}$, —C(=O)R$^9$, —C(=O)N(T$^1$)(T$^2$), —C(=O)OR$^9$, —OC(=O)R$^9$, —OC(=O)N(T$^1$)(T$^2$), —OC(=O)OR$^9$, —S(=O)R$^9$, or —S(=O)$_2$R$^9$;

each R$^9$ is independently —H, —(C$_1$-C$_6$)alkyl, —(C$_2$-C$_6$)alkenyl, —(C$_2$-C$_6$)alkynyl, —(C$_3$-C$_8$)cycloalkyl, —(C$_5$-C$_8$)cycloalkenyl, -phenyl, -benzyl, -(3- to 7-membered)heterocycle, —C(halo)$_3$, —CH(halo)$_2$, or —CH$_2$(halo);

each R$^{12}$ is independently —H or —(C$_1$-C$_4$)alkyl;

R$^{13}$ is selected from:
(a) -halo, —CN, —OH, —CH$_2$OH, —CH$_2$CH$_2$OH, —NO$_2$, —N(R$^6$)$_2$, —S(=O)NH$_2$, —S(=O)$_2$NH$_2$, —C(=O)OV$^1$, and —C(=O)CN; and
(b) —(C$_1$-C$_{10}$)alkyl, —(C$_2$-C$_{10}$)alkenyl, —(C$_2$-C$_{10}$)alkynyl, —O(C$_1$-C$_6$)alkyl, —(C$_3$-C$_7$)cycloalkoxy, —(C$_5$-C$_{10}$)cycloalkenyl, and -(3- to 7-membered)heterocycle, each of which is unsubstituted or substituted with 1, 2, 3, or 4 independently selected R$^8$ groups; and (c)

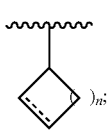

(iv')

and (d) -phenyl and -(5- to 10-membered)heteroaryl, each of which is unsubstituted or substituted with 1, 2, or 3 independently selected $R^7$ groups;

each $T^1$ and $T^2$ is independently —H or —$(C_1\text{-}C_{10})$alkyl which is unsubstituted or substituted with 1, 2, or 3 independently selected $R^5$ groups and, optionally, in which any —$(C_1\text{-}C_{10})$alkyl carbon atom except the carbon atom bonded directly to the atom to which $T^1$ or $T^2$ is attached is independently replaced by O, S, or $N(R^6)$, or $T^1$ and $T^2$ can together form a -(5- to 8-membered)heterocyclic ring wherein the number of atoms in the ring includes the nitrogen atom to which $T^1$ and $T^2$ are bonded, said -(5- to 8-membered)heterocyclic ring is unsubstituted or substituted with 1, 2, or 3 independently selected $R^5$ groups and, optionally, any 1 or 2 carbon atoms in said -(5- to 8-membered)heterocyclic ring is independently replaced by O, S, or $N(R^6)$;

each $T^3$ is independently —H or —$(C_1\text{-}C_{10})$alkyl which is unsubstituted or substituted with 1, 2, or 3 independently selected $R^5$ groups and, optionally, in which any —$(C_1\text{-}C_{10})$ alkyl carbon atom except the carbon atom bonded directly to the atom to which $T^3$ is attached is independently replaced by O, S, or $N(R^{12})$;

each $T^4$ is independently a -(5- or 6-membered)heteroaryl which is unsubstituted or substituted with 1 or 2 independently selected $R^{12}$ groups;

each $V^1$ is independently —H, —$(C_3\text{-}C_7)$cycloalkyl, -phenyl, or -benzyl;

a is an integer selected from 0, 1, and 2;

each b is, independently, an integer selected from 1, 2, 3, 4, 5, and 6;

each d is, independently, an integer selected from 0, 1, 2, and 3;

m is an integer selected from 0, 1, 2, 3, 4, 5, 6, 7, 8, 9, 10, and 11;

n is an integer selected from 0, 1, 2, 3, 4, 5, 6, 7, 8, and 9;

e and f are each an integer independently selected from 0, 1, 2, 3, 4, and 5 provided that $2 \leq (e+f) \leq 5$;

each p is an integer independently selected from 0, 1, 2, 3, and 4; and each halo is independently —F, —Cl, —Br, or —I.

In one embodiment, the compound of formula ($I^\ddagger A$) is a compound of formula ($I^\ddagger A'$):

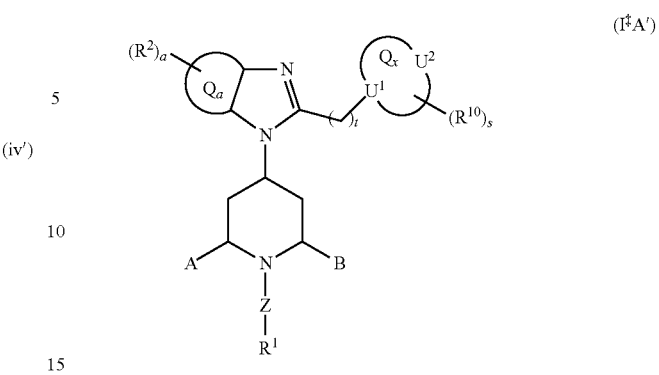

or a pharmaceutically acceptable salt or solvate thereof where $R^1$, $R^2$, $R^{10}$, $Q_a$, $Q_x$, $U^1$, $U^2$, A, B, Z, a, s, and t are as defined for the compounds of formula ($I^\ddagger A$).

In another embodiment, the compound of formula ($I^\ddagger A$) is a compound of formula ($I^\ddagger A''$):

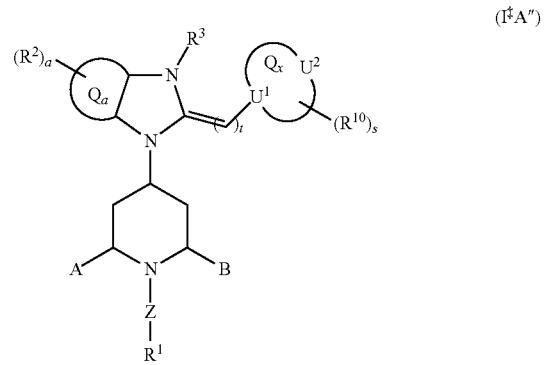

or a pharmaceutically acceptable salt or solvate thereof where $R^1$, $R^2$, $R^{10}$, $Q_a$, $Q_x$, $U^1$, $U^2$, A, B, Z, a, s, and t are as defined for the compounds of formula ($I^\ddagger A$).

In another embodiment, t is 1, 2, or 3, s is 0, 1, or 2, and the $Q_x$ ring is selected from:

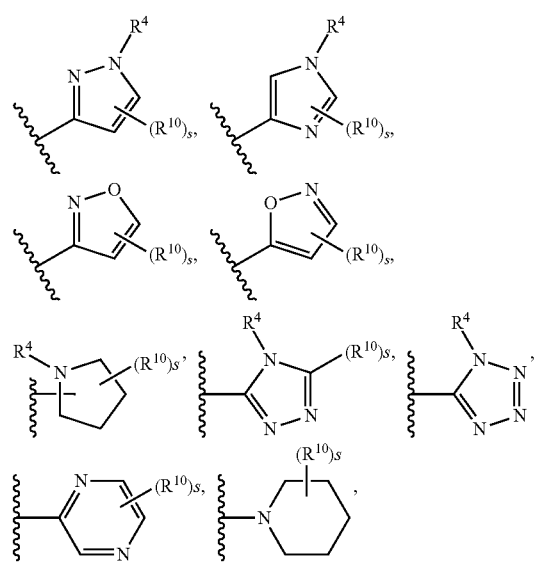

-continued
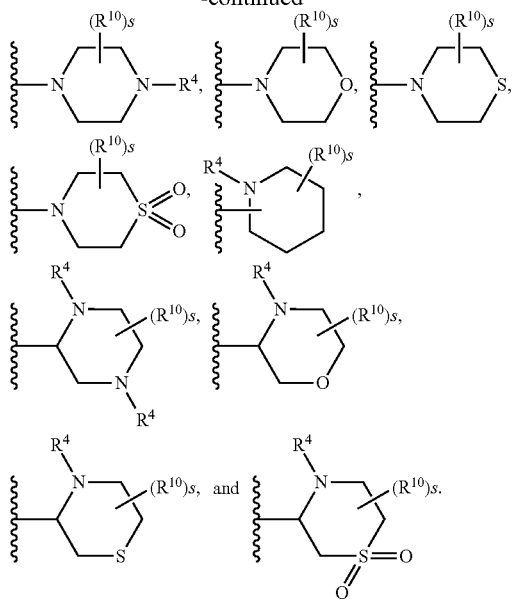
In another embodiment, t is 1, s is 0, 1, or 2, and the $Q_x$ ring is selected from:
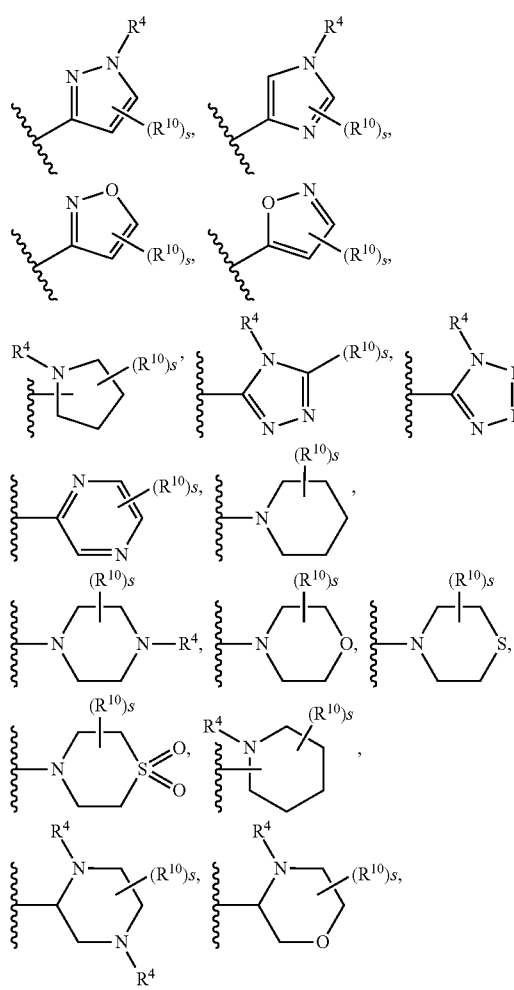
In another embodiment, t is 1, s is 0, 1, or 2, and the $Q_x$ ring is selected from:
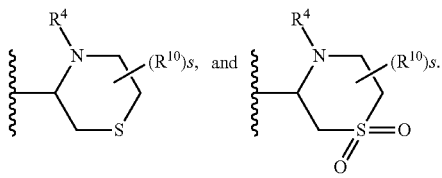
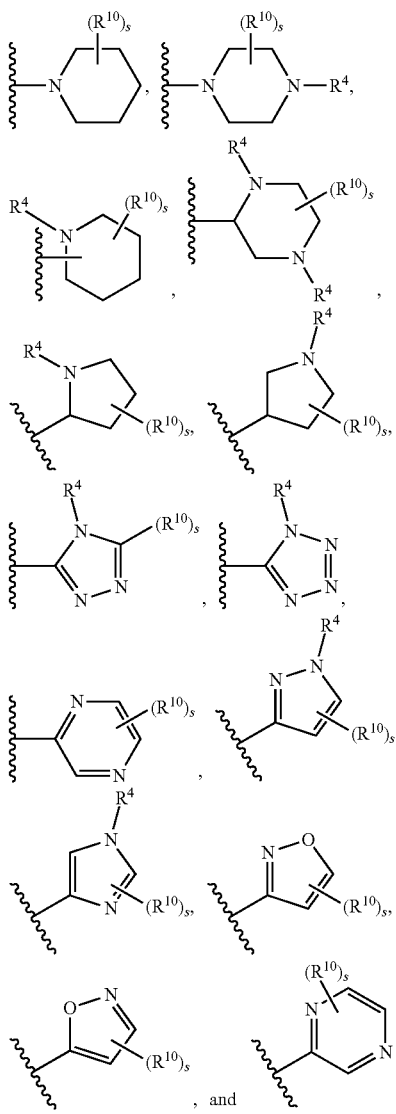
In another embodiment, t is 1, s is 0, 1, or 2, and the $Q_x$ ring is selected from:
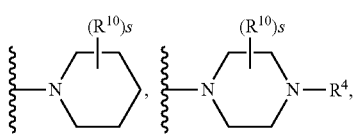

-continued
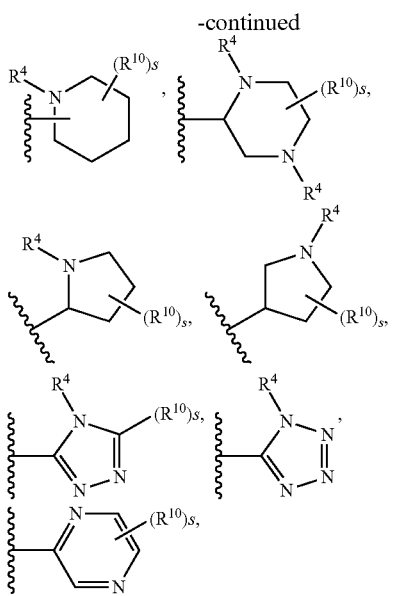
In another embodiment, t is 1 and the $Q_x$ ring is selected from:
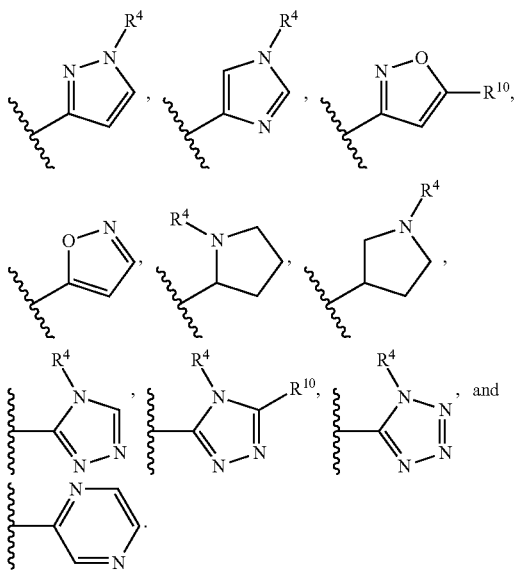
In another embodiment, t is 1 and the $Q_x$ ring is selected from:
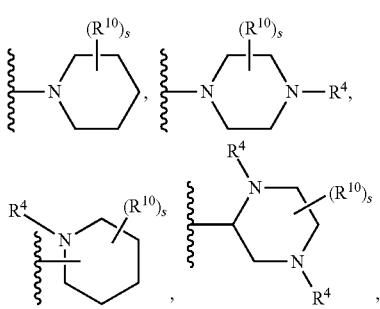
-continued
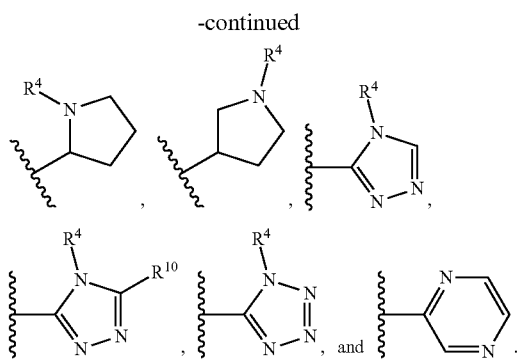
In another embodiment, t is 0, s is 0, 1, or 2, and the $Q_x$ ring is selected from:
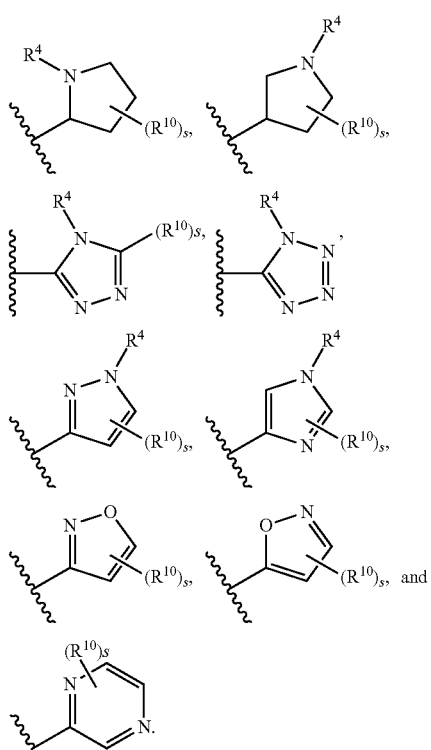
In another embodiment, t is 0, s is 0, 1, or 2, and the $Q_x$ ring is selected from:
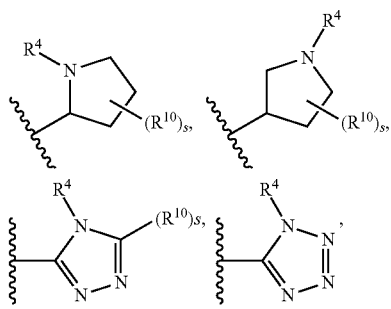

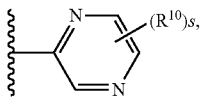

In another embodiment, t is 0 and the $Q_x$ ring is selected from:

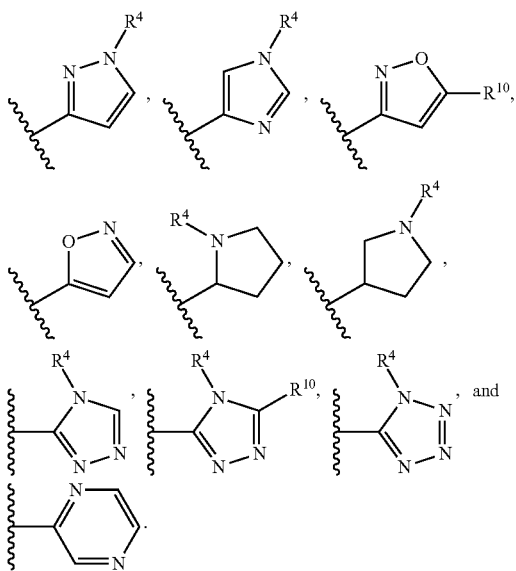

In another embodiment, t is 0 and the $Q_x$ ring is selected from:

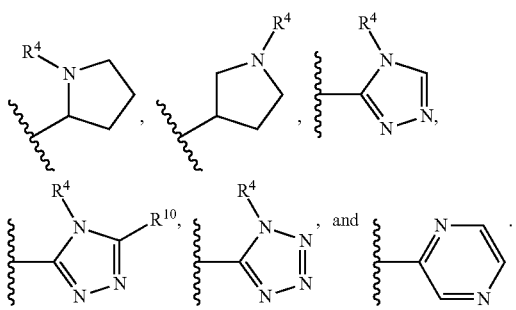

In another embodiment, t is 0 and the $Q_x$ ring is selected from:

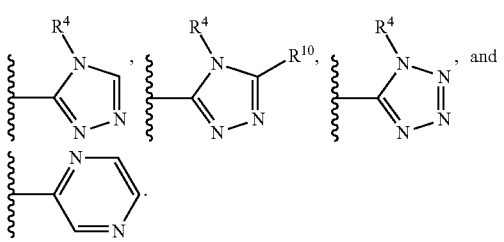

In another embodiment, $R^4$ is H, 2-(1H-imidazole), 2-(1-methyl-1H-imidazole), $CH_2CH_2C(=O)O—(C_1-C_4)$alkyl, $CH_2CH_2C(=O)OH$, $CH_2C(=O)O—(C_1-C_4)$alkyl, $CH_2C(=O)OH$, $C(=O)O—(C_1-C_4)$alkyl, $C(=O)OH$, $CH_2NHS(=O)_2(C_1-C_4)$alkyl, $CH_2CH_2NHS(=O)_2(C_1-C_4)$alkyl, $S(=O)_2$-4-(3,5-dimethylisoxazole), $CH_2C(=O)NH(C_1-C_4)$alkyl, or $CH_2C(=O)N[(C_1-C_4)$alkyl$]_2$. In another embodiment, $R^4$ is H, 2-(1H-imidazole), 2-(1-methyl-1H-imidazole), $CH_2CH_2C(=O)OH$, $CH_2C(=O)O—(C_1-C_4)$alkyl, $CH_2C(=O)OH$, $C(=O)O—(C_1-C_4)$alkyl, $C(=O)OH$, $CH_2NHS(=O)_2(C_1-C_4)$alkyl, $CH_2CH_2NHS(=O)_2(C_1-C_4)$alkyl, $S(=O)_2$-4-(3,5-dimethylisoxazole), $CH_2C(=O)NH(C_1-C_4)$alkyl, or $CH_2C(=O)N[(C_1-C_4)$alkyl$]_2$. In another embodiment, $R^4$ is H, 2-(1H-imidazole), 2-(1-methyl-1H-imidazole), $CH_2CH_2C(=O)O—(C_1-C_4)$alkyl, $CH_2C(=O)O—(C_1-C_4)$alkyl, $CH_2C(=O)OH$, $C(=O)O—(C_1-C_4)$alkyl, $C(=O)OH$, $CH_2NHS(=O)_2(C_1-C_4)$alkyl, $CH_2CH_2NHS(=O)_2(C_1-C_4)$alkyl, $S(=O)_2$-4-(3,5-dimethylisoxazole), $CH_2C(=O)NH(C_1-C_4)$alkyl, or $CH_2C(=O)N[(C_1-C_4)$alkyl$]_2$. In another embodiment, $R^4$ is H, 2-(1H-imidazole), 2-(1-methyl-1H-imidazole), $CH_2CH_2C(=O)O—(C_1-C_4)$alkyl, $CH_2CH_2C(=O)OH$, $CH_2C(=O)OH$, $C(=O)O—(C_1-C_4)$alkyl, $C(=O)OH$, $CH_2NHS(=O)_2(C_1-C_4)$alkyl, $CH_2CH_2NHS(=O)_2(C_1-C_4)$alkyl, $S(=O)_2$-4-(3,5-dimethylisoxazole), $CH_2C(=O)NH(C_1-C_4)$alkyl, or $CH_2C(=O)N[(C_1-C_4)$alkyl$]_2$. In another embodiment, $R^4$ is H, 2-(1H-imidazole), 2-(1-methyl-1H-imidazole), $CH_2CH_2C(=O)O—(C_1-C_4)$alkyl, $CH_2CH_2C(=O)OH$, $CH_2C(=O)O—(C_1-C_4)$alkyl, $C(=O)O—(C_1-C_4)$alkyl, $C(=O)OH$, $CH_2NHS(=O)_2(C_1-C_4)$alkyl, $CH_2CH_2NHS(=O)_2(C_1-C_4)$alkyl, $S(=O)_2$-4-(3,5-dimethylisoxazole), $CH_2C(=O)NH(C_1-C_4)$alkyl, or $CH_2C(=O)N[(C_1-C_4)$alkyl$]_2$. In another embodiment, $R^4$ is H, 2-(1H-imidazole), 2-(1-methyl-1H-imidazole), $CH_2CH_2C(=O)O—(C_1-C_4)$alkyl, $CH_2CH_2C(=O)OH$, $CH_2C(=O)O—(C_1-C_4)$alkyl, $CH_2C(=O)OH$, $C(=O)O—(C_1-C_4)$alkyl, $CH_2NHS(=O)_2(C_1-C_4)$alkyl, $CH_2CH_2NHS(=O)_2(C_1-C_4)$alkyl, $S(=O)_2$-4-(3,5-dimethylisoxazole), $CH_2C(=O)NH(C_1-C_4)$alkyl, or $CH_2C(=O)N[(C_1-C_4)$alkyl$]_2$. In another embodiment, $R^4$ is H, 2-(1H-imidazole), 2-(1-methyl-1H-imidazole), $CH_2CH_2C(=O)O—(C_1-C_4)$alkyl, $CH_2CH_2C(=O)OH$, $CH_2C(=O)O—(C_1-C_4)$alkyl, $CH_2C(=O)OH$, $C(=O)O—(C_1-C_4)$alkyl, $C(=O)OH$, $CH_2NHS(=O)_2(C_1-C_4)$alkyl, or $CH_2CH_2NHS(=O)_2(C_1-C_4)$alkyl.

In another embodiment, $R^4$ is H, 2-(1H-imidazole), 2-(1-methyl-1H-imidazole), $CH_2CH_2C(=O)O—(C_1-C_4)$alkyl, $CH_2CH_2C(=O)OH$, $CH_2NHS(=O)_2(C_1-C_4)$alkyl, or $CH_2CH_2NHS(=O)_2(C_1-C_4)$alkyl. In another embodiment, $R^4$ is H, 2-(1H-imidazole), 2-(1-methyl-1H-imidazole), $CH_2CH_2C(=O)OH$, $CH_2NHS(=O)_2(C_1-C_4)$alkyl, $CH_2CH_2NHS(=O)_2(C_1-C_4)$alkyl, $S(=O)_2$-4-(3,5-dimethylisoxazole), or $CH_2C(=O)O—(C_1-C_4)$alkyl. In another embodiment, $R^4$ is H, 2-(1H-imidazole), 2-(1-methyl-1H-imidazole), $CH_2C(=O)O—(C_1-C_4)$alkyl, $CH_2NHS(=O)_2(C_1-C_4)$alkyl, $CH_2CH_2NHS(=O)_2(C_1-C_4)$alkyl, $S(=O)_2$-4-(3,5-dimethylisoxazole), or $CH_2C(=O)OH$. In another embodiment, $R^4$ is H, 2-(1H-imidazole), 2-(1-methyl-1H-imidazole), $CH_2C(=O)OH$, $CH_2NHS(=O)_2(C_1-C_4)$alkyl, $CH_2CH_2NHS(=O)_2(C_1-C_4)$alkyl, or $C(=O)O—(C_1-C_4)$alkyl. In another embodiment, $R^4$ is H, 2-(1H-imidazole), 2-(1-methyl-1H-imidazole), $C(=O)O—(C_1-C_4)$alkyl, $CH_2NHS(=O)_2(C_1-C_4)$alkyl, $CH_2CH_2NHS(=O)_2(C_1-C_4)$alkyl, $S(=O)_2$-4-(3,5-dimethylisoxazole), or $C(=O)OH$. In another embodiment, $R^4$ is H, 2-(1H-imidazole), 2-(1- methyl-1H-imidazole), $CH_2CH_2C(=O)O—(C_1-C_4)$alkyl, $CH_2NHS(=O)_2(C_1-C_4)$alkyl, $CH_2CH_2NHS(=O)_2(C_1-C_4)$alkyl, $S(=O)_2$-4-(3,5-dimethylisoxazole), $CH_2C(=O)NH(C_1-C_4)$alkyl, or $CH_2C(=O)N[(C_1-C_4)$alkyl$]_2$.

In another embodiment, $R^4$ is H, 2-(1H-imidazole), 2-(1-methyl-1H-imidazole), $CH_2CH_2C(=O)OH$, $CH_2C(=O)O—(C_1-C_4)$alkyl, $CH_2C(=O)OH$, $C(=O)O—(C_1-C_4)$alkyl, $C(=O)OH$, $S(=O)_2$-4-(3,5-dimethylisoxazole), or $CH_2C(=O)NH(C_1-C_4)$alkyl. In another embodiment, $R^4$ is H, 2-(1H-imidazole), 2-(1-methyl-1H-imidazole), $CH_2CH_2C(=O)O—(C_1-C_4)$alkyl, $CH_2C(=O)O—(C_1-C_4)$alkyl, $CH_2C(=O)OH$, $C(=O)O—(C_1-C_4)$alkyl, $C(=O)OH$, $S(=O)_2$-4-(3,5-dimethylisoxazole), or $CH_2C(=O)NH(C_1-C_4)$alkyl. In another embodiment, $R^4$ is H, 2-(1H-imidazole), 2-(1-methyl-1H-imidazole), $CH_2CH_2C(=O)O—(C_1-C_4)$alkyl, $CH_2CH_2C(=O)OH$, $CH_2C(=O)OH$, $C(=O)O—(C_1-C_4)$alkyl, $C(=O)OH$, $S(=O)_2$-4-(3,5-dimethylisoxazole), or $CH_2C(=O)NH(C_1-C_4)$alkyl. In another embodiment, $R^4$ is H, 2-(1H-imidazole), 2-(1-methyl-1H-imidazole), $CH_2CH_2C(=O)O—(C_1-C_4)$alkyl, $CH_2CH_2C(=O)OH$, $CH_2C(=O)OH$, $C(=O)O—(C_1-C_4)$alkyl, $C(=O)OH$, $S(=O)_2$-4-(3,5-dimethylisoxazole), or $CH_2C(=O)NH(C_1-C_4)$alkyl. In another embodiment, $R^4$ is H, 2-(1H-imidazole), 2-(1-methyl-1H-imidazole), $CH_2CH_2C(=O)O—(C_1-C_4)$alkyl, $CH_2C(=O)O—(C_1-C_4)$alkyl, $CH_2C(=O)OH$, $C(=O)O—(C_1-C_4)$alkyl, $C(=O)OH$, $S(=O)_2$-4-(3,5-dimethylisoxazole), or $CH_2C(=O)NH(C_1-C_4)$alkyl. In another embodiment, $R^4$ is H, 2-(1H-imidazole), 2-(1-methyl-1H-imidazole), $CH_2CH_2C(=O)O—(C_1-C_4)$alkyl, $CH_2CH_2C(=O)OH$, $CH_2C(=O)O—(C_1-C_4)$alkyl, $CH_2C(=O)OH$, $S(=O)_2$-4-(3,5-dimethylisoxazole)$C(=O)O—(C_1-C_4)$alkyl, or $CH_2C(=O)NH(C_1-C_4)$alkyl. In another embodiment, $R^4$ is H, 2-(1H-imidazole), 2-(1-methyl-1H-imidazole), $CH_2CH_2C(=O)O—(C_1-C_4)$alkyl, $CH_2CH_2C(=O)OH$, $CH_2C(=O)O—(C_1-C_4)$alkyl, $CH_2C(=O)OH$, $C(=O)O—(C_1-C_4)$alkyl, $C(=O)OH$, or $S(=O)_2$-4-(3,5-dimethylisoxazole).

In another embodiment, $R^4$ is H, 2-(1-methyl-1H-imidazole), $S(=O)_2$-4-(3,5-dimethylisoxazole), $CH_2CH_2C(=O)O—(C_1-C_4)$alkyl, or $CH_2CH_2C(=O)OH$. In another embodiment, $R^4$ is H, 2-(1-methyl-1H-imidazole), $S(=O)_2$-4-(3,5-dimethylisoxazole), $CH_2CH_2C(=O)OH$, or $CH_2C(=O)O—(C_1-C_4)$alkyl. In another embodiment, $R^4$ is H, 2-(1-methyl-1H-imidazole), $S(=O)_2$-4-(3,5-dimethylisoxazole), $CH_2C(=O)O—(C_1-C_4)$alkyl, or $CH_2C(=O)OH$. In another embodiment, $R^4$ is H, 2-(1-methyl-1H-imidazole), $S(=O)_2$-4-(3,5-dimethylisoxazole), $CH_2C(=O)OH$, or $C(=O)O—(C_1-C_4)$alkyl. In another embodiment, $R^4$ is H, 2-(1-methyl-1H-imidazole), $S(=O)_2$-4-(3,5-dimethylisoxazole), $C(=O)O—(C_1-C_4)$alkyl, or $C(=O)OH$. In another embodiment, $R^4$ is H, 2-(1-methyl-1H-imidazole), $S(=O)_2$-4-(3,5-dimethylisoxazole), $CH_2CH_2C(=O)O—(C_1-C_4)$alkyl, or $CH_2C(=O)NH(C_1-C_4)$alkyl.

In another embodiment, $R^4$ is H, $CH_2NHS(=O)_2(C_1-C_4)$alkyl, $CH_2CH_2NHS(=O)_2(C_1-C_4)$alkyl, or $S(=O)_2$-4-(3,5-dimethylisoxazole). In another embodiment, $R^4$ is H, $CH_2NHS(=O)_2(C_1-C_4)$alkyl, or $S(=O)_2$-4-(3,5-dimethylisoxazole). In another embodiment, $R^4$ is H, $CH_2CH_2NHS(=O)_2(C_1-C_4)$alkyl, or $S(=O)_2$-4-(3,5-dimethylisoxazole). In another embodiment, $R^4$ is $CH_2NHS(=O)_2(C_1-C_4)$alkyl, $CH_2CH_2NHS(=O)_2(C_1-C_4)$alkyl, or $S(=O)_2$-4-(3,5-dimethylisoxazole). In another embodiment, $R^4$ is $CH_2NHS(=O)_2(C_1-C_4)$alkyl or $S(=O)_2$-4-(3,5-dimethylisoxazole). In another embodiment, $R^4$ is $CH_2CH_2NHS(=O)_2(C_1-C_4)$alkyl or $S(=O)_2$-4-(3,5-dimethylisoxazole). In another embodiment, $R^4$ is H or $CH_2NHS(=O)_2(C_1-C_4)$alkyl. In another embodiment, $R^4$ is H or $CH_2CH_2NHS(=O)_2(C_1-C_4)$alkyl. In another embodiment, $R^4$ is H or $S(=O)_2$-4-(3,5-dimethylisoxazole). In another embodiment, $R^4$ is $CH_2NHS(=O)_2(C_1-C_4)$alkyl. In another embodiment, $R^4$ is $CH_2CH_2NHS(=O)_2(C_1-C_4)$alkyl. In another embodiment, $R^4$ is $S(=O)_2$-4-(3,5-dimethylisoxazole).

In another embodiment, s is 1 and $R^{10}$ is $CH_3$, $CH_2CH_3$, $OCH_3$, $OCH_2CH_3$, $CH_2C(=O)O—(C_1-C_4)$alkyl, $CH_2C(=O)OH$, $C(=O)O—(C_1-C_4)$alkyl, $C(=O)OH$, or $CH_2C(=O)NH(C_1-C_4)$alkyl. In another embodiment, s is 1 and $R^{10}$ is $CH_3$, $CH_2CH_3$, $OCH_3$, $OCH_2CH_3$, $CH_2C(=O)OH$, $C(=O)O—(C_1-C_4)$alkyl, $C(=O)OH$, or $CH_2C(=O)NH(C_1-C_4)$alkyl. In another embodiment, s is 1 and $R^{10}$ is $CH_3$, $CH_2CH_3$, $OCH_3$, $OCH_2CH_3$, $CH_2C(=O)O—(C_1-C_4)$alkyl, $C(=O)OH$, or $CH_2C(=O)NH(C_1-C_4)$alkyl. In another embodiment, s is 1 and $R^{10}$ is $CH_3$, $CH_2CH_3$, $OCH_3$, $OCH_2CH_3$, $CH_2C(=O)O—(C_1-C_4)$alkyl, $CH_2C(=O)OH$, $C(=O)O—(C_1-C_4)$alkyl, or $CH_2C(=O)NH(C_1-C_4)$alkyl. In another embodiment, s is 1 and $R^{10}$ is $CH_3$, $CH_2CH_3$, $OCH_3$, $OCH_2CH_3$, $CH_2C(=O)O—(C_1-C_4)$alkyl, $CH_2C(=O)OH$, $C(=O)O—(C_1-C_4)$alkyl, or $C(=O)OH$.

In another embodiment, s is 1 and $R^{10}$ is $CH_3$, $CH_2CH_3$, $OCH_3$, $OCH_2CH_3$, $CH_2C(=O)O—(C_1-C_4)$alkyl or $CH_2C(=O)OH$, $C(=O)O—(C_1-C_4)$alkyl. In another embodiment, s is 1 and $R^{10}$ is $CH_3$, $CH_2CH_3$, $OCH_3$, $OCH_2CH_3$, $CH_2C(=O)OH$, $C(=O)O—(C_1-C_4)$alkyl or $C(=O)OH$. In another embodiment, s is 1 and $R^{10}$ is $CH_3$, $CH_2CH_3$, $OCH_3$, $OCH_2CH_3$, $C(=O)OH$ or $CH_2C(=O)NH(C_1-C_4)$alkyl. In another embodiment, s is 1 and $R^{10}$ is $CH_3$, $CH_2CH_3$, $OCH_3$, $OCH_2CH_3$, $CH_2C(=O)O—(C_1-C_4)$alkyl or $CH_2C(=O)NH(C_1-C_4)$alkyl.

In another embodiment, s is 1 and $R^{10}$ is $CH_3$, $CH_2CH_3$, $OCH_3$, $OCH_2CH_3$, $CH_2C(=O)OH$, $C(=O)O—(C_1-C_4)$alkyl, $C(=O)OH$, or $CH_2C(=O)NH(C_1-C_4)$alkyl. In another embodiment, s is 1 and $R^{10}$ is $CH_3$, $CH_2CH_3$, $OCH_3$, $OCH_2CH_3$, $CH_2C(=O)O—(C_1-C_4)$alkyl, $C(=O)OH$, or $CH_2C(=O)NH(C_1-C_4)$alkyl. In another embodiment, s is 1 and $R^{10}$ is $CH_3$, $CH_2CH_3$, $OCH_3$, $OCH_2CH_3$, $CH_2C(=O)O—(C_1-C_4)$alkyl, $CH_2C(=O)OH$, $C(=O)O—(C_1-C_4)$alkyl, or $CH_2C(=O)NH(C_1-C_4)$alkyl. In another embodiment, s is 1 and $R^{10}$ is $CH_3$, $CH_2CH_3$, $OCH_3$, $OCH_2CH_3$, $CH_2C(=O)O—(C_1-C_4)$alkyl, $CH_2C(=O)OH$, $C(=O)O—(C_1-C_4)$alkyl, or $C(=O)OH$.

In another embodiment, s is 1 and $R^{10}$ is $CH_3$, $OCH_3$, $CH_2C(=O)O—(C_1-C_4)$alkyl or $CH_2C(=O)OH$, $C(=O)O—(C_1-C_4)$alkyl. In another embodiment, s is 1 and $R^{10}$ is $CH_3$, $OCH_3$, $CH_2C(=O)OH$, $C(=O)O—(C_1-C_4)$alkyl or $C(=O)OH$. In another embodiment, s is 1 and $R^{10}$ is $CH_3$, $OCH_3$, $C(=O)OH$ or $CH_2C(=O)NH(C_1-C_4)$alkyl. In another embodiment, s is 1 and $R^{10}$ is $CH_3$, $OCH_3$, $CH_2C(=O)O—(C_1-C_4)$alkyl or $CH_2C(=O)NH(C_1-C_4)$alkyl.

In another embodiment, s is 1 and $R^{10}$ is $OCH_3$. In another embodiment, s is 1 and $R^{10}$ is $OCH_2CH_3$.

In another embodiment, s is 2 and each $R^{10}$ is, independently, $OCH_3$, $OCH_2CH_3$, $CH_2C(=O)O—(C_1-C_6)$alkyl, $CH_2C(=O)OH$, $C(=O)O—(C_1-C_6)$alkyl, $C(=O)OH$, or $CH_2C(=O)NH(C_1-C_6)$alkyl. In another embodiment, s is 2 and each $R^{10}$ is, independently, $OCH_3$, $OCH_2CH_3$, $CH_2C(=O)OH$, $C(=O)O—(C_1-C_6)$alkyl, $C(=O)OH$, or $CH_2C(=O)NH(C_1-C_6)$alkyl. In another embodiment, s is 2 and each $R^{10}$ is, independently, $OCH_3$, $OCH_2CH_3$, $CH_2C(=O)O—(C_1-C_6)$alkyl, $C(=O)OH$, or $CH_2C(=O)NH(C_1-C_6)$alkyl. In another embodiment, s is 2 and each $R^{10}$ is, independently, $OCH_3$, $OCH_2CH_3$, $CH_2C(=O)O—(C_1-C_6)$alkyl, $CH_2C(=O)OH$, $C(=O)O—(C_1-C_6)$alkyl, or $CH_2C(=O)NH(C_1-C_6)$alkyl. In another embodiment, s is 2 and each $R^{10}$ is, independently, $OCH_3$, $OCH_2CH_3$, $CH_2C(=O)$O—$(C_1$-$C_6)$alkyl, $CH_2C(=O)OH$, $C(=O)O$—$(C_1$-$C_6)$alkyl, or $C(=O)OH$.

In another embodiment, s is 2 and each $R^{10}$ is, independently, $OCH_3$, $OCH_2CH_3$, $CH_2C(=O)O$—$(C_1$-$C_6)$alkyl, $CH_2C(=O)OH$, or $C(=O)O$—$(C_1$-$C_6)$alkyl. In another embodiment, s is 2 and each $R^{10}$ is, independently, $OCH_3$, $OCH_2CH_3$, $CH_2C(=O)OH$, $C(=O)O$—$(C_1$-$C_6)$alkyl, or $C(=O)OH$. In another embodiment, s is 2 and each $R^{10}$ is, independently, $OCH_3$, $OCH_2CH_3$, $C(=O)OH$, or $CH_2C(=O)NH(C_1$-$C_6)$alkyl. In another embodiment, s is 2 and each $R^{10}$ is, independently, $OCH_3$, $OCH_2CH_3$, $CH_2C(=O)O$—$(C_1$-$C_6)$alkyl, or $CH_2C(=O)NH(C_1$-$C_6)$alkyl.

In another embodiment, s is 2 and each $R^{10}$ is, independently, $OCH_3$, $OCH_2CH_3$, $CH_2C(=O)OH$, $C(=O)O$—$(C_1$-$C_4)$alkyl, $C(=O)OH$, or $CH_2C(=O)NH(C_1$-$C_4)$alkyl. In another embodiment, s is 2 and each $R^{10}$ is, independently, $OCH_3$, $OCH_2CH_3$, $CH_2C(=O)O$—$(C_1$-$C_4)$alkyl, $C(=O)OH$, or $CH_2C(=O)NH(C_1$-$C_4)$alkyl. In another embodiment, s is 2 and each $R^{10}$ is, independently, $OCH_3$, $OCH_2CH_3$, $CH_2C(=O)O$—$(C_1$-$C_4)$alkyl, $CH_2C(=O)OH$, $C(=O)O$—$(C_1$-$C_4)$alkyl, or $CH_2C(=O)NH(C_1$-$C_4)$alkyl. In another embodiment, s is 2 and each $R^{10}$ is, independently, $OCH_3$, $OCH_2CH_3$, $CH_2C(=O)O$—$(C_1$-$C_4)$alkyl, $CH_2C(=O)OH$, $C(=O)O$—$(C_1$-$C_4)$alkyl, or $C(=O)OH$.

In another embodiment, s is 2 and each $R^{10}$ is, independently, $OCH_3$, $CH_2C(=O)O$—$(C_1$-$C_4)$alkyl or $CH_2C(=O)OH$, $C(=O)O$—$(C_1$-$C_4)$alkyl. In another embodiment, s is 2 and each $R^{10}$ is, independently, $OCH_3$, $CH_2C(=O)OH$, $C(=O)O$—$(C_1$-$C_4)$alkyl or $C(=O)OH$. In another embodiment, s is 2 and each $R^{10}$ is, independently, $OCH_3$, $C(=O)OH$ or $CH_2C(=O)NH(C_1$-$C_4)$alkyl. In another embodiment, s is 2 and each $R^{10}$ is, independently, $OCH_3$, $CH_2C(=O)O$—$(C_1$-$C_4)$alkyl or $CH_2C(=O)NH(C_1$-$C_4)$alkyl.

In another embodiment, s is 2 and each $R^{10}$ is, independently, $CH_2C(=O)O$—$(C_1$-$C_6)$alkyl. In another embodiment, s is 2 and each $R^{10}$ is, independently, $CH_2C(=O)OH$. In another embodiment, s is 2 and each $R^{10}$ is, independently, $C(=O)O$—$(C_1$-$C_6)$alkyl. In another embodiment, s is 2 and each $R^{10}$ is, independently, $C(=O)OH$. In another embodiment, s is 2 and each $R^{10}$ is, independently, $CH_2C(=O)NH(C_1$-$C_6)$alkyl. In another embodiment, s is 2 and each $R^{10}$ is, independently, $CH_2C(=O)O$—$(C_1$-$C_4)$alkyl. In another embodiment, s is 2 and each $R^{10}$ is, independently, $C(=O)O$—$(C_1$-$C_4)$alkyl. In another embodiment, s is 1 and $R^{10}$ is $CH_2C(=O)NH(C_1$-$C_4)$alkyl.

In another embodiment, s is 3. In another embodiment, s is 3, two $R^{10}$ groups are gem-dimethyl, gem-difluoro, or $=O$, and the other $R^{10}$ group is —F, —Cl, —$CH_3$, —$CH_2CH_3$, —$OCH_3$, —$OCH_2CH_3$, —$(CH_2)_d$—$C(=Y)YT^3$, or —$(CH_2)_d$—$C(=Y)N(T^1)(T^2)$. In another embodiment, s is 3, two $R^{10}$ groups are gem-dimethyl, gem-difluoro, or $=S$, and the other $R^{10}$ group is —F, —Cl, —$CH_3$, —$CH_2CH_3$, —$OCH_3$, —$OCH_2CH_3$, —$(CH_2)_d$—$C(=Y)YT^3$, or —$(CH_2)_d$—$C(=Y)N(T^1)(T^2)$. In another embodiment, s is 3, two $R^{10}$ groups are gem-dimethyl, $=S$, or $=O$, and the other $R^{10}$ group is —F, —Cl, —$CH_3$, —$CH_2CH_3$, —$OCH_3$, —$OCH_2CH_3$, —$(CH_2)_d$—$C(=Y)YT^3$, or —$(CH_2)_d$—$C(=Y)N(T^1)(T^2)$. In another embodiment, s is 3, two $R^{10}$ groups are gem-difluoro, $=S$, or $=O$, and the other $R^{10}$ group is —F, —Cl, —$CH_3$, —$CH_2CH_3$, —$OCH_3$, —$OCH_2CH_3$, —$(CH_2)_d$—$C(=Y)YT^3$, or —$(CH_2)_d$—$C(=Y)N(T^1)(T^2)$. In another embodiment, s is 3, two $R^{10}$ groups are gem-dimethyl or $=O$, and the other $R^{10}$ group is —F, —Cl, —$CH_3$, —$CH_2CH_3$, —$OCH_3$, —$OCH_2CH_3$, —$(CH_2)_d$—$C(=Y)YT^3$, or —$(CH_2)_d$—$C(=Y)N(T^1)(T^2)$. In another embodiment, s is 3, two $R^{10}$ groups are gem-difluoro or $=O$, and the other $R^{10}$ group is —F, —Cl, —$CH_3$, —$CH_2CH_3$, —$OCH_3$, or —$OCH_2CH_3$.

In another embodiment, s is 3, two $R^{10}$ groups are gem-dimethyl, gem-difluoro, or $=O$, and the other $R^{10}$ group is —F, —Cl, —$CH_3$, —$CH_2CH_3$, —$OCH_3$, or —$OCH_2CH_3$. In another embodiment, s is 3, two $R^{10}$ groups are gem-dimethyl, gem-difluoro, or $=S$, and the other $R^{10}$ group is —F, —Cl, —$CH_3$, —$CH_2CH_3$, —$OCH_3$, or —$OCH_2CH_3$. In another embodiment, s is 3, two $R^{10}$ groups are gem-dimethyl, $=S$, or $=O$, and the other $R^{10}$ group is —F, —Cl, —$CH_3$, —$CH_2CH_3$, —$OCH_3$, or —$OCH_2CH_3$. In another embodiment, s is 3, two $R^{10}$ groups are gem-difluoro, $=S$, or $=O$, and the other $R^{10}$ group is —F, —Cl, —$CH_3$, —$CH_2CH_3$, —$OCH_3$, or —$OCH_2CH_3$. In another embodiment, s is 3, two $R^{10}$ groups are gem-dimethyl or $=O$, and the other $R^{10}$ group is —F, —Cl, —$CH_3$, —$CH_2CH_3$, —$OCH_3$, or —$OCH_2CH_3$. In another embodiment, s is 3, two $R^{10}$ groups are gem-difluoro or $=O$, and the other $R^{13}$ group is —F, —Cl, —$CH_3$, —$CH_2CH_3$, —$OCH_3$, or —$OCH_2CH_3$.

In another embodiment, s is 4. In another embodiment, s is 4, two $R^{10}$ groups are gem-dimethyl, gem-difluoro, or $=O$, and the other two $R^{10}$ groups are independently —F, —Cl, —$CH_3$, —$CH_2CH_3$, —$OCH_3$, —$OCH_2CH_3$, —$(CH_2)_d$—$C(=Y)YT^3$, or —$(CH_2)_d$—$C(=Y)N(T^1)(T^2)$. In another embodiment, s is 4, two $R^{10}$ groups are gem-dimethyl, gem-difluoro, or $=S$, and the other two $R^{10}$ groups are independently —F, —Cl, —$CH_3$, —$CH_2CH_3$, —$OCH_3$, —$OCH_2CH_3$, —$(CH_2)_d$—$C(=Y)YT^3$, or —$(CH_2)_d$—$C(=Y)N(T^1)(T^2)$. In another embodiment, s is 4, two $R^{10}$ groups are gem-dimethyl, $=S$, or $=O$, and the other two $R^{10}$ groups are independently —F, —Cl, —$CH_3$, —$CH_2CH_3$, —$OCH_3$, —$OCH_2CH_3$, —$(CH_2)_d$—$C(=Y)YT^3$, or —$(CH_2)_d$—$C(=Y)N(T^1)(T^2)$. In another embodiment, s is 4, two $R^{10}$ groups are gem-difluoro, $=S$, or $=O$, and the other two $R^{10}$ groups are independently —F, —Cl, —$CH_3$, —$CH_2CH_3$, —$OCH_3$, —$OCH_2CH_3$, —$(CH_2)_d$—$C(=Y)YT^3$, or —$(CH_2)_d$—$C(=Y)N(T^1)(T^2)$. In another embodiment, s is 4, two $R^{10}$ groups are gem-dimethyl or $=O$, and the other two $R^{10}$ groups are independently —F, —Cl, —$CH_3$, —$CH_2CH_3$, —$OCH_3$, —$OCH_2CH_3$, —$(CH_2)_d$—$C(=Y)YT^3$, or —$(CH_2)_d$—$C(=Y)N(T^1)(T^2)$. In another embodiment, s is 4, two $R^{10}$ groups are gem-difluoro or $=O$, and the other two $R^{10}$ groups are independently —F, —Cl, —$CH_3$, —$CH_2CH_3$, —$OCH_3$, or —$OCH_2CH_3$. In another embodiment, s is 4, two $R^{10}$ groups are gem-dimethyl, gem-difluoro, or $=O$, and the other two $R^{10}$ groups are independently —F, —Cl, —$CH_3$, —$CH_2CH_3$, —$OCH_3$, or —$OCH_2CH_3$. In another embodiment, s is 4, two $R^{10}$ groups are gem-dimethyl, gem-difluoro, or $=S$, and the other two $R^{10}$ groups are independently —F, —Cl, —$CH_3$, —$CH_2CH_3$, —$OCH_3$, or —$OCH_2CH_3$. In another embodiment, s is 4, two $R^{10}$ groups are gem-dimethyl, $=S$, or $=O$, and the other two $R^{10}$ groups are independently —F, —Cl, —$CH_3$, —$CH_2CH_3$, —$OCH_3$, or —$OCH_2CH_3$. In another embodiment, s is 4, two $R^{10}$ groups are gem-difluoro, $=S$, or $=O$, and the other two $R^{10}$ groups are independently —F, —Cl, —$CH_3$, —$CH_2CH_3$, —$OCH_3$, or —$OCH_2CH_3$. In another embodiment, s is 4, two $R^{10}$ groups are gem-dimethyl or $=O$, and the other two $R^{10}$ groups are independently —F, —Cl, —$CH_3$, —$CH_2CH_3$, —$OCH_3$, or —$OCH_2CH_3$. In another embodiment, s is 4, two $R^{10}$ groups are gem-difluoro or $=O$, and the other two $R^{10}$ groups are independently —F, —Cl, —$CH_3$, —$CH_2CH_3$, —$OCH_3$, or —$OCH_2CH_3$.

In another embodiment, s is 4, two $R^{10}$ groups are gem-dimethyl, gem-difluoro, or $=O$, and the other two $R^{10}$ groups are gem-dimethyl, gem-difluoro, or =O. In another embodiment, s is 4, two $R^{10}$ groups are gem-dimethyl, gem-difluoro, or =O, and the other two $R^{10}$ groups are gem-dimethyl, gem-difluoro, or =S. In another embodiment, s is 4, two $R^{10}$ groups are gem-dimethyl, gem-difluoro, or =S, and the other two $R^{10}$ groups are gem-dimethyl, gem-difluoro, or =S. In another embodiment, s is 4, two $R^{10}$ groups are gem-dimethyl or =O, and the other two $R^{10}$ groups are gem-dimethyl or =O. In another embodiment, s is 4, two $R^{10}$ groups are gem-difluoro or =O, and the other two $R^{10}$ groups are gem-difluoro or =O. In another embodiment, s is 4, two $R^{10}$ groups are gem-dimethyl or =O, and the other two $R^{10}$ groups are gem-difluoro, or =O. In another embodiment, s is 4, two $R^{10}$ groups are gem-dimethyl, and the other two $R^{10}$ groups are gem-dimethyl, gem-difluoro, or =O. In another embodiment, s is 4, two $R^{10}$ groups are gem-difluoro, and the other two $R^{10}$ groups are gem-dimethyl, gem-difluoro, or =O. In another embodiment, s is 4, two $R^{10}$ groups are =O, and the other two $R^{10}$ groups are gem-dimethyl, gem-difluoro, or =O. In another embodiment, s is 4, two $R^{10}$ groups are =O, and the other two $R^{10}$ groups are gem-dimethy or =O. In another embodiment, s is 4, two $R^{10}$ groups are =O, and the other two $R^{10}$ groups are gem-difluoro or =O. In another embodiment, s is 4, two $R^{10}$ groups are =O, and the other two $R^{10}$ groups are =O. In another embodiment, s is 4, two $R^{10}$ groups are =S, and the other two $R^{10}$ groups are =S.

In another embodiment, $T^4$ is a -(5-membered)heteroaryl which is unsubstituted or substituted with 1 or 2 independently selected $R^{12}$ groups. In another embodiment, $T^4$ is a -(5-membered)heteroaryl which is unsubstituted. In another embodiment, $T^4$ is a -(5-membered)heteroaryl which is substituted with 1 or 2 independently selected $R^{12}$ groups. In another embodiment, $T^4$ is a -(5-membered)heteroaryl which is substituted with 1 $R^{12}$ group. In another embodiment, $T^4$ is a -(5-membered)heteroaryl which is substituted with 2 independently selected $R^{12}$ groups. In another embodiment, $T^4$ is a -(6-membered)heteroaryl which is unsubstituted or substituted with 1 or 2 independently selected $R^{12}$ groups. In another embodiment, $T^4$ is a -(6-membered)heteroaryl which is unsubstituted. In another embodiment, $T^4$ is a -(6-membered)heteroaryl which is substituted with 1 or 2 independently selected $R^{12}$ groups. In another embodiment, $T^4$ is a -(6-membered)heteroaryl which is substituted with 1 $R^{12}$ group. In another embodiment, $T^4$ is a -(6-membered)heteroaryl which is substituted with 2 independently selected $R^{12}$ groups.

In another embodiment, $T^4$ is furyl, pyrrolyl, oxazolyl, imidazolyl, thiazolyl, isoxazolyl, 1,2,3-oxadiazolyl, 1,3,4-oxadiazolyl, 1,2,5 oxadiazolyl, 1,2,3-triazolyl, pyrazolyl, isothiazolyl, 1,2,3 thiadiazolyl, 1,3,4-thiadiazolyl, 1,2,5-thiadiazolyl, or thiophenyl which is unsubstituted or substituted with 1 or 2 independently selected $R^{12}$ groups. In another embodiment, $T^4$ is furyl, pyrrolyl, oxazolyl, imidazolyl, thiazolyl, isoxazolyl, 1,2,3-oxadiazolyl, 1,3,4-oxadiazolyl, 1,2,5 oxadiazolyl, 1,2,3-triazolyl, pyrazolyl, isothiazolyl, 1,2,3 thiadiazolyl, 1,3,4-thiadiazolyl, 1,2,5-thiadiazolyl, or thiophenyl which is unsubstituted. In another embodiment, $T^4$ is furyl, pyrrolyl, oxazolyl, imidazolyl, thiazolyl, isoxazolyl, 1,2,3-oxadiazolyl, 1,3,4-oxadiazolyl, 1,2,5 oxadiazolyl, 1,2,3-triazolyl, pyrazolyl, isothiazolyl, 1,2,3 thiadiazolyl, 1,3,4-thiadiazolyl, 1,2,5-thiadiazolyl, or thiophenyl which is substituted with 1 or 2 independently selected $R^{12}$ groups. In another embodiment, $T^4$ is furyl, pyrrolyl, oxazolyl, imidazolyl, thiazolyl, isoxazolyl, 1,2,3-oxadiazolyl, 1,2,3 thiadiaz-olyl, 1,2,3-triazolyl, pyrazolyl, isothiazolyl, 1,2,3 thiadiazolyl, 1,3,4-thiadiazolyl, 1,2,5-thiadiazolyl, or thiophenyl which is substituted with 1 $R^{12}$ group. In another embodiment, $T^4$ is furyl, pyrrolyl, oxazolyl, imidazolyl, thiazolyl, isoxazolyl, 1,2,3-oxadiazolyl, 1,3,4-oxadiazolyl, 1,2,5 oxadiazolyl, 1,2,3-triazolyl, pyrazolyl, isothiazolyl, 1,2,3 thiadiazolyl, 1,3,4-thiadiazolyl, 1,2,5-thiadiazolyl, or thiophenyl which is substituted with 2 independently selected $R^{12}$ groups.

In another embodiment, $T^4$ is furyl, pyrrolyl, oxazolyl, imidazolyl, thiazolyl, isoxazolyl, 1,2,3-triazolyl, pyrazolyl, isothiazolyl, or thiophenyl which is unsubstituted or substituted with 1 or 2 independently selected $R^{12}$ groups. In another embodiment, $T^4$ is furyl, pyrrolyl, oxazolyl, imidazolyl, thiazolyl, isoxazolyl, 1,2,3-triazolyl, pyrazolyl, isothiazolyl, or thiophenyl which is unsubstituted. In another embodiment, $T^4$ is furyl, pyrrolyl, oxazolyl, imidazolyl, thiazolyl, isoxazolyl, 1,2,3-triazolyl, pyrazolyl, isothiazolyl, or thiophenyl which is substituted with 1 or 2 independently selected $R^{12}$ groups. In another embodiment, $T^4$ is furyl, pyrrolyl, oxazolyl, imidazolyl, thiazolyl, isoxazolyl, 1,2,3-triazolyl, pyrazolyl, isothiazolyl, or thiophenyl which is substituted with 1 $R^{12}$ group. In another embodiment, $T^4$ is furyl, pyrrolyl, oxazolyl, imidazolyl, thiazolyl, isoxazolyl, 1,2,3-triazolyl, pyrazolyl, isothiazolyl, or thiophenyl which is substituted with 2 independently selected $R^{12}$ groups.

In another embodiment, $T^4$ is oxazolyl, imidazolyl, isoxazolyl, 1,2,3-triazolyl, or pyrazolyl which is unsubstituted or substituted with 1 or 2 independently selected $R^{12}$ groups. In another embodiment, $T^4$ is oxazolyl, imidazolyl, isoxazolyl, 1,2,3-triazolyl, or pyrazolyl which is unsubstituted. In another embodiment, $T^4$ is oxazolyl, imidazolyl, isoxazolyl, 1,2,3-triazolyl, or pyrazolyl which is substituted with 1 or 2 independently selected $R^{12}$ groups. In another embodiment, $T^4$ is oxazolyl, imidazolyl, isoxazolyl, 1,2,3-triazolyl, or pyrazolyl which is substituted with 1 $R^{12}$ group. In another embodiment, $T^4$ is oxazolyl, imidazolyl, isoxazolyl, 1,2,3-triazolyl, or pyrazolyl which is substituted with 2 independently selected $R^{12}$ groups.

In one embodiment, the Substituted Benzimidazole-Type Piperidine Compound is not 1-((1-((1R,1'R,3r,3'R,5S,5'S)-[3,9'-bi(9'-azabicyclo[3.3.1]nonan)]-3'-yl)-1H-benzo[d]imidazol-2-yl)methyl)piperidine-4-carboxylic acid. In another embodiment, the Substituted Benzimidazole-Type Piperidine Compound is not 1-((1R,3R,5S)-9-((1R,6S,8r)-bicyclo[4.3.1]decan-8-yl)-9-azabicyclo[3.3.1]nonan-3-yl)-2-(1H-tetrazol-5-yl)-1H-benzo[d]imidazole. In another embodiment, the Substituted Benzimidazole-Type Piperidine Compound is not 1-((1R,3R,5S)-9-((1R,6S,8r)-bicyclo[4.3.1]decan-8-yl)-9-azabicyclo[3.3.1]nonan-3-yl)-2-(5-methoxypyrazin-2-yl)-1H-benzo[d]imidazole. In another embodiment, the Substituted Benzimidazole-Type Piperidine Compound is not (1R,1'R,3r,3'R,5S,5'S)-3'-(2-(5-methoxypyrazin-2-yl)-1H-benzo[d]imidazol-1-yl)-9'-aza-3,9'-bi(bicyclo[3.3.1]nonane). In another embodiment, the Substituted Benzimidazole-Type Piperidine Compound is not 6-((1R,3R,5S)-9-((1R,6S,8r)-bicyclo[4.3.1]decan-8-yl)-9-azabicyclo[3.3.1]nonan-3-yl)-1H-benzo[d]imidazol-2-yl)pyrimidine-2,4(1H,3H)-dione.

In one embodiment, the Substituted Benzimidazole-Type Piperidine Compound is not 1-((1-((1R,1'R,3r,3'R,5S,5'S)-[3,9'-bi(9'-azabicyclo[3.3.1]nonan)]-3'-yl)-1H-benzo[d]imidazol-2-yl)methyl)piperidine-4-carboxylic acid or 1-((1R,3R,5S)-9-((1R,6S,8r)-bicyclo[4.3.1]decan-8-yl)-9-azabicyclo[3.3.1]nonan-3-yl)-2-(1H-tetrazol-5-yl)-1H-benzo[d]imidazole. In another embodiment, the Substituted Benzimidazole-Type Piperidine Compound is not 1-((1-

((1R,1'R,3r,3'R,5S,5'S)-[3,9'-bi(9'-azabicyclo[3.3.1]nonan)]-3'-yl)-1H-benzo[d]imidazol-2-yl)methyl)piperidine-4-carboxylic acid or 1-((1R,3R,5S)-9-((1R,6S,8r)-bicyclo[4.3.1]decan-8-yl)-9-azabicyclo[3.3.1]nonan-3-yl)-2-(5-methoxypyrazin-2-yl)-1H-benzo[d]imidazole. In another embodiment, the Substituted Benzimidazole-Type Piperidine Compound is not 1-((1-((1R,1'R,3r,3'R,5S,5'S)-[3,9'-bi(9'-azabicyclo[3.3.1]nonan)]-3'-yl)-1H-benzo[d]imidazol-2-yl)methyl)piperidine-4-carboxylic acid or (1R,1'R,3r,3'R,5S,5'S)-3'-(2-(5-methoxypyrazin-2-yl)-1H-benzo[d]imidazol-1-yl)-9'-aza-3,9'-bi(bicyclo[3.3.1]nonane). In another embodiment, the Substituted Benzimidazole-Type Piperidine Compound is not 1-((1-((1R,1'R,3r,3'R,5S,5'S)-[3,9'-bi(9'-azabicyclo[3.3.1]nonan)]-3'-yl)-1H-benzo[d]imidazol-2-yl)methyl)piperidine-4-carboxylic acid or 6-(1-((1R,3R,5S)-9-((1R,6S,8r)-bicyclo[4.3.1]decan-8-yl)-9-azabicyclo[3.3.1]nonan-3-yl)-1H-benzo[d]imidazol-2-yl)pyrimidine-2,4(1H,3H)-dione. In another embodiment, the Substituted Benzimidazole-Type Piperidine Compound is not 1-((1R,3R,5S)-9-((1R,6S,8r)-bicyclo[4.3.1]decan-8-yl)-9-azabicyclo[3.3.1]nonan-3-yl)-2-(1H-tetrazol-5-yl)-1H-benzo[d]imidazole or 1-((1R,3R,5S)-9-((1R,6S,8r)-bicyclo[4.3.1]decan-8-yl)-9-azabicyclo[3.3.1]nonan-3-yl)-2-(5-methoxypyrazin-2-yl)-1H-benzo[d]imidazole. In another embodiment, the Substituted Benzimidazole-Type Piperidine Compound is not 1-((1R,3R,5S)-9-((1R,6S,8r)-bicyclo[4.3.1]decan-8-yl)-9-azabicyclo[3.3.1]nonan-3-yl)-2-(1H-tetrazol-5-yl)-1H-benzo[d]imidazole or (1R,1'R,3r,3'R,5S,5'S)-3'-(2-(5-methoxypyrazin-2-yl)-1H-benzo[d]imidazol-1-yl)-9'-aza-3,9'-bi(bicyclo[3.3.1]nonane). In another embodiment, the Substituted Benzimidazole-Type Piperidine Compound is not 1-((1R,3R,5S)-9-((1R,6S,8r)-bicyclo[4.3.1]decan-8-yl)-9-azabicyclo[3.3.1]nonan-3-yl)-2-(1H-tetrazol-5-yl)-1H-benzo[d]imidazole or 6-(1-((1R,3R,5S)-9-((1R,6S,8r)-bicyclo[4.3.1]decan-8-yl)-9-azabicyclo[3.3.1]nonan-3-yl)-1H-benzo[d]imidazol-2-yl)pyrimidine-2,4(1H,3H)-dione. In another embodiment, the Substituted Benzimidazole-Type Piperidine Compound is not 1-((1R,3R,5S)-9-((1R,6S,8r)-bicyclo[4.3.1]decan-8-yl)-9-azabicyclo[3.3.1]nonan-3-yl)-2-(5-methoxypyrazin-2-yl)-1H-benzo[d]imidazole or (1R,1'R,3r,3'R,5S,5'S)-3'-(2-(5-methoxypyrazin-2-yl)-1H-benzo[d]imidazol-1-yl)-9'-aza-3,9'-bi(bicyclo[3.3.1]nonane). In another embodiment, the Substituted Benzimidazole-Type Piperidine Compound is not 1-((1R,3R,5S)-9-((1R,6S,8r)-bicyclo[4.3.1]decan-8-yl)-9-azabicyclo[3.3.1]nonan-3-yl)-2-(5-methoxypyrazin-2-yl)-1H-benzo[d]imidazole or 6-(1-((1R,3R,5S)-9-((1R,6S,8r)-bicyclo[4.3.1]decan-8-yl)-9-azabicyclo[3.3.1]nonan-3-yl)-1H-benzo[d]imidazol-2-yl)pyrimidine-2,4(1H,3H)-dione.

In another embodiment, the Substituted Benzimidazole-Type Piperidine Compound is not (1R,1'R,3r,3'R,5S,5'S)-3'-(2-(5-methoxypyrazin-2-yl)-1H-benzo[d]imidazol-1-yl)-9'-aza-3,9'-bi(bicyclo[3.3.1]nonane) or 6-(1-((1R,3R,5S)-9-((1R,6S,8r)-bicyclo[4.3.1]decan-8-yl)-9-azabicyclo[3.3.1]nonan-3-yl)-1H-benzo[d]imidazol-2-yl)pyrimidine-2,4(1H,3H)-dione.

In one embodiment, the Substituted Benzimidazole-Type Piperidine Compound is not 1-((1-((1R,1'R,3r,3'R,5S,5'S)-[3,9'-bi(9'-azabicyclo[3.3.1]nonan)]-3'-yl)-1H-benzo[d]imidazol-2-yl)methyl)piperidine-4-carboxylic acid, 1-((1R,3R,5S)-9-((1R,6S,8r)-bicyclo[4.3.1]decan-8-yl)-9-azabicyclo[3.3.1]nonan-3-yl)-2-(1H-tetrazol-5-yl)-1H-benzo[d]imidazole, or 1-((1R,3R,5S)-9-((1R,6S,8r)-bicyclo[4.3.1]decan-8-yl)-9-azabicyclo[3.3.1]nonan-3-yl)-2-(5-methoxypyrazin-2-yl)-1H-benzo[d]imidazole. In another embodiment, the Substituted Benzimidazole-Type Piperidine Compound is not 1-((1-((1R,1'R,3r,3'R,5S,5'S)-[3,9'-bi(9'-azabicyclo[3.3.1]nonan)]-3'-yl)-1H-benzo[d]imidazol-2-yl)methyl)piperidine-4-carboxylic acid or 1-((1R,3R,5S)-9-((1R,6S,8r)-bicyclo[4.3.1]decan-8-yl)-9-azabicyclo[3.3.1]nonan-3-yl)-2-(1H-tetrazol-5-yl)-1H-benzo[d]imidazole, or (1R,1'R,3r,3'R,5S,5'S)-3'-(2-(5-methoxypyrazin-2-yl)-1H-benzo[d]imidazol-1-yl)-9'-aza-3,9'-bi(bicyclo[3.3.1]nonane). In another embodiment, the Substituted Benzimidazole-Type Piperidine Compound is not 1-((1-((1R,1'R,3r,3'R,5S,5'S)-[3,9'-bi(9'-azabicyclo[3.3.1]nonan)]-3'-yl)-1H-benzo[d]imidazol-2-yl)methyl)piperidine-4-carboxylic acid, 1-((1R,3R,5S)-9-((1R,6S,8r)-bicyclo[4.3.1]decan-8-yl)-9-azabicyclo[3.3.1]nonan-3-yl)-2-(1H-tetrazol-5-yl)-1H-benzo[d]imidazole, or 6-(1-((1R,3R,5S)-9-((1R,6S,8r)-bicyclo[4.3.1]decan-8-yl)-9-azabicyclo[3.3.1]nonan-3-yl)-1H-benzo[d]imidazol-2-yl)pyrimidine-2,4(1H,3H)-dione. In another embodiment, the Substituted Benzimidazole-Type Piperidine Compound is not 1-((1R,3R,5S)-9-((1R,6S,8r)-bicyclo[4.3.1]decan-8-yl)-9-azabicyclo[3.3.1]nonan-3-yl)-2-(1H-tetrazol-5-yl)-1H-benzo[d]imidazole, 1-((1R,3R,5S)-9-((1R,6S,8r)-bicyclo[4.3.1]decan-8-yl)-9-azabicyclo[3.3.1]nonan-3-yl)-2-(5-methoxypyrazin-2-yl)-1H-benzo[d]imidazole, or (1R,1'R,3r,3'R,5S,5'S)-3'-(2-(5-methoxypyrazin-2-yl)-1H-benzo[d]imidazol-1-yl)-9'-aza-3,9'-bi(bicyclo[3.3.1]nonane). In another embodiment, the Substituted Benzimidazole-Type Piperidine Compound is not 1-((1R,3R,5S)-9-((1R,6S,8r)-bicyclo[4.3.1]decan-8-yl)-9-azabicyclo[3.3.1]nonan-3-yl)-2-(1H-tetrazol-5-yl)-1H-benzo[d]imidazole, 1-((1R,3R,5S)-9-((1R,6S,8r)-bicyclo[4.3.1]decan-8-yl)-9-azabicyclo[3.3.1]nonan-3-yl)-2-(5-methoxypyrazin-2-yl)-1H-benzo[d]imidazole, or 6-(1-((1R,3R,5S)-9-((1R,6S,8r)-bicyclo[4.3.1]decan-8-yl)-9-azabicyclo[3.3.1]nonan-3-yl)-1H-benzo[d]imidazol-2-yl)pyrimidine-2,4(1H,3H)-dione. In another embodiment, the Substituted Benzimidazole-Type Piperidine Compound is not 1-((1R,3R,5S)-9-((1R,6S,8r)-bicyclo[4.3.1]decan-8-yl)-9-azabicyclo[3.3.1]nonan-3-yl)-2-(1H-tetrazol-5-yl)-1H-benzo[d]imidazole, (1R,1'R,3r,3'R,5S,5'S)-3'-(2-(5-methoxypyrazin-2-yl)-1H-benzo[d]imidazol-1-yl)-9'-aza-3,9'-bi(bicyclo[3.3.1]nonane), or 6-(1-((1R,3R,5S)-9-((1R,6S,8r)-bicyclo[4.3.1]decan-8-yl)-9-azabicyclo[3.3.1]nonan-3-yl)-1H-benzo[d]imidazol-2-yl)pyrimidine-2,4(1H,3H)-dione. In another embodiment, the Substituted Benzimidazole-Type Piperidine Compound is not 1-01R,3R,5S)-9-((1R,6S,8r)-bicyclo[4.3.1]decan-8-yl)-9-azabicyclo[3.3.1]nonan-3-yl)-2-(5-methoxypyrazin-2-yl)-1H-benzo[d]imidazole, (1R,1'R,3r,3'R,5S,5'S)-3'-(2-(5-methoxypyrazin-2-yl)-1H-benzo[d]imidazol-1-yl)-9'-aza-3,9'-bi(bicyclo[3.3.1]nonane), or 6-(1-((1R,3R,5S)-9-((1R,6S,8r)-bicyclo[4.3.1]decan-8-yl)-9-azabicyclo[3.3.1]nonan-3-yl)-1H-benzo[d]imidazol-2-yl)pyrimidine-2,4(1H,3H)-dione. In another embodiment, the Substituted Benzimidazole-Type Piperidine Compound is not 1-((1-((1R,1'R,3r,3'R,5S,5'S)-[3,9'-bi(9'-azabicyclo[3.3.1]nonan)]-3'-yl)-1H-benzo[d]imidazol-2-yl)methyl)piperidine-4-carboxylic acid, (1R,1'R,3r,3'R,5S,5'S)-3'-(2-(5-methoxypyrazin-2-yl)-1H-benzo[d]imidazol-1-yl)-9'-aza-3,9'-bi(bicyclo[3.3.1]nonane), or 6-(1-((1R,3R,5S)-9-((1R,6S,8r)-bicyclo[4.3.1]decan-8-yl)-9-azabicyclo[3.3.1]nonan-3-yl)-1H-benzo[d]imidazol-2-yl)pyrimidine-2,4(1H,3H)-dione. In another embodiment, the Substituted Benzimidazole-Type Piperidine Compound is not 1-((1-((1R,1'R,3r,3'R,5S,5'S)-[3,9'-bi(9'-azabicyclo[3.3.1]nonan)]-3'-yl)-1H-benzo[d]imidazol-2-yl)methyl)piperidine-4-carboxylic acid, 1-((1R,3R,5S)-9-((1R,6S,8r)-bicyclo[4.3.1]decan-8-yl)-9-azabicyclo[3.3.1]nonan-3-yl)-2-(5-methoxypyrazin-2-yl)-1H-benzo[d]imidazole, or 6-(1-((1R,3R,5S)-9-((1R,6S,8r)-bicyclo[4.3.1]decan-8-yl)-9-azabicyclo[3.3.1]nonan-3-yl)-1H-benzo[d]imidazol-2-yl)pyrimidine-2,4(1H,3H)-dione. In another embodiment, the Substituted Benzimidazole-Type Piperidine Compound is not 1-((1-(((1R,1'R,3r,3'R,5S,5'S)-[3,9'-bi(9'-azabicyclo[3.3.1]nonan)]-3'-yl)-1H-benzo[d]imidazol-2-yl)methyl)piperidine-4-carboxylic acid, 1-((1R,3R,5S)-9-((1R,6S,8r)-bicyclo[4.3.1]decan-8-yl)-9-azabicyclo[3.3.1]nonan-3-yl)-2-(5-methoxypyrazin-2-yl)-1H-benzo[d]imidazole, or (1R,1'R,3r,3'R,5S,5'S)-3'-(2-(5-methoxypyrazin-2-yl)-1H-benzo[d]imidazol-1-yl)-9'-aza-3,9'-bi(bicyclo[3.3.1]nonane).

In one embodiment, the Substituted Benzimidazole-Type Piperidine Compound is not 1-((1R,3R,5S)-9-((1R,6S,8r)-bicyclo[4.3.1]decan-8-yl)-9-azabicyclo[3.3.1]nonan-3-yl)-2-(1H-tetrazol-5-yl)-1H-benzo[d]imidazole, 1-((1R,3R,5S)-9-((1R,6S,8r)-bicyclo[4.3.1]decan-8-yl)-9-azabicyclo[3.3.1]nonan-3-yl)-2-(5-methoxypyrazin-2-yl)-1H-benzo[d]imidazole, (1R,1'R,3r,3'R,5S,5'S)-3'-(2-(5-methoxypyrazin-2-yl)-1H-benzo[d]imidazol-1-yl)-9'-aza-3,9'-bi(bicyclo[3.3.1]nonane), or 6-(1-((1R,3R,5S)-9-((1R,6S,8r)-bicyclo[4.3.1]decan-8-yl)-9-azabicyclo[3.3.1]nonan-3-yl)-1H-benzo[d]imidazol-2-yl)pyrimidine-2,4(1H,3H)-dione. In another embodiment, the Substituted Benzimidazole-Type Piperidine Compound is not 1-((1-(((1R,1'R,3r,3'R,5S,5'S)-[3,9'-bi(9'-azabicyclo[3.3.1]nonan)]-3'-yl)-1H-benzo[d]imidazol-2-yl)methyl)piperidine-4-carboxylic acid, 1-((1R,3R,5S)-9-((1R,6S,8r)-bicyclo[4.3.1]decan-8-yl)-9-azabicyclo[3.3.1]nonan-3-yl)-2-(5-methoxypyrazin-2-yl)-1H-benzo[d]imidazole, (1R,1'R,3r,3'R,5S,5'S)-3'-(2-(5-methoxypyrazin-2-yl)-1H-benzo[d]imidazol-1-yl)-9'-aza-3,9'-bi(bicyclo[3.3.1]nonane), or 6-(1-((1R,3R,5S)-9-((1R,6S,8r)-bicyclo[4.3.1]decan-8-yl)-9-azabicyclo[3.3.1]nonan-3-yl)-1H-benzo[d]imidazol-2-yl)pyrimidine-2,4(1H,3H)-dione. In another embodiment, the Substituted Benzimidazole-Type Piperidine Compound is not 1-((1-(((1R,1'R,3r,3'R,5S,5'S)-[3,9'-bi(9'-azabicyclo[3.3.1]nonan)]-3'-yl)-1H-benzo[d]imidazol-2-yl)methyl)piperidine-4-carboxylic acid, 1-((1R,3R,5S)-9-((1R,6S,8r)-bicyclo[4.3.1]decan-8-yl)-9-azabicyclo[3.3.1]nonan-3-yl)-2-(1H-tetrazol-5-yl)-1H-benzo[d]imidazole, 1-((1R,3R,5S)-9-((1R,6S,8r)-bicyclo[4.3.1]decan-8-yl)-9-azabicyclo[3.3.1]nonan-3-yl)-2-(5-methoxypyrazin-2-yl)-1H-benzo[d]imidazole, or 6-(1-((1R,3R,5S)-9-((1R,6S,8r)-bicyclo[4.3.1]decan-8-yl)-9-azabicyclo[3.3.1]nonan-3-yl)-1H-benzo[d]imidazol-2-yl)pyrimidine-2,4(1H,3H)-dione. In another embodiment, the Substituted Benzimidazole-Type Piperidine Compound is not 1-((1-(((1R,1'R,3r,3'R,5S,5'S)-[3,9'-bi(9'-azabicyclo[3.3.1]nonan)]-3'-yl)-1H-benzo[d]imidazol-2-yl)methyl)piperidine-4-carboxylic acid, 1-((1R,3R,5S)-9-((1R,6S,80-bicyclo[4.3.1]decan-8-yl)-9-azabicyclo[3.3.1]nonan-3-yl)-2-(1H-tetrazol-5-yl)-1H-benzo[d]imidazole, 1-((1R,3R,5S)-9-((1R,6S,8r)-bicyclo[4.3.1]decan-8-yl)-9-azabicyclo[3.3.1]nonan-3-yl)-2-(5-methoxypyrazin-2-yl)-1H-benzo[d]imidazole, or (1R,1'R,3r,3'R,5S,5'S)-3'-(2-(5-methoxypyrazin-2-yl)-1H-benzo[d]imidazol-1-yl)-9'-aza-3,9'-bi(bicyclo[3.3.1]nonane). In another embodiment, the Substituted Benzimidazole-Type Piperidine Compound is not 1-((1-(((1R,1'R,3r,3R,5S,5'S)-[3,9'-bi(9'-azabicyclo[3.3.1]nonan)]-3'-yl)-1H-benzo[d]imidazol-2-yl)methyl)piperidine-4-carboxylic acid, 1-((1R,3R,5S)-9-((1R,6S,8r)-bicyclo[4.3.1]decan-8-yl)-9-azabicyclo[3.3.1]nonan-3-yl)-2-(1H-tetrazol-5-yl)-1H-benzo[d]imidazole, 1-((1R,3R,5S)-9-((1R,6S,8r)-bicyclo[4.3.1]decan-8-yl)-9-azabicyclo[3.3.1]nonan-3-yl)-2-(5-methoxypyrazin-2-yl)-1H-benzo[d]imidazole, (1R,1'R,3r,3R,5S,5'S)-3'-(2-(5-methoxypyrazin-2-yl)-1H-benzo[d]imidazol-1-yl)-9'-aza-3,9'-bi(bicyclo[3.3.1]nonane), or 6-(1-((1R,3R,5S)-9-((1R,6S,8r)-bicyclo[4.3.1]decan-8-yl)-9-azabicyclo[3.3.1]nonan-3-yl)-1H-benzo[d]imidazol-2-yl)pyrimidine-2,4(1H,3H)-dione.

Each and every embodiment set forth in Sections 4.1, 4.2a, and 4.2b relating to the piperidine ring and the A, B, Z, and $R^1$ substituents thereto, and to the $Q_a$, $Q_x$, $R^2$, $R^3$, $R^4$, $R^{10}$, a, s, and t variable groups referenced therein also relate to the Substituted Benzimidazole-Type Piperidine Compounds in this section; therefore, those embodiments are not repeated here but are instead incorporated by reference in their entirety.

4.3a Substituted Benzimidazole-Type Piperidine Compounds of Formulae (IB), (IB'), and (IB")

As stated above, the disclosure encompasses Substituted Benzimidazole-Type Piperidine Compounds of Formula (IB):

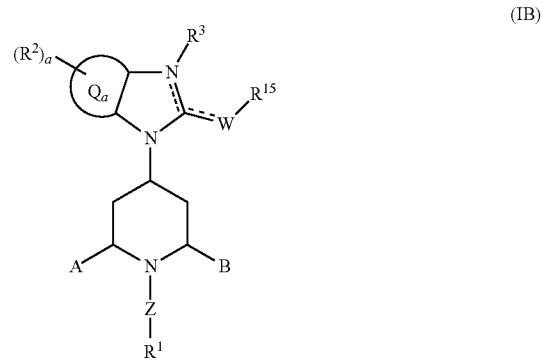

(IB)

or a pharmaceutically acceptable derivative thereof where each dashed line, $Q_a$, $R^1$, $R^2$, $R^3$, $R^{15}$, A, B, W, Z, and a are defined above for the Substituted Benzimidazole-Type Piperidine Compounds of Formula (IB).

In one embodiment, the compound of formula (IB) is a compound of formula (IB'):

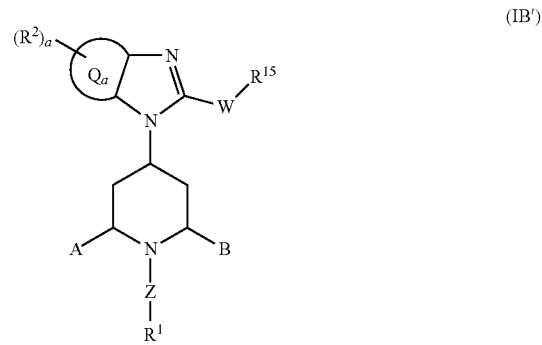

(IB')

or a pharmaceutically acceptable salt or solvate thereof where —W— is a single bond, —$CH_2$—, —NH—, —O—, —CH$_2$—(C$_1$-C$_3$)alkylene-, —NH—(C$_1$-C$_3$)alkylene-, —O—(C$_1$-C$_3$)alkylene-, =CH—(C$_2$-C$_3$)alkenylene-, —CH$_2$—(C$_2$-C$_3$)alkenylene-, —NH—(C$_2$-C$_3$)alkenylene-, —O—(C$_2$-C$_3$)alkenylene-, —CH$_2$—(C$_1$-C$_3$)alkylene-N(R$^{11}$)—, —NH—(C$_1$-C$_3$)alkylene-N(R$^{11}$)—, —O—(C$_1$-C$_3$)alkylene-N(R$^{11}$)—, —CH=N—, —CH$_2$—N(R$^{11}$)—, —CH$_2$—O—, or —CH$_2$—O—(C$_1$-C$_3$)alkylene- and Q$_a$, R$^1$, R$^2$, R$^{11}$, R$^{15}$, A, B, Z, and a are as defined for the compounds of formula (IB).

In another embodiment, the compound of formula (IB) is a compound of formula (IB"):

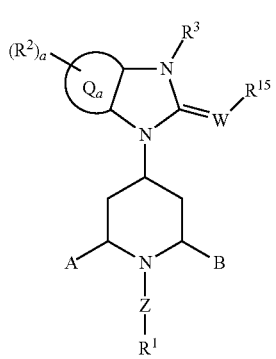

(IB")

or a pharmaceutically acceptable salt or solvate thereof where =W— is a double bond, =CH—, =N—, =CH—(C$_1$-C$_3$)alkylene-, =N—(C$_1$-C$_3$)alkylene-, =CH—(C$_2$-C$_3$)alkenylene-, =N—(C$_2$-C$_3$)alkenylene-, =CH—(C$_1$-C$_3$)alkylene-N(R$^{11}$)—, =N—(C$_1$-C$_3$)alkylene-N(R$^{11}$)—, =CH—N(R$^{11}$)—, =CH—O—, OR=CH—O—(C$_1$-C$_3$)alkylene- and Q$_a$, R$^1$, R$^2$, R$^3$, R$^{11}$, R$^{15}$, A, B, Z, and a are as defined for the compounds of formula (IB).

In another embodiment, =W— is a single bond, double bond, —CH$_2$—, =N—, —CH=N—, or —NH—. In another embodiment, =W— is a single bond, double bond, —CH$_2$—, =N—, or —CH=N—. In another embodiment, =W— is a single bond, double bond, —CH$_2$—, =N—, or —NH—. In another embodiment, =W— is a single bond, double bond, —CH$_2$—, —CH=N—, or —NH—. In another embodiment, =W— is a single bond, double bond, =N—, —CH=N—, or —NH—. In another embodiment, =W— is a single bond, —CH$_2$—, =N—, —CH=N—, or —NH—. In another embodiment, =W— is a double bond, —CH$_2$—, =N—, —CH=N—, or —NH—. In another embodiment, =W— is —CH$_2$—, =N—, —CH=N—, or —NH—. In another embodiment, =W— is a single bond or a double bond. In another embodiment, =W— is a single bond or —NH—. In another embodiment, =W— is a double bond or —CH$_2$—. In another embodiment, =W— is a —CH$_2$— or =N—. In another embodiment, =W— is a =N— or —CH=N—. In another embodiment, =W— is —CH=N— or —NH—. In another embodiment, =W— is a single bond. In another embodiment, =W— is a double bond. In another embodiment, =W— is —CH$_2$—. In another embodiment, =W— is =N—. In another embodiment, =W— is —CH=N—. In another embodiment, =W— is —NH—.

In another embodiment, R$^{15}$ is —OH, —C(=O)OH, —C(=O)OCH$_3$, —C(=O)OC$_2$H$_5$, —C(=O)NH$_2$, —CH$_2$C(=O)OH, —CH$_2$C(=O)OCH$_3$, —CH$_2$C(=O)OC$_2$H$_5$, —OC(=O)CH$_3$, —OC(=O)C$_2$H$_5$, —OCH$_2$C(=O)OH, —OCH$_2$C(=O)OCH$_3$, —OCH$_2$C(=O)OC$_2$H$_5$, —C(=NH)OCH$_3$, —C(=NH)OC$_2$H$_5$, —C(=NH)NHOCH$_3$, or —C(=NH)NHOC$_2$H$_5$. In another embodiment, R$^{15}$ is —C(=O)OH, —C(=O)OCH$_3$, —C(=O)OC$_2$H$_5$, —C(=O)NH$_2$, —CH$_2$C(=O)OH, —CH$_2$C(=O)OCH$_3$, —CH$_2$C(=O)OC$_2$H$_5$, —OC(=O)CH$_3$, —OC(=O)C$_2$H$_5$, —OCH$_2$C(=O)OH, —OCH$_2$C(=O)OCH$_3$, —OCH$_2$C(=O)OC$_2$H$_5$, —C(=NH)OCH$_3$, —C(=NH)OC$_2$H$_5$, —C(=NH)NHOCH$_3$, or —C(=NH)NHOC$_2$H$_5$. In another embodiment, R$^{15}$ is —C(=O)OCH$_3$, —C(=O)OC$_2$H$_5$, —C(=O)NH$_2$, —CH$_2$C(=O)OH, —CH$_2$C(=O)OCH$_3$, —CH$_2$C(=O)OC$_2$H$_5$, —OC(=O)CH$_3$, —OC(=O)C$_2$H$_5$, —OCH$_2$C(=O)OH, —OCH$_2$C(=O)OCH$_3$, —OCH$_2$C(=O)OC$_2$H$_5$, —C(=NH)OCH$_3$, —C(=NH)OC$_2$H$_5$, —C(=NH)NHOCH$_3$, or —C(=NH)NHOC$_2$H$_5$. In another embodiment, R$^{15}$ is —C(=O)OCH$_3$, —C(=O)NH$_2$, —CH$_2$C(=O)OH, —CH$_2$C(=O)OC$_2$H$_5$, —OC(=O)CH$_3$, —OCH$_2$C(=O)OH, —C(=NH)OC$_2$H$_5$, or —C(=NH)NHOCH$_3$.

In another embodiment, =W— is —CH$_2$—, =N—, —CH=N—, or —NH— and R$^{15}$ is —OH, —C(=O)OH, —C(=O)OCH$_3$, —C(=O)OC$_2$H$_5$, —CH$_2$C(=O)OH, —CH$_2$C(=O)OCH$_3$, —CH$_2$C(=O)OC$_2$H$_5$, —OC(=O)CH$_3$, —OC(=O)C$_2$H$_5$, —OCH$_2$C(=O)OH, —OCH$_2$C(=O)OCH$_3$, —OCH$_2$C(=O)OC$_2$H$_5$, —C(=NH)OCH$_3$, —C(=NH)OC$_2$H$_5$, —C(=NH)NHOCH$_3$, or —C(=NH)NHOC$_2$H$_5$. In another embodiment, =W— is —CH$_2$—, =N—, —CH=N—, or —NH— and R$^{15}$ is —C(=O)OH, —C(=O)OCH$_3$, —C(=O)OC$_2$H$_5$, —C(=O)NH$_2$, —CH$_2$C(=O)OH, —CH$_2$C(=O)OCH$_3$, —CH$_2$C(=O)OC$_2$H$_5$, —OC(=O)CH$_3$, —OC(=O)C$_2$H$_5$, —OCH$_2$C(=O)OH, —OCH$_2$C(=O)OCH$_3$, —OCH$_2$C(=O)OC$_2$H$_5$, —C(=NH)OCH$_3$, —C(=NH)OC$_2$H$_5$, —C(=NH)NHOCH$_3$, or —C(=NH)NHOC$_2$H$_5$. In another embodiment, =W— is —CH$_2$—, =N—, —CH=N—, or —NH— and R$^{15}$ is —C(=O)OCH$_3$, —C(=O)NH$_2$, —CH$_2$C(=O)OH, —CH$_2$C(=O)OC$_2$H$_5$, —OC(=O)CH$_3$, —OCH$_2$C(=O)OH, —C(=NH)OC$_2$H$_5$, or —C(=NH)NHOCH$_3$.

In another embodiment, =W— is —CH$_2$— or =N— and R$^{15}$ is —OH, —C(=O)OH, —C(=O)OCH$_3$, —C(=O)OC$_2$H$_5$, —C(=O)NH$_2$, —CH$_2$C(=O)OH, —CH$_2$C(=O)OCH$_3$, —CH$_2$C(=O)OC$_2$H$_5$, —OC(C)CH$_3$, —OC(=O)C$_2$H$_5$, —OCH$_2$C(=O)OH, —OCH$_2$C(=O)OCH$_3$, —OCH$_2$C(=O)OC$_2$H$_5$, —C(=NH)OCH$_3$, —C(=NH)OC$_2$H$_5$, —C(=NH)NHOCH$_3$, or —C(=NH)NHOC$_2$H$_5$. In another embodiment, =W— is —CH$_2$— or =N— and R$^{15}$ is —C(=O)OH, —C(=O)OCH$_3$, —C(=O)OC$_2$H$_5$, —C(=O)NH$_2$, —CH$_2$C(=O)OH, —CH$_2$C(=O)OCH$_3$, —CH$_2$C(=O)OC$_2$H$_5$, —OC(=O)CH$_3$, —OC(=O)C$_2$H$_5$, —OCH$_2$C(=O)OH, —OCH$_2$C(=O)OCH$_3$, —OCH$_2$C(=O)OC$_2$H$_5$, —C(=NH)OCH$_3$, —C(=NH)OC$_2$H$_5$, —C(=NH)NHOCH$_3$, or —C(=NH)NHOC$_2$H$_5$. In another embodiment, =W— is —CH$_2$— or =N— and R$^{15}$ is —C(=O)OCH$_3$, —C(=O)OC$_2$H$_5$, —C(=O)NH$_2$, —CH$_2$C(=O)OH, —CH$_2$C(=O)OCH$_3$, —CH$_2$C(=O)OC$_2$H$_5$, —OC(=O)CH$_3$, —OC(=O)C$_2$H$_5$, —OCH$_2$C(=O)OH, —OCH$_2$C(=O)OCH$_3$, —OCH$_2$C(=O)OC$_2$H$_5$, —C(=NH)OCH$_3$, —C(=NH)OC$_2$H$_5$, —C(=NH)NHOCH$_3$, or —C(=NH)NHOC$_2$H$_5$. In another embodiment, =W— is —CH$_2$— or =N— and R$^{15}$ is —C(=O)OCH$_3$, —C(=O)NH$_2$, —CH$_2$C(=O)OH, —CH$_2$C(=O)OC$_2$H$_5$, —OC(=O)CH$_3$, —OCH$_2$C(=O)OH, —C(=NH)OC$_2$H$_5$, or —C(=NH)NHOCH$_3$.

In another embodiment, =W— is —CH$_2$— or —CH=N— and R$^{15}$ is —OH, —C(=O)OH, —C(=O)OCH$_3$, —C(=O)OC$_2$H$_5$, —C(=O)NH$_2$, —CH$_2$C(=O)OH, —CH$_2$C(=O)OCH$_3$, —CH$_2$C(=O)OC$_2$H$_5$, —OC(=O)CH$_3$, —OC(=O)C$_2$H$_5$, —OCH$_2$C(=O)OH, —OCH$_2$C(=O)OCH$_3$, —OCH$_2$C(=O)OC$_2$H$_5$, —C(=NH)OCH$_3$, —C(=NH)OC$_2$H$_5$, —C(=NH)NHOCH$_3$, or —C(=NH)NHOC$_2$H$_5$. In another embodiment, =W— is —CH$_2$— or —CH=N— and R$^{15}$ is —C(=O)OH, —C(=O)OCH$_3$, —C(=O)OC$_2$H$_5$, —C(=O)NH$_2$, —CH$_2$C(=O)OH, —CH$_2$C(=O)OCH$_3$, —CH$_2$C(=O)OC$_2$H$_5$, —OC(=O)CH$_3$, —OC(=O)C$_2$H$_5$, —OCH$_2$C(=O)OH, —OCH$_2$C(=O)OCH$_3$, —OCH$_2$C(=O)OC$_2$H$_5$, —C(=NH)OCH$_3$, —C(=NH)OC$_2$H$_5$, —C(=NH)NHOCH$_3$, or —C(=NH)NHOC$_2$H$_5$. In another embodiment, =W— is —CH$_2$— or —CH=N— and R$^{15}$ is —C(=O)OCH$_3$, —C(=O)OC$_2$H$_5$, —CH$_2$C(=O)OH, —CH$_2$C(=O)OCH$_3$, —CH$_2$C(=O)OC$_2$H$_5$, —OC(=O)CH$_3$, OC(=O)C$_2$H$_5$, —OCH$_2$C(=O)OH, —OCH$_2$C(=O)OCH$_3$, —OCH$_2$C(=O)OC$_2$H$_5$, —C(=NH)OCH$_3$, —C(=NH)OC$_2$H$_5$, —C(=NH)NHOCH$_3$, or —C(=NH)NHOC$_2$H$_5$. In another embodiment, =W— is —CH$_2$— or —CH=N— and R$^{15}$ is —C(=O)OCH$_3$, —C(=O)NH$_2$, —CH$_2$C(=O)OH, —CH$_2$C(=O)OC$_2$H$_5$, —OC(=O)CH$_3$, —OCH$_2$C(=O)OH, —C(=NH)OC$_2$H$_5$, or —C(=NH)NHOCH$_3$.

In another embodiment, =W— is —CH$_2$— or —NH— and R$^{15}$ is —OH, —C(=O)OH, —C(=O)OCH$_3$, —C(=O)OC$_2$H$_5$, —C(=O)NH$_2$, —CH$_2$C(=O)OH, —CH$_2$C(=O)OCH$_3$, —CH$_2$C(=O)OC$_2$H$_5$, —OC(=O)CH$_3$, —OC(=O)C$_2$H$_5$, —OCH$_2$C(=O)OH, —OCH$_2$C(=O)OCH$_3$, —OCH$_2$C(=O)OC$_2$H$_5$, —C(=NH)OCH$_3$, —C(=NH)OC$_2$H$_5$, —C(=NH)NHOCH$_3$, or —C(=NH)NHOC$_2$H$_5$. In another embodiment, =W— is —CH$_2$— or —NH— and R$^{15}$ is —C(=O)OH, —C(=O)OCH$_3$, —C(=O)OC$_2$H$_5$, —C(=O)NH$_2$, —CH$_2$C(=O)OH, —CH$_2$C(=O)OCH$_3$, —CH$_2$C(=O)OC$_2$H$_5$, —OC(=O)CH$_3$, —OC(=O)C$_2$H$_5$, —OCH$_2$C(=O)OH, —OCH$_2$C(=O)OCH$_3$, —OCH$_2$C(=O)OC$_2$H$_5$, —C(=NH)OCH$_3$, —C(=NH)OC$_2$H$_5$, —C(=NH)NHOCH$_3$, or —C(=NH)NHOC$_2$H$_5$. In another embodiment, =W— is —CH$_2$— or —NH— and R$^{15}$ is —C(=O)OCH$_3$, —C(=O)OC$_2$H$_5$, —C(=O)NH$_2$, —CH$_2$C(=O)OH, —CH$_2$C(=O)OC$_2$H$_5$, —OC(=O)CH$_3$, —OCH$_2$C(=O)OH, —OCH$_2$C(=O)OCH$_3$, —OCH$_2$C(=O)OC$_2$H$_5$, —C(=NH)OCH$_3$, —C(=NH)OC$_2$H$_5$, —C(=NH)NHOCH$_3$, or —C(=NH)NHOC$_2$H$_5$. In another embodiment, =W— is —CH$_2$— or —NH— and R$^{15}$ is —C(=O)OCH$_3$, —C(=O)NH$_2$, —CH$_2$C(=O)OH, —CH$_2$C(=O)OC$_2$H$_5$, —OC(=O)CH$_3$, —OCH$_2$C(=O)OH, —C(=NH)OC$_2$H$_5$, or —C(=NH)NHOCH$_3$.

In another embodiment, =W— is =N— or —CH=N— and R$^{15}$ is —OH, —C(=O)OH, —C(=O)OCH$_3$, —C(=O)OC$_2$H$_5$, —C(=O)NH$_2$, —CH$_2$C(=O)OH, —CH$_2$C(=O)OCH$_3$, —CH$_2$C(=O)OC$_2$H$_5$, —OC(=O)CH$_3$, —OC(=O)C$_2$H$_5$, —OCH$_2$C(=O)OH, —OCH$_2$C(=O)OCH$_3$, —OCH$_2$C(=O)OC$_2$H$_5$, —C(=NH)OCH$_3$, —C(=NH)OC$_2$H$_5$, —C(=NH)NHOCH$_3$, or —C(=NH)NHOC$_2$H$_5$. In another embodiment, =W— is =N— or —CH=N— and R$^{15}$ is —C(=O)OCH$_3$, —C(=O)OC$_2$H$_5$, —C(=O)NH$_2$, —CH$_2$C(=O)OH, —CH$_2$C(=O)OCH$_3$, —CH$_2$C(=O)OC$_2$H$_5$, —OC(=O)CH$_3$, —OC(=O)C$_2$H$_5$, —OCH$_2$C(=O)OH, —OCH$_2$C(=O)OCH$_3$, —OCH$_2$C(=O)OC$_2$H$_5$, —C(=NH)OCH$_3$, —C(=NH)OC$_2$H$_5$, —C(=NH)NHOCH$_3$, or —C(=NH)NHOC$_2$H$_5$. In another embodiment, =W— is =N— or —CH=N— and R$^{15}$ is —C(=O)OCH$_3$, —C(=O)NH$_2$, —CH$_2$C(=O)OH, —CH$_2$C(=O)OC$_2$H$_5$, —OC(=O)CH$_3$, —OCH$_2$C(=O)OH, —C(=NH)OC$_2$H$_5$, or —C(=NH)NHOCH$_3$.

In another embodiment, =W— is =N— or —NH— and R$^{15}$ is —OH, —C(=O)OH, —C(=O)OCH$_3$, —C(=O)OC$_2$H$_5$, —C(=O)NH$_2$, —CH$_2$C(=O)OH, —CH$_2$C(=O)OCH$_3$, —CH$_2$C(=O)OC$_2$H$_5$, —OC(=O)CH$_3$, —OC(=O)C$_2$H$_5$, —OCH$_2$C(=O)OH, —OCH$_2$C(=O)OCH$_3$, —OCH$_2$C(=O)OC$_2$H$_5$, —C(=NH)OCH$_3$, —C(=NH)OC$_2$H$_5$, —C(=NH)NHOCH$_3$, or —C(=NH)NHOC$_2$H$_5$. In another embodiment, =W— is =N— or —NH— and R$^{15}$ is —C(=O)OH, —C(=O)OCH$_3$, —C(=O)OC$_2$H$_5$, —C(=O)NH$_2$, —CH$_2$C(=O)OH, —CH$_2$C(=O)OCH$_3$, —CH$_2$C(=O)OC$_2$H$_5$, —OC(=O)CH$_3$, —OC(=O)C$_2$H$_5$, —OCH$_2$C(=O)OH, —OCH$_2$C(=O)OCH$_3$, —OCH$_2$C(=O)OC$_2$H$_5$, —C(=NH)OCH$_3$, —C(=NH)OC$_2$H$_5$, —C(=NH)NHOCH$_3$, or —C(=NH)NHOC$_2$H$_5$. In another embodiment, =W— is =N— or —NH— and R$^{15}$ is —C(=O)OCH$_3$, —C(=O)OC$_2$H$_5$, —C(=O)NH$_2$, —CH$_2$C(=O)OH, —CH$_2$C(=O)OCH$_3$, —CH$_2$C(=O)OC$_2$H$_5$, —OC(=O)CH$_3$, —OC(=O)C$_2$H$_5$, —OCH$_2$C(=O)OH, —OCH$_2$C(=O)OCH$_3$, —OCH$_2$C(=O)OC$_2$H$_5$, —C(=NH)OCH$_3$, —C(=NH)OC$_2$H$_5$, —C(=NH)NHOCH$_3$, or —C(=NH)NHOC$_2$H$_5$. In another embodiment, =W— is =N— or —NH— and R$^{15}$ is —C(=O)OCH$_3$, —C(=O)NH$_2$, —CH$_2$C(=O)OH, —CH$_2$C(=O)OC$_2$H$_5$, —OC(=O)CH$_3$, —OCH$_2$C(=O)OH, —C(=NH)OC$_2$H$_5$, or —C(=NH)NHOCH$_3$.

In another embodiment, =W— is —CH=N— or —NH— and R$^{15}$ is —OH, —C(=O)OH, —C(=O)OCH$_3$, —C(=O)OC$_2$H$_5$, —C(=O)NH$_2$, —CH$_2$C(=O)OH, —CH$_2$C(=O)OCH$_3$, —CH$_2$C(=O)OC$_2$H$_5$, —OC(=O)CH$_3$, —OC(=O)C$_2$H$_5$, —OCH$_2$C(=O)OH, —OCH$_2$C(=O)OCH$_3$, —OCH$_2$C(=O)OC$_2$H$_5$, —C(=NH)OCH$_3$, —C(=NH)OC$_2$H$_5$, —C(=NH)NHOCH$_3$, or —C(=NH)NHOC$_2$H$_5$. In another embodiment, =W— is —CH=N— or —NH— and R$^{15}$ is —C(=O)OH, —C(=O)OCH$_3$, —C(=O)OC$_2$H$_5$, —C(=O)NH$_2$, —CH$_2$C(=O)OH, —CH$_2$C(=O)OCH$_3$, —CH$_2$C(=O)OC$_2$H$_5$, —OC(=O)CH$_3$, —OC(=O)C$_2$H$_5$, —OCH$_2$C(=O)OH, —OCH$_2$C(=O)OCH$_3$, —OCH$_2$C(=O)OC$_2$H$_5$, —C(=NH)OCH$_3$, —C(=NH)OC$_2$H$_5$, —C(=NH)NHOCH$_3$, or —C(=NH)NHOC$_2$H$_5$. In another embodiment, =W— is —CH=N— or —NH— and R$^{15}$ is —C(=O)OCH$_3$, —C(=O)OC$_2$H$_5$, —C(=O)NH$_2$, —CH$_2$C(=O)OH, —CH$_2$C(=O)OCH$_3$, —CH$_2$C(=O)OC$_2$H$_5$, —OC(=O)CH$_3$, —OC(=O)C$_2$H$_5$, —OCH$_2$C(=O)OH, —OCH$_2$C(=O)OCH$_3$, —OCH$_2$C(=O)OC$_2$H$_5$, —C(=NH)OCH$_3$, —C(=NH)OC$_2$H$_5$, —C(=NH)NHOCH$_3$, or —C(=NH)NHOC$_2$H$_5$. In another embodiment, =W— is —CH=N— or —NH— and R$^{15}$ is —C(=O)OCH$_3$, —C(=O)NH$_2$, —CH$_2$C(=O)OH, —CH$_2$C(=O)OC$_2$H$_5$, —OC(=O)CH$_3$, —OCH$_2$C(=O)OH, —C(=NH)OC$_2$H$_5$, or —C(=NH)NHOCH$_3$.

In another embodiment, =W— is —CH$_2$— and R$^{15}$ is —OH, —C(=O)OH, —C(=O)OCH$_3$, —C(=O)OC$_2$H$_5$, —C(=O)NH$_2$, —CH$_2$C(=O)OH, —CH$_2$C(=O)OCH$_3$, —CH$_2$C(=O)OC$_2$H$_5$, —OC(=O)CH$_3$, —OC(=O)C$_2$H$_5$, —OCH$_2$C(=O)OH, —OCH$_2$C(=O)OCH$_3$, —OCH$_2$C —C(=O)OC$_2$H$_5$, —C(=NH)OCH$_3$, —C(=NH)OC$_2$H$_5$, —C(=NH)NHOCH$_3$, or —C(=NH)NHOC$_2$H$_5$. In another embodiment, =W— is —CH$_2$— and R$^{15}$ is —C(=O)OH, —C(=O)OCH$_3$, —C(=O)OC$_2$H$_5$, —C(=O)NH$_2$, —CH$_2$C(=O)OH, —CH$_2$C(=O)OCH$_3$, —CH$_2$C(=O)OC$_2$H$_5$, —OC(=O)CH$_3$, —OC(=O)C$_2$H$_5$, —OCH$_2$C(=O)OH, —OCH$_2$C(=O)OCH$_3$, —OCH$_2$C(=O)OC$_2$H$_5$, —C(=NH)OCH$_3$, —C(=NH)OC$_2$H$_5$, —C(=NH)NHOCH$_3$, or —C(=NH)NHOC$_2$H$_5$. In another embodiment, =W— is —CH$_2$— and R$^{15}$ is —C(=O)OCH$_3$, —C(=O)OC$_2$H$_5$, —C(=O)NH$_2$, —CH$_2$C(=O)OH, —CH$_2$C(=O)OCH$_3$, —CH$_2$C(=O)OC$_2$H$_5$, —OC(=O)CH$_3$, —OC(=O)C$_2$H$_5$, —OCH$_2$C(=O)OH, —OCH$_2$C(=O)OCH$_3$, —OCH$_2$C(=O)OC$_2$H$_5$, —C(=NH)OCH$_3$, —C(=NH)OC$_2$H$_5$, —C(=NH)NHOCH$_3$, or —C(=NH)NHOC$_2$H$_5$. In another embodiment, =W— is —CH$_2$— and R$^{15}$ is —C(=O)OCH$_3$, —C(=O)NH$_2$, —CH$_2$C(=O)OH, —CH$_2$C(=O)OC$_2$H$_5$, —OC(=O)CH$_3$, —OCH$_2$C(=O)OH, —C(=NH)OC$_2$H$_5$, or —C(=NH)NHOCH$_3$.

In another embodiment, =W— is =N— and R$^{15}$ is —OH, —C(=O)OH, —C(=O)OCH$_3$, —C(=O)OC$_2$H$_5$, —C(=O)NH$_2$, —CH$_2$C(=O)OH, —CH$_2$C(=O)OCH$_3$, —CH$_2$C(=O)OC$_2$H$_5$, —OC(=O)CH$_3$, —OC(=O)C$_2$H$_5$, —OCH$_2$C(=O)OH, —OCH$_2$C(=O)OCH$_3$, —OCH$_2$C(=O)OC$_2$H$_5$, —C(=NH)OCH$_3$, —C(=NH)OC$_2$H$_5$, —C(=NH)NHOCH$_3$, or —C(=NH)NHOC$_2$H$_5$. In another embodiment, =W— is =N— and R$^{15}$ is —C(=O)OH, —C(=O)OCH$_3$, —C(=O)OC$_2$H$_5$, —C(=O)NH$_2$, —CH$_2$C(=O)OH, —CH$_2$C(=O)OCH$_3$, —CH$_2$C(=O)OC$_2$H$_5$, —OC(=O)CH$_3$, —OC(=O)C$_2$H$_5$, —OCH$_2$C(=O)OH, —OCH$_2$C(=O)OCH$_3$, —OCH$_2$C(=O)OC$_2$H$_5$, —C(=NH)OCH$_3$, —C(=NH)OC$_2$H$_5$, —C(=NH)NHOCH$_3$, or —C(=NH)NHOC$_2$H$_5$. In another embodiment, =W— is =N— and R$^{15}$ is —C(=O)OCH$_3$, —C(=O)OC$_2$H$_5$, —C(=O)NH$_2$, —CH$_2$C(=O)OH, —CH$_2$C(=O)OCH$_3$, —CH$_2$C(=O)OC$_2$H$_5$, —OC(=O)CH$_3$, —OC(=O)C$_2$H$_5$, —OCH$_2$C(=O)OH, —OCH$_2$C(=O)OCH$_3$, —OCH$_2$C(=O)OC$_2$H$_5$, —C(=NH)OCH$_3$, —C(=NH)OC$_2$H$_5$, —C(=NH)NHOCH$_3$, or —C(=NH)NHOC$_2$H$_5$. In another embodiment, =W— is =N— and R$^{15}$ is —C(=O)OCH$_3$, —C(=O)NH$_2$, —CH$_2$C(=O)OH, —CH$_2$C(=O)OC$_2$H$_5$, —OC(=O)CH$_3$, —OCH$_2$C(=O)OH, —C(=NH)OC$_2$H$_5$, or —C(=NH)NHOCH$_3$.

In another embodiment, =W— is —CH=N— and R$^{15}$ is —OH, —C(=O)OH, —C(=O)OCH$_3$, —C(=O)OC$_2$H$_5$, —C(=O)NH$_2$, —CH$_2$C(=O)OH, —CH$_2$C(=O)OCH$_3$, —CH$_2$C(=O)OC$_2$H$_5$, —OC(=O)CH$_3$, —OC(=O)C$_2$H$_5$, —OCH$_2$C(=O)OH, —OCH$_2$C(=O)OCH$_3$, —OCH$_2$C(=O)OC$_2$H$_5$, —C(=NH)OCH$_3$, —C(=NH)OC$_2$H$_5$, —C(=NH)NHOCH$_3$, or —C(=NH)NHOC$_2$H$_5$. In another embodiment, =W— is —CH=N— and R$^{15}$ is —C(=O)OH, —C(=O)OCH$_3$, —C(=O)OC$_2$H$_5$, —C(=O)NH$_2$, —CH$_2$C(=O)OH, —CH$_2$C(=O)OCH$_3$, —CH$_2$C(=O)OC$_2$H$_5$, —OC(=O)CH$_3$, —OC(=O)C$_2$H$_5$, —OCH$_2$C(=O)OH, —OCH$_2$C(=O)OCH$_3$, —OCH$_2$C(=O)OC$_2$H$_5$, —C(=NH)OCH$_3$, —C(=NH)OC$_2$H$_5$, —C(=NH)NHOCH$_3$, or —C(=NH)NHOC$_2$H$_5$. In another embodiment, =W— is —CH=N— and R$^{15}$ is —C(=O)OCH$_3$, —C(=O)OC$_2$H$_5$, —C(=O)NH$_2$, —CH$_2$C(=O)OH, —CH$_2$C(=O)OCH$_3$, —CH$_2$C(=O)OC$_2$H$_5$, —OC(=O)CH$_3$, —OC(=O)C$_2$H$_5$, —OCH$_2$C(=O)OH, —OCH$_2$C(=O)OCH$_3$, —OCH$_2$C(=O)OC$_2$H$_5$, —C(=NH)OCH$_3$, —C(=NH)OC$_2$H$_5$, —C(=NH)NHOCH$_3$, or —C(=NH)NHOC$_2$H$_5$. In another embodiment, =W— is —CH=N— and R$^{15}$ is —C(=O)OCH$_3$, —C(=O)NH$_2$, —CH$_2$C(=O)OH, —CH$_2$C(=O)OC$_2$H$_5$, —OC(=O)CH$_3$, —OCH$_2$C(=O)OH, —C(=NH)OC$_2$H$_5$, or —C(=NH)NHOCH$_3$.

In another embodiment, =W— is —NH— and R$^{15}$ is —OH, —C(=O)OH, —C(=O)OCH$_3$, —C(=O)OC$_2$H$_5$, —C(=O)NH$_2$, —CH$_2$C(=O)OH, —CH$_2$C(=O)OCH$_3$, —CH$_2$C(=O)OC$_2$H$_5$, —OC(=O)CH$_3$, —OC(=O)C$_2$H$_5$, —OCH$_2$C(=O)OH, —OCH$_2$C(=O)OCH$_3$, —OCH$_2$C(=O)OC$_2$H$_5$, —C(=NH)OCH$_3$, —C(=NH)OC$_2$H$_5$, —C(=NH)NHOCH$_3$, or —C(=NH)NHOC$_2$H$_5$. In another embodiment, =W— is —NH— and R$^{15}$ is —C(=O)OH, —C(=O)OCH$_3$, —C(=O)OC$_2$H$_5$, —C(=O)NH$_2$, —CH$_2$C(=O)OH, —CH$_2$C(=O)OCH$_3$, —CH$_2$C(=O)OC$_2$H$_5$, —OC(=O)CH$_3$, —OC(=O)C$_2$H$_5$, —OCH$_2$C(=O)OH, —OCH$_2$C(=O)OCH$_3$, —OCH$_2$C(=O)OC$_2$H$_5$, —C(=NH)OCH$_3$, —C(=NH)OC$_2$H$_5$, —C(=NH)NHOCH$_3$, or —C(=NH)NHOC$_2$H$_5$. In another embodiment, =W— is —NH— and R$^{15}$ is —C(=O)OCH$_3$, —C(=O)OC$_2$H$_5$, —C(=O)NH$_2$, —CH$_2$C(=O)OH, —CH$_2$C(=O)OCH$_3$, —CH$_2$C(=O)OC$_2$H$_5$, —OC(=O)CH$_3$, —OC(=O)C$_2$H$_5$, —OCH$_2$C(=O)OH, —OCH$_2$C(=O)OCH$_3$, —OCH$_2$C(=O)OC$_2$H$_5$, —C(=NH)OCH$_3$, —C(=NH)OC$_2$H$_5$, —C(=NH)NHOCH$_3$, or —C(=NH)NHOC$_2$H$_5$. In another embodiment, =W— is —NH— and R$^{15}$ is —C(=O)OCH$_3$, —C(=O)NH$_2$, —CH$_2$C(=O)OH, —CH$_2$C(=O)OC$_2$H$_5$, —OC(=O)CH$_3$, —OCH$_2$C(=O)OH, —C(=NH)OC$_2$H$_5$, or —C(=NH)NHOCH$_3$.

In another embodiment, when =W— is a single bond and R$^{15}$ is (C$_1$)alkyl, R$^8$ is not =O or =S. In another embodiment, when =W— is a single bond and R$^{15}$ is (C$_1$)alkyl, R$^8$ is not —OH or —SH. In another embodiment, when =W— is a single bond and R$^{15}$ is (C$_1$)alkyl, R$^8$ is not halo. In another embodiment, when =W— is a single bond and R$^{15}$ is (C$_1$)alkyl, R$^8$ is not =O, =S, —OH, or —SH. In another embodiment, when =W— is a single bond and R$^{15}$ is (C$_1$)alkyl, R$^8$ is not =O, =S, or halo. In another embodiment, when =W— is a single bond and R$^{15}$ is (C$_1$)alkyl, R$^8$ is not —OH, —SH, or halo. In another embodiment, when =W— is a single bond and R$^{15}$ is (C$_1$)alkyl, R$^8$ is not =O, =S, —OH, —SH, or halo.

Each and every embodiment set forth in Sections 4.1, 4.2a, 4.2b, and 4.2d relating to the piperidine ring and the A, B, Z, and R$^1$ substituents thereto, and to the Q$_a$, R$^2$, R$^3$, R$^{11}$, and a variable groups referenced therein also relate to the Substituted Benzimidazole-Type Piperidine Compounds in this section; therefore, those embodiments are not repeated here but are instead incorporated by reference in their entirety.

4.3b Substituted Benzimidazole-Type Piperidine Compounds of Formulae (IB), (IB'), and (IB")

In another embodiment, R$^{15}$, when present, is selected from:

(a) —H; and (b) —(C$_1$-C$_2$)alkyl which is substituted with 1, 2, or 3 independently selected R$^8$ groups; and (c) —(C$_3$-C$_4$)alkyl and —O—(C$_1$-C$_4$)alkyl, each of which is unsubstituted or substituted with 1, 2, 3, or 4 independently selected R$^8$ groups;

(d) provided that when is a single bond, a double bond, or —O—, R$^{15}$ is not —H.

In another embodiment, each R$^8$ is independently —(C$_1$-C$_4$)alkyl, —(C$_2$-C$_6$)alkenyl, —(C$_2$-C$_6$)alkynyl, -(5- or 6-membered)heteroaryl, —(C$_1$-C$_6$)alkyl-C(=O)OR$^9$, —N(R$^9$)(C$_1$-C$_6$)alkyl-C(=O)OR$^9$, —OR$^9$, —SR$^9$, —C(halo)$_3$, —CH(halo)$_2$, —CH$_2$(halo), —CN, =O, =S, =N(R$^9$), —N$_3$, —NO$_2$, —CH=N(R$^9$), —N(R$^9$)$_2$, —N(R$^9$)OR$^9$, —N(R$^9$)S(=O)R$^{12}$, —N(R$^9$)S(=O)$_2$R$^{12}$, —N(R$^9$)C(=O)R$^{12}$, —N(R$^9$)C(=O)N(T$^1$)(T$^2$), —N(R$^9$)C(=O)

OR$^{12}$, —C(=O)R$^9$, —C(=O)N(T$^1$)(T$^2$), —OC(=O)R$^9$, —OC(=O)N(T$^1$)(T$^2$), —OC(=O)OR$^9$, or —S(=O)R$^9$.

In another embodiment, R$^{11}$ is —H or —(C$_1$-C$_4$)alkyl which is substituted with —OH or —(C$_1$-C$_4$)alkoxy. In another embodiment, R$^{11}$ is —H or —(C$_1$-C$_4$)alkyl which is substituted with —OH. In another embodiment, R$^{11}$ is —H or —(C$_1$-C$_4$)alkyl which is substituted with —(C$_1$-C$_4$)alkoxy. In another embodiment, R$^{11}$ is —H or —CH$_3$ which is substituted with —OH or —(C$_1$-C$_4$)alkoxy. In another embodiment, R$^{11}$ is —H or —CH$_3$ which is substituted with —OH. In another embodiment, R$^{11}$ is —H or —CH$_3$ which is substituted with —(C$_1$-C$_4$)alkoxy. In another embodiment, R$^{11}$ is —H or —CH$_2$CH$_3$ which is substituted with —OH or —(C$_1$-C$_4$)alkoxy. In another embodiment, R$^{11}$ is —H or —CH$_2$CH$_3$ which is substituted with —OH. In another embodiment, R$^{11}$ is —H or —CH$_2$CH$_3$ which is substituted with —(C$_1$-C$_4$)alkoxy. In another embodiment, R$^{11}$ is —H or —CH(CH$_3$)$_2$ which is substituted with —OH or —(C$_1$-C$_4$)alkoxy. In another embodiment, R$^{11}$ is —H or —CH(CH$_3$)$_2$ which is substituted with —OH. In another embodiment, R$^{11}$ is —H or —CH(CH$_3$)$_2$ which is substituted with —(C$_1$-C$_4$)alkoxy. In another embodiment, R$^{11}$ is —H or —(C$_1$-C$_4$)alkyl which is unsubstituted. In another embodiment, R$^{11}$ is —H or —CH$_3$. In another embodiment, R$^{11}$ is —H or —CH$_2$CH$_3$. In another embodiment, R$^{11}$ is —H or —CH(CH$_3$)$_2$. In another embodiment, R$^{11}$ is —CH$_3$. In another embodiment, R$^{11}$ is —CH$_2$CH$_3$. In another embodiment, R$^{11}$ is —CH(CH$_3$)$_2$.

Each and every embodiment set forth in Sections 4.1, 4.2a, 4.2b, 4.2d, and 4.3a relating to the piperidine ring and the A, B, Z, and R$^1$ substituents thereto, and to the W, Q$_a$, R$^2$, R$^3$, R$^{11}$, R$^{15}$, and a variable groups referenced therein also relate to the Substituted Benzimidazole-Type Piperidine Compounds in this section; therefore, those embodiments are not repeated here but are instead incorporated by reference in their entirety.

4.3c Substituted Benzimidazole-Type Piperidine Compounds of Formula (IB)

In other embodiments, the Substituted Benzimidazole-Type Piperidine Compound of Formula (IB) has one of the formulae of Table 17.

TABLE 17

| Formula | Compound |
|---------|----------|
| IBA | 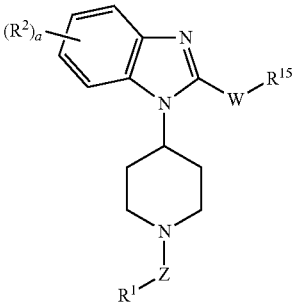 |
| IBB | 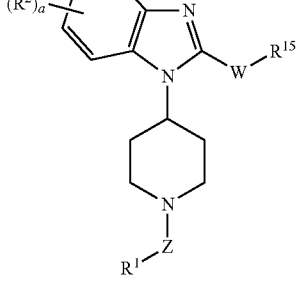 |
| IBC | 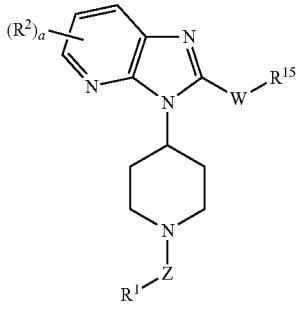 |
| IBD | 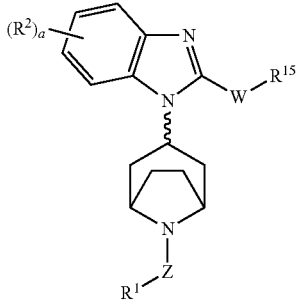 |
| IBD$_1$† | 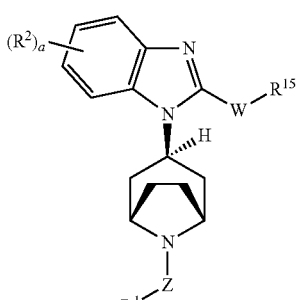 |
| IBD$_2$‡ | 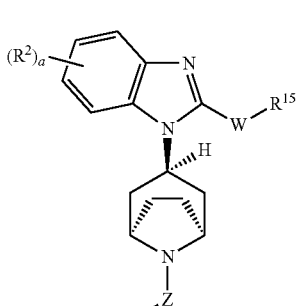 |

TABLE 17-continued

| Formula | Compound |
|---|---|
| IBE | (structure) |
| IBE₁† | (structure) |
| IBE₂‡ | (structure) |
| IBF | (structure) |
| IBF₁† | (structure) |
| IBF₂‡ | (structure) |
| IBG | (structure) |
| IBG₁† | (structure) |
| IBG₂‡ | (structure) |
| IBH | (structure) |

TABLE 17-continued

| Formula | Compound |
| --- | --- |
| IBH₁† | |
| IBH₂‡ | |
| IBJ | |
| IBJ₁† | |
| IBJ₂‡ | |
| IBK | |
| IBK₁† | |
| IBK₂‡ | |
| IBL | |
| IBL₁† | |

TABLE 17-continued

| Formula | Compound |
|---|---|
| IBL$_2$‡ | (structure) |
| IBM | (structure) |
| IBM$_1$† | (structure) |
| IBM$_2$‡ | (structure) |

†indicates the 5-membered, nitrogen-containing ring that is fused to the benzo or pyridino is in the endo-configuration with respect to the alkyl or —CH$_2$—O—CH$_2$— bridge.
‡indicates the 5-membered, nitrogen-containing ring that is fused to the benzo or pyridino is in the exo-configuration with respect to the alkyl or —CH$_2$—O—CH$_2$— bridge.

where $R^1$, $R^2$, $R^{11}$, $R^{15}$, Z, and a are as defined above for the Substituted Benzimidazole-Type Piperidine Compounds of Formula (IB) and —W— is a single bond, —CH$_2$—, —NH—, —O—, —CH$_2$—(C$_1$-C$_3$)alkylene-, —NH—(C$_1$-C$_3$)alkylene-, —O—(C$_1$-C$_3$)alkylene-, —CH$_2$—(C$_2$-C$_3$)alkenylene-, —NH—(C$_2$-C$_3$)alkenylene-, —O—(C$_2$-C$_3$)alkenylene-, —CH$_2$—(C$_1$-C$_3$)alkylene-N(R$^{11}$)—, —NH—(C$_1$-C$_3$)alkylene-N(R$^{11}$)—, —O—(C$_1$-C$_3$)alkylene-N(R$^{11}$)—, —CH═N—, —CH$_2$—N(R$^{11}$)—, —CH$_2$—O—, or —CH$_2$—O—(C$_1$-C$_3$)alkylene-.

4.4 Definitions

As used in connection with the Substituted Benzimidazole-Type Piperidine Compounds herein, the terms used herein have the following meaning:

"—(C$_1$-C$_{10}$)alkyl" means a straight chain or branched non-cyclic hydrocarbon having 1, 2, 3, 4, 5, 6, 7, 8, 9, or 10 carbon atoms. Representative straight chain —(C$_1$-C$_{10}$) alkyls include -methyl, -ethyl, -n-propyl, -n-butyl, -n-pentyl, -n-hexyl, -n-heptyl, -n-octyl, -n-nonyl, and -n-decyl. A branched alkyl means that one or more straight chain —(C$_1$-C$_8$)alkyl groups, such as methyl, ethyl or propyl, replace one or both hydrogens in a —CH$_2$— group of a straight chain alkyl. A branched non-cyclic hydrocarbon means that one or more straight chain —(C$_1$-C$_{10}$)alkyl groups, such as methyl, ethyl or propyl, replace one or both hydrogens in a —CH$_2$— group of a straight chain non-cyclic hydrocarbon. Representative branched —(C$_1$-C$_{10}$)alkyls include -iso-propyl, -sec-butyl, -iso-butyl, -tert-butyl, -iso-pentyl, -neopentyl, 1-methylbutyl, 2-methylbutyl, 3-methylbutyl, 1,1-dimethylpropyl, 1,2-dimethylpropyl, 1-methylpentyl, 2-methylpentyl, 3-methylpentyl, 4-methylpentyl, 1-ethylbutyl, 2-ethylbutyl, 3-ethylbutyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-methylhexyl, 2-methylhexyl, 3-methylhexyl, 4-methylhexyl, 5-methylhexyl, 1,2-dimethylpentyl, 1,3-dimethylpentyl, 1,2-dimethylhexyl, 1,3-dimethylhexyl, 3,3-dimethylhexyl, 1,2-dimethylheptyl, 1,3-dimethylheptyl, and 3,3-dimethylheptyl.

In connection with the Z group, "—(C$_1$-C$_{10}$)alkylene-" means a straight chain or branched non-cyclic hydrocarbon moiety having 1, 2, 3, 4, 5, 6, 7, 8, 9, or 10 carbon atoms where two hydrogen atoms on the same or a different carbon atom of the moiety are each figuratively removed and replaced by a bond to one of the two adjoining groups. Representative —(C$_1$-C$_{10}$)alkylene- moieties include meth-1,1-diyl, eth-1,1-diyl, eth-1,2-diyl, n-prop-1,1-diyl, n-prop-1,2-diyl, n-prop-1,3-diyl, n-but-1,1-diyl, n-but-1,2-diyl, n-but-1,3-diyl, n-but-1,4-diyl, iso-but-1,1-diyl, iso-but-1,2-diyl, iso-but-1,3-diyl, n-deca-1,1-diyl, n-deca-1,2-diyl, n-deca-1,3-diyl, n-deca-1,4-diyl, n-deca-1,5-diyl, n-deca-1,6-diyl, n-deca-1,7-diyl, n-deca-1,8-diyl, n-deca-1,9-diyl, n-deca-1,10-diyl, and the like.

"—(C$_1$-C$_6$)alkyl" means a straight chain or branched non-cyclic hydrocarbon having 1, 2, 3, 4, 5, or 6 carbon atoms. Representative straight chain —(C$_1$-C$_6$)alkyls include -methyl, -ethyl, -n-propyl, -n-butyl, -n-pentyl, and -n-hexyl. Representative branched —(C$_1$-C$_6$)alkyls include -iso-propyl, -sec-butyl, -iso-butyl, -tert-butyl, -iso-pentyl, -neopentyl, 1-methylbutyl, 2-methylbutyl, 3-methylbutyl, 1,1-dimethylpropyl, 1,2-dimethylpropyl, 1-methylpentyl, 2-methylpentyl, 3-methylpentyl, 4-methylpentyl, 1-ethylbutyl, 2-ethylbutyl, 3-ethylbutyl, 1,1-dimethylbutyl, 1,2-dimethylbutyl, 1,3-dimethylbutyl, 2,2-dimethylbutyl, 2,3-dimethylbutyl, and 3,3-dimethylbutyl.

In connection with the Z group, "—(C$_1$-C$_6$)alkylene-" means a straight chain or branched non-cyclic hydrocarbon moiety having 1, 2, 3, 4, 5, or 6 carbon atoms where two hydrogen atoms on the same or a different carbon atom of the moiety are each figuratively removed and replaced by a bond to one of the two adjoining groups. Representative —(C$_1$-C$_6$)alkylene- moieties include meth-1,1-diyl, eth-1,1-diyl, eth-1,2-diyl, n-prop-1,1-diyl, n-prop-1,2-diyl, n-prop-1,3-diyl, n-but-1,1-diyl, n-but-1,2-diyl, n-but-1,3-diyl, n-but-1,4-diyl, iso-but-1,1-diyl, iso-but-1,2-diyl, iso-but-1,3-diyl, and the like.

"—$(C_1-C_4)$alkyl" means a straight chain or branched non-cyclic hydrocarbon having 1, 2, 3, or 4 carbon atoms. Representative straight chain —$(C_1-C_4)$alkyls include -methyl, -ethyl, -n-propyl, and -n-butyl. Representative branched —$(C_1-C_4)$alkyls include -iso-propyl, -sec-butyl, -iso-butyl, and -tert-butyl.

"—$(C_3-C_4)$alkyl" means a straight chain or branched non-cyclic hydrocarbon having 3 or 4 carbon atoms. Representative straight chain —$(C_3-C_4)$alkyls include -n-propyl and -n-butyl. Representative branched —$(C_3-C_4)$alkyls include -iso-propyl, -sec-butyl, -iso-butyl, and -tert-butyl.

In connection with the Z group, "—$(C_1-C_4)$alkylene-" means a straight chain or branched non-cyclic hydrocarbon moiety having 1, 2, 3, or 4 carbon atoms where two hydrogen atoms on the same or a different carbon atom of the moiety are each figuratively removed and replaced by a bond to one of the two adjoining groups. Representative —$(C_1-C_4)$alkylene- moieties include meth-1,1-diyl, eth-1,1-diyl, eth-1,2-diyl, n-prop-1,1-diyl, n-prop-1,2-diyl, n-prop-1,3-diyl, n-but-1,2-diyl, n-but-1,3-diyl, n-but-1,4-diyl, and the like.

"—$(C_1-C_3)$alkyl" means a straight chain or branched non-cyclic hydrocarbon having 1, 2, or 3 carbon atoms. Representative straight chain —$(C_1-C_3)$alkyls include -methyl, -ethyl, -n-propyl. Representative branched —$(C_1-C_3)$alkyls include -iso-propyl.

In connection with the Z group and the ---W— group, "—$(C_1-C_3)$alkylene-" means a straight chain or branched non-cyclic hydrocarbon moiety having 1, 2, or 3 carbon atoms where two hydrogen atoms on the same or a different carbon atom of the moiety are each figuratively removed and replaced by a bond to one of the two adjoining groups. Representative —$(C_1-C_3)$alkylene- moieties include meth-1,1-diyl, eth-1,1-diyl, eth-1,2-diyl, n-prop-1,1-diyl, n-prop-1,2-diyl, n-prop-1,3-diyl, and the like.

"—$(C_1-C_2)$alkyl" means a straight chain non-cyclic hydrocarbon having 1 or 2 carbon atoms. Representative —$(C_1-C_2)$alkyls include -methyl and -ethyl.

In connection with the Z group, "—$(C_1-C_2)$alkylene-" means a straight chain non-cyclic hydrocarbon moiety having 1 or 2 carbon atoms where two hydrogen atoms on the same or a different carbon atom of the moiety are each figuratively removed and replaced by a bond to one of the two adjoining groups. Representative —$(C_1-C_2)$alkylene- moieties include meth-1,1-diyl, eth-1,1-diyl, and eth-1,2-diyl.

"—$(C_2-C_{10})$alkenyl" means a straight chain or branched non-cyclic hydrocarbon having 2, 3, 4, 5, 6, 7, 8, 9, or 10 carbon atoms and including at least one carbon-carbon double bond. A branched alkenyl means that one or more straight chain —$(C_1-C_8)$alkyl groups, such as methyl, ethyl or propyl, replace one or both hydrogens in a —$CH_2$— or —CH= group of a straight chain alkenyl. Representative straight chain and branched $(C_2-C_{10})$alkenyls include -vinyl, -allyl, -1-butenyl, -2-butenyl, -iso-butylenyl, -1-pentenyl, -2-pentenyl, -3-methyl-1-butenyl, -2-methyl-2-butenyl, -2,3-dimethyl-2-butenyl, -1-hexenyl, -2-hexenyl, -3-hexenyl, -1-heptenyl, -2-heptenyl, -3-heptenyl, -1-octenyl, -2-octenyl, -3-octenyl, -1-nonenyl, -2-nonenyl, -3-nonenyl, -1-decenyl, -2-decenyl, -3-decenyl, and the like.

In connection with the Z group, "—$(C_2-C_{10})$alkenylene-" means a straight chain or branched non-cyclic hydrocarbon moiety having 2, 3, 4, 5, 6, 7, 8, 9, or 10 carbon atoms and including at least one carbon-carbon double bond where two hydrogen atoms on the same or a different carbon atom of the moiety are each figuratively removed and replaced by a bond to one of the two adjoining groups. Representative —$(C_2-C_{10})$alkenylene- moieties include vin-1,1-diyl, vin-1,2-diyl, prop-1-en-1,1-diyl, prop-1-en-1,2-diyl, prop-1-en-1,3-diyl, prop-2-en-1,1-diyl, prop-2-en-1,3-diyl, 2-methyl-prop-1-en-3,3-diyl, but-2-en-1,1-diyl, but-1-en-4,4-diyl, but-1-en-1,4-diyl, but-2-en-1,4-diyl, but-3-en-1,4-diyl, but-1-en-1,3-diyl, and the like.

"—$(C_2-C_6)$alkenyl" means a straight chain or branched non-cyclic hydrocarbon having 2, 3, 4, 5, or 6 carbon atoms and including at least one carbon-carbon double bond. Representative straight chain and branched $(C_2-C_6)$alkenyls include -vinyl, -allyl, -1-butenyl, -2-butenyl, -iso-butylenyl, -1-pentenyl, -2-pentenyl, -3-methyl-1-butenyl, -2-methyl-2-butenyl, -2,3-dimethyl-2-butenyl, -hexenyl, -2-hexenyl, -3-hexenyl, and the like.

In connection with the Z group, "—$(C_2-C_6)$alkenylene-" means a straight chain or branched non-cyclic hydrocarbon moiety having 2, 3, 4, 5, or 6 carbon atoms and including at least one carbon-carbon double bond where two hydrogen atoms on the same or a different carbon atom of the moiety are each figuratively removed and replaced by a bond to one of the two adjoining groups. Representative —$(C_2-C_6)$alkenylene- moieties include vin-1,1-diyl, vin-1,2-diyl, prop-1-en-1,2-diyl, prop-1-en-1,3-diyl, prop-2-en-1,1-diyl, prop-2-en-1,3-diyl, 2-methylprop-1-en-3,3-diyl, but-1-en-1,4-diyl, but-2-en-1,4-diyl, but-3-en-1,4-diyl, but-1-en-1,3-diyl, and the like.

"—$(C_2-C_3)$alkenyl" means a straight chain non-cyclic hydrocarbon having 2 or 3 carbon atoms and including at least one carbon-carbon double bond. Representative $(C_2-C_3)$alkenyls include -vinyl, -allyl, and 1-prop-1-enyl.

In connection with the Z group and the ---W— group, "—$(C_2-C_3)$alkenylene-" means a straight chain or branched non-cyclic hydrocarbon moiety having 2 or 3 carbon atoms and including at least one carbon-carbon double bond where two hydrogen atoms on the same or a different carbon atom of the moiety are each figuratively removed and replaced by a bond to one of the two adjoining groups. Representative —$(C_2-C_3)$alkenylene- moieties include vin-1,1-diyl, vin-1,2-diyl, prop-1-en-1,1-diyl, prop-1-en-1,2-diyl, prop-1-en-1,3-diyl, prop-2-en-1,1-diyl, and prop-2-en-1,3-diyl.

"—$(C_1-C_{10})$alkynyl" means a straight chain or branched non-cyclic hydrocarbon having 2, 3, 4, 5, 6, 7, 8, 9, or 10 carbon atoms and including at least one carbon-carbon triple bond. A branched alkynyl means that one or more straight chain —$(C_1-C_8)$alkyl groups, such as methyl, ethyl or propyl, replace one or both hydrogens in a —$CH_2$— group of a straight chain alkynyl. Representative straight chain and branched —$(C_2-C_{10})$alkynyls include -acetylenyl, -propynyl, -1-butynyl, -2-butynyl, -1-pentynyl, -2-pentynyl, -3-methyl-1-butynyl, -4-pentynyl, -1-hexynyl, -2-hexynyl, -5-hexynyl, -1-heptynyl, -2-heptynyl, -6-heptynyl, -1-octynyl, -2-octynyl, -7-octynyl, -1-nonynyl, -2-nonynyl, -8-nonynyl, -1-decynyl, -2-decynyl, -9-decynyl, and the like.

"—$(C_2-C_6)$alkynyl" means a straight chain or branched non-cyclic hydrocarbon having 2, 3, 4, 5, or 6 carbon atoms and including at least one carbon-carbon triple bond. Representative straight chain and branched $(C_2-C_6)$alkynyls include -acetylenyl, -propynyl, -1-butynyl, -2-butynyl, -1-pentynyl, -2-pentynyl, -3-methyl-1-butynyl, -4-pentynyl, -1-hexynyl, -2-hexynyl, -5-hexynyl, and the like.

"—$(C_1-C_6)$alkoxy" means a straight chain or branched non-cyclic hydrocarbon having one or more ether groups and 1, 2, 3, 4, 5, or 6 carbon atoms. Representative straight chain and branched $(C_1-C_6)$alkoxys include -methoxy, -ethoxy, -methoxymethyl, -2-methoxyethyl, -5-methoxypentyl, -3-ethoxybutyl, (methoxymethoxy)methyl-, 1-(methoxy)-1-methoxyethyl-, trimethoxymethyl-, 2-((methoxy)methoxy)-2-methylpropyl-, 3-(1,1,1-trimethoxypropane), (methoxy)trimethoxymethyl-, (2,2,2-trimethoxyethoxy)-, and the like.

"—$(C_1$-$C_4)$alkoxy" means a straight chain or branched non-cyclic hydrocarbon having one or more ether groups and 1, 2, 3, or 4 carbon atoms. Representative straight chain and branched $(C_1$-$C_4)$alkoxys include -methoxy, -ethoxy, -methoxymethyl, -2-methoxyethyl, (methoxymethoxy)methyl-, 1-(methoxy)-1-methoxyethyl-, trimethoxymethyl-, and the like.

"—$(C_3$-$C_{14})$cycloalkyl" means a saturated monocyclic hydrocarbon having 3, 4, 5, 6, 7, 8, 9, 10, 11, 12, 13, or 14 carbon atoms. Representative $(C_3$-$C_{14})$cycloalkyls are -cyclopropyl, -cyclobutyl, -cyclopentyl, -cyclohexyl, -cycloheptyl, -cyclooctyl, -cyclononyl, -cyclodecyl, cycloundecyl, -cyclododecyl, and -cyclotetradecyl.

"—$(C_3$-$C_{12})$cycloalkyl" means a saturated monocyclic hydrocarbon having 3, 4, 5, 6, 7, 8, 9, 10, 11, or 12 carbon atoms. Representative $(C_3$-$C_{12})$cycloalkyls are -cyclopropyl, -cyclobutyl, -cyclopentyl, -cyclohexyl, -cycloheptyl, -cyclooctyl, -cyclononyl, -cyclodecyl, -cycloundecyl, and -cyclododecyl.

"—$(C_6$-$C_{12})$cycloalkyl" means a saturated monocyclic hydrocarbon having 6, 7, 8, 9, 10, 11, or 12 carbon atoms. Representative $(C_6$-$C_{12})$cycloalkyls are -cyclohexyl, -cycloheptyl, -cyclooctyl, -cyclononyl, -cyclodecyl, -cycloundecyl, and -cyclododecyl.

"—$(C_4$-$C_8)$cycloalkyl" or "4- to 8-member cycloalkyl ring" means a saturated monocyclic hydrocarbon having 4, 5, 6, 7, or 8 carbon atoms. Representative —$(C_4$-$C_8)$cycloalkyls are -cyclobutyl, -cyclopentyl, -cyclohexyl, -cycloheptyl, and -cyclooctyl.

"—$(C_3$-$C_8)$cycloalkyl" means a saturated monocyclic hydrocarbon having 3, 4, 5, 6, 7, or 8 carbon atoms. Representative $(C_3$-$C_8)$cycloalkyls include -cyclopropyl, -cyclobutyl, -cyclopentyl, -cyclohexyl, -cycloheptyl, and -cyclooctyl.

"—$(C_3$-$C_7)$cycloalkyl" means a saturated monocyclic hydrocarbon having 3, 4, 5, 6, or 7 carbon atoms. Representative $(C_3$-$C_7)$cycloalkyls include cyclopropyl, -cyclobutyl, -cyclopentyl, -cyclohexyl, and -cycloheptyl.

"—$(C_6$-$C_{14})$bicycloalkyl" means a bicyclic hydrocarbon ring system having 6, 7, 8, 9, 10, 11, 12, 13, or 14 carbon atoms and at least one saturated cyclic alkyl ring. In one embodiment, the —$(C_6$-$C_{14})$bicycloalkyl has one saturated cyclic alkyl ring. In another embodiment, the —$(C_6$-$C_{14})$bicycloalkyl has two saturated cyclic alkyl rings. Representative —$(C_6$-$C_{14})$bicycloalkyls include -indanyl, -norbornyl, -1,2,3,4-tetrahydronaphthalenyl, -5,6,7,8-tetrahydronaphthalenyl, -perhydronaphthalenyl, -bicyclo[2.2.1]hexyl, bicyclo[2.2.1]heptyl, -bicyclo[2.2.2]octyl, -bicyclo[3.3.1]heptyl, -bicyclo[3.2.1]octyl, -bicyclo[3.3.1]nonyl, -bicyclo[3.3.2]decyl, -bicyclo[3.3.3]undecyl, -bicyclo[4.2.2]decyl, -bicyclo[4.3.2]undecyl, -bicyclo[4.3.1]decyl, and the like.

"—$(C_6$-$C_{10})$bicycloalkyl" means a bicyclic hydrocarbon ring system having 6, 7, 8, 9, or 10 carbon atoms and at least one saturated cyclic alkyl ring. In one embodiment, the —$(C_6$-$C_{10})$bicycloalkyl has one saturated cyclic alkyl ring. In another embodiment, the —$(C_6$-$C_{10})$bicycloalkyl has two saturated cyclic alkyl rings. Representative —$(C_6$-$C_{10})$bicycloalkyls include -indanyl, -norbornyl, -1,2,3,4-tetrahydronaphthalenyl, -5,6,7,8-tetrahydronaphthalenyl, -perhydronaphthalenyl, -bicyclo[2.2.1]hexyl, bicyclo[2.2.1.]heptyl, -bicyclo[2.2.2]octyl, -bicyclo[3.3.1]heptyl, -bicyclo[3.2.1]octyl, -bicyclo[3.3.1]nonyl, -bicyclo[3.3.2]decyl, -bicyclo[4.2.2]decyl, -bicyclo[4.3.1]decyl, and the like.

"—$(C_8$-$C_{20})$tricycloalkyl" means a tri-cyclic hydrocarbon ring system having 8, 9, 10, 11, 12, 13, 14, 15, 16, 17, 18, 19, or 20 carbon atoms and at least one saturated cyclic alkyl ring; thus, one of the rings can comprise, e.g., benzo. In one embodiment, the —$(C_8$-$C_{20})$tricycloalkyl has one saturated cyclic alkyl ring. In another embodiment, the —$(C_8$-$C_{20})$tricycloalkyl has two saturated cyclic alkyl rings. In another embodiment, the —$(C_8$-$C_{20})$tricycloalkyl has three saturated cyclic alkyl rings. Representative —$(C_8$-$C_{20})$tricycloalkyls include -pyrenyl, -adamantyl, -noradamantyl, -1,2,3,4-tetrahydroanthracenyl, -1,2,3,4,4a,9,9a,10-octahydroanthracenyl, -perhydroanthracenyl-aceanthrenyl, -1,2,3,4-tetrahydropenanthrenyl, -5,6,7,8-tetrahydrophenanthrenyl, -1,2,3,4,4a,9,10,10a-octahydrophenanthrenyl, -perhydrophenanthrenyl, -tetradecahydro-1H-cyclohepta[a]naphthalenyl, -tetradecahydro-1H-cycloocta[e]indenyl, -tetradecahydro-1H-cyclohepta[e]azulenyl, -hexadecahydrocycloocta[b]naphthalenyl, -hexadecahydrocyclohepta[a]heptalenyl, -tricyclo-pentadecanyl, -tricyclo-octadecanyl, -tricyclo-nonadecanyl, -tricyclo-icosanyl, -2,3-benzobicyclo[2.2.2]octanyl, -6,7-benzobicyclo[3.2.1]octanyl, -9,10-benzobicyclo[3.3.2]decanyl, -2,3,4,4a,9,9a-hexahydro-1H-fluorenyl, -1,2,3,4,4a,8b-hexahydrobiphenylenyl, and the like.

"—$(C_5$-$C_{14})$cycloalkenyl" means a cyclic non-aromatic hydrocarbon having at least one carbon-carbon double bond in the cyclic system and 5, 6, 7, 8, 9, 10, 11, 12, 13, or 14 carbon atoms. Representative $(C_5$-$C_{14})$cycloalkenyls include -cyclopentenyl, -cyclopentadienyl, -cyclohexenyl, -cyclohexadienyl, -cycloheptenyl, -cycloheptadienyl, -cycloheptatrienyl, -cyclooctenyl, -cyclooctadienyl, -cyclooctatrienyl, -cyclooctatetraenyl, -cyclononenyl, -cyclononadienyl, -cyclononatrienyl, -cyclodecenyl, -cyclodecadienyl, -cyclotetradecenyl, -cyclododecadienyl, and the like.

"—$(C_5$-$C_{10})$cycloalkenyl" means a cyclic non-aromatic hydrocarbon having at least one carbon-carbon double bond in the cyclic system and 5, 6, 7, 8, 9, or 10 carbon atoms. Representative $(C_5$-$C_{10})$cycloalkenyls include -cyclopentenyl, -cyclopentadienyl, -cyclohexenyl, -cyclohexadienyl, -cycloheptenyl, -cycloheptadienyl, -cycloheptatrienyl, -cyclooctenyl, -cyclooctadienyl, -cyclooctatrienyl, -cyclooctatetraenyl, -cyclononenyl, -cyclononadienyl, -cyclononatrienyl, -cyclodecenyl, -cyclodecadienyl, and the like.

"—$(C_5$-$C_8)$cycloalkenyl" means a cyclic non-aromatic hydrocarbon having at least one carbon-carbon double bond in the cyclic system and 5, 6, 7, or 8 carbon atoms. Representative $(C_5$-$C_8)$cycloalkenyls include -cyclopentenyl, -cyclopentadienyl, -cyclohexenyl, -cyclohexadienyl, -cycloheptenyl, -cycloheptadienyl, -cycloheptatrienyl, -cyclooctenyl, -cyclooctadienyl, -cyclooctatrienyl, - cyclooctatetraenyl, and the like.

"—$(C_7$-$C_{14})$bicycloalkenyl" means a bicyclic hydrocarbon ring system having at least one carbon-carbon double bond in each ring and 7, 8, 9, 10, 11, 12, 13, or 14 carbon atoms. Representative —$(C_7$-$C_{14})$bicycloalkenyls include -indenyl, -pentalenyl, -naphthalenyl, -azulenyl, -heptalenyl, -1,2,7,8-tetrahydronaphthalenyl, -norbornenyl, and the like.

"—$(C_7$-$C_{10})$bicycloalkenyl" means a bicyclic hydrocarbon ring system having at least one carbon-carbon double bond in each ring and 7, 8, 9, or 10 carbon atoms. Representative —$(C_7$-$C_{10})$bicycloalkenyls include -indenyl, -pentalenyl, -naphthalenyl, -azulenyl, -1,2,7,8-tetrahydronaphthalenyl, -norbornenyl, and the like.

"—$(C_8$-$C_{20})$tricycloalkenyl" means a tricyclic hydrocarbon ring system having at least one carbon-carbon double bond in each ring and 8, 9, 10, 11, 12, 13, 14, 15, 16, 17, 18, 19, or 20 carbon atoms. Representative —$(C_8$-$C_{20})$tricycloalkenyls include -anthracenyl, -phenanthrenyl, -phenalenyl, -acenaphthalenyl, -as-indacenyl, -s-indacenyl, -2,3,6,7,8,9,10,11-octahydro-1H-cycloocta[e]indenyl, 2,3,4,7,8,9,10,11-octahydro-1H-cyclohepta[a]naphthalenyl, -8,9,10,11-tetrahydro-7H-cyclohepta[a]naphthalenyl, -2,3,4,5,6,7,8,9,10,11,12,13-dodecahydro-1H-cyclohepta[a]heptalenyl, -1,2,3,4,5,6,7,8,9,10,11,12,13,14-tetradecahydro-dicyclohepta[a,c]cyclooctenyl, -2,3,4,5,6,7,8,9,10,11,12,13-dodecahydro-1H-dibenzo[a,d]cyclononenyl, and the like.

"-(5- to 8-membered)heterocycle", "-(5- to 8-membered)heterocyclo", or "-(5- to 8-membered)heterocyclic" means a 5- to 8-membered monocyclic heterocyclic ring, i.e., a monocyclic ring comprising at least one heteroatom, which is either saturated, unsaturated non-aromatic or aromatic. A 5-membered heterocycle can contain 1, 2, 3, or 4 heteroatoms, a 6-membered heterocycle can contain 1, 2, 3, or 4 heteroatoms, and a 7- or 8-membered heterocycle can contain 1, 2, 3, 4, or 5 heteroatoms. Each heteroatom is independently selected from nitrogen, which can be quaternized; oxygen; and sulfur, including sulfoxide and sulfone. The -(5- to 8-membered)heterocycle can be attached via a nitrogen or carbon atom. Representative -(5- to 8-membered)heterocycles include pyridyl, furyl, thiophenyl, pyrrolyl, oxazolyl, imidazolyl, thiazolidinyl, thiadiazolyl, thiazolyl, isoxazolyl, pyrazolyl, isothiazolyl, pyridazinyl, pyrimidinyl, triazinyl, morpholinyl, pyrrolidinonyl, pyrrolidinyl, piperidinyl, piperazinyl, 2,3-dihydrofuranyl, dihydropyranyl, hydantoinyl, tetrahydrofuranyl, tetrahydropyranyl, dihydropyridinyl, tetrahydropyridinyl, tetrahydropyrimidinyl, tetrahydrothiophenyl, tetrahydrothiopyranyl, 1,4-oxazepanyl, azocanyl, 1,5-diazocanyl, and the like.

"-(3- to 7-membered)heterocycle" or "-(3- to 7-membered)heterocyclo" means a 3- to 7-membered monocyclic heterocyclic ring, i.e., a monocyclic ring comprising at least one heteroatom, which is either saturated, unsaturated non-aromatic or aromatic. A 3-membered heterocycle contains 1 heteroatom, a 4-membered heterocycle can contain 1 or 2 heteroatoms, a 5-membered heterocycle can contain 1, 2, 3, or 4 heteroatoms, a 6-membered heterocycle can contain 1, 2, 3, or 4 heteroatoms, and a 7-membered heterocycle can contain 1, 2, 3, 4, or 5 heteroatoms. Each heteroatom is independently selected from nitrogen, which can be quaternized; oxygen; and sulfur, including sulfoxide and sulfone. The -(3- to 7-membered)heterocycle can be attached via a nitrogen or carbon atom. Representative -(3- to 7-membered)heterocycles include pyridyl, furyl, thiophenyl, pyrrolyl, oxazolyl, imidazolyl, thiazolidinyl, thiadiazolyl, thiazolyl, isoxazolyl, pyrazolyl, isothiazolyl, pyridazinyl, pyrimidinyl, triazinyl, morpholinyl, pyrrolidinonyl, pyrrolidinyl, piperidinyl, piperazinyl, 2,3-dihydrofuranyl, dihydropyranyl, hydantoinyl, valerolactamyl, oxiranyl, oxetanyl, tetrahydrofuranyl, tetrahydropyranyl, dihydropyridinyl, tetrahydropyridinyl, tetrahydropyrimidinyl, tetrahydrothiophenyl, tetrahydrothiopyranyl, and the like.

"-(4-membered)heterocycle" or "-(4-membered)heterocyclo" means a 4-membered monocyclic heterocyclic ring, i.e., a monocyclic ring comprising at least one heteroatom, which is either saturated or unsaturated non-aromatic. A 4-membered heterocycle can contain 1 or 2 heteroatoms. Each heteroatom is independently selected from nitrogen, which can be quaternized; oxygen; and sulfur, including sulfoxide and sulfone. The -(4-membered)heterocycle can be attached via a nitrogen or carbon atom. Representative -(4-membered)heterocycles include oxetane, thietane, azetine, and the like.

"-(7-membered)heterocycle" or "-(7-membered)heterocyclo" means a 7-membered monocyclic heterocyclic ring, i.e., a monocyclic ring comprising at least one heteroatom, which is either saturated or unsaturated non-aromatic. A 7-membered heterocycle can contain 1, 2, 3, 4, or 5 heteroatoms. Each heteroatom is independently selected from nitrogen, which can be quaternized; oxygen; and sulfur, including sulfoxide and sulfone. The -(7-membered)heterocycle can be attached via a nitrogen or carbon atom. Representative -(7-membered)heterocycles include oxepanyl, 1,4-dioxepanyl, azepanyl, 1,4-oxazepane, thiepanyl, 1,3-oxathiepanyl, 1,3-thiazepanyl, 2,3-dihydro-1,3-thiazepinyl, 2,3,4,5-tetrahydro-1,3-oxazepinyl, and the like.

"-(3- to 5-membered)heterocycle" or "-(3- to 5-membered)heterocyclo" means a 3- to 5-membered monocyclic heterocyclic ring, i.e., a monocyclic ring comprising at least one heteroatom, which is either saturated, unsaturated non-aromatic or aromatic. A 3-membered heterocycle contains 1 heteroatom, a 4-membered heterocycle can contain 1 or 2 heteroatoms, and a 5-membered heterocycle can contain 1, 2, 3, or 4 heteroatoms. Each heteroatom is independently selected from nitrogen, which can be quaternized; oxygen; and sulfur, including sulfoxide and sulfone. The -(3- to 5-membered)heterocycle can be attached via a nitrogen or carbon atom. Representative -(3- to 5-membered)heterocycles include furyl, thiophenyl, pyrrolyl, oxazolyl, imidazolyl, thiazolidinyl, thiadiazolyl, thiazolyl, isoxazolyl, pyrazolyl, isothiazolyl, 2,3-dihydrofuranyl, dihydropyranyl, hydantoinyl, oxiranyl, oxetanyl, tetrahydrofuranyl, tetrahydrothiophenyl, and the like.

"-(5- or 6-membered)heterocycle" or "-(5- or 6-membered)heterocyclo" means a 5- or 6-membered monocyclic heterocyclic ring, i.e., a monocyclic ring comprising at least one heteroatom, which is either saturated, unsaturated non-aromatic or aromatic. A 5-membered heterocycle can contain 1, 2, 3, or 4 heteroatoms and a 6-membered heterocycle can contain 1, 2, 3, or 4 heteroatoms. Each heteroatom is independently selected from nitrogen, which can be quaternized; oxygen; and sulfur, including sulfoxide and sulfone. The -(5- or 6-membered)heterocycle can be attached via a nitrogen or carbon atom. Representative -(5- or 6-membered)heterocycles include pyridyl, furyl, thiophenyl, pyrrolyl, oxazolyl, imidazolyl, thiazolidinyl, thiadiazolyl, thiazolyl, isoxazolyl, pyrazolyl, isothiazolyl, pyridazinyl, pyrimidinyl, triazinyl, morpholinyl, pyrrolidinonyl, pyrrolidinyl, piperidinyl, piperazinyl, 2,3-dihydrofuranyl, dihydropyranyl, hydantoinyl, valerolactamyl, tetrahydrofuranyl, tetrahydropyranyl, dihydropyridinyl, tetrahydropyridinyl, tetrahydropyrimidinyl, tetrahydrothiophenyl, tetrahydrothiopyranyl, tetrazolyl, and the like.

"-(7- to 10-membered)bicycloheterocycle" or "-(7- to 10-membered)bicycloheterocyclo" means a 7- to 10-membered bicyclic, heterocyclic ring, each ring of which is independently either saturated, unsaturated non-aromatic or aromatic, i.e., where at least one ring comprises at least one heteroatom. A -(7- to 10-membered)bicycloheterocycle contains 1, 2, 3, or 4 heteroatoms independently selected from nitrogen, which can be quaternized; oxygen; and sulfur, including sulfoxide and sulfone. The -(7- to 10-membered)bicycloheterocycle can be attached via a nitrogen or carbon atom. Representative -(7- to 10-membered)bicycloheterocycles include -quinolinyl, -isoquinolinyl, -2,3-dihydrobenzofuranyl, -1,3-dihydroisobenzofuranyl, -benzo[d][1,3]dioxolyl, -2,3-dihydrobenzo[b]thiophenyl, -1,3-dihydrobenzo[c]thiophenyl, -benzo[d][1,3]dithiolyl, -chromonyl, -chromanyl, -2,3-dihydrobenzo[b][1,4]dioxinyl, -thiochromonyl, -thiochromanyl, -2,3-dihydrobenzo[b][1,4]dithiinyl, -coumarinyl, -indolyl, -indolizinyl, -benzo[b]furanyl, -benzo[b]thiophenyl, -indazolyl, -purinyl, -4H- quinolizinyl, -isoquinolyl, -quinolyl, -phthalazinyl, -naphthyridinyl, -indolinyl, -isoindolinyl, -1,2,3,4-tetrahydroquinolinyl, -1,2,3,4-tetrahydroisoquinolinyl, and the like.

"—($C_3$-$C_{12}$)cycloalkoxy" means a saturated monocyclic hydrocarbon having 3, 4, 5, 6, 7, 8, 9, 10, 11, or 12 carbon atoms where at least one of the carbon atoms is replaced by an oxygen atom. Representative ($C_3$-$C_{12}$)cycloalkoxy are -oxiranyl, -oxetanyl, -tetrahydrofuranyl, -tetrahydro-2H-pyranyl, -1,4-dioxanyl, -oxepanyl, -1,4-dioxepanyl, -oxocanyl, -1,5-dioxocanyl, -1,3,5-trioxocanyl, -oxonanyl, -1,5-dioxonanyl, -1,4,7-trioxonanyl, -oxacyclododecanyl, -1,7-dioxacyclododecanyl, and -1,5,9-trioxacyclododecanyl.

"—($C_3$-$C_7$)cycloalkoxy" means a saturated monocyclic hydrocarbon having 3, 4, 5, 6, or 7 carbon atoms where at least one of the carbon atoms is replaced by an oxygen atom. Representative ($C_3$-$C_7$)cycloalkoxy are -oxiranyl, -oxetanyl, -tetrahydrofuranyl, -tetrahydro-2H-pyranyl, -1,4-dioxanyl, -oxepanyl, and -1,4-dioxepanyl.

"—($C_{14}$)aryl" means a 14-membered aromatic carbocyclic moiety such as -anthryl or -phenanthryl.

"-(5- to 10-membered)heteroaryl" means an aromatic heterocycle ring of 5 to 10 members, including both mono- and bicyclic ring systems, i.e., a monocyclic aromatic ring comprising at least one heteroatom independently selected from nitrogen, oxygen, and sulfur or a bicyclic aromatic ring where at least one ring comprises at least one heteroatom independently selected from nitrogen, oxygen, and sulfur. In one embodiment, a monocyclic -(5- to 10-membered)heteroaryl comprises at least two heteroatoms independently selected from nitrogen, oxygen, and sulfur. In another embodiment, a bicyclic -(5- to 10-membered)heteroaryl comprises at least two heteroatoms, present in the same or in different rings, each heteroatom being independently selected from nitrogen, oxygen, and sulfur. In another embodiment, one of the -(5- to 10-membered)heteroaryl's rings contain at least one carbon atom. In another embodiment, both of the bicyclic -(5- to 10-membered)heteroaryl's rings contain at least one carbon atom. Representative -(5- to 10-membered)heteroaryls include pyridyl, furyl, benzofuranyl, thiophenyl, benzothiophenyl, quinolinyl, isoquinolinyl, pyrrolyl, indolyl, oxazolyl, benzoxazolyl, imidazolyl, benzimidazolyl, thiazolyl, benzothiazolyl, isoxazolyl, oxadiazolinyl, pyrazolyl, isothiazolyl, pyridazinyl, pyrimidyl, pyrimidinyl, pyrazinyl, thiadiazolyl, triazinyl, thienyl, cinnolinyl, phthalazinyl, and quinazolinyl.

"-(5- or 6-membered)heteroaryl" means a monocyclic aromatic heterocycle ring of 5 or 6 members, i.e., a monocyclic aromatic ring comprising at least one heteroatom independently selected from nitrogen, oxygen, and sulfur. In one embodiment, the -(5- or 6-membered)heteroaryl ring contains at least one carbon atom. Representative -(5- or 6-membered)heteroaryls include pyridyl, furyl, pyrrolyl, oxazolyl, imidazolyl, thiazolyl, isoxazolyl, 1,2,3-oxadiazolyl, 1,3,4-oxadiazolyl, 1,2,5-oxadiazolyl, 1,2,3-triazolyl, pyrazolyl, isothiazolyl, pyridazinyl, pyrimidyl, pyrazinyl, 1,2,3-thiadiazolyl, 1,3,4-thiadiazolyl, 1,2,5-thiadiazolyl, 1,3,5-triazinyl, and thiophenyl.

"—$CH_2$(halo)" means a methyl group where one of the hydrogens of the methyl group has been replaced with a halogen. Representative —$CH_2$(halo) groups include —$CH_2F$, —$CH_2Cl$, —$CH_2Br$, and —$CH_2I$.

"—CH(halo)$_2$" means a methyl group where two of the hydrogens of the methyl group have each been independently replaced with a halogen. Representative —CH(halo)$_2$ groups include —$CHF_2$, —$CHCl_2$, —$CHBr_2$, —CHBrClI, —CHClI, and —$CHI_2$.

"—C(halo)$_3$" means a methyl group where each of the hydrogens of the methyl group has been independently replaced with a halogen. Representative —C(halo)$_3$ groups include —$CF_3$, —$CCl_3$, —$CBr_3$, —$CI_3$, —$CF_2Br$, —$CF_2Cl$, —$CCl_2F$, and —CFClBr.

"—Halogen" or "-halo" means —F, —Cl, —Br, or —I.

"Oxo", "=O", and the like as used herein mean an oxygen atom doubly bonded to carbon or another element.

"Thiooxo", "thioxo", "=S", and the like as used herein mean a sulfur atom doubly bonded to carbon or another element.

"($C_2$-$C_6$)bridge" as used herein means a hydrocarbon chain containing 2 to 6 carbon atoms joining two atoms of the piperidine ring of Formula (I) to form a fused bicyclic ring system. For example, compounds of the disclosure can comprise a ($C_2$-$C_6$)bridge joining positions 2 and 6 of the piperidine ring (A-B can together form a ($C_2$-$C_6$)bridge). Exemplary compounds of the disclosure include those with an unsubstituted ($C_2$)bridge, —$CH_2$—$CH_2$—, joining positions 2 and 6 of the piperidine ring (A-B can together form a ($C_2$)bridge); an unsubstituted ($C_3$)bridge, —$CH_2$—$CH_2$—$CH_2$—, joining positions 2 and 6 of the piperidine ring (A-B can together form a ($C_3$)bridge); an unsubstituted ($C_4$) bridge, —$CH_2$—$CH_2$—$CH_2$—$CH_2$—, joining positions 2 and 6 of the piperidine ring (A-B can together form a ($C_4$)bridge); an unsubstituted ($C_5$)bridge, —$CH_2$—$CH_2$—$CH_2$—$CH_2$—$CH_2$—, joining positions 2 and 6 of the piperidine ring (A-B can together form a ($C_5$)bridge); or an unsubstituted ($C_6$)bridge, —$CH_2$—$CH_2$—$CH_2$—$CH_2$—$CH_2$—$CH_2$—, joining positions 2 and 6 of the piperidine ring (A-B can together form a ($C_6$)bridge). Examples of compounds where A-B can together form a ($C_2$-$C_6$)bridge include compounds comprising the following ring systems: 8-aza-bicyclo[3.2.1]octane; 9-aza-bicyclo[3.3.1]nonane; 10-aza-bicyclo[4.3.1]decane; 11-aza-bicyclo[5.3.1]undecane; and 12-aza-bicyclo[6.3.1]dodecane. Examples of a ($C_2$-$C_6$)bridge which contains —HC=CH— within the ($C_2$-$C_6$)bridge include —HC=CH—, —$CH_2$—HC=CH—, —HC=CH—$CH_2$—, —$CH_2$—HC=CH—$CH_2$—, and the like. Examples of a ($C_2$-$C_6$)bridge which contains —O— within the ($C_2$-$C_6$)bridge include —$CH_2$—O—$CH_2$-(containing 2 carbon atoms), —$CH_2$—O—$CH_2$—$CH_2$— and —$CH_2$—$CH_2$—O—$CH_2$— (each containing 3 carbon atoms), —$CH_2$—$CH_2$—O—$CH_2$—$CH_2$—, —$CH_2$—O—$CH_2$—$CH_2$—$CH_2$— and —$CH_2$—$CH_2$—$CH_2$—O—$CH_2$— (each containing 4 carbon atoms), and the like.

It is to be understood that when t is 0, the compounds of formula (IA) and the like are represented as:

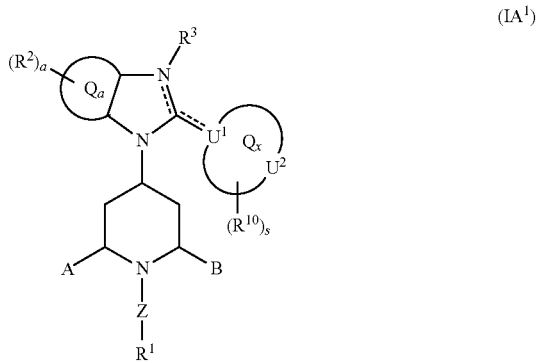

(IA$^1$)

where the $Q_x$ ring is, e.g., a -(4-, 5-, 6-, or 7-membered) heterocycle as defined for formula (IA) above; when t is 0 and the dashed line within the 5-membered, nitrogen-containing ring that is fused to the $Q_a$ ring is present, the compounds of formula (IA) and the like are represented as:

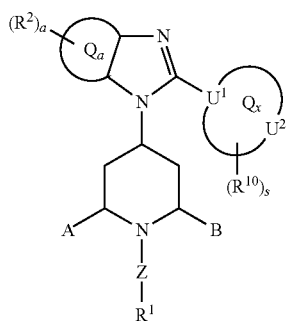

(IA²)

where the $Q_x$ ring is, e.g., a -(4-, 5-, 6-, or 7-membered) heterocycle as defined for formula (IA) above; and when t is 0, the dashed line within the 5-membered, nitrogen-containing ring that is fused to the $Q_a$ ring is absent, and the other dashed line is present, the compounds of formula (IA) and the like are represented as:

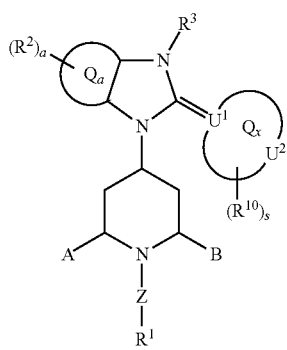

(IA³)

where the $Q_x$ ring is, e.g., a -(4-, 5-, 6-, or 7-membered) heterocycle as defined for formula (IA) above.

It is to be understood that when t is 1, the compounds of formula (IA) and the like are represented as:

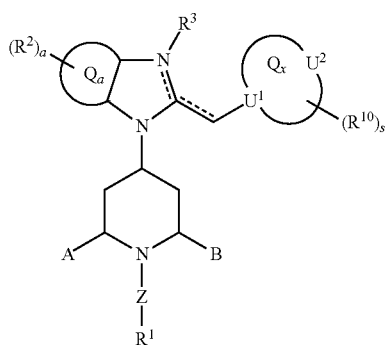

(IA⁴)

where the $Q_x$ ring is, e.g., a (6-membered)heterocycle as defined for formula (IA) above; when t is 1 and the dashed line within the 5-membered, nitrogen-containing ring that is fused to the $Q_a$ ring is present, the compounds of formula (IA) and the like are represented as:

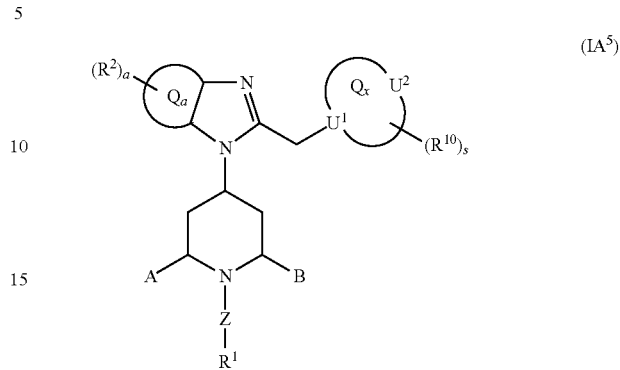

where the $Q_x$ ring is, e.g., a (6-membered)heterocycle as defined for formula (IA) above; and when t is 1, the dashed line within the 5-membered, nitrogen-containing ring that is fused to the $Q_a$ ring is absent, and the other dashed line is present, the compounds of formula (IA) and the like are represented as:

(IA⁶)

where the $Q_x$ ring is, e.g., a (6-membered)heterocycle as defined for formula (IA) above.

It is to be understood that when t is 2, the compounds of formula (IA) and the like are represented as:

(IA⁷)

where the $Q_x$ ring is, e.g., a (6-membered)heterocycle as defined for formula (IA) above; when t is 2 and the dashed line within the 5-membered, nitrogen-containing ring that is fused to the $Q_a$ ring is present, the compounds of formula (IA) and the like are represented as:

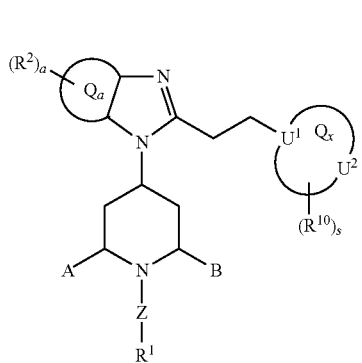
(IA$^8$)

where the $Q_x$ ring is, e.g., a (6-membered)heterocycle as defined for formula (IA) above; and when t is 2, the dashed line within the 5-membered, nitrogen-containing ring that is fused to the $Q_a$ ring is absent, and the other dashed line is present, the compounds of formula (IA) and the like are represented as:

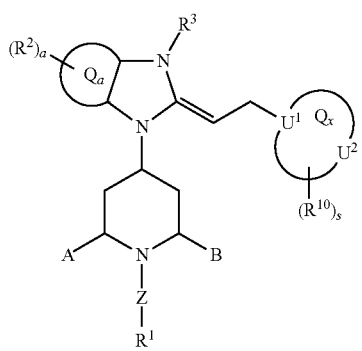
(IA$^9$)

where the $Q_x$ ring is, e.g., a (6-membered)heterocycle as defined for formula (IA) above.

In compounds of the disclosure comprising a bridge joining positions 2 and 6 of the piperidine ring (e.g., A-B can together form a $(C_2-C_6)$bridge), for, e.g., a compound of Formula (I), the exemplary endo bridge:

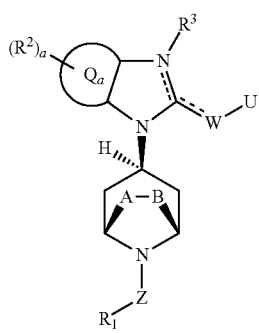

is equivalent to

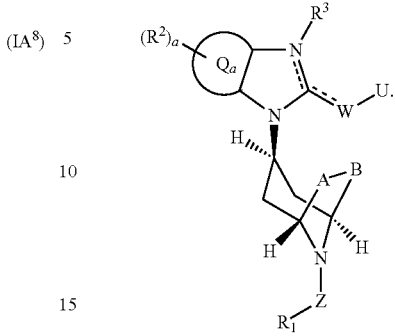

In compounds of the disclosure comprising a bridge joining positions 2 and 6 of the piperidine ring (e.g., A-B can together form a $(C_2-C_6)$bridge), for, e.g., a compound of Formula (I), the exemplary exo bridge:

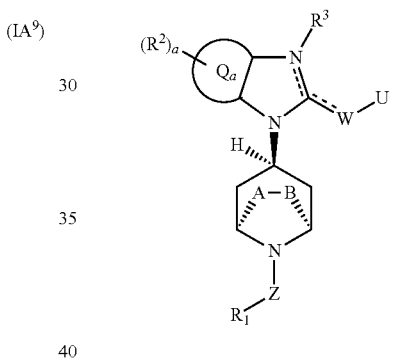

is equivalent to

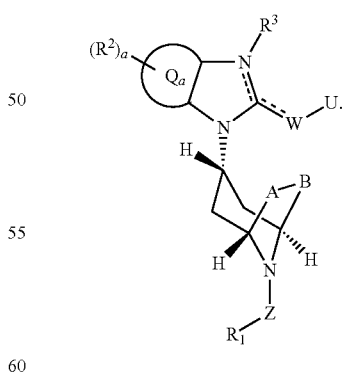

In compounds of the disclosure where the —Z—R$^1$ group comprises a bicyclic group, that bicyclic group can have two orientations. For example, for a —Z—R$^1$ group that is a —(C$_6$-C$_{14}$)bicycloalkyl, e.g., bicyclo[3.3.1]nonanyl, attached directly to the piperidine ring nitrogen, the following orientations are possible:

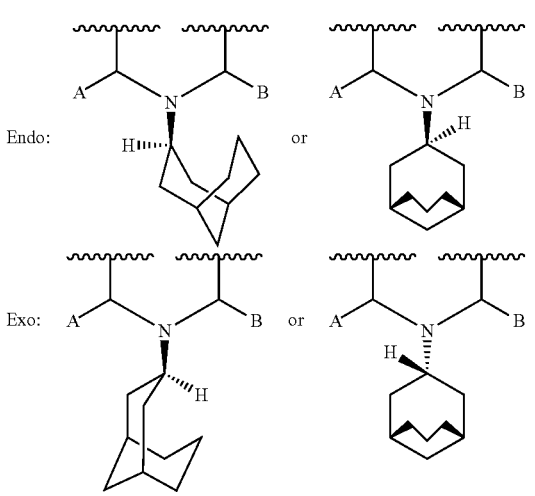

As used herein in connection with "—[(C₁-C₁₀)alkyl optionally substituted by $R^{13}$]$_h$—", when h is 1 means that the Z—$R^1$ bonded to the piperidine ring bearing A and B substituents is understood to appear as follows:

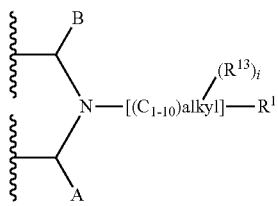

where, when i is 0, the —(C₁-C₁₀)alkyl- is unsubstituted by a $R^{13}$ group and, when i is 1, the —(C₁-C₁₀)alkyl- is substituted by a $R^1$ group at the carbon atom furthest removed from the piperidine ring bearing A and B substituents and substituted by a $R^{13}$ group at any carbon atom of the —(C₁-C₁₀)alkyl- including at the carbon atom furthest removed from the piperidine ring bearing A and B substituents. In one embodiment, $R^{13}$ is selected from:

(a) -halo, —OH, —CH₂OH, —CH₂CH₂OH, —N(R⁶)₂, and —C(=O)OV¹; and (b) —(C₁-C₁₀)alkyl, —(C₂-C₁₀)alkenyl, —O(C₁-C₆)alkyl, —(C₅-C₁₄)cycloalkenyl, and -(5- or 6-membered)heterocycle, each of which is unsubstituted or substituted with 1, 2, 3, or 4 independently selected $R^8$ groups; and (c)

(iv)

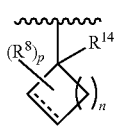

wherein $R^{14}$ is —H and n is an integer selected from 2, 3, 4, 5, 6, and 7;

(d) -phenyl and -(5- or 6-membered)heteroaryl, each of which is unsubstituted or substituted with 1 or 2 independently selected $R^7$ groups.

In another embodiment, $R^{13}$ is selected from:

(a) -halo, —OH, —CH₂OH, —CH₂CH₂OH, —N(R⁶)₂, and —C(=O)OV¹; and (b) —(C₁-C₆)alkyl, —(C₂-C₆)alkenyl, —O(C₁-C₄)alkyl, and -(5- or 6-membered)heterocycle, each of which is unsubstituted or substituted with 1 or 2 independently selected $R^8$ groups; and (c)

(i)

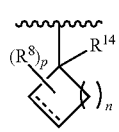

wherein $R^{14}$ is —H and n is an integer selected from 2, 3, 4, 5, 6, and 7;

(d) -phenyl and -(5- or 6-membered)heteroaryl, each of which is unsubstituted or substituted with 1 or 2 independently selected $R^7$ groups.

"[(C₂-C₁₀)alkenyl optionally substituted by $R^{13}$]—" as used herein in connection with Z—$R^1$ means that the Z—$R^1$ bonded to the piperidine ring bearing A and B substituents is understood to appear as follows:

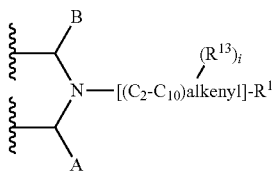

where, when i is 0, the —(C₂-C₁₀)alkenyl- is unsubstituted by a $R^{13}$ group and, when i is 1, the —(C₂-C₁₀)alkenyl- is substituted by a $R^1$ group at the carbon atom furthest removed from the piperidine ring bearing A and B substituents and substituted by a $R^{13}$ group at any carbon atom of the —(C₂-C₁₀)alkenyl- including at the carbon atom furthest removed from the piperidine ring bearing A and B substituents.

As used herein in connection with formula (i) of $R^1$, when the dashed line is present as a bond to provide a double bond at that position, then formula (i) is understood to appear as follows (i)

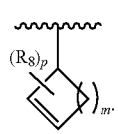

As used herein in connection with formula (i) of $R^1$, when the dashed line is absent, then formula (i) is understood to appear as follows (i)

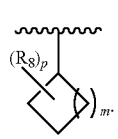

As used herein in connection with formula (iv) of $R^{13}$, when the dashed line is present as a bond to provide a double bond at that position, then formula (iv) is understood to appear as follows

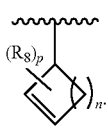
(iv)

As used herein in connection with formula (iv) of $R^{13}$, when the dashed line is absent, then formula (iv) is understood to appear as follows

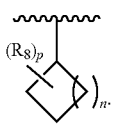
(iv)

The terms "benzo," "benzo group" and the like, when used in connection with the $Q_a$ ring, means

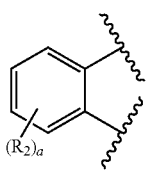

where $R^2$, and a are defined above for the Substituted Benzimidazole-Type Piperidine Compounds of Formula (I).

The terms "pyridino," "pyridino group" and the like, when used in connection with the $Q_a$ ring, means

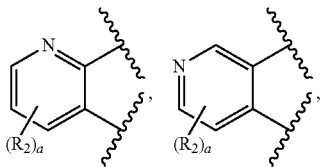

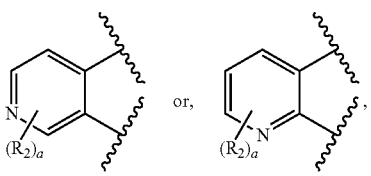

where $R^2$, and a are defined above for the Substituted Benzimidazole-Type Piperidine Compounds of Formula (I).
In one embodiment, the optionally-substituted pyridino $Q_a$ ring is

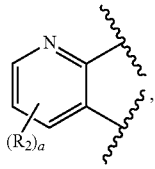

In another embodiment, the optionally-substituted pyridino $Q_a$ ring is

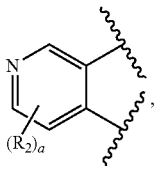

In another embodiment, the optionally-substituted pyridino $Q_a$ ring is

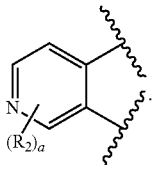

In another embodiment, the optionally-substituted pyridino $Q_a$ ring is

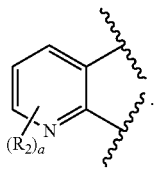

The terms "pyrimidino", "pyrimidino group" and the like, when used in connection with the optionally-substituted $Q_a$ ring, means

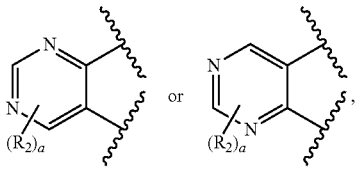

where $R^2$ and a are defined above for the Substituted Benzimidazole-Type Piperidine Compounds of Formula (I).
In one embodiment, the optionally-substituted pyrimidino $Q_a$ ring is

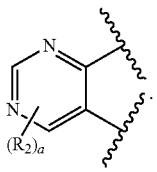

In another embodiment, the optionally-substituted pyrimidino $Q_a$ ring is

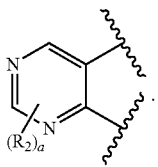

The terms "pyrazino", "pyrazino group" and the like, when used in connection with the optionally-substituted $Q_a$ ring, means

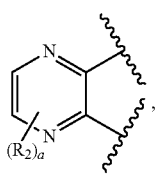

where $R^2$ and a are defined above for the Substituted Benzimidazole-Type Piperidine Compounds of Formula (I).

The terms "pyridazino", "pyridazino group" and the like, when used in connection with the optionally-substituted $Q_a$ ring, means

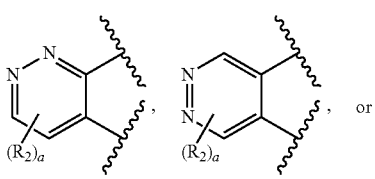, or

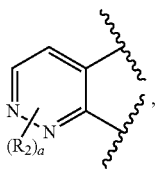

where $R^2$ and a are defined above for the Substituted Benzimidazole-Type Piperidine Compounds of Formula (I).
In one embodiment, the optionally-substituted pyridazino $Q_a$ ring is

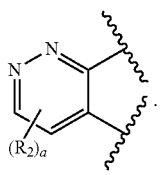

In another embodiment, the optionally-substituted pyridazino $Q_a$ ring is

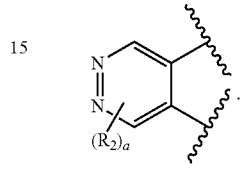

In another embodiment, the optionally-substituted pyridazino $Q_a$ ring is

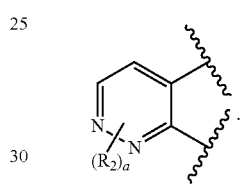

The terms "pyrrolino", "pyrrolino group" and the like, when used in connection with the optionally-substituted $Q_a$ ring, means

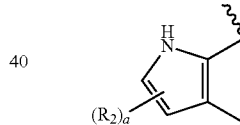, 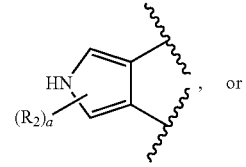, or

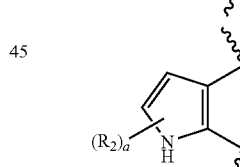

where $R^2$ and a are defined above for the Substituted Benzimidazole-Type Piperidine Compounds of Formula (I).
In one embodiment, the optionally-substituted pyrrolino $Q_a$ ring is

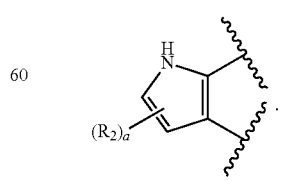

In another embodiment, the optionally-substituted pyrrolino $Q_a$ ring is

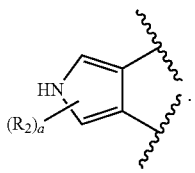

In another embodiment, the optionally-substituted pyrrolino $Q_a$ ring is

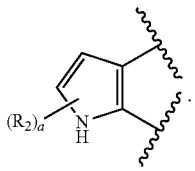

The terms "imidazolino", "imidazolino group" and the like, when used in connection with the optionally-substituted $Q_a$ ring, means

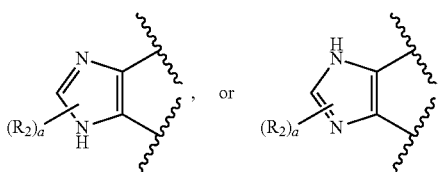

where $R^2$ and a are defined above for the Substituted Benzimidazole-Type Piperidine Compounds of Formula (I). In one embodiment, the optionally-substituted imidazolino $Q_a$ ring is

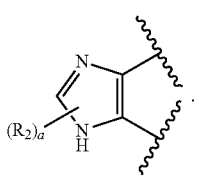

In another embodiment, the optionally-substituted imidazolino $Q_a$ ring is

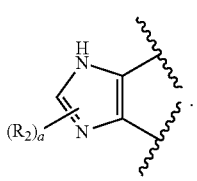

The terms "pyrazolino", "pyrazolino group" and the like, when used in connection with the optionally-substituted $Q_a$ ring, means

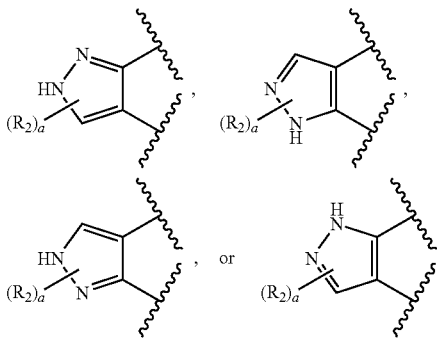

where $R^2$ and a are defined above for the Substituted Benzimidazole-Type Piperidine Compounds of Formula (I). In one embodiment, the optionally-substituted pyrazolino $Q_a$ ring is

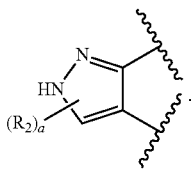

In another embodiment, the optionally-substituted pyrazolino $Q_a$ ring is

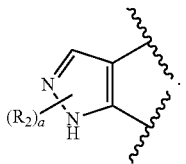

In another embodiment, the optionally-substituted pyrazolino $Q_a$ ring is

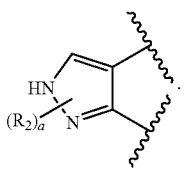

In another embodiment, the optionally-substituted pyrazolino $Q_a$ ring is

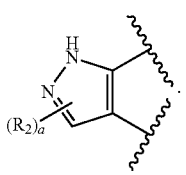

The terms "triazolino", "triazolino group" and the like, when used in connection with the optionally-substituted $Q_a$ ring, means

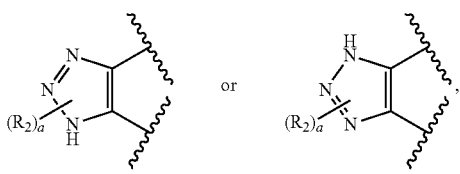

where R² and a are defined above for the Substituted Benzimidazole-Type Piperidine Compounds of Formula (I). In one embodiment, the optionally-substituted triazolino $Q_a$ ring is

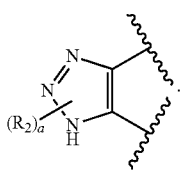

In another embodiment, the optionally-substituted triazolino $Q_a$ ring is

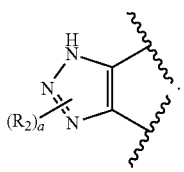

The terms "furano", "furano group" and the like, when used in connection with the optionally-substituted $Q_a$ ring, means

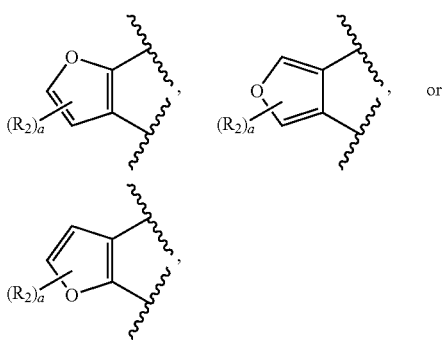

where R² and a are defined above for the Substituted Benzimidazole-Type Piperidine Compounds of Formula (I). In one embodiment, the optionally-substituted furano $Q_a$ ring is

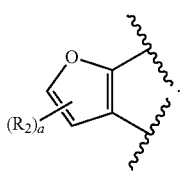

In another embodiment, the optionally-substituted furano $Q_a$ ring is

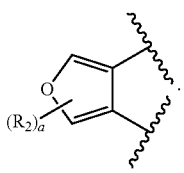

In another embodiment, the optionally-substituted furano $Q_a$ ring is

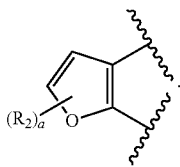

The terms "oxazolino", "oxazolino group" and the like, when used in connection with the optionally-substituted $Q_a$ ring, means

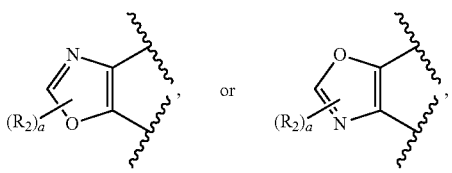

where R² and a are defined above for the Substituted Benzimidazole-Type Piperidine Compounds of Formula (I). In one embodiment, the optionally-substituted oxazolino $Q_a$ ring is

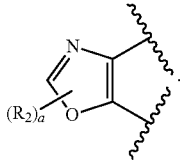

In another embodiment, the optionally-substituted oxazolino $Q_a$ ring is

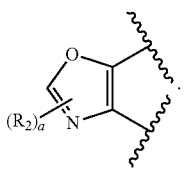

The terms "isoxazolino", "isoxazolino group" and the like, when used in connection with the optionally-substituted $Q_a$ ring, means

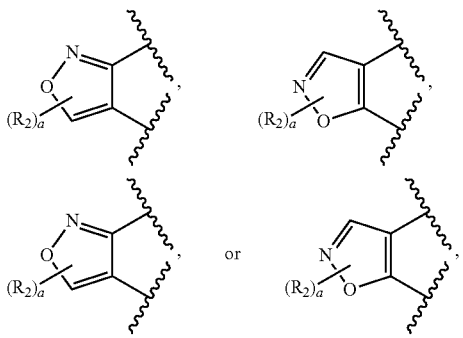

where R² and a are defined above for the Substituted Benzimidazole-Type Piperidine Compounds of Formula (I). In one embodiment, the optionally-substituted isoxazolino Q_a ring is

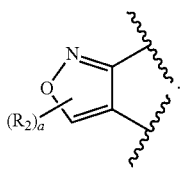

In another embodiment, the optionally-substituted isoxazolino Q_a ring is

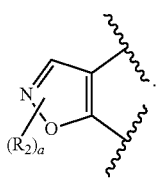

In another embodiment, the optionally-substituted isoxazolino Q_a ring is

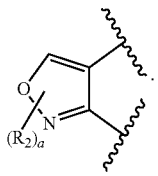

In another embodiment, the optionally-substituted isoxazolino Q_a ring is

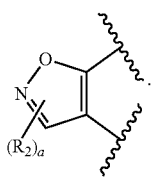

The terms "oxadiazolino", "oxadiazolino group" and the like, when used in connection with the optionally-substituted Q_a ring, means

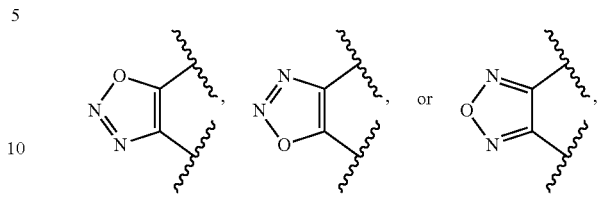

where R² and a are defined above for the Substituted Benzimidazole-Type Piperidine Compounds of Formula (I). In one embodiment, the optionally-substituted oxadiazolino Q_a ring is

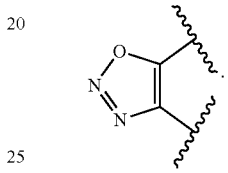

In another embodiment, the optionally-substituted oxadiazolino Q_a ring is

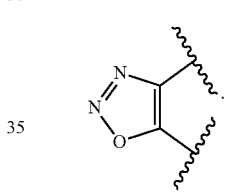

In another embodiment, the optionally-substituted oxadiazolino Q_a ring is

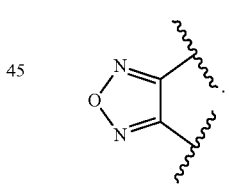

The terms "thiopheno", "thiopheno group" and the like, when used in connection with the optionally-substituted Q_a ring, means

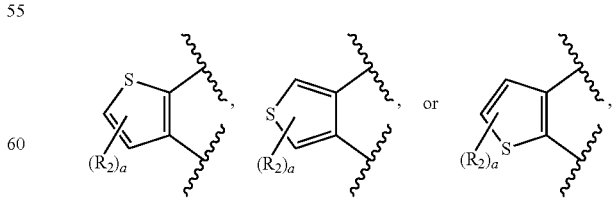

where R² and a are defined above for the Substituted Benzimidazole-Type Piperidine Compounds of Formula (I). In one embodiment, the optionally-substituted thiopheno Q_a ring is

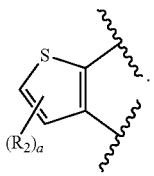

In another embodiment, the optionally-substituted thiopheno $Q_a$ ring is

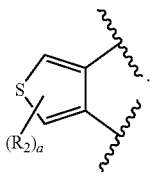

In another embodiment, the optionally-substituted thiopheno $Q_a$ ring is

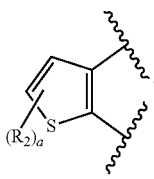

The terms "thiazolino", "thiazolino group" and the like, when used in connection with the optionally-substituted $Q_a$ ring, means

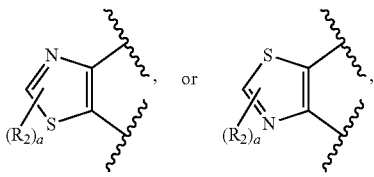

where $R^2$ and a are defined above for the Substituted Benzimidazole-Type Piperidine Compounds of Formula (I). In one embodiment, the optionally-substituted thiazolino $Q_a$ ring is

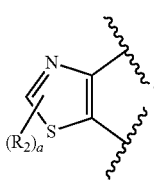

In another embodiment, the optionally-substituted thiazolino $Q_a$ ring is

The terms "isothiazolino", "isothiazolino group" and the like, when used in connection with the optionally-substituted $Q_a$ ring, means

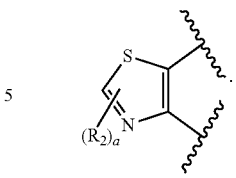

where $R^2$ and a are defined above for the Substituted Benzimidazole-Type Piperidine Compounds of Formula (I). In one embodiment, the optionally-substituted isothiazolino $Q_a$ ring is

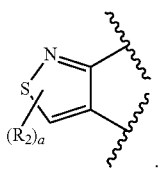

In another embodiment, the optionally-substituted isothiazolino $Q_a$ ring is

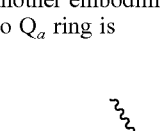

In another embodiment, the optionally-substituted isothiazolino $Q_a$ ring is

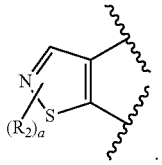

In another embodiment, the optionally-substituted isothiazolino $Q_a$ ring is

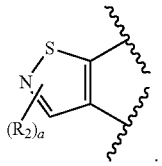

The terms "thiadiazolino", "thiadiazolino group" and the like, when used in connection with the optionally-substituted $Q_a$ ring, means

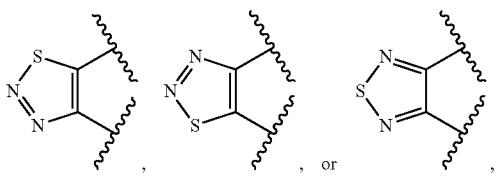

where $R^2$ and a are defined above for the Substituted Benzimidazole-Type Piperidine Compounds of Formula (I). In one embodiment, the optionally-substituted thiadiazolino $Q_a$ ring is

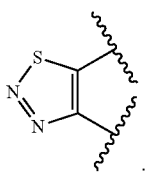

In another embodiment, the optionally-substituted thiadiazolino $Q_a$ ring is

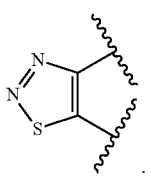

In another embodiment, the optionally-substituted thiadiazolino $Q_a$ ring is

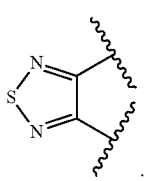 [SMILES: *c1nsnc1*]

In one embodiment, the term "optionally substituted bicyclo[3.3.1]nonyl" and the like when used in connection with the optionally-substituted $R^1$ group is understood to refer to one of the structures below:

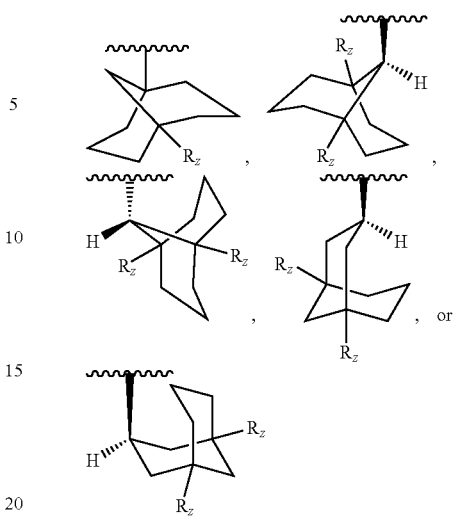

where the substituents are as defined above for the Substituted Benzimidazole-Type Piperidine Compounds of Formula (I); and where in one or more embodiments, the optionally substituted $R^1$ group comprises one or more of the above-recited optionally substituted bicyclo[3.3.1]nonyl structures.

In one embodiment, the term "optionally substituted —$(C_6$-$C_{14})$bicycloalkyl" means

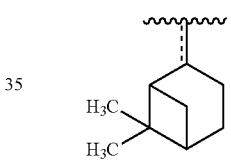

where the dashed line denotes the presence or absence of a bond (i.e., when a dashed line is present there is a double bond at that position and when a dashed line is absent there is a single bond at that position). when the dashed line is present as a bond to provide a double bond at that position, then the group above is understood to appear as follows

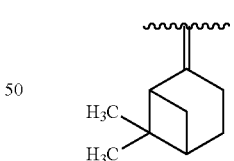

and when the dashed line is absent, then the optionally substituted —$(C_6$-$C_{14})$bicycloalkyl group above is understood to appear as follows

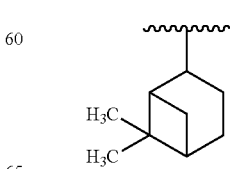

In one embodiment, the term "2-(1H-imidazole)" means

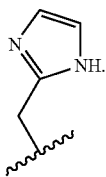 [SMILES: *Cc1ncc[nH]1]

In one embodiment, the term "2-(1-methyl-1H-imidazole)" means

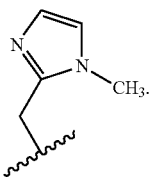 [SMILES: *Cc1nccn1C]

In one embodiment, the term "S(=O)$_2$-4-(3,5-dimethylisoxazole)" means

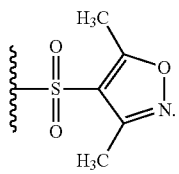

When a first group is "substituted with one or more" second groups, one or more hydrogen atoms of the first group is replaced with a corresponding number of second groups. When the number of second groups is two or greater, each second group can be the same or different. In one embodiment, a first group is substituted with up to three second groups. In another embodiment, a first group is substituted with one or two second groups. In another embodiment, a first group is substituted with two second groups. In another embodiment, a first group is substituted with two second groups and each second group is identical. In another embodiment, a first group is substituted with only one second group.

The term "animal" includes, but is not limited to, a human or a non-human animal, such as a companion animal or livestock, e.g., a cow, monkey, baboon, chimpanzee, horse, sheep, pig, chicken, turkey, quail, cat, dog, mouse, rat, rabbit or guinea pig.

The term "pharmaceutically acceptable derivative", as used herein, includes any pharmaceutically acceptable salt, solvate, radiolabeled form, stereoisomer, enantiomer, diastereomer, other stereoisomeric form, racemic mixture, geometric isomer, and/or tautomer, e.g., of a Substituted Benzimidazole-Type Piperidine Compound of the disclosure.

In one embodiment, the pharmaceutically acceptable derivative is a pharmaceutically acceptable salt, solvate, radiolabeled form, stereoisomer, enantiomer, diastereomer, other stereoisomeric form, racemic mixture, geometric isomer, and/or tautomer, e.g., of a Substituted Benzimidazole-Type Piperidine Compound of the disclosure. The term "pharmaceutically acceptable salt", as used herein, is any pharmaceutically acceptable salt that can be prepared from a Substituted Benzimidazole-Type Piperidine Compound including a salt formed from an acid and a basic functional group, such as a nitrogen group, of a Substituted Benzimidazole-Type Piperidine Compound. Illustrative salts include, but are not limited, to sulfate, citrate, acetate, trifluoroacetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucoronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. The term "pharmaceutically acceptable salt" also includes a salt prepared from a Substituted Benzimidazole-Type Piperidine Compound having an acidic functional group, such as a carboxylic acid functional group, and a pharmaceutically acceptable inorganic or organic base. Suitable bases include, but are not limited to, hydroxides of alkali metals such as sodium, potassium, cesium, and lithium; hydroxides of alkaline earth metal such as calcium and magnesium; hydroxides of other metals, such as aluminum and zinc; ammonia and organic amines, such as unsubstituted or hydroxy-substituted mono-, di-, or trialkylamines; dicyclohexylamine; tributyl amine; pyridine; picoline; N-methyl-N-ethylamine; diethylamine; triethylamine; mono-, bis-, or tris-(2-hydroxy-($C_1$-$C_3$)alkyl amines), such as mono-, bis-, or tris-(2-hydroxyethyl)amine, 2-hydroxy-tert-butylamine, or tris-(hydroxymethyl)methylamine, N,N-di-[($C_1$-$C_3$)alkyl]-N-(hydroxy-($C_1$-$C_3$)alkyl)-amines, such as N,N-dimethyl-N-(2-hydroxyethyl)amine, or tri-(2-hydroxyethyl)amine; N-methyl-D-glucamine; and amino acids such as arginine, lysine, and the like. In one embodiment, the pharmaceutically acceptable salt is a hydrochloride-salt, a sulfate-salt, a sodium-salt, a potassium-salt, a benzene sulfonic acid-salt, a para-toluenesulfonic acid-salt, or a fumaric acid-salt. In another embodiment, the pharmaceutically acceptable salt is a hydrochloride-salt or a sulfate-salt. In another embodiment, the pharmaceutically acceptable salt is a hydrochloride-salt. In another embodiment, the pharmaceutically acceptable salt is a sulfate-salt. In another embodiment, the pharmaceutically acceptable salt is a sodium-salt. In another embodiment, the pharmaceutically acceptable salt is a potassium-salt. In another embodiment, the pharmaceutically acceptable salt is a para-toluenesulfonic acid-salt. In another embodiment, the pharmaceutically acceptable salt is a fumaric acid-salt. In another embodiment, the pharmaceutically acceptable fumaric acid-salt contains about one equivalent of a Substituted Benzimidazole-Type Piperidine Compound and about 0.5 equivalents of fumaric acid, e.g., from about 0.3 to about 0.7 equivalents of fumaric acid in one embodiment, from about 0.4 to about 0.6 equivalents of fumaric acid in another embodiment, from about 0.44 to about 0.56 equivalents of fumaric acid in another embodiment, or from about 0.47 to about 0.53 equivalents of fumaric acid in another embodiment. In another embodiment, the pharmaceutically acceptable fumaric acid-salt contains one equivalent of a Substituted Benzimidazole-Type Piperidine Compound and 0.5 equivalents of fumaric acid. One skilled in the art will recognize that, e.g., acid addition salts, of a Substituted Benzimidazole-Type Piperidine Compound can be prepared by reaction of the compounds with the appropriate acid by a variety of known methods.

The compounds of the disclosure provided herein also encompass all anhydrates of the Substituted Benzimidazole-Type Piperidine Compounds. The term "anhydrate" as used herein, is any crystalline form of a Substituted Benzimidazole-Type Piperidine Compound in which water molecules are a non-integral part of the crystal. An anhydrate of a Substituted Benzimidazole-Type Piperidine Compound can be prepared, for example, by crystallization from a solvent substantially free of water. In one embodiment, the Substituted Benzimidazole-Type Piperidine Compound is present as an anhydrate, i.e., as a free base where the crystal lattice is substantially free of water molecules and any water molecules present are present as "surface water" (e.g., loosely bound to the crystal's surface) as would be discernable and distinguishable to those in the art by, e.g., thermogravimetric analysis (TGA) and/or differential scanning calorimetry (DSC), from water molecules that are an integral part of the crystal (e.g., a hydrate). An anhydrate of a Substituted Benzimidazole-Type Piperidine Compound has less than about 0.2 mole water in one embodiment, less than about 0.15 mole water in another embodiment, less than about 0.12 mole water in another embodiment, less than about 0.1 mole water in another embodiment, less than about 0.085 mole water in another embodiment, less than about 0.075 mole water in another embodiment, less than about 0.06 mole water in another embodiment, less than about 0.057 mole water in another embodiment, less than about 0.05 mole water in another embodiment, less than about 0.03 mole water in another embodiment, less than about 0.025 mole water in another embodiment, less than about 0.02 mole water in another embodiment, less than about 0.01 mole water in another embodiment, less than about 0.005 mole water in another embodiment, and less than about 0.001 mole water in another embodiment, each said embodiment taking into account the presence of surface water and each said embodiment being per 1 mole of a Substituted Benzimidazole-Type Piperidine Compound.

The compounds of the disclosure provided herein also encompass all solvates of the Substituted Benzimidazole-Type Piperidine Compounds. "Solvates" are known in the art and are considered to be a combination, physical association and/or solvation of a Substituted Benzimidazole-Type Piperidine Compound with a solvent molecule. This physical association can involve varying degrees of ionic and covalent bonding, including hydrogen bonding. When the solvate is of the stoichiometric type, there is a fixed ratio of the solvent molecule to Substituted Benzimidazole-Type Piperidine Compound, e.g., a disolvate, monosolvate or hemisolvate when the solvent molecule:Substituted Benzimidazole-Type Piperidine Compound molecule molar ratio is 2:1, 1:1 or 1:2, respectively. In other embodiments, the solvate is of the nonstoichiometric type. For example, the Substituted Benzimidazole-Type Piperidine Compound crystal can contain solvent molecules in the structural voids, e.g., channels, of the crystal lattice. In certain instances, the solvate can be isolated, for example when one or more solvent molecules are incorporated into the crystal lattice of a crystalline solid. Thus, "solvate", as used herein, encompasses both solution-phase and isolatable solvates. A Substituted Benzimidazole-Type Piperidine Compound of the disclosure can be present as a solvated form with a pharmaceutically acceptable solvent, such as water, methanol, ethanol, and the like, and it is intended that the disclosure include both solvated and unsolvated Substituted Benzimidazole-Type Piperidine Compound forms. As "hydrate" relates to a particular subgroup of solvates, i.e., where the solvent molecule is water, hydrates are included within the solvates of the disclosure. In one embodiment, the Substituted Benzimidazole-Type Piperidine Compound is present as a monohydrate, i.e., as a free base where the water: Substituted Benzimidazole-Type Piperidine Compound molar ratio is about 1:1, e.g., from 0.91:1 to 1.09:1 in one embodiment, from 0.94:1 to 1.06:1 in another embodiment, from 0.97:1 to 1.03:1 in another embodiment, and from 0.985:1 to 1.015:1 in another embodiment, each said embodiment taking no account of surface water that might be present, if any.

Preparation of solvates is known in the art. For example, Caira et al., "Preparation and Crystal Characterization of a Polymorph, a Monohydrate, and an Ethyl Acetate Solvate of the Antifungal Fluconazole," *J. Pharmaceut. Sci.*, 93(3): 601-611 (2004), describes the preparation of solvates of fluconazole with ethyl acetate and with water. Similar preparations of solvates, hemisolvate, hydrates, and the like are described by Van Tonder et al., "Preparation and Physicochemical Characterization of 5 Niclosamide Solvates and 1 Hemisolvate," *AAPS Pharm. Sci. Tech.*, 5(1):Article 12 (2004), and Bingham et al., "Over one hundred solvates of sulfathiazole," *Chem. Comm.*, pp. 603-604 (2001). In one embodiment, a non-limiting, process involves dissolving the Substituted Benzimidazole-Type Piperidine Compound in a desired amount of the desired solvent (organic, water or mixtures thereof) at temperatures above about 20° C. to about 25° C., cooling the solution at a rate sufficient to form crystals, and isolating the crystals by known methods, e.g., filtration. Analytical techniques, for example, infrared spectroscopy, can be used to show the presence of the solvent in a crystal of the solvate.

In addition, one or more hydrogen, carbon or other atoms of a Substituted Benzimidazole-Type Piperidine Compound can be replaced by a radioactive isotope of the hydrogen, carbon or other atoms. Such a "radiolabeled", "radiolabeled form", and the like of a Substituted Benzimidazole-Type Piperidine Compound, each of which is encompassed by the disclosure, is useful as a research and/or diagnostic tool in metabolism pharmacokinetic studies and in binding assays. "Radioactive", as used herein with respect to an atom, means an atom that comprises a radioactive atom and therefore the specific radioactivity thereof is above the background level of radioactivity. Examples of radioactive isotopes that can be incorporated into a Substituted Benzimidazole-Type Piperidine Compound of the disclosure include isotopes of hydrogen, carbon, nitrogen, oxygen, phosphorus, sulfur, fluorine, chlorine, bromine, and iodine, such as $^2$H, $^3$H, $^{11}$C, $^{13}$C, $^{14}$C, $^{15}$N, $^{17}$O, $^{18}$O, $^{31}$P, $^{32}$P, $^{35}$S, $^{18}$F, $^{19}$F, $^{36}$Cl, $^{37}$Cl, $^{76}$Br, $^{77}$Br, $^{81}$Br, $^{123}$I, $^{124}$I, $^{125}$I, and $^{131}$I, respectively. In one embodiment, a radiolabeled Substituted Benzimidazole-Type Piperidine Compound contains 1, 2, 3, 4, or more radioactive isotopes, each of which is independently selected from hydrogen, carbon, nitrogen, oxygen, phosphorus, sulfur, fluorine, chlorine, bromine, and iodine. In another embodiment, a radiolabeled Substituted Benzimidazole-Type Piperidine Compound contains 1 or 2 radioactive isotopes, each of which is independently selected from hydrogen, carbon, nitrogen, oxygen, phosphorus, sulfur, fluorine, chlorine, bromine, and iodine. In another embodiment, a radiolabeled Substituted Benzimidazole-Type Piperidine Compound contains 1 radioactive isotope which is selected from hydrogen, carbon, nitrogen, oxygen, phosphorus, sulfur, fluorine, chlorine, bromine, and iodine. In another embodiment, a radiolabeled Substituted Benzimidazole-Type Piperidine Compound contains 1, 2, 3, 4, or more radioactive isotopes, each of which is independently selected from $^2$H, $^3$H, $^{11}$C, $^{13}$C, $^{14}$C, $^{15}$N, $^{17}$O, $^{18}$O, $^{31}$P, $^{32}$P, $^{35}$S, $^{18}$F, $^{19}$F, $^{36}$Cl, $^{37}$Cl, $^{76}$Br, $^{77}$Br, $^{81}$Br, $^{123}$I, $^{124}$I, $^{125}$I, and $^{131}$I. In another embodiment, a radiolabeled Substituted Benzimidazole-Type Piperidine Compound contains 1 or 2 radioactive isotopes, each of which is independently selected from $^{2}H$, $^{3}H$, $^{11}C$, $^{13}C$, $^{14}C$, $^{15}N$, $^{17}O$, $^{18}O$, $^{31}P$, $^{32}P$, $^{35}S$, $^{18}F$, $^{19}F$, $^{36}Cl$, $^{37}Cl$, $^{76}Br$, $^{77}Br$, $^{81}Br$, $^{123}I$, $^{124}I$, $^{125}I$, and $^{131}I$. In another embodiment, a radiolabeled Substituted Benzimidazole-Type Piperidine Compound contains 1 radioactive isotope which is selected from $^{2}H$, $^{3}H$, $^{11}C$, $^{13}C$, $^{14}C$, $^{15}N$, $^{17}O$, $^{18}O$, $^{31}P$, $^{32}P$, $^{35}S$, $^{18}F$, $^{19}F$, $^{36}Cl$, $^{37}Cl$, $^{76}Br$, $^{77}Br$, $^{81}Br$, $^{123}I$, $^{124}I$, $^{125}I$, and $^{131}I$. In another embodiment, a radiolabeled Substituted Benzimidazole-Type Piperidine Compound contains 1, 2, 3, 4, or more radioactive isotopes, each of which is independently selected from $^{2}H$, $^{3}H$, $^{13}C$, $^{14}C$, $^{15}N$, $^{18}O$, $^{32}P$, and $^{125}I$. In another embodiment, a radiolabeled Substituted Benzimidazole-Type Piperidine Compound contains 1 or 2 radioactive isotopes, each of which is independently selected from $^{3}H$, $^{14}C$, $^{15}N$, $^{18}O$, $^{32}P$, and $^{125}I$. In another embodiment, a radiolabeled Substituted Benzimidazole-Type Piperidine Compound contains 1 radioactive isotope which is selected from $^{3}H$, $^{14}C$, $^{15}N$, $^{18}O$, 32P, and $^{125}I$.

Radiolabeled compounds of the disclosure can be prepared by methods known in the art. For example, tritiated Substituted Benzimidazole-Type Piperidine Compounds can be prepared by introducing tritium into the particular Substituted Benzimidazole-Type Piperidine Compound, for example, by catalytic dehalogenation with tritium. This method can include reacting a suitably halogen-substituted precursor of a Substituted Benzimidazole-Type Piperidine Compound with tritium gas in the presence of a suitable catalyst, for example, Pd/C, in the presence or absence of a base. Other suitable methods for preparing tritiated compounds can be found in Filer, "The Preparation and Characterization of Tritiated Neurochemicals," *Isotopes in the Physical and Biomedical Sciences, Vol. 1, Labeled Compounds (Part A)*, E. Buncel et al, eds., Chapter 6, pp. 155-192 (1987). $^{14}C$-labeled compounds can be prepared by employing starting materials having a $^{14}C$ carbon. Compounds containing piperazine isotopically enriched with $^{13}C$ and/or $^{15}N$ can be prepared as described in, e.g., FIG. 5A and the associated description, of U.S. Pat. No. 7,355,045 B2. Radiolabeled compounds containing $^{18}F$ at the 6-position of an aniline ring can be prepared as described in column 27 of U.S. Pat. No. 6,562,319 B2.

An Substituted Benzimidazole-Type Piperidine Compound can contain one or more asymmetric centers and can thus give rise to enantiomers, diastereomers, and other stereoisomeric forms. Unless specifically otherwise indicated, the disclosure encompasses compounds with all such possible forms as well as their racemic and resolved forms or any mixture thereof. When a Substituted Benzimidazole-Type Piperidine Compound contains an olefinic double bond or other center of geometric asymmetry, and unless specifically otherwise indicated, it is intended to include all "geometric isomers", e.g., both E and Z geometric isomers. Unless specifically otherwise indicated, all "tautomers", e.g., lactam-lactim, urea-isourea, ketone-enol, amide-imidic acid, enamine-imine, amine-imine, and enamine-enimine tautomers, are intended to be encompassed by the disclosure as well.

As used herein, the terms "stereoisomer", "stereoisomeric form", and the like are general terms for all isomers of individual molecules that differ only in the orientation of their atoms in space. It includes enantiomers and isomers of compounds with more than one chiral center that are not mirror images of one another ("diastereomers").

The term "chiral center" refers to a carbon atom to which four different groups are attached.

The term "enantiomer" or "enantiomeric" refers to a molecule that is nonsuperimposeable on its mirror image and hence optically active where the enantiomer rotates the plane of polarized light in one direction and its mirror image rotates the plane of polarized light in the opposite direction.

The term "racemic" refers to a mixture of equal parts of enantiomers which is optically inactive.

The term "resolution" refers to the separation or concentration or depletion of one of the two enantiomeric forms of a molecule. Optical isomers of a Substituted Benzimidazole-Type Piperidine Compound can be obtained by known techniques such as chiral chromatography or formation of diastereomeric salts from an optically active acid or base.

Optical purity can be stated in terms of enantiomeric excess (% ee) and/or diastereomeric excess (% de), each which is determined by the appropriate formula below:

$$\% \ ee = \left[\frac{\text{major enantiomer(mol)} - \text{minor enantiomer(mol)}}{\text{major enantiomer(mol)} + \text{minor enantiomer(mol)}}\right] \times 100\%$$

$$\% \ de = \left[\frac{\text{major diastereomer(mol)} - \text{minor diastereomers(mol)}}{\text{major diastereomer(mol)} + \text{minor diastereomers(mol)}}\right] \times 100\%.$$

The term "MeOH" means methanol, i.e., methyl alcohol. The term "EtOH" means ethanol, i.e., ethyl alcohol. The term "Et$_2$O" means diethyl ether, i.e., ethoxyethane. The term "THF" means tetrahydrofuran. The term "DMF" means N,N-dimethylformamide. The term "DCM" means methylene chloride, i.e., dichloromethane or $CH_2Cl_2$. The term "DCE" means 1,2-dichloroethane. The term "EtOAc" means ethyl acetate. The term "MeCN" means acetonitrile. The term "DMSO" means dimethylsulfoxide, i.e., methylsulfinylmethane. The term "NMP" means N-methylpyrrolidinone, i.e., 1-methylpyrrolidin-2-one. The term "MTBE" means tert-butyl methyl ether, i.e., 2-methoxy-2-methylpropane. The term "AcOH" means acetic acid. The term "TFA" means 2,2,2-trifluoroacetic acid. The term "TEA" means triethylamine. The term "DIEA" means diisopropylethylamine, i.e., N-ethyl-N-isopropylpropan-2-amine. The term "Bn" means benzyl, i.e.:

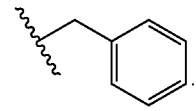

The term "NaOH" means sodium hydroxide. The term "HCl" means hydrochloric acid. The term "EDCI" means 1-ethyl-3-(3-dimethylaminopropyl)carbodiimide, i.e., $N^1$-((ethylimino)methylene)-$N^3$,$N^3$-dimethylpropane-1,3-diamine. The term "CDI" means di(1H-imidazol-1-yl)methanone. The term "BOC" means tert-butyloxycarbonyl, i.e.:

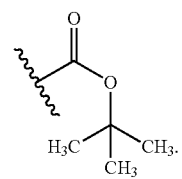

The term "IBD" means inflammatory-bowel disease. The term "IBS" means irritable-bowel syndrome. The term "ALS" means amyotrophic lateral sclerosis.

The term "effective amount", when used in connection with a Substituted Benzimidazole-Type Piperidine Compound, means an amount effective for: (a) treating or preventing a Condition or symptom thereof; (b) detectably inhibiting ORL-1 receptor function in a cell; or (c) detectably activating ORL-1 receptor function in a cell.

The term "effective amount", when used in connection with a second therapeutic agent means an amount for providing the therapeutic effect of the second therapeutic agent.

The terms "modulate", "modulating", and the like as used herein with respect to the ORL-1 receptor mean the mediation of a pharmacodynamic response (e.g., analgesia) in an animal from (i) inhibiting or activating the receptor, or (ii) directly or indirectly affecting the normal regulation of the receptor activity. Compounds that modulate the receptor activity include agonists, partial agonists, antagonists, mixed agonists/antagonists, mixed partial agonists/antagonists and compounds which directly or indirectly affect regulation of the receptor activity.

As used herein, a compound that binds to a receptor and mimics the regulatory effect(s) of an endogenous ligand is defined as an "agonist". As used herein, a compound that binds to a receptor and is only partly effective as an agonist is defined as a "partial agonist". As used herein, a compound that binds to a receptor but produces no regulatory effect, but rather blocks binding of another agent to the receptor is defined as an "antagonist". (See Ross et al., "Pharmacodynamics: Mechanisms of Drug Action and the Relationship Between Drug Concentration and Effect," in *Goodman and Gilman's The Pharmacological Basis of Therapeutics* pp. 31-43 (Goodman et al., eds., 10$^{th}$ Ed., McGraw-Hill, New York 2001)).

The terms "treatment of", "treating", and the like include the amelioration or cessation of a Condition or a symptom thereof. In one embodiment, treating includes inhibiting, for example, decreasing the overall frequency of episodes of a Condition or a symptom thereof.

The terms "prevention of", "preventing", and the like include the avoidance of the onset of a Condition or a symptom thereof.

A "disorder" includes, but is not limited to, the Conditions defined above.

In the event of doubt as to the agreement of a depicted chemical structure and a chemical name, the depicted chemical structure governs.

It is appreciated that various features of the disclosure which are, for clarity, described in the context of separate embodiments, can also be provided in combination in a single embodiment unless otherwise specifically herein excluded. Conversely, various features of the disclosure which are, for brevity, described in the context of a single embodiment, can also be provided separately and/or in any suitable subcombination unless otherwise specifically herein excluded.

4.5 Methods for Making Substituted Benzimidazole-Type Piperidine Compounds of Formula (I)

Substituted Benzimidazole-Type Piperidine Compounds can be made using conventional organic synthesis, in view of the present disclosure, and including the following illustrative methods shown in the schemes below where $R^1$, $R^2$, $R^3$, $Q_a$, W, U, A, B, Z, a, and the dashed lines are defined above, L is a halogen leaving group such as Br or I, L' is F or Cl, R is —($C_1$-$C_4$)alkyl or —$CF_3$, and R' is —($C_1$-$C_4$) alkyl. For simplicity, in the following schemes the exemplary $Q_a$ group is benzo which is sometimes unsubstituted with $R^2$; however, the schemes are also applicable to substituted benzo and any of the (5- or 6-membered) heteroaryl $Q_a$ groups, whether unsubstituted or optionally substituted.

Section 4.5.1 describes methods for making benzene-1,2-diamine compounds. Section 4.5.2 describes methods for making Substituted Benzimidazole-Type Piperidine Compounds of Formula (I) from benzene-1,2-diamine compounds. Section 4.5.3 describes methods for making various stereochemical forms of Substituted Benzimidazole-Type Piperidine Compounds of Formula (I).

4.5.1 Methods for Making Benzene-1,2-diamine Compounds

Preparation of Substituted Benzimidazole-Type Piperidine Compounds of Formula (I) can be carried out by reacting through a benzene-1,2-diamine intermediate compound (e.g., Compound A4). Five alternative methods for preparing benzene-1,2-diamine compounds are shown in Schemes A and C-F below.

4.5.1.1 Synthesis of Compound A4

Method 1 (Scheme A)

Scheme A

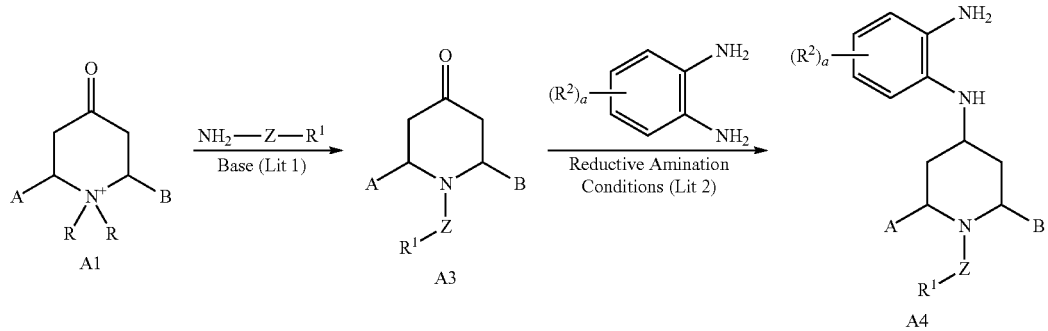

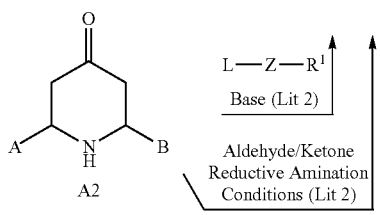

In Scheme A and the other schemes, "Lit 1" refers to the procedures described in the publications Tortolani et al., "A Convenient Synthesis to N-Aryl-Substituted 4-Piperidones," *Org. Lett.* 1:1261-1262 (1999) and/or International PCT Publication No. WO 2005/075459 A1 of Euro-Celtique S.A. and "Lit 2" refers to the procedures described in U.S. Pat. No. 6,635,653 by Goehring et al.

Compounds A1 and A2 are commercially available or can be prepared by methods known to the art.

A piperidinium salt of structure A1 can be reacted with a primary amine in a suitable solvent, such as EtOH, under reflux conditions in the presence of a base, such as potassium carbonate, as described in reference "Lit 1" to provide the 1-(substituted)piperidine-4-one Compound A3. As described in reference "Lit 2," Compound A3 can also be prepared by alkylation of a piperidine-4-one of structure A2 with an alkyl bromide or alkyl iodide in a suitable solvent, such as DMF, MeCN or DMSO, in the presence of an inorganic base, such as potassium carbonate, or an organic base, such as DMA. As described in reference "Lit 2," Compound A3 can also be prepared by reductive amination of Compound A2 with an aldehyde or ketone using either sodium triacetoxyborohydride or sodium cyanoborohydride in a suitable solvent, such as DCM or MeOH, respectively. Compound A3 can then be reductively aminated with a substituted or unsubstituted 1,2-phenylenediamine using sodium triacetoxyborohydride or sodium cyanoborohydride in a suitable solvent, such as DCM or MeOH, respectively, to provide Compound A4, as described in reference "Lit 2."

4.5.1.2 Synthesis of Compound B6

Method 2 (Scheme B)

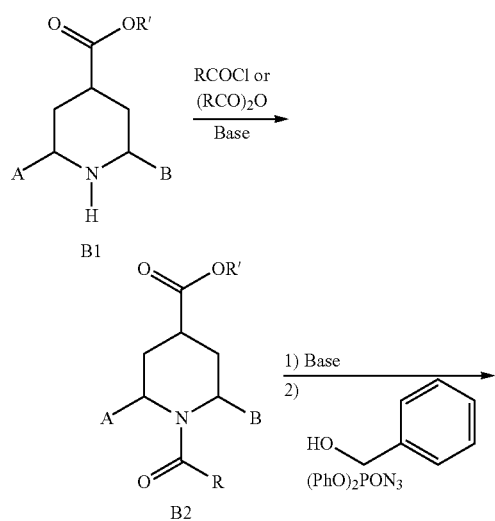

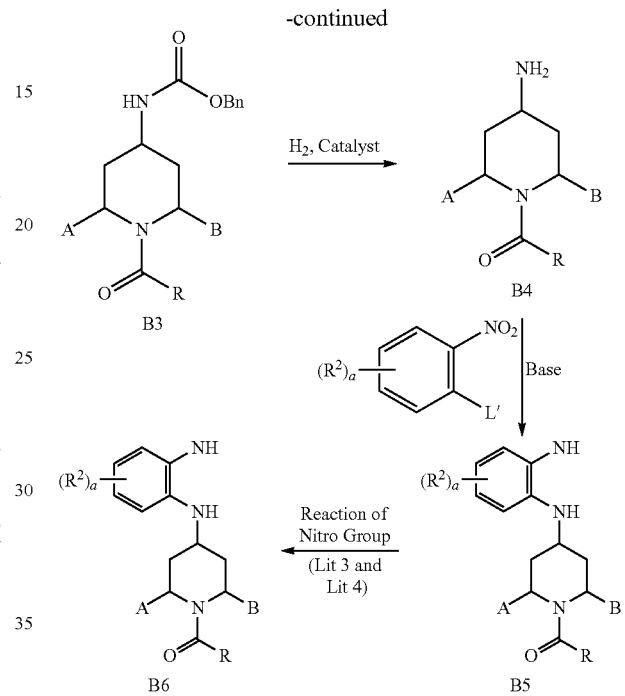

In Scheme B and the other schemes, "Lit 3" refers to the reference Rylander, "Hydrogenation of Nitro Compounds," in *Hydrogenation Methods* pp. 104-116 (Academic Press, London, 1985), which provides a review of the methods available for the reduction of nitro groups, and "Lit 4" refers to the Zinin reduction procedures described in the reference Porter, "The Zinin Reduction of Nitroarenes," *Org. Reactions*, 20:455-481 (1973).

Compound B1 is commercially available or can be prepared by methods known to the art. Compound B1 can be reacted with an acid chloride $RC(=O)Cl$, such as 2,2,2-trifluoroacetyl chloride, or anhydride $(RC(=O))_2O$, such as 2,2,2-trifluoroacetic anhydride, and a base, such as TEA, in a suitable solvent, such as DCM or THF, to provide Compound B2. Compound B2 can be converted to Compound B3 in a two step procedure by hydrolysis of the ester to the carboxylic acid using an appropriate base, such as aqueous NaOH, followed by treatment with diphenyl phosphorazidate ("$(PhO)_2P(=O)N_3$") and phenylmethanol ("BnOH") under Curtius rearrangement conditions. The benzyloxycarbonyl group of Compound B3 can then be removed under hydrogenolysis conditions using a noble metal catalyst, e.g., palladium on carbon, under a hydrogen atmosphere, to provide Compound B4. Compound B4 can be reacted with a substituted or unsubstituted 2-halo-1-nitrobenzene (where the halo is fluoride or chloride) in the presence of a base such as potassium carbonate in a suitable solvent such as MeCN under reflux conditions to provide Compound B5. In the next step, Compound B5 can be converted to Compound B6 using a catalyst, such as Raney nickel, in a suitable solvent, such as EtOH, under a hydrogen atmosphere as described in reference "Lit 3." Compound B5 can also be converted to Compound B6 by chemical means, such as with Zn, Sn(II) chloride or Fe, or using sulfides or polysulfides by the Zinin Reduction as described in reference "Lit 4."

4.5.1.3 Synthesis of Compound C4

Method 3 (Scheme C)

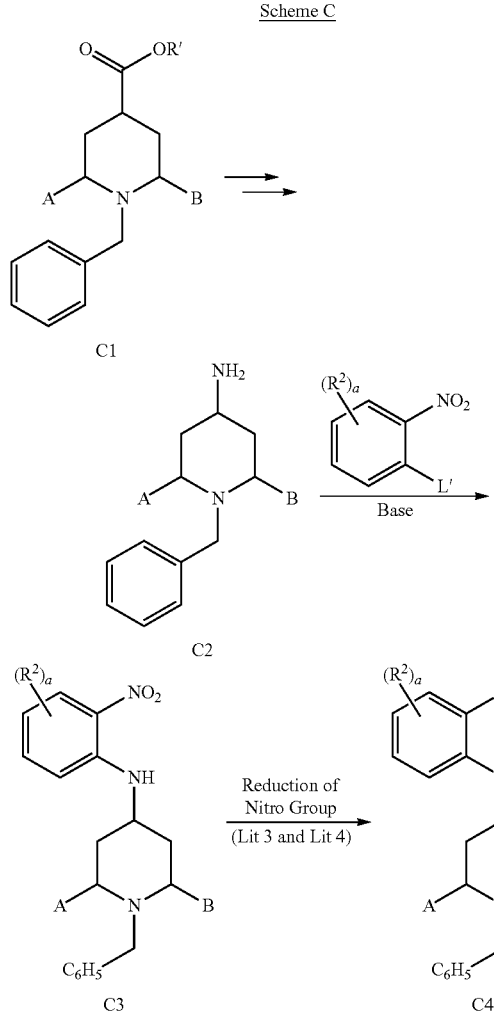

reducing agent, such as Zn, Sn(II) chloride or Fe, or using sulfide or polysulfides by the Zinin Reduction as described in Scheme B.

4.5.1.4 Synthesis of Compound D2

Method 4 (Scheme D)

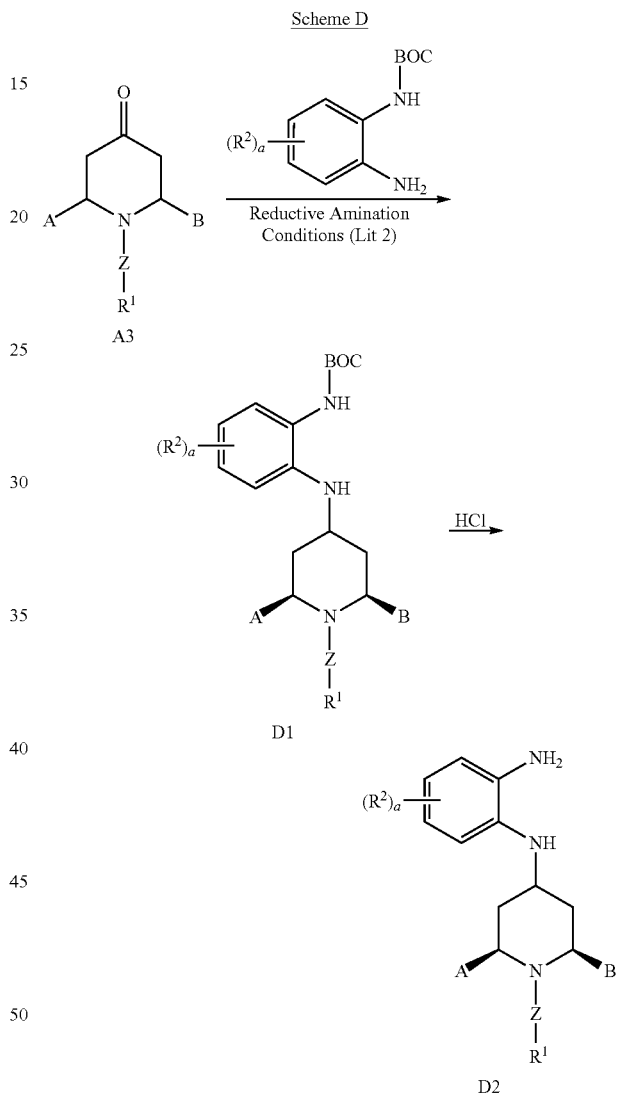

Compound C1 is commercially available or can be prepared from Compound B1 by methods known to the art. Compound C2 can be prepared from Compound C1 in a similar manner to the preparation of Compound B4 from Compound B1 in Scheme B. Compound C2 can be reacted with a substituted or unsubstituted 2-halo-1-nitrobenzene (where the halo is fluoride or chloride) in the presence of a base such as potassium carbonate in a suitable solvent such as MeCN under reflux conditions to provide Compound C3. In the next step, Compound C3 can be converted to Compound C4 by treatment with a hydrogenation catalyst, such as Raney nickel, in a suitable solvent, such as EtOH, under a hydrogen atmosphere, or by chemical means using a As shown in Scheme D, Compound A3 can be converted to Compound D1 under reductive amination conditions using a BOC protected, substituted or unsubstituted 1,2-phenylenediamine and a reducing agent, such as sodium triacetoxyborohydride or sodium cyanoborohydride, in a suitable solvent, such as DCM or MeOH, respectively as described in reference "Lit 2." The BOC protecting group can be removed using acidic conditions, such as using HCl or TFA, to provide Compound D2. Where substituent groups A and B together form a bridge, e.g., a two carbon bridge, the "exo" and "endo" isomers which result can be conveniently separated using flash column chromatography.

4.5.1.5 Synthesis of Compound E3

Method 5 (Scheme E)

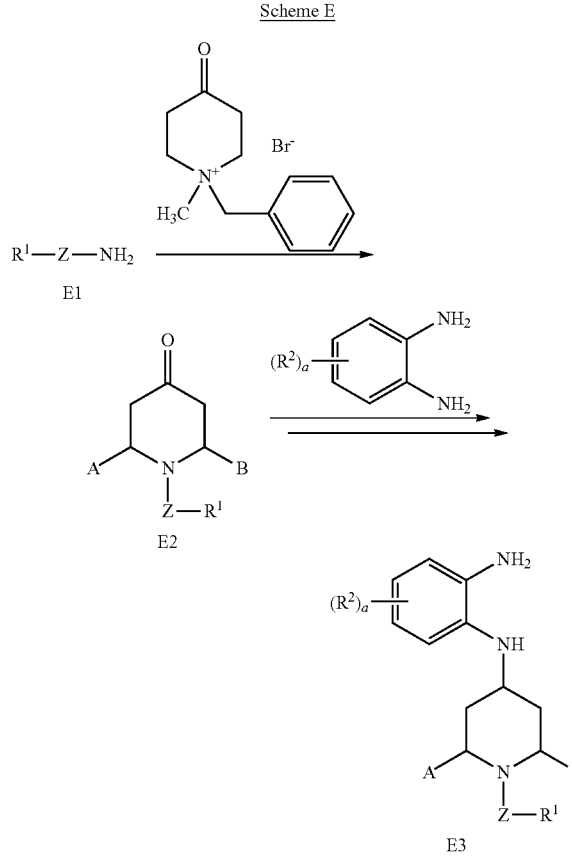

In Scheme E, Compound E3 can be prepared as described in U.S. Pat. App. Pub. No. US 2010/0022519 A1 for example, at paragraph [1364] and thereafter. Briefly, the primary amine E1, where —Z—R$^1$ can be cyclodecyl, adamantyl or noradamantyl, for example, can be treated with a piperidone salt in a polar solvent, such as EtOH or MeOH containing water, and an inorganic base, such as potassium carbonate, under reflux for from about 4 hrs to about 6 hrs to provide Compound E2. Compound E2 can then be treated with a substituted or unsubstituted 1,2-phenylenediamine and AcOH in a solvent, such as THF or 1,2-dimethoxyethane, to provide an imine, which can be reduced with sodium triacetoxyborohydride to provide Compound E3.

4.5.2 Methods for Making Substituted Benzimidazole-Type Piperidine Compounds of Formula (I) from Benzene-1,2-diamine Compounds Methods for converting benzene-1,2-diamine compounds to provide Substituted Benzimidazole-Type Piperidine Compounds of Formula (I) are shown in Schemes F-P below.

4.5.2.1 Synthesis of Substituted Benzimidazole-Type Piperidine Compounds where Q$_x$ is Present and U$^1$ is C or CH (Schemes F-H)

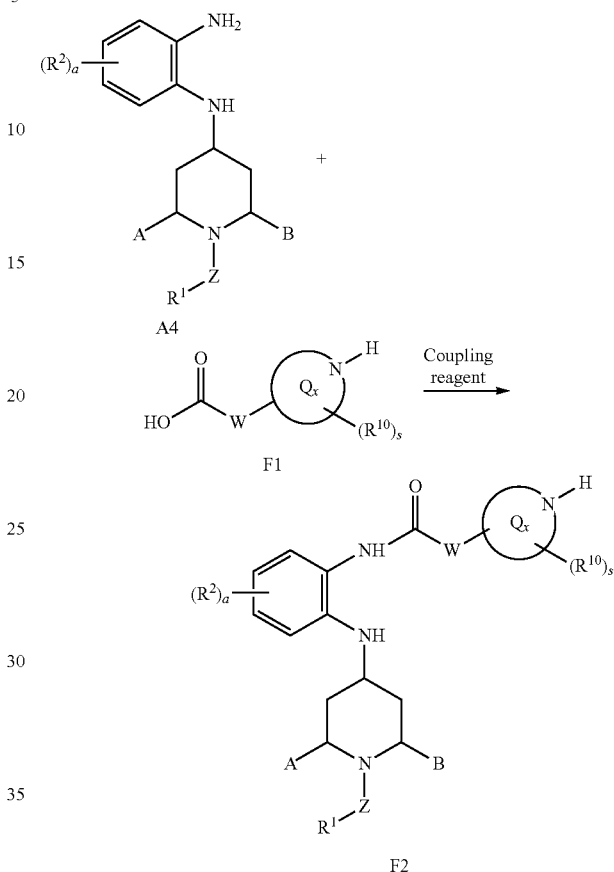

In Scheme F, Compound A4 can be reacted with Compound F1 in the presence of one or more coupling reagents, e.g., 1-hydroxybenzotriazole (HOBT) and/or 1-ethyl-3-(3-dimethylaminopropyl)carbodiimide (EDCI), at a temperature of about 25° C. to provide Compound F2. The reaction can be carried out in the presence of a suitable base, such as DIEA.

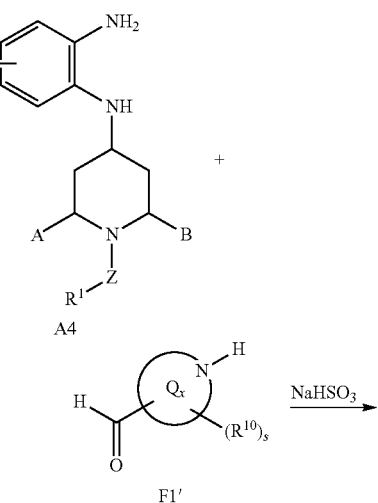

-continued

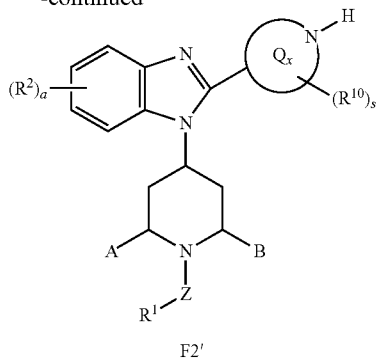

F2'

In Scheme F', Compound A4 can be reacted with Compound F1' in excess sodium bisulfite at an elevated temperature (e.g., greater than about 100° C.) to provide Compound F2'. In certain embodiments, the reaction can be carried out using a microwave apparatus as an energy source.

Scheme G

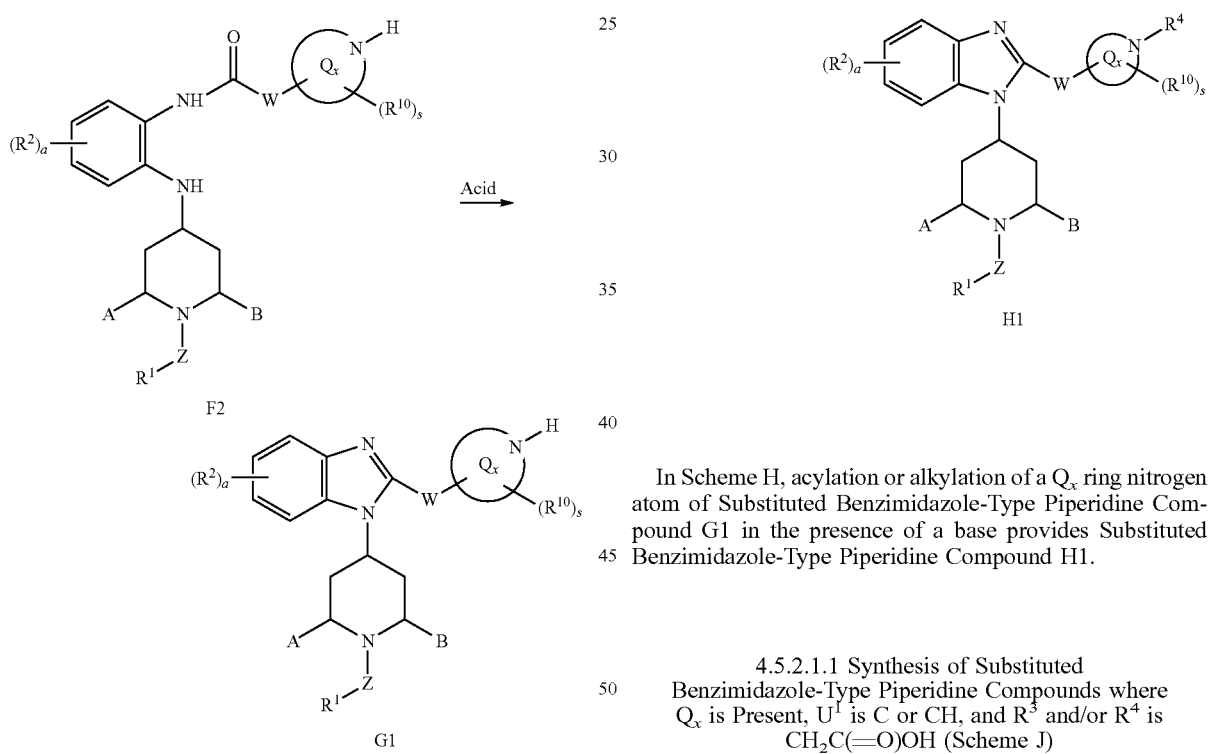

F2

G1

In Scheme G, Compound F2 can be cyclized in the presence of an acid to provide Substituted Benzimidazole-Type Piperidine Compound G1. In certain embodiments, the cyclization reaction is conducted in the presence of AcOH at elevated temperature, e.g., from about 80° C. to about 120° C.

Scheme H

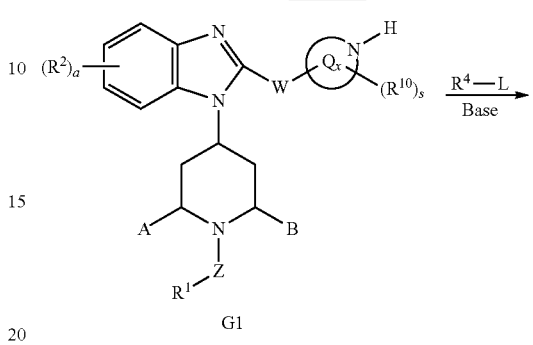

G1

H1

In Scheme H, acylation or alkylation of a $Q_x$ ring nitrogen atom of Substituted Benzimidazole-Type Piperidine Compound G1 in the presence of a base provides Substituted Benzimidazole-Type Piperidine Compound H1.

4.5.2.1.1 Synthesis of Substituted Benzimidazole-Type Piperidine Compounds where $Q_x$ is Present, $U^1$ is C or CH, and $R^3$ and/or $R^4$ is $CH_2C(=O)OH$ (Scheme J)

Scheme J

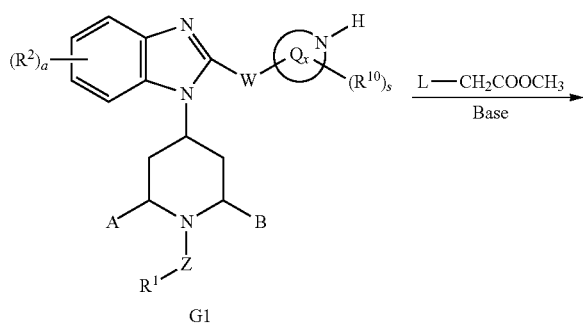

G1

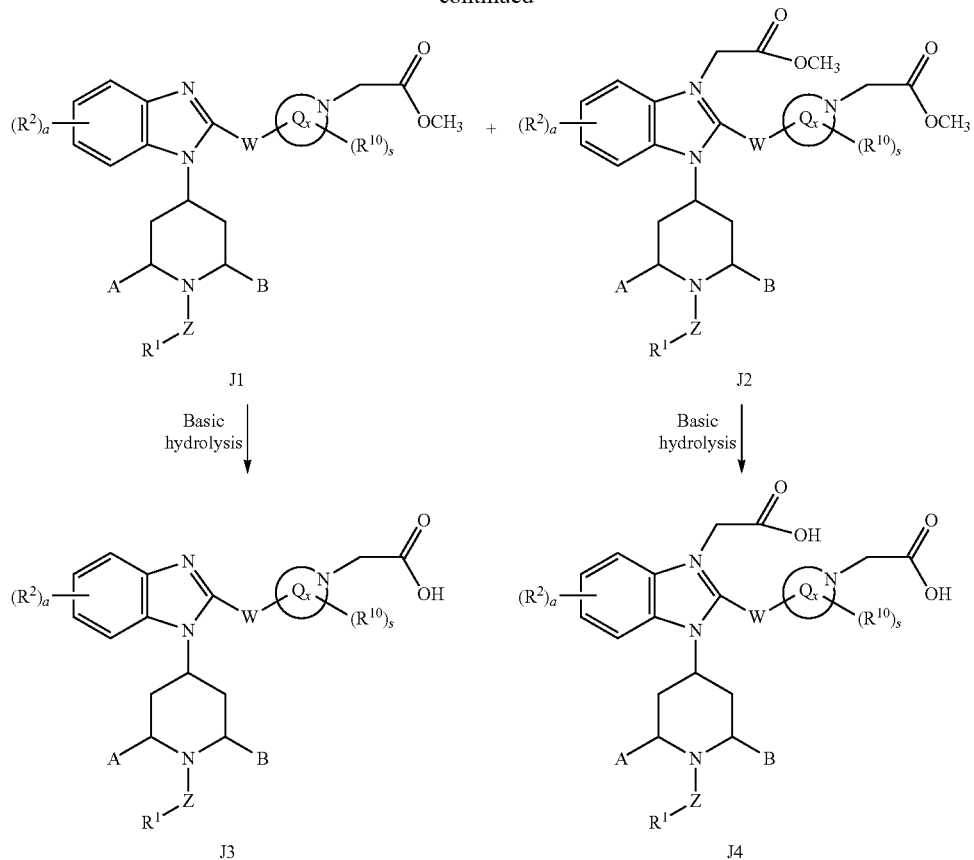

In Scheme J, Substituted Benzimidazole-Type Piperidine Compound G1 is reacted with L-CH$_2$C(=O)OCH$_3$ in the presence of a base to provide Substituted Benzimidazole-Type Piperidine Compounds J1 and J2. Substituted Benzimidazole-Type Piperidine Compound J1 and/or Substituted Benzimidazole-Type Piperidine Compound J2 can then be hydrolyzed by a suitable base, e.g., NaOH, in EtOH to provide Substituted Benzimidazole-Type Piperidine Compound J3 and/or Substituted Benzimidazole-Type Piperidine Compound J4, respectively.

4.5.2.2 Synthesis of Substituted Benzimidazole-Type Piperidine Compounds where --- W— is a Single Bond, Q$_x$ is Present, and U$^1$ is N (Schemes K and L)

Scheme K

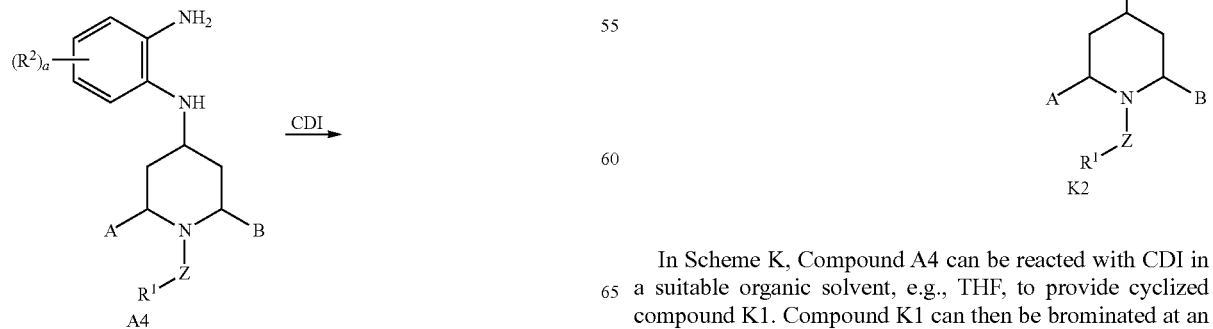

In Scheme K, Compound A4 can be reacted with CDI in a suitable organic solvent, e.g., THF, to provide cyclized compound K1. Compound K1 can then be brominated at an elevated temperature through the addition of phosphorus oxybromide (POBr₃) in a suitable organic solvent, e.g., DCE, to provide Compound K2.

Scheme L

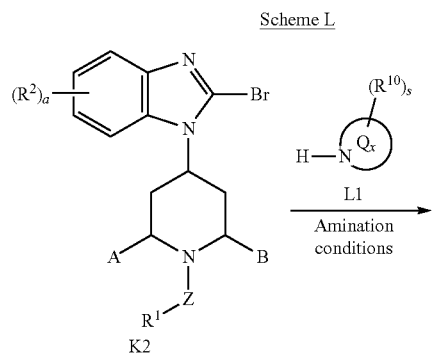

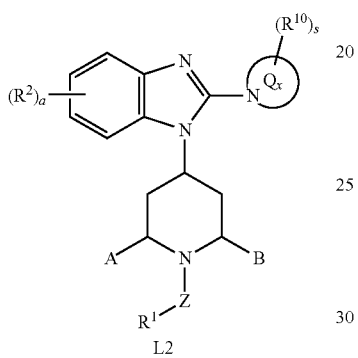

L2

In Scheme L, Compound K2 is reacted with Compound L1 under amination conditions, for example, using an amination agent, such as N,N'-dicyclohexylcarbodiimide, HOBT, or EDCI, and a base, such as TEA or DIEA, in a suitable solvent, such as DCM or THF, to provide Substituted Benzimidazole-Type Piperidine Compound L2. In certain embodiments, the reaction can be conducted in a sealed pressurized tube at elevated temperature, e.g., about 100° C.

4.5.2.3 Synthesis of Substituted Benzimidazole-Type Piperidine Compounds where ꞊꞊꞊ W— is —CH₂—, $Q_x$ is Present, and $U^1$ is N (Scheme M)

Scheme M

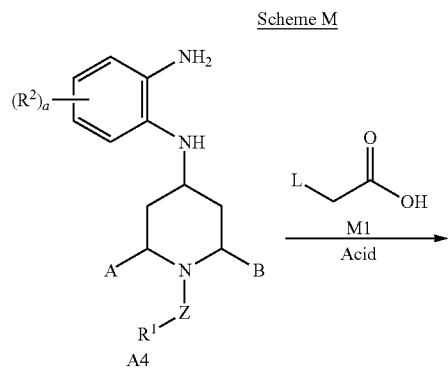

A4

-continued

M2

M3

In Scheme M, Compound A4 can be cyclized at elevated temperature, e.g., from about 70° C. to about 120° C., through the addition of Compound M1 in the presence of a strong acid to provide Substituted Benzimidazole-Type Piperidine Compound M2. Substituted Benzimidazole-Type Piperidine Compound M2 can then be reacted with Compound L1 in the presence of base to provide Substituted Benzimidazole-Type Piperidine Compound M3.

4.5.2.4 Synthesis of Substituted Benzimidazole-Type Piperidine Compounds where ꞊꞊꞊ W— is —NH— and $Q_x$ is Absent (Scheme N)

Scheme N

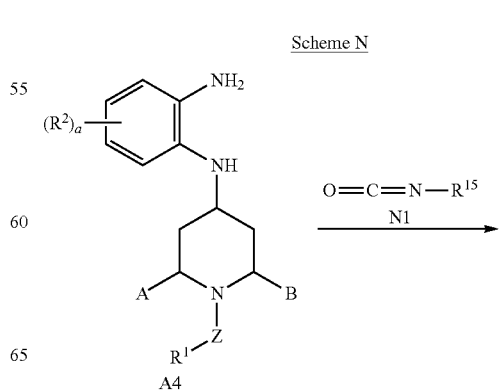

A4

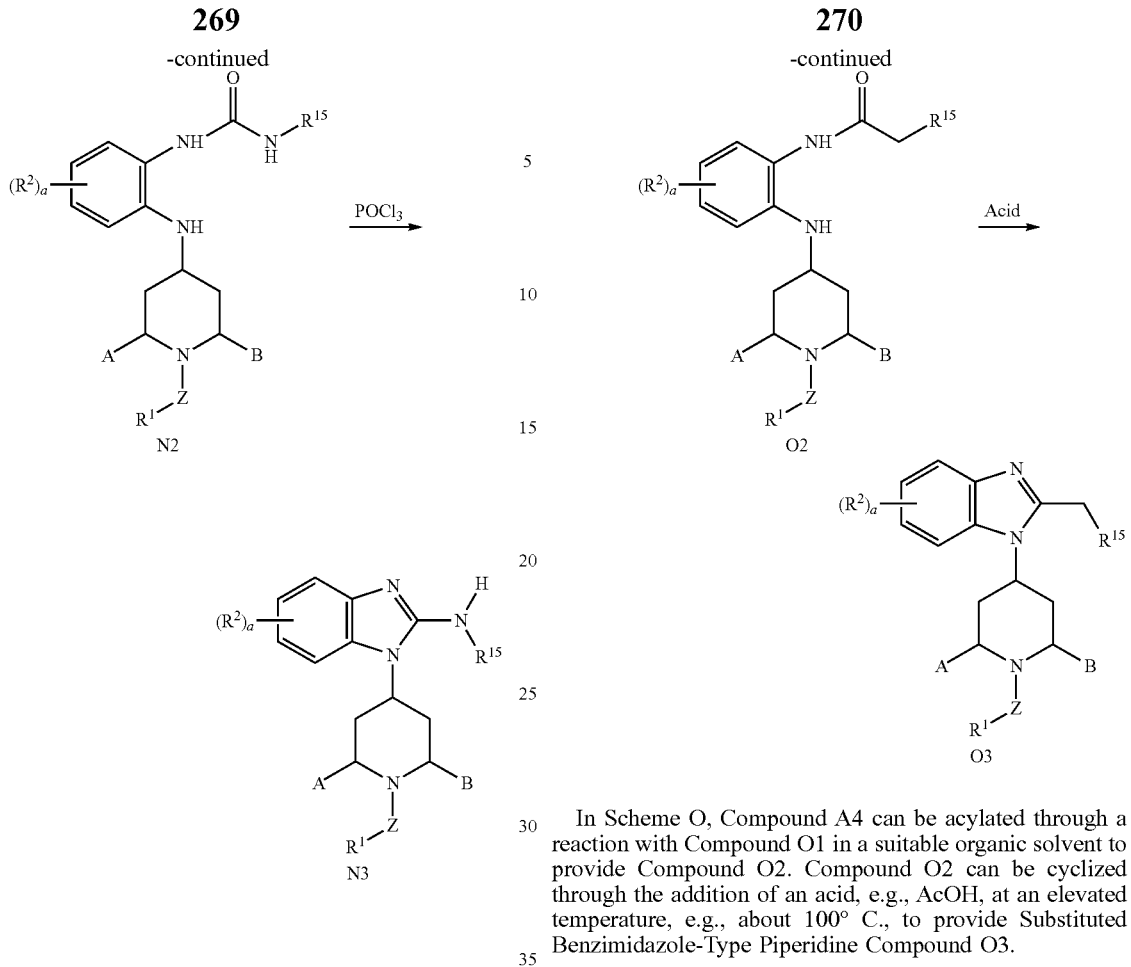

In Scheme N, Compound A4 can be reacted with isocyanate N1 in the presence of a suitable organic solvent, e.g., DCM, to provide compound N2. Compound N2 can then be cyclized through the addition of phosphorus oxychloride (POCl₃) at elevated temperature, e.g., about 100° C., to provide Substituted Benzimidazole-Type Piperidine Compound N3.

4.5.2.5 Synthesis of Substituted Benzimidazole-Type Piperidine Compounds where ---W— is —CH₂— and Q$_x$ is Absent (Scheme O)

In Scheme O, Compound A4 can be acylated through a reaction with Compound O1 in a suitable organic solvent to provide Compound O2. Compound O2 can be cyclized through the addition of an acid, e.g., AcOH, at an elevated temperature, e.g., about 100° C., to provide Substituted Benzimidazole-Type Piperidine Compound O3.

4.5.2.6 Synthesis of Substituted Benzimidazole-Type Piperidine Compounds where ---W— is —CH=N— and Q$_x$ is Absent

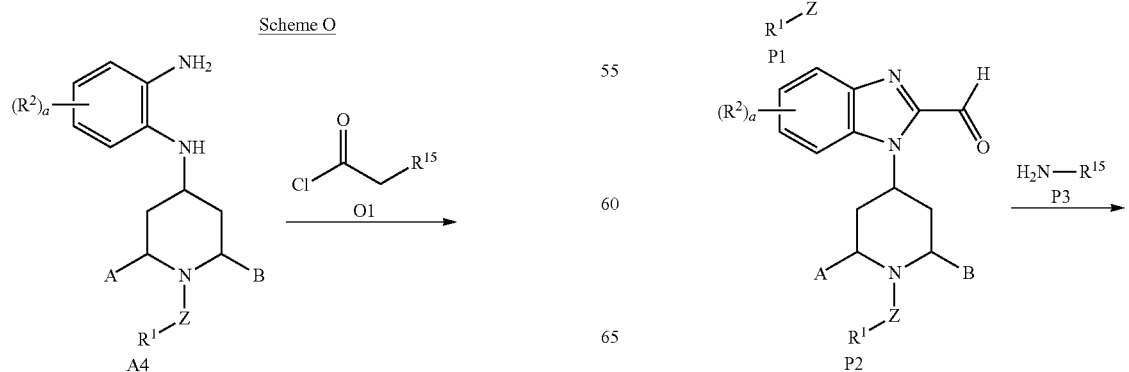

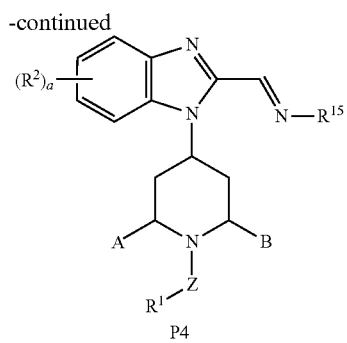

P4

Substituted Benzimidazole-Type Piperidine Compound P1 in Scheme P can be prepared, e.g., by the method in Section 4.5.2.5 above. Substituted Benzimidazole-Type Piperidine Compound P1 can be converted to Substituted Benzimidazole-Type Piperidine Compound P2 through the addition of magnesium dioxide in a suitable organic solvent, e.g., DCM. Substituted Benzimidazole-Type Piperidine Compound P2 can then be reacted with Compound P3 in an alcohol solvent, e.g., MeOH, under reflux conditions to provide Substituted Benzimidazole-Type Piperidine Compound P4.

4.5.3 Methods for Making Specific Stereoisomeric Forms of Substituted Benzimidazole-Type Piperidine Compounds of Formula (I)

Specific stereoisomeric forms of Substituted Benzimidazole-Type Piperidine Compounds of Formula (I) can be prepared using methods described above. As described below, the desired stereochemical form can be introduced into the optionally-bridged piperidine portion of the molecule prior to the addition of the quinoxaline portion of the molecule.

4.5.3.1 Synthesis of Stereoisomeric Forms of Substituted Benzimidazole-Type Piperidine Compound Precursors (Scheme Q)

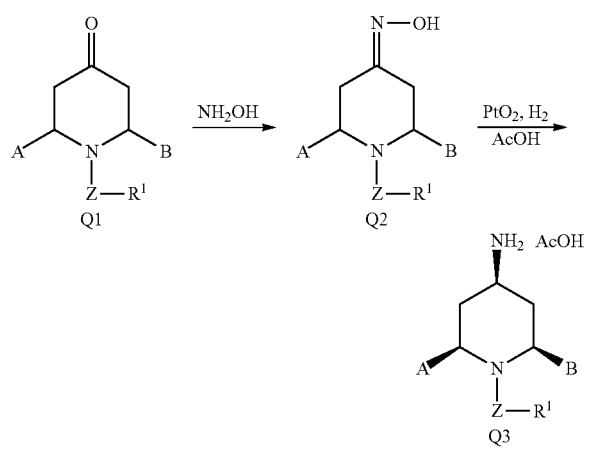

In Scheme Q, Compound Q3 can be prepared according to the methods described in U.S. Pat. App. Pub. No. US 2010/0216726 A1, for example, at paragraph [1745] and thereafter. Briefly, Compound Q1 can be converted to oxime Compound Q2 using aqueous hydroxylamine in an acidic solvent, such as AcOH. Compound Q2 can be reduced to an endo amine Compound Q3 by hydrogenation using a noble metal catalyst, such as platinum oxide, in a solvent, such as AcOH.

4.5.3.2 Alternative Synthesis of Stereoisomeric Forms of Substituted Benzimidazole-Type Piperidine Compound Precursors (Scheme R)

Scheme R

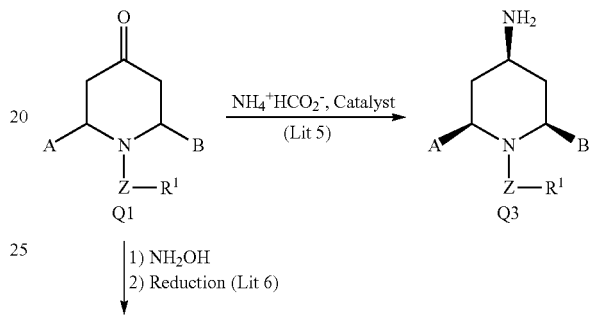

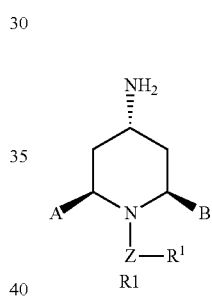

R1

In Scheme R and the other schemes, "Lit 5" refers to Berdini et al., "A Modified Palladium Catalyzed Reductive Amination Procedure," *Tetrahedron,* 58:5669-5674 (2002) and "Lit 6" refers to Lewin et al., "Molecular Features Associated with Polyamine Modulation of NMDA Receptors," *J. Med. Chem.* 41:988-995 (1998).

Compound Q1, where substituent groups A and B together form a bridge, e.g., a two carbon bridge, is commercially available or can be prepared by methods known to the art.

When substituent groups A and B together form a bridge, e.g., a two carbon bridge, Compound Q1 can be converted to Compound Q3, the "endo" isomer, under reductive amination conditions using, e.g., ammonium formate and a noble metal catalyst, e.g., palladium on carbon, in a solvent, such as EtOH or MeOH, as described in reference "Lit 5." Similarly, where substituent groups A and B together form a bridge, e.g., a two carbon bridge, Compound Q1 can be reacted with aqueous hydroxylamine in a solvent, such as hexanes, to form an intermediate hydroxylamine, which can be converted to its oxime by dehydration in a solvent with a high boiling point, such as toluene, under Dean-stark conditions. The oxime intermediate can be converted to Compound R1, the "exo" isomer, by reduction using, e.g., sodium in propanol as described in reference "Lit 6."

4.5.3.3 Synthesis of Stereoisomeric Forms of Substituted Benzimidazole-Type Piperidine Compounds of Formula (I) from Compound Q3 (Scheme S)

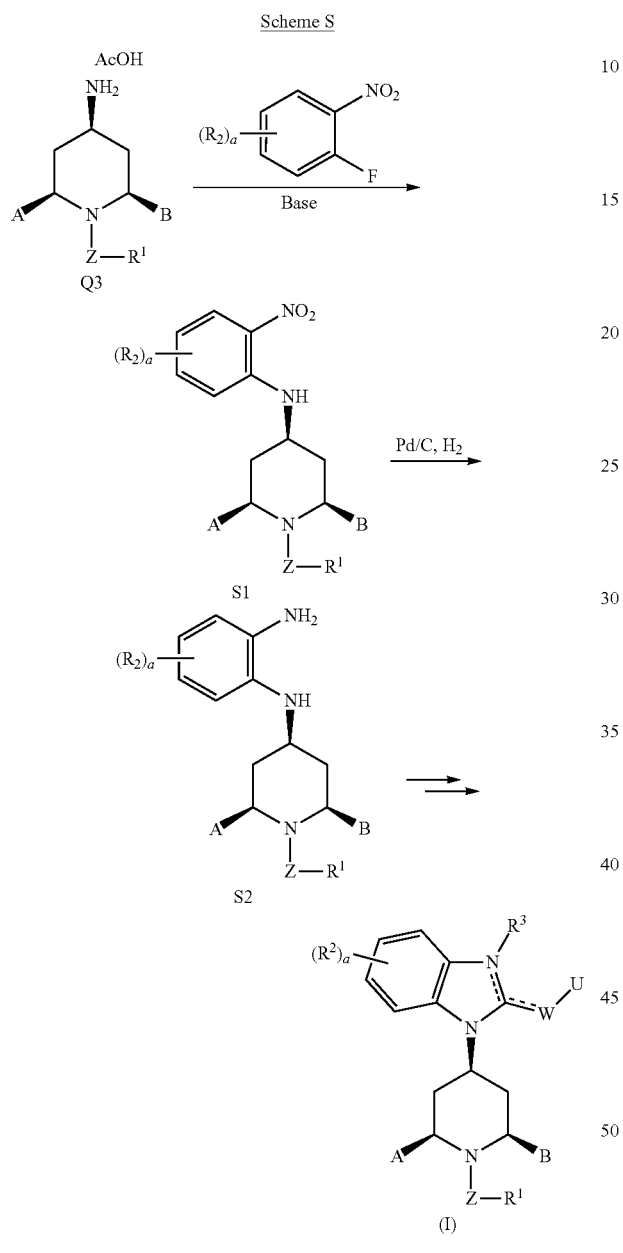

In Scheme S, Compound S2 can be prepared according to the methods described in U.S. Pat. App. Pub. No. US 2010/0216726 A1, for example, at paragraph [1745] and thereafter. Briefly, amine Compound Q3 or its salt, such as the acetate, can be reacted with a substituted or unsubstituted 2-fluoronitrobenzene in a polar solvent, such as MeCN or DMF, and a base, such as TEA or potassium carbonate, to provide Compound S1. Compound S1 can be reduced to Compound S2 by hydrogenation using a noble metal catalyst, such as palladium on charcoal or Raney nickel, in a solvent, such as EtOAc or DCM. Thereafter, a Substituted Benzimidazole-Type Piperidine Compound of Formula (I) can be prepared using methods described in Sections 4.5.1 through 4.5.2.

In these embodiments, the final product of the reaction, i.e., the Substituted Benzimidazole-Type Piperidine Compound of Formula (I), has a percent diastereomeric excess (% de) of at least about 90%. In another embodiment, the final product of the reaction has a % de of at least about 95%. In another embodiment, the final product of the reaction has a % de of at least about 97%. In another embodiment, the final product of the reaction has a % de of at least about 98%. In another embodiment, the final product of the reaction has a % de of at least about 99%. In another embodiment, the final product of the reaction has a % de of greater than 99% (e.g., 99.1% to 99.9%).

4.5.4 Methods for Making 3-Chloroquinoxalin-2(1H)-One Intermediates and Substituted Benzimidazole-Type Piperidine Compounds Comprising a 3-(Bicyclo[3.3.1]nonanyl) $R^1$ Group (Scheme T)

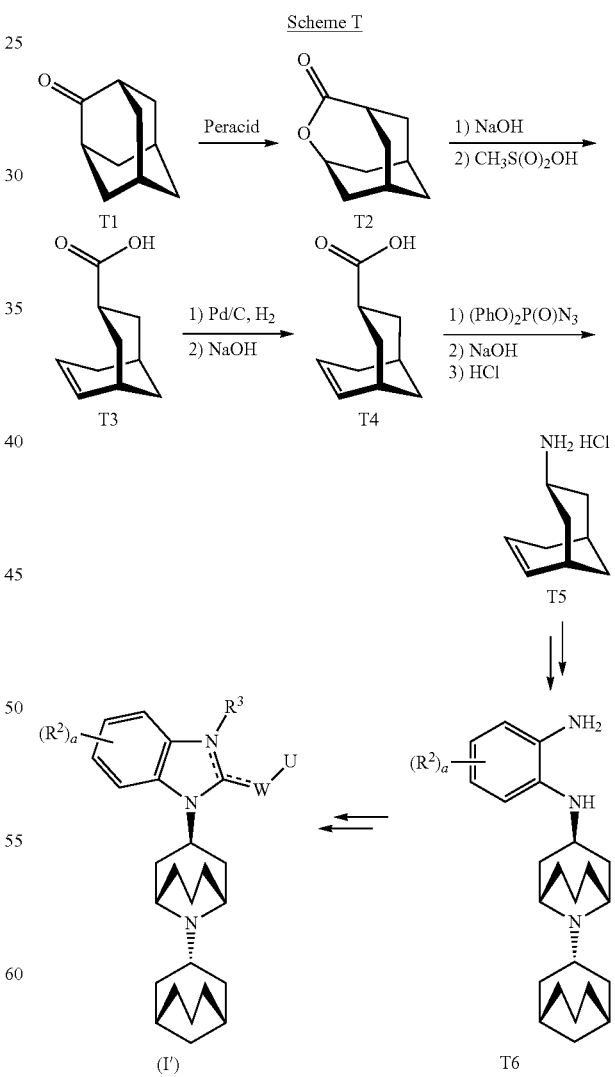

In Scheme T, 2-adamantanone T1 can be dissolved in TFA and treated with a peracid, such sodium percarbonate, at from about 20° C. to about 30° C. to provide a lactone Compound T2. Compound T2 can be hydrolyzed to a hydroxyl acid using NaOH in a solvent, such as MeOH, under reflux. The stereochemistry of the acid epimerizes from endo to exo. The hydroxyl acid can be dehydrated to Compound T3 using an acid, such as methanesulfonic acid, in a solvent, such as toluene, by azeotropic drying. Compound T3 can be hydrogenated using a catalyst, such as palladium on charcoal, in a mixed solvent system, such as MeOH and EtOAc, to provide a mixture of acid Compound T4 and its methyl ester (Compound T4', not shown). The mixture can be hydrolyzed to the acid Compound T4 using NaOH in aqueous MeOH. Compound T4 can be converted to Compound T5 using di-phenyl phosphoryl azide and TEA in a solvent, such as toluene, in a Curtius type reaction to provide an isocyanate that can be hydrolyzed to the amine of Compound T5 using NaOH in aqueous THF or another aprotic water miscible solvent. The isolated amine of Compound T5 can be converted to its hydrochloride salt by treatment with HCl. Compound T5 can be converted to a 2-chloroquinoxaline Compound T6 according to the methods described in Section 4.5.1. Compound T6 can be converted to Substituted Benzimidazole-Type Piperidine Compounds of Formula (I') according to the methods described in Section 4.5.2.

4.5.5 Methods for Making 3-Chloroquinoxalin-2 (1H)-one Intermediates and Substituted Benzimidazole-Type Piperidine Compounds Comprising a 3-(7-Methylbicyclo[3.3.1]nonanyl) $R^1$ Group (Scheme U)

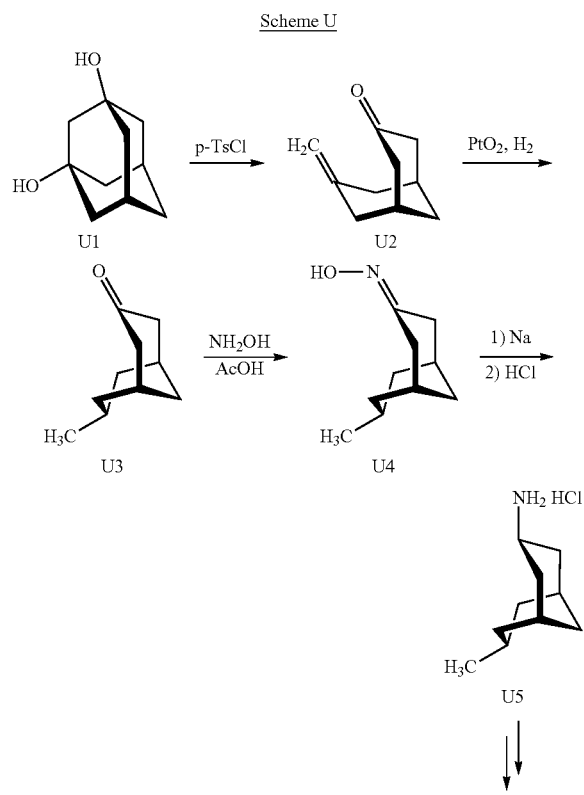

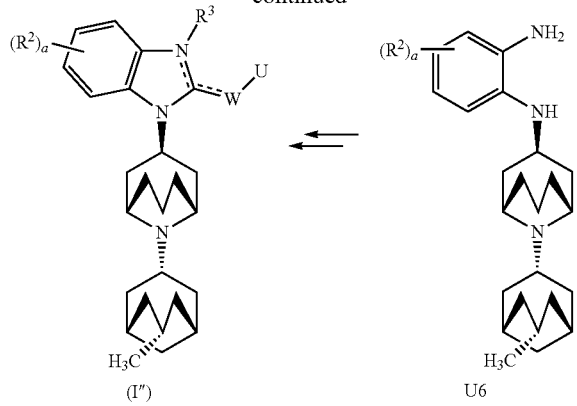

In Scheme U, 1,3-dihydroxyadamantane U1 can be treated with p-toluenesulfonyl chloride in pyridine at a temperature of about 70° C. for from about 2 hr to about 6 hr to provide Compound U2. Compound U2 can be hydrogenated to Compound U3 using platinum oxide in a non-polar solvent, such cyclohexane. Compound U3 can be converted to the oxime Compound U4 using hydroxylamine in AcOH at a temperature from about 25° C. to about 40° C. Compound U4 can be reacted with sodium metal and iso-propanol in a solvent, such as toluene, at a temperature of about 100° C. to provide the amine of Compound U5. The isolated amine of Compound U5 can be converted to its hydrochloride salt by treatment with HCl in a solvent, such as Et$_2$O. Compound U5 can be converted to Compound U6 according to the methods described in Section 4.5.1.1. Compound U6 can be converted to Substituted Benzimidazole-Type Piperidine Compounds of Formula (I") according to the method described in Section 4.5.2.

4.6 Therapeutic Uses of the Substituted Benzimidazole-Type Piperidine Compounds

In accordance with the disclosure, the Substituted Benzimidazole-Type Piperidine Compounds are administered to an animal in need of treatment or prevention of a Condition.

In one embodiment, an effective amount of a Substituted Benzimidazole-Type Piperidine Compound can be used to treat or prevent any condition treatable or preventable by inhibiting the activity of the ORL-1 receptor. Examples of Conditions that are treatable or preventable by inhibiting the activity of the ORL-1 receptor include, but are not limited to: pain (CNS effect), memory disorders, obesity, constipation, depression, dementia, and Parkinsonism.

In another embodiment, an effective amount of a Substituted Benzimidazole-Type Piperidine Compound can be used to treat or prevent any condition treatable or preventable by activating the ORL-1 receptor. Examples of Conditions that are treatable or preventable by activating the ORL-1 receptor include, but are not limited to, pain (PNS effect), anxiety, cough, diarrhea, blood pressure disorder (via vasodilation and via diuresis), epilepsy, anorexia/cachexia, urinary incontinence, drug abuse, a sleep disorder, a metabolic disorder, a renal disorders, and a cardiovascular disorder.

The Substituted Benzimidazole-Type Piperidine Compounds can be used to treat or prevent acute or chronic pain. Examples of pain that can be treated or prevented using a Substituted Benzimidazole-Type Piperidine Compound include, but are not limited to, cancer pain, neuropathic pain, labor pain, myocardial infarction pain, pancreatic pain, colic pain, post-operative pain, headache pain, muscle pain, arthritic pain, and pain associated with a periodontal disease, including gingivitis and periodontitis.

The Substituted Benzimidazole-Type Piperidine Compounds can also be used to treat or prevent pain associated with inflammation or with an inflammatory disease in an animal. Such pain can arise where there is an inflammation of the body tissue which can be a local inflammatory response or a systemic inflammation. For example, a Substituted Benzimidazole-Type Piperidine Compound can be used to treat or prevent pain associated with inflammatory diseases including, but not limited to, organ transplant rejection; reoxygenation injury resulting from organ transplantation (see Grupp et al., "Protection against Hypoxia-reoxygenation in the Absence of Poly (ADP-ribose) Synthetase in Isolated Working Hearts," *J. Mol. Cell Cardiol.* 31:297-303 (1999)) including, but not limited to, transplantation of the heart, lung, liver, or kidney; chronic inflammatory diseases of the joints, including arthritis, rheumatoid arthritis, osteoarthritis and bone diseases associated with increased bone resorption; inflammatory bowel diseases, such as ileitis, ulcerative colitis, Barrett's syndrome, and Crohn's disease; inflammatory lung diseases, such as asthma, adult respiratory distress syndrome, and chronic obstructive airway disease; inflammatory diseases of the eye, including corneal dystrophy, trachoma, onchocerciasis, uveitis, sympathetic ophthalmitis and endophthalmitis; chronic inflammatory disease of the gum, including gingivitis and periodontitis; tuberculosis; leprosy; inflammatory diseases of the kidney, including uremic complications, glomerulonephritis and nephrosis; inflammatory disease of the skin, including sclerodermatitis, psoriasis and eczema; inflammatory diseases of the central nervous system, including chronic demyelinating diseases of the nervous system, multiple sclerosis, AIDS-related neurodegeneration and Alzheimer's disease, infectious meningitis, encephalomyelitis, Parkinson's disease, Huntington's disease, amyotrophic lateral sclerosis and viral or autoimmune encephalitis; autoimmune diseases, including Type I and Type II diabetes mellitus; diabetic complications, including, but not limited to, diabetic cataract, glaucoma, retinopathy, nephropathy (such as microalbuminuria and progressive diabetic nephropathy), gangrene of the feet, atherosclerotic coronary arterial disease, peripheral arterial disease, nonketotic hyperglycemic-hyperosmolar coma, foot ulcers, joint problems, and a skin or mucous membrane complication (such as an infection, a shin spot, a candidal infection or necrobiosis lipoidica diabeticorum), immune-complex vasculitis, and systemic lupus erythematosus (SLE); inflammatory disease of the heart, such as cardiomyopathy, ischemic heart disease hypercholesterolemia, and artherosclerosis; as well as various other diseases that can have significant inflammatory components, including preeclampsia, chronic liver failure, brain and spinal cord trauma, and cancer. An Substituted Benzimidazole-Type Piperidine Compound can also be used to treat or prevent pain associated with inflammatory disease that can, for example, be a systemic inflammation of the body, exemplified by gram-positive or gram negative shock, hemorrhagic or anaphylactic shock, or shock induced by cancer chemotherapy in response to pro-inflammatory cytokines, e.g., shock associated with pro-inflammatory cytokines. Such shock can be induced, e.g., by a chemotherapeutic agent that is administered as a treatment for cancer.

The Substituted Benzimidazole-Type Piperidine Compounds can also be used to treat or prevent pain associated with nerve injury (i.e., neuropathic pain). Chronic neuropathic pain is a heterogenous disease state with an unclear etiology. In chronic neuropathic pain, the pain can be mediated by multiple mechanisms. This type of pain generally arises from injury to the peripheral or central nervous tissue. The syndromes include pain associated with spinal cord injury, multiple sclerosis, post-herpetic neuralgia, trigeminal neuralgia, phantom pain, causalgia, and reflex sympathetic dystrophy and lower back pain. The chronic pain is different from acute pain in that chronic neuropathic pain patients suffer the abnormal pain sensations that can be described as spontaneous pain, continuous superficial burning and/or deep aching pain. The pain can be evoked by heat-, cold-, and mechano-hyperalgesia, or by heat-, cold-, or mechano-allodynia.

Chronic neuropathic pain can be caused by injury or infection of peripheral sensory nerves. It includes, but is not limited to, pain from peripheral nerve trauma, herpes virus infection, diabetes mellitus, causalgia, plexus avulsion, neuroma, limb amputation, and vasculitis. Neuropathic pain can also be caused by nerve damage from chronic alcoholism, human immunodeficiency virus infection, hypothyroidism, uremia, or vitamin deficiencies. Stroke (spinal or brain) and spinal cord injury can also induce neuropathic pain. Cancer-related neuropathic pain results from tumor growth compression of adjacent nerves, brain, or spinal cord. In addition, cancer treatments, including chemotherapy and radiation therapy, can cause nerve injury. Neuropathic pain includes but is not limited to pain caused by nerve injury such as, for example, the pain from which diabetics suffer.

The Substituted Benzimidazole-Type Piperidine Compounds can be used to treat or prevent a migraine including, but not limited to, migraine without aura ("common migraine"), migraine with aura ("classic migraine"), migraine without headache, basilar migraine, familial hemiplegic migraine, migrainous infarction, and migraine with prolonged aura.

The Substituted Benzimidazole-Type Piperidine Compounds can be used to treat or prevent a sleep disorder including, but not limited to, insomnia, hypersomnia, sleep deprivation, sleep apnea, dysomnia, delayed sleep phase syndrome (DSPS), advanced sleep phase syndrome (ASPS), non-24-hour sleep-wake syndrome (e.g., circadian rhythm sleep disorder), situational circadian rhythm sleep disorders (e.g., jet lag, shift work sleep disorders), hypopnea, irregular sleep wake rhythm, nightmares, night terror, parasomnia, restless leg syndrome (RLS), nocturnal mycolonus/periodic limb movement disorder (PLMD), rapid eye movement (REM) sleep disorder, somnambulism/sleep walking, somniloquy/sleep talking, and somniphobia. For example, U.S. Pat. No. 8,003,669 discloses a class of ORL-1 agonists said to be therapeutic agents for circadian rhythm sleep disorder and Miyakawa et al. disclose that administration of the ORL-1 receptor agonist known as W-212393 induces phase advance of locomotor activity circadian rhythm in mice ("ORL1 receptor-mediated down-regulation of mPER2 in the suprachiasmatic nucleus accelerates re-entrainment of the circadian clock following a shift in the environmental light/dark cycle," *Neuropharmacol.* 52:1055-1064 (2007)).

Metabolic disorders can be caused by an abnormal metabolic process and can be acquired, e.g., failure of a metabolically important organ such as the liver or disease of an endocrine organ, or congenital, e.g., an inherited enzyme abnormality. A congenital metabolic disorder can be caused by a defect in a single gene; some of the more well-known inborn metabolic errors include sickle cell anemia, hypothyroidism, Tay-Sachs disease, phenylketonuria, and cystic fibrosis. The Substituted Benzimidazole-Type Piperidine Compounds can be used to treat or prevent a metabolic disorder including, but not limited to, anorexia nervosa, bulimia, and obesity. For example, U.S. Pat. No. 7,241,770 discloses a class of hydronopol derivative ORL-1 agonists said to be therapeutic agents for metabolic disorders.

A renal disorder may be acute or chronic. An acute renal disorder can be caused by impaired blood flow to the kidneys due to, e.g., blood loss, heart attack, or liver failure; kidney damage due to, e.g., blood clots, hemolytic uremic syndrome, or vasculitis; or urine blockage due to, e.g., bladder cancer, an enlarged prostate, or kidney stones. A chronic renal disorder can be caused by, e.g., diabetes mellitus, hypertension, or polycystic kidney disease. The Substituted Benzimidazole-Type Piperidine Compounds can be used to treat or prevent a renal disorder including, but not limited to, those renal disorders characterized by the syndrome of inappropriate antidiuretic hormone secretion (SIADH) or by imbalances of water retention and/or water excretion or salt excretion. For example, U.S. Pat. No. 6,869,960 discloses a class of spiropiperidine ORL-1 ligands said to be therapeutic agents for renal disorders.

Cardiovascular disorders represent the leading cause of death in the United States, responsible for about 27% of yearly deaths. Cardiovascular disorders can be caused by tobacco use, alcohol abuse, obesity, diabetes mellitus, high cholesterol, high blood pressure, and other factors. The Substituted Benzimidazole-Type Piperidine Compounds can be used to treat or prevent a cardiovascular disorder including, but not limited to, myocardial infarction, arrhythmias, bradycardia, hypertension, hypotension, thrombosis, anemia, arteriosclerosis, and angina pectoris. For example, U.S. Pat. No. 7,241,770 discloses a class of hydronopol derivative ORL-1 agonists said to be therapeutic agents for cardiovascular disorders.

According to the disclosure, some of the Substituted Benzimidazole-Type Piperidine Compounds are agonists at the ORL-1 receptor, some of the Substituted Benzimidazole-Type Piperidine Compounds are partial agonists at the ORL-1 receptor, and some of the Substituted Benzimidazole-Type Piperidine Compounds are antagonists at the ORL-1 receptor. In another embodiment, a Substituted Benzimidazole-Type Piperidine Compound is an agonist at the ORL-1 receptor and an agonist at a $\mu$, $\kappa$ and/or $\delta$ opioid receptor, particularly at a $\mu$ opioid receptor. In another embodiment, a Substituted Benzimidazole-Type Piperidine Compound is a partial agonist at the ORL-1 receptor and an agonist at a $\mu$, $\kappa$ and/or $\delta$ opioid receptor, particularly at a $\mu$ opioid receptor. In another embodiment, a Substituted Benzimidazole-Type Piperidine Compound is an antagonist at the ORL-1 receptor and an agonist at a $\mu$, $\kappa$ and/or $\delta$ opioid receptor, particularly at a $\mu$ opioid receptor. In another embodiment, a Substituted Benzimidazole-Type Piperidine Compound is an agonist at the ORL-1 receptor and an antagonist at a $\mu$, $\kappa$ and/or $\delta$ opioid receptor, particularly at a $\mu$ opioid receptor. In another embodiment, a Substituted Benzimidazole-Type Piperidine Compound is a partial agonist at the ORL-1 receptor and an antagonist at a $\mu$, $\kappa$ and/or $\delta$ opioid receptor, particularly at a $\mu$ opioid receptor. In another embodiment, a Substituted Benzimidazole-Type Piperidine Compound is an antagonist at the ORL-1 receptor and an antagonist at a $\mu$, $\kappa$ and/or $\delta$ opioid receptor, particularly at a $\mu$ opioid receptor.

The disclosure also provides methods for inhibiting ORL-1 receptor function in a cell, comprising contacting a cell capable of expressing the ORL-1 receptor with an amount of a Substituted Benzimidazole-Type Piperidine Compound effective to inhibit ORL-1 receptor function in the cell. This method can be adapted for use in vitro as part of an assay to select compounds that can be useful for treating or preventing a Condition in an animal. Alternatively, this method can be adapted for use in vivo, (i.e., in an animal such as a human) by contacting a cell in the animal with an effective amount of a Substituted Benzimidazole-Type Piperidine Compound. In one embodiment, the method is useful for treating or preventing pain in an animal in need of such treatment or prevention. In another embodiment, the method is useful for treating or preventing a memory disorder, obesity, constipation, depression, dementia, or Parkinsonism in an animal in need of such treatment or prevention.

The disclosure also relates to methods for activating ORL-1 receptor function in a cell, comprising contacting a cell capable of expressing the ORL-1 receptor with an amount of a Substituted Benzimidazole-Type Piperidine Compound effective to activate ORL-1 receptor function in the cell. This method can be adapted for use in vitro as part of an assay to select compounds useful for treating or preventing, pain, anxiety, cough, diarrhea, high blood pressure, epilepsy, anorexia/cachexia, urinary incontinence, drug abuse, a sleep disorder, a metabolic disorder, a renal disorders, or a cardiovascular disorder. Alternatively, the method can be adapted for use in vivo (i.e., in an animal such as a human), by contacting a cell in the animal with an effective amount of a Substituted Benzimidazole-Type Piperidine Compound. In one embodiment, the method is useful for treating or preventing pain in an animal in need of such treatment or prevention. In another embodiment, the method is useful for treating or preventing anxiety, cough, diarrhea, high blood pressure, epilepsy, anorexia/chachexia, urinary incontinence, drug abuse, a sleep disorder, a metabolic disorder, a renal disorders, or a cardiovascular disorder in an animal in need of such treatment or prevention.

Examples of tissue comprising cells capable of expressing the ORL-1 receptor include but are not limited to brain, spinal cord, vas deferens, and gastrointestinal tract tissue. Methods for assaying cells that express the ORL-1 receptor are known in the art; for example, see Shimohigashi et al., "Sensitivity of Opioid Receptor-like Receptor ORL1 for Chemical Modification on Nociceptin, a Naturally Occurring Nociceptive Peptide," *J. Biol. Chem.* 271(39):23642-23645 (1996); Narita et al., "Identification of the G-protein Coupled ORL1 Receptor in the Mouse Spinal Cord by [$^{35}$S]-GTPγS Binding and Immunohistochemistry," *Brit. J. Pharmacol.* 128:1300-1306 (1999); Milligan, "Principles: Extending the Utility of [$^{35}$S]GTPγS Binding Assays," *TIPS* 24(2):87-90 (2003); and Lazareno, "Measurement of Agonist-stimulated [$^{35}$S]GTPγS Binding to Cell Membranes," *Methods in Molecular Biology* 106:231-245 (1999).

4.7 Therapeutic/Prophylactic Administration and Compositions of the Disclosure Due to their activity, the Substituted Benzimidazole-Type Piperidine Compounds are advantageously useful in human and veterinary medicine. As described above, the Substituted Benzimidazole-Type Piperidine Compounds are useful for treating or preventing a Condition in an animal in need thereof. The Substituted Benzimidazole-Type Piperidine Compounds of the disclosure can be administered to any animal requiring modulation of the opioid and/or ORL-1 receptors.

When administered to an animal, a Substituted Benzimidazole-Type Piperidine Compound can be administered as a component of a composition that comprises a pharmaceutically acceptable carrier or excipient. The compositions, which comprise a Substituted Benzimidazole-Type Piperidine Compound, can be administered orally. An Substituted Benzimidazole-Type Piperidine Compound can also be administered by any other convenient route, for example, by infusion or bolus injection, by absorption through epithelial or mucocutaneous linings (e.g., oral, rectal, and intestinal mucosa, etc.) and can be administered together with a second therapeutically active agent. Administration can be systemic or local. Various delivery systems are known, e.g., encapsulation in liposomes, microparticles, microcapsules, multiparticulates, capsules, etc., and can be used to administer a Substituted Benzimidazole-Type Piperidine Compound.

Methods of administration include, but are not limited to, intradermal, intramuscular, intraperitoneal, parenteral, intravenous, subcutaneous, intranasal, epidural, oral, sublingual, intracerebral, intravaginal, transdermal (e.g., via a patch), rectal, by inhalation, transmucosal, or topical, particularly to the ears, nose, eyes, or skin. The method of administration is left to the discretion of the practitioner. In some instances, administration will result in the release of a Substituted Benzimidazole-Type Piperidine Compound into the bloodstream. In other instances, administration will result in only local release of a Substituted Benzimidazole-Type Piperidine Compound.

In specific embodiments, it can be desirable to administer a Substituted Benzimidazole-Type Piperidine Compound locally. This can be achieved, for example and not by way of limitation, by local infusion during surgery, topical application, e.g., in conjunction with a wound dressing after surgery, by injection, by means of a catheter, by means of a suppository or enema, or by means of an implant, said implant being of a porous, non-porous, or gelatinous material, including membranes, such as sialastic membranes, or fibers.

In certain embodiments, it can be desirable to introduce a Substituted Benzimidazole-Type Piperidine Compound into the central nervous system or gastrointestinal tract by any suitable route, including intraventricular, intrathecal, and epidural injection, and enema. Intraventricular injection can be facilitated by an intraventricular catheter, for example, attached to a reservoir, such as an Ommaya reservoir.

Pulmonary administration can also be employed, e.g., by use of an inhaler or nebulizer, and formulation with an aerosolizing agent, or via perfusion in a fluorocarbon or synthetic pulmonary surfactant. In certain embodiments, a Substituted Benzimidazole-Type Piperidine Compound can be formulated as a suppository, with traditional binders and excipients such as triglycerides.

When a Substituted Benzimidazole-Type Piperidine Compound of the disclosure is incorporated for parenteral administration by injection (e.g., continuous infusion or bolus injection), the formulation for parenteral administration can be in the form of a suspension, solution, emulsion in an oily or aqueous vehicle, and such formulations can further comprise pharmaceutically necessary additives such as one or more stabilizing agents, suspending agents, dispersing agents, and the like. An Substituted Benzimidazole-Type Piperidine Compound of the disclosure can also be in the form of a powder for reconstitution as an injectable formulation.

In another embodiment, a Substituted Benzimidazole-Type Piperidine Compound can be delivered in a vesicle, in particular a liposome (see Langer, "New Methods of Drug Delivery," *Science* 249:1527-1533 (1990); and Treat et al., "Liposome Encapsulated Doxorubicin Preliminary Results of Phase I and Phase II Trials," pp. 317-327 and 353-365 in *Liposomes in the Therapy of Infectious Disease and Cancer* (1989)).

In yet another embodiment, a Substituted Benzimidazole-Type Piperidine Compound can be delivered in a controlled-release system or sustained-release system (see, e.g., Goodson, "Dental Applications," in *Medical Applications of Controlled Release, Vol. 2, Applications and Evaluation*, Langer and Wise, eds., CRC Press, Chapter 6, pp. 115-138 (1984), hereafter "Goodson"). Other controlled- or sustained-release systems discussed in the review by Langer, *Science* 249:1527-1533 (1990) can be used. In one embodiment, a pump can be used (Langer, *Science* 249:1527-1533 (1990); Sefton, "Implantable Pumps," in *CRC Crit. Rev. Biomed. Eng.* 14(3):201-240 (1987); Buchwald et al., "Long-term, Continuous Intravenous Heparin Administration by an Implantable Infusion Pump in Ambulatory Patients with Recurrent Venous Thrombosis," *Surgery* 88:507-516 (1980); and Saudek et al., "A Preliminary Trial of the Programmable Implantable Medication System for Insulin Delivery," *New Engl. J. Med.* 321:574-579 (1989)). In another embodiment, polymeric materials can be used (see Goodson; Smolen et al., "Drug Product Design and Performance," *Controlled Drug Bioavailability Vol.* 1, John Wiley and Sons, New York (1984); Langer et al., "Chemical and Physical Structure of Polymers as Carriers for Controlled Release of Bioactive Agents: A Review," *J. Macromol. Sci. Rev. Macromol. Chem.* C23(1):61-126 (1983); Levy et al., "Inhibition of Calcification of Bioprosthetic Heart Valves by Local Controlled-Release Diphosphonate," *Science* 228:190-192 (1985); During et al., "Controlled Release of Dopamine from a Polymeric Brain Implant: In Vivo Characterization," *Ann. Neurol.* 25:351-356 (1989); and Howard et al., "Intracerebral drug delivery in rats with lesion-induced memory deficits," *J. Neurosurg.* 71:105-112 (1989)). In yet another embodiment, a controlled- or sustained-release system can be placed in proximity of a target of a Substituted Benzimidazole-Type Piperidine Compound, e.g., the spinal column, brain, or gastrointestinal tract, thus requiring only a fraction of the systemic dose.

The compositions can optionally, but preferably, further comprise a suitable amount of a pharmaceutically acceptable excipient so as to provide the form for proper administration to the animal. Such a pharmaceutical excipient can be a diluent, suspending agent, solubilizer, binder, disintegrant, preservative, coloring agent, lubricant, and the like. The pharmaceutical excipient can be a liquid, such as water or an oil, including those of petroleum, animal, vegetable, or synthetic origin, such as peanut oil, soybean oil, mineral oil, sesame oil, and the like. The pharmaceutical excipient can be saline, gum acacia, gelatin, starch paste, talc, keratin, colloidal silica, urea, and the like. In addition, auxiliary, stabilizing, thickening, lubricating, and coloring agents can be used. In one embodiment, the pharmaceutically acceptable excipient is sterile when administered to an animal. Water is a particularly useful excipient when a Substituted Benzimidazole-Type Piperidine Compound is administered intravenously. Saline solutions and aqueous dextrose and glycerol solutions can also be employed as liquid excipients, particularly for injectable solutions. Suitable pharmaceutical excipients also include starch, glucose, lactose, sucrose, gelatin, malt, rice, flour, chalk, silica gel, sodium stearate, glycerol monostearate, talc, sodium chloride, dried skim milk, glycerol, propylene glycol, water, EtOH, and the like. The compositions, if desired, can also contain minor amounts of wetting or emulsifying agents, or pH buffering agents. Specific examples of pharmaceutically acceptable carriers and excipients that can be used to formulate oral dosage forms are described in the *Handbook of Pharmaceutical Excipients*, (Amer. Pharmaceutical Ass'n, Washington, D.C., 1986), incorporated herein by reference.

The compositions can take the form of solutions, suspensions, emulsions, tablets, pills, pellets, capsules, capsules containing liquids, powders, sustained-release formulations, suppositories, emulsions, aerosols, sprays, suspensions, or any other form suitable for use. In one embodiment, the composition is in the form of a capsule (see, e.g., U.S. Pat. No. 5,698,155). Other examples of suitable pharmaceutical excipients are described by Radebough et al., "Preformulation," pp. 1447-1676 in *Remington's Pharmaceutical Sciences Vol. 2* (Gennaro, ed., $19^{th}$ Ed., Mack Publishing, Easton, Pa., 1995), incorporated herein by reference.

In one embodiment, the Substituted Benzimidazole-Type Piperidine Compounds are formulated in accordance with routine procedures as a composition adapted for oral administration to human beings. An Substituted Benzimidazole-Type Piperidine Compound to be orally delivered can be in the form of tablets, capsules, gelcaps, caplets, lozenges, aqueous or oily solutions, suspensions, granules, powders, emulsions, syrups, or elixirs, for example. When a Substituted Benzimidazole-Type Piperidine Compound is incorporated into oral tablets, such tablets can be compressed, tablet triturates, enteric-coated, sugar-coated, film-coated, multiply compressed or multiply layered. Techniques and compositions for making solid oral dosage forms are described in *Pharmaceutical Dosage Forms: Tablets* (Lieberman et al., eds., $2^{nd}$ Ed., Marcel Dekker, Inc., 1989 and 1990). Techniques and compositions for making tablets (compressed and molded), capsules (hard and soft gelatin) and pills are also described by King, "Tablets, Capsules, and Pills," pp. 1553-1593 in *Remington's Pharmaceutical Sciences* (Osol, ed., $16^{th}$ Ed., Mack Publishing, Easton, Pa., 1980).

Liquid oral dosage forms include aqueous and nonaqueous solutions, emulsions, suspensions, and solutions and/or suspensions reconstituted from non-effervescent granules, optionally containing one or more suitable solvents, preservatives, emulsifying agents, suspending agents, diluents, sweeteners, coloring agents, flavoring agents, and the like. Techniques and composition for making liquid oral dosage forms are described in *Pharmaceutical Dosage Forms: Disperse Systems* (Lieberman et al., eds., $2^{nd}$ Ed., Marcel Dekker, Inc., 1996 and 1998).

When a Substituted Benzimidazole-Type Piperidine Compound is to be injected parenterally, it can be, e.g., in the form of an isotonic sterile solution. Alternatively, when a Substituted Benzimidazole-Type Piperidine Compound is to be inhaled, it can be formulated into a dry aerosol or can be formulated into an aqueous or partially aqueous solution.

An orally administered Substituted Benzimidazole-Type Piperidine Compound can contain one or more agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration and absorption in the gastrointestinal tract thereby providing a sustained action over an extended period of time. Selectively permeable membranes surrounding an osmotically active driving compound are also suitable for orally administered compositions. In these latter platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time-delay material such as glycerol monostearate or glycerol stearate can also be used. Oral compositions can include standard excipients such as mannitol, lactose, starch, magnesium stearate, sodium saccharin, cellulose, and magnesium carbonate. In one embodiment, the excipients are of pharmaceutical grade.

In another embodiment, the Substituted Benzimidazole-Type Piperidine Compounds can be formulated for intravenous administration. In certain embodiments, compositions for intravenous administration comprise sterile isotonic aqueous buffer. Where necessary, the compositions can also include a solubilizing agent. An Substituted Benzimidazole-Type Piperidine Compound for intravenous administration can optionally include a local anesthetic such as benzocaine or prilocaine to lessen pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent. Where a Substituted Benzimidazole-Type Piperidine Compound is to be administered by infusion, it can be dispensed, for example, with an infusion bottle containing sterile pharmaceutical grade water or saline. Where a Substituted Benzimidazole-Type Piperidine Compound is administered by injection, an ampule of sterile water for injection or saline can be provided so that the ingredients can be mixed prior to administration.

An Substituted Benzimidazole-Type Piperidine Compound can be administered by controlled-release or sustained-release means or by delivery devices that are known to those in the art. Examples include, but are not limited to, those described in U.S. Pat. Nos. 3,845,770, 3,916,899, 3,536,809, 3,598,123, 4,008,719, 5,674,533, 5,059,595, 5,591,767, 5,120,548, 5,073,543, 5,639,476, 5,354,556, and 5,733,566, each of which is incorporated herein by reference. Such dosage forms can be used to provide controlled- or sustained-release of one or more active ingredients using, for example, hydropropylmethyl cellulose, ethylcellulose, other polymer matrices, gels, permeable membranes, osmotic systems, multilayer coatings, microparticles, multiparticulates, liposomes, microspheres, or a combination thereof to provide the desired release profile in varying proportions. Suitable controlled- or sustained-release formulations known to those in the art, including those described herein, can be readily selected for use with the active ingredients of the disclosure. The disclosure thus encompasses single unit dosage forms suitable for oral administration such as, but not limited to, tablets, capsules, gelcaps, and caplets that are adapted for controlled- or sustained-release.

Controlled- or sustained-release pharmaceutical compositions can have a common goal of improving drug therapy over that achieved by their non-controlled or non-sustained-release counterparts. In one embodiment, a controlled- or sustained-release composition comprises a minimal amount of a Substituted Benzimidazole-Type Piperidine Compound to treat or prevent the Condition or a symptom thereof in a minimum amount of time. Advantages of controlled- or sustained-release compositions include extended activity of the drug, reduced dosage frequency, and increased compliance. In addition, controlled- or sustained-release compositions can favorably affect the time of onset of action or other characteristics, such as blood levels of the Substituted Benzimidazole-Type Piperidine Compound, and can thus reduce the occurrence of adverse side effects.

Controlled- or sustained-release compositions can initially release an amount of a Substituted Benzimidazole-Type Piperidine Compound that promptly produces the desired therapeutic or prophylactic effect, and gradually and continually release other amounts of the Substituted Benzimidazole-Type Piperidine Compound to maintain this level of therapeutic or prophylactic effect over an extended period of time. To maintain a constant level of the Substituted Benzimidazole-Type Piperidine Compound in the body, the Substituted Benzimidazole-Type Piperidine Compound can be released from the dosage form at a rate that will replace the amount of Substituted Benzimidazole-Type Piperidine Compound being metabolized and excreted from the body. Controlled- or sustained-release of an active ingredient can be stimulated by various conditions, including but not limited to, changes in pH, changes in temperature, concentration or availability of enzymes, concentration or availability of water, or other physiological conditions or compounds.

The amount of the Substituted Benzimidazole-Type Piperidine Compound that is effective for the treatment or prevention of a Condition can be determined by standard clinical techniques. In addition, in vitro and/or in vivo assays can optionally be employed to help identify optimal dosage ranges. The precise dose to be employed will also depend on, e.g., the route of administration and the seriousness of the Condition, and can be decided according to the judgment of a practitioner and/or each animal's circumstances. In other examples thereof, variations will necessarily occur depending upon the weight and physical condition (e.g., hepatic and renal function) of the animal being treated, the affliction to be treated, the severity of the symptoms, the frequency of the dosage interval, the presence of any deleterious side-effects, and the particular compound utilized, among other things.

Suitable effective dosage amounts, however, range from about 0.01 mg/kg of body weight to about 3000 mg/kg of body weight of the animal per day, although they are, in certain embodiments, from about 0.01 mg/kg of body weight to about 2500 mg/kg of body weight of the animal per day or from about 0.01 mg/kg of body weight to about 1000 mg/kg of body weight of the animal per day. In another embodiment, the effective dosage amount is about 100 mg/kg of body weight of the animal per day or less. In another embodiment, the effective dosage amount ranges from about 0.01 mg/kg of body weight to about 100 mg/kg of body weight of the animal per day of a Substituted Benzimidazole-Type Piperidine Compound, in another embodiment, about 0.02 mg/kg of body weight to about 50 mg/kg of body weight of the animal per day, and in another embodiment, about 0.025 mg/kg of body weight to about 20 mg/kg of body weight of the animal per day.

Administration can be as a single dose or as a divided dose. In one embodiment, an effective dosage amount is administered about every 24 hr until the Condition is abated. In another embodiment, an effective dosage amount is administered about every 12 hr until the Condition is abated. In another embodiment, an effective dosage amount is administered about every 8 hr until the Condition is abated. In another embodiment, an effective dosage amount is administered about every 6 hr until the Condition is abated. In another embodiment, an effective dosage amount is administered about every 4 hr until the Condition is abated. The effective dosage amounts described herein refer to total amounts administered; that is, if more than one Substituted Benzimidazole-Type Piperidine Compound is administered, the effective dosage amounts correspond to the total amount administered.

Where a cell capable of expressing the ORL-1 receptor, the μ-opioid receptor, the κ-opioid receptor and/or the δ-opioid receptor is contacted with a Substituted Benzimidazole-Type Piperidine Compound in vitro, the amount effective for inhibiting or activating that receptor function in a cell will, in certain embodiments, range from about $10^{-12}$ mol/L to about $10^{-4}$ mol/L, in one embodiment, from about $10^{-12}$ mol/L to about $10^{-5}$ mol/L, in another embodiment, from about $10^{-12}$ mol/L to about $10^{-6}$ mol/L, and in another embodiment, from about $10^{-12}$ mol/L to about $10^{-9}$ mol/L of a solution or suspension of a pharmaceutically acceptable carrier or excipient. In one embodiment, the volume of solution or suspension comprising the Substituted Benzimidazole-Type Piperidine Compound will be from about 0.01 μL to about 1 mL. In another embodiment, the volume of solution or suspension will be about 200 μL.

An Substituted Benzimidazole-Type Piperidine Compound has a binding affinity ($K_i$) for the human ORL-1 receptor of about 1000 nM or less in one embodiment, or about 500 nM or less in another embodiment, about 100 nM or less in another embodiment, about 50 nM or less in another embodiment, or about 20 nM or less in another embodiment, or about 5 nM or less in another embodiment. The binding affinity $K_i$ can be measured in ways known to the art, e.g., by an assay utilizing membranes from recombinant HEK-293 cells expressing the ORL-1 receptor.

In certain embodiments, a Substituted Benzimidazole-Type Piperidine Compound has a Ki (nM) of about 300 or less for binding to ORL-1 receptors. In one embodiment, a Substituted Benzimidazole-Type Piperidine Compound of the disclosure has a $K_i$ (nM) of about 100 or less. In another embodiment, a Substituted Benzimidazole-Type Piperidine Compound of the disclosure has a $K_i$ (nM) of about 35 or less. In another embodiment, a Substituted Benzimidazole-Type Piperidine Compound of the disclosure has a $K_i$ (nM) of about 20 or less. In another embodiment, a Substituted Benzimidazole-Type Piperidine Compound of the disclosure has a $K_i$ (nM) of about 15 or less. In another embodiment, a Substituted Benzimidazole-Type Piperidine Compound of the disclosure has a $K_i$ (nM) of about 10 or less. In another embodiment, a Substituted Benzimidazole-Type Piperidine Compound of the disclosure has a $K_i$ (nM) of about 4 or less. In another embodiment, a Substituted Benzimidazole-Type Piperidine Compound of the disclosure has a $K_i$ (nM) of about 1 or less. In another embodiment, a Substituted Benzimidazole-Type Piperidine Compound of the disclosure has a $K_i$ (nM) of about 0.4 or less. In another embodiment, a Substituted Benzimidazole-Type Piperidine Compound of the disclosure has a $K_i$ (nM) of about 0.1 or less.

ORL-1 GTP $EC_{50}$ is the concentration of a compound providing 50% of the maximal response for the compound at an ORL-1 receptor. In one embodiment, a Substituted Benzimidazole-Type Piperidine Compound has an ORL-1 GTP $EC_{50}$ (nM) of about 5000 or less to stimulate ORL-1 receptor function. In another embodiment, a Substituted Benzimidazole-Type Piperidine Compound of the disclosure has an ORL-1 GTP $EC_{50}$ (nM) of about 1000 or less. In another embodiment, a Substituted Benzimidazole-Type Piperidine Compound of the disclosure has an ORL-1 GTP $EC_{50}$ (nM) of about 100 or less. In another embodiment, a Substituted Benzimidazole-Type Piperidine Compound of the disclosure has an ORL-1 GTP $EC_{50}$ (nM) of about 80 or less. In another embodiment, a Substituted Benzimidazole-Type Piperidine Compound of the disclosure has an ORL-1

GTP $EC_{50}$ (nM) of about 50 or less. In another embodiment, a Substituted Benzimidazole-Type Piperidine Compound of the disclosure has an ORL-1 GTP $EC_{50}$ (nM) of about 35 or less. In another embodiment, a Substituted Benzimidazole-Type Piperidine Compound of the disclosure has an ORL-1 GTP $EC_{50}$ (nM) of about 15 or less. In another embodiment, a Substituted Benzimidazole-Type Piperidine Compound has an ORL-1 GTP $EC_{50}$ (nM) of about 10 or less. In another embodiment, a Substituted Benzimidazole-Type Piperidine Compound has an ORL-1 GTP $EC_{50}$ (nM) of about 4 or less. In another embodiment, a Substituted Benzimidazole-Type Piperidine Compound has an ORL-1 GTP $EC_{50}$ (nM) of about 1 or less. In another embodiment, a Substituted Benzimidazole-Type Piperidine Compound has an ORL-1 GTP $EC_{50}$ (nM) of about 0.4 or less. In another embodiment, a Substituted Benzimidazole-Type Piperidine Compound has an ORL-1 GTP $EC_{50}$ (nM) of about 0.1 or less.

ORL-1 GTP Emax (%) is the maximal effect elicited by a compound relative to the effect elicited by nociceptin, a standard ORL-1 agonist. In certain embodiments, a Substituted Benzimidazole-Type Piperidine Compound of the disclosure acting as an agonist has an ORL-1 GTP Emax (%) of about 50% or greater. In one embodiment, agonist Substituted Benzimidazole-Type Piperidine Compounds has an ORL-1 GTP Emax (%) of about 75% or greater. In another embodiment, agonist Substituted Benzimidazole-Type Piperidine Compounds has an ORL-1 GTP Emax (%) of about 85% or greater. In another embodiment, agonist Substituted Benzimidazole-Type Piperidine Compounds has an ORL-1 GTP Emax (%) of about 95% or greater. In another embodiment, agonist Substituted Benzimidazole-Type Piperidine Compounds has an ORL-1 GTP Emax (%) of about 100% or greater. In certain embodiments, a Substituted Benzimidazole-Type Piperidine Compound of the disclosure acting as a partial agonist has an ORL-1 GTP Emax (%) of less than about 10%. In one embodiment, partial agonist Substituted Benzimidazole-Type Piperidine Compounds has an ORL-1 GTP Emax (%) of less than about 20%. In another embodiment, partial agonist Substituted Benzimidazole-Type Piperidine Compounds has an ORL-1 GTP Emax (%) of less than about 30%. In another embodiment, partial agonist Substituted Benzimidazole-Type Piperidine Compounds has an ORL-1 GTP Emax (%) of less than about 40%. In another embodiment, partial agonist Substituted Benzimidazole-Type Piperidine Compounds has an ORL-1 GTP Emax (%) of less than about 50%.

In certain embodiments, a Substituted Benzimidazole-Type Piperidine Compound has a binding affinity ($K_i$) for the human μ-opioid receptor of about 1000 nM or less in one embodiment, or about 500 nM or less in another embodiment, about 100 nM or less in another embodiment, about 50 nM or less in another embodiment, or about 20 nM or less in another embodiment, or about 5 nM or less in another embodiment.

In certain embodiments, a Substituted Benzimidazole-Type Piperidine Compound has a $K_i$ (nM) for the human μ-opioid receptor of about 3000 or less for binding to a human μ-opioid receptor, or about 1000 or less, or about 650 or less, or about 525 or less, or about 250 or less, or about 100 or less, or about 10 or less, or about 1 or less. In one embodiment, a Substituted Benzimidazole-Type Piperidine Compound has substantially no activity.

μ GTP $EC_{50}$ is the concentration of a compound providing 50% of the maximal response for the compound at a human μ-opioid receptor. In certain embodiments, a Substituted Benzimidazole-Type Piperidine Compound has a μ GTP $EC_{50}$ (nM) of about 20,000 or less to stimulate human μ-opioid receptor function, or about 10,000 or less. In other embodiments, a Substituted Benzimidazole-Type Piperidine Compound has a μ GTP $EC_{50}$ (nM) of about 5000 or less to stimulate human μ-opioid receptor function, or about 4100 or less, or about 3100 or less, or about 2000 or less, or about 1000 or less, or about 100 or less, or about 10 or less, or about 1 or less, or about 0.4 or less.

μ GTP Emax (%) is the maximal effect elicited by a compound relative to the effect elicited by DAMGO, a standard μ agonist. In certain embodiments, a Substituted Benzimidazole-Type Piperidine Compound has a μ GTP Emax (%) of about 10% or greater, or about 20% or greater, or about 50% or greater, or about 65% or greater, or about 75% or greater, or about 88% or greater. In other embodiments, a Substituted Benzimidazole-Type Piperidine Compound has a μ GTP Emax (%) of about 10% or less, or about 5% or less, or about 2% or less.

In one embodiment, a Substituted Benzimidazole-Type Piperidine Compound has a $K_i$ (nM) of about 20,000 or less for binding to a human κ-opioid receptor. In another embodiment, a Substituted Benzimidazole-Type Piperidine Compound has substantially no activity. In certain embodiments, a Substituted Benzimidazole-Type Piperidine Compound that bind to the human κ-opioid receptor has a $K_i$ (nM) of about 10,000 or less, or about 5000 or less, or about 1000 or less, or about 500 or less, or about 300 or less, or about 100 or less, or about 50 or less, or about 20 or less, or about 15 or less.

κ GTP $EC_{50}$ is the concentration of a compound providing 50% of the maximal response for the compound at a human κ-opioid receptor. In certain embodiments, a Substituted Benzimidazole-Type Piperidine Compound has a κ GTP $EC_{50}$ (nM) of about 20,000 or less to stimulate human κ-opioid receptor function, or about 10,000 or less, or about 5000 or less, or about 2000 or less, or about 1500 or less, or about 800 or less, or about 500 or less, or about 300 or less, or about 100 or less, or about 50 or less, or about 25 or less.

κ GTP Emax (%) is the maximal effect elicited by a compound relative to the effect elicited by U69,593. In certain embodiments, a Substituted Benzimidazole-Type Piperidine Compound has a κ GTP Emax (%) of about 10% or greater, or about 15% or greater, or about 30% or greater, or about 40% or greater, or about 45% or greater, or about 75% or greater, or about 90% or greater. In other embodiments, a Substituted Benzimidazole-Type Piperidine Compound has a κ GTP Emax (%) of about 10% or less, or about 5% or less, or about 2% or less.

In one embodiment, a Substituted Benzimidazole-Type Piperidine Compound has a $K_i$ (nM) of about 20,000 or less for binding to a human δ-opioid receptor. In another embodiment, a Substituted Benzimidazole-Type Piperidine Compound has substantially no activity. In other embodiments, a Substituted Benzimidazole-Type Piperidine Compound that binds to the human δ-opioid receptor has a $K_i$ (nM) of about 10,000 or less, or about 9000 or less, or about 7500 or less, or about 6500 or less, or about 5000 or less, or about 3000 or less, or about 2500 or less, or about 1000 or less, or about 500 or less, or about 350 or less, or about 250 or less, or about 100 or less.

δ GTP $EC_{50}$ is the concentration of a compound providing 50% of the maximal response for the compound at a human δ-opioid receptor. In certain embodiments, a Substituted Benzimidazole-Type Piperidine Compound has a δ GTP $EC_{50}$ (nM) of about 20,000 or less to stimulate human δ-opioid receptor function, or about 10,000 or less, or about 1000 or less, or about 100 or less, or about 90 or less, or about 50 or less, or about 25 or less or less.

δ GTP Emax (%) is the maximal effect elicited by a compound relative to the effect elicited by met-enkephalin. In certain embodiments, a Substituted Benzimidazole-Type Piperidine Compound has a δ GTP Emax (%) of about 10% or greater, or about 30% or greater, or about 50% or greater, or about 75% or greater, or about 90% or greater, or about 100% or greater. In other embodiments, a Substituted Benzimidazole-Type Piperidine Compound has a δ GTP Emax (%) of about 10% or less, or about 5% or less, or about 2% or less.

The Substituted Benzimidazole-Type Piperidine Compounds can be assayed in vitro or in vivo for the desired therapeutic or prophylactic activity prior to use in humans. Animal model systems can be used to demonstrate safety and efficacy.

The methods for treating or preventing a Condition in an animal in need thereof can further comprise co-administering to the animal being administered a Substituted Benzimidazole-Type Piperidine Compound (i.e., a first therapeutic agent) a second therapeutic agent. In one embodiment, the second therapeutic agent is administered in an effective amount.

An effective amount of the second therapeutic agent will be known to those skilled the art depending on the agent. However, it is well within the skilled artisan's purview to determine the second therapeutic agent's optimal effective-amount range. An Substituted Benzimidazole-Type Piperidine Compound and the second therapeutic agent combined can act either additively or synergistically to treat the same Condition, or they may act independently of each other such that the Substituted Benzimidazole-Type Piperidine Compound treats or prevents a first Condition and the second therapeutic agent treats or prevents a second disorder, which can be the same as the first Condition or another disorder. In one embodiment of the disclosure, where a second therapeutic agent is administered to an animal for treatment of a Condition (e.g., pain), the minimal effective amount of the Substituted Benzimidazole-Type Piperidine Compound will be less than its minimal effective amount would be where the second therapeutic agent is not administered. In this embodiment, the Substituted Benzimidazole-Type Piperidine Compound and the second therapeutic agent can act synergistically to treat or prevent a Condition. In one embodiment, a Substituted Benzimidazole-Type Piperidine Compound is administered concurrently with a second therapeutic agent as a single composition comprising an effective amount of a Substituted Benzimidazole-Type Piperidine Compound and an effective amount of the second therapeutic agent. Alternatively, a composition comprising an effective amount of a Substituted Benzimidazole-Type Piperidine Compound and a second composition comprising an effective amount of the second therapeutic agent are concurrently administered. In another embodiment, an effective amount of a Substituted Benzimidazole-Type Piperidine Compound is administered prior or subsequent to administration of an effective amount of the second therapeutic agent. In this embodiment, the Substituted Benzimidazole-Type Piperidine Compound is administered while the second therapeutic agent exerts its therapeutic effect, or the second therapeutic agent is administered while the Substituted Benzimidazole-Type Piperidine Compound exerts its therapeutic effect for treating or preventing a Condition.

The second therapeutic agent can be, but is not limited to, an opioid agonist, a non-opioid analgesic, a non-steroidal anti-inflammatory agent, an antimigraine agent, a Cox-II inhibitor, a 5-lipoxygenase inhibitor, an anti-emetic, a β-adrenergic blocker, an anticonvulsant, an antidepressant, a $Ca^{2+}$-channel blocker, an anti-cancer agent, an agent for treating or preventing UI, an agent for treating or preventing anxiety, an agent for treating or preventing a memory disorder, an agent for treating or preventing obesity, an agent for treating or preventing constipation, an agent for treating or preventing cough, an agent for treating or preventing diarrhea, an agent for treating or preventing high blood pressure, an agent for treating or preventing epilepsy, an agent for treating or preventing anorexia/cachexia, an agent for treating or preventing drug abuse, an agent for treating or preventing an ulcer, an agent for treating or preventing IBD, an agent for treating or preventing IBS, an agent for treating or preventing addictive disorder, an agent for treating or preventing Parkinson's disease and parkinsonism, an agent for treating or preventing a stroke, an agent for treating or preventing a seizure, an agent for treating or preventing a pruritic condition, an agent for treating or preventing psychosis, an agent for treating or preventing Huntington's chorea, an agent for treating or preventing ALS, an agent for treating or preventing a cognitive disorder, an agent for treating or preventing a migraine, an agent for inhibiting vomiting, an agent for treating or preventing dyskinesia, an agent for treating or preventing depression, or any mixture thereof.

Examples of useful opioid agonists include, but are not limited to, alfentanil, allylprodine, alphaprodine, anileridine, benzylmorphine, bezitramide, buprenorphine, butorphanol, clonitanne, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papaveretum, pentazocine, phenadoxone, phenomorphan, phenazocine, phenoperidine, piminodine, piritramide, proheptazine, promedol, properidine, propiram, propoxyphene, sufentanil, tilidine, tramadol, pharmaceutically acceptable salts or solvates thereof, or any mixture thereof.

In certain embodiments, the opioid agonist is codeine, hydromorphone, hydrocodone, oxycodone, dihydrocodeine, dihydromorphine, morphine, tramadol, oxymorphone, pharmaceutically acceptable salts or solvates thereof, or any mixture thereof.

Examples of useful non-opioid analgesics include, but are not limited to, non-steroidal anti-inflammatory agents, such as aspirin, ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidometacin, acemetacin, fentiazac, clidanac, oxpinac, mefenamic acid, meclofenamic acid, flufenamic acid, niflumic acid, tolfenamic acid, diflurisal, flufenisal, piroxicam, sudoxicam, isoxicam, a pharmaceutically acceptable salt thereof, or any mixture thereof. Other suitable non-opioid analgesics include the following, non-limiting, chemical classes of analgesic, antipyretic, non-steroidal anti-inflammatory drugs; salicylic acid derivatives, including aspirin, sodium salicylate, choline magnesium trisalicylate, salsalate, diflunisal, salicylsalicylic acid, sulfasalazine, and olsalazin; para-aminophenol derivatives including acetaminophen and phenacetin; indole and indene acetic acids, including indomethacin, sulindac, and etodolac; heteroaryl acetic acids, including tolmetin, diclofenac, and ketorolac; anthranilic acids (fenamates), including mefenamic acid and meclofenamic acid; enolic acids, including oxicams (piroxicam, tenoxicam), and pyrazolidinediones (phenylbutazone, oxyphenthartazone); alkanones, including nabumetone; a pharmaceutically acceptable salt thereof; or any mixture thereof. For a more detailed description of the NSAIDs, see Insel, "Analgesic-Antipyretic and Anti-inflammatory Agents and Drugs Employed in the Treatment of Gout," pp. 617-657 in *Goodman* and *Gilman's The Pharmacological Basis of Therapeutics* (Goodman et al., eds., 9$^{th}$ Ed., McGraw-Hill, New York 1996), and Hanson, "Analgesic, Antipyretic and Anti-Inflammatory Drugs," pp. 1196-1221 in *Remington: The Science and Practice of Pharmacy Vol. II* (Gennaro, ed., 19$^{th}$ Ed., Mack Publishing, Easton, Pa., 1995), which are hereby incorporated by reference in their entireties.

Examples of useful Cox-II inhibitors and 5-lipoxygenase inhibitors, as well as combinations thereof, are described in U.S. Pat. No. 6,136,839, which is hereby incorporated by reference in its entirety. Examples of useful Cox-II inhibitors include, but are not limited to, celecoxib, DUP-697, flosulide, meloxicam, 6-MNA, L-745337, rofecoxib, nabumetone, nimesulide, NS-398, SC-5766, T-614, L-768277, GR-253035, JTE-522, RS-57067-000, SC-58125, SC-078, PD-138387, NS-398, flosulide, D-1367, SC-5766, PD-164387, etoricoxib, valdecoxib, parecoxib, a pharmaceutically acceptable salt thereof, or any mixture thereof.

Examples of useful antimigraine agents include, but are not limited to, alpiropride, bromocriptine, dihydroergotamine, dolasetron, ergocornine, ergocominine, ergocryptine, ergonovine, ergot, ergotamine, flumedroxone acetate, fonazine, ketanserin, lisuride, lomerizine, methylergonovine, methysergide, metoprolol, naratriptan, oxetorone, pizotyline, propranolol, risperidone, rizatriptan, sumatriptan, timolol, trazodone, zolmitriptan, a pharmaceutically acceptable salt thereof, or any mixture thereof.

Examples of useful anticonvulsants include, but are not limited to, acetylpheneturide, albutoin, aloxidone, aminoglutethimide, 4-amino-3-hydroxybutyric acid, atrolactamide, beclamide, buramate, calcium bromide, carbamazepine, cinromide, clomethiazole, clonazepam, decimemide, diethadione, dimethadione, doxenitroin, eterobarb, ethadione, ethosuximide, ethotoin, felbamate, fluoresone, gabapentin, 5-hydroxytryptophan, lamotrigine, magnesium bromide, magnesium sulfate, mephenytoin, mephobarbital, metharbital, methetoin, methsuximide, 5-methyl-5-(3-phenanthryl)-hydantoin, 3-methyl-5-phenyl-hydantoin, narcobarbital, nimetazepam, nitrazepam, oxcarbazepine, paramethadione, phenacemide, phenetharbital, pheneturide, phenobarbital, phensuximide, phenylmethylbarbituric acid, phenytoin, phethenylate sodium, potassium bromide, pregabaline, primidone, progabide, sodium bromide, solanum, strontium bromide, suclofenide, sulthiame, tetrantoin, tiagabine, topiramate, trimethadione, valproic acid, valpromide, vigabatrin, zonisamide, a pharmaceutically acceptable salt thereof, or any mixture thereof.

Examples of useful Ca$^{2+}$-channel blockers include, but are not limited to, bepridil, clentiazem, diltiazem, fendiline, gallopamil, mibefradil, prenylamine, semotiadil, terodiline, verapamil, amlodipine, aranidipine, barnidipine, benidipine, cilnidipine, efonidipine, elgodipine, felodipine, isradipine, lacidipine, lercanidipine, manidipine, nicardipine, nifedipine, nilvadipine, nimodipine, nisoldipine, nitrendipine, cinnarizine, flunarizine, lidoflazine, lomerizine, bencyclane, etafenone, fantofarone, perhexiline, a pharmaceutically acceptable salt thereof, or any mixture thereof.

Examples of useful therapeutic agents for treating or preventing UI include, but are not limited to, propantheline, imipramine, hyoscyamine, oxybutynin, dicyclomine, a pharmaceutically acceptable salt thereof, or any mixture thereof.

Examples of useful therapeutic agents for treating or preventing anxiety include, but are not limited to, benzodiazepines, such as alprazolam, brotizolam, chlordiazepoxide, clobazam, clonazepam, clorazepate, demoxepam, diazepam, estazolam, flumazenil, flurazepam, halazepam, lorazepam, midazolam, nitrazepam, nordazepam, oxazepam, prazepam, quazepam, tanazepam, and triazolam; non-benzodiazepine agents, such as buspirone, gepirone, ipsapirone, tiospirone, zolpicone, zolpidem, and zaleplon; tranquilizers, such as barbituates, e.g., amobarbital, aprobarbital, butabarbital, butalbital, mephobarbital, methohexital, pentobarbital, phenobarbital, secobarbital, and thiopental; propanediol carbamates, such as meprobamate and tybamate; a pharmaceutically acceptable salt thereof; or any mixture thereof.

Examples of useful therapeutic agents for treating or preventing diarrhea include, but are not limited to, diphenoxylate, loperamide, a pharmaceutically acceptable salt thereof, or any mixture thereof.

Examples of useful therapeutic agents for treating or preventing epilepsy include, but are not limited to, carbamazepine, ethosuximide, gabapentin, lamotrigine, phenobarbital, phenytoin, primidone, valproic acid, trimethadione, benzodiazepines, γ vinyl GABA, acetazolamide, felbamate, a pharmaceutically acceptable salt thereof, or any mixture thereof.

Examples of useful therapeutic agents for treating or preventing drug abuse include, but are not limited to, methadone, desipramine, amantadine, fluoxetine, buprenorphine, an opiate agonist, 3-phenoxypyridine, levomethadyl acetate hydrochloride, serotonin antagonists, a pharmaceutically acceptable salt thereof, or any mixture thereof.

Examples of non-steroidal anti-inflammatory agents, 5-lipoxygenase inhibitors, anti-emetics, β-adrenergic blockers, antidepressants, and anti-cancer agents are known in the art and can be selected by those skilled in the art. Examples of useful therapeutic agents for treating or preventing memory disorder, obesity, constipation, cough, high blood pressure, anorexia/cachexia, an ulcer, IBD, IBS, addictive disorder, Parkinson's disease and parkinsonism, a stroke, a seizure, a pruritic condition, psychosis, Huntington's chorea, ALS, a cognitive disorder, a migraine, dyskinesia, depression, and/or treating, preventing or inhibiting vomiting include those that are known in the art and can be selected by those skilled in the art.

A composition of the disclosure is prepared by a method comprising admixing a Substituted Benzimidazole-Type Piperidine Compound or a pharmaceutically acceptable salt or solvate thereof with a pharmaceutically acceptable carrier or excipient. Admixing can be accomplished using methods known for admixing a compound (or derivative) and a pharmaceutically acceptable carrier or excipient. In one embodiment, the Substituted Benzimidazole-Type Piperidine Compound is present in the composition in an effective amount.

4.8 Kits

The disclosure further provides kits that can simplify the handling and administration of a Substituted Benzimidazole-Type Piperidine Compound to an animal.

A typical kit of the disclosure comprises a unit dosage form of a Substituted Benzimidazole-Type Piperidine Compound. In one embodiment, the unit dosage form comprises a first container, which can be sterile, containing an effective amount of a Substituted Benzimidazole-Type Piperidine Compound and a pharmaceutically acceptable carrier or excipient. The kit can further comprise a label or printed instructions instructing the use of the Substituted Benzimidazole-Type Piperidine Compound to treat or prevent a Condition. The kit can further comprise a unit dosage form of a second therapeutic agent, for example, a second container containing an effective amount of the second therapeutic agent and a pharmaceutically acceptable carrier or excipient. In another embodiment, the kit comprises a container containing an effective amount of a Substituted Benzimidazole-Type Piperidine Compound, an effective amount of a second therapeutic agent and a pharmaceutically acceptable carrier or excipient. Examples of second therapeutic agents include, but are not limited to, those listed above.

Kits of the disclosure can further comprise a device that is useful for administering the unit dosage forms. Examples of such a device include, but are not limited to, a syringe, a drip bag, a patch, an inhaler, and an enema bag.

The following examples are set forth to assist in understanding the invention and should not be construed as specifically limiting the invention described and claimed herein. Such variations of the invention, including the substitution of all equivalents now known or later developed, that would be within the purview of those skilled in the art, and changes in formulation or changes in experimental design, are to be considered to fall within the scope of the invention incorporated herein.

5. EXAMPLES

Certain Examples below relate to the synthesis of illustrative Substituted Benzimidazole-Type Piperidine Compounds.

5.1 Example 1

Synthesis of Substituted Benzimidazole-Type Piperidine Compounds ZA01-ZA03 and H30b(i)

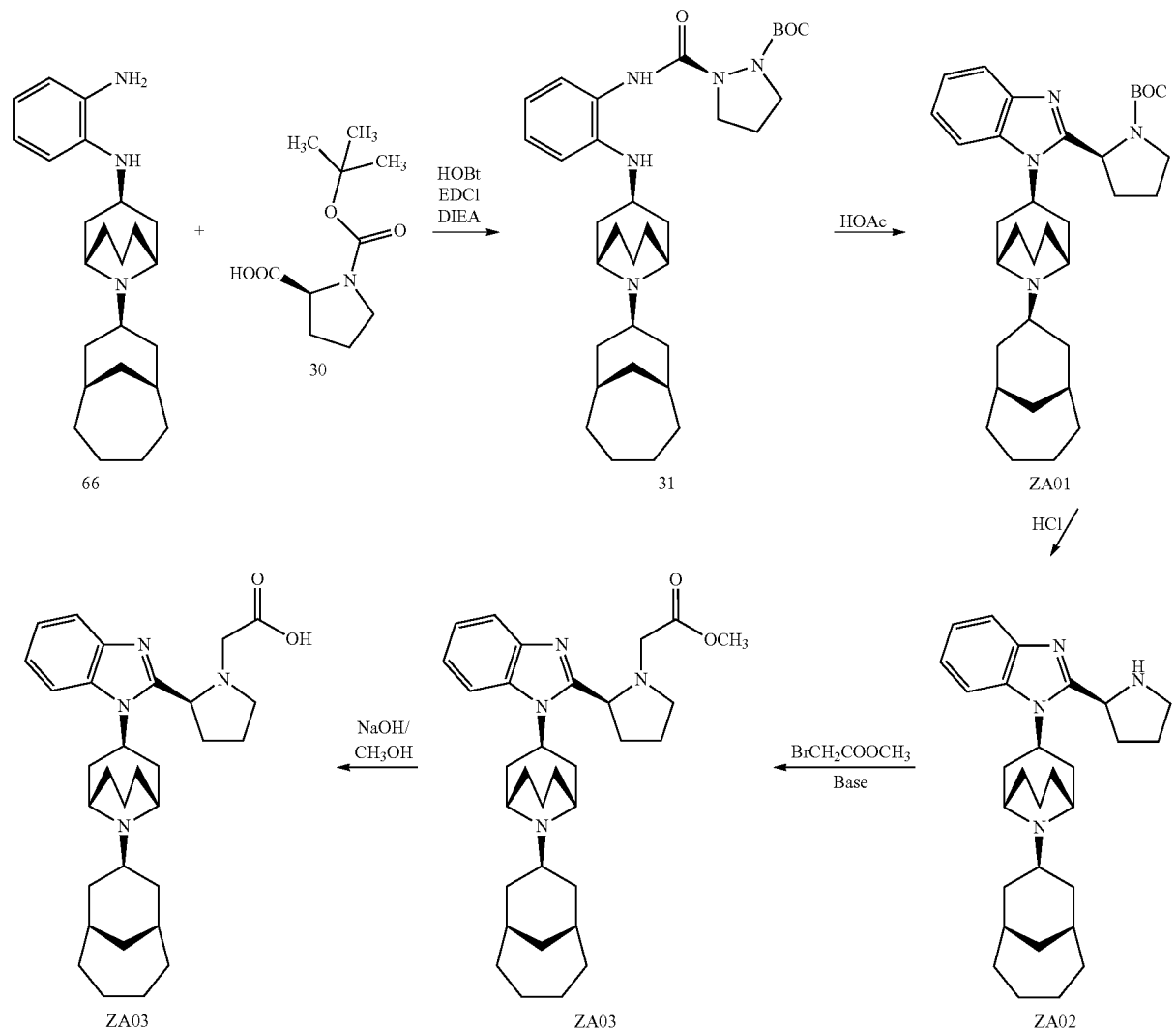

Compound 66, N¹-((1R,3R,5S)-9-((1R,6S,8s)-bicyclo[4.3.1]decan-8-yl)-9-azabicyclo[3.3.1]nonan-3-yl)benzene-1,2-diamine, was prepared as described in Example 6.

To a solution of Compound 66 (0.57 g, 1.57 mmol) and ((S)-1-(tert-butoxycarbonyl)pyrrolidine-2-carboxylic acid (Compound 30, 0.44 g, 2.04 mmol, Sigma-Aldrich, St. Louis, Mo.) in DCM (10 mL) at a temperature of about 25° C. was added HOBT (0.35 g, 2.59 mmol, Sigma-Aldrich), EDCI hydrochloride (0.50 g, 2.59 mmol, Sigma-Aldrich), and DIEA (0.70 mL, Sigma-Aldrich). The resulting reaction mixture was stirred at that temperature for 16 hrs. Thereafter, the mixture was quenched with water and extracted twice with DCM (50 mL for each extraction). The organic portions were combined, dried (over $Na_2SO_4$), and evaporated to dryness under reduced pressure to provide Compound 31, (S)-tert-butyl 2-((2-(((1R,3R,5S)-9-((1R,6S,8s)-bicyclo[4.3.1]decan-8-yl)-9-azabicyclo[3.3.1]nonan-3-yl)amino)phenyl)carbamoyl)pyrrolidine-1-carboxylate.

The identity of Compound 31 was confirmed using MS.

Compound 31: MS: m/z=565.4 $[M+H]^+$.

To a solution of Compound 31 (1.57 mmol) in toluene (15 mL) at a temperature of about 25° C. was added AcOH (0.45 mL) The resulting reaction mixture was heated to 100° C. and stirred at that temperature for 16 hrs. Thereafter, the mixture was cooled to a temperature of about 25° C., quenched with water, and extracted twice with DCM (50 mL for each extraction). The organic portions were combined, washed with an aqueous $NaHCO_3$ solution, dried (over $Na_2SO_4$), and evaporated to dryness under reduced pressure to provide a product which was chromatographed on a flash column eluted with a gradient of from 0:100 MeOH:DCM to 10:90 MeOH:DCM. The fractions containing the product were combined and, under reduced pressure, evaporated and dried to provide Substituted Benzimidazole-Type Piperidine Compound ZA01, (S)-tert-butyl 2-(1-((1R,3R,5S)-9-((1R,6S,8s)-bicyclo[4.3.1]decan-8-yl)-9-azabicyclo[3.3.1]nonan-3-yl)-1H-benzo[d]imidazol-2-yl)pyrrolidine-1-carboxylate (80% yield from Compound 66).

The identity of Substituted Benzimidazole-Type Piperidine Compound ZA01 was confirmed using MS.

Substituted Benzimidazole-Type Piperidine Compound ZA01: MS: m/z=547.4 $[M+H]^+$.

To a solution of Substituted Benzimidazole-Type Piperidine Compound ZA01 (1.5 mmol) in MeOH (3 mL) at a temperature of about 25° C. was added 4 mol/L HCl in 1,4-dioxane (3 mL). The resulting reaction mixture was stirred at that temperature for 2 hrs then evaporated to dryness under reduced pressure. To the residue was added an aqueous $NaHCO_3$ solution (50 mL). The resulting mixture was extracted twice with DCM (50 mL for each extraction). The organic portions were combined, washed with brine, dried (over $Na_2SO_4$), and evaporated to dryness under reduced pressure to provide a product which was chromatographed on a flash column eluted with a gradient of from 0:100 MeOH (10% $NH_4OH$):DCM to 30:70 MeOH (10% $NH_4OH$):DCM. The fractions containing the product were combined and, under reduced pressure, evaporated and dried to provide Substituted Benzimidazole-Type Piperidine Compound ZA02, 1-((1R,3R,5S)-9-((1R,6S,8s)-bicyclo[4.3.1]decan-8-yl)-9-azabicyclo[3.3.1]nonan-3-yl)-2-((S)-pyrrolidin-2-yl)-1H-benzo[d]imidazole (yield 95%).

The identity of Substituted Benzimidazole-Type Piperidine Compound ZA02 was confirmed using MS.

Substituted Benzimidazole-Type Piperidine Compound ZA02: MS: m/z=447.4 $[M+H]^+$.

An alkylation reaction was performed as follows. To a solution of Substituted Benzimidazole-Type Piperidine Compound ZA02 (0.50 mmol) and methyl 2-bromoacetate (0.75 mmol, Sigma-Aldrich) in DMF (2 mL) at a temperature of about 25° C. was added DIEA (2.0 mmol). The resulting reaction mixture was heated to 45° C. and stirred at that temperature for 2 hrs. Thereafter, the mixture was evaporated to dryness under reduced pressure to provide a product which was chromatographed on a flash column eluted with a gradient of from 0:100 MeOH:DCM to 10:90 MeOH:DCM to provide Substituted Benzimidazole-Type Piperidine Compound ZA03, methyl 2-((S)-2-(1-((1R,3R,5S)-9-((1R,6S,8s)-bicyclo[3.3.1]decan-8-yl)-9-azabicyclo[3.3.1]nonan-3-yl)-1H-benzo[d]imidazol-2-yl)pyrrolidin-1-yl)acetate (yield 80%).

The identity of Substituted Benzimidazole-Type Piperidine Compound ZA03 was confirmed using MS.

Substituted Benzimidazole-Type Piperidine Compound ZA03: MS: m/z=519.4 $[M+H]^+$.

An alternate alkylation reaction was performed as follows. To a solution of Substituted Benzimidazole-Type Piperidine Compound ZA02 (0.50 mmol) and methyl 2-bromoacetate (0.75 mmol) in DMF (2 mL) at a temperature of about 25° C. was added $K_2CO_3$ (2.0 mmol). The resulting reaction mixture was heated to 85° C. and stirred at that temperature for 1.5 hrs. Thereafter, the mixture was evaporated to dryness under reduced pressure to provide a product which was chromatographed on a flash column eluted with a gradient of from 0:100 MeOH:DCM to 10:90 MeOH:DCM to provide Substituted Benzimidazole-Type Piperidine Compound ZA03 (yield 50%).

To a solution of Substituted Benzimidazole-Type Piperidine Compound ZA03 (0.37 mmol) in MeOH (2.0 mL) at a temperature of about 25° C. was added 1 mol/L NaOH (0.5 mmol, 0.5 mL) solution. The resulting reaction mixture was stirred at that temperature for 1.5 hrs. Thereafter, the mixture was evaporated to dryness under reduced pressure to provide a residue. Water was added to the residue, the resulting mixture was acidified with 1 mol/L HCl to a pH of about 4.0, and the mixture was evaporated to dryness under reduced pressure to provide a product which was chromatographed on a flash column eluted with a gradient of from 0:100 MeOH (10% $NH_4OH$):DCM to 30:70 MeOH (10% $NH_4OH$):DCM. The fractions containing the product were combined and, under reduced pressure, evaporated and dried to provide Substituted Benzimidazole-Type Piperidine Compound H30b(i), 2-((S)-2-(1-((1R,3R,5S)-9-((1R,6S,8s)-bicyclo[4.3.1]decan-8-yl)-9-azabicyclo[3.3.1]nonan-3-yl)-1H-benzo[d]imidazol-2-yl)pyrrolidin-1-yl)acetic acid (yield 75%).

The identity of Substituted Benzimidazole-Type Piperidine Compound H30b(i) was confirmed using $^1$H-NMR and MS.

Substituted Benzimidazole-Type Piperidine Compound H30b(i): $\delta_H$ (ppm, $CD_3OD$): 7.66 (m, 2H), 7.30 (m, 2H), 6.48 (br, s, 1H), 4.40 (br, s, 1H), 4.18 (br, s, 2H), 3.76 (br, s, 1H), 3.33 (m, 1H), 3.10 (m, 2H), 2.61 (m, 4H), 2.46 (m, 6H), 2.07-1.88 (m, 10H), 1.87-1.41 (m, 11H); MS: m/z=505.2 $[M+H]^+$.

5.2 Example 2

Synthesis of Substituted Benzimidazole-Type Piperidine Compound H36b(i)

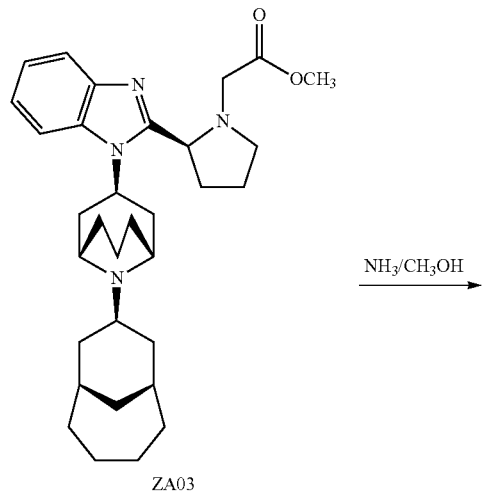

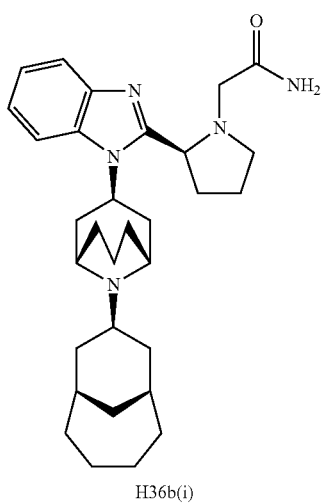

Substituted Benzimidazole-Type Piperidine Compound ZA03 was prepared as described in Example 1 herein.

To a solution of Substituted Benzimidazole-Type Piperidine Compound ZA03 (0.37 mmol) in MeOH (1.0 mL) at a temperature of about 25° C. was added a 7 mol/L ammonia solution in MeOH (3.5 mmol, 0.5 mL). The resulting reaction mixture was stirred at that temperature for 24 hrs. Thereafter, the mixture was evaporated to dryness under reduced pressure to provide a product which was chromatographed on a flash column eluted with a gradient of from 0:100 MeOH (10% NH$_4$OH):DCM to 30:70 MeOH (10% NH$_4$OH):DCM. The fractions containing the product were combined and, under reduced pressure, evaporated and dried to provide Substituted Benzimidazole-Type Piperidine Compound H36b(i), 2-((S)-2-(1-((1R,3R,5S)-9-((1R,6S,8s)-bicyclo[4.3.1]decan-8-yl)-9-azabicyclo[3.3.1]nonan-3-yl)-1H-benzo[d]imidazol-2-yl)pyrrolidin-1-yl)acetamide (yield 60%).

The identity of Substituted Benzimidazole-Type Piperidine Compound H36b(i) was confirmed using $^1$H-NMR and MS.

Substituted Benzimidazole-Type Piperidine Compound H36b(i): $^1$H-NMR: $\delta_H$ (ppm, CD$_3$OD): 7.76 (d, J=7.8 Hz, 1H), 7.66 (d, J=7.8 Hz, 1H), 7.28 (m, 2H), 5.35 (br, s, 1H), 4.60 (br, s, 1H), 4.11 (m, 1H), 3.67 (br, s, 1H), 3.40 (m, 2H), 2.94 (m, 1H), 2.46-2.06 (m, 10H), 2.02-1.52 (m, 15H), 1.29 (m, 5H); MS: m/z=504.3 [M+H]$^+$.

5.3 Example 3

Synthesis of Substituted Benzimidazole-Type Piperidine Compounds ZA04-ZA06, H56d(ii), and O85d

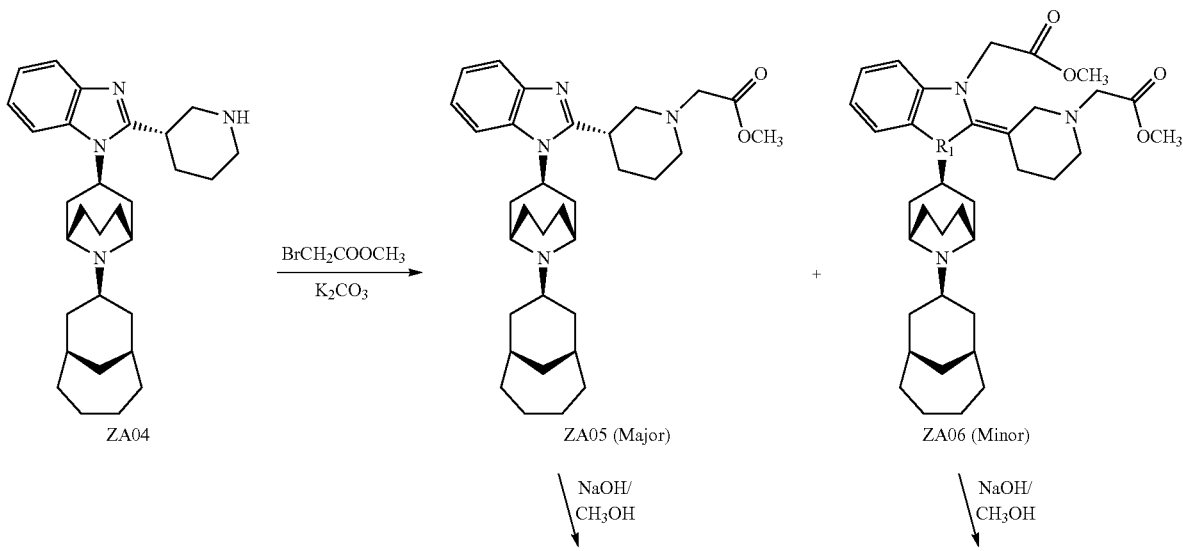

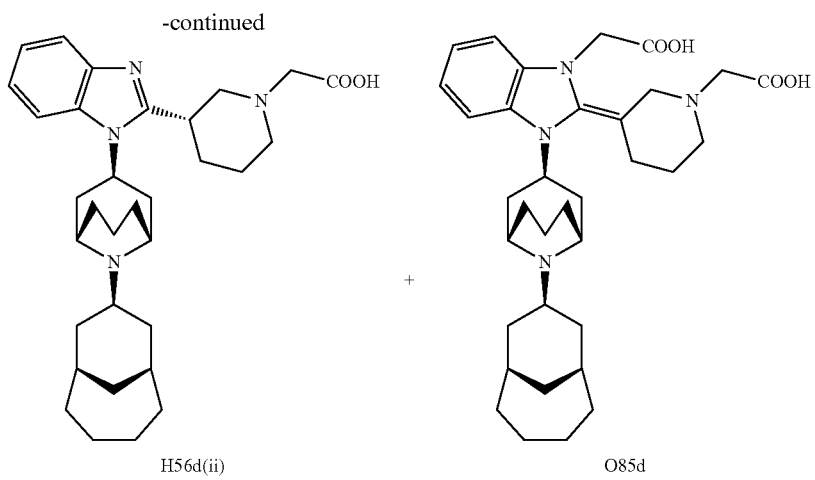

H56d(ii)  O85d

Substituted Benzimidazole-Type Piperidine Compound ZA04, 1-((1R,3R,5S)-9-((1R,6S,8s)-bicyclo[4.3.1]decan-8-yl)-9-azabicyclo[3.3.1]nonan-3-yl)-2-((S)-piperidin-3-yl)-1H-benzo[d]imidazole, was prepared from Compound 66 in a similar manner to the previously-described preparation of Compound ZA02 in Example 1 except that (S)-1-(tert-butoxycarbonyl)piperidine-3-carboxylic acid (Sigma-Aldrich) was used in place of Compound 30.

Thereafter, in a similar manner to the previously-described preparation of Compound ZA03 in Example 1, the alkylation step was performed. This provided, simultaneously, the major mono-alkylation product Substituted Benzimidazole-Type Piperidine Compound ZA05, methyl 2-((S)-3-(1-((1R,3R,5S)-9-((1R,6S,8s)-bicyclo[4.3.1]decan-8-yl)-9-azabicyclo[3.3.1]nonan-3-yl)-1H-benzo[d]imidazol-2-yl)piperidin-1-yl)acetate, and the minor di-alkylation product Substituted Benzimidazole-Type Piperidine Compound ZA06, methyl 2-((E)-3-((1R,3R,5S)-9-((1R,6S,8s)-bicyclo[4.3.1]decan-8-yl)-9-azabicyclo[3.3.1]nonan-3-yl)-2-(1-(2-methoxy-2-oxoethyl)piperidin-3-ylidene)-2,3-dihydro-1H-benzo[d]imidazol-1-yl)acetate.

In a similar manner to the previously-described preparation of Compound H30b(i) in Example 1, the hydrolysis step was performed with Substituted Benzimidazole-Type Piperidine Compounds ZA05 and ZA06 to provide, simultaneously, Substituted Benzimidazole-Type Piperidine Compound H56d(ii), 2-((S)-3-(1-((1R,6S,8s)-bicyclo[3.3.1]decan-8-yl)-9-azabicyclo[3.3.1]nonan-3-yl)-1H-benzo[d]imidazol-2-yl)piperidin-1-yl)acetic acid and Substituted Benzimidazole-Type Piperidine Compound O85d, 2-((E)-3-((1R,3R,5S)-9-((1R,6S,8s)-bicyclo[4.3.1]decan-8-yl)-9-azabicyclo[3.3.1]nonan-3-yl)-2-(1-(carboxymethyl)piperidin-3-ylidene)-2,3-dihydro-1H-benzo[d]imidazol-1-yl)acetic acid, respectively.

The identity of Substituted Benzimidazole-Type Piperidine Compound H56d(ii) was confirmed using $^1$H-NMR and MS.

Substituted Benzimidazole-Type Piperidine Compound H56d(ii): $^1$H-NMR: $\delta_H$ (ppm, CD$_3$OD): 7.81 (d, J=7.8 Hz, 1H), 7.72 (d, J=7.8 Hz, 1H), 7.38 (m, 2H), 5.40 (m, 1H), 4.30 (m, 2H), 4.02-3.75 (m, 3H), 3.77 (m, 2H), 3.58 (m, 1H), 3.36 (m, 1H), 2.81-2.48 (m, 4H), 2.37 (m, 3H), 2.13-1.60 (m, 16H), 1.57-1.38 (m, 5H); MS: m/z=519.3 [M+H]$^+$.

The identity of Substituted Benzimidazole-Type Piperidine Compound O85d was confirmed using $^1$H-NMR and MS.

Substituted Benzimidazole-Type Piperidine Compound O85d: $^1$H-NMR: $\delta_H$ (ppm, CD$_3$OD): 7.80 (d, J=7.8 Hz, 1H), 7.71 (d, J=7.8 Hz, 1H), 7.34 (m, 2H), 5.56 (br, s, 1H), 4.39 (br, s, 2H), 4.23 (m, 1H), 4.05 (m, 2H), 3.85 (m, 1H), 3.60 (m, 1H), 3.44 (m, 1H), 3.19 (m, 1H), 3.03 (m, 2H), 2.68 (m, 4H), 2.49 (m, 3H), 2.20-1.75 (m, 16H), 1.56 (m, 5H); MS: m/z=577.2 [M+H]$^+$.

5.4 Example 4

Synthesis of Compound 44

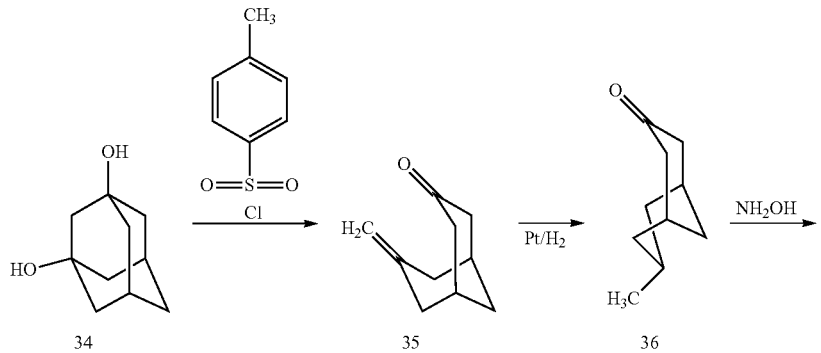

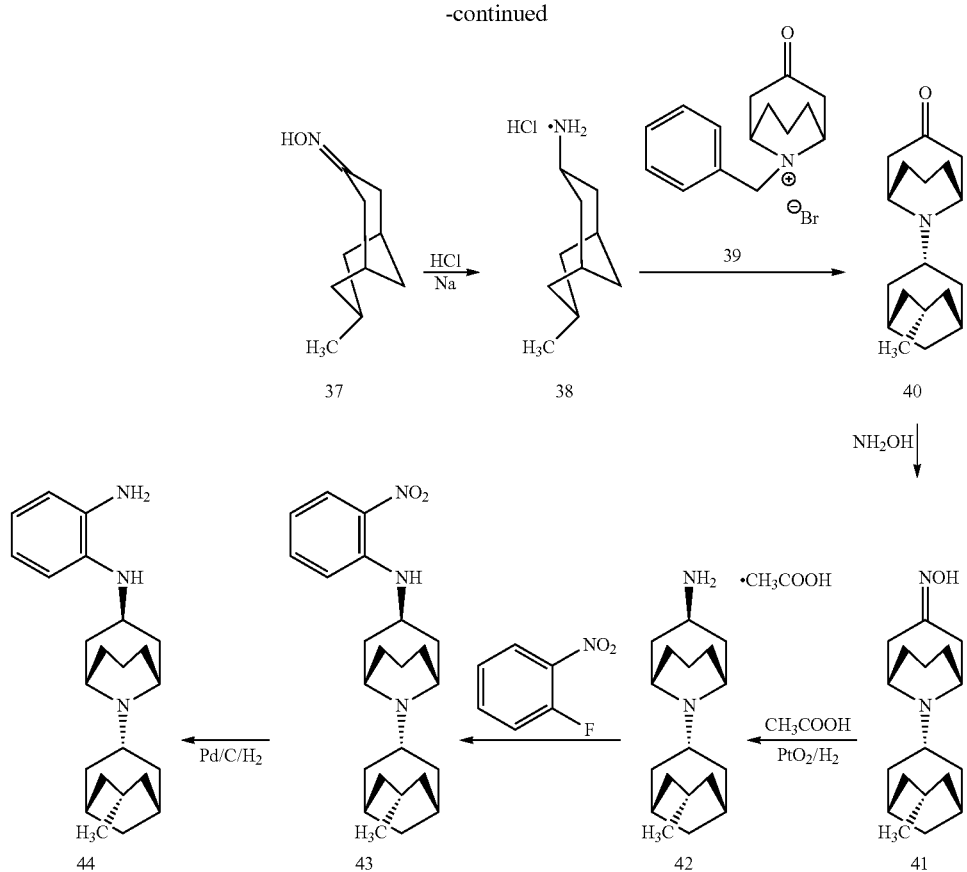

2-Adamantanediol (Compound 34, 500 g, 2.97 mol, Sigma-Aldrich), p-tosyl chloride (624 g, 3.27 mol, Sigma-Aldrich), and pyridine (1.5 L) were combined and stirred under an argon atmosphere. The reaction mixture was heated to a temperature in the range of 68-71° C. and remained at that temperature for 2.5 hrs. The reaction mixture was cooled to a temperature of about 25° C. and poured into saturated brine (6 L). The resulting mixture was extracted three times with MTBE (4 L for each extraction). The organic portions were combined, dried (over MgSO$_4$), filtered, and concentrated onto 1 kg silica gel (pre-treated with hexanes:TEA). The adsorbed material was chromatographed on 1.5 kg silica eluted sequentially with 1:10 EtOAc: hexanes (5 L) then 2:10 EtOAc:hexanes (5 L). All product fractions were combined and evaporated under reduced pressure to provide a residue. The residue was suspended in deionized water (2 L), stirred for 10 min, and filtered under reduced pressure to remove any excess reactants. The remaining solids were taken up in MTBE (2 L), dried (over MgSO$_4$), filtered, and evaporated under reduced pressure to provide 301 g of Compound 35, (1R,5S)-7-methylenebicyclo[3.3.1]nonan-3-one, as a white crystalline solid (yield 67%).

The identity of Compound 35 was confirmed using $^1$H-NMR and TLC.

Compound 35: $^1$H-NMR: $\delta_H$ (ppm, 400 MHz, CDCl$_3$): 4.79 (2H, s), 2.51 (8H, m), 2.29 (2H, m), 1.94 (2H, m), 1.60 (1H, m); TLC (SiO$_2$) 1:10 EtOAc:hexanes: R$_f$=0.25 (visualized with KMnO$_4$ spray reagent).

Compound 35 (250 g, 1.66 mol) was divided into five equal batches. Under a hydrogen atmosphere, the first batch was hydrogenated over platinum black (5 g, Sigma-Aldrich) at 50 psi in dry 99:1 cyclohexane:EtOAc (200 mL) for 2 hrs. The reaction mixture was decanted and the remaining catalyst washed with cyclohexane until no product remained as determined by TLC. The reaction flask was then recharged with the next batch of Compound 35, cyclohexane (200 mL), and hydrogen and the reaction mixture was hydrogenated at 50 psi for 2 hrs. This procedure was repeated until all batches were reacted. All filtrates were combined, filtered through CELITE, and concentrated at a temperature of about 25° C. to provide Compound 36, 7-methylbicyclo[3.3.1]nonan-3-one, as a colorless oil.

The identity of Compound 36 was confirmed using $^1$H-NMR and TLC.

Compound 36: $^1$H-NMR: $\delta_H$ (ppm, 400 MHz, CDCl$_3$): 2.42 (4H, m), 2.26 (2H, m), 1.98-2.00 (3H, m), 1.65 (1H, m), 1.54 (1H, m), 0.80 (1H, m); TLC (SiO$_2$) 2:10 EtOAc: hexanes: R$_f$=0.30 (visualized with KMnO$_4$ spray reagent).

Compound 36, taken directly from the previous step, was taken up in AcOH (1 L). To this was added 50% aqueous NH$_2$OH (100 mL, Sigma-Aldrich). With stirring, the reaction mixture was heated to a gentle reflux and refluxed for 1 hr. The mixture was cooled to a temperature of about 25° C. and slowly poured into 2.5M Na$_2$CO$_3$ aqueous solution (5 L) with stirring. Thereafter, the mixture was stirred vigorously for 1 hr. Deionized water (1 L) was added and the mixture was stirred for another 0.5 hrs. The precipitate that formed was collected by filtering under reduced pressure and washed with deionized water (2 L). The residue was taken up in DCM (1 L), dried (over MgSO$_4$), filtered, and evaporated under reduced pressure to provide 231.5 g of Compound 37, 7-methylbicyclo[3.3.1]nonan-3-one oxime, as a white fluffy solid (85% yield from Compound 35).

The identity of Compound 37 was confirmed using $^1$H-NMR.

Compound 37: $^1$H-NMR: $\delta_H$ (ppm, 400 MHz, CDCl$_3$): 3.21 (1H, d), 2.05-2.41 (4H, m), 1.73-2.11 (4H, m), 1.51-1.73 (2H, m), 1.33 (1H, d), 0.82 (4H, m), 0.63 (1H, t).

To a three neck 5 L round bottom flask equipped with an overhead stirrer, 1 L pressure equalizing dropping funnel, and temperature probe was added toluene (about 3 L) and Na metal (67.17 g, 2.8 mol, Sigma-Aldrich). Under an argon atmosphere, the mixture was heated to a gentle reflux until the Na metal became molten. A solution of a portion of Compound 37 (66.66 g, 0.40 mol) in dry isopropyl alcohol (230 mL) was then added dropwise via the dropping funnel over 1.5 hrs. With stirring, the resulting reaction mixture was heated to reflux and refluxed for 16 hrs. After cooling to a temperature of about 25° C., the following materials were added in sequential order: EtOH (164 mL) dropwise over 15 min, 1:1 EtOH:H$_2$O (164 mL) dropwise over 15 min, and water (500 mL) dropwise over 30 min. The resulting mixture was stirred for 2 hrs. The mixture was poured into a 6 L separatory funnel and the organic layer was separated. The aqueous portion was extracted three times with Et$_2$O (1 L for each extraction).

The process just described was repeated twice more with 66.66 g of Compound 37 being used each time. All organic portions were combined, dried (over MgSO$_4$), and filtered into a 6 L Erlenmeyer flask. To the mixture was added 2M HCl in Et$_2$O (1.5 L, 2.5 eq). The mixture was allowed to stir and cool in an ice:MeOH bath for 1 hr. The solids that formed were filtered under reduced pressure and dried under reduced pressure at 50° C. for 18 hr to provide 100.01 g of Compound 38, (3s,7s)-7-methylbicyclo[33.1]nonan-3-amine hydrochloride, as a white crystalline solid. The filtrate was evaporated under reduced pressure to provide a residue which was triturated with Et$_2$O (2 L). The solids that remained were filtered and washed with Et$_2$O (2 L) to provide 87.1 g of a second crop of Compound 38 after drying (overall yield 39%).

The identity of Compound 38 was confirmed using $^1$H-NMR.

Compound 38: $^1$H-NMR: $\delta_H$ (ppm, 400 MHz, CDCl$_3$): 8.28 (3H, bs), 3.55 (1H, m), 2.25 (2H, m), 1.81-2.09 (4H, m), 1.85 (1H, m), 1.61 (3H, m) 1.08 (1H, d), 0.70-0.88 (5H, m).

Compound 38 (87.1 g, 0.463 mol), 9-benzyl-3-oxo-9-azoniabicyclo[3.3.1]nonane bromide (Compound 39, 165.20 g, 0.509 mol, Sigma-Aldrich), potassium carbonate (67.83 g, 0.491 mol), EtOH (1.07 L), and water (346 mL) were combined. The resulting reaction mixture was stirred for about 16 hrs at a temperature of about 25° C. The reaction mixture was then heated to reflux and refluxed for 3 hrs. Thereafter, the mixture was cooled to a temperature of about 25° C. then further cooled to 5° C. in an ice/MeOH bath and allowed to stir for 30 min at that temperature. The solids that formed were filtered under reduced pressure, washed with deionized water, and dried under reduced pressure to provide 102.1 g of Compound 40, (1R,3r,5S,7s)-7-methyl-9'-aza[3,9'-bi(bicyclo[3.3.1]nonan)]-3'-one, as an off-white crystalline solid (yield 80%).

The identity of Compound 40 was confirmed using $^1$H-NMR.

Compound 40: $^1$H-NMR: $\delta_H$ (ppm, 400 MHz, CDCl$_3$): 3.68 (2H, m), 3.05 (1H, m), 2.61 (2H, m), 2.25 (4H, m), 1.98 (1H, m), 1.85 (4H, m), 1.49-1.78 (7H, m), 1.25 (2H, m), 1.07 (1H, d), 0.86 (3H, d), 0.78 (2H, t).

Compound 40 (67 g, 0.243 mol), THF (500 mL), and AcOH (41.78 mL, 0.730 mol) were combined. To this mixture was added 50% aqueous NH$_2$OH (45 mL, 0.730 mol). With stirring, the resulting reaction mixture was heated to reflux and refluxed for 1 hr. The mixture was cooled to a temperature of about 25° C. and deionized water was added (500 mL). Potassium carbonate (100 g, 0.730 mol) in deionized water (500 mL) was then added in one portion. The resulting mixture was stirred and cooled in an ice bath for 1 hr. The solids that formed were filtered under reduced pressure and dried under reduced pressure at 60° C. to provide Compound 41, (1R,3r,5S,7 s)-7-methyl-9'-aza[3,9'-bi(bicyclo[3.3.1]nonan)]-3'-one oxime (yield>99%).

The identity of Compound 41 was confirmed using $^1$H-NMR.

Compound 41: $^1$H-NMR: $\delta_H$ (ppm, 400 MHz, CD$_3$OD): 3.76 (1H, m), 3.45 (2H, m), 3.18 (1H, m), 3.02 (1H, m), 2.62 (1H, m), 2.27 (4H, m), 1.78-2.08 (7H, m), 1.67 (1H, m), 1.58 (2H, m), 1.46 (1H, m), 1.22 (2H, t), 1.09 (1H, d), 0.85 (5H, m).

Compound 41 (70.01 g, 0.241 mol) was taken up in AcOH (400 mL). This mixture was divided into two batches. Under a hydrogen atmosphere, to each batch was added platinum (IV) oxide (5.98 g, 0.2 eq, Sigma-Aldrich) and each batch was then hydrogenated at 50 psi for 16 hrs to 18 hrs. The batches were combined and filtered through CELITE. The filter cake was washed with AcOH (500 mL). The filtrate was concentrated under reduced pressure at 70° C. to provide an oil. To the oil was added MTBE (6 L). The mixture was stirred and cooled to 0° C. for 1 hr. The white precipitate that formed was filtered under reduced pressure, washed with Et$_2$O (2 L), and dried under reduced pressure to provide 76.2 g of Compound 42, (1R,1'R,3r,3'R,5S,5'S,7S)-7-methyl-9'-aza[3,9'-bi(bicyclo[3.3.1]nonan)]-3'-amine acetate, as a white solid (yield 94%).

The identity of Compound 42 was confirmed using $^1$H-NMR and LC/MS.

Compound 42: $^1$H-NMR: $\delta_H$ (ppm, 400 MHz, CD$_3$OD): 3.73 (2H, m), 3.55 (1H, m), 2.46 (2H, m), 2.24 (2H, m), 1.75-2.12 (11H, m), 1.45-1.75 (4H, m), 1.28 (4H, m), 1.06 (1H, d), 0.89 (3H, d), 0.80 (2H, t); LC/MS (t$_r$=1.689 min): m/z=277.3 [M+H]$^+$ (Calc.: 276.5).

Compound 42 (80.0 g, 0.23 mol), 1-fluoro-2-nitrobenzene (35.69 g, 0.253 mol, Sigma-Aldrich), and potassium carbonate (95.36 g, 0.69 mol) were combined in dry DMF (400 mL). The reaction mixture was heated to 110° C. under an argon atmosphere for 1 hr then cooled to a temperature of about 25° C. Deionized water (2 L) was added and the mixture was stirred and cooled in an ice/MeOH bath for 1 hr. The resulting solids were filtered under reduced pressure, washed with deionized water (4 L), and dried under reduced pressure to provide 66.81 g of Compound 43, (1R,1'R,3r,3'R,5S,5'S,7S)-7-methyl-N-(2-nitrophenyl)-9'-aza[3,9'-bi(bicyclo[3.3.1]nonan)]-3'-amine, as a orange solid (yield 73%).

The identity of Compound 43 was confirmed using $^1$H-NMR and LC/MS.

Compound 43: $^1$H-NMR: $\delta_H$ (ppm, 400 MHz, CDCl$_3$): 8.17 (1H, d), 8.01 (1H, m), 7.43 (1H, t), 6.93 (1H, d), 6.61 (1H, t), 3.95 (1H, m), 3.45 (2H, m), 3.06 (1H, m), 2.48 (2H, m), 2.20 (2H, m), 1.87-2.08 (4H, m), 1.45-1.89 (6H, m), 1.35 (2H, t), 0.95-1.22 (5H, m), 0.87 (5H, m); LC/MS (t$_r$=2.732 min): m/z=398.4 [M+H]$^+$ (Calc.: 397.6).

Compound 43 (30.0 g, 75.57 mmol) was taken up in DCM (100 mL). Under a hydrogen atmosphere, to this was added Pd/C (3 g) and, with stirring, the reaction mixture was hydrogenated at 50 psi for 2 hr at a temperature of about 25°

C. to provide Compound 44, N$^1$—((1R,3r,3'R,5S,5'S,7S)-7-methyl-[3,9'-bi(9'-azabicyclo[3.3.1]nonan)]-3'-yl)benzene-1,2-diamine.

The identity of Compound 44 was confirmed using LC/MS.

Compound 44: LC/MS (t$_r$=2.045 min): m/z=368.9 [M+H]$^+$ (Calc.: 367.6).

5.5 Example 5

Synthesis of Compound 56

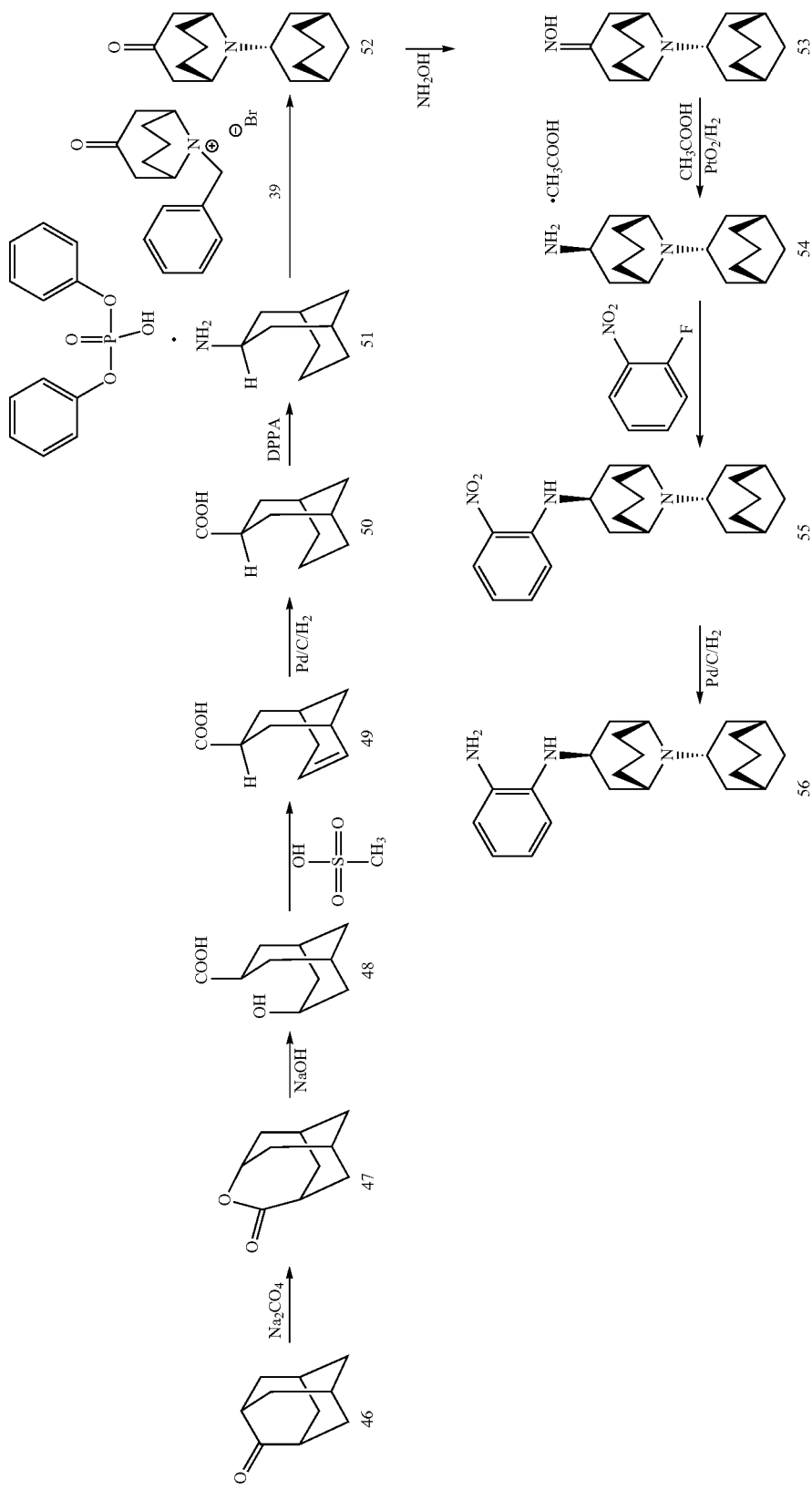

2-Adamantanone (Compound 46, 1000 g, 6.66 mol, Sigma-Aldrich) was dissolved in TFA (3 L, Sigma-Aldrich). To this mechanically stirred mixture surrounded by a cooling bath with a temperature maintained at 20° C. was added sodium percarbonate (1254.8 g, 7.99 mol, Sigma-Aldrich) portion-wise over 1 hr; the temperature of the reaction mixture increased to 60° C. during the addition. After 2 hrs additional stirring, deionized water (4 L) was added followed by four extractions with DCM (2 L for each extraction). The organic portions were combined, dried (over $MgSO_4$), filtered, and evaporated under reduced pressure to provide 1180 g of Compound 47, (1R,3r,6s,8S)-4-oxatricyclo[4.3.1.13,8]undecan-5-one, as a white crystalline solid (yield 97%).

The identity of Compound 47 was confirmed using $^1$H-NMR and TLC.

Compound 47: $^1$H-NMR: $\delta_H$ (ppm, 400 MHz, $CDCl_3$): 4.48 (1H, s), 3.06 (1H, m), 2.09 (2H, m), 2.00 (3H, m), 1.95 (2H, m), 1.81 (2H, m), 1.70 (2H, m); TLC ($SiO_2$) 1:1 EtOAc:hexanes: $R_f$=0.8 (visualized with molybdenum blue spray reagent).

Compound 47 (1572.7 g, 9.46 mol) was taken up in MeOH (2 L). To this was added NaOH (2270 g, 56.7 mol) in deionized water (6 L); the temperature of the mixture increased from about 25° C. to 54° C. during the addition. With stirring, the resulting reaction mixture was heated to a gentle reflux and refluxed for 36 hrs. After cooling to a temperature of about 25° C., the MeOH was removed by vacuum distillation at 60° C. The resulting solution was stirred and acidified with concentrated HCl to a pH of about 2.5. The white precipitate that formed was allowed to stir for 18 hrs at a temperature of about 25° C. then filtered under reduced pressure to provide partially dried Compound 48, (1R,3r,5S,7r)-7-hydroxybicyclo[3.3.1]nonane-3-carboxylic acid.

The identity of Compound 48 was confirmed using $^1$H-NMR and TLC.

Compound 48: $^1$H-NMR: $\delta_H$ (ppm, 400 MHz, d6-DMSO): 11.88 (1H, s), 4.44 (1H, s), 3.73 (1H, m), 1.95 (4H, m), 1.63 (2H, m), 1.41 (3H, m), 1.22 (2H, m), 1.16 (1H, m); TLC ($SiO_2$) 2:1:0.1 EtOAc:hexanes:AcOH: $R_f$=0.3 (visualized with molybdenum blue spray reagent).

Compound 48, taken directly from the previous step, was suspended in toluene (8 L). To this was added methane sulfonic acid (367 mL, 4.73 mol, Sigma-Aldrich). With stirring, the resulting reaction mixture was heated to reflux and water removed azeotropically for 5 hrs. After cooling to a temperature of about 25° C., deionized water (4 L) was added with stirring. The organic layer was separated, dried (over $MgSO_4$), filtered, and concentrated to provide Compound 49, (1R,3S,5S)-bicyclo[3.3.1]non-6-ene-3-carboxylic acid.

The identity of Compound 49 was confirmed using $^1$H-NMR and TLC.

Compound 49: $^1$H-NMR: $\delta_H$ (ppm, 400 MHz, $CDCl_3$): 10.45 (1H, bs), 5.85 (1H, m), 5.70 (1H, m), 2.79 (1H, m), 2.37 (2H, m), 2.11 (1H, m), 1.81 (3H, m), 1.61 (41-1, m); TLC ($SiO_2$) 1:1:0.1 EtOAc:hexanes:AcOH: $R_f$=0.8 (visualized with molybdenum blue spray reagent).

Compound 49, taken directly from the previous step, was taken up in MeOH (1 L). This was divided into six batches and to each, under a hydrogen atmosphere, was added 10% Pd/C (0.01 mol). The reaction mixtures were each hydrogenated at 50 psi until hydrogen uptake ceased (10 hrs to 15 hrs). The mixtures were combined, filtered through CELITE, and NaOH (1 kg) in deionized water (400 mL) was added. The mixture was stirred for 4 h at a temperature of about 25° C. The mixture was concentrated under reduced pressure and deionized water (4 L) was added. Concentrated HCl was added until a pH within the range of 3-4 was achieved. The white solid that formed was allowed to stir for 1 hr at a temperature of about 25° C. and then was filtered under reduced pressure to provide 1.232 kg of Compound 50, (1R,3r,5S)-bicyclo[3.3.1]nonane-3-carboxylic acid, as an off-white crystalline solid (78% yield from Compound 47).

The identity of Compound 50 was confirmed using $^1$H-NMR and TLC.

Compound 50: $^1$H-NMR: $\delta_H$ (ppm, 400 MHz, $CDCl_3$): 9.25 (1H, bs), 3.13 (1H, m), 1.97 (4H, m), 1.80 (2H, m), 1.70 (5H, m), 1.57 (3H, m); TLC ($SiO_2$) 1:1:0.1 EtOAc:hexanes: AcOH: $R_f$=0.8 (visualized with molybdenum blue spray reagent).

Compound 50 (1108.5 g, 6.59 mol) was taken up in toluene (5 L) in a 20 L reaction vessel. To this was added TEA (1013.3 mL, 7.26 mol). The resulting mixture was stirred and heated to 75° C. under a nitrogen atmosphere. The diphenyl phosphoryl azide (DPPA, 1564 mL, 7.26 mol, Sigma-Aldrich) was diluted with toluene to 2 L total volume and added slowly via addition funnel over 1.5 hrs; during this addition the temperature increased by about 10° C. to 15° C. The resulting reaction mixture was allowed to stir for 3 hrs at 75° C. The mixture was then concentrated to a brownish-yellow oil by vacuum distillation at 90° C. The oil was cooled to 5° C. and THF (2.5 L) was added. The mixture was allowed to stir and cool to 0° C. NaOH (792 g, 19.80 mol) in deionized water (3 L) was added over 1 hr keeping the temperature below 5° C. The mixture was stirred for 18 hrs at 5° C. The resulting mixture was then extracted twice with $Et_2O$ (4 L for each extraction). To the remaining aqueous mixture at 5° C. was slowly added concentrated HCl until a pH of about 6-7 was reached; no significant change in temperature occurred during this neutralization. The resulting white precipitate was allowed to stir for 2 hrs at 0° C. The precipitate was then filtered under reduced pressure and dried under reduced pressure at 50° C. to provide 1.875 kg of Compound 51, (1R,3r,5S)-bicyclo[3.3.1]nonan-3-amine diphenyl phosphate salt, as a white solid (yield 73.1%).

The identity of Compound 51 was confirmed using $^1$H-NMR.

Compound 51: $^1$H-NMR: $\delta_H$ (ppm, 400 MHz, d6-DMSO): 7.78 (2H, s), 7.22 (4H, t), 7.11 (4H, m), 6.93 (2H, t), 3.61 (1H, m), 3.31 (1H, s), 1.93 (4H, m), 1.33-1.60 (10H, m).

Compound 51 (1037.5 g, 2.67 mol) and Compound 39 (1000 g, 3.08 mol) were suspended in EtOH (6.2 L) and deionized water (2 L). To this stirred mixture was added potassium carbonate (390.72 g, 2.83 mol) in deionized water (800 mL). The resulting reaction mixture was stirred for 18 hrs at a temperature of about 25° C. The reaction mixture was then heated to reflux, about 81° C., and refluxed for 3 hrs. Thereafter, the mixture was allowed to cool slowly over 4 h to a temperature of about 25° C. with vigorous stirring during which time a white precipitate formed. The mixture was then cooled to 5° C. and allowed to stir for 2 hrs at that temperature. The white precipitate was filtered under reduced pressure, washed with deionized water (8 L), and dried under reduced pressure at 60° C. to provide 580.1 g of Compound 52, (1R,1'R,3r,5S,5'S)-9'-aza[3,9'-bi(bicyclo[3.3.1]nonan)]-3'-one, as a white crystalline solid (yield 83.1%).

The identity of Compound 52 was confirmed using $^1$H-NMR and TLC.

Compound 52: $^1$H-NMR: $\delta_H$ (ppm, 400 MHz, $CDCl_3$): 3.69 (2H, s), 3.38 (1H, m), 2.62 (2H, m), 2.21 (2H, d), 2.12 (4H, m), 1.85 (2H, m), 1.41-1.78 (14H, m); TLC ($SiO_2$) 7:3 hexanes:EtOAc: $R_f$=0.4 (visualized with potassium iodoplatinate spray).

Compound 52 (580.1 g, 2.22 mol) and THF (4 L) were introduced into a reactor; the reactor temperature control was set to 18° C. 50% Aqueous NH₂OH (415 mL, 6.66 mol) was added followed by the slow addition of AcOH (381.25 mL, 6.66 mol). The temperature of the reaction mixture increased to 28° C. during the addition. The reaction mixture was stirred for 16 hrs at a temperature of about 25° C. then heated to a gentle reflux and refluxed for 1 hr. The mixture was cooled to a temperature of about 25° C. and deionized water (4 L) and DCM (4 L) were added. With vigorous stirring, solid NaHCO₃ (560 g, 6.66 mol) was then slowly added over 30 min and the mixture was allowed to stir until effervescence ceased. The white precipitate that formed was filtered under reduced pressure, washed with deionized water (1 L), and dried under reduced pressure at 60° C. for 72 hrs to provide 432.5 g of Compound 53, (1R,1'R,3r,5S,5'S)-9'-aza[3,9'-bi(bicyclo[3.3.1]nonan)]-3'-one oxime, as a white solid (yield 70.6%). The filtrate was allowed to form layers and the organic layer was separated. The aqueous layer was washed three times with DCM (2 L for each wash). The organic portions were combined, dried (over MgSO₄), filtered, and evaporated under reduced pressure to provide a pale yellow solid. The solid was triturated with 10:1 Et₂O:EtOAc (1 L), stirred for 1 hr, and filtered under reduced pressure to provide a residue which was dried under reduced pressure at 60° C. for 72 hrs to provide an additional 138.4 g of Compound 53 as a white solid (yield 22.6%, overall yield 93.2%).

Compound 53 (570.9 g, 2.07 mol) was taken up in AcOH (3 L). This mixture, with a total dissolved volume of 3.3 L, was divided into ten 330 mL batches. Under a hydrogen atmosphere, to each batch was added platinum (IV) oxide (9.40 g, 0.041 mol) and each batch was then hydrogenated at 50 psi for 16 hrs to 18 hrs. The batches were combined and filtered through CELITE. The filter cake was washed with AcOH (500 mL). The filtrate was concentrated under reduced pressure at 70° C. to provide an oil. To the oil was added Et₂O (6 L). The mixture was stirred and cooled to 0° C. for 1 hr. The white precipitate that formed was filtered under reduced pressure and washed with Et₂O (2 L) to provide 253.4 g of Compound 54, (1R,1'R,3r,3'R,5S,5'S)-9'-aza[3,9'-bi(bicyclo[3.3.1]nonan)]-3'-amine acetate (yield 35.3%). The filtrate was evaporated under reduced pressure to provide a residue which was subjected to the same treatment with Et₂O. A second crop of 213.7 g of Compound 54 was isolated (yield 32.1%). The filtrate was again evaporated under reduced pressure to provide 201.1 g of Compound 54 (yield 25.4%, overall yield 92.8%).

The identity of Compound 54 was confirmed using ¹H-NMR.

Compound 54: ¹H-NMR: δ$_H$ (ppm, 400 MHz, CD₃OD): 3.63 (3H, m), 3.42 (1H, m), 2.36 (2H, m), 2.01 (5H, m), 1.89 (5H, m), 1.39-1.78 (13H, m), 1.12 (2H, m).

In part 1, Compound 54 (439.0 g, 1.36 mol) and MeCN (4 L) were introduced into a reactor; the reactor temperature control was set to 25° C. To this mixture were added TEA (412.9 g, 4.08 mol, 3 eq) and 1-fluoro-2-nitrobenzene (194.2 g, 1.38 mol, 1 eq). The reaction mixture was heated to reflux, refluxed for 6 days, then cooled to 0° C. The yellow precipitate that formed was collected by filtration under reduced pressure. The filter cake was washed four times with DCM (2 L for each wash) and the filtrates were set aside. The remaining 91 g of solids, comprising recovered Compound 54, were dried and set aside.

In part 2, the reaction described in part 1 above was repeated using the recovered Compound 54 starting material except DMF (2 L) and K₂CO₃ (3 eq) were used. After stirring for 2 hrs at 110° C., the reaction mixture was cooled to a temperature of about 25° C. and poured into deionized water (4 L).

This mixture was extracted six times with Et₂O (2 L for each extraction). The organic portions were combined and evaporated under reduced pressure to provide a residue.

The residue from part 2 and the filtrates from part 1 were combined and the resulting combination was evaporated under reduced pressure to provide an oil which was triturated with deionized water (4 L). The solids that formed were filtered under reduced pressure and washed with further deionized water. The solids were then dried under reduced pressure at 60° C. for 48 hrs to provide 402 g of Compound 55, (1R,1'R,3r,3'R,5S,5'S)—N-(2-nitrophenyl)-9'-aza[3,9'-bi(bicyclo[3.3.1]nonan)]-3'-amine, as a bright yellow solid (yield 77%).

Compound 55 (402 g, 1.05 mol) was taken up in MeOH (2.5 L). This mixture was divided into ten batches. Under a hydrogen atmosphere, to each batch was added 10% Pd/C (0.04 mol) and, with stirring, each batch was hydrogenated at 50 psi for 3 hrs at a temperature of about 25° C. The batches were filtered through CELITE and the filter cake washed with MeOH. The filtrate was evaporated under reduced pressure to provide a residue which was triturated with Et₂O then filtered under reduced pressure to provide Compound 56, N¹-((1R,1'R,3r,3'R,5S,5'S)-[3,9'-bi(9'-azabicyclo[3.3.1]nonan)]-3'-yl)benzene-1,2-diamine, as a light brown solid (yield>99%).

5.6 Example 6

Synthesis of Compound 66

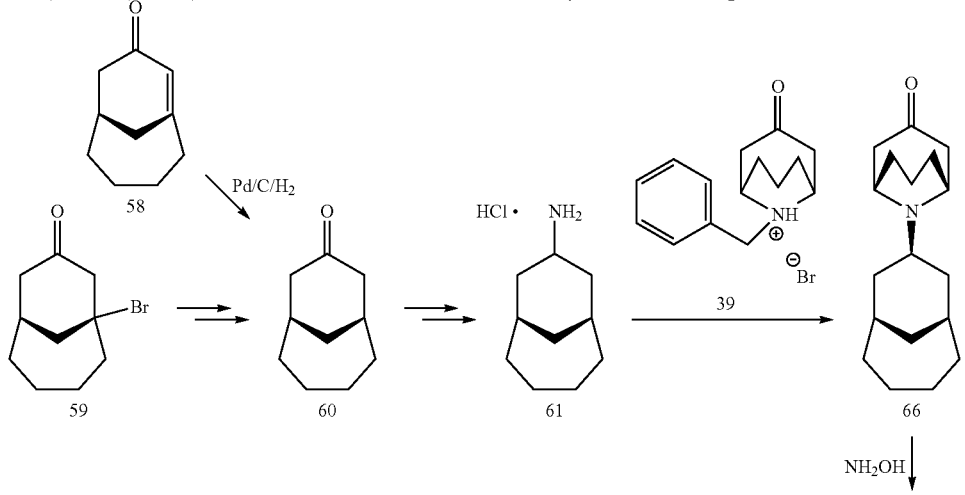

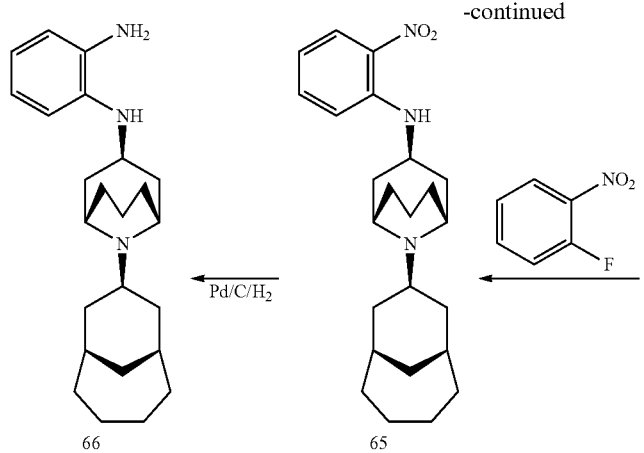
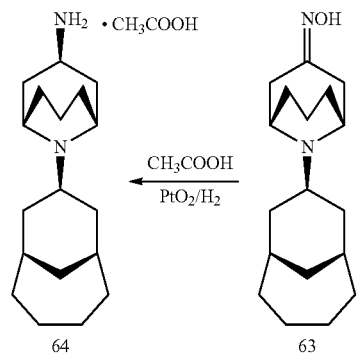

Using procedures similar to those described in Examples 4 and 5, Compound 66 was prepared from Compound 60.

The identity of Compound 61, (1R,6S)-bicyclo[4.3.1]decan-8-amine, was confirmed using MS.

Compound 61: MS: m/z=154.4 [M+H]$^+$.

The identity of Compound 62, (1R,5S)-9-((1R,6S,8s)-bicyclo[4.3.1]decan-8-yl)-9-azabicyclo[3.3.1]nonan-3-one, was confirmed using $^1$H-NMR and MS.

Compound 62: $^1$H-NMR: $\delta_H$ (ppm, CD$_3$OD): 3.76 (br, 2H), 3.45 (m, 1H), 3.13 (m, 1H), 2.70 (m, 2H), 2.38-2.20 (m, 4H), 1.99-1.76 (m, 9H), 1.75-1.34 (m, 10H); MS: m/z=276.4 [M+H]$^+$.

The identity of Compound 63, (1R,5S)-9-((1R,6S,8s)-bicyclo[4.3.1]decan-8-yl)-9-azabicyclo[3.3.1]nonan-3-one oxime, was confirmed using $^1$H-NMR and MS.

Compound 63: $^1$H-NMR: $\delta_H$ (ppm, CDCl$_3$): 8.29 (br, 1H), 3.52 (br, 2H), 3.03 (m, 2H), 2.63 (m, 1H), 2.27 (m, 4H), 1.95-1.26 (m, 20H); MS: m/z=291.4 [M+H]$^+$.

The identity of Compound 64, (1R,3R,5S)-9-((1R,6S,8s)-bicyclo[4.3.1]decan-8-yl)-9-azabicyclo[3.3.1]nonan-3-amine acetate, was confirmed using $^1$H-NMR and MS.

Compound 64: $^1$H-NMR: $\delta_H$ (ppm, CD$_3$OD): 3.49 (m, 2H), 3.20 (m, 1H), 3.05 (m, 1H), 2.27 (m, 4H), 2.04 (m, 1H), 1.91 (s, 3H), 1.81 (m, 7H), 1.71-1.42 (m, 8H), 1.31-1.15 (m, 61-1); MS: m/z=277.4 [M+H]$^+$.

The identity of Compound 65, (1R,3R,5S)-9-((1R,6S,8s)-bicyclo[4.3.1]decan-8-yl)-N-(2-nitrophenyl)-9-azabicyclo[3.3.1]nonan-3-amine, was confirmed using $^1$H-NMR and MS.

Compound 65: $^1$H-NMR: $\delta_H$ (ppm, CDCl$_3$): 8.17 (dd, J=1.7, 8.4 Hz, 1H), 8.04 (d, J=7.3 Hz, 1H), 7.41 (m, 1H), 6.94 (d, J=8.4 Hz, 1H), 6.60 (m, 1H), 3.98 (m, 1H), 3.51 (m, 2H), 3.05 (m, 1H), 2.46 (m, 2H), 2.27 (m, 2H), 2.02 (m, 1H), 1.86-1.52 (m, 12H), 1.49-1.32 (m, 4H), 1.25 (m, 2H), 1.13 (m, 2H); MS: m/z=398.4 [M+H]$^+$.

The identity of Compound 66 was confirmed using $^1$H-NMR and MS.

Compound 66: $^1$H-NMR: $\delta_H$ (ppm, CDCl$_3$): 6.78 (m, 4H), 6.60 (m, 1H), 4.46 (m, 1H), 3.91 (m, 3H), 3.74 (m, 1H), 3.11 (m, 2H), 2.79 (m, 2H), 2.55 (m, 1H), 2.42 (m, 4H), 2.02-1.55 (m, 12H), 1.52-1.27 (m, 5H); MS: m/z=368.4 [M+H]$^+$.

Compound 60, (1R,6S)-bicyclo[4.3.1]decan-8-one, was prepared by hydrogenating Compound 58 using palladium on carbon under a hydrogen atmosphere, for example, similarly to the preparation of Compound 50 in Example 5. Alternately, Compound 60 can be prepared by protecting the oxo group of Compound 59 followed by debromination with n-butyl lithium, quenching with water, and deprotection of the oxo group.

The identity of Compound 60 was confirmed using MS.

Compound 60: MS: m/z=153.4 [M+H]$^+$.

Compound 58, (R)-bicyclo[4.3.1]dec-6-en-8-one, was prepared by methods known to the art, e.g., as described in House et al., *J. Org. Chem.* 4-((16):2819-2824 (1979) and House et al., *J. Org. Chem.* 45(10):1800-1806 (1980). These House et al. references also describe the preparation of Compound 59, (1S,6S)-1-bromobicyclo[4.3.1]decan-8-one.

The identity of Compound 58 was confirmed using MS.

Compound 58: MS: m/z=151.4 [M+H]$^+$.

5.7 Example 7

Synthesis of Substituted Benzimidazole-Type Piperidine Compounds where ---W— is a Single Bond and $Q_x$ is Present Using procedures similar to those described above in Example 1, the following Substituted Benzimidazole-Type Piperidine Compounds were prepared from Compound 66. The co-reactant compounds are commercially available from, e.g., Sigma-Aldrich, or can be prepared by methods known to the art.

H56b(i)

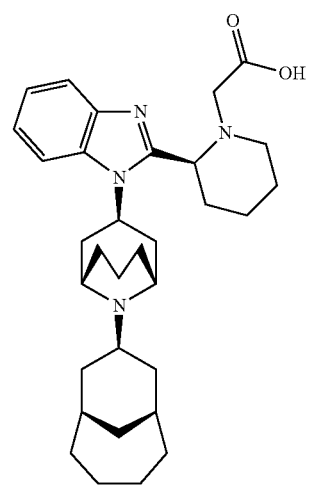

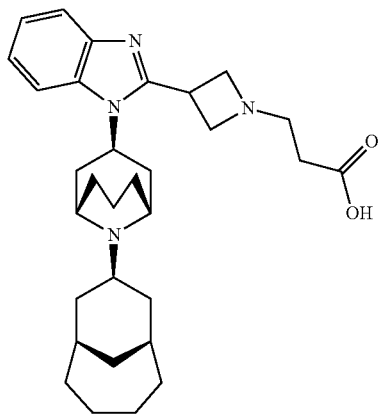
H6d

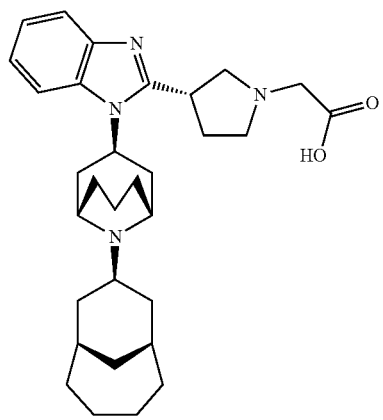
H30d(ii)

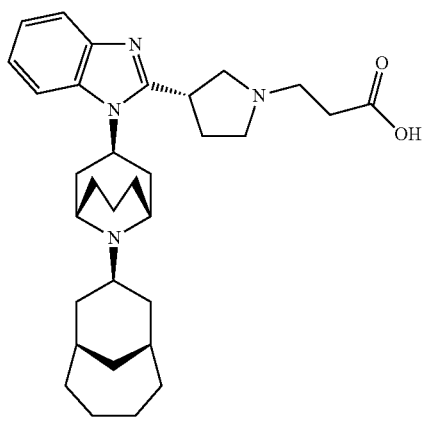
H32d(ii)

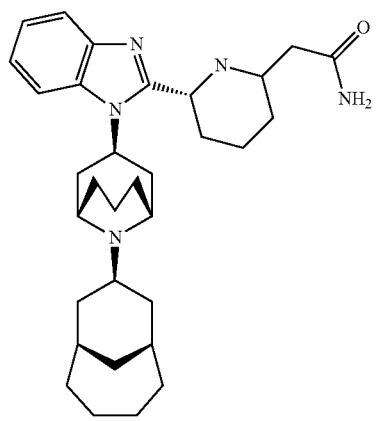
H62d(ii)

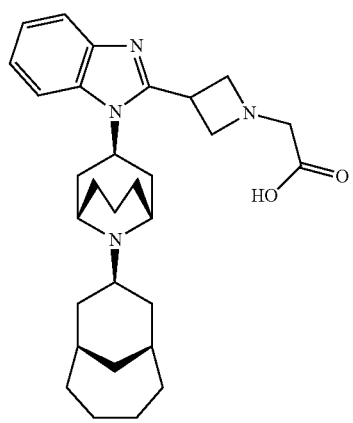
H4d

H56b(i): 2-((S)-2-(1-((1R,3R,5S)-9-((1R,6S,8s)-bicyclo[3.3.1]decan-8-yl)-9-azabicyclo[3.3.1]nonan-3-yl)-1H-benzo[d]imidazol-2-yl)piperidin-1-yl)acetic acid.

H56b(i): $^1$H-NMR: $\delta_H$ (ppm, CD$_3$OD): 7.71 (m, 2H), 7.31 (m, 2H), 6.58 (br, s, 1H), 4.25 (m, 2H), 4.10 (br, s, 1H), 3.91 (m, 1H), 3.42 (m, 1H), 2.99 (m, 2H), 2.66 (m, 3H), 2.47 (m, 5H), 2.23-1.91 (m, 11H), 1.85-1.76 (m, 8H), 1.63-1.42 (m, 6H); MS: m/z=519.3 [M+H]$^+$.

H6d: 3-(3-(1-((1R,3R,5S)-9-((1R,6S,8s)-bicyclo[4.3.1]decan-8-yl)-9-azabicyclo[3.3.1]nonan-3-yl)-1H-benzo[d]imidazol-2-yl)azetidin-1-yl)propanoic acid.

H6d: $^1$H-NMR: $\delta_H$ (ppm, CD$_3$OD): 7.81 (d, J=7.8 Hz, 1H), 7.50 (d, J=7.8 Hz, 1H), 7.36 (m, 2H), 5.69 (m, 1H), 4.55 (m, 2H), 4.37 (m, 2H), 4.01 (m, 1H), 3.58 (m, 2H), 2.64 (m, 6H), 2.47 (m, 3H), 2.34 (m, 2H), 2.15 (m, 2H), 2.04 (m, 3H), 1.79 (m, 8H), 1.56 (m, 4H); MS: m/z=505.2 [M+H]$^+$.

H32d(ii): 3-((S)-3-(1-((1R,3R,5S)-9-((1R,6'R,8s)-bicyclo[4.3.1]decan-8-yl)-9-azabicyclo[3.3.1]nonan-3-yl)-1H-benzo[d]imidazol-2-yl)pyrrolidin-1-yl)propanoic acid.

H32d(ii): $^1$H-NMR: $\delta_H$ (ppm, CD$_3$OD): 7.80 (d, J=7.8 Hz, 1H), 7.71 (d, J=7.8 Hz, 1H), 7.34 (m, 2H), 5.84 (m, 1H), 4.62 (m, 2H), 4.41 (m, 2H), 4.01 (m, 2H), 3.88 (m, 1H), 3.82 (m, 1H), 3.83 (m, 3H), 2.89-2.53 (m, 6H), 2.48-2.25 (m, 6H), 2.17 (m, 2H), 2.05 (br, s, 3H), 1.96-1.62 (m, 8H), 1.55 (m, 4H); MS: m/z=519.3 [M+H]$^+$.

H30d(ii): 2-((S)-3-(1-((1R,3R,5S)-9-((1R,6S,8s)-bicyclo[4.3.1]decan-8-yl)-9-azabicyclo[3.3.1]nonan-3-yl)-1H-benzo[d]imidazol-2-yl)pyrrolidin-1-yl)acetic acid.

H30d(ii): $^1$H-NMR: $\delta_H$ (ppm, CD$_3$OD): 7.70 (d, J=7.8 Hz, 1H), 7.62 (d, J=7.8 Hz, 1H), 7.24 (m, 2H), 5.33 (m, 1H), 4.26 (m, 4H), 4.13 (m, 1H), 4.06 (m, 1H), 3.86 (m, 2H), 3.51 (m, 2H), 2.58 (m, 5H), 2.37 (m, 3H), 2.20-1.70 (m, 15H), 1.48 (m, 5H); MS: m/z=505.2 [M+H]$^+$.

H62d(ii): 2-4S)-3-(1-((1R,3R,5S)-9-((1R,6S,8s)-bicyclo[4.3.1]decan-8-yl)-9-azabicyclo[3.3.1]nonan-3-yl)-1H-benzo[d]imidazol-2-yl)piperidin-1-yl)acetamide.

H62d(ii): $^1$H-NMR: $\delta_H$ (ppm, CD$_3$OD): 7.75 (d, J=8.0 Hz, 1H), 7.67 (d, J=8.0 Hz, 1H), 7.31 (m, 2H), 5.34 (m, 1H), 4.29 (m, 4H), 3.81 (m, 1H), 3.40 (m, 1H), 2.76 (m, 1H), 2.59 (m, 3H), 2.36 (m, 3H), 2.09-1.56 (m, 19H), 1.48 (m, 5H); MS: m/z=518.2 [M+H]$^+$.

H4d: 2-(3-(1-((1R,3R,5S)-9-((1R,6S,8s)-bicyclo[4.3.1]decan-8-yl)-9-azabicyclo[3.3.1]nonan-3-yl)-1H-benzo[d]imidazol-2-yl)azetidin-1-yl)acetic acid.

H4d: $^1$H-NMR: $\delta_H$ (ppm, CD$_3$OD): 7.68 (m, 2H), 7.26 (m, 2H), 5.17 (br, s, 1H), 4.61 (m, 4H), 4.26 (br, 4H), 3.87 (br, s, 1H), 2.60 (m, 4H), 2.37 (m, 3H), 2.06-1.61 (m, 14H), 1.47 (m, 5H); MS: m/z=491.2 [M+H]$^+$.

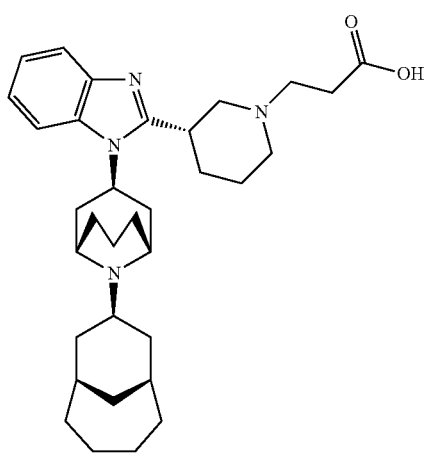

H58d(ii)

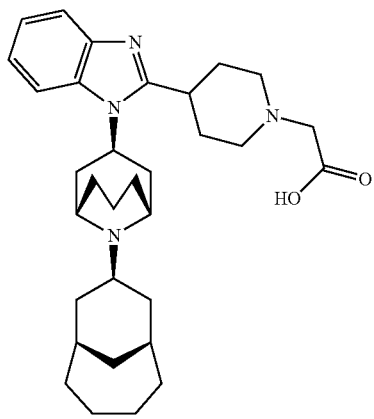

ZA07

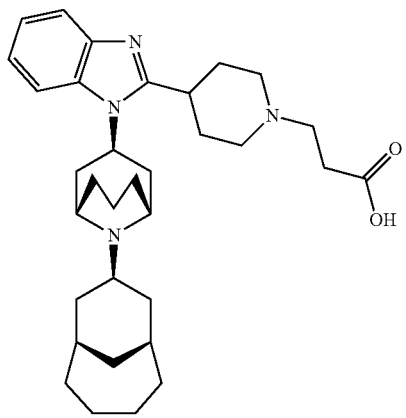

ZA08

H58d(ii): 3-((S)-3-(1-((1R,3R,5S)-9-((1R,6S,8s)-bicyclo[4.3.1]decan-8-yl)-9-azabicyclo[3.3.1]nonan-3-yl)-1H-benzo[d]imidazol-2-yl)piperidin-1-yl)propanoic acid.

H58d(ii): $^1$H-NMR: $\delta_H$ (ppm, CD$_3$OD): 7.72 (d, J=8.0 Hz, 1H), 7.65 (d, J=8.0 Hz, 1H), 7.28 (m, 2H), 5.32 (br, s, 1H), 4.27 (br, s, 2H), 3.87 (m, 3H), 3.39 (m, 4H), 2.88 (m, 2H), 2.69 (m, 1H), 2.56 (m, 3H), 2.36 (m, 3H), 2.06 (m, 3H), 1.95 (m, 4H), 1.82-1.66 (m, 11H), 1.46 (m, 5H); MS: m/z=533.4 [M+H]$^+$.

ZA07: 2-(4-(1-((1R,3R,5S)-9-((1R,6S,8s)-bicyclo[3.3.1]decan-8-yl)-9-azabicyclo[3.3.1]nonan-3-yl)-1H-benzo[d]imidazol-2-yl)piperidin-1-yl)acetic acid.

ZA07: $^1$H-NMR: $\delta_H$ (ppm, CD$_3$OD): 7.80 (d, J=8.0 Hz, 1H), 7.69 (d, J=8.0 Hz, 1H), 7.35 (m, 2H), 5.92 (m, 1H), 4.38 (m, 2H), 4.04 (m, 2H), 3.77 (m, 4H), 3.52 (m, 2H), 2.75 (m, 2H), 2.61 (m, 2.48 (m, 3H), 2.39 (m, 2H), 2.38-1.65 (m, 16H), 1.54 (m, 4H); MS: m/z=519.3 [M+H]$^+$.

ZA08: 3-(4-(1-((1R,3R,5S)-9-((1R,6S,8s)-bicyclo[4.3.1]decan-8-yl)-9-azabicyclo[3.3.1]nonan-3-yl)-1H-benzo[d]imidazol-2-yl)piperidin-1-yl)propanoic acid.

ZA08: $^1$H-NMR: $\delta_H$(ppm, CD$_3$OD): 7.80 (d, J=8.0 Hz, 1H), 7.68 (d, J=8.0 Hz, 1H), 7.34 (m, 2H), 5.92 (m, 1H), 4.38 (m, 2H), 4.08 (m, 2H), 3.71 (m, 2H), 3.48 (m, 4H), 2.71 (m, 6H), 2.48 (m, 3H), 2.34 (m, 2H), 2.26 (m, 5H), 2.03 (m, 3H), 1.83 (m, 8H), 1.56 (m, 4H); MS: m/z=533.4 [M+H]$^+$.

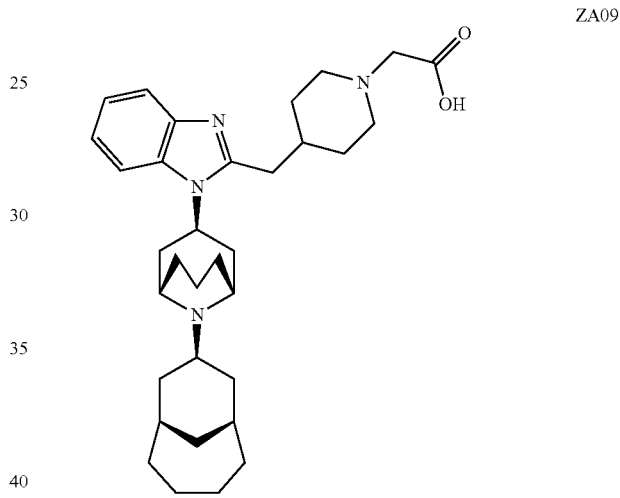

ZA09

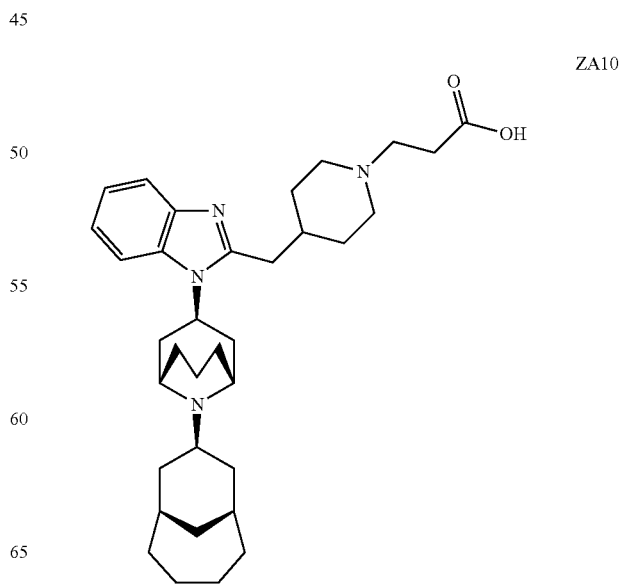

ZA10

319
-continued

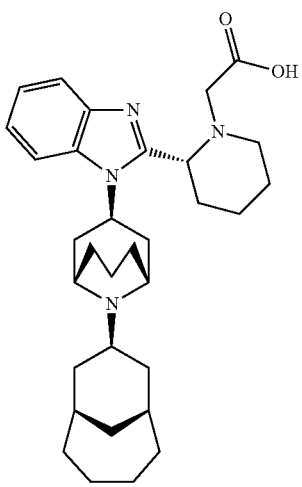

H56b(ii)

320
-continued

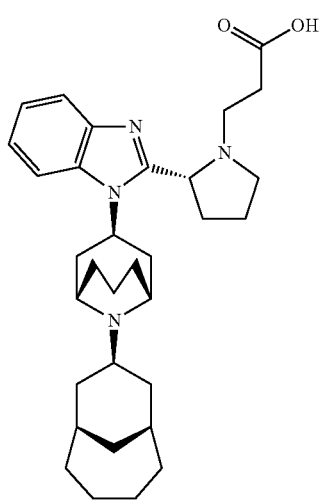

H32d(ii)

ZA09: 2-(4-((1-((1R,3R,5S)-9-((1R,6S,8s)-bicyclo[4.3.1]decan-8-yl)-9-azabicyclo[3.3.1]nonan-3-yl)-1H-benzo[d]imidazol-2-yl)methyl)piperidin-1-yl)acetic acid.

ZA09: $^1$H-NMR: $\delta_H$ (ppm, CD$_3$OD): 7.82 (d, J=8.0 Hz, 1H), 7.64 (d, J=8.0 Hz, 1H), 7.38 (m, 2H), 5.40 (m, 1H), 4.27 (m, 2H), 3.95 (m, 3H), 3.57 (m, 2H), 3.01 (m, 4H), 2.65 (m, 4H), 2.36 (m, 3H), 2.21 (m, 1H), 2.08 (m, 2H), 1.96 (m, 5H), 1.70 (m, 11H), 1.47 (m, 5H); MS: m/z=533.4 [M+H]$^+$.

ZA10: 3-(4-((1-((1R,3R,5S)-9-((1R,6S,8s)-bicyclo[4.3.1]decan-8-yl)-9-azabicyclo[3.3.1]nonan-3-yl)-1H-benzo[d]imidazol-2-yl)methyl)piperidin-1-yl)propanoic acid.

ZA10: $^1$H-NMR: $\delta_H$ (ppm, CD$_3$OD): 7.68 (d, J=7.8 Hz, 1H), 7.54 (d, J=7.8 Hz, 1H), 7.22 (m, 2H), 5.67 (m, 1H), 4.28 (m, 2H), 3.90 (m, 1H), 3.47 (m, 2H), 3.25 (m, 2H), 3.12-2.95 (m, 4H), 2.78 (m, 2H), 2.58 (m, 6H), 2.37 (m, 3H), 2.28-1.53 (m, 17H), 1.45 (m, 4H); MS: m/z 547.3 [M+H]$^+$.

H56b(ii): 2-((R)-2-(1-((1R,3R,5S)-9-((1R,6S,8s)-bicyclo[4.3.1]decan-8-yl)-9-azabicyclo[3.3.1]nonan-3-yl)-1H-benzo[d]imidazol-2-yl)piperidin-1-yl)acetic acid.

H56b(ii): $^1$H-NMR: $\delta_H$ (ppm, CD$_3$OD): 7.77 (d, J=8.0 Hz, 1H), 7.68 (d, J=8.0 Hz, 1H), 7.33 (m, 2H), 6.55 (br, s, 1H), 4.34 (br, s, 1H), 4.24 (m, 1H), 4.10 (br, s, 1H), 3.91 (m, 1H), 3.35 (m, 1H), 3.01 (m, 2H), 2.67 (m, 2H), 2.47 (m, 5H), 2.20-1.86 (m, 11H), 1.77 (m, 7H), 1.60 (m, 6H); MS: m/z=519.3 [M+H]$^+$.

H30b(ii)

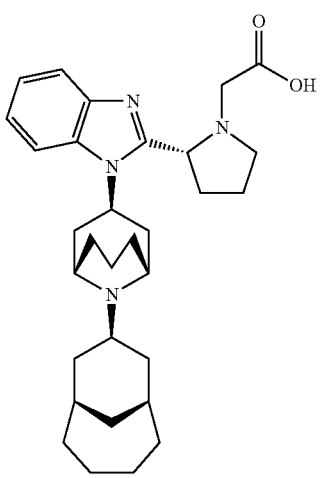

H30b(ii): 2-((R)-2-(1-((1R,3R,5S)-9-((1R,6S,8s)-bicyclo[4.3.1]decan-8-yl)-9-azabicyclo[3.3.1]nonan-3-yl)-1H-benzo[d]imidazol-2-yl)pyrrolidin-1-yl)acetic acid.

H30b(ii): $^1$H-NMR: $\delta_H$ (ppm, CD$_3$OD): 7.66 (d, J=8.0 Hz, 1H), 7.56 (d, J=8.0 Hz, 1H), 7.22 (m, 2H), 6.34 (br, s, 1H), 4.33 (m, 1H), 4.12 (m, 2H), 3.73 (m, 1H), 3.26 (m, 1H), 3.02 (m, 2H), 2.53 (m, 4H), 2.28 (m, 6H), 1.95 (m, 10H), 1.66 (m, 7H), 1.45 (m, 4H); MS: m/z=505.4 [M+H]$^+$.

H32b(ii): 3-((R)-2-(1-((1R,3R,5S)-9-((1R,6S,8s)-bicyclo[4.3.1]decan-8-yl)-9-azabicyclo[3.3.1]nonan-3-yl)-1H-benzo[d]imidazol-2-yl)pyrrolidin-1-yl)propanoic acid.

H32b(ii): $^1$H-NMR: $\delta_H$ (ppm, CD$_3$OD): 7.80-7.73 (m, 1H), 7.70-7.61 (m, 1H), 7.36-7.19 (m, 2H), 5.84-5.70 (m, 1H), 4.34-4.26 (m, 1H), 4.24-4.16 (m, 1H), 4.14-4.05 (m, 1H), 3.76-3.64 (m, 1H), 3.10-3.00 (m, 1H), 2.95-2.83 (m, 1H), 2.77-2.65 (m, 2H), 2.58-2.34 (m, 10H), 2.32-2.20 (m, 1H), 2.16-1.67 (m, 14H), 1.67-1.45 (m, 7H); MS: m/z=519.3 [M+H]$^+$.

5.8 Example 8

Synthesis of Substituted Benzimidazole-Type Piperidine Compounds where ⸗W— is a Single Bond and Q$_x$ is Present Using procedures similar to those described above in Example 1, the following Substituted Benzimidazole-Type Piperidine Compounds were prepared from Compound 56 and the appropriate co-reactants. The co-reactant compounds are commercially available from, e.g., Sigma-Aldrich, or can be prepared by methods known to the art.

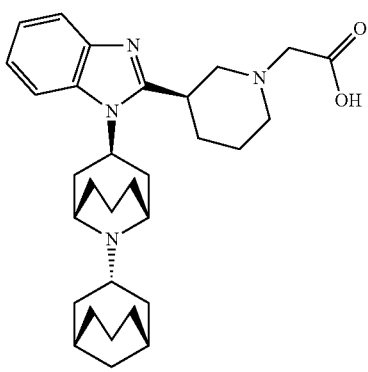 [SMILES: O=C(O)CN1CCC[C@@H](c2nc3ccccc3n2[C@H]2C[C@H]3CCC[C@@H](C2)N3[C@H]2C[C@@H]3CCC[C@@H](C3)C2)C1]

B56c(i)

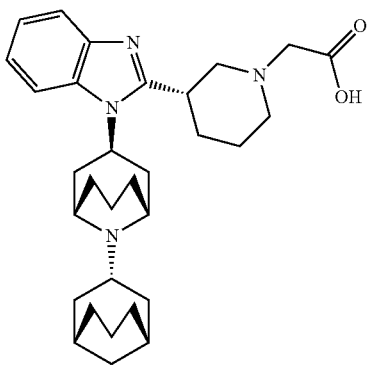 [SMILES: O=C(O)CN1CCC[C@H](c2nc3ccccc3n2[C@H]2C[C@H]3CCC[C@@H](C2)N3[C@H]2C[C@@H]3CCC[C@@H](C3)C2)C1]

B56c(ii)

B56c(i): 2-((R)-3-(1-((1R,1'R,3r,3'R,5S,5'S)-[3,9'-bi(9'-azabicyclo[3.3.1]nonan)]-3'-yl)-1H-benzo[d]imidazol-2-yl)piperidin-1-yl)acetic acid.

B56c(i): $^1$H-NMR: $\delta_H$ (ppm, CD$_3$OD): 7.98 (d, J=7.6 Hz, 1H), 7.81 (d, J=7.6 Hz, 1H), 7.56 (m, 2H), 6.08 (br, s, 1H), 4.42-4.30 (m, 5H), 3.90 (m, 1H), 3.71 (m, 2H), 2.78 (m, 4H), 2.43 (m, 3H), 2.28 (m, 9H), 2.05 (m, 2H), 1.85 (m, 8H), 1.77 (m, 2H); MS: m/z=505.6 [M+H]$^+$.

B56c(ii): 2-((S)-3-(1-((1R,1R,3r,3'R,5S,5'S)-[3,9'-bi(9'-azabicyclo[3.3.1]nonan)]-3'-yl)-1H-benzo[d]imidazol-2-yl)piperidin-1-yl)acetic acid.

B56c(ii): $^1$H-NMR: $\delta_H$ (ppm, CD$_3$OD): 7.79 (d, J=7.8 Hz, 1H), 7.70 (d, J=7.8 Hz, 1H), 7.34 (m, 2H), 5.71 (br, s, 1H), 4.23 (m, 2H), 3.99 (br, s, 1H), 3.65 (m, 3H), 3.45 (br, s, 1H), 3.01 (m, 2H), 2.65 (m, 4H), 2.39 (m, 1H), 2.19-1.98 (m, 13H), 1.72-1.53 (m, 10H); MS: m/z=505.6 [M+H]$^+$.

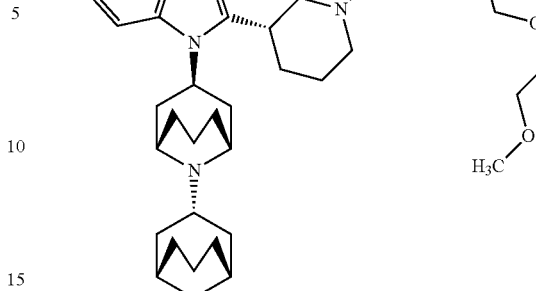

ZA11

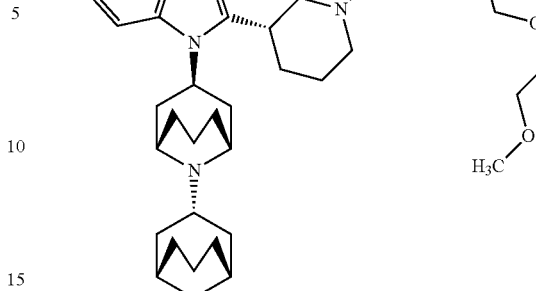

ZA12

ZA11: (1R,1'R,3r,3'R,5S,5'S)-3'-(2-((R)-1-(2-(2-(2-methoxyethoxy)ethoxy)ethyl)piperidin-3-yl)-1H-benzo[d]imidazol-1-yl)-9'-aza-3,9'-bi(bicyclo[3.3.1]nonane).

ZA11: $^1$H-NMR: $\delta_H$ (ppm, CD$_3$OD): 7.78 (d, J=7.7 Hz, 1H), 7.64 (d, J=7.7 Hz, 1H), 7.28 (m, 2H), 5.06 (m, 1H), 3.71-3.56 (m, 11H), 3.40 (m, 4H), 3.09 (m, 1H), 2.73 (br s, 2H), 2.48-2.18 (m, 7H), 2.13-1.92 (m, 7H), 1.90-1.57 (m, 14H), 1.21 (m, 2H); MS: m/z=593.3 [M+H]$^+$.

ZA12: (1R,1'R,3r,3'R,5S,5'S)-3'-(2-((S)-1-(2-(2-(2-methoxyethoxy)ethoxy)ethyl)piperidin-3-yl)-1H-benzo[d]imidazol-1-yl)-9'-aza-3,9'-bi(bicyclo[3.3.1]nonane).

ZA12: $^1$H-NMR: $\delta_H$ (ppm, CD$_3$OD): 7.79 (d, J=7.8 Hz, 1H), 7.67 (d, J=7.8 Hz, 1H), 7.30 (m, 2H), 5.25 (m, 1H), 3.96-3.76 (m, 5H), 3.65 (m, 4H), 3.54 (m, 2H), 3.42 (m, 2H), 3.32 (m, 3H), 3.03 (br s, 3H), 2.62-2.32 (m, 5H), 2.12 (m, 7H), 2.02-1.86 (m, 7H), 1.82-1.63 (m, 10H), 1.43 (m, 2H); MS: m/z=593.3 [M+H]$^+$.

5.9 Example 9

Synthesis of Substituted Benzimidazole-Type Piperidine Compounds where ---W— is a Single Bond and Q$_x$ is Present

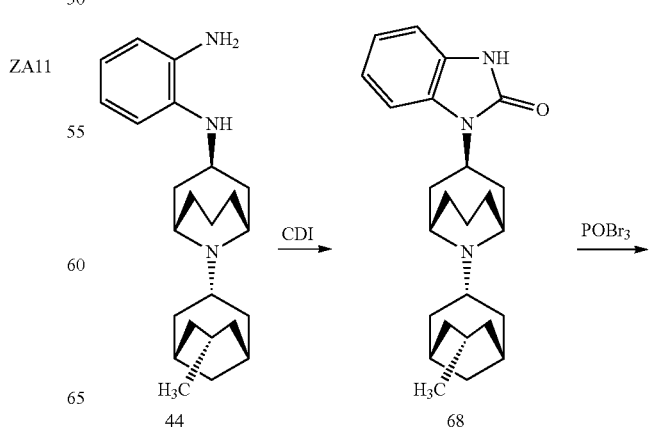

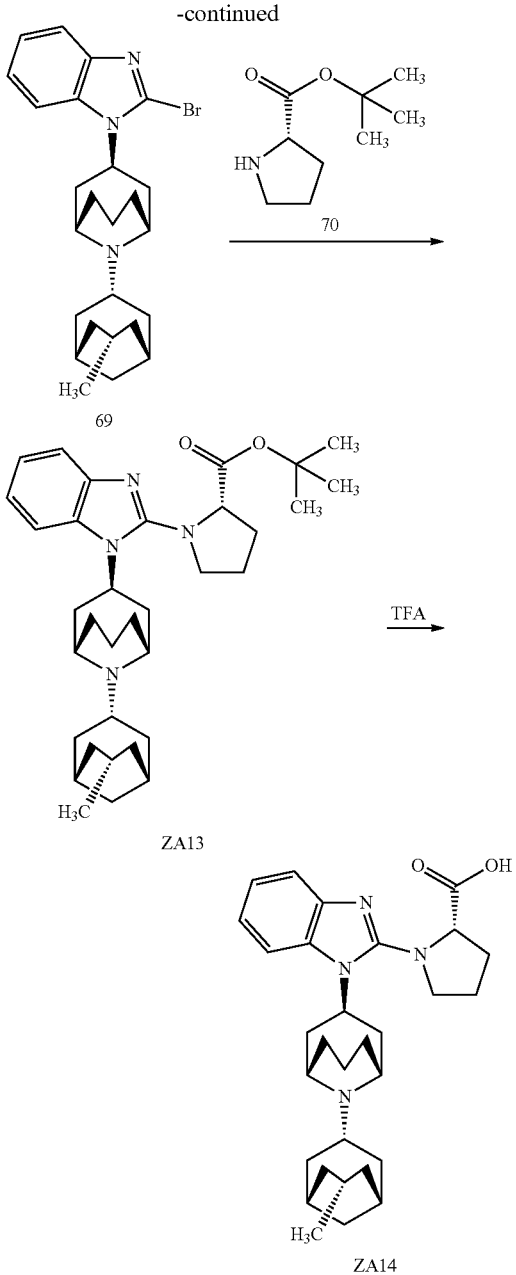

Under an argon atmosphere, in a dry flask containing a solution of Compound 44 (3.92 g, 10.68 mmol), prepared in Example 5, in THF (20 mL) at −10° C. was added portionwise a solution of CDI (2.42 g, 14.95 mmol, Sigma-Aldrich) in THF (37 mL). The resulting reaction mixture was stirred for 1 hr while it gradually warmed to 5° C. Thereafter, the mixture was cooled to 0° C. and water was added. The mixture was extracted with EtOAc, washed with brine, and concentrated to provide 3.7 g of a residue. The residue was chromatographed on a silica gel column eluted with a gradient of from 100:0 hexanes:EtOAc to 90:10 hexanes:EtOAc followed by elution with 10:90 MeOH:chloroform to provide 3.35 g of Compound 68, 1-((1R,1'R,3r,3'R,5S,5'S,7S)-7-methyl-[3,9'-bi(9'-azabicyclo[3.3.1]nonane)]-3'-yl)-1H-benzo[d]imidazol-2(3H)-one (yield 79.8%).

The identity of Compound 68 was confirmed using LC/MS.

Compound 68: LC/MS: m/z=394 [M+H]$^+$ (Calc.: 395).

In a 30 mL pressure tube containing a suspension of Compound 68 (0.50 g, 1.27 mmol) in DCE (3.8 mL) at a temperature of about 25° C. was added in one portion POBr$_3$ (1.82 g, 6.36 mmol, Sigma-Aldrich). The tube was sealed and the resulting reaction mixture kept for 22 hrs in an oil bath set at 100° C. The mixture was then poured onto an ice and water slurry, extracted with DCM, neutralized with 10% aqueous Na$_2$CO$_3$, washed with brine, and concentrated to provide 0.61 g of Compound 69, (1R,1'R,3r,3'R,5S,5'S,7S)-3'-(2-bromo-1H-benzo[d]imidazol-1-yl)-7-methyl-9'-aza-3,9'-bi(bicyclo[3.3.1]nonane), as a solid which was used directly in the next step.

The identity of Compound 69 was confirmed using LC/MS.

Compound 69: LC/MS: m/z=456 [M+H]$^+$ (Calc.: 455).

Into a 10 mL pressure tube containing Compound 69 (0.30 g, 0.66 mmol) was added (S)-tert-butyl pyrrolidine-2-carboxylate (Compound 70, 1.5 mL, 5.84 mmol, Sigma-Aldrich). The tube was sealed and the resulting reaction mixture was kept for 9 hrs in an oil bath set at 125° C. Thereafter, the resulting brownish residue was dissolved in DCM and chromatographed on a silica gel column eluted with a gradient of from 0:100 EtOAc:hexanes to 20:80 EtOAc:hexanes to provide 81 mg of Substituted Benzimidazole-Type Piperidine Compound ZA13, (S)-tert-butyl 1-(1-((1R,1'R,3r,3'R,5S,5'S,7R)-7-methyl-[3,9'-bi(9'-azabicyclo[3.3.1]nonan)]-3'-yl)-1H-benzo[d]imidazol-2-yl)pyrrolidine-2-carboxylate, as an amber semi-solid (yield 22.5%).

The identity of Substituted Benzimidazole-Type Piperidine Compound ZA13 was confirmed using LC/MS.

Substituted Benzimidazole-Type Piperidine Compound ZA13: LC/MS: m/z=547 [M+H]$^+$ (Calc.: 546).

To a solution of Compound ZA13 (80 mg, 0.146 mmol) in DCM (0.8 mL) at a temperature of about 25° C. was added TFA (0.17 mL, 2.19 mmol). The resulting reaction mixture was kept at a temperature of about 25° C. for 16 hrs then evaporated to dryness. The residue was triturated with Et$_2$O to provide a solid which was chromatographed by preparative HPLC to provide 35 mg of the TFA salt of Substituted Benzimidazole-Type Piperidine Compound ZA14. This salt was neutralized with 10% aqueous Na$_2$CO$_3$ and extracted with DCM to provide 20 mg of Substituted Benzimidazole-Type Piperidine Compound ZA14, (S)-1-(1-((1R,1'R,3r,3'R,5S,5'S,7R)-7-methyl-[3,9'-bi(9'-azabicyclo[3.3.1]nonan)]-3'-yl)-1H-benzo[d]imidazol-2-yl)pyrrolidine-2-carboxylic acid (yield 27.9%).

The identity of Substituted Benzimidazole-Type Piperidine Compound ZA14 was confirmed using $^1$H-NMR and LC/MS.

Substituted Benzimidazole-Type Piperidine Compound ZA14: $^1$H-NMR: δ$_H$ (ppm, 300 MHz, CD$_3$OD): 7.70-7.64 (m, 1H), 7.54-7.49 (m, 1H), 7.47-7.41 (m, 2H), 5.45-5.32 (m, 1H), 4.96 (t, J=7.0 Hz, 1H), 4.32 (d, J=7.8 Hz, 1H), 4.27-4.20 (m, 1H), 4.04-3.97 (q, J=6.4 Hz, 1H), 3.93-3.83 (m, 1H), 3.71-3.64 (t, J=10.3 Hz, 1H), 2.87-2.77 (m, 1H), 2.74-2.56 (m, 4H), 2.45-2.29 (m, 3H), 2.28-2.20 (m, 2H), 2.19-2.06 (m, 6H), 2.02-1.88 (m, 2H), 1.88-1.66 (m, 6H), 1.14-1.08 (d, J=12.5 Hz, 1H), 0.92 (d, J=6.4 Hz, 3H), 0.75-0.64 (t, J=12.3 Hz, 2H); LC/MS: m/z=491 [M+H]$^+$ (Calc.: 490).

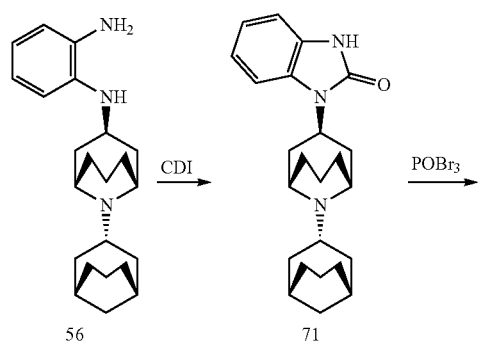

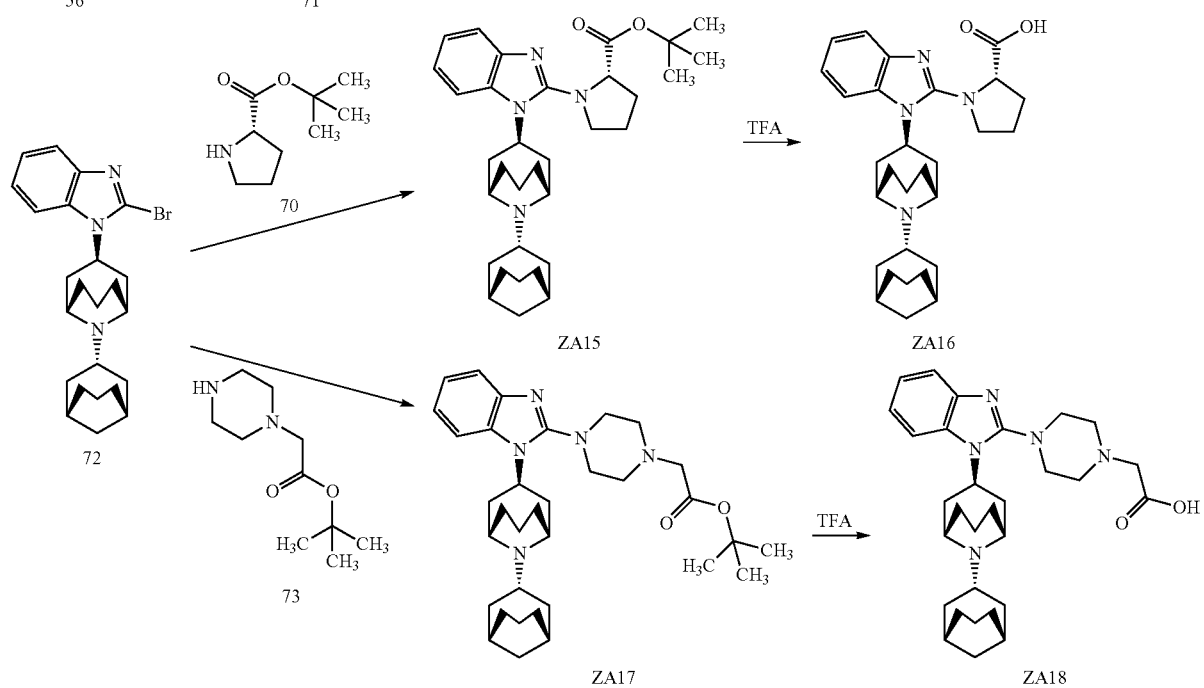

Compound 72, (1R,1'R,3r,3'R,5S,5'S)-3'-(2-bromo-1H-benzo[d]imidazol-1-yl)-9'-aza-3,9'-bi(bicyclo[3.3.1]nonane), was prepared in a similar manner to the previously-described preparation of Compound 69 except that Compound 56 was used in place of Compound 44.

The identity of Compound 71, 1-((1R,1'R,3r,3'R,5S,5'S)-[3,9'-bi(9'-azabicyclo[3.3.1]nonan)]-3'-yl)-1H-benzo[d]imidazol-2(3H)-one, was confirmed using LC/MS.

Compound 71: LC/MS: m/z=380 [M+H]$^+$ (Calc.: 379).

The identity of Compound 72 was confirmed using LC/MS.

Compound 72: LC/MS: m/z=442 [M+H]$^+$ (Calc.: 441).

Thereafter, Substituted Benzimidazole-Type Piperidine Compound ZA15, (S)-tert-butyl 1-(1-((1R,1'R,3r,3'R,5S,5'S)-[3,9'-bi(9'-azabicyclo[3.3.1]nonan)]-3'-yl)-1H-benzo[d]imidazol-2-yl)pyrrolidine-2-carboxylate (yield 11.1%), was prepared from Compounds 72 and 70 in a similar manner to the previously-described preparation of Compound ZA13.

The identity of Substituted Benzimidazole-Type Piperidine Compound ZA15 was confirmed using LC/MS.

Substituted Benzimidazole-Type Piperidine Compound ZA15: LC/MS: m/z=533 [M+H]$^+$ (Calc.: 532).

Substituted Benzimidazole-Type Piperidine Compound ZA16, (S)-1-(1-((1R,1'R,3r,3'R,5S,5'S)-[3,9'-bi(9'-azabicyclo[3.3.1]nonan)]-3'-yl)-1H-benzo[d]imidazol-2-yl)pyrrolidine-2-carboxylic acid (yield 48.3%), was prepared in a similar manner to the previously-described preparation of Compound ZA14.

The identity of Substituted Benzimidazole-Type Piperidine Compound ZA16 was confirmed using $^1$H-NMR and LC/MS.

Substituted Benzimidazole-Type Piperidine Compound ZA16: $^1$H-NMR: $\delta_H$ (ppm, 300 MHz, CD$_3$OD): 7.62-7.68 (m, 1H), 7.55-7.48 (m, 1H), 7.46-7.39 (m, 2H), 5.43-5.30 (m, 1H), 4.93 (t, J=7.5 Hz, 1H), 4.36-4.27 (m, 2H), 4.27-4.20 (m, 1H), 4.03-3.95 (q, J=9.0 Hz, 1H), 3.70-3.62 (m, 1H), 2.86-2.75 (m, 1H), 2.73-2.56 (m, 4H), 2.40-2.29 (m, 2H), 2.28-2.02 (m, 9H), 2.02-1.92 (m, 2H), 1.88-1.70 (m, 7H), 1.68-1.58 (m, 2H), 1.54-1.41 (m, 1H); LC/MS: m/z=477 [M+H]$^+$ (Calc.: 476).

Compound 72 (0.73 g, 1.65 mmol) and tert-butyl 2-(piperazin-1-yl)acetate (Compound 7, 1.18 g, 5.90 mmol, Sigma-Aldrich) were combined in a pressure tube and the resulting reaction mixture was kept for 9 hrs on an oil bath set at 125° C. The mixture was then cooled to a temperature of about 25° C. and the resulting residue was chromatographed on a silica gel column eluted with a gradient of from 10:90 EtOAc:hexanes to 30:70 EtOAc:hexanes to provide 0.20 g of Substituted Benzimidazole-Type Piperidine Compound ZA17, tert-butyl 2-(4-(1-((1R,1'R,3r,3'R,5S,5'S)-[3, 9'-bi(9'-azabicyclo[3.3.1]nonan)]-3'-yl)-1H-benzo[d]imidazol-2-yl)piperazin-1-yl)acetate.

The identity of Substituted Benzimidazole-Type Piperidine Compound ZA17 was confirmed using LC/MS.

Substituted Benzimidazole-Type Piperidine Compound ZA17: LC/MS: m/z=562 [M+H]+ (Calc.: 561).

To a solution of Substituted Benzimidazole-Type Piperidine Compound ZA17 (0.198 g, 0.35 mmol) in DCM (1.9 mL) at a temperature of about 25° C. was added TFA (0.41 mL, 5.28 mmol). The resulting reaction mixture was kept at a temperature of about 25° C. for 16 hrs then evaporated to dryness. The residue was chromatographed by preparative HPLC, neutralized with 10% aqueous $Na_2CO_3$, and extracted with DCM to provide 55 mg of Substituted Benzimidazole-Type Piperidine Compound ZA18, 2-(4-(1R,1'R,3r,3'R,5S,5'S)-[3,9'-bi(9'-azabicyclo[3.3.1]nonan)]-3'-yl)-1H-benzo[d]imidazol-2-yl)piperazin-1-yl)acetic acid (yield 31%).

The identity of Substituted Benzimidazole-Type Piperidine Compound ZA18 was confirmed using $^1$H-NMR and LC/MS.

Substituted Benzimidazole-Type Piperidine Compound ZA18: $^1$H-NMR: $\delta_H$ (ppm, 300 MHz, $CD_3OD$): 7.65-7.60 (m, 2H), 7.37-7.29 (m, 2H), 5.48-5.36 (m, 1H), 4.37-4.29 (m, 1H), 4.28-4.21 (m, 2H), 3.92 (s, 2H), 3.57-3.47 (m, 8H), 2.70-2.62 (m, 4H), 2.50-2.35 (m, 1H), 2.27-1.96 (m, 9H), 1.85-1.71 (m, 7H), 1.69-1.56 (q, J=9.9 Hz, 2H), 1.54-1.42 (m, 1H); LC/MS: m/z=506 [M+H]+ (Calc.: 505).

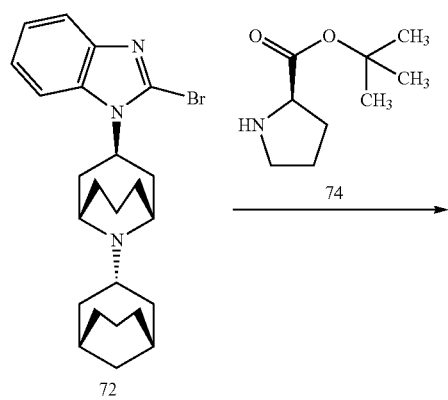

72

74
→

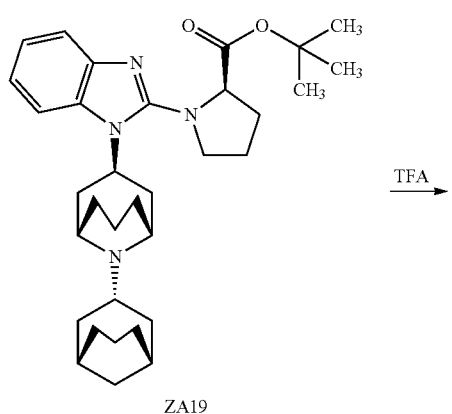

ZA19

TFA
→

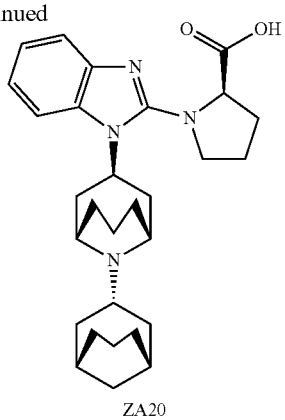

ZA20

Substituted Benzimidazole-Type Piperidine Compound ZA19, (R)-tert-butyl 1-(1-((1R,1'R,3r,3'R,5S,5'S)-[3,9'-bi(9'-azabicyclo[3.3.1]nonan)]-3'-yl)-1H-benzo[d]imidazol-2-yl)pyrrolidine-2-carboxylate (yield 18.8%), was prepared in a similar manner to the previously-described preparation of Substituted Benzimidazole-Type Piperidine Compound ZA13 except that a molar excess of (R)-tert-butyl pyrrolidine-2-carboxylate (Compound 74, Sigma-Aldrich) was used in place of Compound 70.

The identity of Substituted Benzimidazole-Type Piperidine Compound ZA19 was confirmed using LC/MS.

Substituted Benzimidazole-Type Piperidine Compound ZA19: LC/MS: m/z=562 [M+H]+ (Calc.: 561).

Thereafter, Substituted Benzimidazole-Type Piperidine Compound ZA20, (R)-1-(1-((1R,1'R,3r,3'R,5S,5'S)-[3,9'-bi(9'-azabicyclo[3.3.1]nonan)]-3'-yl)-1H-benzo[d]imidazol-2-yl)pyrrolidine-2-carboxylic acid, was prepared in a similar manner to the previously-described preparation of Substituted Benzimidazole-Type Piperidine Compound ZA14 (yield 16%).

The identity of Substituted Benzimidazole-Type Piperidine Compound ZA20 was confirmed using $^1$H-NMR and LC/MS.

Substituted Benzimidazole-Type Piperidine Compound ZA20: $^1$H-NMR: $\delta_H$ (ppm, 300 MHz, $CD_3OD$): 7.72-7.66 (m, 1H), 7.55-7.49 (m, 1H), 7.48-7.41 (m, 2H), 5.43-5.31 (m, 1H), 4.96 (t, J=7.5 Hz, 1H), 4.36-4.27 (m, 2H), 4.27-4.20 (m, 1H), 4.06-3.97 (q, J=9.0 Hz, 1H), 3.73-3.66 (t, J=9.0 Hz, 1H), 2.88-2.77 (m, 1H), 2.75-2.55 (m, 4H), 2.42-2.28 (m, 2H), 2.28-2.03 (m, 9H), 2.02-1.92 (m, 2H), 1.88-1.70 (m, 7H), 1.68-1.58 (m, 2H), 1.55-1.41 (m, 1H); LC/MS: m/z=506 [M+H]+ (Calc.: 505).

5.10 Example 10

Synthesis of Substituted Benzimidazole-Type Piperidine Compounds where ---W— is a Single Bond and $Q_x$ is Present Using procedures similar to those described above in Example 1, the following Substituted Benzimidazole-Type Piperidine Compounds were prepared from the appropriate diamine, e.g., 1'-benzene-1,2-diamine, 3'-pyridine-2,3-diamine, 4'-pyridine-3,4-diamine, or 3'-pyridine-3,4-diamine, and the appropriate co-reactants. Said diamines are commercially available or can be prepared by methods known to the art, e.g., as described in U.S. Pat. App. Pub. Nos. US 2010/0216726 A1 (see, e.g., Examples 3, 14, 30, 32, 35, 38, 40, and 42-44), US 2011/0178090 A1 (see, e.g., Examples 1, 2, 4, 5, and 9), and/or International PCT Publication No. WO 2012/085648 A1 (see, e.g., Examples 12 and 13), which are hereby incorporated by reference in their entireties. The co-reactant compounds are commercially available from, e.g., Sigma-Aldrich, or can be prepared by methods known to the art.

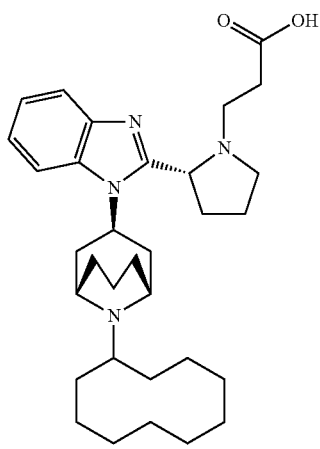

E32c(ii)

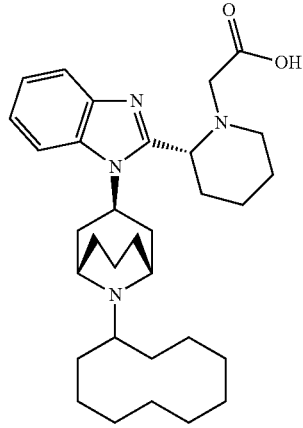 [SMILES: O=C(O)CN1CCCC[C@@H]1c1nc2ccccc2n1[C@H]1C[C@H]2CCC[C@@H](C1)N2C1CCCCCCCCC1]

E56c(ii)

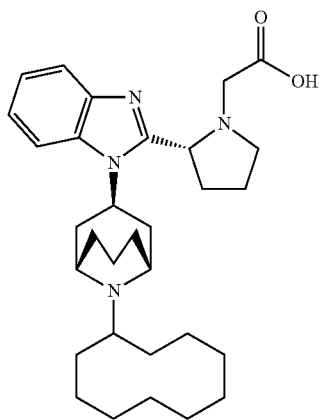

E30c(ii)

E32c(ii): 3-((R)-2-(1-((1R,3r,5S)-9-cyclodecyl-9-azabicyclo[3.3.1]nonan-3-yl)-1H-benzo[d]imidazol-2-yl)pyrrolidin-1-yl)propanoic acid.

E32c(ii): $^1$H-NMR: $\delta_H$ (ppm, CD$_3$OD): 7.82-7.74 (m, 1H), 7.69-7.61 (m, 1H), 7.36-7.22 (m, 2H), 5.75-5.59 (m, 1H), 4.24-4.11 (m, 1H), 4.06-3.86 (m, 2H), 3.53-3.40 (m, 1H), 3.21-3.11 (m, 1H), 3.11-2.96 (m, 1H), 2.73-2.18 (m, 10H), 2.15-1.70 (m, 11H), 1.69-1.42 (m, 13H), 1.37-1.23 (m, 1H), 0.94-0.83 (m, 1H); MS: m/z=521.4 [M+H]$^+$.

E30c(ii): 2-((R)-2-(1-((1R,3r,5S)-9-cyclodecyl-9-azabicyclo[3.3.1]nonan-3-yl)-1H-benzo[d]imidazol-2-yl)pyrrolidin-1-yl)acetic acid.

E30c(ii): $^1$H-NMR: $\delta_H$ (ppm, CD$_3$OD): 7.81-7.69 (m, 1H), 7.65-7.53 (m, 1H), 7.36-7.17 (m, 2H), 6.18-5.71 (m, 1H), 4.40-4.20 (m, 1H), 4.09-3.86 (m, 2H), 3.72-3.51 (m, 1H), 3.45-3.33 (m, 1H), 3.11-2.97 (m, 1H), 2.66-2.27 (m, 6H), 2.27-1.74 (m, 12H), 1.73-1.45 (m, 16H); MS: m/z=507.3 [M+H]$^+$.

E56c(ii): 2-((R)-2-(1-((1R,3r,5S)-9-cyclodecyl-9-azabicyclo[3.3.1]nonan-3-yl)-1H-benzo[d]imidazol-2-yl)piperidin-1-yl)acetic acid.

E56c(ii): $^1$H-NMR: $\delta_H$ (ppm, CD$_3$OD): 7.80-7.71 (m, 1H), 7.69-7.59 (m, 1H), 7.38-7.20 (m, 2H), 6.51-6.30 (m, 1H), 4.26-3.95 (m, 3H), 3.92-3.74 (m, 1H), 3.27-3.02 (m, 2H), 2.98-2.82 (m, 1H), 2.73-2.52 (m, 3H), 2.52-2.28 (m, 3H), 2.26-1.80 (m, 12H), 1.80-1.46 (m, 17H); MS: m/z=521.4 [M+H]$^+$.

5.11 Example 11

Synthesis of Substituted Benzimidazole-Type Piperidine Compounds where ---W— is —CH₂— and Q_x is Present

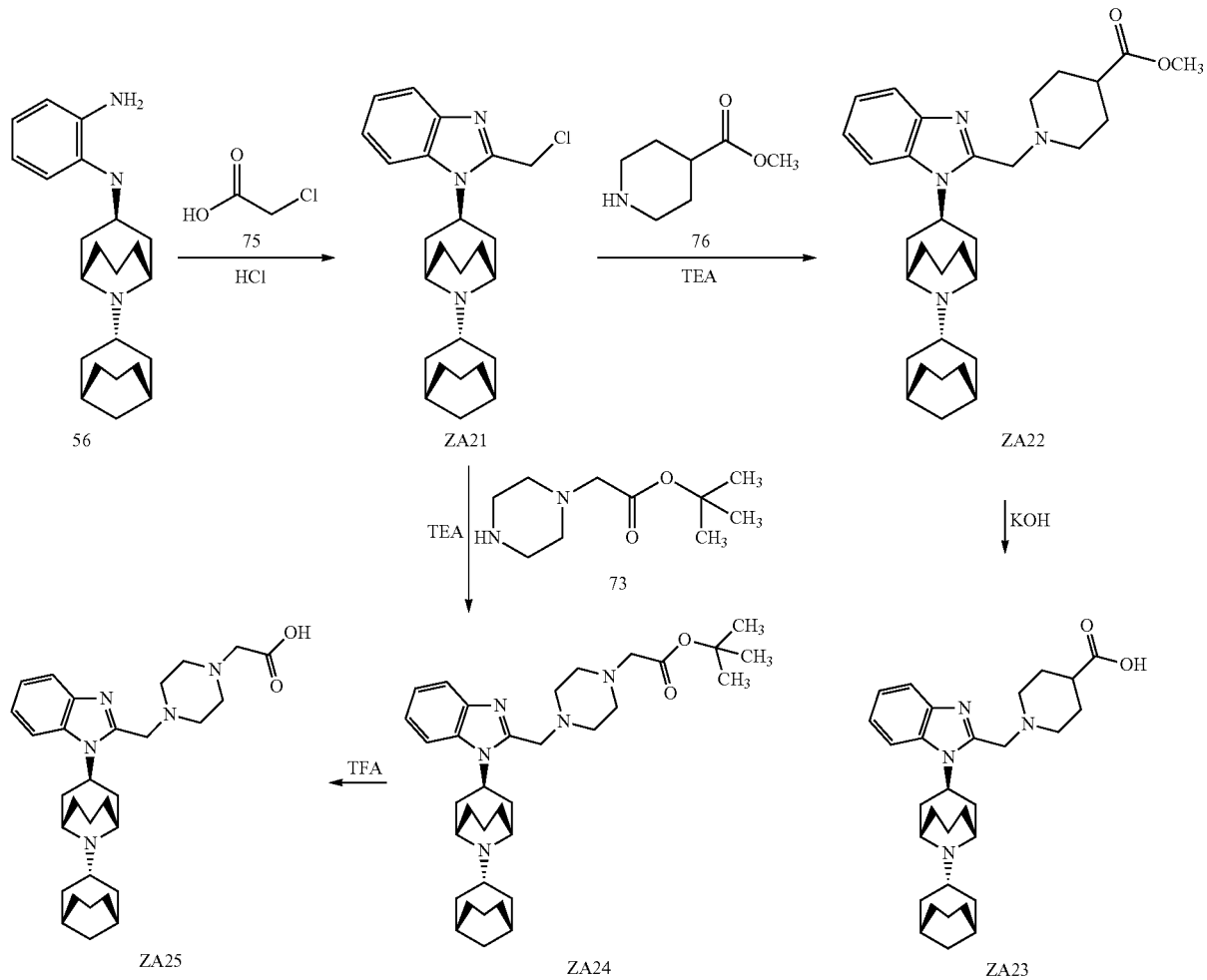

To a round-bottomed flask was added Compound 56 (353 mg, 1.0 mmol), prepared in Example 6, 2-chloroacetic acid (Compound 75, 113 mg, 1.2 mmol, Sigma-Aldrich), and 6 mol/L HCl (5 mL). The resulting reaction mixture was heated to 90° C. and stirred at that temperature for 16 hrs. Thereafter, the mixture was cooled to a temperature of about 25° C., neutralized with 2 mol/L NaOH to a pH of about pH7. The precipitate that formed was filtered, washed with water, and dried to provide 206 mg of Substituted Benzimidazole-Type Piperidine Compound ZA21, (1R,1'R,3r,3'R, 5S,5'S)-3'-(2-(chloromethyl)-1H-benzo[d]imidazol-1-yl)-9'-aza-3,9'-bi(bicyclo[3.3.1]nonane), as a brown solid (yield 50%) which was used directly in the next step.

To a solution of Substituted Benzimidazole-Type Piperidine Compound ZA21 (412 mg, 1.0 mmol) in DMF (4 mL) was added methyl piperidine-4-carboxylate (Compound 76, 143 mg, 1.0 mmol, Sigma-Aldrich) and TEA (0.5 mL). The resulting reaction mixture was heated to 40° C. and stirred at that temperature for 12 hrs. Thereafter, the mixture was cooled to a temperature of about 25° C., diluted with EtOAc (200 mL), washed with brine, dried (over Na₂SO₄), and evaporated to dryness. The residue was chromatographed on a COMBIFLASH apparatus eluted with a gradient of from 0:100 MeOH:DCM to 5:95 MeOH:DCM to provide 100 mg of Substituted Benzimidazole-Type Piperidine Compound ZA22, methyl 1-((1-((1R,1'R,3r,3'R,5S,5'S)-[3,9'-bi(9'-azabicyclo[3.3.1]nonan)]-3'-yl)-1H-benzo[d]imidazol-2-yl)methyl)piperidine-4-carboxylate, as a brown solid (yield 20%) which was used directly in the next step.

To a round-bottomed flask was added Substituted Benzimidazole-Type Piperidine Compound ZA22 (100 mg, 0.19 mmol) and 2 mol/L aqueous KOH (2 mL). The resulting mixture was heated to 40° C. and stirred at that temperature for 3 days. Thereafter, the mixture was cooled to a temperature of about 25° C. then 1 mol/L HCl was added to achieve a pH of about pH5. After twice extracting with 20:1 DCM: MeOH (50 mL for each extraction), the organic portions were combined, dried, and evaporated to dryness to provide 70 mg of Substituted Benzimidazole-Type Piperidine Compound ZA23, 1-((1-((1R,1R,3r,3'R,5S,5'S)-[3,9'-bi(9'-azabicyclo[3.3.1]nonan)]-3'-yl)-1H-benzo[d]imidazol-2-yl)methyl)piperidine-4-carboxylic acid, as a pale-yellow solid (yield 72%).

The identity of Substituted Benzimidazole-Type Piperidine Compound ZA23 was confirmed using $^1$H-NMR and LC/MS.

Substituted Benzimidazole-Type Piperidine Compound ZA23: $^1$H-NMR: $\delta_H$ (ppm, 400 MHz, MeOH-d$_4$): 7.87 (1H, d, J=8.5 Hz), 7.76 (1H, d, J=8.1 Hz), 7.44 (1H, t, J=7.5 Hz), 7.36 (1H, t, J=7.7 Hz), 5.89 (1H, m), 4.76 (2H, m), 4.40 (1H, m), 4.30 (2H, m), 3.60 (2H, m), 3.20 (1H, m), 2.69 (5H, m), 2.39 (3H, m), 2.21 (8H, m), 2.01 (4H, m), 1.87-1.58 (10H, m); LC/MS: m/z=505.4 [M+H]$^+$ (Calc.: 504.7).

To a solution of Substituted Benzimidazole-Type Piperidine Compound ZA21 (412 mg, 10 mmol) in DMF (4 mL) was added Compound 73 (198 mg, 1.5 mmol) and TEA (0.5 mL). The resulting reaction mixture kept at a temperature of about 25° C. for 12 hrs and then diluted with EtOAc (200 mL), washed with brine, dried (over Na$_2$SO$_4$), and evaporated to dryness. The residue was chromatographed on a COMBIFLASH apparatus eluted with a gradient of from 0:100 DCM:MeOH to 5:95 DCM:MeOH to provide 113 mg of Substituted Benzimidazole-Type Piperidine Compound ZA24, tert-butyl 2-(4-((1-((1R,1'R,3r,3'R,5S,5'S)-[3,9'-bi(9'-azabicyclo[3.3.1]nonan)]-3'-yl)-1H-benzo[d]imidazol-2-yl)methyl)piperazin-1-yl)acetate, as a solid (yield 20%) which was used directly in the next step.

To a solution of Substituted Benzimidazole-Type Piperidine Compound ZA24 (100 mg, 0.17 mmol) in DCM (4 mL) was added TFA (2 mL). The resulting reaction mixture was stirred at a temperature of about 25° C. for 10 hrs then 1 mol/L NaOH was added to achieve a pH of about pH4. After twice extracting with 20:1 DCM:MeOH (50 mL for each extraction), the organic portions were combined, dried, and evaporated to dryness. The residue was chromatographed on a COMBIFLASH apparatus eluted with a gradient of from 0:100 MeOH:DCM to 5:95 MeOH:DCM to provide 30 mg of Substituted Benzimidazole-Type Piperidine Compound ZA25, 2-(4-((1-((1R,1'R,3r,3'R,5S,5'S)-[3,9'-bi(9'-azabicyclo[3.3.1]nonan)]-3'-yl)-1H-benzo[d]imidazol-2-yl)methyl)piperazin-1-yl)acetic acid, as a white foam (yield 33%).

The identity of Substituted Benzimidazole-Type Piperidine Compound ZA25 was confirmed using $^1$H-NMR and LC/MS.

Substituted Benzimidazole-Type Piperidine Compound ZA25: $^1$H-NMR: $\delta_H$ (ppm, 400 MHz, MeOH-d$_4$): 7.79 (1H, d, J=8.3 Hz), 7.65 (1H, d, J=8.1 Hz), 7.35 (2H, m), 5.34 (1H, m), 4.35-4.15 (3H, m), 3.94 (4H, m), 3.33 (4H, m), 2.78 (2H, m), 2.62 (6H, m), 2.32 (1H, m), 2.11 (6H, m), 1.99-1.79 (3H, m), 1.75-1.47 (10H, m); LC/MS: m/z=520.3 [M+H]$^+$ (Calc.: 519.7).

5.12 Example 12

Synthesis of Substituted Benzimidazole-Type Piperidine Compounds where --- W— is =N— and Q$_x$ is Absent

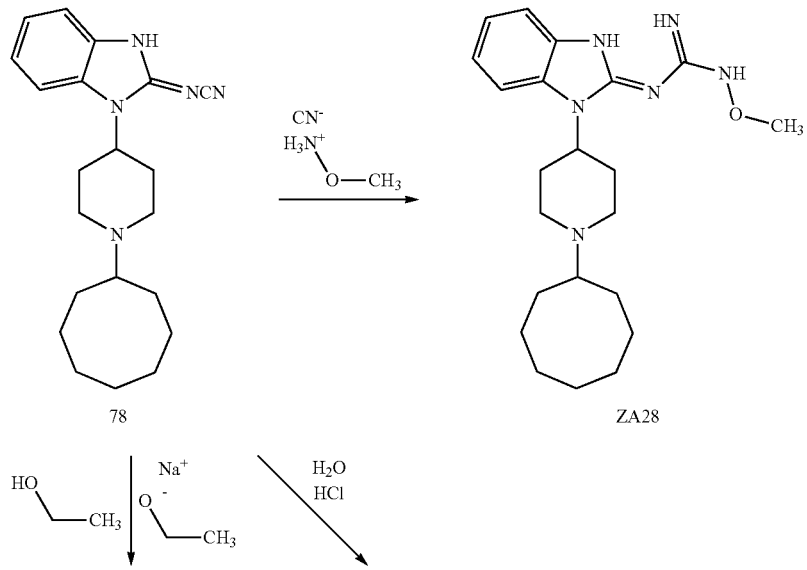

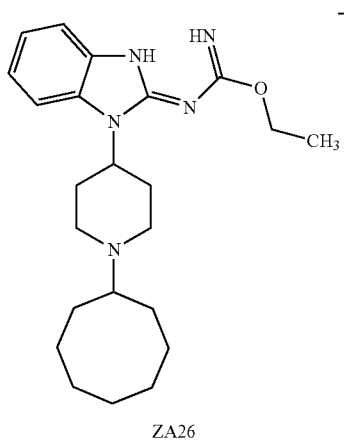 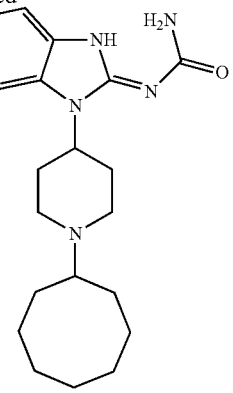

ZA26          ZA27

Compound 78, N-(1-(1-cyclooctylpiperidin-4-yl)-1H-benzo[d]imidazol-2(3H)-ylidene)cyanamide, was prepared from readily available materials according to known methods, such as those disclosed in EP 0029707 B1, e.g., Reference Examples 19 and 20, and U.S. Pat. No. 6,867,222 B2, e.g., Examples 13 and 14, which are hereby incorporated by reference in their entireties.

To a mixture of Compound 78 (200 mg, 26 mmol) and EtOH (10 mL) at a temperature of about 25° C. was added 20% sodium ethoxide in EtOH (0.2 mL). After stirring at a temperature of about 25° C. for 30 min, the reaction mixture was warmed to a temperature of 70° C. and stirred for 3 hrs. After cooling to a temperature of about 25° C., the reaction mixture was diluted with EtOAc (40 mL) and water (4 mL). The organic portion was separated, concentrated under reduced pressure, and chromatographed with a silica gel column eluted with 1:10 MeOH:DCM to provide 100 mg of Substituted Benzimidazole-Type Piperidine Compound ZA26 as a white solid (yield 45%).

The identity of Substituted Benzimidazole-Type Piperidine Compound ZA26, ethyl 1-(1-cyclooctylpiperidin-4-yl)-1H-benzo[d]imidazol-2(3H)-ylidenecarbamimidate, was confirmed using $^1$H NMR and LC/MS.

Substituted Benzimidazole-Type Piperidine Compound ZA26: $^1$H NMR: $\delta_H$ (400 MHz, CDCl$_3$): 9.4 (br, 1H), 7.48-7.53 (m, 2H), 7.04-7.12 (m, 2H), 5.3 (br, 1H), 4.62-4.71 (m, 1H), 4.37 (q, 2H, 7.2 Hz), 2.94-2.98 (m, 2H), 2.66-2.71 (m, 1H), 2.48-2.55 (m, 2H), 2.34-2.42 (m, 2H), 1.74-1.84 (m, 6H), 1.46-1.64 (m, 10H), 1.37 (t, 3H, 7.1 Hz); LC/MS (100%, t$_r$=4.902 min): m/z=398.5 [M+H]$^+$ (Calc.: 397.5).

To a mixture of Compound 78 (200 mg, 26 mmol) in THF (10 mL) at a temperature of about 25° C. was added 2 mol/L aqueous HCl (2 mL). After stirring at a temperature of about 25° C. for 30 min, the reaction mixture was warmed to a temperature of 70° C. and stirred for 3 hrs. After cooling to a temperature of about 25° C., the reaction mixture was diluted with EtOAc (40 mL) and neutralized with 2 mol/L aqueous NaOH. The organic portion was separated, concentrated under reduced pressure, and chromatographed with a silica gel column eluted with 1:10 MeOH:DCM to provide 120 mg of Substituted Benzimidazole-Type Piperidine Compound ZA27 as a white solid (yield 55%).

The identity of Substituted Benzimidazole-Type Piperidine Compound ZA27, 1-(1-(1-cyclooctylpiperidin-4-yl)-1H-benzo[d]imidazol-2(3H)-ylidene)urea, was confirmed using $^1$H NMR and LC/MS.

Substituted Benzimidazole-Type Piperidine Compound ZA27: $^1$H NMR: $\delta_H$ (400 MHz, CDCl$_3$): 11.8 (s, 1H, —NH), 7.48 (br, 1H), 7.08-7.22 (m, 3H), 4.96 (br, 2H, —NH$_2$), 2.92-2.98 (m, 2H), 2.64-2.68 (m, 1H), 2.40-2.52 (m, 4H), 1.40-1.82 (m, 16H); LC/MS (100%, t$_r$=4.612 min): m/z=370.5 [M+H]$^+$ (Calc.: 369.5).

In a manner similar to the preparation of Substituted Benzimidazole-Type Piperidine Compound ZA26, 120 mg of Substituted Benzimidazole-Type Piperidine Compound ZA28 was prepared as a white solid (yield 54%) except that O-methylhydroxylamine hydrochloride (Sigma-Aldrich) was used in place of sodium ethoxide.

The identity of Substituted Benzimidazole-Type Piperidine Compound ZA28, 1-(1-(1-cyclooctylpiperidin-4-yl)-1H-benzo[d]imidazol-2(3H)-ylidene)-3-methoxyguanidine, was confirmed using $^1$H NMR and LC/MS.

Substituted Benzimidazole-Type Piperidine Compound ZA28: $^1$H NMR: $\delta_H$ (400 MHz, CDCl$_3$): 7.04-7.60 (m, 4H), 4.42-4.61 (m, 2H), 3.82 (s, 3H), 3.76 (s, 1H), 3.68 (s, 1H), 2.92-2.96 (m, 2H), 2.64-2.71 (m, 1H), 2.38-2.52 (m, 4H), 1.44-1.84 (m, 16H); LC/MS (100%, t$_r$=4.716 min): m/z=399.6 [M+H]$^+$ (Calc.: 398.6).

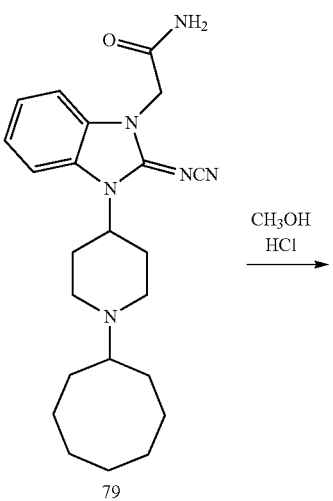

79

CH$_3$OH
HCl
⟶

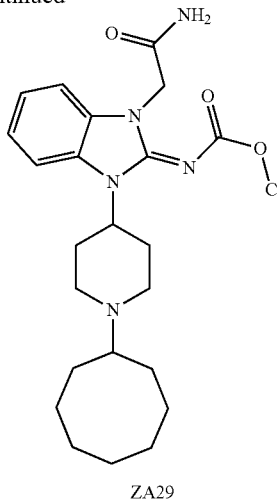

ZA29

Compound 79, 2-(2-(cyanoimino)-3-(1-cyclooctylpiperidin-4-yl)-2,3-dihydro-1H-benzo[d]imidazol-1-yl)acetamide, was prepared from readily available materials according to known methods, such as those disclosed in EP 0029707 B1, e.g., Reference Examples 19 and 20, and U.S. Pat. No. 6,867,222 B2, e.g., Examples 13 and 14, which are hereby incorporated by reference in their entireties.

In a manner similar to the preparation of Substituted Benzimidazole-Type Piperidine Compound ZA26, 180 mg of Substituted Benzimidazole-Type Piperidine Compound ZA29 was prepared as a white solid (yield 70%) by using MeOH in place of EtOH and 4 mol/L HCl in 1,4-dioxane in place of 2 mol/L aqueous HCl.

The identity of Substituted Benzimidazole-Type Piperidine Compound ZA29, (E)-methyl 1-(2-amino-2-oxoethyl)-3-(1-cyclooctylpiperidin-4-yl)-1H-benzo[d]imidazol-2(3H)-ylidenecarbamate, was confirmed using $^1$H NMR and LC/MS.

Substituted Benzimidazole-Type Piperidine Compound ZA29: $^1$H NMR: $\delta_H$ (400 MHz, CDCl$_3$): 7.6 (br, 1H), 7.16-7.22 (m, 2H), 7.04-7.07 (m, 1H), 4.84 (s, 2H), 4.76 (br, 2H, —NH$_2$), 4.56 (br, 1H), 3.8 (s, 3H, —OCH$_3$), 2.92-2.98 (m, 2H), 2.64-2.68 (m, 1H), 2.40-2.92 (m, 5H), 1.40-1.92 (m, 18H); LC/MS (100%, t$_r$=4.518 min): m/z=442.5 [M+H]$^+$ (Calc.: 441.5).

5.13 Example 13

Synthesis of Substituted Benzimidazole-Type Piperidine Compounds where ---W--- is —NH— and Q$_x$ is Absent

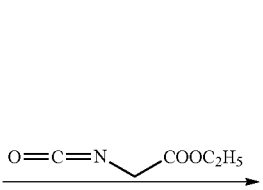

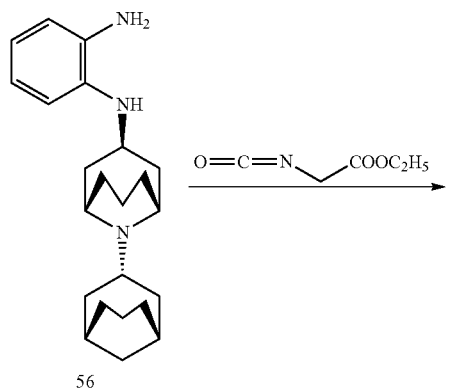

56

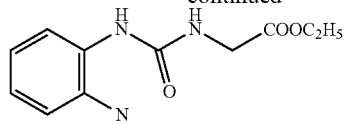

80

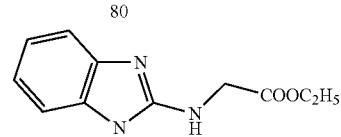

ZA30

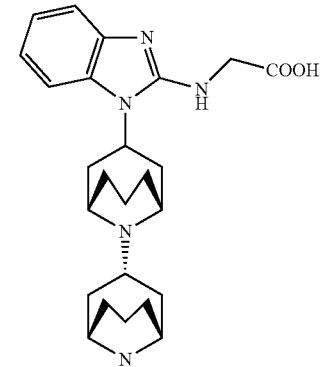

ZA31

To a solution of Compound 56 (200 mg, 0.566 mmol) in DCM (2.0 mL) in ice bath was added with stirring ethyl 2-isocyanatoacetate (88 mg, 0.679 mmol, Sigma Aldrich). The resulting reaction mixture was allowed to warm to a temperature of about 25° C. and then stirred for 1.5 hrs at that temperature. Thereafter, evaporation to dryness and drying under reduced pressure provided 280 mg of Compound 80, ethyl 2-(3-(2-(((1R,1'R,3r,3'R,5S,5'S)-[3,9'-bi(9'-azabicyclo[3.3.1]nonan)]-3'-ylamino)phenyl)ureido)acetate, which was used directly in the next step.

To Compound 80, taken directly from the previous step, was added POCl$_3$ (2.0 mL, Sigma Aldrich). The resulting reaction mixture was heated to 100° C. and stirred at that temperature for 2 hrs. Thereafter, the mixture was cooled to a temperature of about 25° C., diluted with chloroform, and neutralized with a saturated NaHCO$_3$ aqueous solution. The aqueous portion was separated and extracted twice with chloroform. The organic portions were combined, dried (over MgSO$_4$), filtered, and concentrated to dryness. The residue was chromatographed on a silica gel column eluted with n-hexane and EtOAc to provide 223 mg of Substituted Benzimidazole-Type Piperidine Compound ZA30, ethyl 2-((1-((1R,1'R,3r,5S,5'S)-[3,9'-bi(9'-azabicyclo[3.3.1]nonan)]-3'-yl)-1H-benzo[d]imidazol-2-yl)amino)acetate (yield 85% for two steps).

The identity of Substituted Benzimidazole-Type Piperidine Compound ZA30 was confirmed using $^1$H-NMR.

Substituted Benzimidazole-Type Piperidine Compound ZA30: $^1$H-NMR: $\delta_H$ (ppm, 400 MHz, CDCl$_3$): 1.08-2.30 (m, 27H), 3.48-3.63 (m, 3H), 4.28 (m, 2H), 4.40 (s, 2H), 4.61 (m, 1H), 4.92 (brs, 1H), 7.01-7.15 (m, 2H), 7.41 (m, 1H), 7.52 (m, 1H).

To a suspension of Substituted Benzimidazole-Type Piperidine Compound ZA30 (220 mg, 0.473 mmol) in THF (1.5 mL) and EtOH (1.5 mL) was added a 2 mol/L NaOH solution (0.71 mL, 1.42 mmol). The resulting reaction mixture was stirred at a temperature of about 25° C. for 2 hrs. Thereafter, 2 mol/L aqueous HCl (0.71 mL, 1.42 mmol) was added. The resulting precipitate was collected by filtration and dried under reduced pressure to provide 173 mg of Substituted Benzimidazole-Type Piperidine Compound ZA31, 2-((1-((1R,1'R,3r,5S,5'S)-[3,9'-bi(9'-azabicyclo[3.3.1]nonan)]-3'-yl)-1H-benzo[d]imidazol-2-yl)amino)acetic acid (yield 84%).

The identity of Substituted Benzimidazole-Type Piperidine Compound ZA31 was confirmed using $^1$H-NMR and LC/MS.

Substituted Benzimidazole-Type Piperidine Compound ZA31: $^1$H-NMR: $\delta_H$ (ppm, 400 MHz, CD$_3$OD): 1.59-2.68 (m, 24H), 4.14 (s, 2H), 4.26-4.33 (m, 3H), 5.69 (m, 1H), 7.30 (m, 2H), 7.67 (m, 1H), 8.11 (m, 1H); LC/MS: m/z=437.3 [M+H]$^+$ (Calc.: 436).

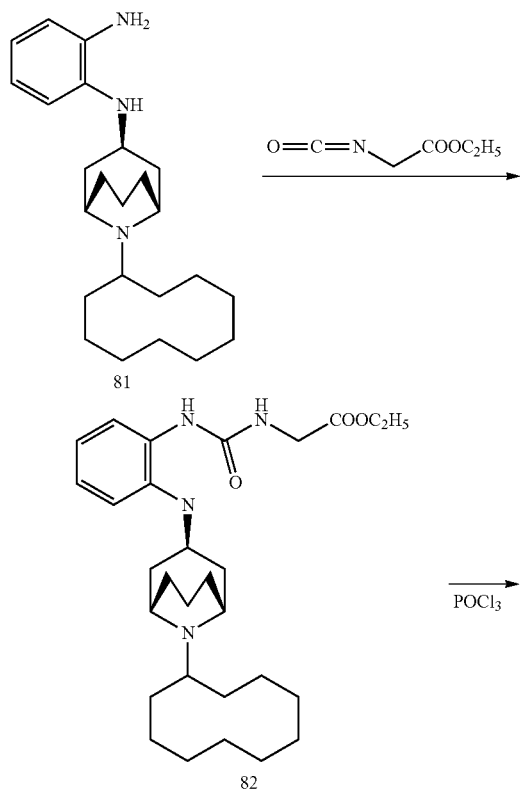

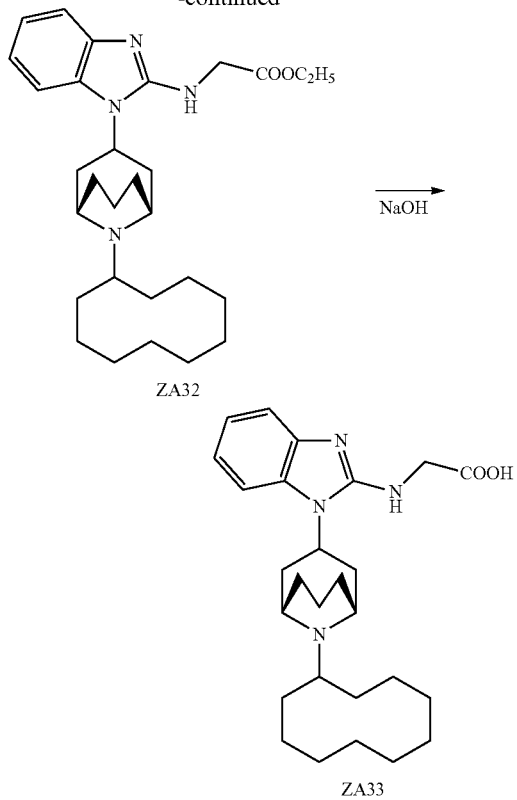

Compound 82, ethyl 2-(3-(2-(((1R,3r,5S)-9-cyclodecyl-9-azabicyclo[3.3.1]nonan-3-yl)amino)phenyl)ureido)acetate (265 mg), was prepared from Compound 81, N$^1$-((1R,3r,5S)-9-cyclodecyl-9-azabicyclo[3.3.1]nonan-3-ylbenzene-1,2-diamine (200 mg) by a procedure similar to that for preparing Compound 80 from Compound 56. Compound 81 is commercially available or can be prepared by methods known to the art, e.g., as described in U.S. Pat. App. Pub. Nos. US 2010/0216726 A1 (see, e.g., Examples 3, 14, 30, 32, 35, 38, 40, and 42-44), US 2011/0178090 A1 (see, e.g., Examples 1, 2, 4, 5, and 9), and/or International PCT Publication No. WO 2012/085648 A1 (see, e.g., Examples 12 and 13), which are hereby incorporated by reference in their entireties.

Substituted Benzimidazole-Type Piperidine Compound ZA32, ethyl 2-((1-((1R,5S)-9-cyclodecyl-9-azabicyclo[3.3.1]nonan-3-yl)-1H-benzo[d]imidazol-2-yl)amino)acetate (171 mg, yield 66%), was prepared from Compound 82 (265 mg) by a procedure similar to that for preparing Substituted Benzimidazole-Type Piperidine Compound ZA30 from Compound 80.

The identity of Substituted Benzimidazole-Type Piperidine Compound ZA32 was confirmed using $^1$H-NMR.

Substituted Benzimidazole-Type Piperidine Compound ZA32: $^1$H-NMR: $\delta_H$ (ppm, 400 MHz, CDCl$_3$): 1.16-2.30 (m, 31H), 3.07 (brs, 1H), 3.56 (brs, 2H), 4.29 (m, 2H), 4.39 (s, 2H), 4.57 (m, 1H), 4.88 (s, 1H), 7.00-7.19 (m, 2H), 7.34 (m, 1H), 7.48 (m, 1H).

Substituted Benzimidazole-Type Piperidine Compound ZA33, 2-((1-((1R,5S)-9-cyclodecyl-9-azabicyclo[3.3.1]nonan-3-yl)-1H-benzo[d]imidazol-2-yl)amino)acetic acid (120 mg, yield 75%), was prepared from Substituted Benzimidazole-Type Piperidine Compound ZA32 (170 mg) by a procedure similar to that for preparing Substituted Benzimidazole-Type Piperidine Compound ZA31 from Compound ZA30.

The identity of Substituted Benzimidazole-Type Piperidine Compound ZA33 was confirmed using ¹H-NMR and LC/MS.

Substituted Benzimidazole-Type Piperidine Compound ZA33: ¹H-NMR: δ$_H$ (ppm, 400 MHz, CD$_3$OD): 1.56-2.49 (m, 28H), 3.69 (brs, 1H), 4.05 (m, 4H), 5.22 (m, 1H), 7.04-7.11 (m, 214), 7.33 (m, 1H), 7.44 (m, 1H); LC/MS: m/z=453.3 [M+H]⁺ (Calc.: 452).

5.14 Example 14

Synthesis of Substituted Benzimidazole-Type Piperidine Compounds where ---W--- is —CH$_2$— or —CH=N— and Q$_x$ is Absent

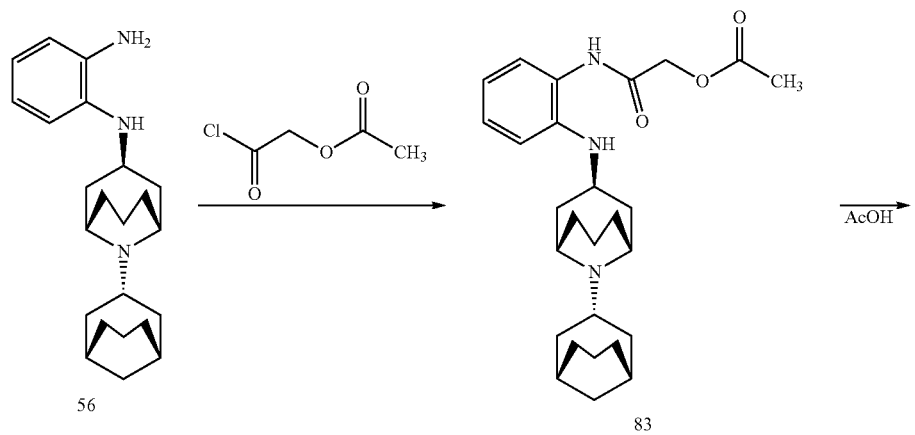

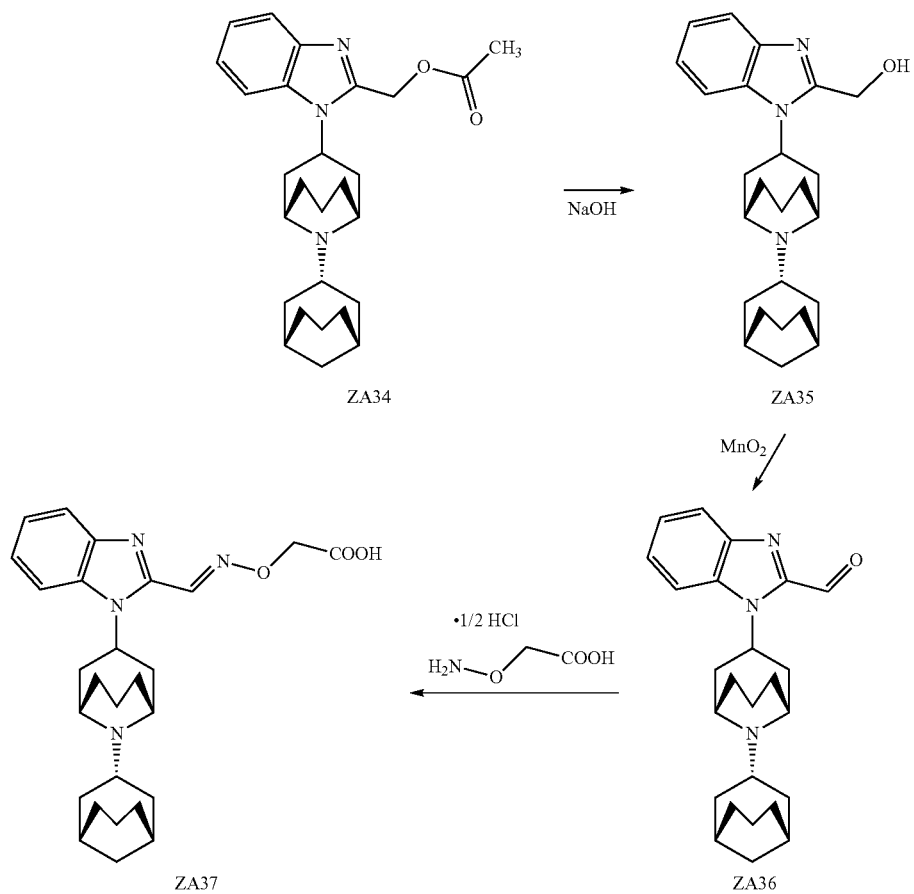

To a solution of Compound 56 (300 mg, 0.849 mmol) in DCM (3.0 mL) in ice bath was added with stirring 2-chloro-2-oxoethyl acetate (122 mg, 0.891 mmol, Sigma Aldrich). The resulting reaction mixture was stirred in ice bath for 30 min then diluted with chloroform and a saturated NaHCO$_3$ aqueous solution. The aqueous portion was extracted with chloroform. The organic portions were combined, dried (over MgSO$_4$), filtered, and concentrated to dryness to provide 435 mg of Compound 83, 2-((2-((1R,1'R,3r,3'R,5S,5'S)-[3,9'-bi(9'-azabicyclo[3.3.1]nonan)]-3'-ylamino)phenyl)amino)-2-oxoethyl acetate (yield>99.5%), which was used directly in the next step.

To a solution of Compound 83 (435 mg) in toluene (2.0 mL) and 1,4-dioxane (2.0 mL) was added AcOH (0.097 mL, 1.70 mmol). The resulting reaction mixture was heated to 100° C., and stirred at that temperature for 13 hrs. Thereafter, the mixture was cooled to a temperature of about 25° C. and poured into chloroform and a saturated NaHCO$_3$ aqueous solution. The aqueous portion was extracted with chloroform. The organic portions were combined, dried (over MgSO$_4$), filtered, and concentrated to dryness. The residue was chromatographed on a silica gel column eluted with n-hexane and EtOAc containing 5% TEA to provide 220 mg of Substituted Benzimidazole-Type Piperidine Compound ZA34, (1-((1R,1'R,3r,5S,5'S)-[3,9'-bi(9'-azabicyclo[3.3.1]nonan)]-3'-yl)-1H-benzo[d]imidazol-2-yl) methyl acetate (yield 59% for two steps).

The identity of Substituted Benzimidazole-Type Piperidine Compound ZA34 was confirmed using $^1$H-NMR.

Substituted Benzimidazole-Type Piperidine Compound ZA34: $^1$H-NMR: $\delta_H$ (ppm, 400 MHz, CDCl$_3$): 1.09-2.33 (m, 27H), 3.41-3.61 (m, 3H), 4.86 (1H, m), 5.40 (s, 2H), 7.27 (m, 2H), 7.68-7.82 (m, 2H).

To a solution of Substituted Benzimidazole-Type Piperidine Compound ZA34 (220 mg, 0.505 mmol) in MeOH (4.0 mL) was added 2 mol/L aqueous NaOH (0.758 mL, 1.515 mmol). The resulting reaction mixture was stirred at a temperature of about 25° C. for 2 hrs. Thereafter, 2 mol/L aqueous HCl (0.758 mL, 1.515 mmol) was added and the mixture was poured into chloroform and water. The aqueous portion was extracted twice with chloroform. The organic portions were combined, dried (over MgSO$_4$), filtered, and concentrated to dryness. The residue was chromatographed on a silica gel column eluted with n-hexane and EtOAc containing 5% TEA to provide 180 mg of Substituted Benzimidazole-Type Piperidine Compound ZA35, (1-((1R,1'R,3r,5S,5'S)-[3,9'-bi(9'-azabicyclo[3.3.1]nonan)]-3'-yl)-1H-benzo[d]imidazol-2-yl)methanol (yield 91%).

The identity of Substituted Benzimidazole-Type Piperidine Compound ZA35 was confirmed using $^1$H-NMR and LC/MS.

Substituted Benzimidazole-Type Piperidine Compound ZA35: $^1$H-NMR: $\delta_H$ (ppm, 400 MHz, CDCl$_3$): 1.13-2.26 (m, 24H), 3.49-3.78 (m, 4H), 4.85 (m, 1H), 4.92 (s, 2H), 7.26 (m, 2H), 7.67 (m, 1H), 7.74 (m, 1H); LC/MS: m/z=394.4 [M+H]$^+$ (Calc.: 393).

To a solution of Substituted Benzimidazole-Type Piperidine Compound ZA35 (100 mg, 0.254 mmol) in DCM (3.0 mL) was added manganese dioxide (88 mg, 1.02 mmol, Sigma Aldrich). The resulting reaction mixture was heated to reflux and refluxed with stirring for 3 hrs. Thereafter, the insoluble material was removed by filtration through CELITE. The filtrate was concentrated and dried under reduced pressure to provide 86 mg of Substituted Benzimidazole-Type Piperidine Compound ZA36, 1-((1R,1'R,3r,5S,5'S)-[3,9'-bi(9'-azabicyclo[3.3.1]nonan)]-3 t-yl)-1H-benzo[d]imidazole-2-carbaldehyde (yield 86%).

The identity of Substituted Benzimidazole-Type Piperidine Compound ZA36 was confirmed using $^1$H-NMR.

Substituted Benzimidazole-Type Piperidine Compound ZA36: $^1$H-NMR: $\delta_H$ (ppm, 400 MHz, CDCl$_3$): 1.13-2.41 (m, 24H), 3.49-3.68 (m, 3H), 5.90 (m, 1H), 7.35-7.50 (m, 2H), 7.79 (m, 1H), 7.91 (m, 1H), 10.1 (s, 1H).

To a solution of Substituted Benzimidazole-Type Piperidine Compound ZA36 (84 mg, 0.215 mmol) in MeOH (1.5 mL) and water (0.5 mL) was added 2-(aminooxy)acetic acid hemihydrochloride (28 mg, 0.257 mmol, Sigma Aldrich). The resulting reaction mixture was heated to reflux and refluxed with stirring for 2 hrs. Thereafter, a 2 mol/L aqueous NaOH solution (0.13 mL) was added followed by evaporation to dryness. The resulting residue was diluted with chloroform and MeOH. The solution was dried (over MgSO$_4$), filtered, and concentrated to dryness. The residue was chromatographed on a silica gel column eluted with DCM and MeOH containing 10% NH$_4$OH to provide 42 mg of Substituted Benzimidazole-Type Piperidine Compound ZA37, 2-(((E)-((1-((1R,1'R,3r,5S,5'S)-[3,9'-bi(9'-azabicyclo[3.3.1]nonan)]-3'-yl)-1H-benzo[d]imidazol-2-yl)methylene)amino)oxy)acetic acid (yield 42%).

The identity of Substituted Benzimidazole-Type Piperidine Compound ZA37 was confirmed using $^1$H-NMR and LC/MS.

Substituted Benzimidazole-Type Piperidine Compound ZA37: $^1$H-NMR: $\delta_H$ (ppm, 400 MHz, CDCl$_3$): 1.35-2.65 (m, 22H), 2.98 (m, 2H), 4.08-4.30 (m, 3H), 4.69 (s, 2H), 6.65 (m, 1H), 7.31 (m, 2H), 7.59 (m, 1H), 7.80 (m, 1H), 8.20 (s, 1H); LC/MS: m/z=465.3 [M+H]$^+$ (Calc.: 464).

5.15 Example 15

Synthesis of Substituted Benzimidazole-Type Piperidine Compounds where t is 0 and the Q$_x$ Ring is a 5- or 6-Membered Heterocycle Using procedures similar to those described in Example 1, the following Substituted Benzimidazole-Type Piperidine Compounds were prepared from Compound 66. The co-reactant compounds are commercially available from, e.g., Sigma-Aldrich, or can be prepared by methods known to the art.

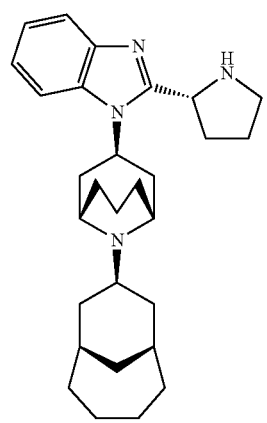

H27b(i)

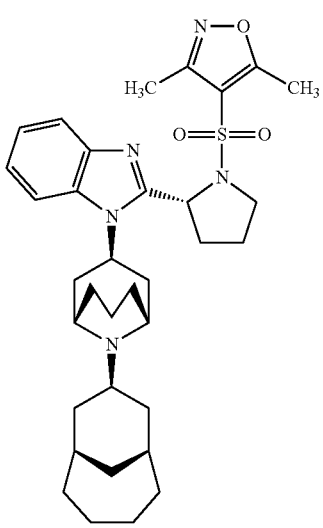

ZA38

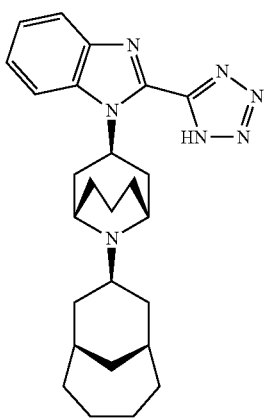

ZA39

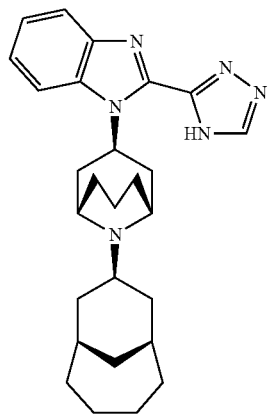

ZA40

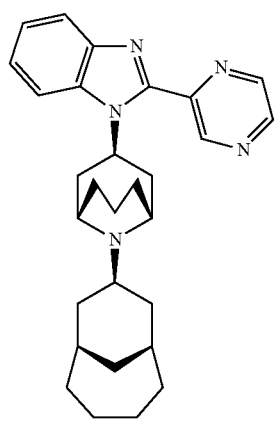

ZA41

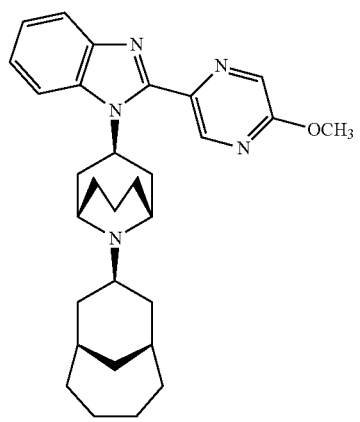

ZA42

H27b(i): 1-((1R,3R,5S)-9-((1R,6S,8r)-bicyclo[4.3.1]decan-8-yl)-9-azabicyclo[3.3.1]nonan-3-yl)-2-((R)-pyrrolidin-2-yl)-1H-benzo[d]imidazole.

H27b(i): $^1$H-NMR: $\delta_H$ (ppm, CD$_3$OD): 7.74 (m, 1H), 7.67 (m, 1H), 7.27 (m, 2H), 4.95 (m, 1H), 4.50 (m, 1H), 3.69 (m, 2H), 3.23 (m, 1H), 3.02 (m, 1H), 2.43-2.23 (m, 8H), 2.06-1.81 (m, 10H), 1.79-1.56 (m, 6H), 1.50 (m, 2H), 1.32 (m, 2H); MS: m/z=447.3 [M+H]$^+$.

ZA38: 4-(((R)-2-(1-((1R,3R,5S)-9-((1R,6S,8r)-bicyclo[3.3.1]decan-8-yl)-9-azabicyclo[3.3.1]nonan-3-yl)-1H-benzo[d]imidazol-2-yl)pyrrolidin-1-yl)sulfonyl)-3,5-dimethylisoxazole.

ZA38: $^1$H-NMR: $\delta_H$ (ppm, CD$_3$OD): 7.80 (m, 1H), 7.60 (m, 1H), 7.37 (m, 2H), 5.42 (m, 2H), 4.31 (m, 2H), 3.91 (m, 114), 3.62 (m, 2H), 2.70 (m, 3H), 2.44 (m, 3H), 2.30 (s, 3H), 2.10 (m, 5H), 2.00 (s, 3H), 1.96 (m, 3H), 1.77 (m, 6H), 1.67 (m, 4H), 1.50 (m, 5H); MS: m/z=606.3 [M+H]$^+$.

ZA39: 1-((1R,3R,5S)-9-((1R,6S,8r)-bicyclo[3.3.1]decan-8-yl)-9-azabicyclo[3.3.1]nonan-3-yl)-2-(1H-tetrazol-5-yl)-1H-benzo[d]imidazole.

ZA39: $^1$H-NMR: $\delta_H$ (ppm, CD$_3$OD): 7.77 (m, 1H), 7.67 (m, 1H), 7.33 (m, 2H), 5.72 (m, 1H), 4.31 (m, 2H), 3.90 (m, 1H), 2.75 (m, 4H), 2.44 (m, 3H), 2.10 (m, 3H), 1.94 (m, 4H), 1.76 (m, 7H), 1.51 (m, 5H); MS: m/z=446.3 [M+H]$^+$.

ZA40: 1-((1R,3R,5S)-9-((1R,6S,8r)-bicyclo[4.3.1]decan-8-yl)-9-azabicyclo[3.3.1]nonan-3-yl)-2-(4H-1,2,4-triazol-3-yl)-1H-benzo[d]imidazole.

ZA40: $^1$H-NMR: $\delta_H$ (ppm, CD$_3$OD): 8.39 (s, 1H), 7.77 (m, 1H), 7.68 (m, 1H), 7.25 (m, 2H), 5.52 (m, 1H), 3.54 (br, 2H), 3.05 (m, 1H), 2.34-2.12 (m, 7H), 1.87-1.30 (m, 14H), 1.21 (m, 4H); MS: m/z=445.4 [M+H]$^+$.

ZA41: 1-((1R,3R,5S)-9-((1R,6S,8r)-bicyclo[4.3.1]decan-8-yl)-9-azabicyclo[3.3.1]nonan-3-yl)-2-(pyrazin-2-yl)-1H-benzo[d]imidazole.

ZA41: $^1$H-NMR: $\delta_H$ (ppm, CD$_3$OD): 9.37 (s, 1H), 9.08 (s, 1H), 9.00 (s, 1H), 8.42 (d, J=8 Hz, 1H), 8.04 (d, J=8 Hz, 1H), 7.79 (m, 2H), 6.32 (m, 1H), 4.33 (m, 2H), 3.91 (m, 1H), 2.95 (m, 2H), 2.76 (m, 2H), 2.43 (m, 3H), 2.13 (m, 5H), 1.97-1.59 (m, 10H), 1.48 (m, 4H); MS: m/z=456.3 [M+H]$^+$.

ZA42: 1-((1R,3R,5S)-9-((1R,6S,8r)-bicyclo[3.3.1]decan-8-yl)-9-azabicyclo[3.3.1]nonan-3-yl)-2-(5-methoxypyrazin-2-yl)-1H-benzo[d]imidazole.

ZA42: $^1$H-NMR: $\delta_H$ (ppm, CD$_3$OD): 8.75 (s, 1H), 8.35 (s, 1H), 7.86 (m, 1H), 7.75 (m, 1H), 7.34 (m, 2H), 5.34 (m, 1H), 4.48 (m, 3H), 4.08 (s, 3H), 3.57 (br, s, 2H), 3.05 (m, 1H), 2.36 (m, 5H), 2.23 (m, 5H), 1.92-1.46 (m, 8H), 1.39 (m, 2H), 1.26 (m, 3H); MS: m/z=486.3 [M+H]$^+$.

5.16 Example 16

Synthesis of Substituted Benzimidazole-Type Piperidine Compounds where t is 1 and the Q$_x$ Ring is a 5- or 6-Membered Heterocycle Using procedures similar to those described in Example 1, the following Substituted Benzimidazole-Type Piperidine Compounds were prepared from Compound 66. The co-reactant compounds are commercially available from, e.g., Sigma-Aldrich, or can be prepared by methods known to the art.

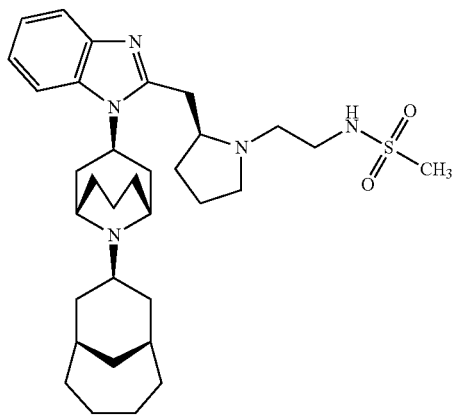

ZA43

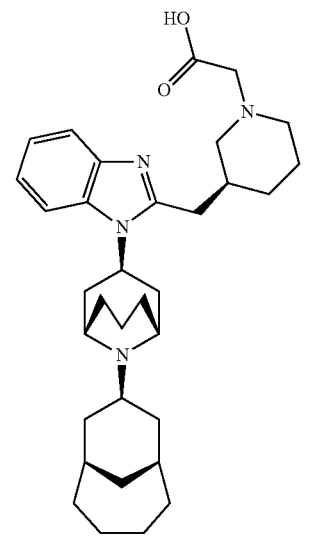

ZA45

ZA43: N-(2-((S)-2-((1-((1R,3R,5S)-9-((1R,6S,8r)-bicyclo[4.3.1]decan-8-yl)-9-azabicyclo[3.3.1]nonan-3-yl)-1H-benzo[d]imidazol-2-yl)methyl)pyrrolidin-1-yl)ethyl)methanesulfonamide.

ZA43: $^1$H-NMR: $\delta_H$ (ppm, CD$_3$OD): 7.67 (m, 1H), 7.49 (m, 1H), 7.12 (m, 2H), 4.86 (m, 1H), 3.57 (m, 2H), 3.17-2.84 (m, 8H), 2.79 (s, 3H), 2.46-2.11 (m, 8H), 1.90-1.47 (m, 16H), 1.41 (m, 2H), 1.28-1.07 (m, 4H); MS: m/z=582.3 [M+H]$^+$.

ZA44: 2-((S)-2-((1-((1R,3R,5S)-9-((1R,6S,8r)-bicyclo[4.3.1]decan-8-yl)-9-azabicyclo[3.3.1]nonan-3-yl)-1H-benzo[d]imidazol-2-yl)methyl)pyrrolidin-1-yl)-N,N-diethylacetamide.

ZA44: $^1$H-NMR: $\delta_H$ (ppm, CD$_3$OD): 7.64 (d, J=8 Hz, 1H), 7.50 (d, J=8 Hz, 1H), 7.15 (m, 2H), 4.88 (br, s, 1H), 3.62 (m, 3H), 3.28 (m, 2H), 3.05 (m, 4H), 2.81 (m, 1H), 2.42 (m, 1H), 2.25 (m, 6H), 1.96-1.36 (m, 14H), 1.15 (m, 3H), 0.98 (m, 6H); MS: m/z=574.5 [M+H]$^+$.

ZA45: 2-((S)-3-((1-((1R,3R,5S)-9-((1R,6S,8r)-bicyclo[4.3.1]decan-8-yl)-9-azabicyclo[3.3.1]nonan-3-yl)-1H-benzo[d]imidazol-2-yl)methyl)piperidin-1-yl)acetic acid.

ZA45: $^1$H-NMR: $\delta_H$ (ppm, CD$_3$OD): 7.80-7.71 (m, 1H), 7.66-7.59 (m, 1H), 7.36-7.23 (m, 2H), 5.54-5.38 (m, 1H), 4.33-4.15 (m, 2H), 3.96-3.78 (m, 1H), 3.69-3.53 (m, 4H), 3.17-2.88 (m, 4H), 2.77-2.35 (m, 8H), 2.33-1.34 (m, 23H); MS: m/z=533.4 [M+H]$^+$.

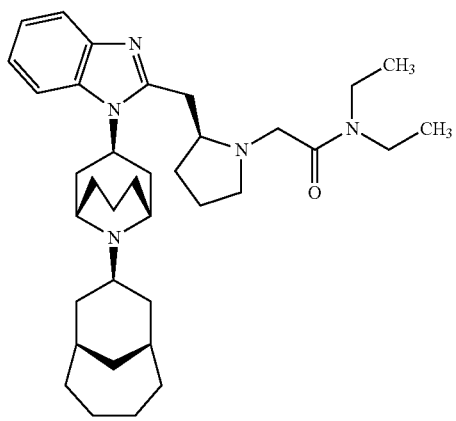

ZA44

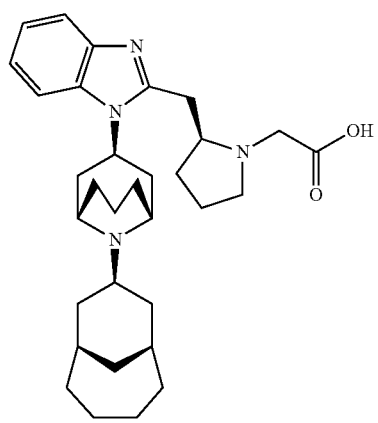

ZA46

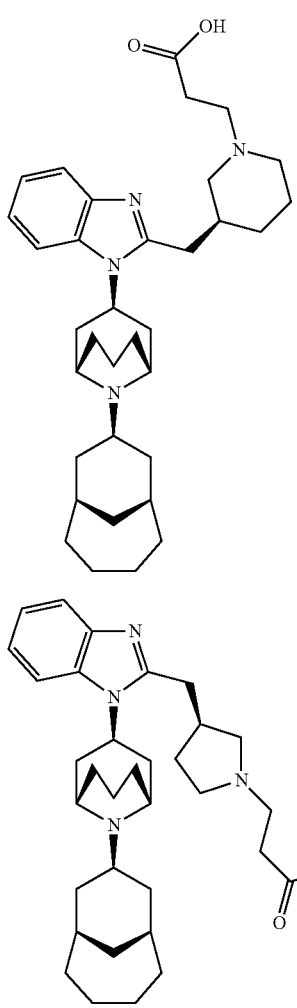

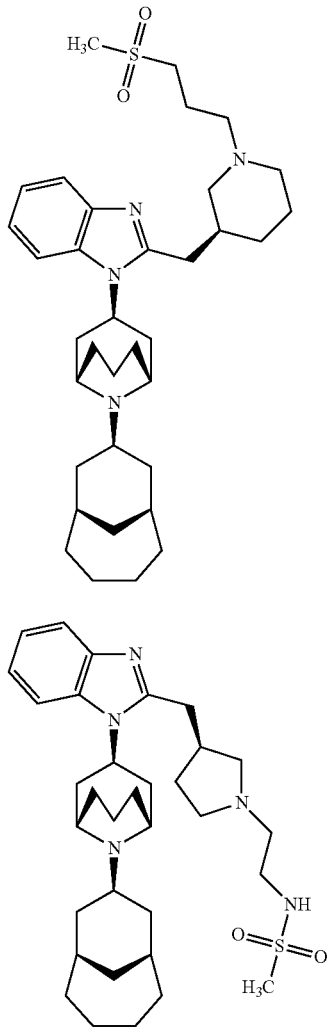

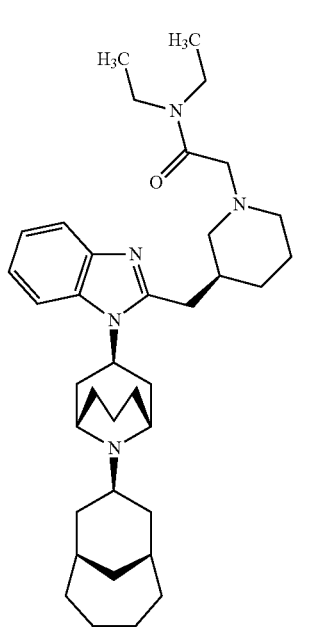

ZA46: 2-((S)-3-((1-((1R,3R,5S)-9-((1R,6S,8r)-bicyclo[4.3.1]decan-8-yl)-9-azabicyclo[3.3.1]nonan-3-yl)-1H-benzo[d]imidazol-2-yl)methyl)pyrrolidin-1-yl)acetic acid.

ZA46: $^1$H-NMR: $\delta_H$ (ppm, CD$_3$OD): 7.79-7.73 (m, 1H), 7.72-7.66 (m, 1H), 7.34-7.21 (m, 2H), 5.13-4.97 (m, 1H), 3.96-3.82 (m, 2H), 3.82-3.71 (m, 2H), 3.71-3.54 (m, 2H), 3.53-3.04 (m, 6H), 2.57-2.29 (m, 8H), 2.08-1.37 (m, 20H); MS: m/z=519.3 [M+H]$^+$.

ZA47: 3-((S)-3-((1-((1R,3R,5S)-9-((1R,6S,8r)-bicyclo[3.3.1]decan-8-yl)-9-azabicyclo[3.3.1]nonan-3-yl)-1H-benzo[d]imidazol-2-yl)methyl)piperidin-1-yl)propanoic acid.

ZA47: $^1$H-NMR: $\delta_H$ (ppm, CD$_3$OD): 7.83-7.74 (m, 1H), 7.68-7.61 (m, 1H), 7.39-7.25 (m, 2H), 5.54-5.33 (m, 1H), 4.40-4.27 (m, 2H), 4.00-3.71 (m, 2H), 3.55-3.33 (m, 2H), 3.28-2.95 (m, 4H), 2.89-2.33 (m, 10H), 2.24-1.27 (m, 24H); MS: m/z=547.3 [M+H]$^+$.

ZA48: 3-((S)-3-((1-((1R,3R,5S)-9-((1R,6S,8r)-bicyclo[4.3.1]decan-8-yl)-9-azabicyclo[3.3.1]nonan-3-yl)-1H-benzo[d]imidazol-2-yl)methyl)pyrrolidin-1-yl)propanoic acid.

ZA48: $^1$H-NMR: $\delta_H$ (ppm, CD$_3$OD): 7.87-7.65 (m, 2H), 7.48-7.21 (m, 2H), 5.82-5.56 (m, 1H), 4.47-4.26 (m, 2H), 4.15-3.83 (m, 1H), 3.79-3.56 (m, 2H), 3.55-3.22 (m, 6H), 3.22-3.03 (m, 1H), 2.85-2.51 (m, 6H), 2.55-2.28 (m, 4H), 2.28-2.08 (m, 4H), 2.08-1.44 (m, 16H); MS: m/z=533.4 [M+H]$^+$.

ZA49: N-(2-((S)-3-((1-((1R,3R,5S)-9-((1R,6S,8r)-bicyclo[4.3.1]decan-8-yl)-9-azabicyclo[3.3.1]nonan-3-yl)-1H-benzo[d]imidazol-2-yl)methyl)piperidin-1-yl)ethyl)methanesulfonamide.

ZA49: $^1$H-NMR: $\delta_H$ (ppm, CD$_3$OD): 7.83-7.69 (m, 1H), 7.65-7.54 (m, 1H), 7.33-7.17 (m, 2H), 4.97-4.79 (m, 1H), 3.77-3.57 (m, 2H), 3.27-3.09 (m, 3H), 3.00-2.77 (m, 7H), 2.59-2.46 (m, 2H), 2.45-2.00 (m, 9H), 2.00-1.41 (m, 18H), 1.41-1.04 (m, 5H); MS: m/z=596.4 [M+H]$^+$.

ZA50: N-(2-((S)-3-((1-((1R,3R,5S)-9-((1R,6S,8r)-bicyclo[4.3.1]decan-8-yl)-9-azabicyclo[3.3.1]nonan-3-yl)-1H-benzo[d]imidazol-2-yl)methyl)pyrrolidin-1-yl)ethyl)methanesulfonamide.

ZA50: $^1$H-NMR: $\delta_H$ (ppm, CD$_3$OD): 7.81-7.71 (m, 1H), 7.64-7.57 (m, 1H), 7.32-7.17 (m, 2H), 4.97-4.81 (m, 1H), 3.72-3.60 (m, 2H), 3.24-3.11 (m, 3H), 3.09-2.99 (m, 2H), 2.98-2.91 (m, 3H), 2.91-2.56 (m, 7H), 2.50-2.17 (m, 8H), 2.18-2.01 (m, 1H), 2.01-1.41 (m, 15H), 1.42-1.19 (m, 4H); MS: m/z=582.3 [M+H]$^+$.

ZA51: 2-((S)-3-((1-((1R,3R,5S)-9-((1R,6S,8r)-bicyclo[4.3.1]decan-8-yl)-9-azabicyclo[3.3.1]nonan-3-yl)-1H-benzo[d]imidazol-2-yl)methyl)piperidin-1-yl)-N,N-diethylacetamide.

ZA51: $^1$H-NMR: $\delta_H$ (ppm, CD$_3$OD): 7.81-7.70 (m, 1H), 7.65-7.53 (m, 1H), 7.31-7.15 (m, 2H), 4.97-4.82 (m, 1H), 3.76-3.59 (m, 2H), 3.52-3.07 (m, 6H), 2.99-2.69 (m, 4H), 2.50-2.04 (m, 9H), 2.02-1.42 (m, 19H), 1.42-1.01 (m, 9H), 1.01-0.83 (m, 3H); MS: m/z=588.5 [M+H]$^+$.

ZA52

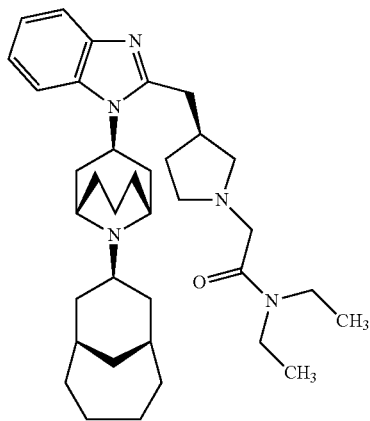

ZA53

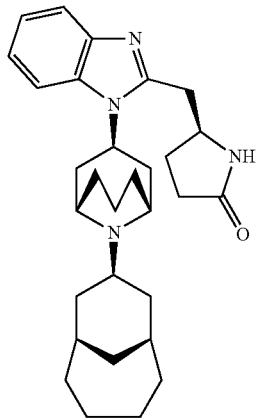

ZA54

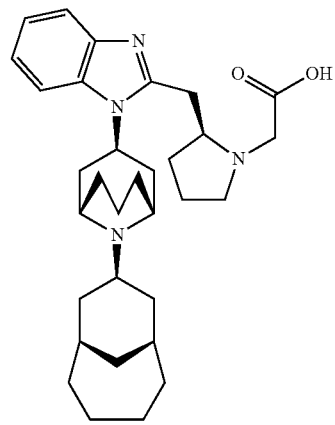

ZA52: 2-((S)-3-((1-((1R,3R,5S)-9-((1R,6S,8r)-bicyclo[4.3.1]decan-8-yl)-9-azabicyclo[3.3.1]nonan-3-yl)-1H-benzo[d]imidazol-2-yl)methyl)pyrrolidin-1-yl)-N,N-diethylacetamide.

ZA52: $^1$H-NMR: $\delta_H$ (ppm, CD$_3$OD): 7.81-7.70 (m, 1H), 7.67-7.53 (m, 1H), 7.34-7.16 (m, 2H), 4.97-4.82 (m, 1H), 3.74-3.59 (m, 2H), 3.48-3.33 (m, 4H), 3.27-3.14 (m, 1H), 3.10-2.99 (m, 2H), 2.95-2.85 (m, 1H), 2.85-2.65 (m, 3H), 2.54-2.00 (m, 9H), 1.99-1.40 (m, 16H), 1.40-1.23 (m, 4H), 1.25-1.15 (m, 4H), 1.15-0.98 (m, 4H); MS: m/z=574.3 [M+H]$^+$.

ZA53: (S)-5-((1-((1R,3R,5S)-9-((1R,6S,8r)-bicyclo[4.3.1]decan-8-yl)-9-azabicyclo[3.3.1]nonan-3-yl)-1H-benzo[d]imidazol-2-yl)methyl)pyrrolidin-2-one.

ZA53: $^1$H-NMR: $\delta_H$ (ppm, CD$_3$OD): 7.80 (m, 1H), 7.70 (m, 1H), 7.33 (m, 2H), 5.59 (br, s, 1H), 4.35 (m, 3H), 4.00 (m, 1H), 3.31 (m, 2H), 2.83-2.31 (m, 9H), 2.23-1.67 (m, 14H), 1.60 (m, 4H); MS: m/z=475.4 [M+H]$^+$.

ZA54: 2-((S)-2-((1-((1R,3R,5S)-9-((1R,6S,8r)-bicyclo[4.3.1]decan-8-yl)-9-azabicyclo[3.3.1]nonan-3-yl)-1H-benzo[d]imidazol-2-yl)methyl)pyrrolidin-1-yl)acetic acid.

ZA54: $^1$H-NMR: $\delta_H$ (ppm, CD$_3$OD): 7.95 (d, 3=8 Hz, 1H), 7.84 (d, 3=8 Hz, 1H), 7.62 (m, 2H), 6.10 (m, 1H), 4.67 (m, 1H), 4.54 (m, 1H), 4.42 (m, 2H), 4.32 (m, 2H), 4.09-3.83 (m, 3H), 3.41 (m, 1H), 2.93 (m, 1H), 2.78 (m, 1H), 2.63 (m, 2H), 2.40 (m, 2H), 2.35-2.00 (m, 7H), 1.98-1.76 (m, 7H), 1.69 (m, 4H), 1.41 (m, 5H); MS: m/z=519.3 [M+H]$^+$.

ZA55

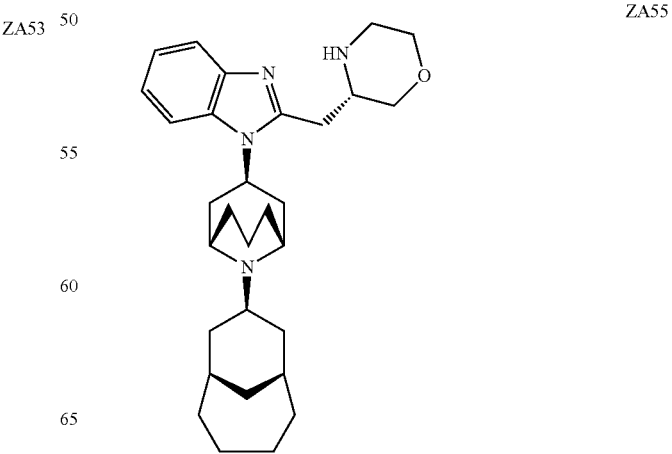

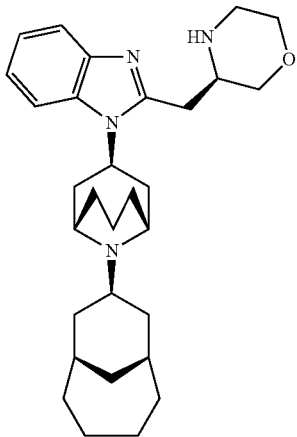

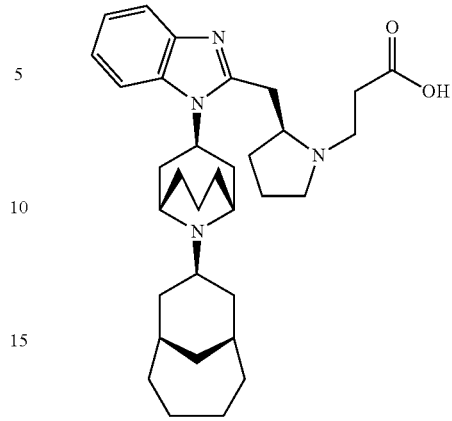

ZA55: (S)-3-((1-((1R,3R,5S)-9-((1R,6S,8r)-bicyclo[3.3.1]decan-8-yl)-9-azabicyclo[3.3.1]nonan-3-yl)-1H-benzo[d]imidazol-2-yl)methyl)morpholine.

ZA55: $^1$H-NMR: $\delta_H$ (ppm, CD$_3$OD): 7.81 (d, J=8 Hz, 1H), 7.70 (d, J=8 Hz, 1H), 7.34 (m, 2H), 5.49 (br, s, 1H), 4.21 (m, 2H), 4.02 (m, 1H), 3.95 (m, 1H), 3.80 (m, 1H), 3.74 (m, 1H), 3.64 (m, 2H), 3.27 (m, 2H), 3.19 (m, 2H), 2.65 (m, 2H), 2.55 (m, 2H), 2.46 (m, 3H), 2.17-1.52 (m, 19H); MS: m/z=477.3 [M+H]$^+$.

ZA56: (R)-3-((1R,3R,5S)-9-((1R,6S,8r)-bicyclo[4.3.1]decan-8-yl)-9-azabicyclo[3.3.1]nonan-3-yl)-1H-benzo[d]imidazol-2-yl)methyl)morpholine.

ZA56: $^1$H-NMR: $\delta_H$ (ppm, CD$_3$OD): 7.81 (m, 1H), 7.70 (m, 1H), 7.34 (m, 2H), 5.65 (br, s, 1H), 4.27 (m, 2H), 4.02 (m, 1H), 3.94 (m, 1H), 3.87 (m, 1H), 3.75 (m, 1H), 3.34 (m, 2H), 3.21 (m, 1H), 2.64 (m, 4H), 2.47 (m, 3H), 2.20-1.51 (m, 19H); MS: m/z=477.3 [M+H]$^+$.

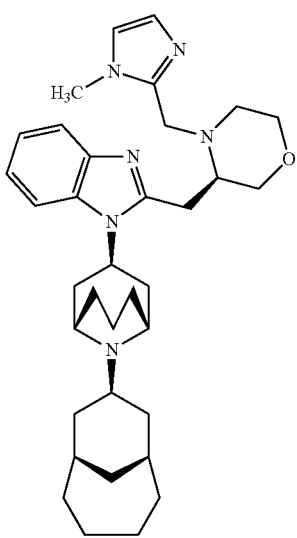

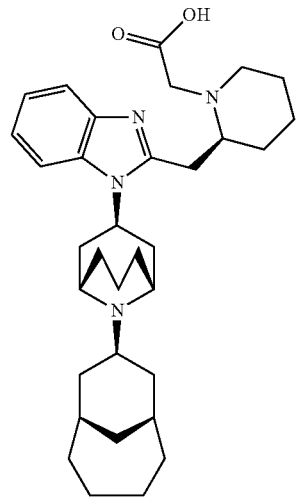

ZA57: (R)-3-((1-((1R,3R,5S)-9-((1R,6S,8r)-bicyclo[4.3.1]decan-8-yl)-9-azabicyclo[3.3.1]nonan-3-yl)-1H-benzo[d]imidazol-2-yl)methyl)-4-((1-methyl-1H-imidazol-2-yl)methyl)morpholine.

ZA57: $^1$H-NMR: $\delta_H$ CD$_3$OD): 7.81 (d, J=8 Hz, 1H), 7.64 (d, J=8 Hz, 1H), 7.43 (m, 2H), 7.36 (m, 2H), 5.50 (m, 1H), 4.30 (m, 2H), 4.12 (m, 2H), 3.89 (m, 1H), 3.76 (s, 3H), 3.70 (m, 2H), 3.50 (m, 1H), 3.41 (m, 3H), 2.98 (m, 1H), 2.64 (m, 4H), 2.38 (m, 4H), 2.01 (m, 5H), 1.75 (m, 9H), 1.48 (m, 5H); MS: m/z=571.3 [M+H]$^+$.

ZA58: 3-((S)-2-((1-((1R,3R,5S)-9-((1R,6S,8r)-bicyclo[4.3.1]decan-8-yl)-9-azabicyclo[3.3.1]nonan-3-yl)-1H-benzo[d]imidazol-2-yl)methyl)pyrrolidin-1-yl)propanoic acid.

ZA58: $^1$H-NMR: $\delta_H$ (ppm, CD$_3$OD): 7.70 (d, J=7.8 Hz, 1H), 7.59 (d, J=7.8 Hz, 1H), 7.24 (m, 2H), 5.48 (br, s, 1H), 4.28 (m, 2H), 4.12 (m, 1H), 3.86 (m, 1H), 3.71 (s, 2H), 3.61 (m, 1H), 3.47 (m, 1H), 3.31 (m, 2H), 2.96 (m, 2H), 2.78-2.47 (m, 5H), 2.35 (m, 4H), 2.06 (m, 4H), 1.98-1.61 (m, 9H), 1.48 (m, 5H), 1.22 (m, 2H); MS: m/z=533.4 [M+H]$^+$.

ZA59: 2-((S)-2-((1-((1R,3R,5S)-9-((1R,6S,8r)-bicyclo[4.3.1]decan-8-yl)-9-azabicyclo[3.3.1]nonan-3-yl)-1H-benzo[d]imidazol-2-yl)methyl)piperidin-1-yl)acetic acid.

ZA59: $^1$H-NMR: $\delta_H$ (ppm, CD$_3$OD): 8.04 (d, J=8 Hz, 1H), 7.81 (d, J=8 Hz, 1H), 7.62 (m, 2H), 5.92 (br, s, 1H), 4.60 (m, 3H), 4.24 (m, 3H), 3.91 (m, 2H), 3.61 (m, 1H), 3.28 (m, 1H), 2.80 (m, 3H), 2.35 (m, 4H), 1.99 (m, 6H), 1.77 (m, 10H), 1.48 (m, 5H); MS: m/z=533.4 [M+H]$^+$.

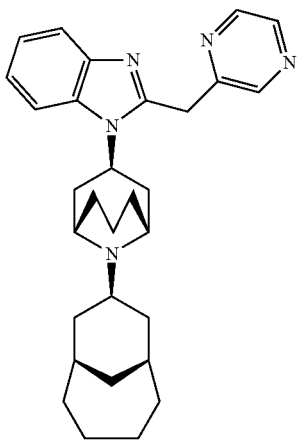

ZA60

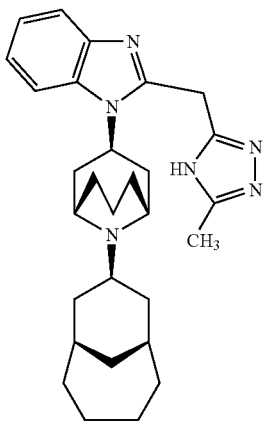

ZA61

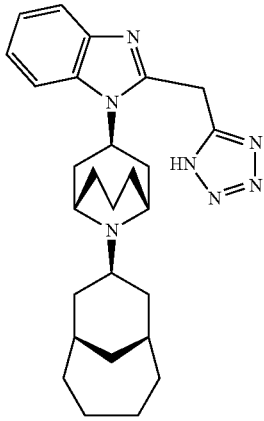

ZA62

ZA60: 1-((1R,3R,5S)-9-((1R,6S,8r)-bicyclo[4.3.1]decan-8-yl)-9-azabicyclo[3.3.1]nonan-3-yl)-2-(pyrazin-2-ylmethyl)-1H-benzo[d]imidazole.

ZA60: $^1$H-NMR: $\delta_H$ (ppm, CD$_3$OD): 8.99 (s, 1H), 8.69 (m, 1H), 8.58 (m, 1H), 8.08 (m, 1H), 7.79 (m, 1H), 7.62 (m, 2H), 6.13 (m, 1H), 4.25 (m, 2H), 3.86 (m, 1H), 2.70 (m, 4H), 2.33 (m, 3H), 2.03 (m, 5H), 1.88 (m, 2H), 1.88 (m, 2H), 1.84-1.60 (m, 8H), 1.43 (m, 4H); MS: m/z=470.4 [M+H]$^+$.

ZA61: 1-((1R,3R,5S)-9-((1R,6S,8r)-bicyclo[4.3.1]decan-8-yl)-9-azabicyclo[3.3.1]nonan-3-yl)-2-((5-methyl-4H-1,2,4-triazol-3-yl)methyl)-1H-benzo[d]imidazole.

ZA61: $^1$H-NMR: $\delta_H$ (ppm, CD$_3$OD): 7.67 (d, J=8 Hz, 1H), 7.52 (d, J=8 Hz, 1H), 7.17 (m, 2H), 4.81 (m, 1H), 4.32 (s, 2H), 3.61 (m, 1H), 2.30 (s, 3H), 2.22 (m, 7H), 1.87-1.64 (m, 6H), 1.56 (m, 2H), 1.46 (m, 3H), 1.30 (m, 6H); MS: m/z=473.2 [M+H].

ZA62: 2-((1H-tetrazol-5-yl)methyl)-1-((1R,3R,5S)-9-((1R,6S,8r)-bicyclo[4.3.1]decan-8-yl)-9-azabicyclo[3.3.1]nonan-3-yl)-1H-benzo[d]imidazole.

ZA62: $^1$H-NMR: $\delta_H$ (ppm, CD$_3$OD): 7.68 (m, 1H), 7.61 (m, 1H), 7.57 (m, 1H), 7.27 (m, 2H), 5.25 (m, 1H), 4.51 (s, 2H), 4.22 (m, 2H), 3.89 (m, 1H), 2.52 (m, 4H), 2.26 (m, 3H), 2.06 (m, 5H), 1.90 (m, 3H), 1.78 (m, 5H), 1.48 (m, 5H); MS: m/z=460.4 [M+H]$^+$.

5.17 Example 17

Synthesis of Substituted Benzimidazole-Type Piperidine Compounds where t is 0 and the $Q_x$ Ring is a 5- or 6-Membered Heterocycle Using procedures similar to those described in Example 1, the following Substituted Benzimidazole-Type Piperidine Compounds were prepared from Compound 56. The co-reactant compounds are commercially available from, e.g., Sigma-Aldrich, or can be prepared by methods known to the art.

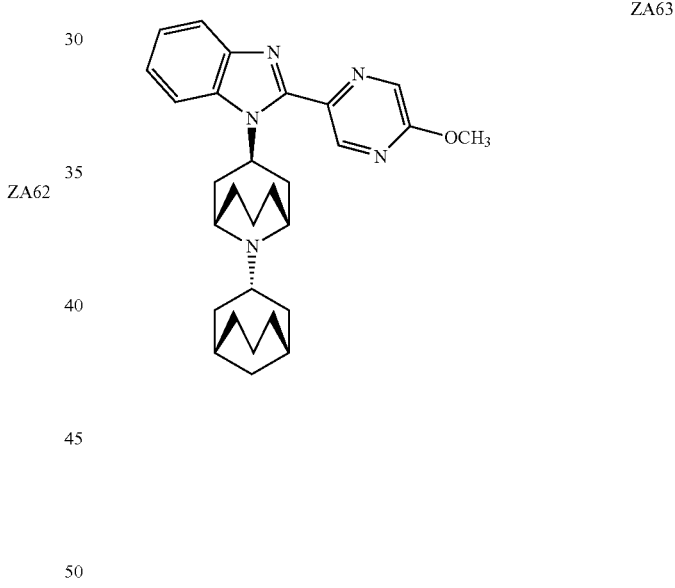

ZA63

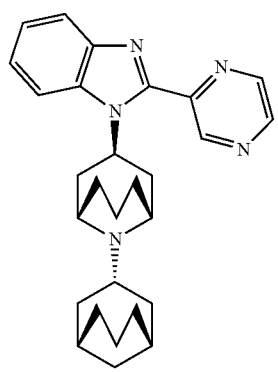

ZA64

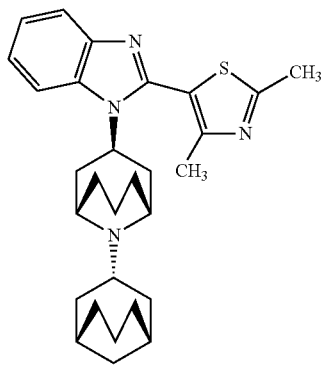

ZA65

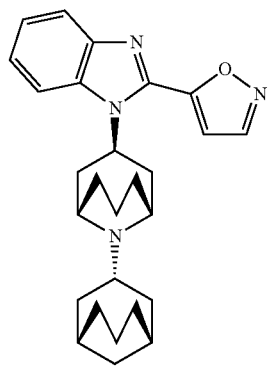

ZA66

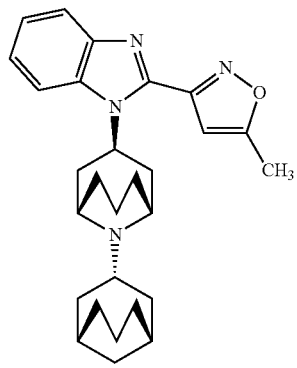

ZA67

ZA63: (1R,1'R,3r,3'R,5S,5'S)-3'-(2-(5-methoxypyrazin-2-yl)-1H-benzo[d]imidazol-1-yl)-9'-aza-3,9'-bi(bicyclo[3.3.1]nonane).

ZA63: $^1$H-NMR: $\delta_H$ (ppm, CD$_3$OD): 8.78-8.69 (m, 1H), 8.42-8.33 (m, 1H), 7.93-7.82 (m, 1H), 7.77-7.68 (m, 1H), 7.43-7.25 (m, 2H), 5.47-5.29 (m, 1H), 4.15 (s, 3H), 3.70-3.41 (m, 2H), 2.45-2.26 (m, 6H), 2.06-1.83 (m, 6H), 1.83-1.72 (m, 1H), 1.72-1.45 (m, 7H), 1.45-1.32 (m, 2H), 1.32-1.16 (m, 2H); MS: m/z=472.4 [M+H]$^+$.

ZA64: (1R,1'R,3r,3'R,5S,5'S)-3'-(2-(pyrazin-2-yl)-1H-benzo[d]imidazol-1-yl)-9'-aza-3,9'-bi(bicyclo[3.3.1]nonane).

ZA64: $^1$H-NMR: $\delta_H$ (ppm, CD$_3$OD): 9.44-9.39 (m, 1H), 9.14-9.07 (m, 1H), 9.04-8.99 (m, 1H), 8.45-8.37 (m, 1H), 8.09-8.00 (m, 1H), 7.89-7.74 (m, 2H), 6.26-6.10 (m, 1H), 4.38-4.19 (m, 3H), 2.99-2.87 (m, 2H), 2.82-2.70 (m, 2H), 2.43-2.27 (m, 1H), 2.27-2.06 (m, 8H), 2.06-1.96 (m, 1H), 1.84-1.45 (m, 10H); MS: m/z=442.2 [M+H]$^+$.

ZA65: 5-(1-((1R,1'R,3r,3'R,5S,5'S)-[3,9'-bi(9'-azabicyclo[3.3.1]nonan)]-3'-yl)-1H-benzo[d]imidazol-2-yl)-2,4-dimethylthiazole.

ZA65: $^1$H-NMR: $\delta_H$ (ppm, CD$_3$OD): 8.25-8.17 (m, 1H), 8.04-7.98 (m, 1H), 7.89-7.82 (m, 1H), 7.82-7.74 (m, 1H), 6.02-5.88 (m, 1H), 4.37-4.17 (m, 3H), 3.16 (s, 3H), 2.88-2.66 (m, 4H), 2.66 (s, 3H), 2.42-2.23 (m, 3H), 2.23-1.99 (m, 7H), 1.87-1.77 (m, 2H), 1.77-1.60 (m, 6H), 1.60-1.47 (m, 2H); MS: m/z=475.2 [M+H]$^+$.

ZA66: 5-(1-((1R,1'R,3r,3'R,5S,5'S)-[3,9'-bi(9'-azabicyclo[3.3.1]nonan)]-3'-yl)-1H-benzo[d]imidazol-2-yl)isoxazole.

ZA66: $^1$H-NMR: $\delta_H$ (ppm, CD$_3$OD): 8.75-8.69 (m, 1H), 8.00-7.91 (m, 1H), 7.84-7.77 (m, 1H), 7.54-7.37 (m, 2H), 7.17-7.10 (m, 1H), 5.61-5.44 (m, 1H), 4.42-3.83 (m, 3H), 2.81-2.52 (m, 4H), 2.52-2.02 (m, 8H), 2.02-1.43 (m, 12H); MS: m/z=431.3 [M+H]$^+$.

ZA67: 3-(1-((1R,1'R,3r,3'R,5S,5'S)-[3,9'-bi(9'-azabicyclo[3.3.1]nonan)]-3'-yl)-1H-benzo[d]imidazol-2-yl)-5-methylisoxazole.

ZA67: $^1$H-NMR: $\delta_H$ (ppm, CD$_3$OD): 7.95-7.89 (m, 1H), 7.86-7.76 (m, 1H), 7.54-7.33 (m, 2H), 6.89-6.72 (m, 1H), 6.48-6.30 (m, 1H), 4.46-4.13 (m, 3H), 2.93-2.51 (m, 9H), 2.51-1.55 (m, 18H); MS: m/z=445.4 [M+H]$^+$.

5.19 Example 19

Synthesis of Substituted Benzimidazole-Type Piperidine Compound ZA68 where t is 0 and the Q$_x$ Ring is a 5-Membered Heterocycle

5.18 Example 18

Synthesis of Substituted Benzimidazole-Type Piperidine Compounds where t is 0 and the Q$_x$ Ring is a 5-Membered Heterocycle Using procedures similar to those described in Example 14, the following Substituted Benzimidazole-Type Piperidine Compounds were prepared from Compound 56. The co-reactant compounds are commercially available from, e.g., Sigma-Aldrich, or can be prepared by methods known to the art.

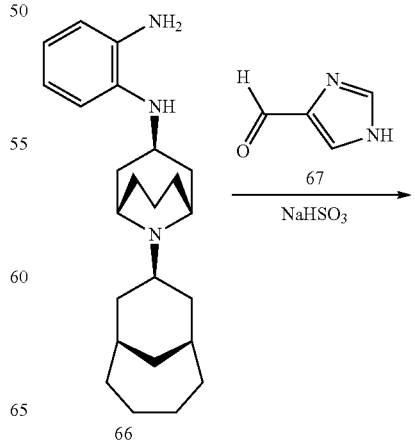

66

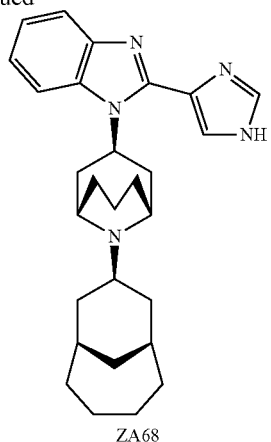

ZA68

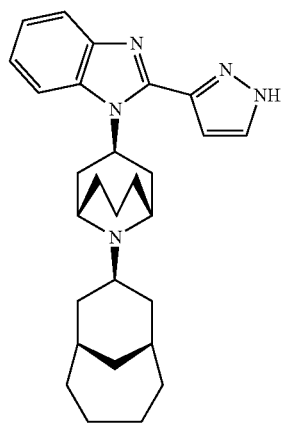

ZA69

To a solution of Compound 66 (0.184 g, 0.5 mmol) in EtOH (1 mL) at a temperature of about 25° C. was added 1H-imidazole-4-carbaldehyde (Compound 67, 0.048 g, 0.5 mmol, Sigma-Aldrich) and 40% aq. NaHSO₃ (1.1 mL). The resulting reaction mixture was then irradiated for 60 min at 150° C. using a BIOTAGE Initiator microwave synthesizer apparatus (Biotage, LLC, Charlotte, N.C.) operating at 2.45 GHz and a maximum of 400 Watts. Thereafter, the mixture was evaporated to dryness under reduced pressure to provide a product which was chromatographed on a flash column eluted with a gradient of from 0:100 MeOH (10% NH₄OH):DCM to 30:70 MeOH (10% NH₄OH):DCM. The fractions containing the product were combined and, under reduced pressure, evaporated and dried to provide Substituted Benzimidazole-Type Piperidine Compound ZA68, 1-((1R,3R,5S)-9-((1R,6S,8r)-bicyclo[4.3.1]decan-8-yl)-9-azabicyclo[3.3.1]nonan-3-yl)-2-(1H-imidazol-4-yl)-1H-benzo[d]imidazole (yield 40%).

The identity of Substituted Benzimidazole-Type Piperidine Compound ZA68 was confirmed using ¹H-NMR and MS.

ZA68: ¹H-NMR: δ$_H$ (ppm, CD₃OD): 7.83 (m, 2H), 7.68 (m, 1H), 7.62 (m, 1H), 7.29 (m, 2H), 5.46 (br, s, 1H), 3.65 (br, s, 2H), 3.17 (m, 1H), 2.48-2.22 (m, 7H), 1.97-1.49 (m, 12H), 1.43 (m, 2H), 1.29 (m, 4H); MS: m/z=444.3 [M+H]⁺.

5.20 Example 20

Synthesis of Substituted Benzimidazole-Type Piperidine Compounds where t is 0 and the Q$_x$ Ring is a 5- or 6-Membered Heterocycle Using procedures similar to those described in Example 19, the following Substituted Benzimidazole-Type Piperidine Compounds were prepared from Compound 66. The co-reactant compounds are commercially available from, e.g., Sigma-Aldrich, or can be prepared by methods known to the art.

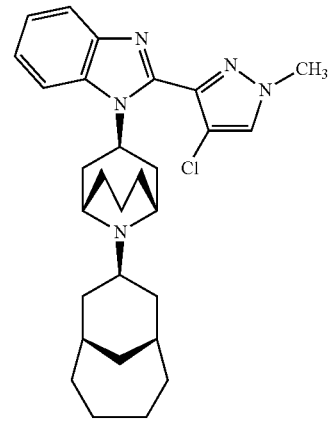

ZA70

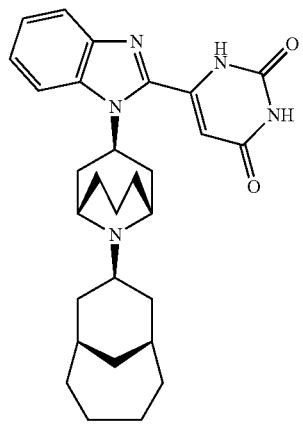

ZA71

ZA69: 1-((1R,3R,5S)-9-((1R,6S,8r)-bicyclo[3.3.1]decan-8-yl)-9-azabicyclo[3.3.1]nonan-3-yl)-2-(1H-pyrazol-3-yl)-1H-benzo[d]imidazole.

ZA69: ¹H-NMR: δ$_H$ (ppm, CD₃OD): 7.95 (m, 2H), 7.74 (m, 1H), 7.52 (m, 2H), 7.01 (m, 1H), 5.78 (m, 1H), 4.24 (m, 2H), 3.87 (m, 1H), 2.85 (m, 2H), 2.65 (m, 2H), 2.42 (m, 3H), 2.02 (m, 5H), 1.80 (m, 4H), 1.66 (m, 5H), 1.49 (m, 5H); MS: m/z=444.3 [M+H]⁺.

ZA70: 1-((1R,3R,5S)-9-((1R,6S,8r)-bicyclo[3.3.1]decan-8-yl)-9-azabicyclo[3.3.1]nonan-3-yl)-2-(4-chloro-1-methyl-1H-pyrazol-3-yl)-1H-benzo[d]imidazole.

ZA70: ¹H-NMR: δ$_H$ (ppm, CD₃OD): 7.98 (s, 1H), 7.85 (m, 1H), 7.73 (m, 1H), 7.43 (m, 2H), 5.38 (m, 1H), 4.21 (br, 2H), 3.97 (s, 3H), 3.84 (m, 1H), 2.64 (m, 4H), 2.35 (m, 2H), 2.17-1.56 (m, 16H), 1.45 (m, 4H); MS: m/z=492.4 [M+H]⁺.

ZA71: 6-(1-((1R,3R,5S)-9-((1R,6S,8r)-bicyclo[4.3.1]decan-8-yl)-9-azabicyclo[3.3.1]nonan-3-yl)-1H-benzo[d]imidazol-2-yl)pyrimidine-2,4(1H,3H)-dione.

ZA71: $^1$H-NMR: $\delta_H$ (ppm, CD$_3$OD): 7.81 (m, 1H), 7.73 (m, 1H), 7.38 (m, 2H), 5.91 (s, 1H), 5.14 (m, 1H), 4.22 (m, 2H), 3.87 (m, 1H), 2.64 (m, 4H), 2.38 (m, 3H), 2.03 (m, 5H), 1.76 (m, 7H), 1.51 (m, 7H); MS: m/z=488.3 [M+H]$^+$.

5.21 Example 21

In Vitro ORL-1 Receptor Binding Assay

ORL-1 Receptor Binding Assay Procedures: Membranes from recombinant HEK-293 cells expressing the human opioid receptor-like receptor (ORL-1) (Receptor Biology) were prepared by lysing cells in ice-cold hypotonic buffer (2.5 mM MgCl$_2$, 50 mM HEPES, pH 7.4) (10 mL/10 cm dish) followed by homogenization with a tissue grinder/Teflon pestle. Membranes were collected by centrifugation at 30,000×g for 15 min at 4° C. and pellets resuspended in hypotonic buffer to a final concentration 1-3 mg/mL. Protein concentrations were determined using the BioRad protein assay reagent with bovine serum albumen as a standard. Aliquots of the ORL-1 receptor membranes were stored at −80° C.

Radioligand binding assays (screening and dose-displacement) used 0.1 nM [$^3$H]-nociceptin (NEN; 87.7 Ci/mmole) with 10-20 µg membrane protein in a final volume of 500 µL binding buffer (10 mM MgCl$_2$, 1 mM EDTA, 5% DMSO, 50 mM HEPES, pH 7.4). Non-specific binding was determined in the presence of 10 nM unlabeled nociceptin (American Peptide Company). All reactions were performed in 96-deep well polypropylene plates for 1 h at about 25° C. Binding reactions were terminated by rapid filtration onto 96-well Unifilter GF/C filter plates (Packard) presoaked in 0.5% polyethylenimine (Sigma-Aldrich). Harvesting was performed using a 96-well tissue harvester (Packard) followed by three filtration washes with 500 µL ice-cold binding buffer. Filter plates were subsequently dried at 50° C. for 2-3 hrs. Fifty µL/well scintillation cocktail (BetaScint; Wallac) was added and plates were counted in a Packard Top-Count for 1 min/well. The data from screening and dose-displacement experiments were analyzed using Microsoft Excel and the curve fitting functions in GraphPad PRISM™, v. 3.0, respectively, or an in-house function for one-site competition curve-fitting.

ORL-1 Receptor Binding Data: An Substituted Benzimidazole-Type Piperidine Compound has a binding affinity (K$_1$) for the human ORL-1 receptor of about 1000 nM or less in one embodiment, or about 500 nM or less in another embodiment. In certain embodiments, a Substituted Benzimidazole-Type Piperidine Compound has a K$_i$ (nM) of about 300 or less for binding to ORL-1 receptors. In one embodiment, a Substituted Benzimidazole-Type Piperidine Compound has a K$_i$ (nM) of about 100 or less. In another embodiment, a Substituted Benzimidazole-Type Piperidine Compound of the disclosure has a K$_i$ (nM) of about 35 or less. In another embodiment, a Substituted Benzimidazole-Type Piperidine Compound of the disclosure has a K$_i$ (nM) of about 20 or less. In another embodiment, a Substituted Benzimidazole-Type Piperidine Compound of the disclosure has a K$_i$ (nM) of about 15 or less. In another embodiment, a Substituted Benzimidazole-Type Piperidine Compound of the disclosure has a K$_i$ (nM) of about 10 or less. In another embodiment, a Substituted Benzimidazole-Type Piperidine Compound of the disclosure has a K$_i$ (nM) of about 4 or less. In another embodiment, a Substituted Benzimidazole-Type Piperidine Compound of the disclosure has a K$_i$ (nM) of about 1 or less. In another embodiment, a Substituted Benzimidazole-Type Piperidine Compound of the disclosure has a K$_i$ (nM) of about 0.4 or less. In another embodiment, a Substituted Benzimidazole-Type Piperidine Compound of the disclosure has a K$_i$ (nM) of about 0.1 or less.

5.22 Example 22

In Vitro ORL-1 Receptor Functional Assay

ORL-1 Receptor [$^{35}$S]GTPγS Binding Assay Procedures: Membranes from recombinant HEK-293 cells expressing the human opioid receptor-like (ORL-1) (Receptor Biology) were prepared by lysing cells in ice-cold hypotonic buffer (2.5 mM MgCl$_2$, 50 mM HEPES, pH 7.4) (10 mL/10 cm dish) followed by homogenization with a tissue grinder/Teflon pestle. Membranes were collected by centrifugation at 30,000×g for 15 min at 4° C., and pellets resuspended in hypotonic buffer to a final concentration of 1-3 mg/mL. Protein concentrations were determined using the BioRad protein assay reagent with bovine serum albumen as a standard. Aliquots of the ORL-1 receptor membranes were stored at −80° C.

Functional binding assays were conducted as follows. ORL-1 membrane solution was prepared by sequentially adding final concentrations of 0.066 µg/µL ORL-1 membrane protein, 10 µg/mL saponin, 3 µM GDP and 0.20 nM [35S]GTPγS to binding buffer (100 mM NaCl, 10 mM MgCl$_2$, 20 mM HEPES, pH 7.4) on ice. The prepared membrane solution (190 µL/well) was transferred to 96-shallow well polypropylene plates containing 10 µL of 20× concentrated stock solutions of agonist/nociceptin prepared in DMSO. Plates were incubated for 30 min at about 25° C. with shaking. Reactions were terminated by rapid filtration onto 96-well Unifilter GF/B filter plates (Packard) using a 96-well tissue harvester (Packard) and followed by three filtration washes with 200 µL ice-cold binding buffer (10 mM NaH$_2$PO$_4$, 10 mM Na$_2$HPO$_4$, pH 7.4). Filter plates were subsequently dried at 50° C. for 2-3 hrs. Fifty µL/well scintillation cocktail (BetaScint; Wallac) was added and plates were counted in Packard Top-Count for 1 min/well. Data are analyzed using the sigmoidal dose-response curve fitting functions in GraphPad PRISM v. 3.0, or an in-house function for non-linear, sigmoidal dose-response curve-fitting.

ORL-1 Receptor Functional Data: ORL-1 GTP EC$_{50}$ is the concentration of a compound providing 50% of the maximal response for the compound at an ORL-1 receptor. In one embodiment, a Substituted Benzimidazole-Type Piperidine Compound has an ORL-1 GTP EC$_{50}$ (nM) of about 5000 or less to stimulate ORL-1 receptor function. In another embodiment, a Substituted Benzimidazole-Type Piperidine Compound has an ORL-1 GTP EC$_{50}$ (nM) of about 1000 or less. In another embodiment, a Substituted Benzimidazole-Type Piperidine Compound has an ORL-1 GTP EC$_{50}$ (nM) of about 100 or less. In another embodiment, a Substituted Benzimidazole-Type Piperidine Compound has an ORL-1 GTP EC$_{50}$ (nM) of about 80 or less. In another embodiment, a Substituted Benzimidazole-Type Piperidine Compound has an ORL-1 GTP EC$_{50}$ (nM) of about 50 or less. In another embodiment, a Substituted Benzimidazole-Type Piperidine Compound has an ORL-1 GTP EC$_{50}$ (nM) of about 35 or less. In another embodiment, a Substituted Benzimidazole-Type Piperidine Compound has an ORL-1 GTP EC$_{50}$ (nM) of about 15 or less. In another embodiment, a Substituted Benzimidazole-Type Piperidine Compound has an ORL-1 GTP $EC_{50}$ (nM) of about 10 or less. In another embodiment, a Substituted Benzimidazole-Type Piperidine Compound has an ORL-1 GTP $EC_{50}$ (nM) of about 4 or less. In another embodiment, a Substituted Benzimidazole-Type Piperidine Compound has an ORL-1 GTP $EC_{50}$ (nM) of about 1 or less. In another embodiment, a Substituted Benzimidazole-Type Piperidine Compound has an ORL-1 GTP $EC_{50}$ (nM) of about 0.4 or less. In another embodiment, a Substituted Benzimidazole-Type Piperidine Compound has an ORL-1 GTP $EC_{50}$ (nM) of about 0.1 or less.

ORL-1 GTP Emax (%) is the maximal effect elicited by a compound relative to the effect elicited by nociceptin, a standard ORL-1 agonist. In one embodiment, a Substituted Benzimidazole-Type Piperidine Compound has an ORL-1 GTP Emax (%) of about 50% or greater. In another embodiment, a Substituted Benzimidazole-Type Piperidine Compound has an ORL-1 GTP Emax (%) of about 75% or greater. In another embodiment, a Substituted Benzimidazole-Type Piperidine Compound has an ORL-1 GTP Emax (%) of about 85% or greater. In another embodiment, a Substituted Benzimidazole-Type Piperidine Compound has an ORL-1 GTP Emax (%) of about 95% or greater. In another embodiment, a Substituted Benzimidazole-Type Piperidine Compound has an ORL-1 GTP Emax (%) of about 100% or greater. In another embodiment, a Substituted Benzimidazole-Type Piperidine Compound has an ORL-1 GTP Emax (%) of about 110% or greater. In certain embodiments, a Substituted Benzimidazole-Type Piperidine Compound acting as a partial agonist has an ORL-1 GTP Emax (%) of less than about 10%. In one embodiment, partial agonist Substituted Benzimidazole-Type Piperidine Compounds has an ORL-1 GTP Emax (%) of less than about 20%. In another embodiment, partial agonist Substituted Benzimidazole-Type Piperidine Compounds has an ORL-1 GTP Emax (%) of less than about 30%. In another embodiment, partial agonist Substituted Benzimidazole-Type Piperidine Compounds has an ORL-1 GTP Emax (%) of less than about 40%. In another embodiment, partial agonist Substituted Benzimidazole-Type Piperidine Compounds has an ORL-1 GTP Emax (%) of less than about 50%.

5.23 Example 23

In Vitro Mu-Opioid Receptor Binding Assays

μ-Opioid Receptor Binding Assay Procedures: Radioligand binding assays were conducted using freshly thawed membranes expressing human μ-receptors (Perkin Elmer, Shelton, Conn.). Radioligand dose-displacement binding assays for human μ-opioid receptors used 0.2 nM [$^{3}$H]-diprenorphine (NEN, Boston, Mass.), with 5-20 mg membrane protein/well in a final volume of 500 μL, binding buffer (10 mM $MgCl_2$, 1 mM EDTA, 5% DMSO, 50 mM HEPES, pH 7.4). Reactions were carried out in the absence or presence of increasing concentrations of unlabeled naloxone. All reactions were conducted in 96-deep well polypropylene plates for 1-2 hrs at about 25° C. Binding reactions were terminated by rapid filtration onto 96-well Unifilter GF/C filter plates (Packard, Meriden, Conn.) presoaked in 0.5% polyethylenimine using a 96-well tissue harvester (Brandel, Gaithersburg, Md.) followed by performing three filtration washes with 5004 of ice-cold binding buffer. Filter plates were subsequently dried at 50° C. for 2-3 hrs. BetaScint scintillation cocktail (Wallac, Turku, Finland) was added (50 μL/well), and plates were counted using a Packard Top-Count for 1 min/well. The data were analyzed using the one-site competition curve fitting functions in GraphPad PRISM v. 3.0 (San Diego, Calif.), or an in-house function for one-site competition curve-fitting.

μ-Opioid Receptor Binding Data: In certain embodiments, a Substituted Benzimidazole-Type Piperidine Compound has a $K_i$ (nM) of about 3000 or less for binding to μ-opioid receptors, or about 1000 or less, or about 650 or less, or about 525 or less, or about 250 or less, or about 100 or less, or about 10 or less, or about 1 or less, or about 0.1 or less.

5.24 Example 24

In vitro Mu-Opioid Receptor Functional Assays

μ-Opioid Receptor Functional Assay Procedures: [$^{35}$S] GTPγS functional assays were conducted using freshly thawed membranes expressing human μ-receptors. Assay reactions were prepared by sequentially adding the following reagents to binding buffer (100 mM NaCl, 10 mM $MgCl_2$, 20 mM HEPES, pH 7.4) on ice (final concentrations indicated): membrane protein (0.026 mg/mL), saponin (10 mg/mL), GDP (3 mM) and [$^{35}$S]GTPγS (0.20 nM; NEN). The prepared membrane solution (190 μL/well) was transferred to 96-shallow well polypropylene plates containing 10 μL of 20× concentrated stock solutions of the agonist DAMGO ([D-Ala2, N-methyl-Phe4 Gly-ol5]-enkephalin) prepared in DMSO. Plates were incubated for 30 min at about 25° C. with shaking. Reactions were terminated by rapid filtration onto 96-well Unifilter GF/B filter plates (Packard, Meriden, Conn.) using a 96-well tissue harvester (Brandel, Gaithersburg, Md.) followed by three filtration washes with 200 μL of ice-cold wash buffer (10 mM $NaH_2PO_4$, 10 mM $Na_2HPO_4$, pH 7.4). Filter plates were subsequently dried at 50° C. for 2-3 hrs. BetaScint scintillation cocktail (Wallac, Turku, Finland) was added (50 μL/well) and plates were counted using a Packard Top-Count for 1 min/well. Data were analyzed using the sigmoidal dose-response curve fitting functions in GraphPad PRISM v. 3.0, or an in-house function for non-linear, sigmoidal dose-response curve-fitting.

μ-Opioid Receptor Functional Data: μGTP $EC_{50}$ is the concentration of a compound providing 50% of the maximal response for the compound at a μ-opioid receptor. In certain embodiments, a Substituted Benzimidazole-Type Piperidine Compound has a μ GTP $EC_{50}$ (nM) of about 5000 or less, or about 4100 or less, or about 3100 or less, or about 2000 or less, or about 1000 or less, or about 100 or less, or about 10 or less, or about 1 or less, or about 0.4 or less, or about 0.1 or less.

μ GTP Emax (%) is the maximal effect elicited by a compound relative to the effect elicited by DAMGO, a standard μ agonist. In certain embodiments, a Substituted Benzimidazole-Type Piperidine Compound has a μ GTP Emax (%) of about 10% or greater, or about 20% or greater, or about 50% or greater, or about 65% or greater, or about 75% or greater, or about 88% or greater, or about 100% or greater. In other embodiments, a Substituted Benzimidazole-Type Piperidine Compound has a μ GTP Emax (%) of about 10% or less, or about 5% or less, or about 2% or less.

5.25 Example 25

In Vitro Kappa-Opioid Receptor Binding Assays

κ-Opioid Receptor Binding Assay Procedures: Membranes from recombinant HEK-293 cells expressing the human kappa opioid receptor (kappa) (cloned in house) were prepared by lysing cells in ice cold hypotonic buffer (2.5 mM $MgCl_2$, 50 mM HEPES, pH 7.4) (10 mL/10 cm dish) followed by homogenization with a tissue grinder/Teflon pestle. Membranes were collected by centrifugation at 30,000×g for 15 min at 4° C. and pellets resuspended in hypotonic buffer to a final concentration of 1-3 mg/mL. Protein concentrations were determined using the BioRad protein assay reagent with bovine serum albumen as a standard. Aliquots of kappa receptor membranes were stored at −80° C.

Radioligand dose displacement assays used 0.4-0.8 nM [$^3$H]-U69,593 (NEN; 40 Ci/mmole) with 10-20 µg membrane protein (recombinant kappa opioid receptor expressed in HEK 293 cells; in-house prep) in a final volume of 200 µL, binding buffer (5% DMSO, 50 mM Trizma base, pH 7.4). Non-specific binding was determined in the presence of 10 µM unlabeled naloxone or U69,593. All reactions were performed in 96-well polypropylene plates for 1 h at a temperature of about 25° C. Binding reactions were determined by rapid filtration onto 96-well Unifilter GF/C filter plates (Packard) presoaked in 0.5% polyethylenimine (Sigma-Aldrich). Harvesting was performed using a 96-well tissue harvester (Packard) followed by five filtration washes with 200 µL, ice-cold binding buffer. Filter plates were subsequently dried at 50° C. for 1-2 hrs. Fifty µL/well scintillation cocktail (MicroScint20, Packard) was added and plates were counted in a Packard Top-Count for 1 min/well.

κ-Opioid Receptor Binding Data: In one embodiment, a Substituted Benzimidazole-Type Piperidine Compound has substantially no activity at a κ-opioid receptor. In certain embodiments, a Substituted Benzimidazole-Type Piperidine Compound has a Ki (nM) of about 20,000 or less, or about 10,000 or less, or about 5000 or less, or about 500 or less, or about 300 or less, or about 100 or less, or about 50 or less, or about 20 or less, or about 15 or less, or about 10 or less.

5.26 Example 26

In Vitro Kappa-Opioid Receptor Functional Assays

κ-Opioid Receptor Functional Assay Procedures: Functional [$^{35}$S]GTPγS binding assays were conducted as follows. Kappa opioid receptor membrane solution was prepared by sequentially adding final concentrations of 0.026 µg/µL kappa membrane protein (in-house), 10 µg/mL saponin, 3 µM GDP and 0.20 nM [$^{35}$S]GTPγS to binding buffer (100 mM NaCl, 10 mM $MgCl_2$, 20 mM HEPES, pH 7.4) on ice. The prepared membrane solution (190 µL/well) was transferred to 96-shallow well polypropylene plates containing 10 µL of 20× concentrated stock solutions of agonist prepared in DMSO. Plates were incubated for 30 min at a temperature of about 25° C. with shaking. Reactions were terminated by rapid filtration onto 96-well Unifilter GF/B filter plates (Packard) using a 96-well tissue harvester (Packard) and followed by three filtration washes with 2004, ice-cold binding buffer (10 mM $NaH_2PO_4$, 10 mM $Na_2HPO_4$, pH 7.4). Filter plates were subsequently dried at 50° C. for 2-3 hrs. Fifty µL/well scintillation cocktail (MicroScint20, Packard) was added and plates were counted in a Packard Top-Count for 1 min/well.

κ-Opioid Receptor Functional Data: κ GTP $EC_{50}$ is the concentration of a compound providing 50% of the maximal response for the compound at a κ-opioid receptor. In certain embodiments, a Substituted Benzimidazole-Type Piperidine Compound has a κ GTP $EC_{50}$ (nM) of about 20,000 or less, or about 10,000 or less, or about 5000 or less, or about 2000 or less, or about 1500 or less, or about 800 or less, or about 500 or less, or about 300 or less, or about 100 or less, or about 50 or less, or about 10 or less.

κ GTP Emax (%) is the maximal effect elicited by a compound relative to the effect elicited by U69,593. In certain embodiments, a Substituted Benzimidazole-Type Piperidine Compound has a κ GTP Emax (%) of about 10% or greater, or about 15% or greater, or about 30% or greater, or about 40% or greater, or about 45% or greater, or about 75% or greater, or about 90% or greater, or about 100% or greater. In other embodiments, a Substituted Benzimidazole-Type Piperidine Compound has a κ GTP Emax (%) of about 10% or less, or about 5% or less, or about 2% or less.

5.27 Example 27

In Vitro Delta-Opioid Receptor Binding Assays

δ-Opioid Receptor Binding Assay Procedures: Radioligand dose-displacement assays used 0.2 nM [$^3$H]-Naltrindole (NEN; 33.0 Ci/mmole) with 10-20 µg membrane protein (recombinant delta opioid receptor expressed in CHO-K1 cells; Perkin Elmer) in a final volume of 500 µL binding buffer (5 mM $MgCl_2$, 5% DMSO, 50 mM Trizma base, pH 7.4). Non-specific binding was determined in the presence of 25 µM unlabeled naloxone. All reactions were performed in 96-deep well polypropylene plates for 1 h at a temperature of about 25° C. Binding reactions were determined by rapid filtration onto 96-well Unifilter GF/C filter plates (Packard) presoaked in 0.5% polyethylenimine (Sigma-Aldrich). Harvesting was performed using a 96-well tissue harvester (Packard) followed by five filtration washes with 500 µL ice-cold binding buffer. Filter plates were subsequently dried at 50° C. for 1-2 hrs. Fifty µL/well scintillation cocktail (MicroScint20, Packard) was added and plates were counted in a Packard Top-Count for 1 min/well.

δ-Opioid Receptor Binding Data: In one embodiment, a Substituted Benzimidazole-Type Piperidine Compound has substantially no activity at a δ-opioid receptor. In certain embodiments, a Substituted Benzimidazole-Type Piperidine Compound has a Ki (nM) of about 20,000 or less, or about 10,000 or less, or about 7500 or less, or about 6500 or less, or about 5000 or less, or about 3000 or less, or about 2500 or less, or about 1000 or less, or about 500 or less, or about 350 or less, or about 250 or less, or about 100 or less, or about 10 or less.

5.28 Example 28

In vitro Delta-Opioid Receptor Functional Assays

δ-Opioid Receptor Functional Assay Procedures: Functional [$^{35}$S]GTPγS binding assays were conducted as follows using membranes expressing human δ-opioid receptors. Delta opioid receptor membrane solution was prepared by sequentially adding final concentrations of 0.026 µg/pt delta membrane protein (Perkin Elmer), 10 µg/mL saponin, 3 µM GDP and 0.20 nM [$^{35}$S]GTPγS to binding buffer (100 mM NaCl, 10 mM $MgCl_2$, 20 mM HEPES, pH 7.4) on ice. The prepared membrane solution (190 µL/well) was transferred to 96-shallow well polypropylene plates containing 10 µL of 20× concentrated stock solutions of agonist prepared in DMSO. Plates were incubated for 30 min at a temperature of about 25° C. with shaking. Reactions were terminated by rapid filtration onto 96-well Unifilter GF/B filter plates (Packard) using a 96-well tissue harvester (Packard) and followed by three filtration washes with 200 µL ice-cold binding buffer (10 mM $NaH_2PO_4$, 10 mM $Na_2HPO_4$, pH 7.4). Filter plates were subsequently dried at 50° C. for 1-2 hrs. Fifty μL/well scintillation cocktail (MicroScint20, Packard) was added and plates were counted in a Packard Top-count for 1 min/well.

δ-Opioid Receptor Functional Data: δ GTP $EC_{50}$ is the concentration of a compound providing 50% of the maximal response for the compound at a δ receptor. In certain embodiments, a Substituted Benzimidazole-Type Piperidine Compound has a δ GTP $EC_{50}$ (nM) of about 20,000 or less, or about 10,000 or less, or about 100 or less, or about 1000 or less, or about 90 or less, or about 50 or less, or about 25 or less, or about 10 or less.

δ GTP Emax (%) is the maximal effect elicited by a compound relative to the effect elicited by met-enkephalin. In certain embodiments, a Substituted Benzimidazole-Type Piperidine Compound has a δ GTP Emax (%) of about 10% or greater, or about 30% or greater, or about 50% or greater, or about 75% or greater, or about 90% or greater, or about 100% or greater, or about 110% or greater. In other embodiments, a Substituted Benzimidazole-Type Piperidine Compound has a δ GTP Emax (%) of about 10% or less, or about 5% or less, or about 2% or less.

5.29 Example 29

Efficacy of Receptor Binding and Activity Response

The following Tables provide, for several Substituted Benzimidazole-Type Piperidine Compounds and certain other compounds of interest, results on the efficacy of binding and activity response to the ORL-1 receptor, the mu-opioid receptor, the kappa-opioid receptor, and/or the delta-opioid receptor and CYP2D6 response.

In Table 18, binding efficacy to the ORL-1 receptor was determined by the procedure in Example 21. Binding efficacy to the mu-opioid receptor was determined by the procedure in Example 23. Binding efficacy to the kappa-opioid receptor was determined by the procedure in Example 25. Binding efficacy to the delta-opioid receptor was determined by the procedure in Example 27.

In Table 19, activity response to the ORL-1 receptor was determined by the procedure in Example 22. Activity response to the mu-opioid receptor was determined by the procedure in Example 24. Activity response to the kappa-opioid receptor was determined by the procedure in Example 26. Activity response to the delta-opioid receptor can be determined by the procedure in Example 28.

TABLE 18

Efficacy of Receptor Binding of Substituted Benzimidazole-Type Piperidine Compounds and Certain Other Compounds of Interest

| | | $K_i$ [Average ± Std Deviation] (nM) | | | |
| --- | --- | --- | --- | --- | --- |
| | | | Opioid Receptor | | |
| Ref. No. | Compound | ORL-1 | Mu | Kappa | Delta |
| B56c(i) | [structure] | 2068 ± 98 | — | — | — |
| B56c(ii) | [structure] | 220 ± 24 | >20,000 | 353 ± 39 | >20,000 |

TABLE 18-continued

Efficacy of Receptor Binding of Substituted Benzimidazole-Type Piperidine Compounds and Certain Other Compounds of Interest

| | | $K_i$ [Average ± Std Deviation] (nM) | | | |
|---|---|---|---|---|---|
| | | | Opioid Receptor | | |
| Ref. No. | Compound | ORL-1 | Mu | Kappa | Delta |
| E30c(ii) | | 37.9 ± 4.1 | — | — | — |
| E32c(ii) | | 690 ± 84 | — | — | — |
| E56c(ii) | | 583 ± 40 | — | — | — |

TABLE 18-continued
Efficacy of Receptor Binding of Substituted Benzimidazole-Type Piperidine Compounds and Certain Other Compounds of Interest
| | | $K_i$ [Average ± Std Deviation] (nM) | | | |
| | | | Opioid Receptor | | |
| Ref. No. | Compound | ORL-1 | Mu | Kappa | Delta |
| H4d | 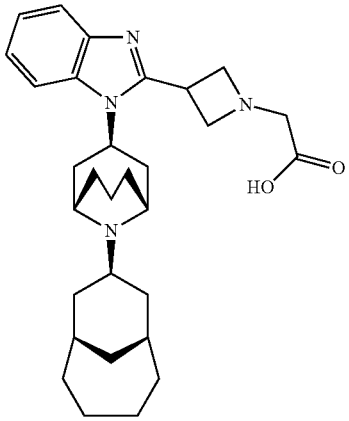 [SMILES: O=C(O)CN1CC(c2nc3ccccc3n2[C@H]2C[C@H]3CCC[C@@H](C2)N3[C@@H]2C[C@@H]3CCCC[C@@H](C3)C2)C1] | 4.73 ± 0.07 | — | — | — |
| H6d | 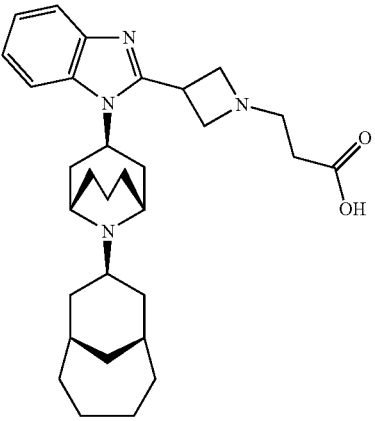 [SMILES: O=C(O)CCN1CC(c2nc3ccccc3n2[C@H]2C[C@H]3CCC[C@@H](C2)N3[C@@H]2C[C@@H]3CCCC[C@@H](C3)C2)C1] | 8.9 ± 0.3 | — | — | — |
| H27b(i) | 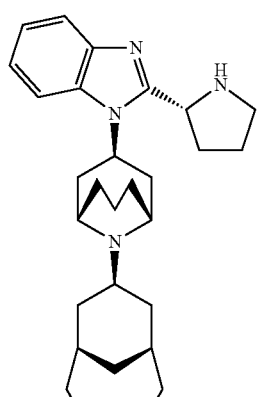 | 1.9 ± 0.4 | — | — | — |

TABLE 18-continued

Efficacy of Receptor Binding of Substituted Benzimidazole-Type Piperidine Compounds and Certain Other Compounds of Interest

| | | K$_i$ [Average ± Std Deviation] (nM) | | | |
| --- | --- | --- | --- | --- | --- |
| | | | Opioid Receptor | | |
| Ref. No. | Compound | ORL-1 | Mu | Kappa | Delta |
| H30b(i) | | 18.2 ± 5.7 | 3560 ± 790 | 150 ± 44 | 16,200 |
| H30b(ii) | | 9.0 ± 2.2 | 1112 ± 297 | 65.2 ± 14.1 | 5275 ± 1863 |
| H30d(ii) | | 18.6 ± 2.4 | — | — | — |

TABLE 18-continued
Efficacy of Receptor Binding of Substituted Benzimidazole-Type Piperidine
Compounds and Certain Other Compounds of Interest
| | | | $K_i$ [Average ± Std Deviation] (nM) | | | |
| | | | | Opioid Receptor | | |
| Ref. No. | Compound | ORL-1 | Mu | Kappa | Delta |
|---|---|---|---|---|---|
| H32b(ii) | 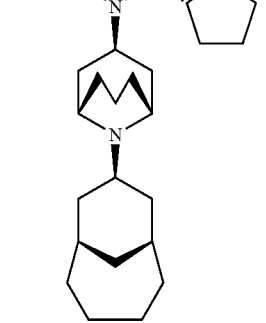 | 96.9 ± 13.9 | 5540 ± 1640 | 828 ± 98 | >20,000 |
| H32d(ii) | 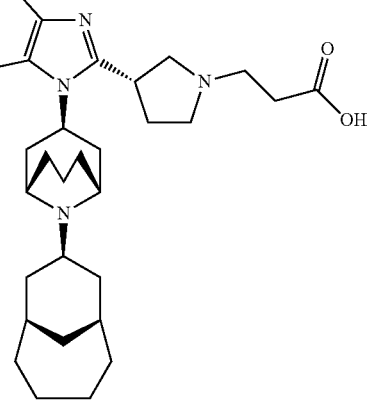 | 86 ± 20 | — | — | — |
| H36b(i) | 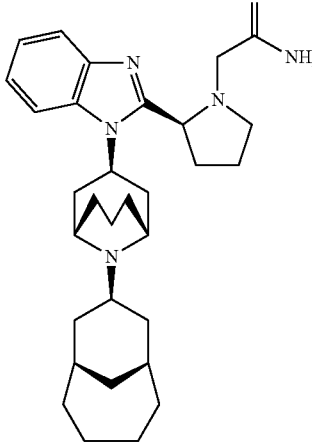 | 19.0 ± 1.3 | 1670 ± 360 | 123 ± 19 | >20,000 |

TABLE 18-continued

Efficacy of Receptor Binding of Substituted Benzimidazole-Type Piperidine
Compounds and Certain Other Compounds of Interest

| | | $K_i$ [Average ± Std Deviation] (nM) | | | |
| | | | Opioid Receptor | | |
| Ref. No. | Compound | ORL-1 | Mu | Kappa | Delta |
|---|---|---|---|---|---|
| H56b(i) | | 45.5 ± 3.6 | 4640 ± 1150 | 108 ± 8 | 6790 ± 1270 |
| H56b(ii) | | 55 ± 11 | 11,320 ± 3,780 | 16.3 ± 5.3 | >20,000 |
| H56d(ii) | | 43.4 ± 10.7 | 7450 ± 1460 | 700 ± 180 | >20,000 |

TABLE 18-continued
Efficacy of Receptor Binding of Substituted Benzimidazole-Type Piperidine
Compounds and Certain Other Compounds of Interest
| | | K$_i$ [Average ± Std Deviation] (nM) | | | |
| | | | Opioid Receptor | | |
| Ref. No. | Compound | ORL-1 | Mu | Kappa | Delta |
|---|---|---|---|---|---|
| H58d(ii) | 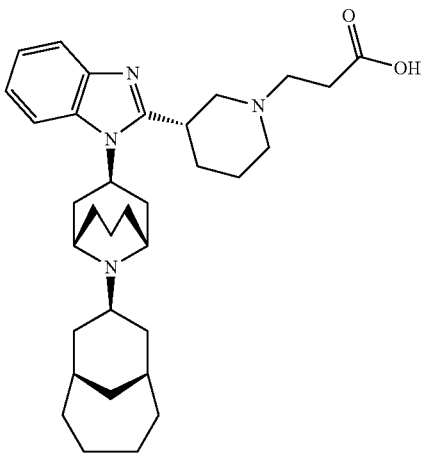 [SMILES: O=C(O)CCN1CCC[C@H](c2nc3ccccc3n2[C@H]2C[C@H]3CCC[C@@H](C2)N3[C@@H]2C[C@@H]3CCCC[C@@H](C3)C2)C1] | 86 ± 8 | >20,000 | 254 ± 57 | >20,000 |
| H62d(ii) | 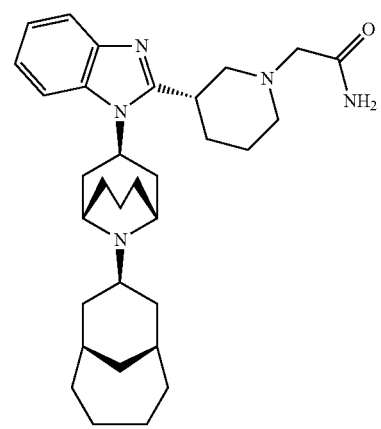 [SMILES: NC(=O)CN1CCC[C@H](c2nc3ccccc3n2[C@H]2C[C@H]3CCC[C@@H](C2)N3[C@@H]2C[C@@H]3CCCC[C@@H](C3)C2)C1] | 15.7 ± 2.4 | — | — | — |
| O85d | 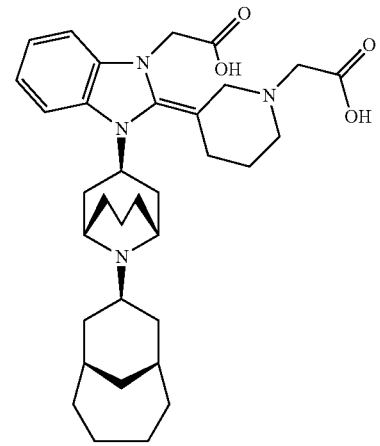 [SMILES: O=C(O)CN1CCC/C(=C2/N(CC(=O)O)c3ccccc3N2[C@H]2C[C@H]3CCC[C@@H](C2)N3[C@@H]2C[C@@H]3CCCC[C@@H](C3)C2)C1] | 21.7 ± 3.2 | 11,770 | 41.3 ± 16.5 | 12,140 |

TABLE 18-continued

Efficacy of Receptor Binding of Substituted Benzimidazole-Type Piperidine Compounds and Certain Other Compounds of Interest

| | | $K_i$ [Average ± Std Deviation] (nM) | | | |
| | | | Opioid Receptor | | |
| Ref. No. | Compound | ORL-1 | Mu | Kappa | Delta |
| ZA07 | | 42.7 ± 5.6 | — | — | — |
| ZA08 | | 92 ± 16 | — | — | — |
| ZA09 | | 14.2 ± 1.2 | — | — | — |

TABLE 18-continued

Efficacy of Receptor Binding of Substituted Benzimidazole-Type Piperidine Compounds and Certain Other Compounds of Interest

| | | $K_i$ [Average ± Std Deviation] (nM) | | | |
|---|---|---|---|---|---|
| | | | Opioid Receptor | | |
| Ref. No. | Compound | ORL-1 | Mu | Kappa | Delta |
| ZA10 | | 23.5 ± 3.0 | >20,000 | 822 ± 260 | >20,000 |
| ZA11 | | 182 ± 25 | — | — | — |
| ZA12 | | 117 ± 15 | — | — | — |

TABLE 18-continued
Efficacy of Receptor Binding of Substituted Benzimidazole-Type Piperidine
Compounds and Certain Other Compounds of Interest
| | | $K_i$ [Average ± Std Deviation] (nM) | | | |
| | | | Opioid Receptor | | |
| Ref. No. | Compound | ORL-1 | Mu | Kappa | Delta |
|---|---|---|---|---|---|
| ZA14 | 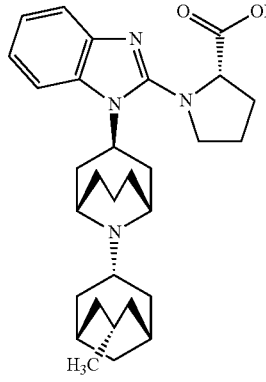 | 505 ± 29 | — | — | — |
| ZA16 | 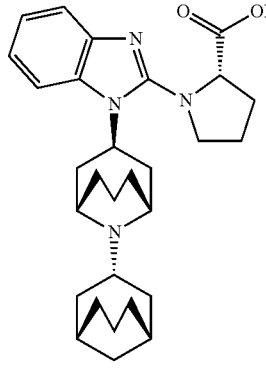 | 3250 ± 303 | — | — | — |
| ZA18 | 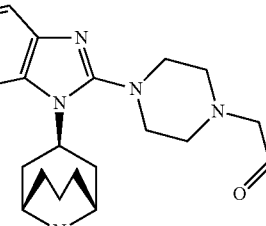 | 251 ± 10 | — | — | — |

TABLE 18-continued
Efficacy of Receptor Binding of Substituted Benzimidazole-Type Piperidine Compounds and Certain Other Compounds of Interest
| | | $K_i$ [Average ± Std Deviation] (nM) | | | |
| | | | Opioid Receptor | | |
| Ref. No. | Compound | ORL-1 | Mu | Kappa | Delta |
| ZA20 | 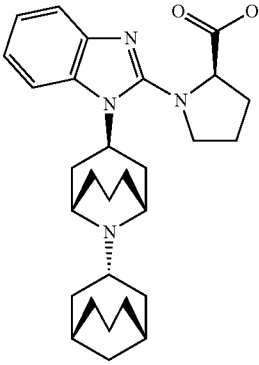 | 1250 ± 97 | — | — | — |
| ZA23 | 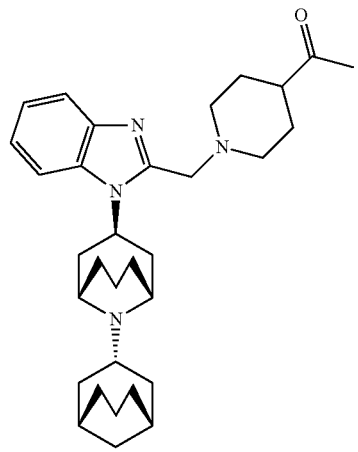 [SMILES: CC(=O)C1CCN(Cc2nc3ccccc3n2[C@H]2C[C@H]3CCC[C@@H](C2)N3[C@H]2C[C@@H]3CCC[C@@H](C3)C2)CC1] | 27.7 ± 0.4 | — | — | — |
| ZA25 | 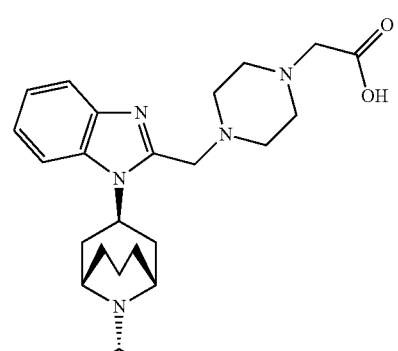 | 66 ± 14 | >20,000 | 6800 ± 710 | 10,900 |

TABLE 18-continued

Efficacy of Receptor Binding of Substituted Benzimidazole-Type Piperidine Compounds and Certain Other Compounds of Interest

| | | $K_i$ [Average ± Std Deviation] (nM) | | | |
| --- | --- | --- | --- | --- | --- |
| | | | Opioid Receptor | | |
| Ref. No. | Compound | ORL-1 | Mu | Kappa | Delta |
| ZA26 | | 17.5 ± 2.7 | 511 ± 73 | 59 ± 21 | 1616 ± 213 |
| ZA27 | | 36.7 ± 2.0 | 339 ± 21 | 33.7 ± 3.2 | 10,260 ± 390 |
| ZA28 | | 22.4 ± 2.6 | 2473 ± 733 | 26.2 ± 8.0 | 5655 ± 677 |

TABLE 18-continued

Efficacy of Receptor Binding of Substituted Benzimidazole-Type Piperidine
Compounds and Certain Other Compounds of Interest

| | | $K_i$ [Average ± Std Deviation] (nM) | | | |
| --- | --- | --- | --- | --- | --- |
| | | | Opioid Receptor | | |
| Ref. No. | Compound | ORL-1 | Mu | Kappa | Delta |
| ZA29 | *(structure)* | 37.1 ± 6.6 | 2771 ± 854 | 594 ± 160 | — |
| ZA31 | *(structure)* | 65.0 ± 11.1 | — | — | — |
| ZA33 | *(structure)* | 59.1 ± 7.3 | 1183 ± 173 | 265 ± 21 | 13,600 ± 1,960 |

TABLE 18-continued

Efficacy of Receptor Binding of Substituted Benzimidazole-Type Piperidine
Compounds and Certain Other Compounds of Interest

| | | $K_i$ [Average ± Std Deviation] (nM) | | | |
| --- | --- | --- | --- | --- | --- |
| | | | Opioid Receptor | | |
| Ref. No. | Compound | ORL-1 | Mu | Kappa | Delta |
| ZA35 | | 2.68 ± 0.12 | 1577 ± 204 | 246 ± 77 | >20,000 |
| ZA37 | | 102 ± 19 | 1497 ± 228 | 1543 ± 92 | 3960 ± 710 |
| ZA38 | | 780 ± 165 | — | — | — |

TABLE 18-continued

Efficacy of Receptor Binding of Substituted Benzimidazole-Type Piperidine
Compounds and Certain Other Compounds of Interest

| | | K$_i$ [Average ± Std Deviation] (nM) | | | |
| | | | Opioid Receptor | | |
| Ref. No. | Compound | ORL-1 | Mu | Kappa | Delta |
|---|---|---|---|---|---|
| ZA39 | | 5.1 ± 0.7 | — | 566 ± 71 | — |
| ZA40 | | 2.20 ± 0.63 | — | — | — |
| ZA41 | | 1.15 ± 0.23 | — | — | — |

TABLE 18-continued

Efficacy of Receptor Binding of Substituted Benzimidazole-Type Piperidine
Compounds and Certain Other Compounds of Interest

| | | $K_i$ [Average ± Std Deviation] (nM) | | | |
| --- | --- | --- | --- | --- | --- |
| | | | Opioid Receptor | | |
| Ref. No. | Compound | ORL-1 | Mu | Kappa | Delta |
| ZA42 | | 0.92 ± 0.10 | — | — | — |
| ZA43 | | 14.9 ± 0.7 | 1837 ± 476 | 43.7 ± 11.1 | >20,000 |
| ZA44 | | 167.1 ± 2.5 | — | — | — |

TABLE 18-continued
Efficacy of Receptor Binding of Substituted Benzimidazole-Type Piperidine
Compounds and Certain Other Compounds of Interest
| | | $K_i$ [Average ± Std Deviation] (nM) | | | |
| | | | Opioid Receptor | | |
| Ref. No. | Compound | ORL-1 | Mu | Kappa | Delta |
| ZA45 | 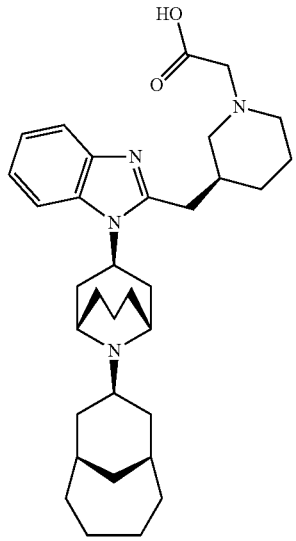 [SMILES: O=C(O)CN1CCC[C@@H](Cc2nc3ccccc3n2[C@H]2C[C@H]3CCC[C@@H](C2)N3[C@@H]2C[C@@H]3CCCC[C@@H](C3)C2)C1] | 120 ± 14 | — | — | — |
| ZA46 | 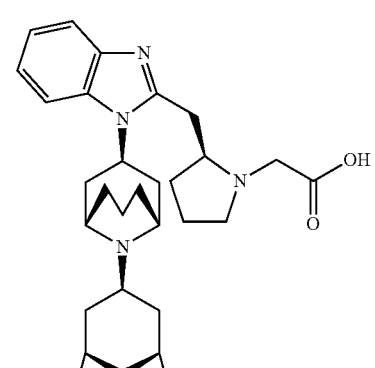 | 17.0 ± 2.3 | 4006 ± 796 | 344 ± 63 | >20,000 |

TABLE 18-continued
Efficacy of Receptor Binding of Substituted Benzimidazole-Type Piperidine Compounds and Certain Other Compounds of Interest
| | | $K_i$ [Average ± Std Deviation] (nM) | | | |
|---|---|---|---|---|---|
| | | | Opioid Receptor | | |
| Ref. No. | Compound | ORL-1 | Mu | Kappa | Delta |
| ZA47 | 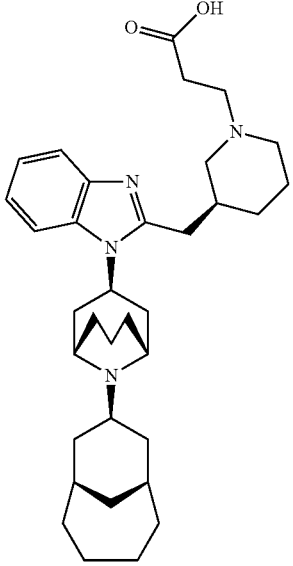 [SMILES: O=C(O)CCN1CCC[C@@H](Cc2nc3ccccc3n2[C@H]2C[C@H]3CCC[C@@H](C2)N3[C@@H]2C[C@@H]3CCCC[C@@H](C3)C2)C1] | 117 ± 38 | — | — | — |
| ZA48 | 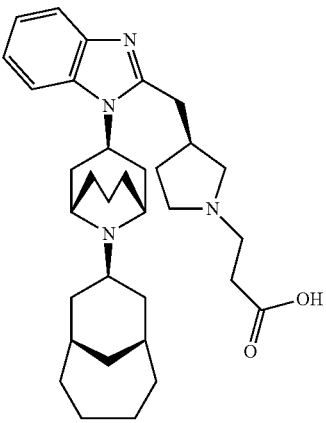 [SMILES: O=C(O)CCN1CC[C@@H](Cc2nc3ccccc3n2[C@H]2C[C@H]3CCC[C@@H](C2)N3[C@@H]2C[C@@H]3CCCC[C@@H](C3)C2)C1] | 36.0 ± 4.9 | 4497 ± 1124 | 614 ± 92 | >20,000 |

TABLE 18-continued

Efficacy of Receptor Binding of Substituted Benzimidazole-Type Piperidine Compounds and Certain Other Compounds of Interest

| | | $K_i$ [Average ± Std Deviation] (nM) | | | |
| | | | Opioid Receptor | | |
| Ref. No. | Compound | ORL-1 | Mu | Kappa | Delta |
| ZA49 | | 11.5 ± 1.4 | — | — | — |
| ZA50 | | 6.14 ± 0.73 | 1879 ± 120 | 58.3 ± 3.0 | 20,000 |

TABLE 18-continued

Efficacy of Receptor Binding of Substituted Benzimidazole-Type Piperidine Compounds and Certain Other Compounds of Interest

| | | K$_i$ [Average ± Std Deviation] (nM) | | | |
| | | | Opioid Receptor | | |
| Ref. No. | Compound | ORL-1 | Mu | Kappa | Delta |
| --- | --- | --- | --- | --- | --- |
| ZA51 | | 47.9 ± 4.6 | — | — | — |
| ZA52 | | 15.8 ± 1.6 | 3007 ± 242 | 30.4 ± 4.4 | >20,000 |
| ZA53 | | 0.80 ± 0.26 | — | — | — |

TABLE 18-continued

Efficacy of Receptor Binding of Substituted Benzimidazole-Type Piperidine Compounds and Certain Other Compounds of Interest

| Ref. No. | Compound | $K_i$ [Average ± Std Deviation] (nM) | | | |
| --- | --- | --- | --- | --- | --- |
| | | | Opioid Receptor | | |
| | | ORL-1 | Mu | Kappa | Delta |
| ZA54 | | 49 ± 15 | 2846 ± 629 | 254 ± 61 | >20,000 |
| ZA55 | | 5.4 ± 0.8 | 1914 ± 292 | 31.3 ± 4.9 | >20,000 |
| ZA56 | | 2.05 ± 0.47 | 1669 ± 612 | 50.1 ± 5.9 | >20,000 |

TABLE 18-continued

Efficacy of Receptor Binding of Substituted Benzimidazole-Type Piperidine
Compounds and Certain Other Compounds of Interest

| | | $K_i$ [Average ± Std Deviation] (nM) | | | |
| | | | Opioid Receptor | | |
| Ref. No. | Compound | ORL-1 | Mu | Kappa | Delta |
|---|---|---|---|---|---|
| ZA57 | | 8.5 ± 1.1 | — | — | — |
| ZA58 | | 19.9 ± 3.9 | 4335 ± 546 | 444 ± 113 | >20,000 |
| ZA59 | | 29.5 ± 2.2 | 3003 ± 112 | 169 ± 13 | >20,000 |

TABLE 18-continued

Efficacy of Receptor Binding of Substituted Benzimidazole-Type Piperidine
Compounds and Certain Other Compounds of Interest

| | | $K_i$ [Average ± Std Deviation] (nM) | | | |
| | | | Opioid Receptor | | |
| Ref. No. | Compound | ORL-1 | Mu | Kappa | Delta |
|---|---|---|---|---|---|
| ZA60 | | 4.5 ± 0.2 | — | 114.8 ± 2.9 | — |
| ZA61 | | 3.8 ± 0.7 | — | 130 ± 26 | — |
| ZA62 | | 47.2 ± 3.7 | — | — | — |

TABLE 18-continued

Efficacy of Receptor Binding of Substituted Benzimidazole-Type Piperidine Compounds and Certain Other Compounds of Interest

| | | $K_i$ [Average ± Std Deviation] (nM) | | | |
| | | | Opioid Receptor | | |
| Ref. No. | Compound | ORL-1 | Mu | Kappa | Delta |
|---|---|---|---|---|---|
| ZA63 | | 4.11 ± 0.45 | — | — | — |
| ZA64 | | 21.6 ± 4.2 | — | — | — |
| ZA65 | | 40 ± 8 | — | — | — |
| ZA66 | | 7.1 ± 1.2 | — | — | — |

TABLE 18-continued

Efficacy of Receptor Binding of Substituted Benzimidazole-Type Piperidine
Compounds and Certain Other Compounds of Interest

| | | K$_i$ [Average ± Std Deviation] (nM) | | | |
| --- | --- | --- | --- | --- | --- |
| | | | Opioid Receptor | | |
| Ref. No. | Compound | ORL-1 | Mu | Kappa | Delta |
| ZA67 | | 4.2 ± 0.7 | — | — | — |
| ZA68 | | 6.0 ± 1.1 | 520 ± 46 | 89.6 ± 9.1 | >20,000 |
| ZA69 | | 4.9 ± 0.9 | 529 ± 34 | 51 ± 14 | 6160 ± 1450 |

TABLE 18-continued

Efficacy of Receptor Binding of Substituted Benzimidazole-Type Piperidine Compounds and Certain Other Compounds of Interest

| Ref. No. | Compound | $K_i$ [Average ± Std Deviation] (nM) ORL-1 | Opioid Receptor Mu | Kappa | Delta |
|---|---|---|---|---|---|
| ZA70 | | 6.7 ± 1.0 | 952 ± 67 | 79 ± 6 | 4170 ± 495 |
| ZA71 | | 20.8 ± 4.2 | — | — | — |

TABLE 19

Activity Response of Substituted Benzimidazole-Type Piperidine Compounds

GTPγS ($EC_{50}$: nM, Emax: %) [mean ± SEM]

| | ORL-1 | | Opioid Receptor $EC_{50}$ | |
|---|---|---|---|---|
| Ref. No. | $EC_{50}$ | $E_{max}$ | Mu | Kappa |
| B56c(ii) | 1034 ± 30 | 31.3 ± 2.7 | — | — |
| E30c(ii) | 336 ± 27 | 125.3 ± 4.3 | — | — |
| H4d | 37.7 ± 11.3 | 102 ± 1 | — | — |
| H6d | 38.9 ± 7.0 | 101.7 ± 3.4 | — | — |
| H27b(i) | 23.2 ± 2.2 | 98.3 ± 2.0 | — | — |
| H30b(i) | 16.2 ± 2.2 | 55.7 ± 3.7 | — | — |
| H30b(ii) | 39.6 ± 6.3 | 41 ± 1 | — | >20,000 |
| H30d(ii) | 65 ± 28 | 85.3 ± 4.3 | — | — |
| H32b(ii) | 139 ± 23 | 49.7 ± 9.3 | — | >20,000 |
| H32d(ii) | 160 ± 35 | 90 ± 3 | — | — |
| H36b(i) | 38 ± 8 | 35.3 ± 1.5 | — | >20,000 |
| H56b(i) | 121 ± 17 | 40.3 ± 2.2 | — | >20,000 |
| H56b(ii) | 104 ± 21 | 38.5 ± 2.1 | — | 1533 ± 147 |
| H56d(ii) | 95 ± 20 | 66.7 ± 5.5 | — | >20,000 |
| H58d(ii) | 78 ± 15 | 41.7 ± 3.8 | — | >20,000 |
| H62d(ii) | 6.2 ± 0.8 | 18.7 ± 3.2 | — | — |
| O85d | 67 ± 18 | 60 ± 1 | — | >20,000 |
| ZA07 | 140 ± 17 | 106 ± 3.8 | — | — |
| ZA08 | 253 ± 20 | 104.3 ± 5.9 | — | — |
| ZA09 | 37.0 ± 6.3 | 85.0 ± 2.6 | — | — |
| ZA10 | 138.7 ± 8.3 | 75.67 ± 0.88 | — | >20,000 |
| ZA11 | 502 ± 99 | 23.0 ± 0.6 | — | — |
| ZA12 | 390 ± 34 | 24.3 ± 0.9 | — | — |
| ZA23 | >20,000 | — | — | — |
| ZA25 | 136 ± 15 | 36.0 ± 3.2 | — | — |
| ZA26 | 46.7 ± 16.3 | 106.3 ± 8.8 | 3813 ± 821 | 721 ± 97 |
| ZA27 | 91.4 ± 13.3 | 90.7 ± 3.5 | 2764 ± 1459 | 824 ± 94 |
| ZA28 | 70.8 ± 11.2 | 107.3 ± 4.2 | — | 1011 ± 112 |
| ZA29 | 124 ± 21 | 66.0 ± 4.7 | — | 5418 ± 820 |
| ZA31 | 64.8 ± 2.5 | 21.67 ± 0.33 | — | — |

TABLE 19-continued

Activity Response of Substituted Benzimidazole-
Type Piperidine Compounds

| | GTPγS (EC$_{50}$: nM, Emax: %) [mean ± SEM] | | Opioid Receptor EC$_{50}$ | |
|---|---|---|---|---|
| | ORL-1 | | | |
| Ref. No. | EC$_{50}$ | E$_{max}$ | Mu | Kappa |
| ZA33 | 219.9 ± 8.6 | 120.7 ± 6.7 | — | >20,000 |
| ZA35 | 17.5 ± 1.5 | 33.0 ± 1.3 | — | >20,000 |
| ZA37 | 84.2 ± 2.2 | 34.7 ± 1.5 | — | — |
| ZA39 | >20,000 | — | — | >20,000 |
| ZA40 | 5.8 ± 0.5 | 22.3 ± 1.3 | — | — |
| ZA41 | 3.0 ± 1.3 | 10.3 ± 0.9 | — | — |
| ZA42 | >20,000 | — | — | — |
| ZA43 | 59.3 ± 3.9 | 58.3 ± 2.3 | — | >20,000 |
| ZA44 | 355 ± 114 | 48.7 ± 1.8 | — | — |
| ZA45 | 22.8 ± 3.2 | 15 ± 1 | — | — |
| ZA46 | 43.1 ± 9.3 | 51.7 ± 1.7 | — | >20,000 |
| ZA47 | 82 ± 18 | 22.8 ± 0.8 | — | — |
| ZA48 | 62.5 ± 4.6 | 63.3 ± 3.8 | — | >20,000 |
| ZA49 | 12.5 ± 4.0 | 16.3 ± 0.3 | — | — |
| ZA50 | 8.9 ± 1.8 | 43 ± 3 | — | >20,000 |
| ZA51 | 40 ± 15 | 11 ± 1 | — | — |
| ZA52 | 28.4 ± 7.4 | 31.7 ± 3.3 | — | >20,000 |
| ZA53 | 3.6 ± 0.8 | 14.3 ± 1.0 | — | — |
| ZA54 | 72.5 ± 9.3 | 40.7 ± 0.9 | — | >20,000 |
| ZA55 | 17.0 ± 1.2 | 61.3 ± 1.5 | — | >20,000 |
| ZA56 | 4.7 ± 0.4 | 56.0 ± 2.1 | — | >20,000 |
| ZA57 | 26.9 ± 2.5 | 23.3 ± 0.9 | — | — |
| ZA58 | 103.9 ± 2.3 | 66 ± 2 | — | >20,000 |
| ZA59 | 101 ± 15 | 40.3 ± 0.7 | — | >20,000 |
| ZA60 | 12.6 ± 1.5 | 53.7 ± 4.2 | — | — |
| ZA61 | 5.61 ± 0.25 | 28.8 ± 2.5 | — | — |
| ZA62 | 38.4 ± 8.3 | 17.3 ± 0.3 | — | — |
| ZA63 | >20,000 | — | — | — |
| ZA64 | 8 ± 3 | 7.0 ± 0.7 | — | — |
| ZA65 | 71.7 ± 5.2 | 21 ± 1 | — | — |
| ZA66 | 16.6 ± 1.0 | 22.7 ± 1.2 | — | — |
| ZA67 | 14.3 ± 3.7 | 23.3 ± 0.9 | — | — |
| ZA68 | 28.4 ± 2.3 | 26 ± 2 | 564 ± 189 | >20,000 |
| ZA69 | 10.4 ± 1.1 | 31.7 ± 0.9 | 466 ± 165 | >20,000 |
| ZA70 | 22.6 ± 5.2 | 29.3 ± 0.9 | 4750 ± 1270 | >20,000 |
| ZA71 | >20,000 | — | — | — |

5.30 Example 30

In Vivo Assays for Prevention or Treatment of Pain

Test Animals: Each experiment uses rats weighing between 200-260 g at the start of the experiment. The rats are group-housed and have free access to food and water at all times, except prior to oral administration of a Substituted Benzimidazole-Type Piperidine Compound when food is removed for 16 hrs before dosing. A control group acts as a comparison to rats treated with a Substituted Benzimidazole-Type Piperidine Compound. The control group is administered the carrier for the Substituted Benzimidazole-Type Piperidine Compound. The volume of carrier administered to the control group is the same as the volume of carrier and Substituted Benzimidazole-Type Piperidine Compound administered to the test group.

Acute Pain: To assess the actions of a Substituted Benzimidazole-Type Piperidine Compound for the treatment or prevention of acute pain, the rat tail flick test can be used. Rats are gently restrained by hand and the tail exposed to a focused beam of radiant heat at a point 5 cm from the tip using a tail flick unit (Model 7360, commercially available from Ugo Basile of Italy). Tail flick latencies are defined as the interval between the onset of the thermal stimulus and the flick of the tail. Animals not responding within 20 seconds are removed from the tail flick unit and assigned a withdrawal latency of 20 seconds. Tail flick latencies are measured immediately before (pre-treatment) and 1, 3, and 5 hrs following administration of a Substituted Benzimidazole-Type Piperidine Compound. Data are expressed as tail flick latency(s) and the percentage of the maximal possible effect (% MPE), i.e., 20 seconds, is calculated as follows:

$$\% MPE = \frac{[(\text{post administration latency}) - (\text{pre-administration latency})]}{(20 \text{ s pre-administration latency})} \times 100$$

The rat tail flick test is described in D'Amour et al., "A Method for Determining Loss of Pain Sensation," *J. Pharmacol. Exp. Ther.* 72:74-79 (1941).

Inflammatory Pain: To assess the actions of a Substituted Benzimidazole-Type Piperidine Compound for the treatment or prevention of inflammatory pain, the Freund's complete adjuvant ("FCA") model of inflammatory pain can be used. FCA-induced inflammation of the rat hind paw is associated with the development of persistent inflammatory mechanical hyperalgesia and provides reliable prediction of the anti-hyperalgesic action of clinically useful analgesic drugs (Bartho et al., "Involvement of capsaicin-sensitive neurons in hyperalgesia and enhanced opioid antinociception in inflammation," *Naunyn-Schmiedeberg's Arch. Pharmacol.* 342:666-670 (1990)). The left hind paw of each animal is administered a 50 μL intraplantar injection of 50% FCA. 24 hr post injection, the animal is assessed for response to noxious mechanical stimuli by determining the PWT, as described below. Rats are then administered a single injection of 1, 3, 10 or 30 mg/kg of either a Substituted Benzimidazole-Type Piperidine Compound; 30 mg/kg of a control selected from Celebrex, indomethacin, and naproxen; or carrier. Responses to noxious mechanical stimuli are then determined 1, 3, 5 and 24 hrs post administration. Percentage reversal of hyperalgesia for each animal is defined as:

$$\% \text{Reversal} = \frac{[(\text{post administration } PWT) - (\text{pre-administration } PWT)]}{[(\text{baseline } PWT) - (\text{pre-administration } PWT)]} \times 100$$

Neuropathic Pain: To assess the actions of a Substituted Benzimidazole-Type Piperidine Compound for the treatment or prevention of neuropathic pain, either the Seltzer model or the Chung model can be used.

In the Seltzer model, the partial sciatic nerve ligation model of neuropathic pain is used to produce neuropathic hyperalgesia in rats (Seltzer et al., "A Novel Behavioral Model of Neuropathic Pain Disorders Produced in Rats by Partial Sciatic Nerve Injury," *Pain* 43:205-218 (1990)). Partial ligation of the left sciatic nerve is performed under isoflurane/O$_2$ inhalation anaesthesia. Following induction of anesthesia, the left thigh of the male, 6-7 week old Jcl:SD rat is shaved. The sciatic nerve is exposed at high thigh level through a small incision and is carefully cleared of surrounding connective tissues at a site near the trocanther just distal to the point at which the posterior biceps semitendinosus nerve branches off of the common sciatic nerve. A 7-0 silk suture is inserted into the nerve with a ⅜ curved, reversed-cutting mini-needle and tightly ligated so that the dorsal ⅓ to ½ of the nerve thickness is held within the ligature. The wound is closed with a single muscle suture (4-0 nylon (Vicryl)) and vetbond tissue glue. The wound area is then dusted with antibiotic powder. Sham treatment involves an identical surgical procedure except that the sciatic nerve is not manipulated or ligated.

Following surgery, animals are weighed and placed on a warm pad until they recovered from anesthesia. Animals are then returned to their home cages until behavioral testing began. The animal is assessed for response to noxious mechanical stimuli by determining PWT for the rear paw of the animal, as described below, prior to surgery (baseline), then immediately prior to and 1, 3, and 5 hrs after oral drug-in-vehicle administration (for day 1). Thus, the 24 hr time point is the start of the next day when drug-in-vehicle is again orally administered (24 hrs after the prior administration). On days 4 and 7, PWT response is determined 1, 3, and 5 hrs thereafter. Percentage reversal of neuropathic hyperalgesia at each of the specified times after administration is defined as:

$$\% \text{ Reversal} = \frac{[(\text{post administration } PWT) - (\text{pre-administration } PWT)]}{[(\text{baseline } PWT) - (\text{pre-administration } PWT)]} \times 100$$

Additionally, 10 mg/kg of pregabalin (Kemprotec, Ltd., Middlesbrough, UK), an anticonvulsant accepted for relief of particular neuropathic pain, in vehicle and the vehicle alone (0.5% weight/volume methylcellulose (400 cP, Wako Pure Chemical Industries, Ltd.)/aqueous solution) are orally administered as controls. Eight rats that underwent partial ligation of the left sciatic nerve are used for each treatment group except for pregabalin, where six rats are treated. Dunnett's test is conducted for the % reversal; values with p<0.05 are considered to be statistically significant. Additionally, as a control the rats undergo sham surgery in which an identical surgical procedure is followed with regard to the right thigh but the sciatic nerve is neither manipulated nor ligated.

In the Chung model, the spinal nerve ligation model of neuropathic pain is used to produce mechanical hyperalgesia, thermal hyperalgesia and tactile allodynia in rats. Surgery is performed under isoflurane/$O_2$ inhalation anaesthesia. Following induction of anaesthesia, a 3 cm incision is made and the left paraspinal muscles are separated from the spinous process at the $L_4$-$S_2$ levels. The $L_6$ transverse process is carefully removed with a pair of small rongeurs to identify visually the $L_4$-$L_6$ spinal nerves. The left $L_5$ (or $L_5$ and $L_6$) spinal nerve(s) is isolated and tightly ligated with silk thread. A complete hemostasis is confirmed and the wound is sutured using non-absorbable sutures, such as nylon sutures or stainless steel staples. Sham-treated rats undergo an identical surgical procedure except that the spinal nerve(s) is not manipulated. Following surgery animals are weighed, administered a subcutaneous (s.c.) injection of saline or ringers lactate, the wound area is dusted with antibiotic powder and they are kept on a warm pad until they recover from the anesthesia. Animals are then returned to their home cages until behavioral testing begins. The animals are assessed for response to noxious mechanical stimuli by determining PWT, as described below, prior to surgery (baseline), then immediately prior to and 1, 3, and 5 hrs after being administered a Substituted Benzimidazole-Type Piperidine Compound for the left rear paw of the animal. The animal can also be assessed for response to noxious thermal stimuli or for tactile allodynia, as described below. The Chung model for neuropathic pain is described in Kim, "An Experimental Model for Peripheral Neuropathy Produced by Segmental Spinal Nerve Ligation in the Rat," Pain 50(3):355-363 (1992).

Response to Mechanical Stimuli as an Assessment of Mechanical Hyperalgesia: The paw pressure assay can be used to assess mechanical hyperalgesia. For this assay, hind paw withdrawal thresholds (PWT) to a noxious mechanical stimulus are determined using an analgesymeter (Model 37215, commercially available from Ugo Basile of Italy) as described in Stein, "Unilateral Inflammation of the Hindpaw in Rats as a Model of Prolonged Noxious Stimulation: Alterations in Behavior and Nociceptive Thresholds," Pharmacol. Biochem. Behavior 31:451-455 (1988). The maximum weight that can be applied to the hind paw is set at 250 g and the end point is taken as complete withdrawal of the paw. PWT is determined once for each rat at each time point and either only the affected (ipsilateral) paw is tested, or both the ipsilateral and contralateral (non-injured) paw are tested.

Response to Thermal Stimuli as an Assessment of Thermal Hyperalgesia: The plantar test can be used to assess thermal hyperalgesia. For this test, hind paw withdrawal latencies to a noxious thermal stimulus are determined using a plantar test apparatus (commercially available from Ugo Basile of Italy) following the technique described by Hargreaves et al., "A New and Sensitive Method for Measuring Thermal Nociception in Cutaneous Hyperalgesia," Pain 32(1):77-88 (1988). The maximum exposure time is set at 32 seconds to avoid tissue damage and any directed paw withdrawal from the heat source is taken as the end point. Three latencies are determined at each time point and averaged. Either only the affected (ipsilateral) paw is tested, or both the ipsilateral and contralateral (non-injured) paw are tested.

Assessment of Tactile Allodynia: To assess tactile allodynia, rats are placed in clear, plexiglass compartments with a wire mesh floor and allowed to habituate for a period of at least 15 min. After habituation, a series of von Frey monofilaments are presented to the plantar surface of the left (operated) foot of each rat. The series of von Frey monofilaments consists of six monofilaments of increasing diameter, with the smallest diameter fiber presented first. Five trials are conducted with each filament with each trial separated by approximately 2 minutes. Each presentation lasts for a period of 4-8 seconds or until a nociceptive withdrawal behavior is observed. Flinching, paw withdrawal or licking of the paw are considered nociceptive behavioral responses.

The invention is not to be limited in scope by the specific embodiments disclosed in the examples that are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims. A number of references have been cited, the entire disclosures of which are incorporated herein by reference for all purposes.

What is claimed:
1. A compound of Formula (IB):

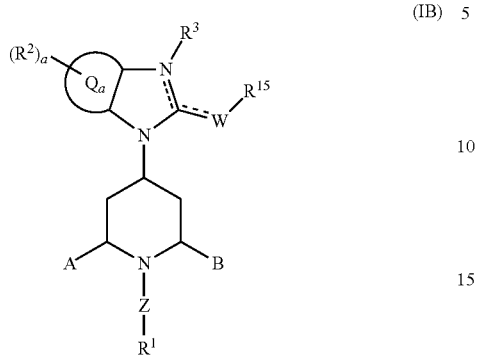

or a pharmaceutically acceptable salt or solvate thereof wherein:
the $Q_a$ ring is fused benzo or fused (5- or 6-membered) heteroaryl;
each $R^2$ is independently selected from:
(a) -halo, —CN, —NO$_2$, —OT$^3$, —C(=O)T$^3$, —C(=O)OT$^3$, —C(=O)N(T$^1$)(T$^2$), —S(=O)$_2$OT$^3$, —S(=O)T$^3$, —S(=O)$_2$T$^3$, —O—S(=O)$_2$T$^3$, —S(=O)$_2$N(T$^1$)(T$^2$), —N(T$^1$)(T$^2$), —N(T$^3$)C(=O)T$^3$, —N(T$^3$)C(=O)N(T$^1$)(T$^2$), —N(T$^3$)S(=O)T$^3$, —N(T$^3$)S(=O)$_2$T$^3$, —N(T$^3$)C(=O)OT$^3$, and —N(T$^3$)S(=O)$_2$N(T$^1$)(T$^2$); and
(b) —(C$_1$-C$_6$)alkyl, —(C$_2$-C$_6$)alkenyl, —(C$_2$-C$_6$)alkynyl, —(C$_1$-C$_6$)alkoxy, —(C$_3$-C$_7$)cycloalkyl, —(C$_6$-C$_{10}$)bicycloalkyl, —(C$_5$-C$_{10}$)cycloalkenyl, —(C$_7$-C$_{10}$)bicycloalkenyl, and -(5- or 6-membered)heterocycle, each of which is unsubstituted or substituted with 1, 2, or 3 independently selected R$^8$ groups; and
(c) -phenyl, -naphthalenyl, and -(5- or 6-membered) heteroaryl, each of which is unsubstituted or substituted with 1, 2, or 3 independently selected R$^7$ groups;
each dashed line denotes the presence or absence of a bond, provided that:
(a) one dashed line must denote the presence of a bond;
(b) when one dashed line denotes the presence of a bond then the other dashed line denotes the absence of a bond;
(c) when the dashed line within the 5-membered, nitrogen-containing ring that is fused to the $Q_a$ ring is present, then R$^3$ is absent; and
(d) when the dashed line within the 5-membered, nitrogen-containing ring that is fused to the $Q_a$ ring is absent, then R$^3$ is present;
R$^3$, when present, is:
(a) —H; or
(b) —(C$_1$-C$_4$)alkyl which is unsubstituted or substituted with 1, 2, or 3 groups independently selected from —OH, —(C$_1$-C$_4$)alkoxy, —N(R$^6$)$_2$, —C(=O)OR$^9$, and —C(=O)N(R$^6$)$_2$; or
(c) —(C$_3$-C$_7$)cycloalkyl which is unsubstituted or substituted with 1, 2, or 3 groups independently selected from —OH, —(C$_1$-C$_4$)alkyl, —(C$_1$-C$_4$)alkoxy, —N(R$^6$)$_2$, —C(=O)OR$^9$, and —C(=O)N(R$^6$)$_2$;

--- W— is a single bond, a double bond, =CH—, —CH$_2$—, =N—, —NH—, —O—, =CH—(C$_1$-C$_3$)alkylene-, —CH$_2$—(C$_1$-C$_3$)alkylene-, =N—(C$_1$-C$_3$)alkylene-, —NH—(C$_1$-C$_3$)alkylene-, —O—(C$_1$-C$_3$)alkylene-, =CH—(C$_2$-C$_3$)alkenylene-, —CH$_2$—(C$_2$-C$_3$)alkenylene-, =N—(C$_2$-C$_3$)alkenylene-, —NH—(C$_2$-C$_3$)alkenylene-, —O—(C$_2$-C$_3$)alkenylene-, =CH—(C$_1$-C$_3$)alkylene-N(R$^{11}$)—, —CH$_2$—(C$_1$-C$_3$)alkylene-N(R$^{11}$)—, =N—(C$_1$-C$_3$)alkylene-N(R$^{11}$)—, —NH—(C$_1$-C$_3$)alkylene-N(R$^{11}$)—, —O—(C$_1$-C$_3$)alkylene-N(R$^{11}$)—, =CH—N(R$^{11}$)—, —CH=N—, —CH$_2$—N(R$^{11}$)—, =CH—O—, —CH$_2$—O—, =CH—O—(C$_1$-C$_3$)alkylene-, or —CH$_2$—O—(C$_1$-C$_3$)alkylene-;
R$^{15}$ is selected from:
(a) —H; and
(b) —(C$_1$-C$_4$)alkyl and —O—(C$_1$-C$_4$)alkyl, each of which is unsubstituted or substituted with 1, 2, 3, or 4 independently selected R$^8$ groups;
(c) provided that when --- W— is a single bond, a double bond, or —O—, R$^{15}$ is not —H;
A and B together form a (C$_2$-C$_6$)bridge, which is unsubstituted or substituted with 1, 2, 3, 4, 5, 6, 7, or 8 substituents independently selected from —OH, —(C$_1$-C$_4$)alkyl, -halo, and —C(halo)$_3$, and which bridge optionally contains —HC=CH— or —O— within the (C$_2$-C$_6$)bridge;
wherein the 5-membered, nitrogen-containing ring that is fused to the $Q_a$ ring can be in the endo- or exo-configuration with respect to the A-B bridge;
Z is —[(C$_4$-C$_{10}$)alkyl optionally substituted by R$^{13}$]$_h$—, wherein h is 0;
Y is O or S;
R$^1$ is selected from:
(a) —H, -halo, —CN, —OH, —CH$_2$OH, —CH$_2$CH$_2$OH, —NO$_2$, —N(R$^6$)$_2$, —S(=O)NH$_2$, —S(=O)$_2$NH$_2$, and —C(=O)CN; and
(b) —(C$_2$-C$_{10}$)alkenyl, —(C$_2$-C$_{10}$)alkynyl, —O(C$_1$-C$_6$)alkyl, —(C$_3$-C$_7$)cycloalkoxy, —(C$_6$-C$_{14}$)bicycloalkyl, —(C$_8$-C$_{20}$)tricycloalkyl, —(C$_5$-C$_{10}$)cycloalkenyl, —(C$_7$-C$_{14}$)bicycloalkenyl, —(C$_8$-C$_{20}$)tricycloalkenyl, and -(3- to 7-membered) heterocycle, each of which is unsubstituted or substituted with 1, 2, 3, or 4 independently selected R$^8$ groups; and
(c)

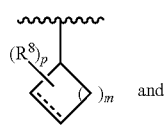

and

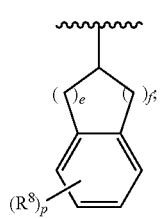

and
(d) -phenyl, -naphthalenyl, —(C$_{14}$)aryl, and -(5- to 10-membered)heteroaryl, each of which is unsubstituted or substituted with 1, 2, 3, or 4 independently selected $R^7$ groups;

each $R^5$ is independently —$(C_1-C_4)$alkyl, —$(C_2-C_6)$alkenyl, —$(C_2-C_6)$alkynyl, -(5- or 6-membered)heteroaryl, —$(C_1-C_6)$alkyl-C(=O)OR$^9$, —OR$^9$, —SR$^9$, —C(halo)$_3$, —CH(halo)$_2$, —CH$_2$(halo), —CN, =O, =S, -halo, —N$_3$, —NO$_2$, —CH=N(R$^9$), —N(R$^9$)(C$_1$-C$_6$)alkyl-C(=O)OR$^9$, —N(R$^9$)$_2$, —N(R$^9$)OH, —N(R$^9$)S(=O)R$^{12}$, —N(R$^9$)S(=O)$_2$R$^{12}$, —N(R$^9$)C(=O)R$^{12}$, —N(R$^9$)C(=O)OR$^{12}$, —C(=O)R$^9$, —C(=O)OR$^9$, —OC(=O)R$^9$, —OC(=O)OR$^9$, —S(=O)R$^9$, or —S(=O)$_2$R$^9$;

each $R^6$ is independently —H, —$(C_1-C_6)$alkyl, or —$(C_3-C_7)$cycloalkyl, or two $R^6$ groups attached to the same nitrogen atom can together form a -(5- to 8-membered)heterocyclic ring, wherein the number of atoms in the ring includes the nitrogen atom, and in which one of the -(5- to 8-membered)heterocyclic ring carbon atoms is optionally replaced by O, S, or N(T$^3$);

each $R^7$ is independently —$(C_1-C_4)$alkyl, —$(C_2-C_6)$alkenyl, —$(C_2-C_6)$alkynyl, —SR$^9$, —C(halo)$_3$, —CH(halo)$_2$, —CH$_2$(halo), —CN, -halo, —N$_3$, —NO$_2$, —CH=N(R$^9$), —N(R$^9$)$_2$, —N(R$^9$)OH, —N(R$^9$)S(=O)R$^{12}$, —N(R$^9$)S(=O)$_2$R$^{12}$, —N(R$^9$)C(=O)R$^{12}$, —N(R$^9$)C(=O)N(T$^1$)(T$^2$), —N(R$^9$)C(=O)OR$^{12}$, —C(=O)R$^9$, —C(=O)N(T$^1$)(T$^2$), —C(=O)OR$^9$, —OC(=O)R$^9$, —OC(=O)N(T$^1$)(T$^2$), —OC(=O)OR$^9$, —S(=O)R$^9$, or —S(=O)$_2$R$^9$;

each $R^8$ is independently —$(C_1-C_4)$alkyl, —$(C_2-C_6)$alkenyl, —$(C_2-C_6)$alkynyl, $(C_1-C_6)$alkyl-C(=O)OR$^9$, —N(R$^9$)(C$_1$-C$_6$)alkyl-C(=O)OR$^9$, —OR$^9$, —SR$^9$, —C(halo)$_3$, —CH(halo)$_2$, —CH$_2$(halo), —CN, =O, =S, =N(R$^9$), -halo, —N$_3$, —NO$_2$, —CH=N(R$^9$), —N(R$^9$)$_2$, —N(R$^9$)OR$^9$, —N(R$^9$)S(=O)R$^{12}$, —N(R$^9$)S(=O)$_2$R$^{12}$, —N(R$^9$)C(=O)R$^{12}$, —N(R$^9$)C(=O)N(T$^1$)(T$^2$), —N(R$^9$)C(=O)OR$^{12}$, —C(=O)R$^9$, —C(=O)N(T$^1$)(T$^2$), —C(=O)OR$^9$, —OC(=O)R$^9$, —OC(=O)N(T$^1$)(T$^2$), —OC(=O)OR$^9$, —S(=O)R$^9$, or —S(=O)$_2$R$^9$;

each $R^9$ is independently —H, —$(C_1-C_6)$alkyl, —$(C_2-C_6)$alkenyl, —$(C_2-C_6)$alkynyl, —$(C_3-C_8)$cycloalkyl, —$(C_5-C_8)$cycloalkenyl, -phenyl, -benzyl, -(3- to 7-membered)heterocycle, —C(halo)$_3$, —CH(halo)$_2$, or —CH$_2$(halo);

$R^{11}$ is —H, —CN, or —C(=O)N(R$^6$)$_2$ or $R^{11}$ is —$(C_1-C_4)$alkyl which is unsubstituted or substituted with —OH, —$(C_1-C_4)$alkoxy, or —N(R$^6$)$_2$;

each $R^{12}$ is independently —H or —$(C_1-C_4)$alkyl;

$R^{13}$ is selected from:
(a) -halo, —CN, —OH, —CH$_2$OH, —CH$_2$CH$_2$OH, —NO$_2$, —N(R$^6$)$_2$, —S(=O)NH$_2$, —S(=O)$_2$NH$_2$, —C(=O)OV$^1$, and —C(=O)CN; and
(b) —$(C_1-C_{10})$alkyl, —$(C_2-C_{10})$alkenyl, —$(C_2-C_{10})$alkynyl, —O(C$_1$-C$_6$)alkyl, —$(C_3-C_7)$cycloalkoxy, —$(C_5-C_{10})$cycloalkenyl, and -(3- to 7-membered)heterocycle, each of which is unsubstituted or substituted with 1, 2, 3, or 4 independently selected $R^8$ groups; and
(c)

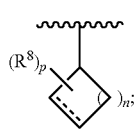

(iv)

and
(d) -phenyl and -(5- to 10-membered)heteroaryl, each of which is unsubstituted or substituted with 1, 2, or 3 independently selected $R^7$ groups;

each $T^1$ and $T^2$ is independently —H or —$(C_1-C_{10})$alkyl which is unsubstituted or substituted with 1, 2, or 3 independently selected $R^5$ groups and, optionally, in which any —$(C_1-C_{10})$alkyl carbon atom except the carbon atom bonded directly to the atom to which $T^1$ or $T^2$ is attached is independently replaced by O, S, or N(R$^6$), or $T^1$ and $T^2$ can together form a -(5- to 8-membered)heterocyclic ring wherein the number of atoms in the ring includes the nitrogen atom to which $T^1$ and $T^2$ are bonded, said -(5- to 8-membered)heterocyclic ring is unsubstituted or substituted with 1, 2, or 3 independently selected $R^5$ groups and, optionally, any 1 or 2 carbon atoms in said -(5- to 8-membered)heterocyclic ring is independently replaced by O, S, or N(R$^6$);

each $T^3$ is independently —H or —$(C_1-C_{10})$alkyl which is unsubstituted or substituted with 1, 2, or 3 independently selected $R^5$ groups and, optionally, in which any —$(C_1-C_{10})$alkyl carbon atom except the carbon atom bonded directly to the atom to which $T^3$ is attached is independently replaced by O, S, or N(R$^{12}$);

each $V^1$ is independently —H, —$(C_1-C_6)$alkyl, —$(C_3-C_7)$cycloalkyl, -phenyl, or -benzyl;

a is an integer selected from 0, 1, and 2;

m is an integer selected from 0, 1, 2, 3, 4, 5, 6, 7, 8, 9, 10, and 11;

n is an integer selected from 0, 1, 2, 3, 4, 5, 6, 7, 8, and 9;

e and f are each an integer independently selected from 0, 1, 2, 3, 4, and 5 provided that $2 \leq (e+f) \leq 5$;

each p is an integer independently selected from 0, 1, 2, 3, and 4; and each halo is independently —F, —Cl, —Br, or —I.

2. The compound of claim 1 or a pharmaceutically acceptable salt or solvate thereof, wherein $Q_a$ is benzo, pyridino, pyrimidino, pyrazino, or pyridazino wherein the 2- and 3-positions of the pyridino are fused to the 5-membered, nitrogen-containing ring.

3. The compound of claim 2 or a pharmaceutically acceptable salt or solvate thereof, wherein =W— is a single bond, a double bond, —CH$_2$—, =N—, —CH=N—, or —NH—.

4. The compound of claim 3 or a pharmaceutically acceptable salt or solvate thereof, wherein $R^{15}$ is —CH$_2$OH, —C(=O)OH, —C(=O)OCH$_3$, —C(=O)OC$_2$H$_5$, —C(=O)NH$_2$, —CH$_2$C(=O)OH, —CH$_2$C(=O)OCH$_3$, —CH$_2$C(=O)OC$_2$H$_5$, —OC(=O)CH$_3$, —OC(=O)C$_2$H$_5$, —OCH$_2$C(=O)OH, —OCH$_2$C(=O)OCH$_3$, —OCH$_2$C(=O)OC$_2$H$_5$, —C(=NH)OCH$_3$, —C(=NH)OC$_2$H$_5$, —C(=NH)NHOCH$_3$, or —C(=NH)NHOC$_2$H$_5$.

5. The compound of claim 3 or a pharmaceutically acceptable salt or solvate thereof, wherein =W— is =N— or —NH— and $R^{15}$ is —C(=O)OCH$_3$, —C(=O)OC$_2$H$_5$, —C(=O)NH$_2$, —CH$_2$C(=O)OH, —CH$_2$C(=O)OCH$_3$, —CH$_2$C(=O)OC$_2$H$_5$, —OC(=O)CH$_3$, —OC(=O)C$_2$H$_5$, —OCH$_2$C(=O)OH, —OCH$_2$C(=O)OCH$_3$, —OCH$_2$C(=O)OC$_2$H$_5$, —C(=NH)OCH$_3$, —C(=NH)OC$_2$H$_5$, —C(=NH)NHOCH$_3$, or —C(=NH)NHOC$_2$H$_5$.

6. The compound of claim 3 or a pharmaceutically acceptable salt or solvate thereof, wherein:

$Q_a$ is benzo;

a is 0; and $R^1$ is selected from:
(a) —CN, —OH, —CH$_2$OH, —CH$_2$CH$_2$OH, —NO$_2$, —N(R$^6$)$_2$, —S(=O)NH$_2$, —S(=O)$_2$NH$_2$, and —C(=O)CN; and
(b) —O(C$_1$-C$_6$)alkyl, —(C$_3$-C$_7$)cycloalkoxy, —(C$_3$-C$_{14}$)cycloalkyl, —(C$_6$-C$_{14}$)bicycloalkyl, —(C$_8$-C$_{20}$)tricycloalkyl, —(C$_5$-C$_{14}$)cycloalkenyl, —(C$_7$-C$_{14}$)bicycloalkenyl, —(C$_8$-C$_{20}$)tricycloalkenyl, and -(3- to 7-membered)heterocycle, each of which is unsubstituted or substituted with 1, 2, 3, or 4 independently selected R$^8$ groups; and
(c)

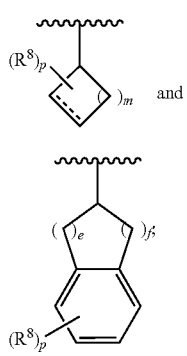

and
(d) -phenyl and -(5- to 10-membered)heteroaryl, each of which is unsubstituted or substituted with 1, 2, or 3 independently selected R$^7$ groups.

7. The compound of claim 6 or a pharmaceutically acceptable salt or solvate thereof, wherein =W— is —CH$_2$—, =N—, —CH=N—, or —NH— and R$^{15}$ is —C(=O)OH, —C(=O)OCH$_3$, —C(=O)OC$_2$H$_5$, —C(=O)NH$_2$, —CH$_2$C(=O)OH, —CH$_2$C(=O)OCH$_3$, —CH$_2$C(=O)OC$_2$H$_5$, —OC(=O)CH$_3$, —OC(=O)C$_2$H$_5$, —OCH$_2$C(=O)OH, —OCH$_2$C(=O)OCH$_3$, —OCH$_2$C(=O)OC$_2$H$_5$, —C(=NH)OCH$_3$, —C(=NH)OC$_2$H$_5$, —C(=NH)NHOCH$_3$, or —C(=NH)NHOC$_2$H$_5$.

8. The compound of claim 7 or a pharmaceutically acceptable salt or solvate thereof, wherein R$^{15}$ is —C(=O)OCH$_3$, —C(=O)NH$_2$, —CH$_2$C(=O)OH, —CH$_2$C(=O)OC$_2$H$_5$, —OC(=O)CH$_3$, —OCH$_2$C(=O)OH, —C(=NH)OC$_2$H$_5$, or —C(=NH)NHOCH$_3$.

9. The compound of claim 6 or a pharmaceutically acceptable salt or solvate thereof, wherein =W— is —CH=N— or —NH— and R$^{15}$ is —C(=O)OCH$_3$, —C(=O)OC$_2$H$_5$, —C(=O)NH$_2$, —CH$_2$C(=O)OH, —CH$_2$C(=O)OCH$_3$, —CH$_2$C(=O)OC$_2$H$_5$, —OC(=O)CH$_3$, —OC(=O)C$_2$H$_5$, —OCH$_2$C(=O)OH, —OCH$_2$C(=O)OCH$_3$, —OCH$_2$C(=O)OC$_2$H$_5$, —C(=NH)OCH$_3$, —C(=NH)OC$_2$H$_5$, —C(=NH)NHOCH$_3$, or —C(=NH)NHOC$_2$H$_5$.

10. The compound of claim 3 or a pharmaceutically acceptable salt or solvate thereof, wherein A and B together form a bridge such that the bridged-piperidine is:

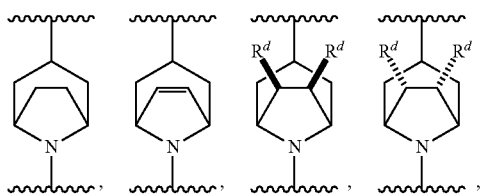

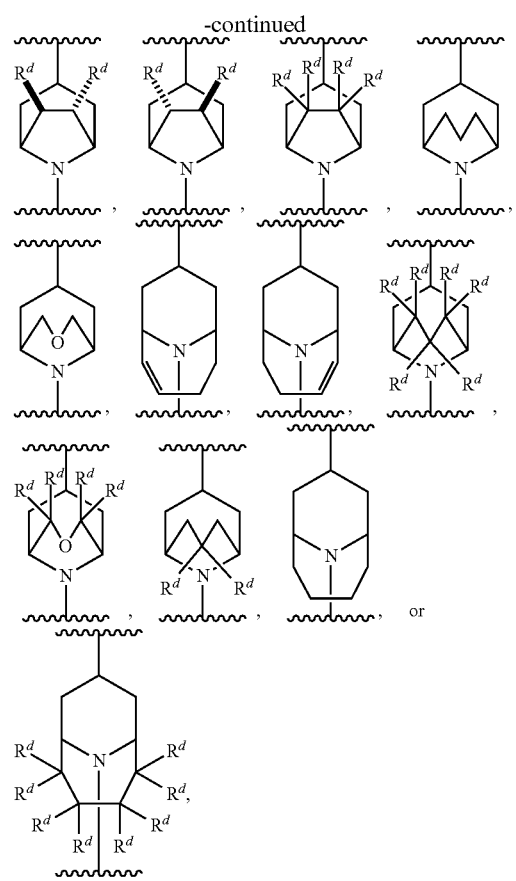

wherein each R$^d$ is independently —H, —(C$_1$-C$_4$)alkyl, -halo, or —C(halo)$_3$.

11. The compound of claim 10 or a pharmaceutically acceptable salt or solvate thereof, wherein A and B together form a bridge such that the bridged-piperidine is:

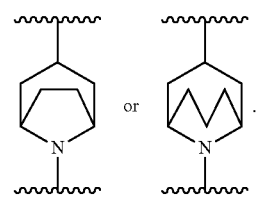 [SMILES: *C1CC2CCC(C1)N2* ; *C1CC2CCCC(C1)N2*]

wherein the A-B bridge of the bridged-piperidine is in the endo-configuration with respect to the 5-membered, nitrogen-containing ring that is fused to the $Q_a$ ring.

12. The compound of claim 6 or a pharmaceutically acceptable salt or solvate thereof, wherein:
(a) R$^1$ is —(C$_3$-C$_{14}$)cycloalkyl, —(C$_8$-C$_{14}$)cycloalkenyl, —(C$_6$-C$_{14}$)bicycloalkyl, —(C$_7$-C$_{14}$)bicycloalkenyl, or —(C$_8$-C$_{20}$)tricycloalkyl, each of which is unsubstituted or substituted with 1, 2, 3, or 4 independently selected R$^8$ groups; and
(b) each R$^8$ is independently —(C$_1$-C$_4$)alkyl, —(C$_1$-C$_6$)alkyl-C(=O)OR$^9$, —N(R$^9$)(C$_1$-C$_6$)alkyl-C(=O)OR$^9$, —OR$^9$, —C(halo)$_3$, —CH(halo)$_2$, —CH$_2$(halo), -halo, —N(R$^9$)$_2$, —C(=O)N(T$^1$)(T$^2$), or —C(=O)OR$^9$.

13. The compound of claim 12 or a pharmaceutically acceptable salt or solvate thereof, wherein —Z—R$^1$ is:

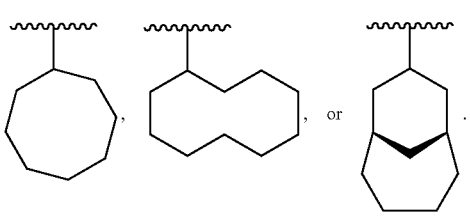
14. The compound of claim 12 or a pharmaceutically acceptable salt or solvate thereof, wherein —Z—R$^1$ is:
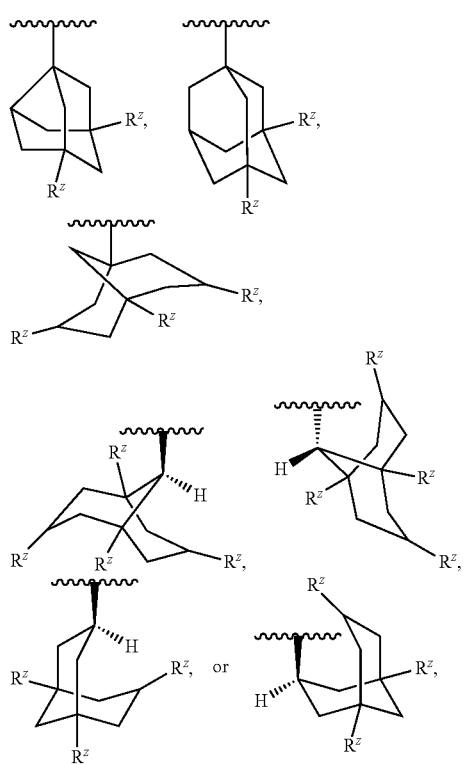
wherein each R$^z$ is independently —H, —CH$_3$, or —CH$_2$CH$_3$.
15. The compound of claim 10 or a pharmaceutically acceptable salt or solvate thereof, wherein the R$^1$ group is in the exo-configuration with respect to the A-B bridge of the bridged piperidine.
16. A compound which is:
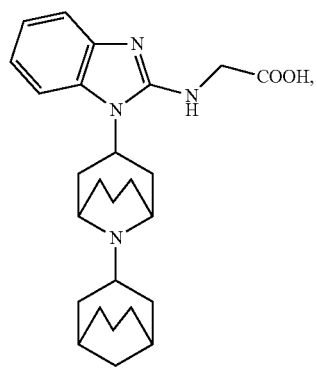
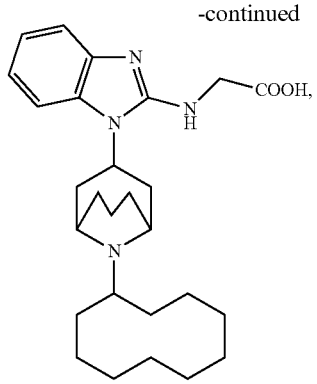
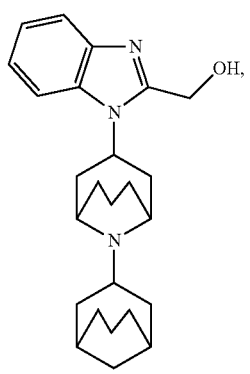
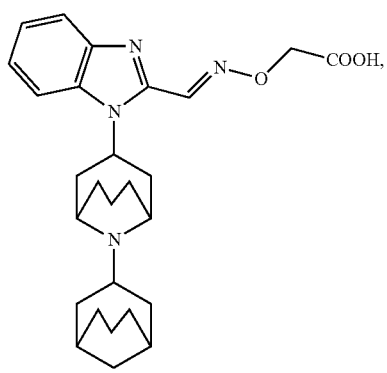
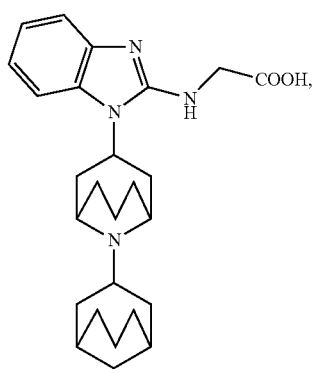

-continued

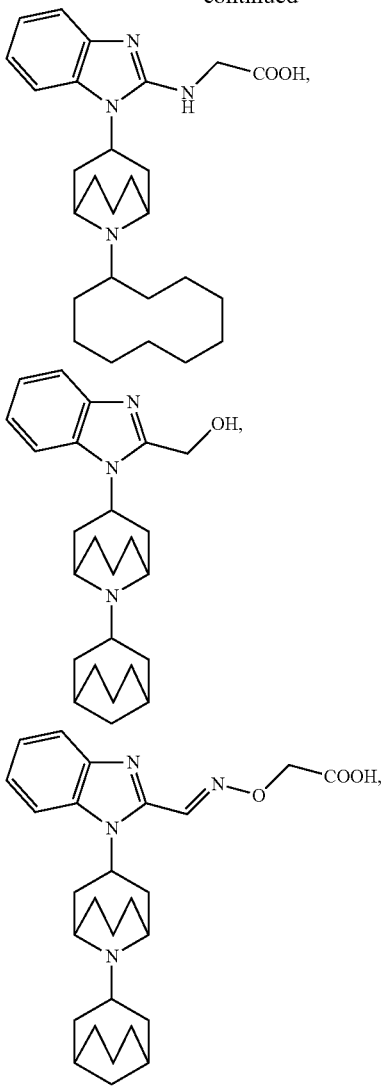

or a pharmaceutically acceptable salt thereof.

17. The compound of claim 1, wherein the compound is present as the compound or as a pharmaceutically acceptable salt of the compound wherein the pharmaceutically acceptable salt is a hydrochloride-salt, a sodium-salt, a potassium-salt, or a para-toluenesulfonic acid-salt.

18. A composition comprising an effective amount of the compound or a pharmaceutically acceptable salt of the compound of claim 1 and a pharmaceutically acceptable carrier or excipient.

19. A method for modulating ORL-1 receptor function in a cell, comprising contacting a cell capable of expressing the ORL-1 receptor with an effective amount of the compound or a pharmaceutically acceptable salt of the compound of claim 1.

20. The compound of claim 16 which is:

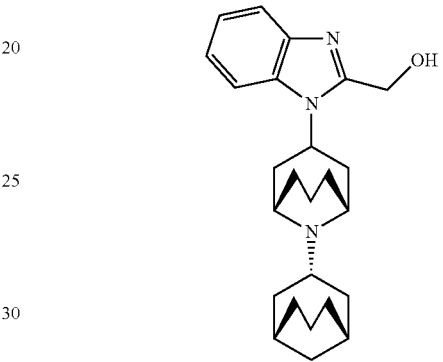

or a pharmaceutically acceptable salt thereof.

21. The compound of claim 20, wherein the pharmaceutically acceptable salt is a hydrochloride-salt, a sodium-salt, a potassium-salt, or a para-toluenesulfonic acid-salt.

22. A method for modulating ORL-1 receptor function in a cell, comprising contacting a cell capable of expressing the ORL-1 receptor with an effective amount of the compound or a pharmaceutically acceptable salt of the compound of claim 16.

* * * * *

UNITED STATES PATENT AND TRADEMARK OFFICE
CERTIFICATE OF CORRECTION

PATENT NO. : 9,598,411 B2
APPLICATION NO. : 14/800475
DATED : March 21, 2017
INVENTOR(S) : Nobuyuki Tanaka et al.

It is certified that error appears in the above-identified patent and that said Letters Patent is hereby corrected as shown below:

In the Claims

In Column 424, Line 32, Claim 1, "-[(C$_4$-C$_{10}$)alkyl" should read -- -[(C$_1$-C$_{10}$)alkyl --.

In Column 425, Line 21, Claim 1, "-SR$^9$" should read -- -OR$^9$, -SR$^9$ --.

In Column 428, Line 56, Claim 12, "-(C$_8$-C$_{14}$)cycloalkenyl," should read -- -(C$_5$-C$_{14}$)cycloalkenyl, --.

In Column 430, Line 35 to Column 431, Line 43, Claim 16, " 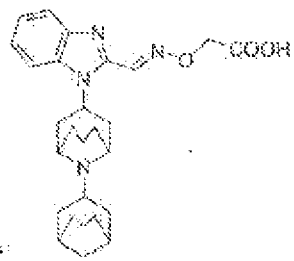 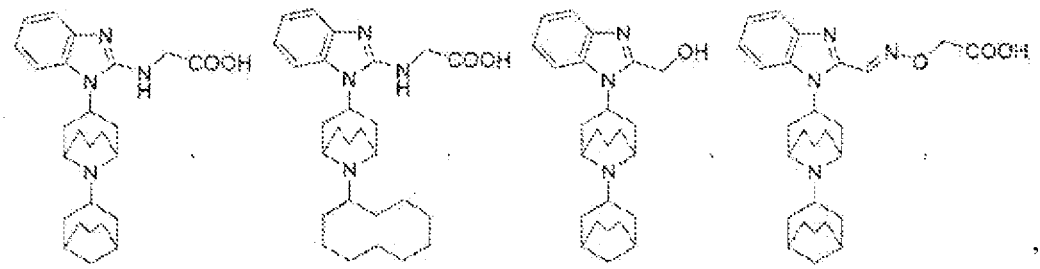 " should Signed and Sealed this
Twenty-fourth Day of October, 2017

Joseph Matal
*Performing the Functions and Duties of the
Under Secretary of Commerce for Intellectual Property and
Director of the United States Patent and Trademark Office* read -- 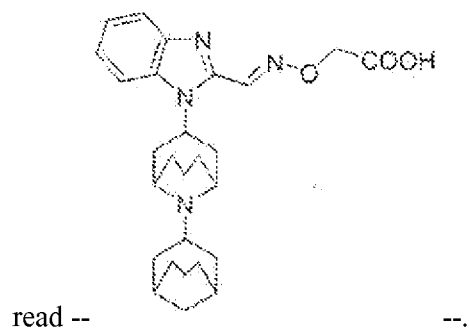 --.